(12) United States Patent
Cooper et al.

(10) Patent No.: US 11,465,992 B2
(45) Date of Patent: Oct. 11, 2022

(54) SULFONAMIDE CARBOXAMIDE COMPOUNDS

(71) Applicant: Inflazome Limited, Dublin (IE)

(72) Inventors: Matthew Cooper, Cambridge (GB); David Miller, Cambridge (GB); Angus MacLeod, Cambridge (GB); Jimmy Van Wiltenburg, Groningen (NL); Stephen Thom, Nottingham (GB); Stephen St-Gallay, Nottingham (GB); Jonathan Shannon, Nottingham (GB)

(73) Assignee: INFLAZOME LIMITED, Dublin (IE)

( * ) Notice: Subject to any disclaimer, the term of this patent is extended or adjusted under 35 U.S.C. 154(b) by 0 days.

(21) Appl. No.: 16/629,006

(22) PCT Filed: Jul. 4, 2018

(86) PCT No.: PCT/EP2018/068077
§ 371 (c)(1),
(2) Date: Jan. 6, 2020

(87) PCT Pub. No.: WO2019/008025
PCT Pub. Date: Jan. 10, 2019

(65) Prior Publication Data
US 2020/0291003 A1    Sep. 17, 2020

(30) Foreign Application Priority Data

Jul. 7, 2017 (GB) ................................ 1710943
Aug. 15, 2017 (GB) ................................ 1713079
Aug. 15, 2017 (GB) ................................ 1713082
Nov. 9, 2017 (GB) ................................ 1718561
Nov. 9, 2017 (GB) ................................ 1718563
Dec. 22, 2017 (GB) ................................ 1721726

(51) Int. Cl.
| | | |
|---|---|---|
| *C07D 409/04* | (2006.01) |
| *C07D 205/04* | (2006.01) |
| *C07D 205/12* | (2006.01) |
| *C07D 207/12* | (2006.01) |
| *C07D 211/54* | (2006.01) |
| *C07D 211/96* | (2006.01) |
| *C07D 215/36* | (2006.01) |
| *C07D 223/06* | (2006.01) |
| *C07D 239/60* | (2006.01) |
| *C07D 241/18* | (2006.01) |
| *C07D 401/04* | (2006.01) |
| *C07D 401/06* | (2006.01) |
| *C07D 401/12* | (2006.01) |
| *C07D 401/14* | (2006.01) |

(Continued)

(52) U.S. Cl.
CPC ......... *C07D 409/04* (2013.01); *C07D 205/04* (2013.01); *C07D 205/12* (2013.01); *C07D 207/12* (2013.01); *C07D 211/54* (2013.01); *C07D 211/96* (2013.01); *C07D 215/36* (2013.01); *C07D 223/06* (2013.01); *C07D 239/60* (2013.01); *C07D 241/18* (2013.01); *C07D 401/04* (2013.01); *C07D 401/06* (2013.01); *C07D 401/12* (2013.01); *C07D 401/14* (2013.01); *C07D 405/04* (2013.01); *C07D 405/06* (2013.01); *C07D 453/02* (2013.01); *C07D 471/08* (2013.01)

(58) Field of Classification Search
None
See application file for complete search history.

(56) References Cited

U.S. PATENT DOCUMENTS

| 3,242,174 A | 3/1966 | McManus et al. |
| 3,305,556 A | 2/1967 | McManus et al. |

(Continued)

FOREIGN PATENT DOCUMENTS

| AU | 2015900507 | 8/2016 |
| CA | 1292738 C | 12/1991 |

(Continued)

OTHER PUBLICATIONS

Abou Ouf, et al., "Sulphonyl Ureas and Thioureas of 1,3,4—Thiodiazole to be tested as Hypoglycomic Agents," Egypt. J. Pharm. Sci., 21(3-4):189-198, (1980).

(Continued)

*Primary Examiner* — Samantha L Shterengarts
(74) *Attorney, Agent, or Firm* — Alston & Bird LLP

(57) ABSTRACT

The present invention relates to compounds of formula (I):

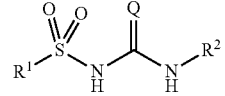

Formula (I)

wherein Q is selected from O or S; $R^1$ is a non-aromatic heterocyclic group comprising at least one ring nitrogen atom, wherein $R^1$ is attached to the sulfur atom of the sulfonylurea group by a ring carbon atom, and wherein $R^1$ may optionally be substituted; and $R^2$ is a cyclic group substituted at the α-position, wherein $R^2$ may optionally be further substituted.

The present invention further relates to salts, solvates and prodrugs of such compounds, to pharmaceutical compositions comprising such compounds, and to the use of such compounds in the treatment and prevention of medical disorders and diseases, most especially by the inhibition of NLRP3.

37 Claims, No Drawings

(51) Int. Cl.
    *C07D 405/04*     (2006.01)
    *C07D 405/06*     (2006.01)
    *C07D 453/02*     (2006.01)
    *C07D 471/08*     (2006.01)

(56) References Cited

U.S. PATENT DOCUMENTS

| | | |
|---|---|---|
| 4,018,929 A | 4/1977 | Delarge et al. |
| 4,723,991 A | 2/1988 | Holyoke, Jr. et al. |
| 4,741,760 A | 5/1988 | Meyer et al. |
| 4,802,908 A | 2/1989 | Hillemann |
| 5,169,860 A | 12/1992 | Mohamadi et al. |
| 5,219,856 A | 6/1993 | Olson |
| 5,486,618 A | 1/1996 | Hagen et al. |
| 10,538,487 B2 | 1/2020 | O'Neill et al. |
| 2002/0034764 A1 | 3/2002 | Gabel et al. |
| 2002/0077486 A1 | 6/2002 | Scarborough et al. |
| 2006/0069093 A1 | 3/2006 | Scarborough et al. |
| 2019/0192478 A1 | 6/2019 | Hacini-Rachinel |
| 2019/0359564 A1 | 11/2019 | O'Neill et al. |

FOREIGN PATENT DOCUMENTS

| | | |
|---|---|---|
| CN | 1245490 A | 2/2000 |
| CN | 104513239 A | 4/2015 |
| DK | 2006/00313 L | 3/2006 |
| EP | 125864 A1 | 11/1984 |
| EP | 176304 A1 | 4/1986 |
| EP | 177163 A2 | 4/1986 |
| EP | 189069 A2 | 7/1986 |
| EP | 224842 A2 | 6/1987 |
| EP | 249938 A2 | 12/1987 |
| EP | 262096 A1 | 3/1988 |
| EP | 318602 A1 | 6/1989 |
| EP | 0467613 A1 | 1/1992 |
| EP | 610653 A1 | 8/1994 |
| EP | 795548 A1 | 9/1997 |
| EP | 885890 A1 | 12/1998 |
| EP | 976742 A1 | 2/2000 |
| EP | 1236468 A1 | 9/2002 |
| EP | 1995240 A1 | 11/2008 |
| EP | 2543670 A1 | 1/2013 |
| EP | 2781216 A1 | 9/2014 |
| EP | 2962692 A1 | 1/2016 |
| FR | 2068472 A1 | 8/1971 |
| GB | 797474 A | 7/1958 |
| GB | 1146979 A | 3/1969 |
| GB | 1147403 A | 4/1969 |
| GB | 1155936 A | 6/1969 |
| GB | 1322980 A | 7/1973 |
| JP | S60-45573 A | 3/1985 |
| JP | S62-148482 A | 7/1987 |
| JP | H06-199053 A | 7/1994 |
| JP | H06-199054 A | 7/1994 |
| JP | 2000-053649 A | 2/2000 |
| JP | 2000-095796 A | 4/2000 |
| JP | 2000-511200 A | 8/2000 |
| JP | 2002-275062 A | 9/2002 |
| PL | 221813 B1 | 5/2016 |
| RU | 2022963 C1 | 11/1994 |
| WO | WO 1991/10668 A1 | 7/1991 |
| WO | WO 1992/04319 A1 | 3/1992 |
| WO | WO 1992/008694 A1 | 5/1992 |
| WO | WO 1993/004045 A1 | 3/1993 |
| WO | WO 1993/004046 A1 | 3/1993 |
| WO | WO 1997/011057 A1 | 3/1997 |
| WO | WO 1998/032733 A1 | 7/1998 |
| WO | WO 2000/055126 A2 | 9/2000 |
| WO | WO 2001/019390 A1 | 3/2001 |
| WO | WO 2001/57037 A1 | 8/2001 |
| WO | WO 2002/006246 A1 | 1/2002 |
| WO | WO 2002/094176 A2 | 11/2002 |
| WO | WO 2003/031194 A1 | 4/2003 |
| WO | WO 2003/031397 A1 | 4/2003 |
| WO | WO 2003/035076 A1 | 5/2003 |
| WO | WO 2003/045400 A1 | 6/2003 |
| WO | WO 2003/099805 A1 | 12/2003 |
| WO | WO 2005/032488 A2 | 4/2005 |
| WO | WO 2005/035520 A1 | 4/2005 |
| WO | WO 2006/039212 A2 | 4/2006 |
| WO | WO 2006/085815 A1 | 8/2006 |
| WO | WO 2006/097293 A2 | 9/2006 |
| WO | WO 2008/090382 A1 | 7/2008 |
| WO | WO 2009/065096 A1 | 5/2009 |
| WO | WO 2011/041694 A2 | 4/2011 |
| WO | WO 2016/119349 A1 | 8/2016 |
| WO | WO 2016/131098 A1 | 8/2016 |
| WO | WO 2016/131098 A8 | 8/2016 |
| WO | WO 2016/138473 A1 | 9/2016 |
| WO | WO 2017/106957 A1 | 6/2017 |
| WO | WO 2017/129897 A1 | 8/2017 |
| WO | WO 2017/140778 A1 | 8/2017 |
| WO | WO 2017/184604 A1 | 10/2017 |
| WO | WO 2017/189651 A1 | 11/2017 |
| WO | WO 2017/189652 A1 | 11/2017 |
| WO | WO 2017/189663 A1 | 11/2017 |
| WO | WO 2017/201150 A1 | 11/2017 |
| WO | WO 2017/201152 A1 | 11/2017 |
| WO | WO 2018/215818 A1 | 11/2018 |
| WO | WO 2019/008025 A1 | 1/2019 |
| WO | WO 2019/008029 A1 | 1/2019 |
| WO | WO 2019/034686 A1 | 2/2019 |

OTHER PUBLICATIONS

Abou Ouf, et al., "Thiophene Sulphonylureas Structurally Related to Antidiabetic Drugs", J. Drug Res. Egypt, 6(2):123-129, (1974).

Alsante et al., "Pharmaceutical Impurity Identification: A Case Study Using a Multidisciplinary Approach," Journal of Pharmaceutical Sciences, 93(9):2296-2309, (2004).

Baldwin et al, "Inhibiting the Inflammasome: A Chemical Perspective," Journal of Medicinal Chemistry, doi: 10.1021/acs.jmedchem. 5b01091, 59(5):1691-1710, received Jul. 13, 2015, (2016).

Booth et al., "A new and efficient approach to the synthesis of 6-amidino-2-oxopurines," Journal of the Chemical Society, Perkin Transactions 1, 1241-1251, (2001).

Braddock et al., "Targeting IL-1 in Inflammatory Disease: New Opportunities for Therapeutic Intervention," Nature Reviews, Drug Discovery, 3:1-10, (2004).

CAS RN 10238-21-8; STN Entry Date: Nov. 16, 1984; Benzamide, 5-chloro-N-[2-[4-[[[(cyclohexylamino)carbonyl]amino]sulfonyl]phenyl]ethyl]-2-methoxy-.

CAS RN 110311-27-8; STN Entry Date: Sep. 19, 1987; 1H-Indene-5-sulfonamide, N-[[(4-chlorophenyl)amino]carbonyl]-2,3-dihydro-.

CAS RN 210826-40-7; STN Entry Date: Sep. 3, 1998; 2-Furansulfonamide, N-[[(1,2,3,5,6,7-hexahydro-s-indacen-4-yl)amino]carbonyl]-4-(1-hydroxy-1-methylethyl)-.

CAS RN 210826-41-8; STN Entry Date: Sep. 3, 1998; 2-Furansulfonamide, N-[[(8-chloro-1,2,3,5,6,7-hexahydro-s-indacen-4-yl)amino]carbonyl]-4-(1-hydroxy-1-methylethyl)-.

CAS RN 210826-47-4; STN Entry Date: Sep. 3, 1998; 2-Furansulfonamide, N-[[[4-chloro-2,6-bis(1-methylethyl) phenyl]amino]carbonyl]-4-(1-hydroxy-1-methylethyl)-.

CAS RN 29094-61-9; STN Entry Date: Nov. 16, 1984; 2-Pyrazinecarboxamide, N-[2-[4-[[[(cyclohexylamino)carbonyl]amino]sulfonyl]phenyl]ethyl]-5-methyl-.

CAS RN 309742-96-9; STN Entry date Dec. 19, 2000; N-[[(4-chlorophenyl)amino]carbonyl]-1-(phenylmethyl)-1 H-1,2,4-Triazole-3-sulfonamide.

CAS RN 33342-05-1; STN Entry Date: Nov. 16, 1984; Benzenesulfonamide, N-[(cyclohexylamino)carbonyl]-4-[2-(3,4-dihydro-7-methoxy-4,4-dimethyl-1,3-dioxo-2(1H)-isoquinolinyl)ethyl]-.

CAS RN 663215-37-0; STN Entry date Mar. 15, 2004; N-(2-chlorophenyl)-5-[[[[(2-chlorophenyl)amino]carbonyl]amino]sulfonyl]-1 H-1,2,4-Triazole-1-carboxamide.

CAS RN 93479-97-1; STN Entry Date: Dec. 18, 1984; 1H-Pyrrole-1-carboxamide, 3-ethyl-2,5-dihydro-4-methyl-N-[2-[4-[[[[(trans-4-methylcyclohexyl)amino]carbonyl]amino]sulfonyl]phenyl] ethyl]-2-oxo-.

(56) References Cited

OTHER PUBLICATIONS

CAS RN 968-81-0; STN Entry Date: Nov. 16, 1984; Benzenesulfonamide, 4-acetyl-N-[(cyclohexylamino)carbonyl]-.
Coll et al., "A small-molecule inhibitor of the NLRP3 inflammasome for the treatment of inflammatory diseases," Nature Medicine, 21(3):248-255, (2015).
Cook et al., "Immunotherapy and vaccines—The NLRP3 inflammasome, a target for therapy in diverse disease states," Eur. J. Immunol., 40(3): 631-634, (2010).
Croker et al., "C5a, but not C5a-des Arg, induces upregulation of heteromer formation between complement C5a receptors C5aR and C5L2," Immunology and Cell Biology, 91(10):625-633, doi:10.1038/icb.2013.48, (2013).
Cubrilovic et al., "Determination of Protein-Ligand Binding Constants of a Cooperatively Regulated Tetrameric Enzyme Using Electrospray Mass Spectrometry," ACS Chem. Biol., 9(1):218-226, (2014).
Database Caplus [Online]: Chemical Abstracts Service, Columbus, Ohio, US; Dymek et al., Database citation for: "Synthesis of some pyrazolylureas," Abstract, XP002785804, Database Accession No. 1975:57600, Compounds with the Registry Nos. 54569-73-2, 54569-74-3, 54569-75-4, 54569-76-5, 54569-77-6, and 54644-70-1, (1975).
Database Caplus [Online]: Chemical Abstracts Service, Columbus, Ohio, US; Grandberg et al., Database citation for: "3-(p-Bromophenyl)-5-aminopyrazole and some derivatives," Abstract, XP002785801, Database Accession No. 2004:153241, Compound with the Registry No. 786688-48-0, (2003).
Database Caplus [Online]: Chemical Abstracts Service, Columbus, Ohio, US; Nam et al., Database citation of: "Acyl derivatives of 3-(p-aminophenyl)-5-aminopyrazole and its N(1)-substituted derivatives," Abstract, XP002785803, Database Accession No. 1999:126025, Compounds with the Registry Nos. 223518-59-0, 223518-69-2, and 223518-80-7, (1998).
Database Caplus [Online]: Chemical Abstracts Service, Columbus, Ohio, US; Roychowdhury et al., Database citation of: "Synthesis of some new 1,3,5-triazinylbarbiturates," Abstract, XP002785802, Database Accession No. 2003:321536, Compounds with the Registry Nos. 566135-48-6; 566135-49-7; 566135-50-0; and 566135-51-1, (2003).
Dias et al., "Synthesis of new imidazo[4,5-d][1,3]diazepine derivatives from 5-amino-4-(cyanoformimidoyl)imidazoles," Journal of Heterocyclic Chemistry, 33(3):855-862, (1996).
Doitsh et al., "Cell death by pyroptosis drives CD4 T-cell depletion in HIV-1 infection," Nature, 505:509-514, doi:10.1038/nature12940, (2014).
Eggler et al., "Synthesis of Covalent [14C]-Labeled Diarylsulfonylurea (DASU) Inhibitors of The Processing and Release of IL-1," Journal of Labelled Compounds and Radiopharmaceuticals, 45(9):785-794, doi: 10.1002/JLCR.602, (2002).
El-Telbany et al., "Synthesis of Thiophenesulphonylureas and Thioureas Structurally Related to Certain Oral Hypoglycemic drugs. Part 1," Egypt. J. Pharm. Sci., 16(4):397-401, (1975).
Fleming et al., "Novel axially chiral bis-arylthiourea-based organocatalysts for asymmetric Friedel-Crafts type reactions," Tetrahedron Letters, 47(39):7037-7042, (2006).
Foroumadi et al., "Synthesis of certain diarylsulfonylurea derivatives as new potential antitumor agents," Chemistry: An Indian Journal, 1(12):745-748, (2005).
Goda et al., "Development of some 1,2,4-triazole derivatives as potential hypoglycemic agents," Alex. Journal of Pharm. Sci., 1(2):63-66, (1987).
Grishman et al., "Toll-like receptors, the NLRP3 inflammasome, and interleukin-1β in the development and progression of type 1 diabetes," Pediatric Research, 71(6):626-632, (2012).
Hebeisen et al., "Orally active Aminopyridines as inhibitors of tetrameric fructose-1,6-bisphosphatase," Bioorganic & Medicinal Chemistry Letters, 21 (11): 3237-3242, (2011).
Holland, "Preparation of Some Additional Sulfonylureas," Journal of Organic Chemistry, 26(5): 1662-1665, (1961).

Howbert et al., "Novel Agents Effective Against Solid Tumors: The Diarylsulfonylureas. Synthesis, Activities, and Analysis of Quantitative Structure-Activity Relationships," J. Med. Chern., 33(9):2393-2407, doi: 10.1021/JM00171A013, (1990).
Khelili et al., "Synthesis and vasodilator effects of 3- and 7-sulfonylurea-1,2,4-benzothiadiazin-1,1-dioxides on rat aorta," Bioorganic & Medicinal Chemistry, 3(5):495-503, (1995).
Khuntwal et al., "Credential Role of van der Waal Volumes and Atomic Masses in Modeling Hepatitis C Virus NS5B Polymerase Inhibition by Tetrahydrobenzo-Thiophenes Using SVM and MLR Aided QSAR Studies," Current Bioinformatics, 8:465-471, (2013).
Krishnan et al., "Inflammasome activity is essential for one kidney/deoxycorticosterone acetate/salt-induced hypertension in mice," British Journal of Pharmacology, 173:752-765, (2016).
Kumar et al., "Sulfonamide bearing oligonucleotides: Simple synthesis and efficient RNA recognition," Bioorganic & Medicinal Chemistry, 20(12): 3843-3849, (2012).
Laliberte et al., "Glutathione S-Transferase Omega 1-1 Is a Target of Cytokine Release Inhibitory Drugs and May Be Responsible for Their Effect on Interleukin-1β Posttranslational Processing," J. Biol. Chem., 278(19):16567-16578, doi: 10.1074/jbc.M211596200, (2003).
Lamkanfi et al., "Glyburide inhibits the Cryopyrin/Nalp3 inflammasome," J. Cell Biol., 187(1):61-70, (2009).
Laporte, et al., "Tetrahydrobenzothiophene inhibitors of hepatitis C Virus NS5B polymerase," Bioorganic & Medicinal Chemistry Letters, 16(1): 100-103, (2006).
Li et al., "Click Chemistry to Fluorescent Amino Esters: Synthesis and Spectroscopic Studies," Eur. J. Org. Chem., 2395-2405, (2010).
Li et al., "Discovery of the first SecA inhibitors using structure-based virtual screening," Biochemical and Biophysical Research Communications, 368(4):839-845, (2008).
López-Castejón et al., "Current status of inflammasome blockers as anti-inflammatory drugs," Expert Opin. Investig. Drugs, 21 (7):995-1007, (2012).
Luckhurst et al., "A convenient synthesis of sulfonylureas from carboxylic acids and sulfonamides via an in situ Curtius rearrangement," Tetrahedron Letters, 48(50):8878-8882, (2007).
McManus et al, "Sulfamylurea Hypoglycemic Agents. 1. Synthesis and Screening," Journal of Medicinal Chemistry, 8(6):766-776, (1965).
Menu et al., "The NLRP3 inflammasome in health and disease: the good, the bad and the ugly," Clinical and Experimental Immunology, 166:1-15, (2011).
Mohamadi et al., "Sulfonylureas: A New Class of Cancer Chemotherapeutic Agents," J. Med. Chem., 35(16):3012-3016, (1992).
Mokhtar et al., "Synthesis of Nitrogenous Compounds, Part-III," Pakistan Journal of Scientific and Industrial Research, 34(1):9-15, (1991).
Monte et al., "Dihydrobenzofuran Analogues of Hallucinogens. 3. Models of 4-Substituted (2,5-Dimethoxyphenyl)alkylamine Derivatives with Rigidified Methoxy Groups," J. Med. Chem., 39(15):2953-2961, (1996).
Mu et al., "Fluorescent Logic Gates Chemically Attached to Silicon Nanowires," Angew. Chern. Int. Ed., 48(19):3469-3472, (2009).
Nair et al., "Unexpected binding Mode of the Sulfonamide fluorophore 5-Dimethylamino-1-naphthalene Sulfonamide to Human Carbonic Anhydrase II," Journal of Biological Chemistry, 271 (2):1003-1007, (1996).
Ozaki et al., "Targeting the NLRP3 inflammasome in chronic inflammatory diseases: current perspectives," Journal of Inflammation Research, 8:15-27, (2015).
Pacini et al., "2-(3-Thienyl)-5,6-dihydroxypyrimidine-4-carboxylic acids as inhibitors of HCV NS5B RdRp," Bioorganic& Medicinal Chemistry Letters, 19(21):6245-6249, (2009).
Perregaux et al., "Identification and Characterization of a Novel Class of Interleukin-1 Post-Translational Processing Inhibitors," Journal of Pharmacology and Experimental Therapeutics, 299(1):187-197, (2001).
Plé et al., "Discovery of a New Class of Anilinoquinazoline Inhibitors with High Affinity and Specificity for the Tyrosine Kinase Domain of c-Src," J. Med. Chem. 47(4):871-887, (2004).

(56) References Cited

OTHER PUBLICATIONS

Rotroff et al., "Predictive Endocrine Testing in the 21st Century Using in Vitro Assays of Estrogen Receptor Signaling Responses," Environmental Science & Technology, published by American Chemical Society, 48(15):8706-8716, (2014).
Saczewski et al., "Synthesis of Novel Aryl(heteroaryl)sulfonyl Ureas of Possible Biological Interest," Molecules, 15:1113-1126, (2010).
Shah et al., "Analysis of Pfizer Compounds in EPA's ToxCast Chemicals-Assay Space," Chemical Research in Toxicology, published by American Chemical Society, 27:86-98, (2014).
Shah et al., "Setting Clinical Exposure Levels of Concern for Drug-Induced Liver Injury (DILI) Using Mechanistic in vitro Assays," Toxicological Sciences, 147(2):500-514, (2015).
Sipes et al., "Profiling 976 ToxCast Chemicals across 331 Enzymatic and Receptor Signaling Assays," Chemical Research in Toxicology, published by American Chemical Society, 26(6):878-895, (2013).
Urban et al., "Novel Synthesis of 1-(1,2,3,5,6,7-Hexahydro-s-indacen-4-yl)-3-[4-(1-hydroxy-1-methyl-ethyl)-furan-2-sulfonyl]urea, an Anti-inflammatory Agent," Synthetic Communications, 33(12):2029-2043, doi: 10.1081/SCC-120021029 (2003).
Wambaugh et al., High-Throughput Models for Exposure-Based chemical Prioritization in the ExpoCast Project, Environmental Science & Technology, published by American Chemical Society, 47:8479-8488, (2013).
Waterman et al., "Improved Protocol and Data Analysis for Accelerated Shelf-Life Estimation of Solid Dosage Forms," Pharmaceutical Research, 24(4): 780-790, (2007).
Wen et al., "A role for the NLRP3 inflammasome in metabolic diseases—did Warburg miss inflammation?," Nature Immunology, 13(4):352-357, (2012).
Wu et al., "Recent advances in discovery and development of promising therapeutics against hepatitis C virus NS5B RNA-dependent RNA polymerase," Mini-Reviews in Medicinal Chemistry, 5(12):1103-1112, (2005).
Yamazaki et al., "Design, Synthesis and Biological Activity of Novel Non-Peptidyl Endothelin Converting Enzyme Inhibitors, 1-Phenyl-tetrazole-formazan Analogues," Bioorganic& Medicinal Chemistry Letters, 12(9):1275-1278, (2002).
Youssef et al., "Synthesis of certain diarylsulfonylureas as antitumor agents," Medicinal Chemistry Research, 10(6):404-418, (2001).
Youssef et al., "N1, N3-Diaryl sulfonylureas as Possible Anticancer Agents," Alex. J. Pharm. Sci., 8(3): 223-225, (1994).
Youssef et al., "Synthesis of Sulofenur Analoges as Antitumour Agents: Part II," Med. Chem. Res., 11 (9):81-503, (2002).
AU 2015900507 Australian Patent Office International-Type Search Report dated Jul. 30, 2015.
EP Application No. 16751821.6 (Published as EP3259253A1), Examination Report dated Feb. 1, 2019.
EP Application No. 16751821.6 (Published as EP3259253A1), Examination Report dated Aug. 5, 2019.
EP Application No. 16751821.6 (Published as EP3259253A1), Supplementary European Search Report and European Search Opinion dated Jun. 21, 2018.
EP Application No. 19187141.7 (Published as EP3578547A1), European Search Report and European Search Opinion dated Aug. 23, 2019.
EP Application No. 19187141.7 (Published as EP3578547A1), Examination Report dated Apr. 28, 2020.
GB Application No. 1710943.0, Search Report dated Apr. 17, 2018.
GB Application No. 1713082.4, Search Report dated Apr. 30, 2018.
RU Application No. 2017128287, Exam Report dated Jul. 31, 2019.
Singapore Application No. 11201706664Q, Written Opinion dated Jun. 7, 2018.
U.S. Appl. No. 15/551,264, Final Office Action dated May 22, 2019.
U.S. Appl. No. 15/551,264, Non-Final Office Action dated Dec. 26, 2018.
U.S. Appl. No. 15/551,264, Notice of Allowance dated Jul. 31, 2019.
U.S. Appl. No. 15/551,264, Notice of Allowance dated Oct. 22, 2019.
U.S. Appl. No. 15/551,264, Requirement for Restriction/Election dated May 3, 2018.
U.S. Appl. No. 16/535,002, Non-Final Office Action dated Mar. 16, 2020.
U.S. Appl. No. 16/535,002, Notice of Allowance dated May 15, 2020.
U.S. Appl. No. 16/535,002, Notice of Allowance dated Jul. 15, 2020.
U.S. Appl. No. 16/535,002, Requirement for Restriction/Election dated Nov. 26, 2019.
WIPO Application No. PCT/AU2016/050103, PCT International Preliminary Report on Patentability dated Aug. 31, 2017.
WIPO Application No. PCT/AU2016/050103, PCT International Search Report dated May 17, 2016.
WIPO Application No. PCT/AU2016/050103, PCT Written Opinion of the International Searching Authority dated May 17, 2016.
WIPO Application No. PCT/EP2018/068077, PCT International Preliminary Report on Patentability dated Jan. 16, 2020.
WIPO Application No. PCT/EP2018/068077, PCT International Search Report and Written Opinion of the International Searching Authority dated Oct. 5, 2018.
WIPO Application No. PCT/EP2018/072111, PCT International Preliminary Report on Patentability dated Feb. 27, 2020.
WIPO Application No. PCT/EP2018/072111, PCT International Search Report dated Nov. 6, 2018.
WIPO Application No. PCT/EP2018/072111, PCT Written Opinion of the International Searching Authority dated Nov. 6, 2018.
Akri, et ai., "Physicochemical 2D-Qsar and 3D Molecular Docking Studies on N-Chlorosulfonyl Isocyanate Analogs as Sterol O-Acyl-Transferase-1 "Soat-1" Inhibitors," Open Journal of Medicinal Chemistry, 3, 100-120, (2013).
CAS 959361-83-2; STN Entry Date: Dec. 21, 2007; CN Compound Name: Benzo[b]thiophene-3-carboxylic acid, 4,5,6,7-tetrahydro-2-[[[(1-pyrrolidinylsulfonyl)amino]carbonyl]amino]-, ethyl ester (CA Index Name).
Lather, et al., "Predicting Acyl-Coenzyme A: Cholesterol O-Acyltransferase Inhibitory Activity: Computational Approach Using Topological Descriptors," Drug Design and Discovery, 18:117-122, (2003).
Patankar, et al., "Prediction of IC50 Values for ACAT Inhibitors from Molecular Structure," J. Chern. Inf. Comput. Sci, 40, 706-723, (2000).
Picard et al., "Inhibitors of Acyl-CoA:Cholesterol O-Acyltransferase. 17. Structure-Activity Relationships of Several Series of Compounds Derived from N-Chlorosulfonyl Isocyanate," J. Med. Chem., 39(6): 1243-1252, doi: 10.1021/JM9509455, (1996).
Sarges, et al., "Sulfamylurea Hypoglycemic Agents. 6. High-Potency Derivatives," Journal of Medicinal Chemistry, vol. 19, No. 5, 695-709 (1976).
Belikov, et al., "MEDpress-inform," Pharmaceutical Chemistry, Text Book, 4th Edition, Moscow, 622 pages, 11, 27-29, (2007), Brief statement of relevance.
Disease—Wikipedia, retrieved from the internet on Jan. 5, 2022 at: https://en.wikipedia.org/wiki/Disease.
Parajuli, et al., "Prodrug as a Novel Approach of Drug Delivery—A Review," Journal of Drug Delivery & Therapeutics, 5(3):5-9, (2015).
Solvation—Wikipedia, retrieved from the internet on Jan. 5, 2022 at: https://en.wikipedia.org/wiki/Solvation.
Zawilska, et al., "Prodrugs: A challenge for the drug development," Pharmacological Reports, 65, 1-14, (2013).
Ahapkina, et al., "The fundamentals of the modulator concept and classification of modulatory drugs," Valenta Pharmaceuticals and The Serbsky State Research Center for Social and Forensic Psychiatry, p. 933, No. 19, 2012, English abstract.
Basic Non-disclosure Agreement, in Opposition against EP 3259253 on Jul. 23, 2021.
Brown, "Bioisosteres in Medicinal Chemistry" Published by Wiley-VCH Verlag & Co, KGaA, Weinheim, Germany, (2012).
CAS 210826-40-7; STN Entry Date: Sep. 30, 1998; CN Compound Name: 2-Furansulfonamide, N-[[(1,2,3,5,6,7-hexahydro-s-indacen-4-yl)amino]carbonyl]-4-(1-hydroxy-1-methylethyl)—(CA Index Name).

(56) References Cited

OTHER PUBLICATIONS

Coll, "In their own words . . . 2012 IEIIS Young Invesigator Awardees," Endotoxin Newsletter, vol. 19, No. 1, Editor Jerold Weiss, PhD, Dept. of Internal Medicine, University of Iowa, (Oct. 2013).

Coll, "Characterisation of CRID3 and Bayer-31 as Inflammasome Inhibitors and Analysis of the Role of the CRID3 Targets GSTO1 and CLIC1 in Innate Immune Signalling," Catalogue search only, retrieved from internet at: library.catalogue.tcd.ie/search~S7?/aColl/acoll/1??%2C52%2C52%2CB/frameset&FF=acoll=Rebecca=c&1%2C1%2C, on Oct. 11 and 12, 2020.

Coll, et al., "Correction: The Cytokine Release Inhibitory Drug CRID3 Targets ASC Oligomerisation in the NLRP3 and AIM2 Inflammasomes," PloS One, vol. 6, Issue 12, e29539, (Feb. 27, 2013).

Coll, et al., "Supporting Information: The Cytokine Release Inhibitory Drug CRID3 Targets ASC Oligomerisation in the NLRP3 and AIM2 Inflammasomes," PloS One, vol. 6, Issue 12, e29539, (Feb. 27, 2013).

Coll, et al., "The Cytokine Release Inhibitory Drug CRID3 Targets ASC Oligomerisation in the NLRP3 and AIM2 Inflammasomes," PloS One, vol. 6, Issue 12, e29539, (Dec. 2011).

Cross, "Could an NLRP3 inhibitor be the one drug to conquer common diseases?", Drug Discovery, vol. 98, Issue 7, (Feb. 17, 2020).

Dalvie, et al., "Biotransformation Reactions of Five-Membered Aromatic Heterocyclic Rings," Chem. Res. Toxicol., vol. 15, No. 3, 269-299, (2002).

Declaration of Marie Christina Gates, European Patent Attorney of Tomkins & Co., Dublin, Ireland, dated Jan. 5, 2021.

Declaration of Peter Dudley, Sub-Librarian for Reading Room Services & Space at The Library of Trinity College, Dublin (TCD), May 5, 2021.

Dempsey, et al., "Cytokine release inhibitor drug, CRID3, inhibits the NLRP3 inflammasome in glia," Journal of Neuroimmunology, vol. 275(1-2), p. 147, (2014).

Email from CAS Customer Center, Subject: RE: Case #00345503: question of Indexing, Sent: Oct. 9, 2020.

Extract from the Register of European Patents, About this File: EP3578547, in Opposition against EP 3259253 on Jul. 23, 2021.

Febbraio, "Role of interleukins in obesity: implictions for metabolic disease," Trends in Endocrinology and Metabolism, vol. 25, No. 6, pp. 312-319, (Jun. 2014).

Gavrilov, et al., Pharmaceutical Technology, Preparation of Medicaments, Text Book, Moscow Publishing group "GEOTAR-Media", 2010, 624, p. 20, Brief statement of relevance.

Guo, et al., "Inflammasomes: mechanism ofaction, role in disease, and therapeutics," Nature Medicine, vol. 21, No. 7, pp. 677-687, (Jul. 2015).

Haneklaus, et al., "Modulatory mechanisms controlling the NLRP3 inflammasome in inflammation: recent developments," Current opinion in immunology, 25, (1), p. 40-45, (2013).

Harkevic, et al., Pharmacology, 10th Edition, Moscow, "GEOTAR-Media", p. 73-74, (2010), Brief statement of relevance.

Himiceskij, Chemical Encyclopedia, (1983), p. 130-131, Brief statement of relevance.

Lowe, et al., "Synthesis of Heterocyclic Sulfonylureas," J. Heterocyclic Chem., 33, 763-766, (1996).

Maskovskjj, "Medicaments", Moscow Medicina p. 8, part 1, (1993), Brief statement of relevance.

Mullen, et al., "Pattern recognition receptors as potential therapeutic targets in inflammatory rheumatic disease," Arthritis Research & Therapy, 17:122, (2015).

Opposition against EP 3259253, Consolidated List of Cited Opposition Documents, submitted Aug. 20, 2021.

Opposition against EP 3259253, Table 2 of the patent with compound structures shown, on May 5, 2021.

Opposition against EP 3259253, Technical Annex, on May 5, 2021.

Opposition against EP 3259253, Summons to attend Oral Proceedings on Mar. 22, 2022 and Preliminary Opinion mailed Aug. 13, 2021.

Rowland, et al., "Concepts and Applications," Clinical Pharmacokinetics and Pharmacodynamics, 4th Edition, pp. 19-20, 28, 52, 54, 62, 75-79, and 85, (2011).

RU Application No. 2020 142 002 Office Action dated May 31, 2021, English translation only.

St Jean, et al., "Mitigating Heterocycle Metabolism in Drug Discovery," Journal of Medicinal Chemistry, 55, 6002-6020, (2012).

Stalla, et al., "Identification, Synthesis, and Biological Evaluation of the Major Human Metabolite of NLRP3 Inflammasome Inhibitor MCC950," ACS Medicinal Chemistry Letters, 7, 1034-1038, (2016).

Stocks, et al., "On Chemistry, On Medical Chemistry," Published in Great Britain by Sci-Ink Limited, ISBN 978-0-9550072-3-1, pp. 214-215, (2007).

The Library of Trinity Colege Dublin—Trinity College Dublin, Classic Catalogue, Thesis 9801 unavailable, retrived from the internet at: library.catalogue.tcd.ie/search on Nov. 26, 2020 and Jan. 7, 2021.

The Library of Trinity College Dublin—Trinity College Dublin, Classic Catalogue, Thesis 9801 recalled Oct. 27, 2020, retrived from the internet at: library.catalogue.tcd.ie/record-b15328246 on Nov. 3, 2020.

The Library of Trinity College Dublin—Trinity College Dublin, Classic Catalogue, Thesis 9801 unavailable, retrived from the internet at: library.catalogue.tcd.ie/search on Jul. 19, 2021.

The Library of Trinity College Dublin—Trinity College Dublin, Using the Library/Admissions, retrieved from the internet at: https://www.tcd.ie/library/using-library/admissions.php, on Dec. 22, 2020.

U.S. Appl. No. 16/535,002 Information Disclosure Statement Transmittal filed Feb. 1, 2021, in Opposition against EP 3259253 on Jul. 23, 2021.

Zulenko, et al., Pharmacology, Moscow KolosS, p. 34-35, (2008). Brief statement of relevance.

EP 3259253 Notice of Opposition filed Oct. 15, 2020.

EP 3259253 Statement of Opposition filed Oct. 15, 2020.

Balant, et al., "Metabolic Considerations in Prodrug Design," Burger's Medicinal Chemistry and Drug Discovery, 5th Edition, vol. 1; Principles and Practice, pp. 949-982, Editied by Manfred E. Wolff, © 1995 John Wiley & Sons, Inc.

Banker et al., Prodrugs, Modern Pharmaceutics, 3rd edition, Revised and Expanded, pp. 451 and 596, (1995).

Bundgaard, "Design of Prodrugs," Chapter1, p. 1, (1985).

EP 1169038 Decision of the Opposition Division of the European Patent Office posted Feb. 9, 2016.

Ettmayer, et al.," Perspective, Lessons Learned from Marketed and Investigational Prodrugs," Journal of Medicinal Chemistry, vol. 47, No. 10, 2393-2404, (May 6, 2004).

Han, "Targeted prodrug design to optimize drug delivery" AAPS Pharmsci. 2(1) Article 6: 1-11, (2000).

Luo, et al., "NLRP3 gene silencing ameliorates diabetic cardiomyopathy in a type 2 diabetes rat model", PloS One, vol. 9(8), e104771, (2014).

Pan, et al., "Microglial NLRP3 inflammasome activation mediates IL-1β-related inflammation in prefrontal cortex of depressive rats", Brain, Behavior, and Immunity, vol. 41, pp. 90-100, (2014).

Silverman, "The Organic Chemistry of Drug Design and Drug Action," Prodrugs and Drug Delivery Stystem, The Organic Chemistry of Drug Design and Drug Action, Chapter 8, pp. 352-400, (1992).

Stella, Valentino. "Prodrugs as theraputics" Expert Opinion of theraputic patents, 14(3): 277-280 (2004).

Testa, "Prodrug research: futile or fertile," Biochemical Pharmacology, 68, 2097-2106, (2004).

WO 1998/032733 A1, Claim 5 structures, in opposition of EP1169038.

WO 2001/019390 A1, Claim 14 structures, in opposition of EP1169038.

Zhao, et al., "Bay11-7082 attenuates murine lupus nephritis via inhibiting NLRP3 inflammasome and NF-kB activation", International Immunopharmacology, vol. 17, pp. 116-122, (2013).

EP Application No. 21204857.3 Extended European Search Report dated Feb. 21, 2022.

IL 273065 Examination Report dated Jan. 17, 2022.

(56) References Cited

OTHER PUBLICATIONS

TW Application No. 107123161 Search Report dated Feb. 17, 2022.
The Library of Trinity College Dublin—Trinity College Dublin, Classic Catalogue, Thesis 9801 unavailable, retrived from the internet at: library.catalogue.tcd.ie/search on Jan. 17, 2022.

SULFONAMIDE CARBOXAMIDE COMPOUNDS

CROSS-REFERENCE TO RELATED APPLICATION

This application is the US national stage of PCT/EP2018/068077 filed Jul. 4, 2018, which claims priority to GB 1710943.0 filed Jul. 7, 2017, GB 1713079.0 filed Aug. 15, 2017, GB 1713082.4 filed Aug. 15, 2017, GB 1718561.2 filed Nov. 9, 2017, GB 1718563.8 filed Nov. 9, 2017, and GB 1721726.6 filed Dec. 22, 2017.

FIELD OF THE INVENTION

The present invention relates to sulfonylureas and sulfonylthioureas comprising a non-aromatic heterocyclic group comprising at least one ring nitrogen atom, and further comprising a second cyclic group substituted at the α-position, and to associated salts, solvates, prodrugs and pharmaceutical compositions. The present invention further relates to the use of such compounds in the treatment and prevention of medical disorders and diseases, most especially by NLRP3 inhibition.

BACKGROUND

The NOD-like receptor (NLR) family, pyrin domain-containing protein 3 (NLRP3) inflammasome is a component of the inflammatory process, and its aberrant activity is pathogenic in inherited disorders such as cryopyrin-associated periodic syndromes (CAPS) and complex diseases such as multiple sclerosis, type 2 diabetes, Alzheimer's disease and atherosclerosis.

NLRP3 is an intracellular signalling molecule that senses many pathogen-derived, environmental and host-derived factors. Upon activation, NLRP3 binds to apoptosis-associated speck-like protein containing a caspase activation and recruitment domain (ASC). ASC then polymerises to form a large aggregate known as an ASC speck. Polymerised ASC in turn interacts with the cysteine protease caspase-1 to form a complex termed the inflammasome. This results in the activation of caspase-1, which cleaves the precursor forms of the proinflammatory cytokines IL-1β and IL-18 (termed pro-IL-1p and pro-IL-18 respectively) to thereby activate these cytokines. Caspase-1 also mediates a type of inflammatory cell death known as pyroptosis. The ASC speck can also recruit and activate caspase-8, which can process pro-IL-1p and pro-IL-18 and trigger apoptotic cell death.

Caspase-1 cleaves pro-IL-1β and pro-IL-18 to their active forms, which are secreted from the cell. Active caspase-1 also cleaves gasdermin-D to trigger pyroptosis. Through its control of the pyroptotic cell death pathway, caspase-1 also mediates the release of alarmin molecules such as IL-33 and high mobility group box 1 protein (HMGB1). Caspase-1 also cleaves intracellular IL-1R2 resulting in its degradation and allowing the release of IL-1α. In human cells caspase-1 may also control the processing and secretion of IL-37. A number of other caspase-1 substrates such as components of the cytoskeleton and glycolysis pathway may contribute to caspase-1-dependent inflammation.

NLRP3-dependent ASC specks are released into the extracellular environment where they can activate caspase-1, induce processing of caspase-1 substrates and propagate inflammation.

Active cytokines derived from NLRP3 inflammasome activation are important drivers of inflammation and interact with other cytokine pathways to shape the immune response to infection and injury. For example, IL-1β signalling induces the secretion of the pro-inflammatory cytokines IL-6 and TNF. IL-1β and IL-18 synergise with IL-23 to induce IL-17 production by memory CD4 Th17 cells and by γδ T cells in the absence of T cell receptor engagement. IL-18 and IL-12 also synergise to induce IFN-γ production from memory T cells and NK cells driving a Th1 response.

The inherited CAPS diseases Muckle-Wells syndrome (MWS), familial cold autoinflammatory syndrome (FCAS) and neonatal-onset multisystem inflammatory disease (NOMID) are caused by gain-of-function mutations in NLRP3, thus defining NLRP3 as a critical component of the inflammatory process. NLRP3 has also been implicated in the pathogenesis of a number of complex diseases, notably including metabolic disorders such as type 2 diabetes, atherosclerosis, obesity and gout.

A role for NLRP3 in diseases of the central nervous system is emerging, and lung diseases have also been shown to be influenced by NLRP3. Furthermore, NLRP3 has a role in the development of liver disease, kidney disease and aging. Many of these associations were defined using Nlrp3$^{-/-}$ mice, but there have also been insights into the specific activation of NLRP3 in these diseases. In type 2 diabetes mellitus (T2D), the deposition of islet amyloid polypeptide in the pancreas activates NLRP3 and IL-1β signaling, resulting in cell death and inflammation.

Several small molecules have been shown to inhibit the NLRP3 inflammasome. Glyburide inhibits IL-1β production at micromolar concentrations in response to the activation of NLRP3 but not NLRC4 or NLRP1. Other previously characterised weak NLRP3 inhibitors include parthenolide, 3,4-methylenedioxy-β-nitrostyrene and dimethyl sulfoxide (DMSO), although these agents have limited potency and are nonspecific.

Current treatments for NLRP3-related diseases include biologic agents that target IL-1. These are the recombinant IL-1 receptor antagonist anakinra, the neutralizing IL-1β antibody canakinumab and the soluble decoy IL-1 receptor rilonacept. These approaches have proven successful in the treatment of CAPS, and these biologic agents have been used in clinical trials for other IL-1β-associated diseases.

Some diarylsulfonylurea-containing compounds have been identified as cytokine release inhibitory drugs (CRIDs) (Perregaux et al.; J. Pharmacol. Exp. Ther. 299, 187-197, 2001). CRIDs are a class of diarylsulfonylurea-containing compounds that inhibit the post-translational processing of IL-1β. Post-translational processing of IL-1β is accompanied by activation of caspase-1 and cell death. CRIDs arrest activated monocytes so that caspase-1 remains inactive and plasma membrane latency is preserved.

Certain sulfonylurea-containing compounds are also disclosed as inhibitors of NLRP3 (see for example, Baldwin et al., J. Med. Chem., 59(5), 1691-1710, 2016; and WO 2016/131098 A1, WO 2017/129897 A1, WO 2017/140778 A1, WO 2017/184604 A1, WO 2017/184623 A1, WO 2017/184624 A1 and WO 2018/015445 A1).

There is a need to provide compounds with improved pharmacological and/or physiological and/or physicochemical properties and/or those that provide a useful alternative to known compounds.

SUMMARY OF THE INVENTION

A first aspect of the invention provides a compound of formula (I):

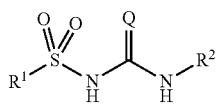

Formula (I)

wherein:

Q is selected from O or S;

R$^1$ is a non-aromatic heterocyclic group comprising at least one ring nitrogen atom, wherein R$^1$ is attached to the sulfur atom of the sulfonylurea group by a ring carbon atom, and wherein R$^1$ may optionally be substituted; and R$^2$ is a cyclic group substituted at the α-position, wherein R$^2$ may optionally be further substituted.

In the context of the present specification, a "hydrocarbyl" substituent group or a hydrocarbyl moiety in a substituent group only includes carbon and hydrogen atoms but, unless stated otherwise, does not include any heteroatoms, such as N, O or S, in its carbon skeleton. A hydrocarbyl group/moiety may be saturated or unsaturated (including aromatic), and may be straight-chained or branched, or be or include cyclic groups wherein, unless stated otherwise, the cyclic group does not include any heteroatoms, such as N, O or S, in its carbon skeleton. Examples of hydrocarbyl groups include alkyl, alkenyl, alkynyl, cycloalkyl, cycloalkenyl and aryl groups/moieties and combinations of all of these groups/moieties. Typically a hydrocarbyl group is a $C_1$-$C_{20}$ hydrocarbyl group. More typically a hydrocarbyl group is a $C_1$-$C_{15}$ hydrocarbyl group. More typically a hydrocarbyl group is a $C_1$-$C_{10}$ hydrocarbyl group. A "hydrocarbylene" group is similarly defined as a divalent hydrocarbyl group.

In the context of the present specification, unless otherwise stated, an "alkyl" substituent group or an alkyl moiety in a substituent group may be linear or branched. Examples of alkyl groups/moieties include methyl, ethyl, n-propyl, i-propyl, n-butyl, i-butyl, t-butyl and n-pentyl groups/moieties. Unless stated otherwise, the term "alkyl" does not include "cycloalkyl". Typically an alkyl group is a $C_1$-$C_{12}$ alkyl group. More typically an alkyl group is a $C_1$-$C_6$ alkyl group. An "alkylene" group is similarly defined as a divalent alkyl group.

An "alkenyl" substituent group or an alkenyl moiety in a substituent group refers to an unsaturated alkyl group or moiety having one or more carbon-carbon double bonds. Examples of alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1,4-hexadienyl groups/moieties. Unless stated otherwise, the term "alkenyl" does not include "cycloalkenyl". Typically an alkenyl group is a $C_2$-$C_{12}$ alkenyl group. More typically an alkenyl group is a $C_2$-$C_6$ alkenyl group. An "alkenylene" group is similarly defined as a divalent alkenyl group.

An "alkynyl" substituent group or an alkynyl moiety in a substituent group refers to an unsaturated alkyl group or moiety having one or more carbon-carbon triple bonds. Examples of alkynyl groups/moieties include ethynyl, propargyl, but-1-ynyl and but-2-ynyl. Typically an alkynyl group is a $C_2$-$C_{12}$ alkynyl group. More typically an alkynyl group is a $C_2$-$C_6$ alkynyl group. An "alkynylene" group is similarly defined as a divalent alkynyl group.

A "cyclic" substituent group or a cyclic moiety in a substituent group refers to any hydrocarbyl ring, wherein the hydrocarbyl ring may be saturated or unsaturated (including aromatic) and may include one or more heteroatoms, e.g. N, O or S, in its carbon skeleton. Examples of cyclic groups include cycloalkyl, cycloalkenyl, heterocyclic, aryl and heteroaryl groups as discussed below. A cyclic group may be monocyclic, bicyclic (e.g. bridged, fused or spiro), or polycyclic. Typically, a cyclic group is a 3- to 12-membered cyclic group, which means it contains from 3 to 12 ring atoms. More typically, a cyclic group is a 3- to 7-membered monocyclic group, which means it contains from 3 to 7 ring atoms.

As used herein, where it is stated that a cyclic group is monocyclic, it is to be understood that the cyclic group is not substituted with a divalent bridging substituent (e.g. —O—, —S—, —NH—, —N(R$^β$)— or —R$^α$—) so as to form a bridged, fused or spiro substituent. However, unless stated otherwise, a substituted monocyclic group may be substituted with one or more monovalent cyclic groups. Similarly, where it is stated that a group is bicyclic, it is to be understood that the cyclic group including any bridged, fused or spiro divalent bridging substituents attached to the cyclic group, but excluding any monovalent cyclic substituents, is bicyclic.

A "heterocyclic" substituent group or a heterocyclic moiety in a substituent group refers to a cyclic group or moiety including one or more carbon atoms and one or more heteroatoms, e.g. N, O or S, in the ring structure. Examples of heterocyclic groups include heteroaryl groups as discussed below and non-aromatic heterocyclic groups such as azetidinyl, azetinyl, tetrahydrofuranyl, pyrrolidinyl, tetrahydrothiophenyl, tetrahydropyranyl, piperidinyl, piperazinyl, morpholinyl, thiomorpholinyl, oxetanyl, thietanyl, pyrazolidinyl, imidazolidinyl, dioxolanyl, oxathiolanyl, thianyl, and dioxanyl groups.

A "cycloalkyl" substituent group or a cycloalkyl moiety in a substituent group refers to a saturated hydrocarbyl ring containing, for example, from 3 to 7 carbon atoms, examples of which include cyclopropyl, cyclobutyl, cyclopentyl and cyclohexyl. Unless stated otherwise, a cycloalkyl substituent group or moiety may include monocyclic, bicyclic or polycyclic hydrocarbyl rings.

A "cycloalkenyl" substituent group or a cycloalkenyl moiety in a substituent group refers to a non-aromatic unsaturated hydrocarbyl ring having one or more carbon-carbon double bonds and containing, for example, from 3 to 7 carbon atoms, examples of which include cyclopent-1-en-1-yl, cyclohex-1-en-1-yl and cyclohex-1,3-dien-1-yl. Unless stated otherwise, a cycloalkenyl substituent group or moiety may include monocyclic, bicyclic or polycyclic hydrocarbyl rings.

An "aryl" substituent group or an aryl moiety in a substituent group refers to an aromatic hydrocarbyl ring. The term "aryl" includes monocyclic aromatic hydrocarbons and polycyclic fused ring aromatic hydrocarbons wherein all of the fused ring systems (excluding any ring systems which are part of or formed by optional substituents) are aromatic. Examples of aryl groups/moieties include phenyl, naphthyl, anthracenyl and phenanthrenyl. Unless stated otherwise, the term "aryl" does not include "heteroaryl".

A "heteroaryl" substituent group or a heteroaryl moiety in a substituent group refers to an aromatic heterocyclic group or moiety. The term "heteroaryl" includes monocyclic aromatic heterocycles and polycyclic fused ring aromatic heterocycles wherein all of the so fused ring systems (excluding any ring systems which are part of or formed by optional substituents) are aromatic. Examples of heteroaryl groups/moieties include the following:

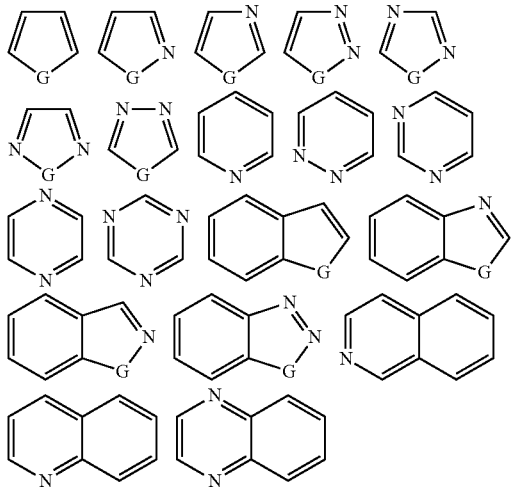

wherein G=O, S or NH.

Unless stated otherwise, where a cyclic group or moiety is stated to be non-aromatic, such as a cycloalkyl, cycloalkenyl or non-aromatic heterocyclic group, it is to be understood that the group or moiety, excluding any ring systems which are part of or formed by optional substituents, is non-aromatic. Similarly, where a cyclic group or moiety is stated to be aromatic, such as an aryl or a heteroaryl group, it is to be understood that the group or moiety, excluding any ring systems which are part of or formed by optional substituents, is aromatic. Typically, a cyclic group or moiety is considered non-aromatic, when it does not have any tautomers that are aromatic. Typically, when a cyclic group or moiety has a tautomer that is aromatic, it is considered aromatic, even if it has tautomers that are not aromatic.

For the purposes of the present specification, where a combination of moieties is referred to as one group, for example, arylalkyl, arylalkenyl, arylalkynyl, alkylaryl, alkenylaryl or alkynylaryl, the last mentioned moiety contains the atom by which the group is attached to the rest of the molecule. An example of an arylalkyl group is benzyl.

For the purposes of the present specification, in an optionally substituted group or moiety:

(i) each hydrogen atom may optionally be replaced by a group independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —Si(R$^\beta$)$_3$; —O—Si(R$^\beta$)$_3$; —R$^\alpha$—Si(R$^\beta$)$_3$; —R$^\alpha$—O—Si(R$^\beta$)$_3$; —NH$_2$; —NHR$^\beta$; —N(R$^\beta$)$_2$; —N(O)(R$^\beta$)$_2$; —N$^+$(R$^\beta$)$_3$; —R$^\alpha$—NH$_2$; —R$^\alpha$—NHR$^\beta$; —R$^\alpha$—N(R$^\beta$)$_2$; —R$^\alpha$—N(O)(R$^\beta$)$_2$; —R$^\alpha$—N$^+$(R$^\beta$)$_3$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —C(=NH)R$^\beta$; —C(=NH)NH$_2$; —C(=NH)NHR$^\beta$; —C(=NH)N(R$^\beta$)$_2$; —C(=NR$^\beta$)R$^\beta$; —C(=NR$^\beta$)NHR$^\beta$; —C(=NR$^\beta$)N(R$^\beta$)$_2$; —C(=NOH)R$^\beta$; —C(N$_2$)R$^\beta$; —R$^\alpha$—C(=NH)R$^\beta$; —R$^\alpha$—C(=NH)NH$_2$; —R$^\alpha$—C(=NH)NHR$^\beta$; —R$^\alpha$—C(=NH)N(R$^\beta$)$_2$; —R$^\alpha$—C(=NR$^\beta$)R$^\beta$; —R$^\alpha$—C(=NR$^\beta$)NHR$^\beta$; —R$^\alpha$—C(=NR$^\beta$)N(R$^\beta$)$_2$; —R$^\alpha$—C(=NOH)R$^\beta$; —R$^\alpha$—C(N$_2$)R$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —O—R$^\alpha$—N(O)(R$^\beta$)$_2$; —O—R$^\alpha$—N$^+$(R$^\beta$)$_3$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NH—R$^\alpha$—N(O)(R$^\beta$)$_2$; —NH—R$^\alpha$—N$^+$(R$^\beta$)$_3$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; —NR$^\beta$—R$^\alpha$—N(R$^\beta$)$_2$; —NR$^\beta$—R$^\alpha$—N(O)(R$^\beta$)$_2$; —NR$^\beta$—R$^\alpha$—N$^+$(R$^\beta$)$_3$; —N(O)R$^\beta$—R$^\alpha$—OH; —N(O)R$^\beta$—R$^\alpha$—OR$^\beta$; —N(O)R$^\beta$—R$^\alpha$—NH$_2$; —N(O)R$^\beta$—R$^\alpha$—NHR$^\beta$; —N(O)R$^\beta$—R$^\alpha$—N(R$^\beta$)$_2$; —N(O)R$^\beta$—R$^\alpha$—N(O)(R$^\beta$)$_2$; —N(O)R$^\beta$—R$^\alpha$—N$^+$(R$^\beta$)$_3$; —N$^+$(R$^\beta$)$_2$—R$^\alpha$—OH; —N$^+$(R$^\beta$)$_2$—R$^\alpha$—OR$^\beta$; —N$^+$(R$^\beta$)$_2$—R$^\alpha$—NH$_2$; —N$^+$(R$^\beta$)$_2$—R$^\alpha$—NHR$^\beta$; —N$^+$(R$^\beta$)$_2$—R$^\alpha$—N(R$^\beta$)$_2$; or —N$^+$(R$^\beta$)$_2$—R$^\alpha$—N(O)(R$^\beta$)$_2$; and/or (ii) any two hydrogen atoms attached to the same atom may optionally be replaced by a π-bonded substituent independently selected from oxo (=O), =S, =NH or =NR$^\beta$; and/or (iii) any two hydrogen atoms attached to the same or different atoms, within the same optionally substituted group or moiety, may optionally be replaced by a bridging substituent independently selected from —O—, —S—, —NH—, —N=N—, —N(R$^\beta$)—, —N(O)(R$^\beta$)—, —N$^+$(R$^\beta$)$_2$$^-$ or —R$^\alpha$—;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, wherein one or more —CH$_2$— groups in the backbone of the alkylene, alkenylene or alkynylene group may optionally be replaced by one or more —N(O)(R$^\beta$)— or —N$^+$(R$^\beta$)$_2$— groups, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, or wherein any two or three —R$^\beta$ attached to the same nitrogen atom may, together with the nitrogen atom to which they are attached, form a C$_2$-C$_7$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, C$_3$-C$_7$ halocycloalkyl, —O(C$_1$-C$_4$ alkyl), —O(C$_1$-C$_4$ haloalkyl), —O(C$_3$-C$_7$ cycloalkyl), —O(C$_3$-C$_7$ halocycloalkyl), —CO(C$_1$-C$_4$ alkyl), —CO(C$_1$-C$_4$ haloalkyl), —COO(C$_1$-C$_4$ alkyl), —COO(C$_1$-C$_4$ haloalkyl), halo, —OH, —NH$_2$, —CN, —C≡CH, oxo (=O), or 4- to 6-membered heterocyclic group.

Typically, the compounds of the present invention comprise at most one quaternary ammonium group such as —N$^+$(R$^\beta$)$_3$ or —N$^+$(R$^\beta$)$_2$—.

Where reference is made to a —R$^\alpha$—C(N$_2$)R$^\beta$ group, what is intended is:

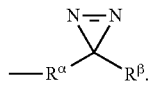

Typically, in an optionally substituted group or moiety:

(i) each hydrogen atom may optionally be replaced by a group independently selected from halo; —CN; —NO$_2$; —N$_3$; —R$^\beta$; —OH; —OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; —NR$^\beta$—R$^\alpha$—N(R$^\beta$)$_2$; a C$_3$-C$_7$ cycloalkyl group optionally substituted with one or more C$_1$-C$_3$ alkyl or C$_1$-C$_3$ haloalkyl groups; a C$_3$-C$_7$ cycloalkenyl group optionally substituted with one or more C$_1$-C$_3$ alkyl or C$_1$-C$_3$ haloalkyl groups; or a 3- to 7-membered non-aromatic heterocyclic group optionally substituted with one or more C$_1$-C$_6$ alkyl or C$_1$-C$_3$ haloalkyl groups; and/or (ii) any two hydrogen atoms attached to the same carbon atom may optionally be replaced by a π-bonded substituent independently selected from oxo (=O), =S, =NH or =NR$^\beta$; and/or (iii) any two hydrogen atoms attached to the same or different atoms, within the same optionally substituted group or moiety, may optionally be replaced by a bridging substituent independently selected from —O—, —S—, —NH—, —N(R$^\beta$)— or —R$^\alpha$—;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, and wherein any —R$^\beta$ may optionally be substituted with one or more C$_1$-C$_3$ alkyl, C$_1$-C$_3$ haloalkyl, C$_3$-C$_7$ cycloalkyl, —O(C$_1$-C$_3$ alkyl), halo, —CN, —C≡CH or oxo (=O) groups.

Typically, in an optionally substituted group or moiety:

(i) each hydrogen atom may optionally be replaced by a group independently selected from halo; —CN; —NO$_2$; —N$_3$; —R$^\beta$; —OH; —OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; a C$_3$-C$_7$ cycloalkyl group optionally substituted with one or more C$_1$-C$_3$ alkyl or C$_1$-C$_3$ haloalkyl groups; a C$_3$-C$_7$ cycloalkenyl group optionally substituted with one or more C$_1$-C$_3$ alkyl or C$_1$-C$_3$ haloalkyl groups;

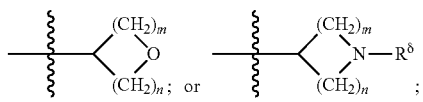

(ii) any two hydrogen atoms attached to the same carbon atom may optionally be replaced by a π-bonded substituent independently selected from (oxo) =O, =S, =NH or =NR$^\beta$; and/or (iii) any two hydrogen atoms attached to the same or different atoms, within the same optionally substituted group or moiety, may optionally be replaced by a bridging substituent independently selected from —O—, —S—, —NH—, —N(R$^\beta$)— or —R$^\alpha$—;

wherein each —R$^\alpha$— is independently selected from an alkylene, alkenylene or alkynylene group, wherein the alkylene, alkenylene or alkynylene group contains from 1 to 6 carbon atoms in its backbone, and wherein the alkylene, alkenylene or alkynylene group may optionally be substituted with one or more halo and/or —R$^\beta$ groups;

wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, and wherein any —R$^\beta$ may optionally be substituted with one or more C$_1$-C$_3$ alkyl, C$_1$-C$_3$ haloalkyl, C$_3$-C$_7$ cycloalkyl, —O(C$_1$-C$_3$ alkyl), halo, —CN, —C≡CH or oxo (=O) groups;

wherein each —R$^\beta$ is independently selected from a C$_1$-C$_6$ alkyl or C$_1$-C$_3$ haloalkyl group;

wherein each m is independently selected from 1, 2 or 3; and wherein each n is independently selected from 1, 2 or 3.

Typically a substituted group comprises 1, 2, 3 or 4 substituents, more typically 1, 2 or 3 substituents, more typically 1 or 2 substituents, and more typically 1 substituent.

Unless stated otherwise, any divalent bridging substituent (e.g. —O—, —S—, —NH—, —N(R$^\beta$)—, —N(O)(R$^\beta$)—, —N$^+$(R$^\beta$)$_2$— or —R$^\alpha$—) of an optionally substituted group or moiety (e.g. R$^1$) must only be attached to the specified group or moiety and may not be attached to a second group or moiety (e.g. R$^2$), even if the second group or moiety can itself be optionally substituted.

The term "halo" includes fluoro, chloro, bromo and iodo.

Unless stated otherwise, any reference to an element is to be considered a reference to all isotopes of that element. Thus, for example, unless stated otherwise any reference to hydrogen is considered to encompass all isotopes of hydrogen including deuterium and tritium.

Where reference is made to a hydrocarbyl or other group including one or more heteroatoms N, O or S in its carbon skeleton, or where reference is made to a carbon atom of a hydrocarbyl or other group being replaced by an N, O or S atom, what is intended is that:

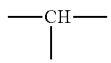

is replaced by

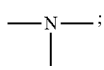

—CH$_2$— is replaced by —NH—, —O— or —S—;
—CH$_3$ is replaced by —NH$_2$, —OH, or —SH;
—CH═ is replaced by —N═;
CH$_2$═ is replaced by NH═, O═ or S═; or
CH≡ is replaced by N≡;
provided that the resultant group comprises at least one carbon atom. For example, methoxy, dimethylamino and aminoethyl groups are considered to be hydrocarbyl groups including one or more heteroatoms N, O or S in their carbon skeleton.

Where reference is made to a —CH$_2$— group in the backbone of a hydrocarbyl or other group being replaced by a —N(O)(R$^\beta$)— or —N$^+$(R$^\beta$)$_2$— group, what is intended is that:
—CH$_2$— is replaced by

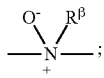

or
—CH$_2$— is replaced by

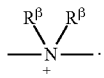

In the context of the present specification, unless otherwise stated, a C$_x$-C$_y$ group is defined as a group containing from x to y carbon atoms. For example, a C$_1$-C$_4$ alkyl group is defined as an alkyl group containing from 1 to 4 carbon atoms. Optional substituents and moieties are not taken into account when calculating the total number of carbon atoms in the parent group substituted with the optional substituents and/or containing the optional moieties. For the avoidance of doubt, replacement heteroatoms, e.g. N, O or S, are not to be counted as carbon atoms when calculating the number of carbon atoms in a C$_x$-C$_y$ group. For example, a morpholinyl group is to be considered a C$_4$ heterocyclic group, not a C$_6$ heterocyclic group.

For the purposes of the present specification, where it is stated that a first atom or group is "directly attached" to a second atom or group it is to be understood that the first atom or group is covalently bonded to the second atom or group with no intervening atom(s) or groups being present. So, for example, for the group (C═O)N(CH$_3$)$_2$, the carbon atom of each methyl group is directly attached to the nitrogen atom and the carbon atom of the carbonyl group is directly attached to the nitrogen atom, but the carbon atom of the carbonyl group is not directly attached to the carbon atom of either methyl group.

R$^1$ is a non-aromatic heterocyclic group which may optionally be substituted. For the avoidance of doubt, it is noted that it is a ring atom of the non-aromatic heterocyclic group of R$^1$ that is directly attached to the sulfur atom of the sulfonylurea group, not any optional substituent.

R$^1$ is a non-aromatic heterocyclic group which may be monocyclic, bicyclic (including bridged, fused and spiro), tricyclic or polycyclic. The bicyclic, tricyclic and polycyclic ring structures may be partially aromatic. For the avoidance of doubt, it is noted that when R$^1$ is a partially aromatic bicyclic, tricyclic or polycyclic group, the ring of R$^1$ that is directly attached to the sulfur atom of the sulfonylurea group is non-aromatic. For the avoidance of doubt, it is also noted that when R$^1$ is a bicyclic, tricyclic or polycyclic group, the at least one ring nitrogen atom of R$^1$ is in a non-aromatic ring, but not necessarily in the non-aromatic ring of R$^1$ that is directly attached to the sulfur atom of the sulfonylurea group. In one embodiment, when R$^1$ is a bicyclic, tricyclic or polycyclic group, the at least one ring nitrogen atom of R$^1$ is in the non-aromatic ring of R$^1$ that is directly attached to the sulfur atom of the sulfonylurea group.

Typically R$^1$ is monocyclic or bicyclic. In one embodiment, R$^1$ is a 4-, 5-, 6- or 7-membered monocyclic ring or a 7-, 8-, 9- or 10-membered bicyclic ring, wherein R$^1$ may optionally be substituted. In one embodiment, R$^1$ is a 4-, 5- or 6-membered monocyclic ring or a 7-, 8-, 9- or 10-membered bicyclic ring, wherein R$^1$ may optionally be substituted.

The non-aromatic heterocyclic group of R$^1$ may be fully saturated or partially unsaturated. In one embodiment, the non-aromatic heterocyclic group of R$^1$ is fully saturated.

In one embodiment, the non-aromatic heterocyclic group of R$^1$ is monocyclic. Where the non-aromatic heterocyclic group of R$^1$ is monocyclic, it may optionally be substituted with any monovalent substituent or any divalent α-bonded substituent, such as those defined above, but may not be substituted with a divalent bridging substituent (e.g. —O—, —S—, —NH—, —N(R$^\beta$)— or —R$^\alpha$—) so as to form a bridged, fused or spiro substituent. Examples of monocyclic non-aromatic heterocyclic groups include:

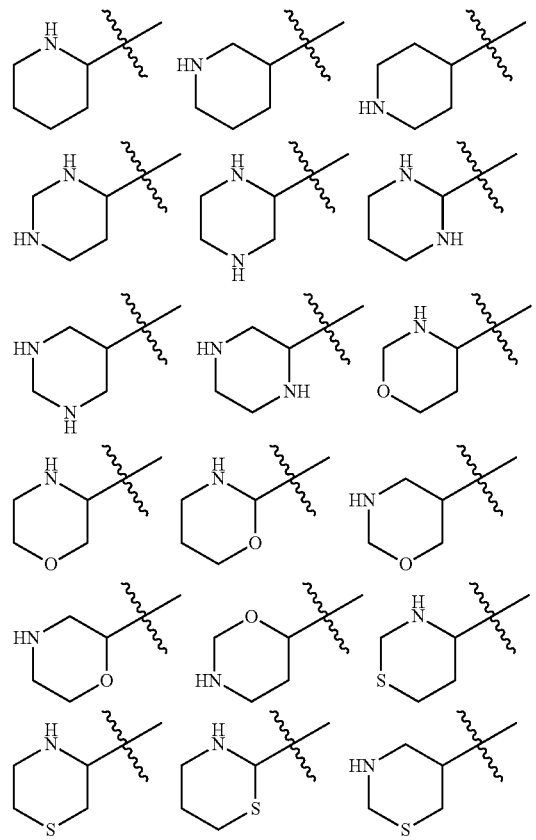

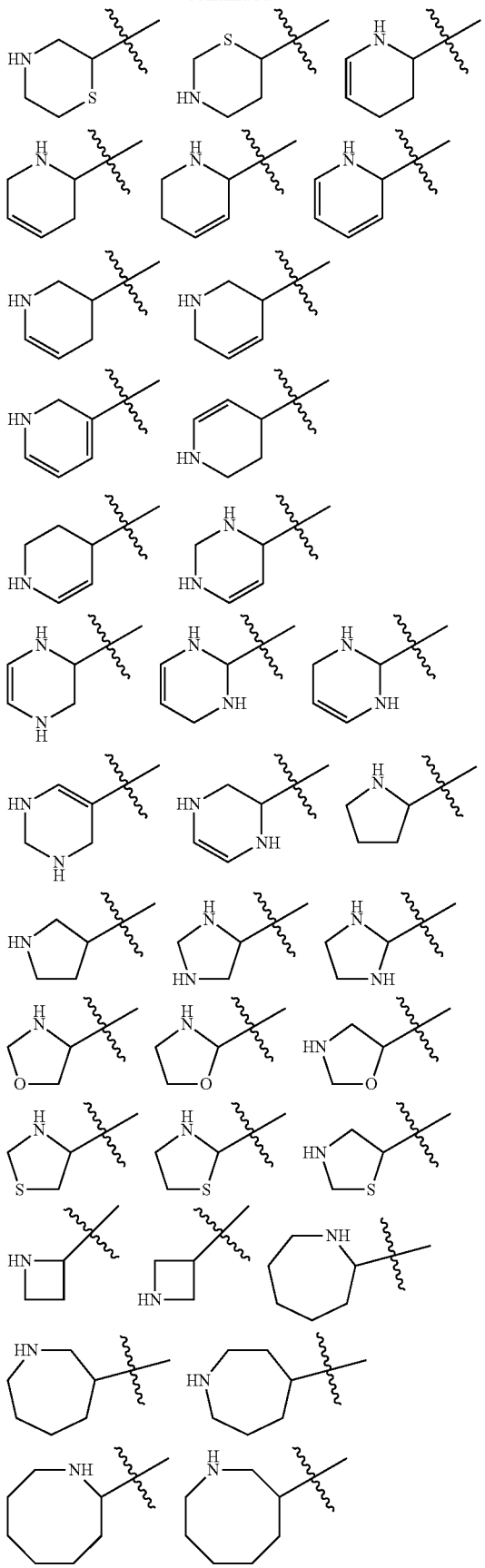

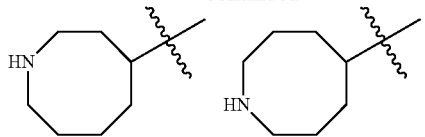

The non-aromatic heterocyclic group of $R^1$ may comprise one or more double bonds in the heterocyclic ring, provided the heterocyclic ring is non-aromatic. The non-aromatic heterocyclic group of $R^1$ does not have any tautomers that are aromatic.

The following are considered aromatic heterocyclic groups, because they have an aromatic tautomer:

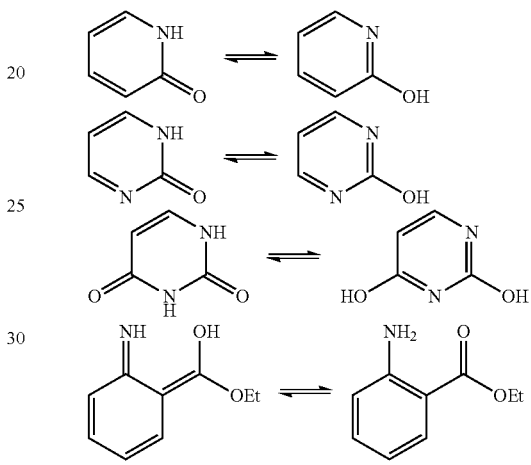

For the avoidance of doubt, the term "non-aromatic heterocyclic group" does not exclude heterocyclic groups or moieties which may possess aromatic character only by virtue of mesomeric charge separation. For example, the following is considered a non-aromatic heterocyclic group, because it does not have an aromatic tautomer:

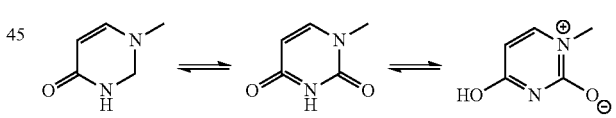

because the last shown tautomer is not taken into consideration because of mesomeric charge separation.

In one embodiment, the non-aromatic heterocyclic group of $R^1$ is monocyclic and is selected from:

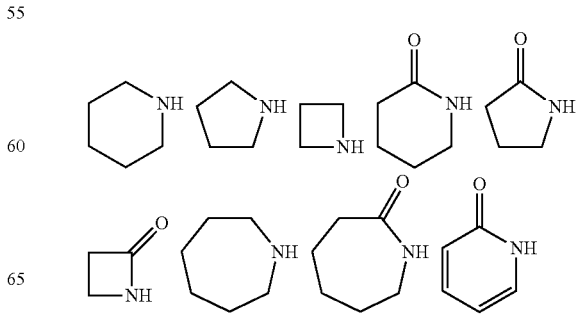

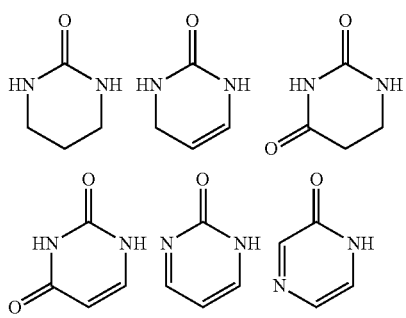

wherein R¹ may optionally be substituted or further substituted. Such non-aromatic heterocyclic R¹ groups are attached to the sulfur atom of the sulfonylurea group by any suitable ring carbon atom. Where the non-aromatic heterocyclic group of R¹ is monocyclic and is selected from:

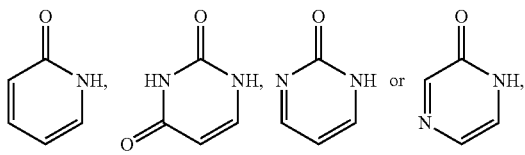

at least one ring nitrogen atom which is adjacent to a carbonyl group is substituted, so that the non-aromatic heterocyclic group of R¹ does not have any tautomers that are aromatic.

In another embodiment, the non-aromatic heterocyclic group of R¹ may be substituted with one or more fused cycloalkyl, cycloalkenyl, non-aromatic heterocyclic, aryl or heteroaryl rings such that the resultant group is bicyclic, tricyclic or polycyclic. For example, the non-aromatic heterocyclic group of R¹ may optionally be substituted with —R$^\alpha$— as defined above. The resultant group may optionally be further substituted with any monovalent substituent or any divalent π-bonded substituent, such as those defined above. Typically in such an embodiment, the resultant group is bicyclic or tricyclic, most typically bicyclic. Examples of such resultant bicyclic groups include:

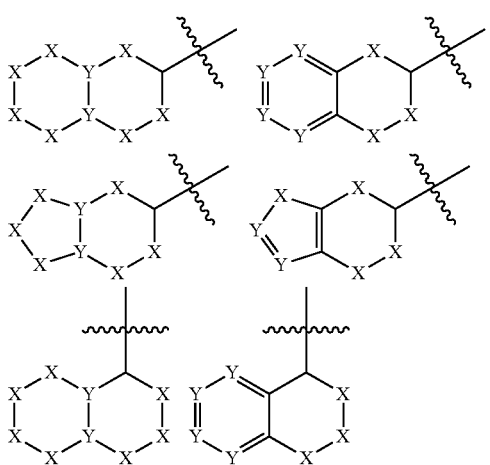

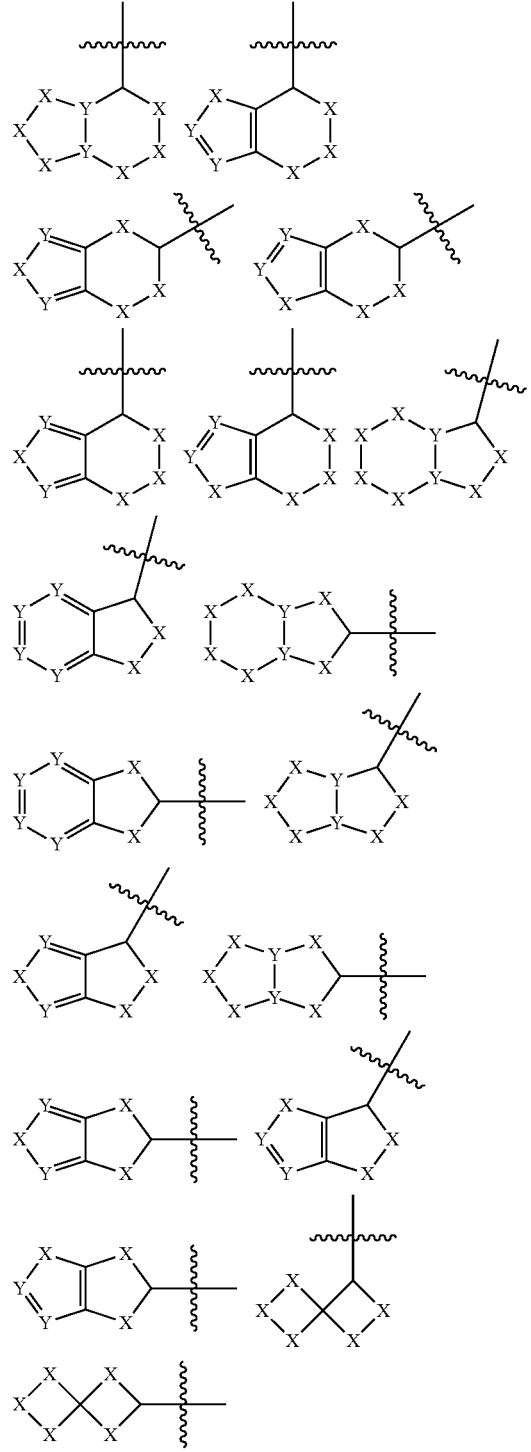

wherein each X is independently $CH_2$, NH, O or S, and each Y is independently CH or N, and wherein the at least one ring nitrogen atom of R¹ is in a non-aromatic ring, and provided that non-aromatic heteroatoms are not adjacent each other. Typically such bicyclic groups comprise 1, 2 or 3 ring heteroatoms N, O or S. In one embodiment, the at least one ring nitrogen atom of R¹ is in the non-aromatic ring of R¹ that is directly attached to the sulfur atom of the sulfonylurea group.

In one embodiment, the non-aromatic heterocyclic group of $R^1$ is a fused bicyclic ring. For example, the non-aromatic heterocyclic group of $R^1$ may be:

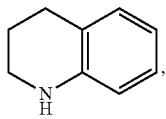

wherein $R^1$ may optionally be substituted. Such a non-aromatic heterocyclic $R^1$ group is attached to the sulfur atom of the sulfonylurea group by any suitable non-aromatic ring carbon atom.

In another embodiment, the non-aromatic heterocyclic group of $R^1$ is a bridged bicyclic ring. For example, the non-aromatic heterocyclic group of $R^1$ may be:

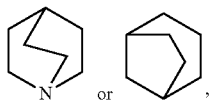

wherein $R^1$ may optionally be substituted. Such non-aromatic heterocyclic $R^1$ groups are attached to the sulfur atom of the sulfonylurea group by any suitable ring carbon atom.

In yet another embodiment, the non-aromatic heterocyclic group of $R^1$ is a spiro bicyclic ring. For example, the non-aromatic heterocyclic group of $R^1$ may be:

wherein $R^1$ may optionally be substituted. Such a non-aromatic heterocyclic $R^1$ group is attached to the sulfur atom of the sulfonylurea group by any suitable ring carbon atom.

In one embodiment, the non-aromatic heterocyclic group of $R^1$ is selected from:

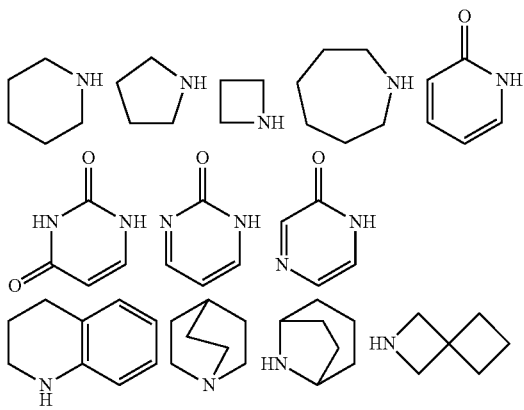

wherein $R^1$ may optionally be substituted or further substituted. Such non-aromatic heterocyclic $R^1$ groups are attached to the sulfur atom of the sulfonylurea group by any suitable non-aromatic ring carbon atom. Where the non-aromatic heterocyclic group of $R^1$ is selected from:

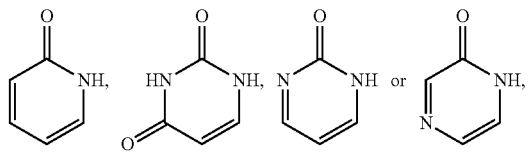

at least one ring nitrogen atom which is adjacent to a carbonyl group is substituted, so that the non-aromatic heterocyclic group of $R^1$ does not have any tautomers that are aromatic.

In one embodiment, the non-aromatic heterocyclic group of $R^1$ is selected from:

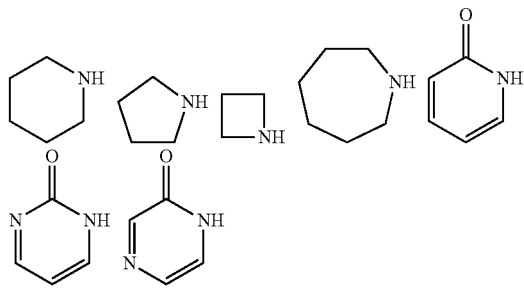

wherein $R^1$ may optionally be substituted or further substituted. Such non-aromatic heterocyclic $R^1$ groups are attached to the sulfur atom of the sulfonylurea group by any suitable ring carbon atom. Where the non-aromatic heterocyclic group of $R^1$ is selected from:

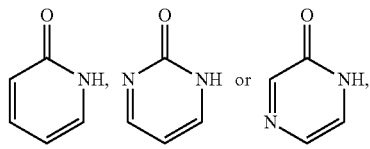

at least one ring nitrogen atom which is adjacent to a carbonyl group is substituted, so that the non-aromatic heterocyclic group of $R^1$ does not have any tautomers that are aromatic.

In one embodiment, the non-aromatic heterocyclic group of $R^1$ is selected from:

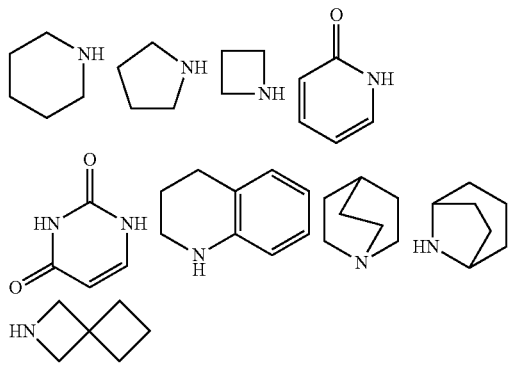

wherein $R^1$ may optionally be substituted or further substituted. Such non-aromatic heterocyclic $R^1$ groups are attached to the sulfur atom of the sulfonylurea group by any suitable non-aromatic ring carbon atom. Where the non-aromatic heterocyclic group of $R^1$ is selected from:

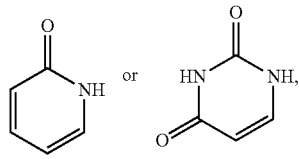 [SMILES: O=c1cccc[nH]1 ; O=c1cc[nH]c(=O)[nH]1]

at least one ring nitrogen atom is substituted, so that the non-aromatic heterocyclic group of $R^1$ does not have any tautomers that are aromatic.

In one embodiment, the non-aromatic heterocyclic group of $R^1$ is selected from:

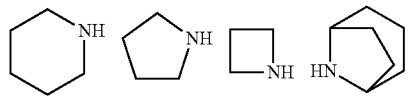

wherein $R^1$ may optionally be substituted or further substituted. Such non-aromatic heterocyclic $R^1$ groups are attached to the sulfur atom of the sulfonylurea group by any suitable ring carbon atom.

$R^1$ is a non-aromatic heterocyclic group comprising at least one ring nitrogen atom. In one embodiment, $R^1$ comprises one, two or three ring nitrogen, oxygen or sulfur atoms. In another embodiment, $R^1$ comprises one or two ring nitrogen or oxygen atoms. In another embodiment, $R^1$ comprises one or two ring nitrogen atoms. In yet another embodiment, $R^1$ comprises one ring nitrogen atom.

$R^1$ may optionally be substituted with one or more substituents, such as those defined above.

In one embodiment, $R^1$ is substituted with one or more (such as one, two or three) substituents independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —Si(R$^\beta$)$_3$; —O—Si(R$^\beta$)$_3$; —R$^\alpha$—Si(R$^\beta$)$_3$; —R$^\alpha$—O—Si(R$^\beta$)$_3$; —NH$_2$; —NHR$^\beta$; —N(R$^\beta$)$_2$; —N(O)(R$^\beta$)$_2$; —N$^+$(R$^\beta$)$_3$; —R$^\alpha$—NH$_2$; —R$^\alpha$—NHR$^\beta$; —R$^\alpha$—N(R$^\beta$)$_2$; —R$^\alpha$—N(O)(R$^\beta$)$_2$; —R$^\alpha$—N$^+$(R$^\beta$)$_3$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —C(=NH)R$^\beta$; —C(=NH)NH$_2$; —C(=NH)NHR$^\beta$; —C(=NH)N(R$^\beta$)$_2$; —C(=NR$^\beta$)R$^\beta$; —C(=NR$^\beta$)NHR$^\beta$; —C(=NR$^\beta$)N(R$^\beta$)$_2$; —C(=NOH)R$^\beta$; —C(N2)R$^\beta$; —R$^\alpha$—C(=NH)R$^\beta$; —R$^\alpha$—C(=NH)NH$_2$; —R$^\alpha$—C(=NH)NHR$^\beta$; —R$^\alpha$—C(=NH)N(R$^\beta$)$_2$; —R$^\alpha$—C(=NR$^\beta$)R$^\beta$; —R$^\alpha$—C(=NR$^\beta$)NHR$^\beta$; —R$^\alpha$—C(=NR$^\beta$)N(R$^\beta$)$_2$; —R$^\alpha$—C(=NOH)R$^\beta$; —R$^\alpha$—C(N$_2$)R$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(RF)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(RF)$_2$; —O—R$^\alpha$—N(O)(R$^\beta$)$_2$; —O—R$^\alpha$—N$^+$(R$^\alpha$)$_3$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NH—R$^\alpha$—N(O)(R$^\beta$)$_2$; —NH—R$^\alpha$—N$^+$(R$^\beta$)$_3$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; —NR$^\beta$—R$^\alpha$—N(R$^\beta$)$_2$; —NR$^\beta$—R$^\alpha$—N(O)(R$^\beta$)$_2$; —NR$^\beta$—R$^\alpha$—N$^+$(R$^\beta$)$_3$; —N(O)R$^\beta$—R$^\alpha$—OH; —N(O)R$^\beta$—R$^\alpha$—OR$^\beta$; —N(O) R$^\beta$—R$^\alpha$—NH$_2$; —N(O)R$^\beta$—R$^\alpha$—NHR$^\beta$; —N(O)R$^\beta$—R$^\alpha$—N(R$^\beta$)$_2$; —N(O)R—R$^\alpha$—N(O)(R$^\beta$)$_2$; —N(O)R$^\beta$—R$^\alpha$—N$^+$(R$^\beta$)$_3$; —N$^+$(R$^\beta$)$_2$—R$^\alpha$—OH; —N$^+$(R$^\beta$)$_2$—R$^\alpha$—OR$^\beta$; —N$^+$(R$^\beta$)$_2$—R$^\alpha$—NH$_2$; —N$^+$(R$^\beta$)$_2$—R$^\alpha$—NHR$^\beta$; —N$^+$(R$^\beta$)$_2$—R$^\alpha$—N(R$^\beta$)$_2$; or —N$^+$(R$^\beta$)$_2$—R$^\alpha$—N(O)(R$^\beta$)$_2$;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, wherein one or more —CH$_2$— groups in the backbone of the alkylene, alkenylene or alkynylene group may optionally be replaced by one or more —N(O)(R$^\beta$)— or —N$^+$(R$^\beta$)$_2$— groups, and wherein the alkylene, alkenylene or alkynylene group may optionally be substituted with one or more halo and/or —R$^\beta$ groups; and wherein each —R is independently selected from a C$_1$-C$_6$ alkyl, C$_2$-C$_6$ alkenyl, C$_2$-C$_6$ alkynyl or C$_2$-C$_6$ cyclic group, or wherein any two or three —R$^\beta$ attached to the same nitrogen atom may, together with the nitrogen atom to which they are attached, form a C$_2$-C$_7$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, C$_3$-C$_7$ halocycloalkyl, —O(C$_1$-C$_4$ alkyl), —O(C$_1$-C$_4$ haloalkyl), —O(C$_3$-C$_7$ cycloalkyl), —O(C$_3$-C$_7$ halocycloalkyl), —CO(C$_1$-C$_4$ alkyl), —CO(C$_1$-C$_4$ haloalkyl), —COO(C$_1$-C$_4$ alkyl), —COO(C$_1$-C$_4$ haloalkyl), halo, —OH, —NH$_2$, —CN, —C≡CH, oxo (=O), or 4- to 6-membered heterocyclic group.

Typically, $R^1$ is substituted on one or more ring nitrogen atoms with such a substituent.

In another embodiment, $R^1$ is substituted with one or more (such as one, two or three) substituents independently selected from halo; —CN; —NO$_2$; —N$_3$; —R$^\beta$; —OH; —OR$^\beta$; —SH; —SR$^\beta$; —SO$_2$R$^\beta$; —NH$_2$; —NHR$^\beta$; —N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(RF)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; —NR$^\beta$—R$^\alpha$—N(R$^\beta$)$_2$; a C$_3$-C$_7$ cycloalkyl group optionally substituted with one or more C$_1$-C$_3$ alkyl or C$_1$-C$_3$ haloalkyl groups; a C$_3$-C$_7$ cycloalkenyl group optionally substituted with one or more C$_1$-C$_3$ alkyl or C$_1$-C$_3$ haloalkyl groups; a 3- to 7-membered non-aromatic heterocyclic group optionally substituted with one or more C$_1$-C$_6$ alkyl or C$_1$-C$_3$ haloalkyl groups; oxo (=O); or a C$_1$-C$_4$ alkylene bridge;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —$R^\beta$ groups; and wherein each —$R^\beta$ is independently selected from a $C_1$-$C_6$ alkyl, $C_2$-$C_6$ alkenyl, $C_2$-$C_6$ alkynyl or $C_2$-$C_6$ cyclic group, and wherein any —$R^\beta$ may optionally be substituted with one or more $C_1$-$C_3$ alkyl, $C_1$-$C_3$ haloalkyl, $C_3$-$C_7$ cycloalkyl, —O($C_1$-$C_3$ alkyl), halo, —CN, —C≡CH or oxo (=O) groups.

Typically, $R^1$ is substituted on one or more ring nitrogen atoms with such a substituent.

In another embodiment, $R^1$ is substituted with one or more (such as one, two or three) substituents independently selected from halo; —CN; —$NO_2$; —$N_3$; —$R^\beta$; —OH; —$OR^\beta$; —SH; —$SR^\beta$; —$SO_2R^\beta$; —$NH_2$; —$NHR^\beta$; —$N(R^\beta)_2$; —CHO; —$COR^\beta$; —COOH; —$COOR^\beta$; —$OCOR^\beta$; —$R^\alpha$—CHO; —$R^\alpha$—$COR^\beta$; —$R^\alpha$—COOH; —$R^\alpha$—$COOR^\beta$; —$R^\alpha$—$OCOR^\beta$; —NH—CHO; —$NR^\beta$—CHO; —NH—$COR^\beta$; —$NR^\beta$—$COR^\beta$; —$CONH_2$; —$CONHR^\beta$; —$CON(R^\beta)_2$; —$R^\alpha$—NH—CHO; —$R^\alpha$—$NR^\beta$—CHO; —$R^\alpha$—NH—$COR^\beta$; —$R^\alpha$—$NR^\beta$—$COR^\beta$; —$R^\alpha$—$CONH_2$; —$R^\alpha$—$CONHR^\beta$; —$R^\alpha$—$CON(R^\beta)_2$; a $C_3$-$C_7$ cycloalkyl group optionally substituted with one or more $C_1$-$C_3$ alkyl or $C_1$-$C_3$ haloalkyl groups; a $C_3$-$C_7$ cycloalkenyl group optionally substituted with one or more $C_1$-$C_3$ alkyl or $C_1$-$C_3$ haloalkyl groups;

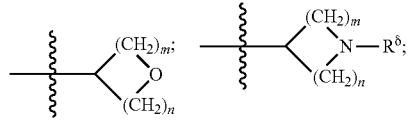

oxo (=O); or a $C_1$-$C_4$ alkylene bridge;
  wherein each —$R^\alpha$— is independently selected from an alkylene, alkenylene or alkynylene group, wherein the alkylene, alkenylene or alkynylene group contains from 1 to 6 carbon atoms in its backbone, and wherein the alkylene, alkenylene or alkynylene group may optionally be substituted with one or more halo and/or —$R^\beta$ groups;
  wherein each —$R^\beta$ is independently selected from a $C_1$-$C_6$ alkyl, $C_2$-$C_6$ alkenyl, $C_2$-$C_6$ alkynyl or $C_2$-$C_6$ cyclic group, and wherein any —$R^\beta$ may optionally be substituted with one or more $C_1$-$C_3$ alkyl, $C_1$-$C_3$ haloalkyl, $C_3$-$C_7$ cycloalkyl, —O($C_1$-$C_3$ alkyl), halo, —CN, —C≡CH or oxo (=O) groups;
  wherein each —$R^\delta$ is independently selected from a $C_1$-$C_6$ alkyl or $C_1$-$C_3$ haloalkyl group;
  wherein each m is independently selected from 1, 2 or 3; and
  wherein each n is independently selected from 1, 2 or 3.

Typically, $R^1$ is substituted on one or more ring nitrogen atoms with such a substituent.

In another embodiment, $R^1$ is substituted with one or more (such as one, two or three) substituents independently selected from halo; —CN; —$N_3$; —$R^\beta$; —$SO_2R^\beta$; —$NH_2$; —$NHR^\beta$; —$N(R^\beta)_2$; —CHO; —$COR^\beta$; —$COOR^\beta$; —$OCOR^\beta$; —$R^\alpha$—CHO; —$R^\alpha$—$COR^\beta$; —$R^\alpha$—$COOR^\beta$; —$R^\alpha$—$OCOR^\beta$; —NH—CHO; —$NR^\beta$—CHO; —NH—$COR^\beta$; —$NR^\beta$—$COR^\beta$; —$CONH_2$; —$CONHR^\beta$; —$CON(R^\beta)_2$;

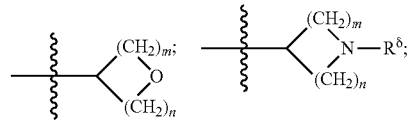

or oxo (=O);
  wherein each —$R^\alpha$— is independently selected from a $C_1$-$C_3$ alkylene group;
  wherein each —R is independently selected from a $C_1$-$C_6$ alkyl or $C_3$-$C_6$ cycloalkyl group, and wherein any —$R^\beta$ may optionally be substituted with one or more $C_3$-$C_6$ cycloalkyl, —O($C_1$-$C_3$ alkyl), halo, —CN or —C≡CH groups;
  wherein each —$R^\delta$ is independently selected from a $C_1$-$C_6$ alkyl group;
  wherein each m is independently selected from 1 or 2; and
  wherein each n is independently selected from 1 or 2.

Typically, $R^1$ is substituted on one or more ring nitrogen atoms with such a substituent.

In one embodiment, $R^1$ is substituted with one or more (such as one, two or three) substituents independently selected from halo; $C_1$-$C_6$ alkyl; $C_1$-$C_6$ haloalkyl; $C_2$-$C_6$ alkenyl; $C_2$-$C_6$ haloalkenyl; $C_2$-$C_6$ alkynyl; $C_2$-$C_6$ haloalkynyl; —$R^5$—CN; —$R^5$—$N_3$; —$R^5$—$NO_2$; —$R^5$—$N(R^6)_2$; —$R^5$—$OR^6$; —$R^5$—$SR^6$; —$R^5$—$Si(R^6)_3$; —$R^5$—O—Si$(R^6)_3$; —$R^5$—$COR^6$; —$R^5$—$COOR^6$; —$R^5$—CO—$R^5$—$OR^6$; —$R^5$—$CON(R^6)_2$; —$R^5$—CO—$R^5$—$N(R^6)_2$; —$R^5$—C(=$NR^6$)$R^6$; —$R^5$—C(=$NR^6$)$N(R^6)_2$; —$R^5$—C(=NOH)$R^6$; —$R^5$—$SO_2R^6$; —$R^5$-phenyl; —$R^5$-(Het);

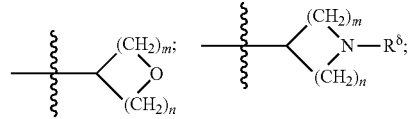

oxo (=O); —$CH_2CH_2$—; —$CH_2CH_2CH_2$—; —$CH_2CH_2CH_2CH_2$—; —CH=CH—CH=$CH_2$—; or —$R^5$—($C_3$-$C_6$ cycloalkyl) wherein the $C_3$-$C_6$ cycloalkyl group is optionally substituted with one or two substituents independently selected from $C_1$-$C_3$ alkyl; wherein
  $R^5$ is independently selected from a bond or $C_1$-$C_5$ alkylene;
  $R^6$ is independently selected from hydrogen, $C_1$-$C_5$ alkyl, $C_1$-$C_5$ haloalkyl, $C_3$-$C_6$ cycloalkyl, —CO—($C_1$-$C_3$ alkyl), —COO—($C_1$-$C_4$ alkyl) or benzyl;
  Het is selected from a pyridinyl, 2-oxo-1,2-dihydropyridinyl, pyridazinyl, pyrimidinyl, pyrazinyl, pyrrolyl, pyrazolyl, imidazolyl or diazirinyl group, each of which may optionally be substituted with one or two substituents independently selected from halo, $C_1$-$C_4$ alkyl, $C_2$-$C_4$ alkenyl or $C_2$-$C_4$ alkynyl;
  X is selected from O, S, SO or $SO_2$;
  m is 1, 2 or 3;
  n is 1, 2 or 3; and
  p is 0, 1 or 2.

Typically, $R^1$ is substituted on one or more ring nitrogen atoms with such a substituent.

In one embodiment, $R^1$ is substituted on one or more (such as one, two or three) ring nitrogen atoms with a substituent independently selected from halo; $C_1$-$C_6$ alkyl; $C_1$-$C_6$ haloalkyl; $C_2$-$C_6$ alkenyl; $C_2$-$C_6$ haloalkenyl; $C_2$-$C_6$ alkynyl; $C_2$-$C_6$ haloalkynyl; —$R^5$—CN; —$R^5$—$N_3$; —$R^5$—

$NO_2$; —$R^5$—$N(R^6)_2$; —$R^5$—$OR^6$; —$R^5$—$SR^6$; —$R^5$—$Si(R^6)_3$; —$R^5$—$O$—$Si(R^6)_3$; —$R^5$—$COR^6$; —$R^5$—$COOR^6$; —$R^5$—$CO$—$R^5$—$OR^6$; —$R^5$—$CON(R^6)_2$; —$R^5$—$CO$—$R^5$—$N(R^6)_2$; —$R^5$—$C(=NR^6)R^6$; —$R^5$—$C(=NR^6)N(R^6)_2$; —$R^5$—$C(=NOH)R^6$; —$R^5$—$SO_2R^6$; —$R^5$-phenyl; —$R^5$-(Het);

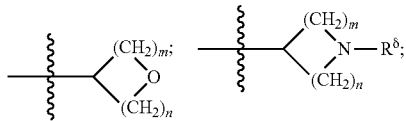

oxo (=O); —$CH_2CH_2$—; —$CH_2CH_2CH_2$—; —$CH_2CH_2CH_2CH_2$—; or —$R^5$—($C_3$-$C_6$ cycloalkyl) wherein the $C_3$-$C_6$ cycloalkyl group is optionally substituted with one or two substituents independently selected from $C_1$-$C_3$ alkyl; wherein
  $R^5$ is independently selected from a bond or $C_1$-$C_5$ alkylene;
  $R^6$ is independently selected from hydrogen, $C_1$-$C_5$ alkyl, $C_1$-$C_5$ haloalkyl, $C_3$-$C_6$ cycloalkyl, —CO—($C_1$-$C_3$ alkyl), —COO—($C_1$-$C_4$ alkyl) or benzyl;
  Het is selected from a pyridinyl, 2-oxo-1,2-dihydropyridinyl, pyridazinyl, pyrimidinyl, pyrazinyl, pyrrolyl, pyrazolyl, imidazolyl or diazirinyl group, each of which may optionally be substituted with one or two substituents independently selected from halo, $C_1$-$C_4$ alkyl, $C_2$-$C_4$ alkenyl or $C_2$-$C_4$ alkynyl;
  X is selected from O, S, SO or $SO_2$;
  m is 1, 2 or 3;
  n is 1, 2 or 3; and
  p is 0, 1 or 2.

In one embodiment, $R^1$ is substituted on one or more (such as one, two or three) ring nitrogen atoms with a substituent independently selected from halo; $C_1$-$C_6$ alkyl; $C_1$-$C_6$ haloalkyl; $C_2$-$C_6$ alkenyl; $C_2$-$C_6$ haloalkenyl; $C_2$-$C_6$ alkynyl; $C_2$-$C_6$ haloalkynyl; —$R^5$—CN; —$R^5$—$N_3$; —$R^5$—$NO_2$; —$R^5$—$N(R^6)_2$; —$R^5$—$OR^6$; —$R^5$—$COR^6$; —$R^5$—$COOR^6$; —$R^5$—$CO$—$R^5$—$OR^6$; —$R^5$—$CON(R^6)_2$; —$R^5$—$CO$—$R^5$—$N(R^6)_2$; —$R^5$—$SO_2R^6$; —$R^5$-phenyl; —$R^5$-pyridinyl; —R—($C_3$-$C_6$ cycloalkyl);

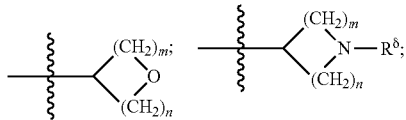

oxo (=O); —$CH_2CH_2CH_2$—; or —$CH_2CH_2CH_2CH_2$—; wherein
  $R^5$ is independently selected from a bond or $C_1$-$C_5$ alkylene;
  $R^6$ is independently selected from hydrogen, $C_1$-$C_5$ alkyl, $C_1$-$C_5$ haloalkyl, $C_3$-$C_6$ cycloalkyl, —CO—($C_1$-$C_3$ alkyl) or benzyl;
  m is 1, 2 or 3; and
  n is 1, 2 or 3.

In one embodiment, $R^1$ is substituted on one or more (such as one, two or three) ring carbon atoms with a substituent independently selected from oxo (=O); —$CH_2CH_2$—; —$CH_2CH_2CH_2$—; —$CH_2CH_2CH_2CH_2$—; —CH=CH—CH=$CH_2$—; —$OR^7$ or —$CON(R^7)_2$; wherein $R^7$ is independently selected from hydrogen or $C_1$-$C_3$ alkyl.

In one embodiment, $R^1$ is substituted on one or more (such as one, two or three) ring carbon atoms with a substituent independently selected from oxo (=O); —$CH_2CH_2CH_2$—; —$CH_2CH_2CH_2CH_2$—; or —CH=CH—CH=$CH_2$—.

In one aspect of any of the above embodiments, $R^1$ contains from 4 to 25 atoms other than hydrogen. More typically, $R^1$ contains from 4 to 20 atoms other than hydrogen. More typically, $R^1$ contains from 4 to 17 atoms other than hydrogen.

$R^2$ is a cyclic group substituted at the α-position, wherein $R^2$ may optionally be further substituted. For the avoidance of doubt, it is noted that it is a ring atom of the cyclic group of $R^2$ that is directly attached to the nitrogen atom of the urea or thiourea group, not any substituent.

In one embodiment of the first aspect of the invention, $R^2$ is an aryl or a heteroaryl group, wherein the aryl or the heteroaryl group is substituted at the α-position, and wherein $R^2$ may optionally be further substituted. Typically, $R^2$ is a phenyl or a 5- or 6-membered heteroaryl group, wherein the phenyl or the heteroaryl group is substituted at the α-position, and wherein $R^2$ may optionally be further substituted. Typically, $R^2$ is an aryl or a heteroaryl group, wherein the aryl or the heteroaryl group is substituted at the α and α' positions, and wherein $R^2$ may optionally be further substituted. Typically, $R^2$ is a phenyl or a 5- or 6-membered heteroaryl group, wherein the phenyl or the heteroaryl group is substituted at the α and α' positions, and wherein $R^2$ may optionally be further substituted. For example, $R^2$ may be a phenyl group substituted at the 2- and 6-positions or a phenyl group substituted at the 2-, 4- and 6-positions.

As used herein, the nomenclature α, β, α', β' refers to the position of the atoms of a cyclic group, such as —$R^2$, relative to the point of attachment of the cyclic group to the remainder of the molecule. For example, where —$R^2$ is a 1,2,3,5,6,7-hexahydro-s-indacen-4-yl moiety, the α, β, α' and β' positions are as follows:

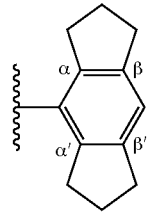 [SMILES: *c1c2c(cc3c1CCC3)CCC2]

In another embodiment, $R^2$ is a cyclic group substituted at the α and α' positions, wherein $R^2$ may optionally be further substituted. For example, $R^2$ may be a cycloalkyl, cycloalkenyl or non-aromatic heterocyclic group substituted at the α and α' positions.

In any of the above embodiments, typical substituents at the α and/or α' positions of the parent cyclic group of $R^2$ comprise a carbon atom. For example, typical substituents at the α and/or α' positions of the parent cyclic group of $R^2$ may be independently selected from —$R^4$, —$OR^4$ and —$COR^4$ groups, wherein each $R^4$ is independently selected from a $C_1$-$C_6$ alkyl, $C_2$-$C_6$ alkenyl, $C_2$-$C_6$ alkynyl or $C_2$-$C_6$ cyclic group and wherein each $R^4$ is optionally further substituted with one or more halo groups. More typically, the substituents at the α and/or α' positions are independently selected from alkyl and cycloalkyl groups, such as $C_3$-$C_6$ branched alkyl and $C_3$-$C_6$ cycloalkyl groups, e.g. isopropyl, cyclopropyl, cyclohexyl or t-butyl groups, wherein the alkyl and cycloalkyl groups are optionally further substituted with one or more fluoro and/or chloro groups.

In one aspect of any of the above embodiments, each substituent at the α and α' positions comprises a carbon atom.

In one embodiment, —R² has a formula selected from:

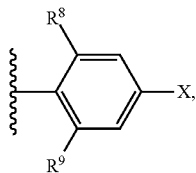

wherein R⁸ and R⁹ are independently selected from $C_1$-$C_4$ alkyl, and X is hydrogen or halo.

Typically, —R² has a formula selected from:

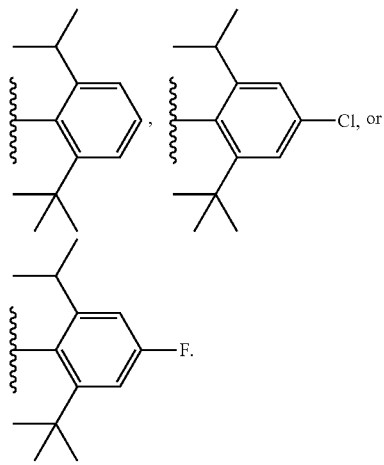

Other typical substituents at the α and/or α' positions of the parent cyclic group of R² may include cycloalkyl, cycloalkenyl, non-aromatic heterocyclic, aryl or heteroaryl rings which are fused to the parent cyclic group across the α, β and/or α', β' positions respectively. Such fused cyclic groups are described in greater detail below.

In one embodiment, R² is a fused aryl or a fused heteroaryl group, wherein the aryl or heteroaryl group is fused to one or more cycloalkyl, cycloalkenyl, non-aromatic heterocyclic, aryl or heteroaryl rings, wherein R² may optionally be further substituted.

In another embodiment, R² is a fused aryl or a fused heteroaryl group, wherein the aryl or heteroaryl group is fused to two or more independently selected cycloalkyl, cycloalkenyl, non-aromatic heterocyclic, aryl or heteroaryl rings, wherein R² may optionally be further substituted. Typically, the two or more cycloalkyl, cycloalkenyl, non-aromatic heterocyclic, aryl or heteroaryl rings are each ortho-fused to the aryl or heteroaryl group, i.e. each fused cycloalkyl, cycloalkenyl, non-aromatic heterocyclic, aryl or heteroaryl ring has only two atoms and one bond in common with the aryl or heteroaryl group. Typically, R² is tricyclic.

In yet another embodiment, R² is a fused aryl or a fused heteroaryl group, wherein a first cycloalkyl, cycloalkenyl, non-aromatic heterocyclic, aryl or heteroaryl ring is fused to the aryl or heteroaryl group across the α, β positions and a second cycloalkyl, cycloalkenyl, non-aromatic heterocyclic, aryl or heteroaryl ring is fused to the aryl or heteroaryl group across the α',β' positions, wherein R² may optionally be further substituted.

In one embodiment, —R² has a formula selected from:

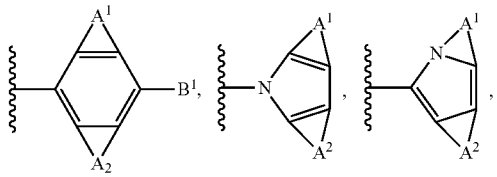

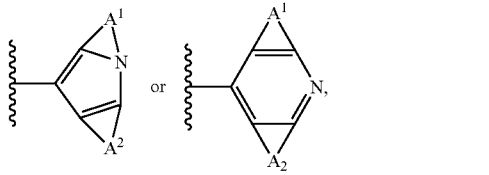

wherein A¹ and A² are each independently selected from an optionally substituted alkylene or alkenylene group, wherein one or more carbon atoms in the backbone of the alkylene or alkenylene group may optionally be replaced by one or more heteroatoms N, O or S, and wherein B¹ is hydrogen or any optional substituent. B¹ and any optional substituent attached to A¹ or A² may together with the atoms to which they are attached form a further fused cycloalkyl, cycloalkenyl, non-aromatic heterocyclic, aryl or heteroaryl ring which may itself be optionally substituted. Similarly, any optional substituent attached to A¹ and any optional substituent attached to A² may also together with the atoms to which they are attached form a further fused cycloalkyl, cycloalkenyl, non-aromatic heterocyclic, aryl or heteroaryl ring which may itself be optionally substituted.

Typically, B¹ is hydrogen or a halo, hydroxyl, —CN, —NO₂, —B² or —OB² group, wherein B² is a $C_1$-$C_4$ alkyl group which may optionally be halo-substituted.

Typically, any ring containing A¹ or A² is a 5- or 6-membered ring. Typically, A¹ and A² are unsubstituted or substituted with one or more halo, hydroxyl, —CN, —NO₂, —B³ or —OB³ groups, wherein B³ is a $C_1$-$C_4$ alkyl group which may optionally be halo-substituted.

In a further embodiment, —R² has a formula selected from:

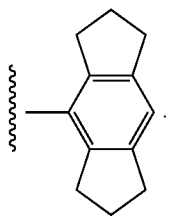

Typically, —R² has the formula:

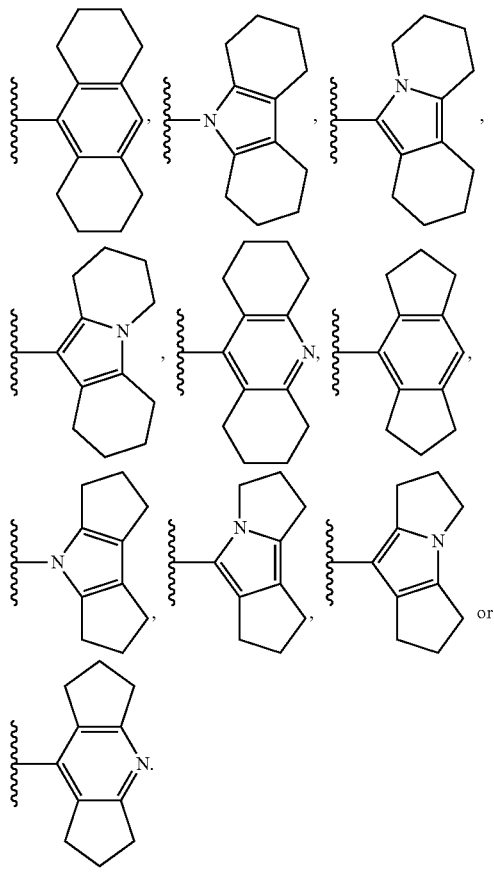

Yet other typical substituents at the α-position of the parent cyclic group of R² may include monovalent heterocyclic groups and monovalent aromatic groups, wherein a ring atom of the heterocyclic or aromatic group is directly attached via a single bond to the α-ring atom of the parent cyclic group, wherein the heterocyclic or aromatic group may optionally be substituted, and wherein the parent cyclic group may optionally be further substituted. Such R² groups are described in greater detail below.

In one embodiment, the α-substituted parent cyclic group of R² is a 5- or 6-membered cyclic group, wherein the cyclic group may optionally be further substituted. In one embodiment, the α-substituted parent cyclic group of R² is an aryl or a heteroaryl group, all of which may optionally be further substituted. In one embodiment, the α-substituted parent cyclic group of R² is a phenyl or a 5- or 6-membered heteroaryl group, all of which may optionally be further substituted. In one embodiment, the α-substituted parent cyclic group of R² is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl or oxadiazolyl group, all of which may optionally be further substituted. In one embodiment, the α-substituted parent cyclic group of R² is a phenyl group, which may optionally be further substituted.

In one embodiment, the α-substituted parent cyclic group of R² is substituted at the α and α' positions, and may optionally be further substituted. For example, the α-substituted parent cyclic group of R² may be a phenyl group substituted at the 2- and 6-positions or a phenyl group substituted at the 2-, 4- and 6-positions.

In one embodiment, R² is a parent cyclic group substituted at the α-position with a monovalent heterocyclic group or a monovalent aromatic group, wherein the heterocyclic or aromatic group may optionally be substituted, and wherein the parent cyclic group may optionally be further substituted. In one embodiment, the monovalent heterocyclic or aromatic group at the α-position is phenyl or a 5- or 6-membered heterocyclic group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl, oxadiazolyl, azetinyl, azetidinyl, oxetanyl, thietanyl, pyrrolidinyl, tetrahydrofuranyl, tetrahydrothiophenyl, pyrazolidinyl, imidazolidinyl, 1,3-dioxolanyl, 1,2-oxathiolanyl, 1,3-oxathiolanyl, piperidinyl, tetrahydropyranyl, thianyl, piperazinyl, 1,4-dioxanyl, morpholinyl or thiomorpholinyl group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, piperidinyl or tetrahydropyranyl group, all of which may optionally be substituted. In one embodiment, the monovalent heterocyclic or aromatic group at the α-position is a phenyl, pyridinyl, pyrimidinyl, pyrazolyl, imidazolyl, isoxazolyl, thiazolyl or tetrahydropyranyl group, all of which may optionally be substituted. In one embodiment, the monovalent heterocyclic or aromatic group at the α-position is a phenyl, pyridinyl, pyrimidinyl or pyrazolyl group, all of which may optionally be substituted with one or two substituents independently selected from halo, —OH, —NH₂, —CN, —NO₂, —B⁴, —OB⁴, —NHB⁴ or —N(B⁴)₂, wherein B⁴ is independently selected from a $C_1$-$C_4$ alkyl, $C_2$-$C_4$ alkenyl or $C_2$-$C_4$ alkynyl group all of which may optionally be halo-substituted. In one embodiment, the monovalent heterocyclic or aromatic group at the α-position is an unsubstituted phenyl, pyridinyl, pyrimidinyl or pyrazolyl group. In one embodiment, the monovalent heterocyclic group at the α-position is a pyridin-2-yl, pyridin-3-yl or pyridin-4-yl group, all of which may optionally be substituted with one or two substituents independently selected from halo, —OH, —NH₂, —CN, —NO₂, —B⁴, —OB⁴, —NHB⁴ or —N(B⁴)₂, wherein B⁴ is independently selected from a $C_1$-$C_4$ alkyl, $C_2$-$C_4$ alkenyl or $C_2$-$C_4$ alkynyl group all of which may optionally be halo-substituted. In one embodiment, the monovalent heterocyclic group at the α-position is an unsubstituted pyridin-3-yl group or a pyridin-4-yl group optionally substituted with one or two substituents independently selected from halo, —OH, —NH₂, —CN, —NO₂, —B⁴, —OB⁴, —NHB⁴ or —N(B⁴)₂, wherein B⁴ is independently selected from a $C_1$-$C_4$ alkyl, $C_2$-$C_4$ alkenyl or $C_2$-$C_4$ alkynyl group all of which may optionally be halo-substituted. Alternatively, any of these the monovalent heterocyclic groups at the α-position may optionally be substituted with one or two substituents independently selected from halo, —OH, —NH₂, —CN, $C_1$-$C_4$ alkyl, $C_2$-$C_4$ alkenyl, $C_2$-$C_4$ alkynyl, $C_1$-$C_4$ haloalkyl, —OB⁸ or —N(B⁸)₂, wherein B⁸ is independently selected from $C_1$-$C_4$ alkyl which may optionally be halo-substituted.

In one embodiment, R² is a parent cyclic group substituted at the α-position with a monovalent heterocyclic group or a monovalent aromatic group, wherein the heterocyclic or aromatic group may optionally be substituted, and wherein the parent cyclic group may optionally be further substituted. In one embodiment, such further substituents are in the α' position of the α-substituted parent cyclic group of R².

Such further substituents may be independently selected from halo, —R$^6$, —OR$^6$ or —COR$^6$ groups, wherein each R$^6$ is independently selected from a C$_1$-C$_6$ alkyl, C$_2$-C$_6$ alkenyl, C$_2$-C$_6$ alkynyl or C$_2$-C$_6$ cyclic group and wherein each R$^6$ is optionally further substituted with one or more halo groups. Typically, such further substituents on the α-substituted parent cyclic group of R$^2$ are independently selected from halo, C$_1$-C$_6$ alkyl (in particular C$_3$-C$_6$ branched alkyl) or C$_3$-C$_6$ cycloalkyl groups, e.g. fluoro, chloro, isopropyl, cyclopropyl, cyclohexyl or t-butyl groups, wherein the alkyl and cycloalkyl groups are optionally further substituted with one or more fluoro and/or chloro groups.

In one embodiment, —R$^2$ has a formula selected from:

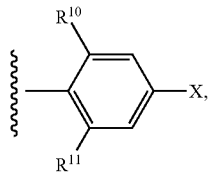

wherein R$^{10}$ is C$_1$-C$_4$ alkyl, R$^{11}$ is a 5- or 6-membered, optionally substituted heterocyclic or aromatic group, and X is hydrogen or halo. In one embodiment, the optional substituents on the heterocyclic or aromatic group are selected from halo, —OH, —NH$_2$, —CN, —NO$_2$, —B$^5$, —OB$^5$, —NHB$^5$ or —N(B$^5$)$_2$, wherein B$^5$ is independently selected from a C$_1$-C$_4$ alkyl, C$_2$-C$_4$ alkenyl or C$_2$-C$_4$ alkynyl group all of which may optionally be halo-substituted. Alternatively, the optional substituents on the heterocyclic or aromatic group are selected from halo, —OH, —NH$_2$, —CN, C$_1$-C$_4$ alkyl, C$_2$-C$_4$ alkenyl, C$_2$-C$_4$ alkynyl, C$_1$-C$_4$ haloalkyl, —OB$^8$ or —N(B$^8$)$_2$, wherein B$^8$ is independently selected from C$_1$-C$_4$ alkyl which may optionally be halo-substituted.

Typically, —R$^2$ has a formula selected from:

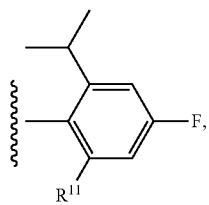

wherein R$^{11}$ is a 5- or 6-membered, optionally substituted heterocyclic or aromatic group. In one embodiment, the optional substituents on the heterocyclic or aromatic group are selected from halo, —OH, —NH$_2$, —CN, —NO$_2$, —B$^6$, —OB$^6$, —NHB$^6$ or —N(B$^6$)$_2$, wherein B$^6$ is independently selected from a C$_1$-C$_4$ alkyl, C$_2$-C$_4$ alkenyl or C$_2$-C$_4$ alkynyl group all of which may optionally be halo-substituted. Alternatively, the optional substituents on the heterocyclic or aromatic group are selected from halo, —OH, —NH$_2$, —CN, C$_1$-C$_4$ alkyl, C$_2$-C$_4$ alkenyl, C$_2$-C$_4$ alkynyl, C$_1$-C$_4$ haloalkyl, —OB$^8$ or —N(B$^8$)$_2$, wherein B$^8$ is independently selected from C$_1$-C$_4$ alkyl which may optionally be halo-substituted.

In one embodiment, R$^2$ is a parent cyclic group substituted at the α-position with a monovalent heterocyclic group or a monovalent aromatic group, wherein the heterocyclic or aromatic group may optionally be substituted, and wherein the parent cyclic group may optionally be further substituted. The further substituents on the α-substituted parent cyclic group of R$^2$ also include cycloalkyl, cycloalkenyl, non-aromatic heterocyclic, aryl or heteroaryl rings which are fused to the α-substituted parent cyclic group of R$^2$. Typically, the cycloalkyl, cycloalkenyl, non-aromatic heterocyclic, aryl or heteroaryl rings are ortho-fused to the α-substituted parent cyclic group of R$^2$, i.e. each fused cycloalkyl, cycloalkenyl, non-aromatic heterocyclic, aryl or heteroaryl ring has only two atoms and one bond in common with the α-substituted parent cyclic group of R$^2$. Typically, the cycloalkyl, cycloalkenyl, non-aromatic heterocyclic, aryl or heteroaryl rings are ortho-fused to the α-substituted parent cyclic group of R$^2$ across the α',β' positions.

In one embodiment, —R$^2$ has a formula selected from:

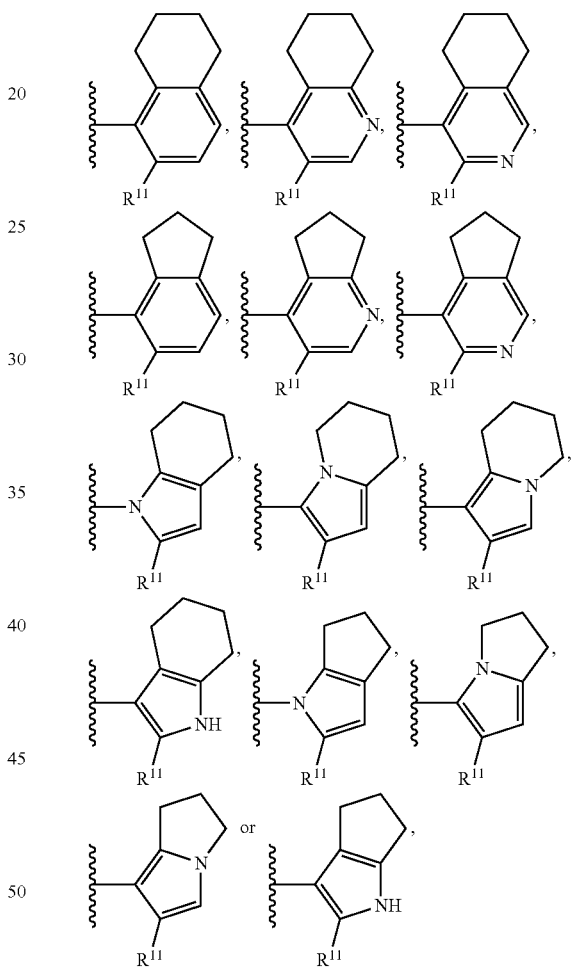

wherein R$^{11}$ is a 5- or 6-membered, optionally substituted heterocyclic or aromatic group. In one embodiment, the optional substituents on the heterocyclic or aromatic group are selected from halo, —OH, —NH$_2$, —CN, —NO$_2$, —B$^7$, —OB$^7$, —NHB$^7$ or —N(B$^7$)$_2$, wherein B$^7$ is independently selected from a C$_1$-C$_4$ alkyl, C$_2$-C$_4$ alkenyl or C$_2$-C$_4$ alkynyl group all of which may optionally be halo-substituted. Alternatively, the optional substituents on the heterocyclic or aromatic group are selected from halo, —OH, —NH$_2$, —CN, C$_1$-C$_4$ alkyl, C$_2$-C$_4$ alkenyl, C$_2$-C$_4$ alkynyl, C$_1$-C$_4$ haloalkyl, —OB$^8$ or —N(B$^8$)$_2$, wherein B$^8$ is independently selected from C$_1$-C$_4$ alkyl which may optionally be halo-substituted.

In one embodiment, $R^2$ is phenyl or a 5- or 6-membered heteroaryl group (such as phenyl, pyridinyl, pyridazinyl, pyrimidinyl or pyrazinyl); wherein
- (i) the phenyl or 5- or 6-membered heteroaryl group is substituted at the α position with a substituent selected from $-R^{14}$, $-OR^{14}$ and $-COR^{14}$, wherein $R^{14}$ is selected from a $C_1$-$C_6$ alkyl, $C_2$-$C_6$ alkenyl, $C_2$-$C_6$ alkynyl or $C_2$-$C_6$ cyclic group and wherein $R^{14}$ is optionally substituted with one or more halo groups; and
- optionally the phenyl or 5- or 6-membered heteroaryl group is further substituted at the α' position with a substituent selected from $-R^{14}$, $-OR^{14}$ and $-COR^{14}$, wherein $R^{14}$ is selected from a $C_1$-$C_6$ alkyl, $C_2$-$C_6$ alkenyl, $C_2$-$C_6$ alkynyl or $C_2$-$C_6$ cyclic group and wherein $R^{14}$ is optionally substituted with one or more halo groups; and
- optionally the phenyl or 5- or 6-membered heteroaryl group is further substituted (typically with one, two or three substituents independently selected from halo, $-NO_2$, $-CN$, $-COOR^{15}$, $-CONH_2$, $-CONHR^{15}$ or $-CON(R^{15})_2$, wherein each $-R^{15}$ is independently selected from a $C_1$-$C_4$ alkyl or $C_1$-$C_4$ haloalkyl group); or
- (ii) the phenyl or 5- or 6-membered heteroaryl group is substituted with a cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and
- optionally the phenyl or 5- or 6-membered heteroaryl group is further substituted at the α' position with a substituent selected from $-R^4$, $-OR^4$ and $-COR^4$, wherein $R^4$ is selected from a $C_1$-$C_6$ alkyl, $C_2$-$C_6$ alkenyl, $C_2$-$C_6$ alkynyl or $C_2$-$C_6$ cyclic group and wherein $R^4$ is optionally substituted with one or more halo groups; and
- optionally the phenyl or 5- or 6-membered heteroaryl group is further substituted (typically with one or two substituents independently selected from halo, $-NO_2$, $-CN$, $-COOR^{15}$, $-CONH_2$, $-CONHR^{15}$ or $-CON(R^{15})_2$, wherein each $-R^{15}$ is independently selected from a $C_1$-$C_4$ alkyl or $C_1$-$C_4$ haloalkyl group); or
- (iii) the phenyl or 5- or 6-membered heteroaryl group is substituted with a first cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and
- the phenyl or 5- or 6-membered heteroaryl group is substituted with a second cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and
- optionally the phenyl group is further substituted (typically with a substituent selected from halo, $-NO_2$, $-CN$, $-COOR^{15}$, $-CONH_2$, $-CONHR^{15}$ or $-CON(R^{15})_2$, wherein each $-R^{15}$ is independently selected from a $C_1$-$C_4$ alkyl or $C_1$-$C_4$ haloalkyl group); or
- (iv) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, $C_1$-$C_3$ alkyl, $C_1$-$C_3$ haloalkyl, $-R^{12}-OR^{13}$, $-R^{12}-N(R^{13})_2$, $-R^{12}-CN$ or $-R^{12}-C\equiv CR^{13}$, and wherein a ring atom of the monovalent heterocyclic or aromatic group is directly attached to the α-ring atom of the parent phenyl or 5- or 6-membered heteroaryl group; wherein $R^{12}$ is independently selected from a bond or a $C_1$-$C_3$ alkylene group; and $R^{13}$ is independently selected from hydrogen or a $C_1$-$C_3$ alkyl or $C_1$-$C_3$ haloalkyl group; and
- optionally the phenyl or 5- or 6-membered heteroaryl group is further substituted at the α' position with a substituent selected from $-R^4$, $-OR^4$ and $-COR^4$, wherein $R^4$ is selected from a $C_1$-$C_6$ alkyl, $C_2$-$C_6$ alkenyl, $C_2$-$C_6$ alkynyl or $C_2$-$C_6$ cyclic group and wherein $R^4$ is optionally substituted with one or more halo groups; and
- optionally the phenyl or 5- or 6-membered heteroaryl group is further substituted (typically with one, two or three substituents independently selected from halo, $-NO_2$, $-CN$, $-COOR^{15}$, $-CONH_2$, $-CONHR^{15}$ or $-CON(R^{15})_2$, wherein each $-R^{15}$ is independently selected from a $C_1$-$C_4$ alkyl or $C_1$-$C_4$ haloalkyl group); or
- (v) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, $C_1$-$C_3$ alkyl, $C_1$-$C_3$ haloalkyl, $-R^{12}-OR^{13}$, $-R^{12}-N(R^{13})_2$, $-R^{12}-CN$ or $-R^{12}-C\equiv CR^{13}$, and wherein a ring atom of the monovalent heterocyclic or aromatic group is directly attached to the α-ring atom of the parent phenyl or 5- or 6-membered heteroaryl group; wherein $R^{12}$ is independently selected from a bond or a $C_1$-$C_3$ alkylene group; and $R^{13}$ is independently selected from hydrogen or a $C_1$-$C_3$ alkyl or $C_1$-$C_3$ haloalkyl group; and
- optionally the phenyl or 5- or 6-membered heteroaryl group is further substituted with a cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and
- optionally the phenyl or 5- or 6-membered heteroaryl group is further substituted (typically with one or two substituents independently selected from halo, $-NO_2$, $-CN$, $-COOR^{15}$, $-CONH_2$, $-CONHR^{15}$ or $-CON(R^{15})_2$, wherein each $-R^{15}$ is independently selected from a $C_1$-$C_4$ alkyl or $C_1$-$C_4$ haloalkyl group).

In the embodiment directly above, where a group or moiety is optionally substituted with one or more halo groups, it may be substituted for example with one, two, three, four, five or six halo groups.

In one aspect of any of the above embodiments, $R^2$ contains from 15 to 50 atoms. More typically, $R^2$ contains from 20 to 40 atoms. Most typically, $R^2$ contains from 25 to 35 atoms.

In another aspect of any of the above embodiments, $R^2$ contains from 10 to 50 atoms other than hydrogen. More typically, $R^2$ contains from 10 to 40 atoms other than hydrogen. More typically, $R^2$ contains from 10 to 35 atoms other than hydrogen. Most typically, $R^2$ contains from 12 to 30 atoms other than hydrogen.

Q is selected from O or S. In one embodiment of the first aspect of the invention, Q is O.

In one specific embodiment, the invention provides a compound of formula (I), wherein:

Q is O;

$R^1$ is a non-aromatic heterocyclic group selected from:

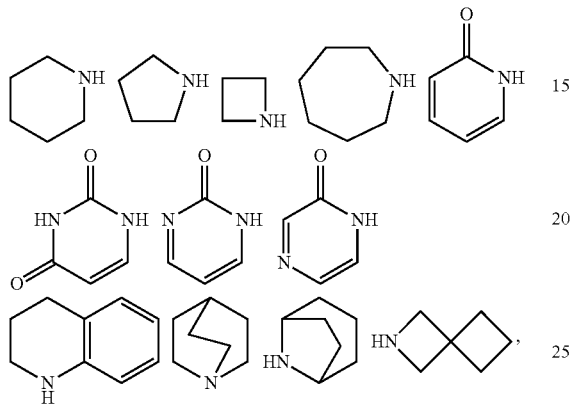

wherein $R^1$ is attached to the sulfur atom of the sulfonylurea group by a non-aromatic ring carbon atom, and wherein $R^1$ may optionally be substituted; and $R^2$ is phenyl or a 5- or 6-membered heteroaryl group; wherein (i) the phenyl or 5- or 6-membered heteroaryl group is substituted at the α position with a substituent selected from —$R^4$, —$OR^4$ and —$COR^4$, wherein $R^4$ is selected from a $C_1$-$C_6$ alkyl, $C_2$-$C_6$ alkenyl, $C_2$-$C_6$ alkynyl or $C_2$-$C_6$ cyclic group and wherein $R^4$ is optionally substituted with one or more halo groups; and optionally the phenyl or 5- or 6-membered heteroaryl group is further substituted at the α' position with a substituent selected from —$R^{14}$, —$OR^{14}$ and —$COR^{14}$, wherein $R^{14}$ is selected from a $C_1$-$C_6$ alkyl, $C_2$-$C_6$ alkenyl, $C_2$-$C_6$ alkynyl or $C_2$-$C_6$ cyclic group and wherein $R^{14}$ is optionally substituted with one or more halo groups; and optionally the phenyl or 5- or 6-membered heteroaryl group is further substituted (typically with one, two or three substituents independently selected from halo, —$NO_2$, —CN, —$COOR^{15}$, —$CONH_2$, —$CONHR^{15}$ or —$CON(R^{15})_2$, wherein each —$R^{15}$ is independently selected from a $C_1$-$C_4$ alkyl or $C_1$-$C_4$ haloalkyl group); or (ii) the phenyl or 5- or 6-membered heteroaryl group is substituted with a cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and optionally the phenyl or 5- or 6-membered heteroaryl group is further substituted at the α' position with a substituent selected from —$R^4$, —$OR^4$ and —$COR^4$, wherein $R^4$ is selected from a $C_1$-$C_6$ alkyl, $C_2$-$C_6$ alkenyl, $C_2$-$C_6$ alkynyl or $C_2$-$C_6$ cyclic group and wherein $R^4$ is optionally substituted with one or more halo groups; and optionally the phenyl or 5- or 6-membered heteroaryl group is further substituted (typically with one or two substituents independently selected from halo, —$NO_2$, —CN, —$COOR^{15}$, —$CONH_2$, —$CONHR^{15}$ or —$CON(R^{15})_2$, wherein each —$R^{15}$ is independently selected from a $C_1$-$C_4$ alkyl or $C_1$-$C_4$ haloalkyl group); or (iii) the phenyl or 5- or 6-membered heteroaryl group is substituted with a first cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and the phenyl or 5- or 6-membered heteroaryl group is substituted with a second cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl group is further substituted (typically with a substituent selected from halo, —$NO_2$, —CN, —$COOR^{15}$, —$CONH_2$, —$CONHR^{15}$ or —$CON(R^{15})_2$, wherein each —$R^{15}$ is independently selected from a $C_1$-$C_4$ alkyl or $C_1$-$C_4$ haloalkyl group); or (iv) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, $C_1$-$C_3$ alkyl, $C_1$-$C_3$ haloalkyl, —$R^{12}$—$OR^{13}$, —$R^{12}$—$N(R^{13})_2$, —$R^{12}$—CN or —$R^{12}$—C≡$CR^{13}$, and wherein a ring atom of the monovalent heterocyclic or aromatic group is directly attached to the α-ring atom of the parent phenyl or 5- or 6-membered heteroaryl group; wherein $R^{12}$ is independently selected from a bond or a $C_1$-$C_3$ alkylene group; and $R^{13}$ is independently selected from hydrogen or a $C_1$-$C_3$ alkyl or $C_1$-$C_3$ haloalkyl group; and optionally the phenyl or 5- or 6-membered heteroaryl group is further substituted at the α' position with a substituent selected from —$R^4$, —$OR^4$ and —$COR^4$, wherein $R^4$ is selected from a $C_1$-$C_6$ alkyl, $C_2$-$C_6$ alkenyl, $C_2$-$C_6$ alkynyl or $C_2$-$C_6$ cyclic group and wherein $R^4$ is optionally substituted with one or more halo groups; and optionally the phenyl or 5- or 6-membered heteroaryl group is further substituted (typically with one, two or three substituents independently selected from halo, —$NO_2$, —CN, —$COOR^{15}$, —$CONH_2$, —$CONHR^{15}$ or —$CON(R^{15})_2$, wherein each —$R^{15}$ is independently selected from a $C_1$-$C_4$ alkyl or $C_1$-$C_4$ haloalkyl group); or (v) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, $C_1$-$C_3$ alkyl, $C_1$-$C_3$ haloalkyl, —$R^{12}$—$OR^{13}$, —$R^{12}$—$N(R^{13})_2$, —$R^{12}$—CN or —$R^{12}$—C≡$CR^{13}$, and wherein a ring atom of the monovalent heterocyclic or aromatic group is directly attached to the α-ring atom of the parent phenyl or 5- or 6-membered heteroaryl group; wherein $R^{12}$ is independently selected from a bond or a $C_1$-$C_3$ alkylene group; and $R^{13}$ is independently selected from hydrogen or a $C_1$-$C_3$ alkyl or $C_1$-$C_3$ haloalkyl group; and optionally the phenyl or 5- or 6-membered heteroaryl group is further substituted with a cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl or 5- or 6-membered heteroaryl group is further substituted (typically with one or two substituents independently selected from halo, —$NO_2$, —CN, —$COOR^{15}$, —$CONH_2$, —$CONHR^{15}$ or —$CON(R^{15})_2$, wherein each —$R^{15}$ is independently selected from a $C_1$-$C_4$ alkyl or $C_1$-$C_4$ haloalkyl group);

provided that when the non-aromatic heterocyclic group of $R^1$ is selected from:

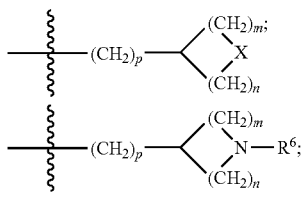

at least one ring nitrogen atom which is adjacent to a carbonyl group is substituted.

In this specific embodiment directly above, where a group or moiety is optionally substituted with one or more halo groups, it may be substituted for example with one, two, three, four, five or six halo groups.

In this specific embodiment directly above, the parent phenyl or 5- or 6-membered heteroaryl group of $R^2$ may be selected from phenyl, pyridinyl, pyridazinyl, pyrimidinyl or pyrazinyl.

In this specific embodiment directly above, $R^1$ may optionally be substituted with one or more (such as one, two or three) substituents independently selected from halo; $C_1$-$C_6$ alkyl; $C_1$-$C_6$ haloalkyl; $C_2$-$C_6$ alkenyl; $C_2$-$C_6$ haloalkenyl; $C_2$-$C_6$ alkynyl; $C_2$-$C_6$ haloalkynyl; —$R^5$—CN; —$R^5$—$N_3$; —$R^5$—$NO_2$; —$R^5$—$N(R^6)_2$; —$R^5$—$OR^6$; —$R^5$—$SR^6$; —$R^5$—$Si(R^6)_3$; —$R^5$—O—$Si(R^6)_3$; —$R^5$—$COR^6$; —$R^5$—$COOR^6$; —$R^5$—CO—$R^5$—$OR^6$; —$R^5$—$CON(R^6)_2$; —$R^5$—CO—$R^5$—$N(R^6)_2$; —$R^5$—C(=$NR^6$)$R^6$; —$R^5$—C(=$NR^6$)$N(R^6)_2$; —$R^5$—C(=NOH)$R^6$; —$R^5$—$SO_2R^6$; —$R^5$-phenyl; —$R^5$-(Het);

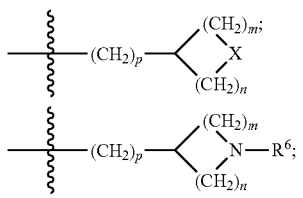

oxo (=O); —$CH_2CH_2$—; —$CH_2CH_2CH_2$—; —$CH_2CH_2CH_2CH_2$—; —CH=CH—CH=$CH_2$—; or —$R^5$—($C_3$-$C_6$ cycloalkyl) wherein the $C_3$-$C_6$ cycloalkyl group is optionally substituted with one or two substituents independently selected from $C_1$-$C_3$ alkyl; wherein $R^5$ is independently selected from a bond or $C_1$-$C_5$ alkylene;

$R^6$ is independently selected from hydrogen, $C_1$-$C_5$ alkyl, $C_1$-$C_5$ haloalkyl, $C_3$-$C_6$ cycloalkyl, —CO—($C_1$-$C_3$ alkyl), —COO—($C_1$-$C_4$ alkyl) or benzyl;

Het is selected from a pyridinyl, 2-oxo-1,2-dihydropyridinyl, pyridazinyl, pyrimidinyl, pyrazinyl, pyrrolyl, pyrazolyl, imidazolyl or diazirinyl group, each of which may optionally be substituted with one or two substituents independently selected from halo, $C_1$-$C_4$ alkyl, $C_2$-$C_4$ alkenyl or $C_2$-$C_4$ alkynyl;

X is selected from O, S, SO or $SO_2$;

m is 1, 2 or 3;

n is 1, 2 or 3; and p is 0, 1 or 2.

Typically, $R^1$ is substituted on one or more (such as one, two or three) ring nitrogen atoms with such a substituent.

In one aspect of any of the above embodiments, the compound of formula (I) has a molecular weight of from 250 to 2000 Da. Typically, the compound of formula (I) has a molecular weight of from 280 to 900 Da. More typically, the compound of formula (I) has a molecular weight of from 310 to 550 Da.

A second aspect of the invention provides a compound selected from the group consisting of:

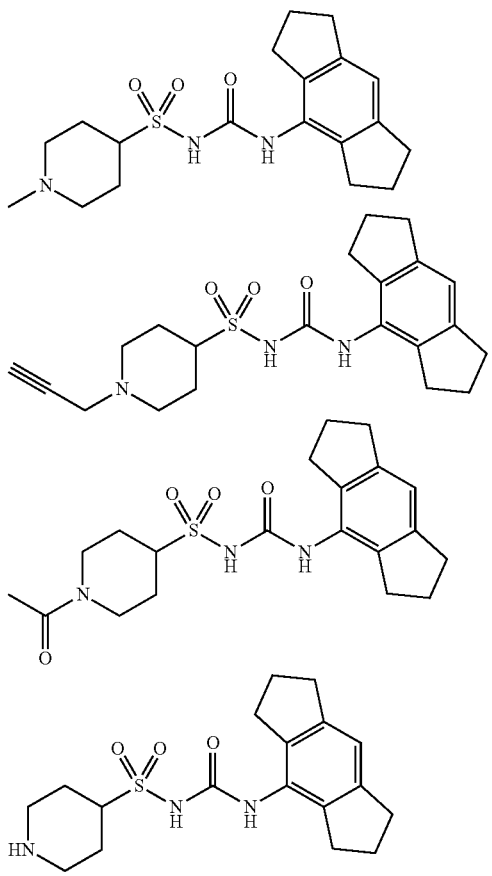

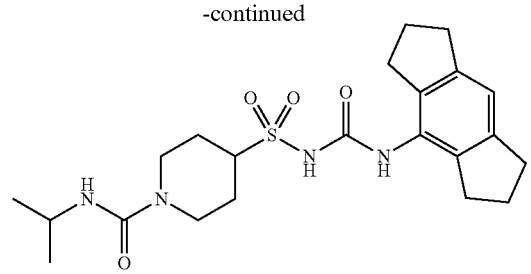
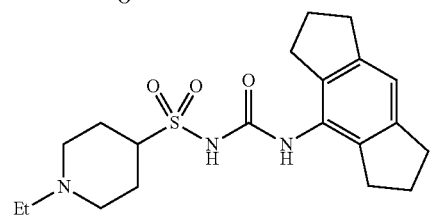
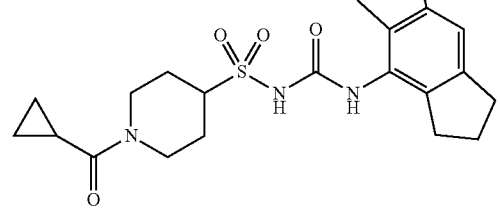
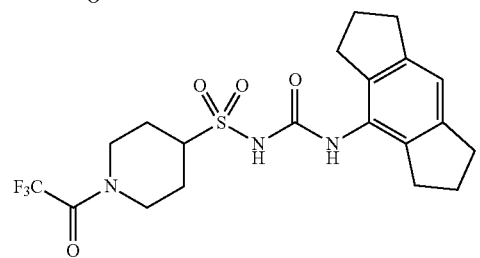
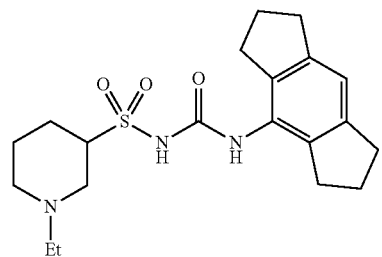
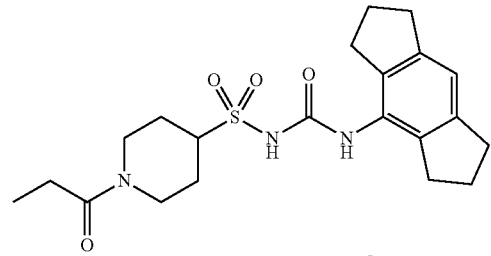
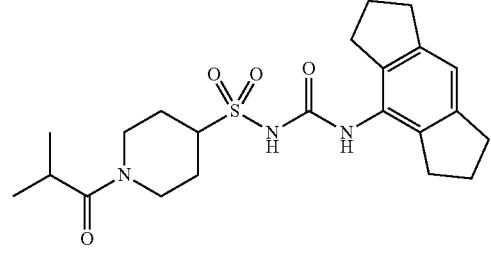
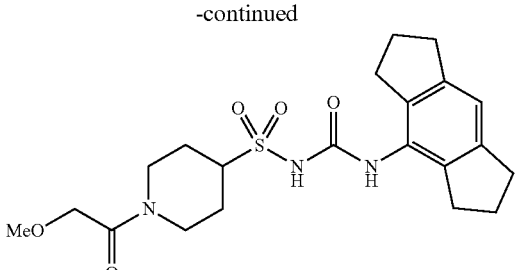
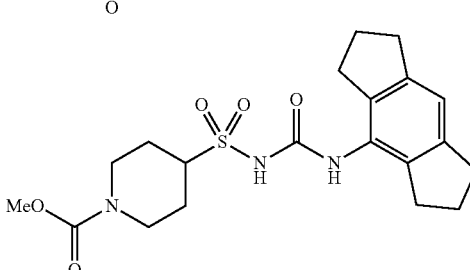
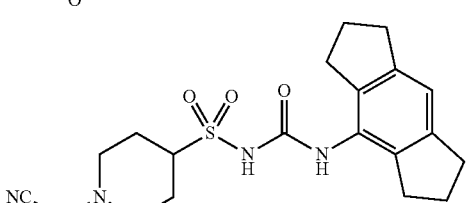
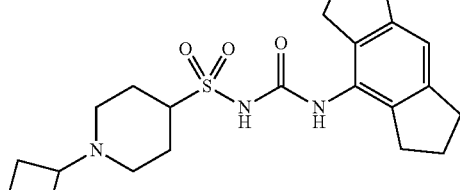
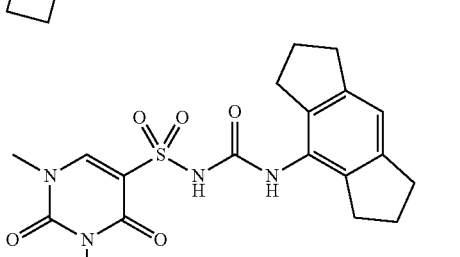
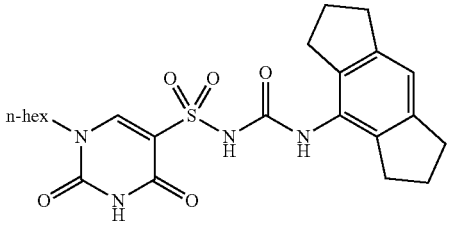
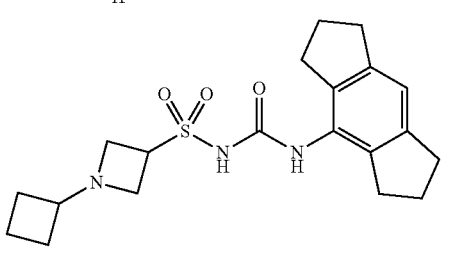

37
-continued
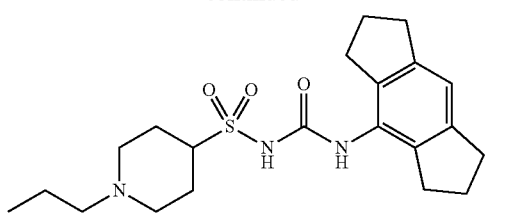
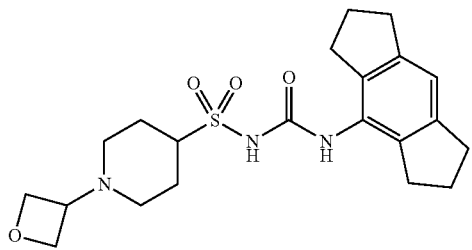
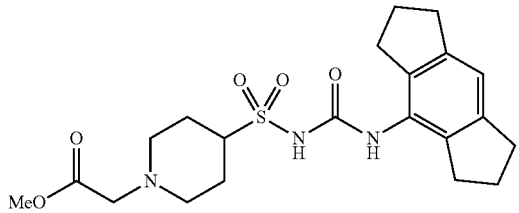
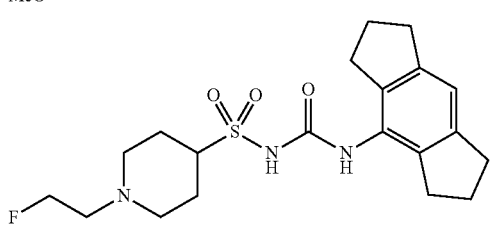
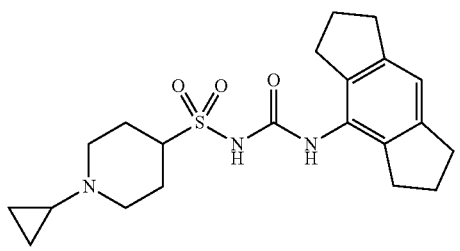
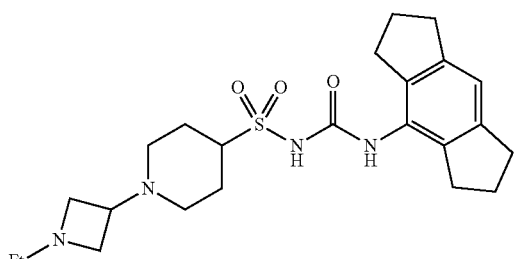
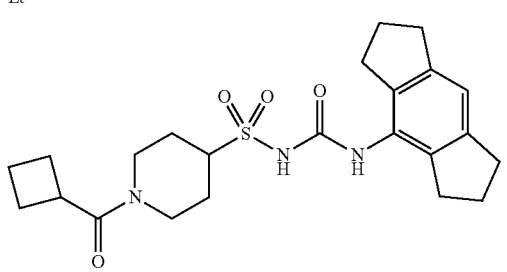
38
-continued
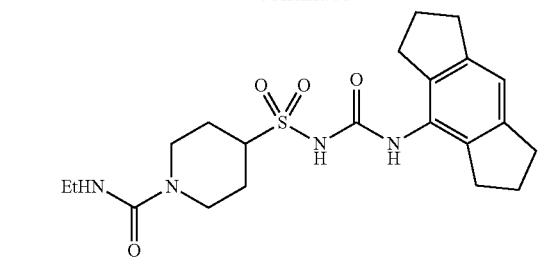
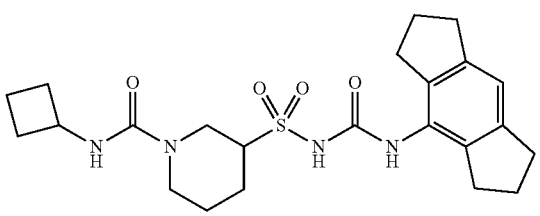
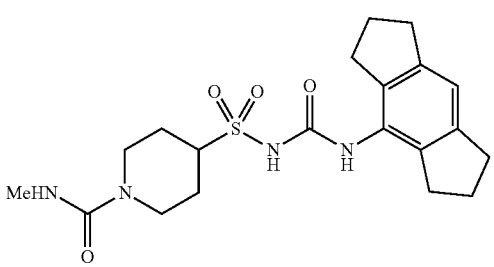
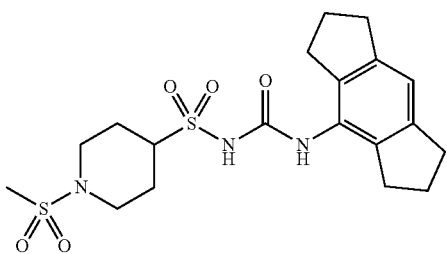
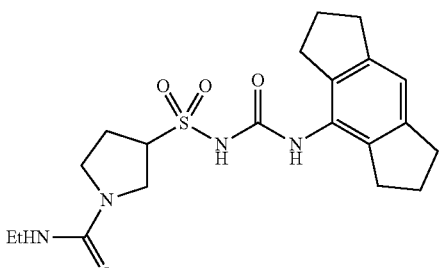
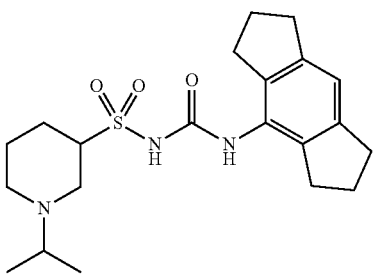

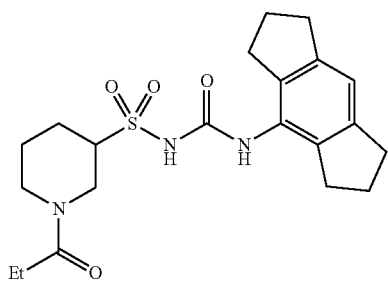
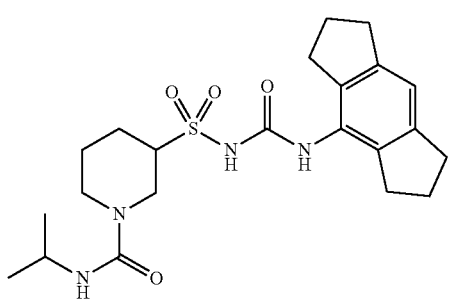
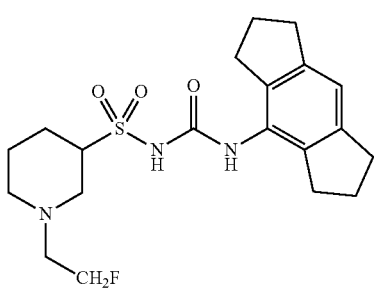
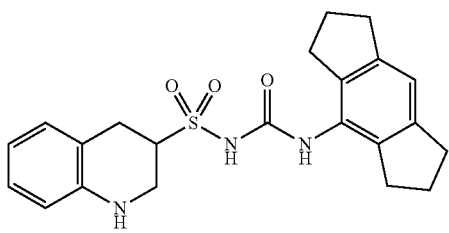
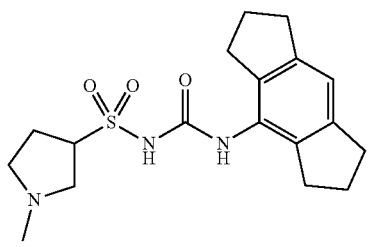
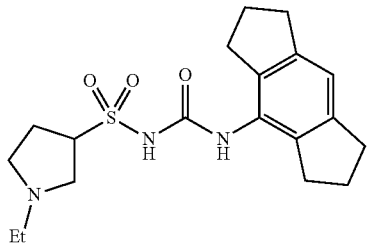
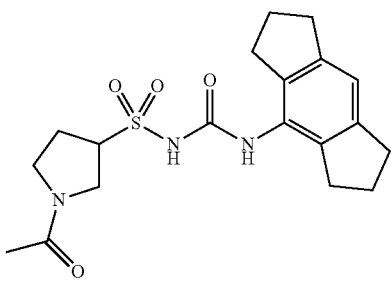
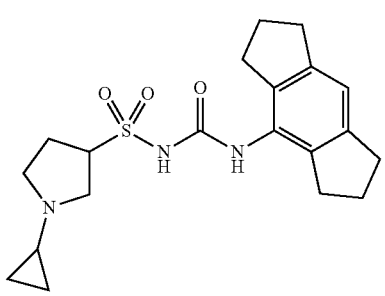
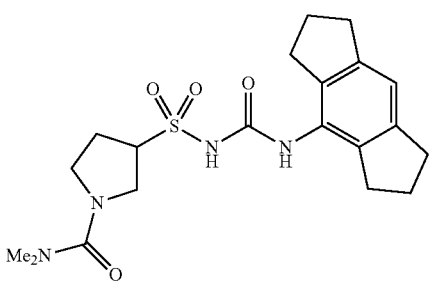
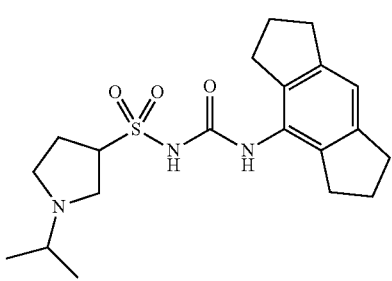
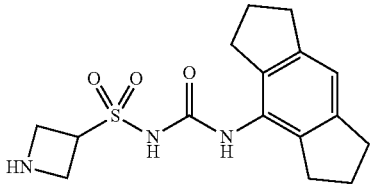
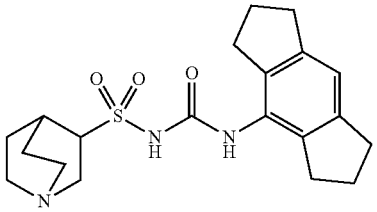

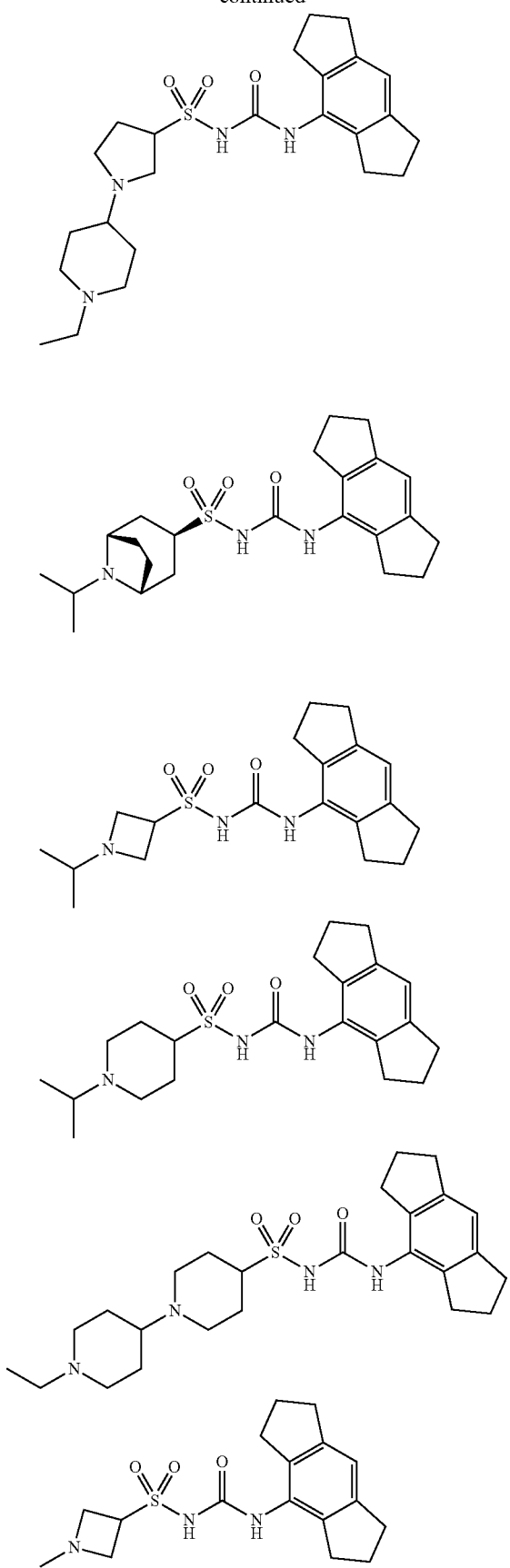
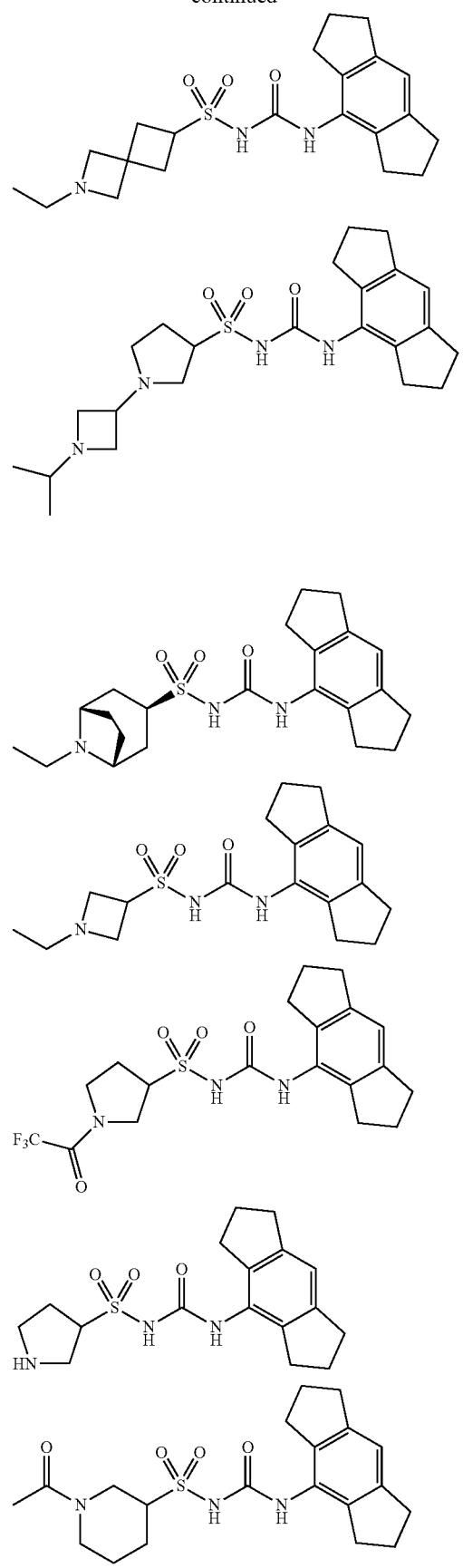

43
-continued
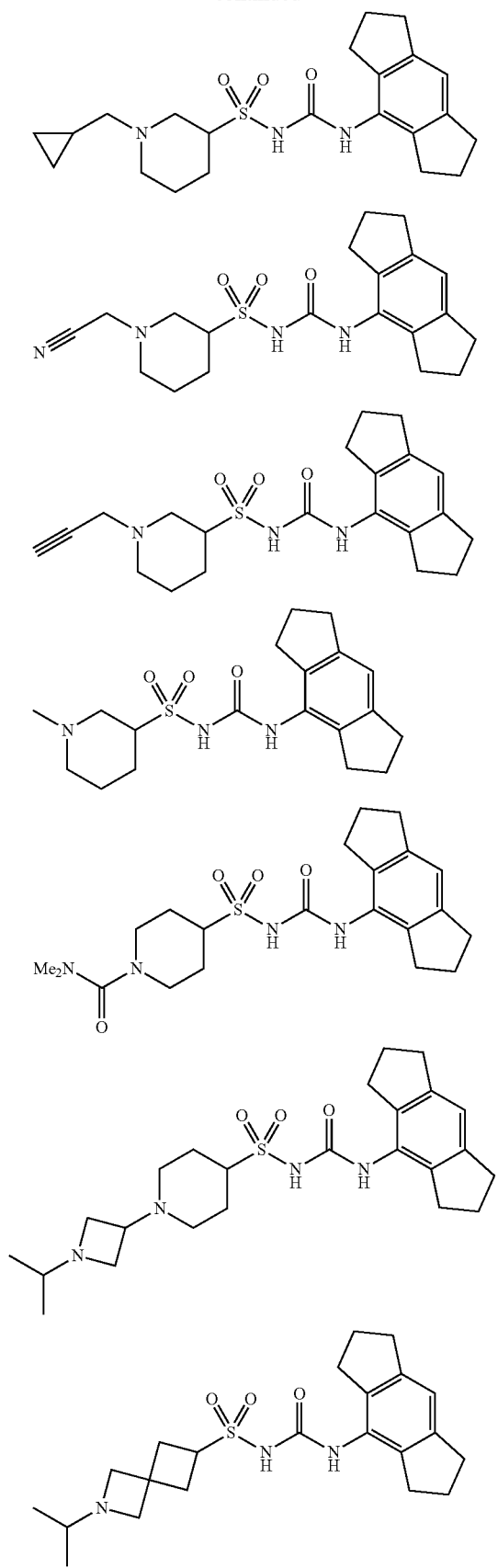
44
-continued
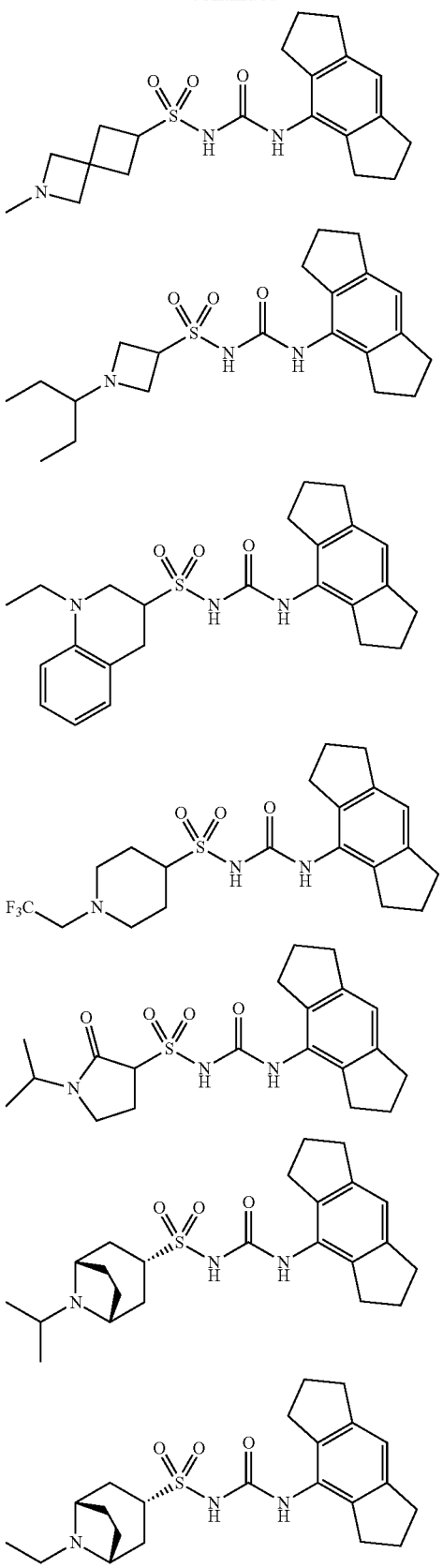

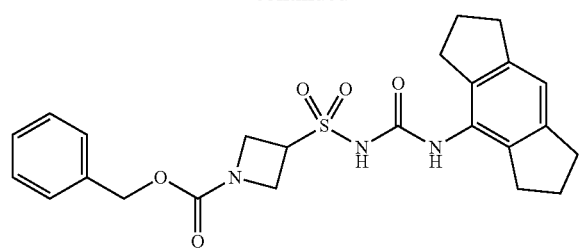
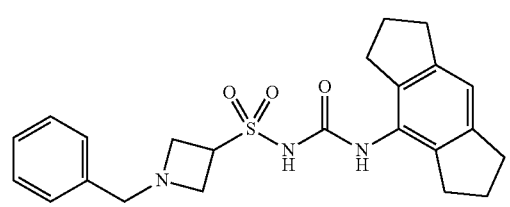
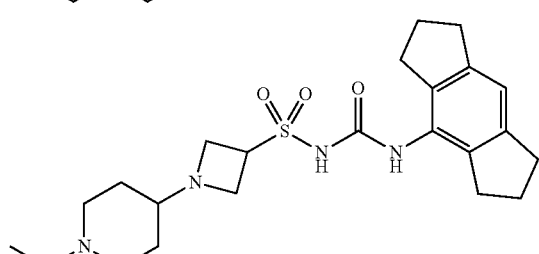
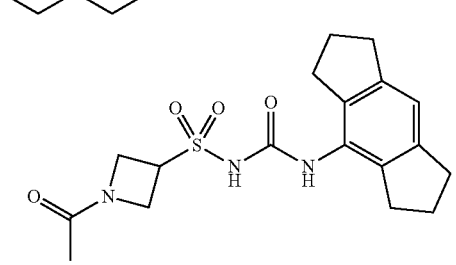
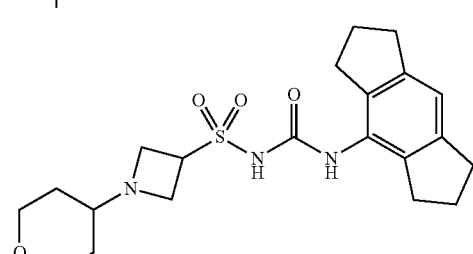
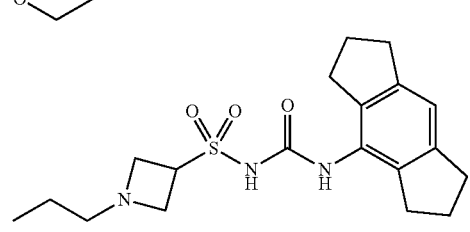
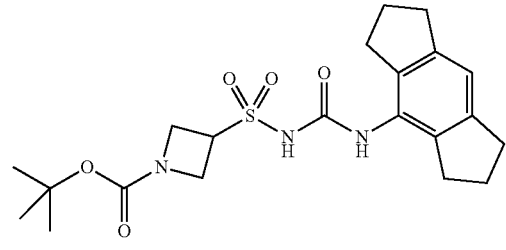
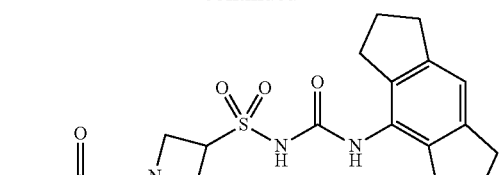
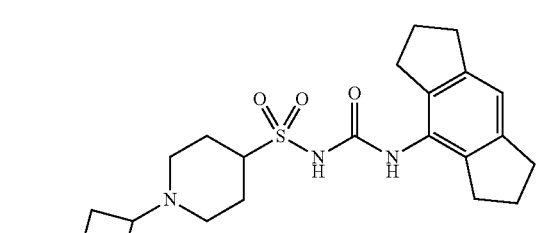
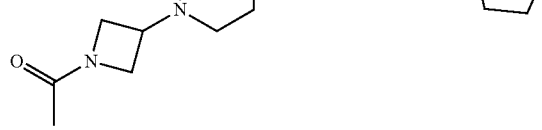
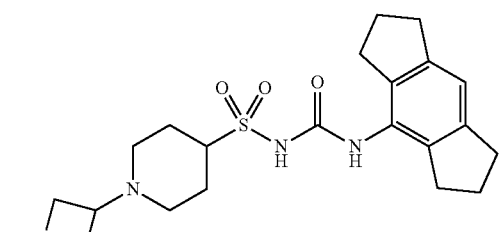
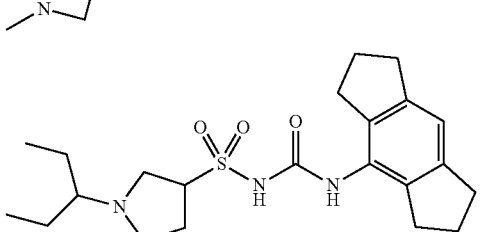
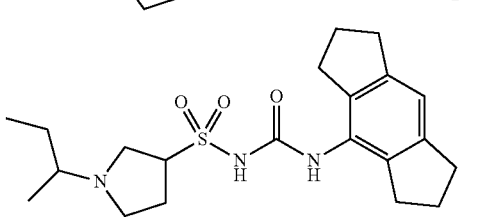
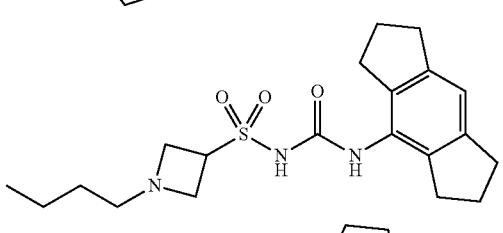
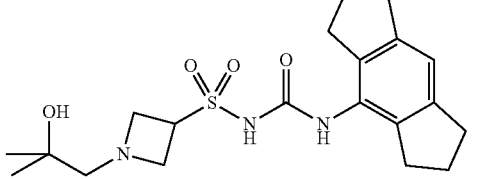

47
-continued
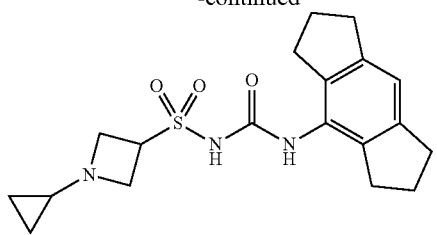
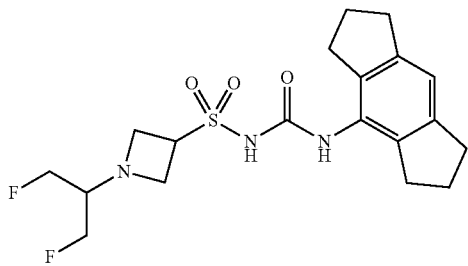
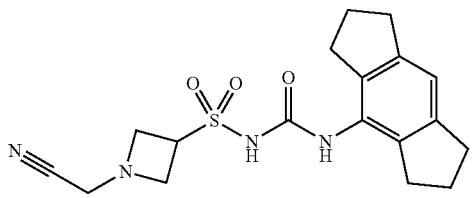
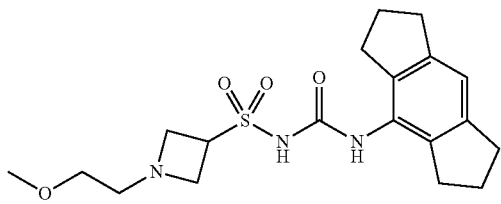
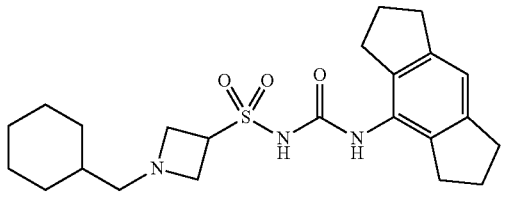
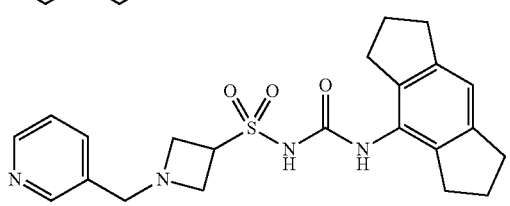
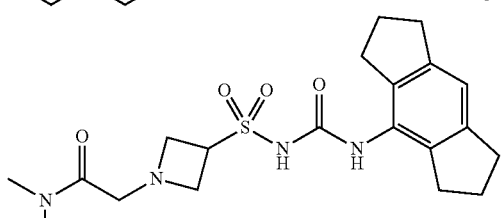
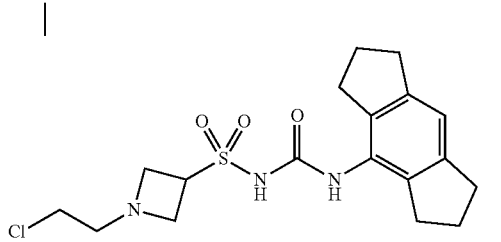
48
-continued
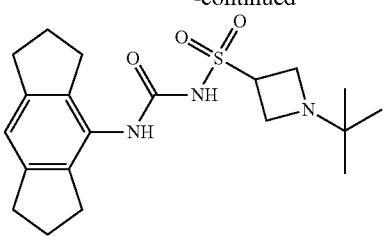
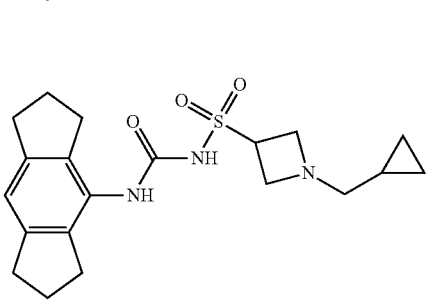
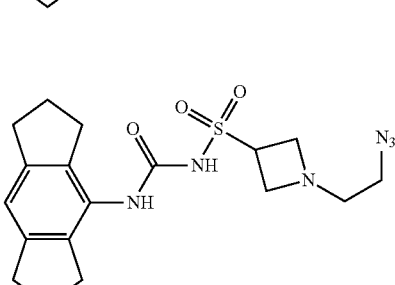
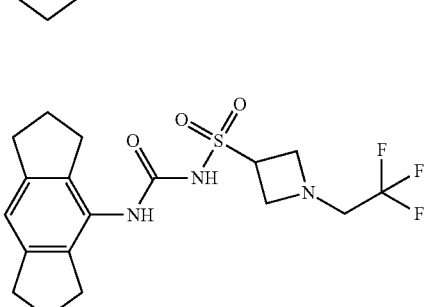
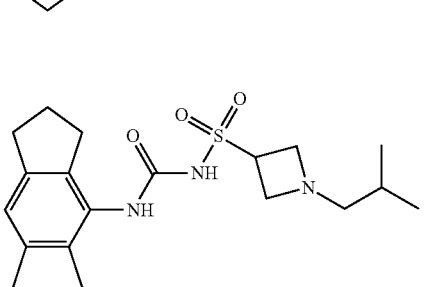
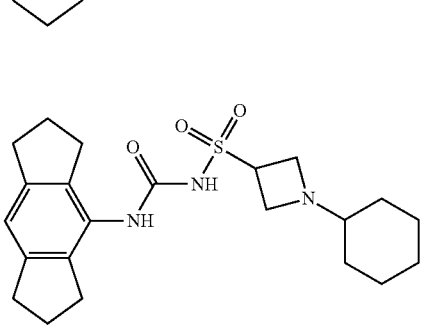

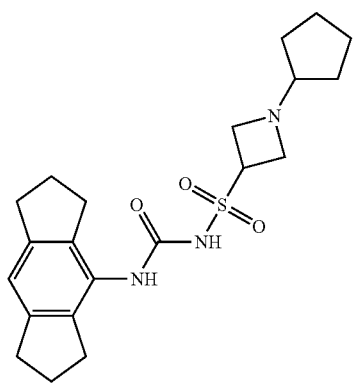
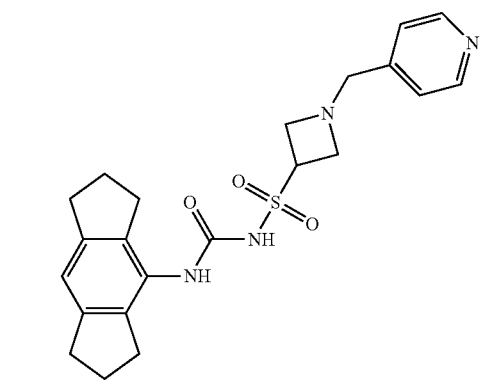
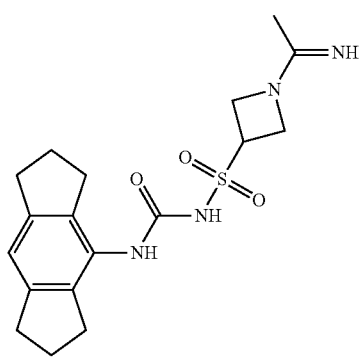
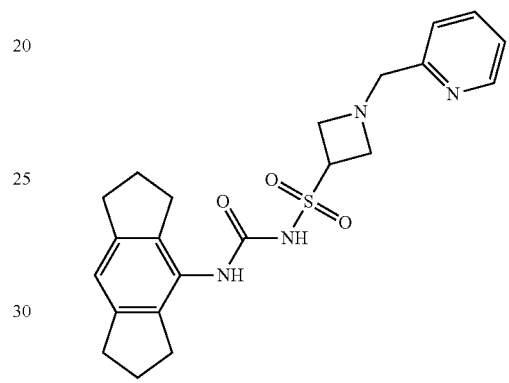
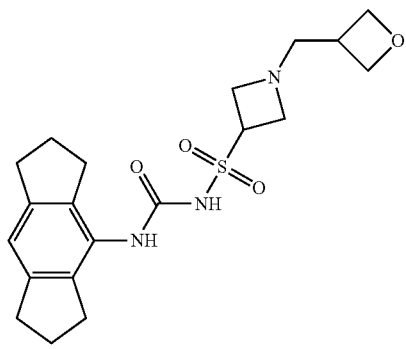
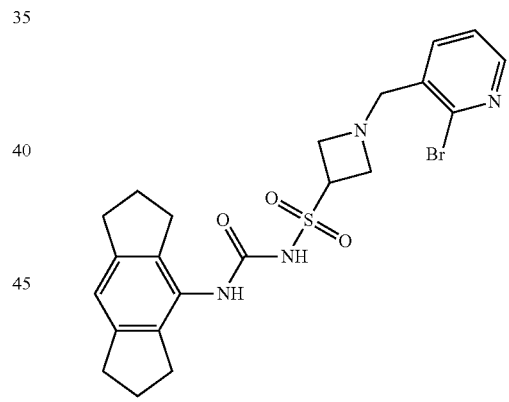
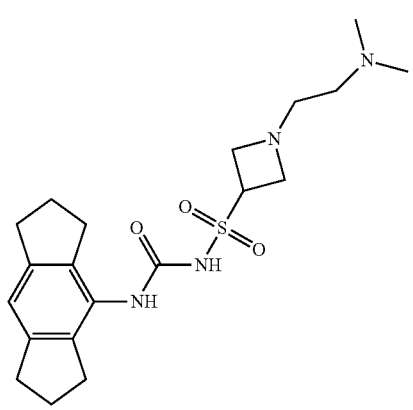
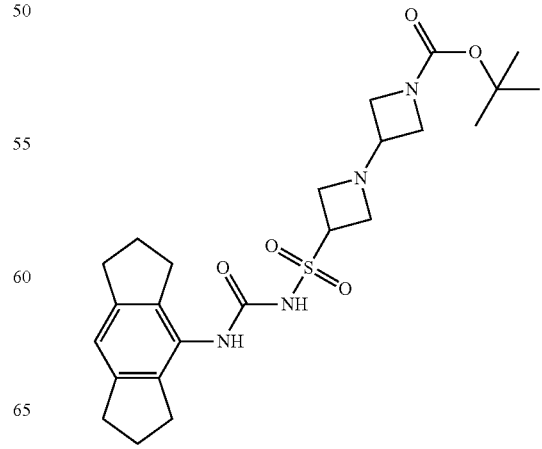

51
-continued
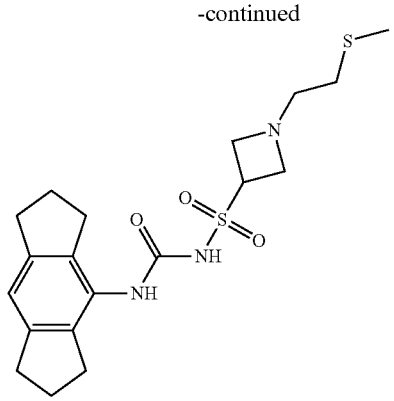
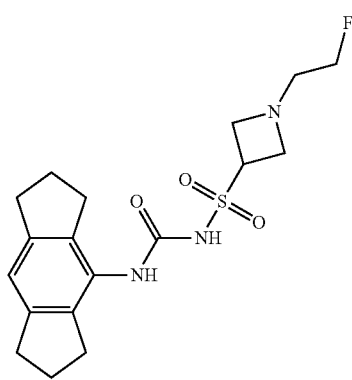
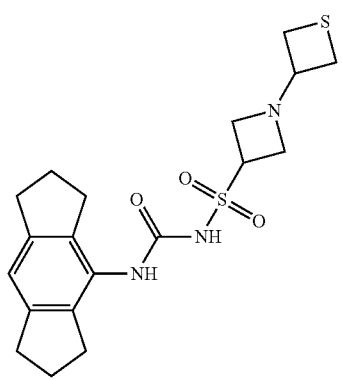
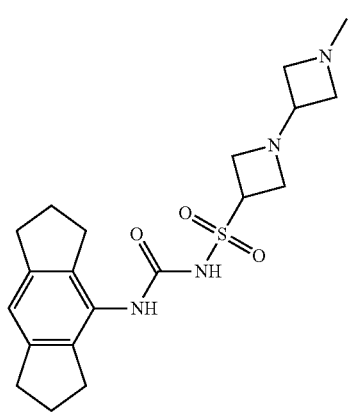
52
-continued
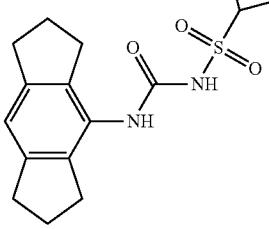
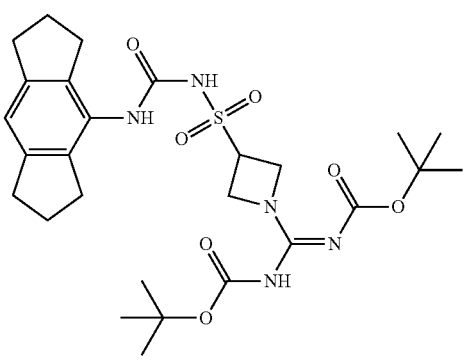
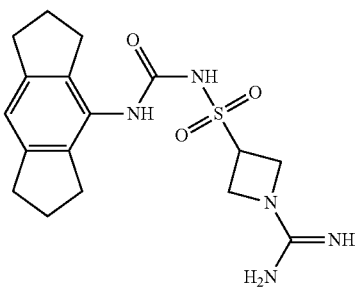
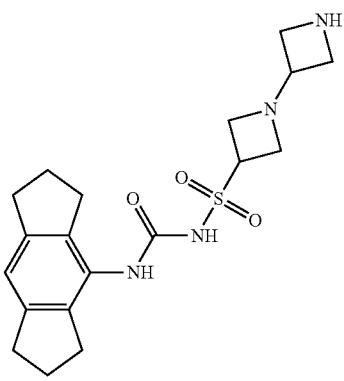

53
-continued
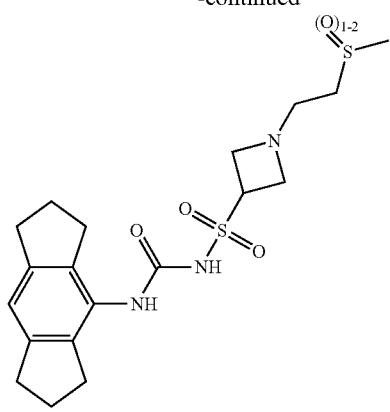
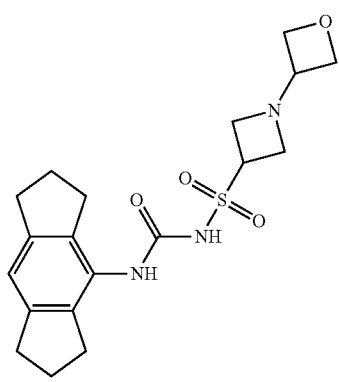
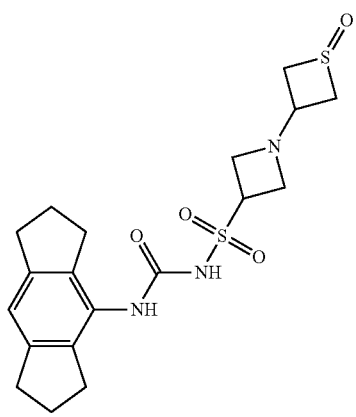
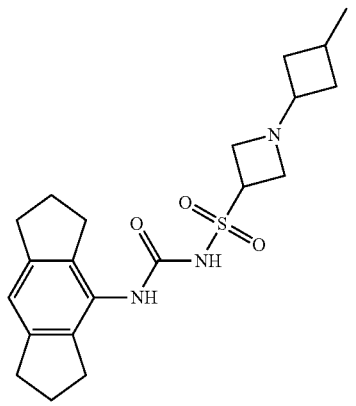
54
-continued
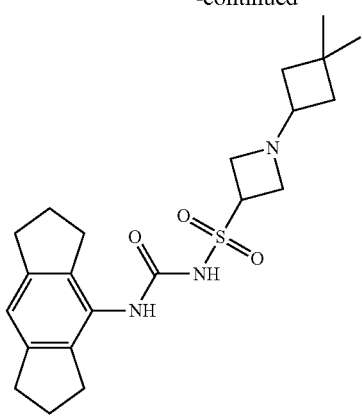
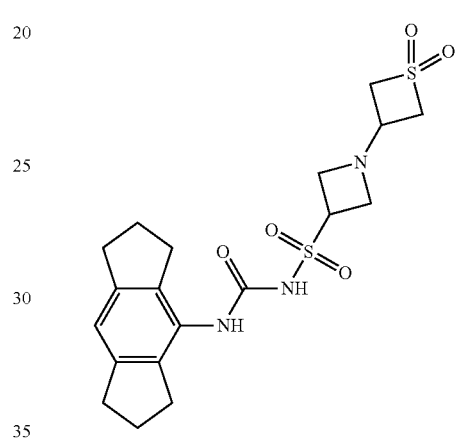
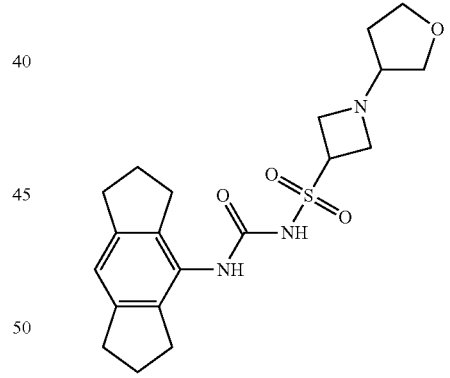
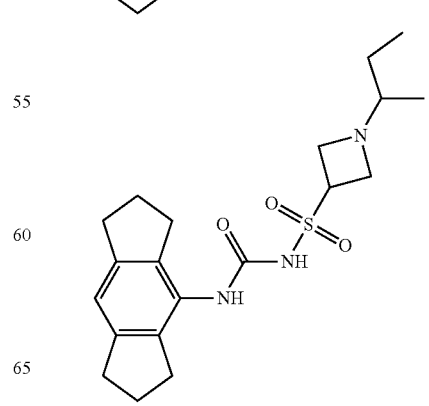

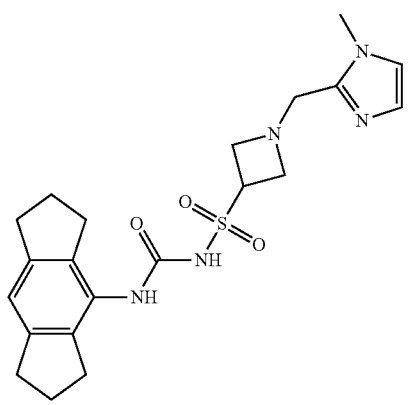
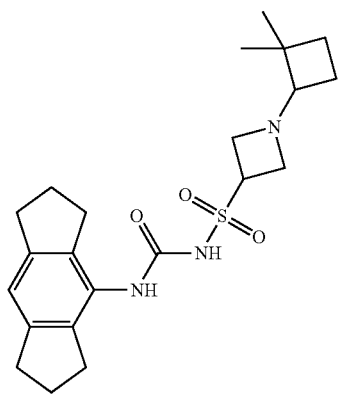
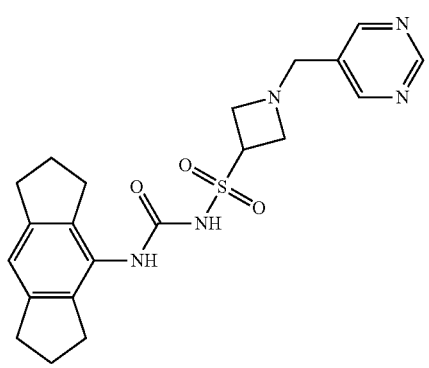
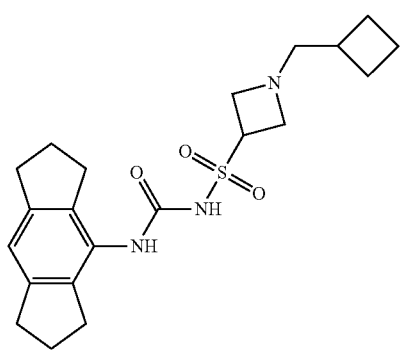
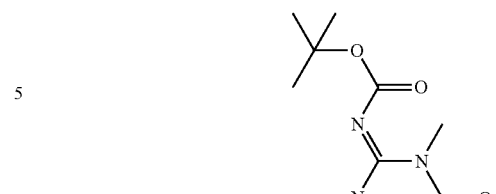
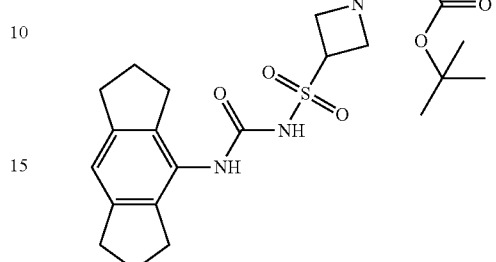
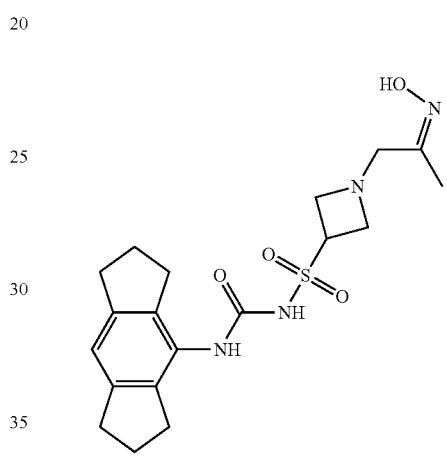
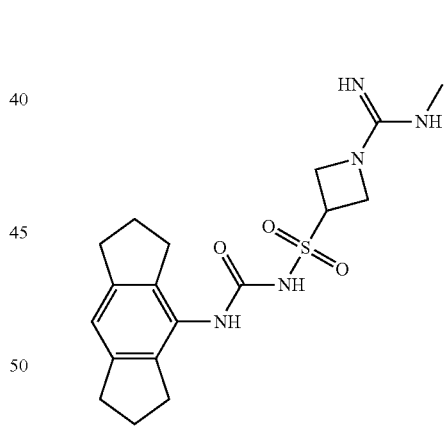
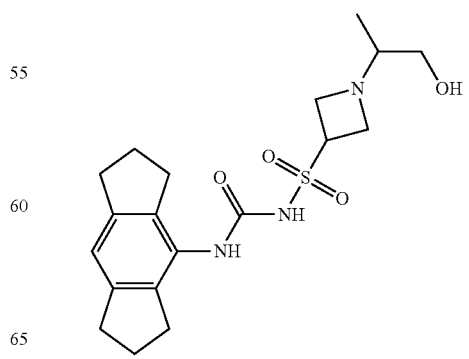

57
-continued
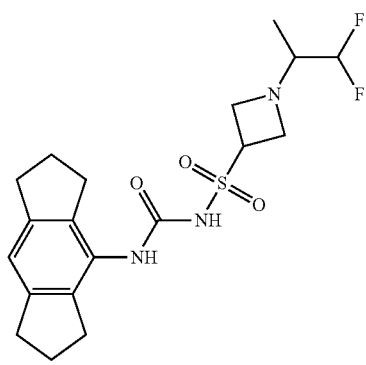
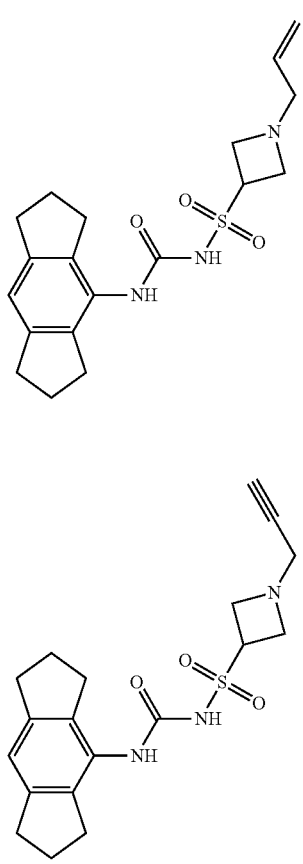
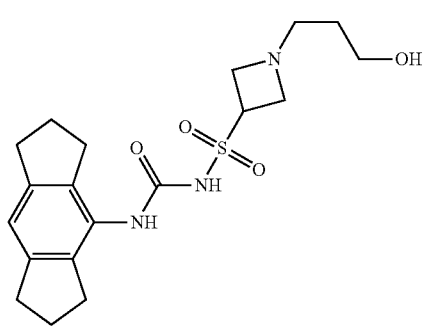
58
-continued
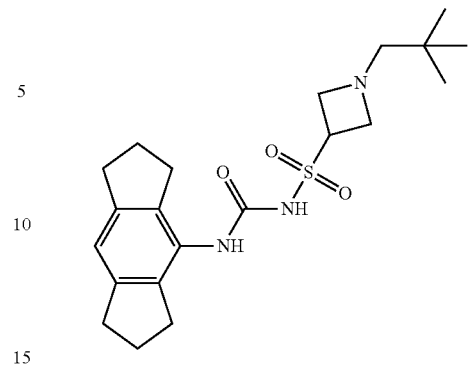
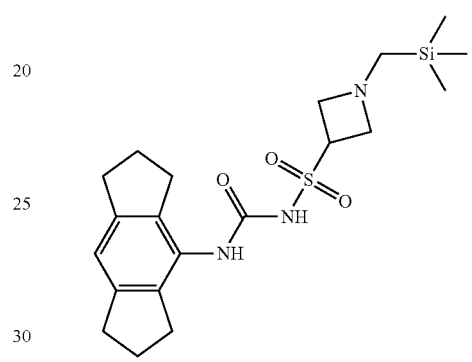
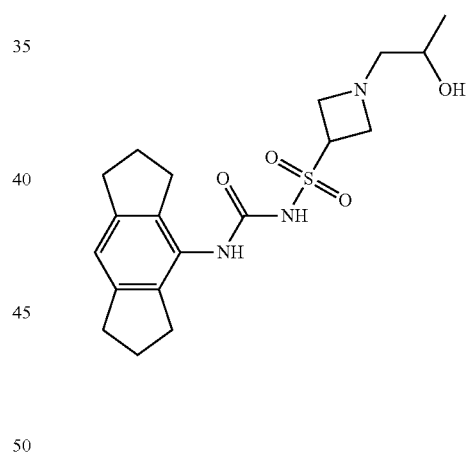
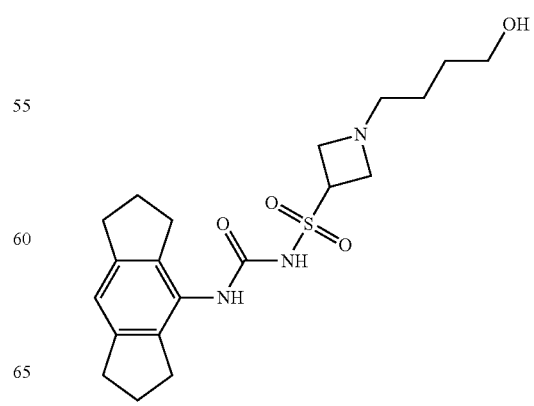

59
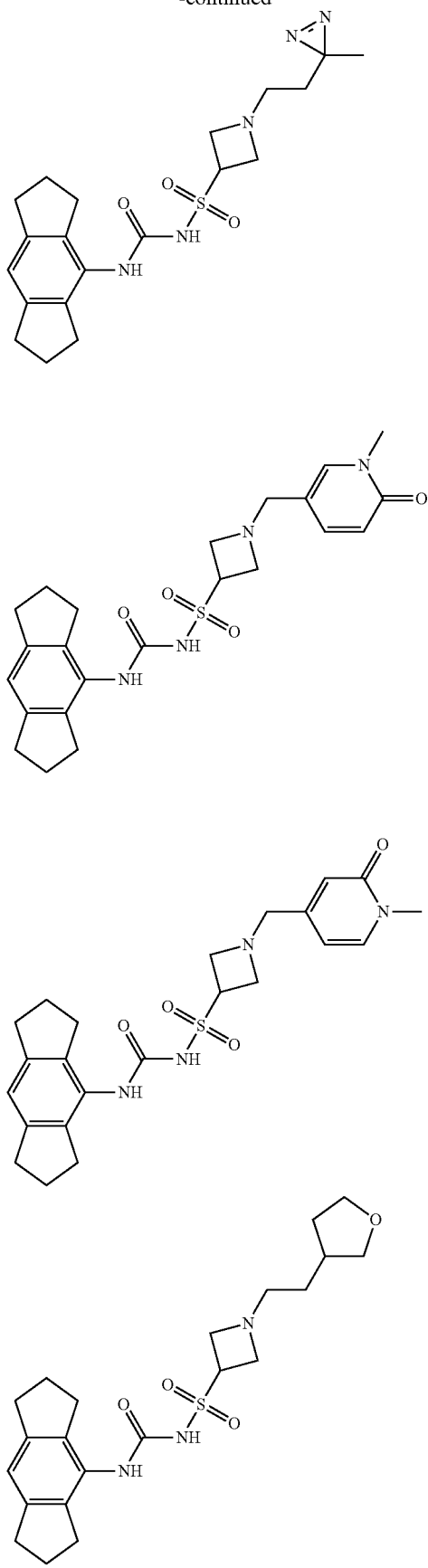
60
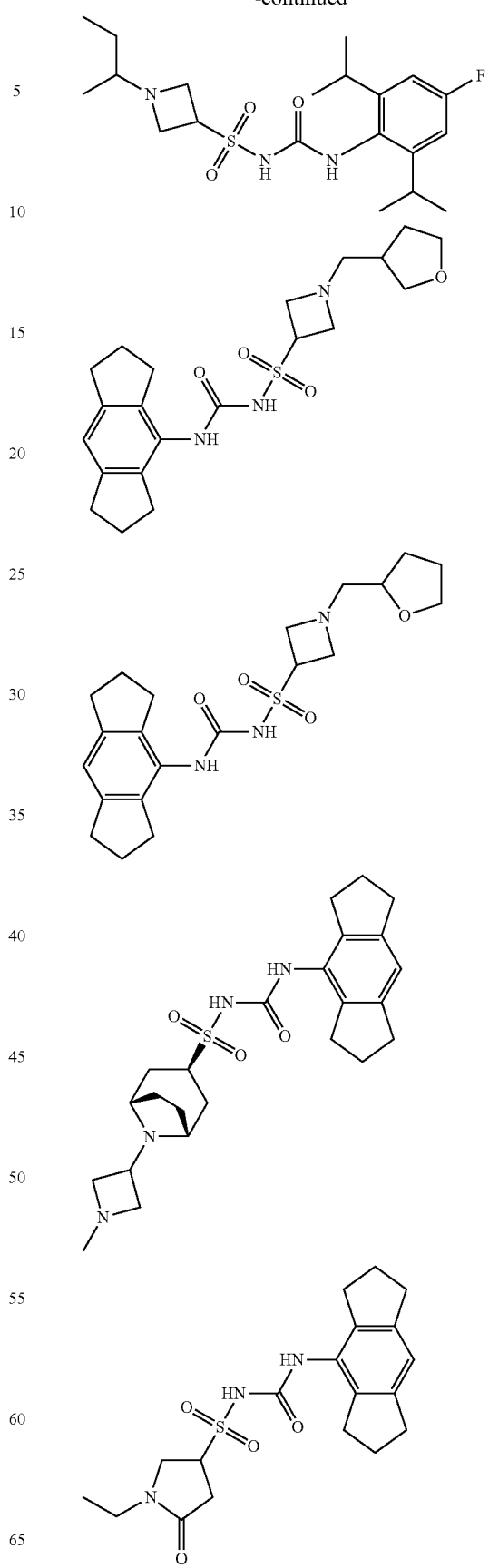

61
-continued
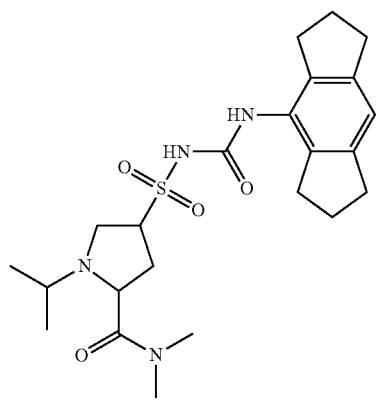
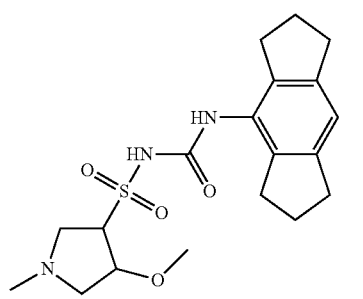
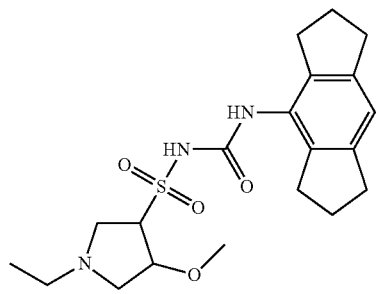
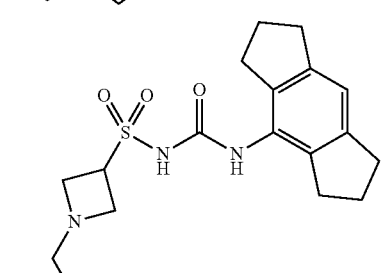
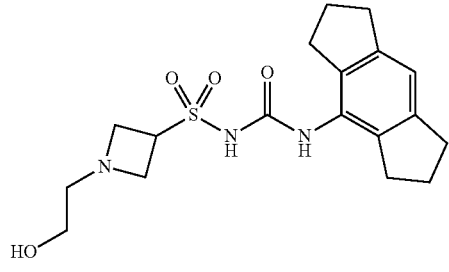
62
-continued
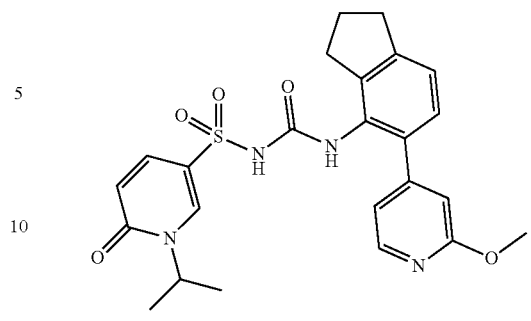
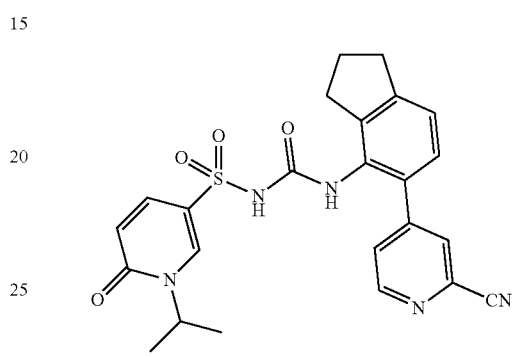
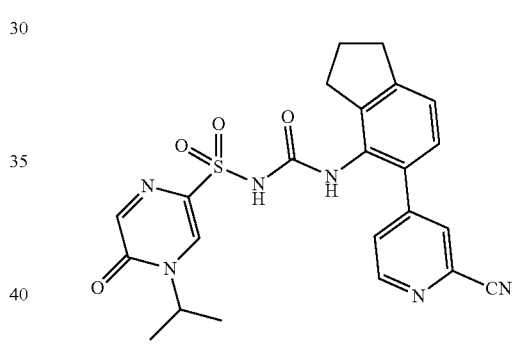
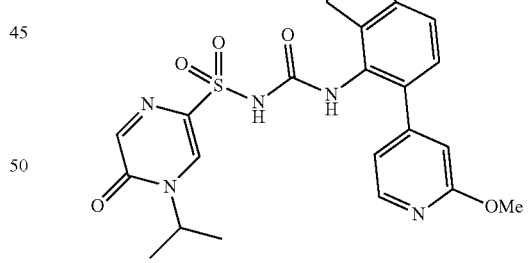
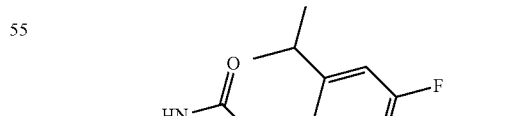
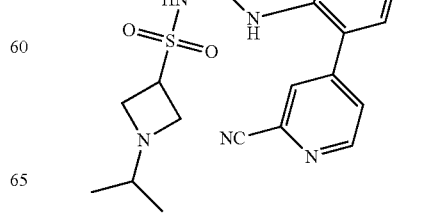

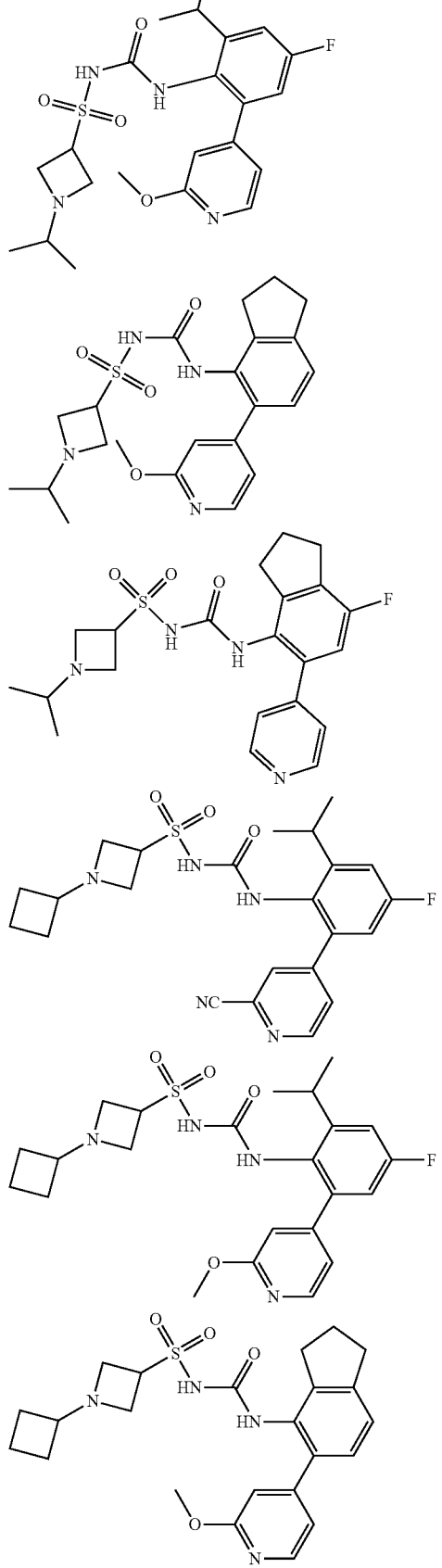
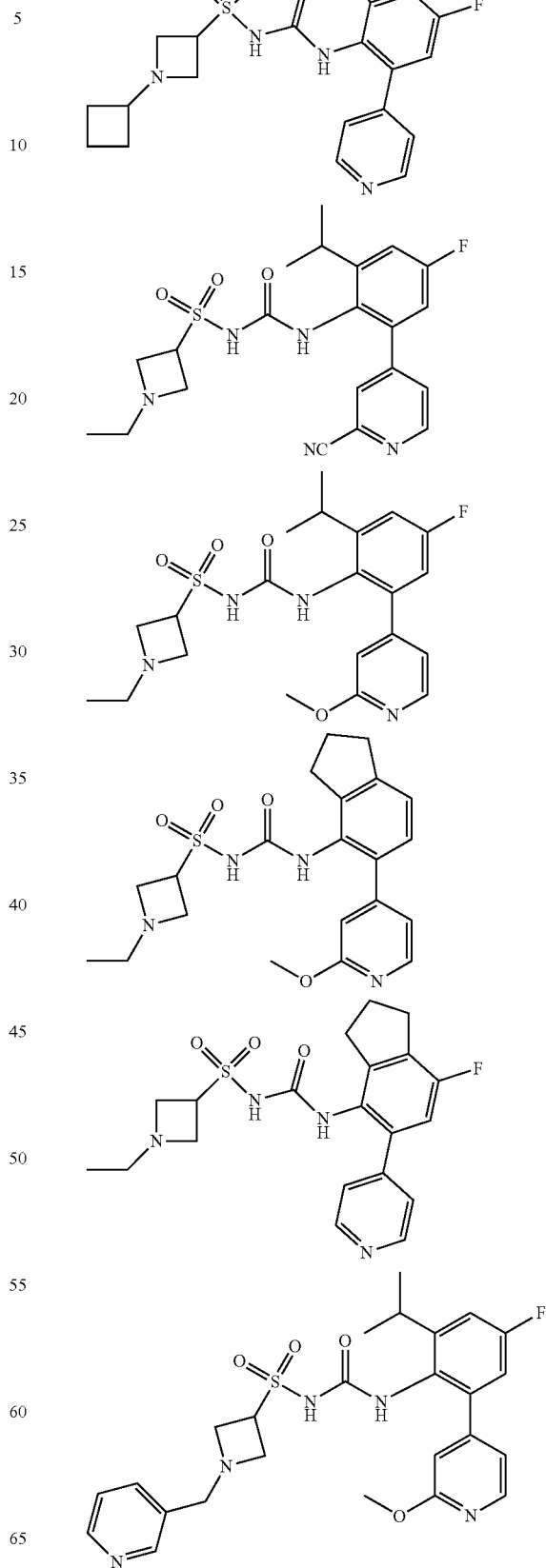

65
-continued
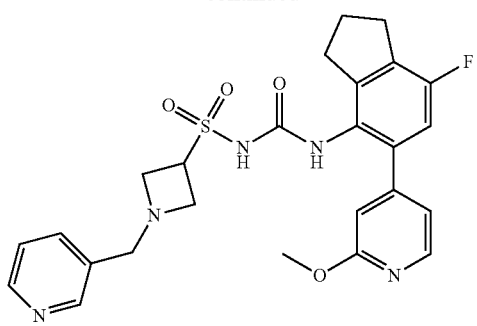
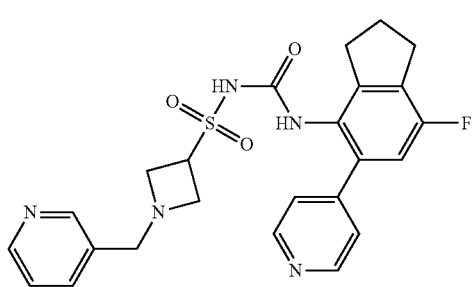
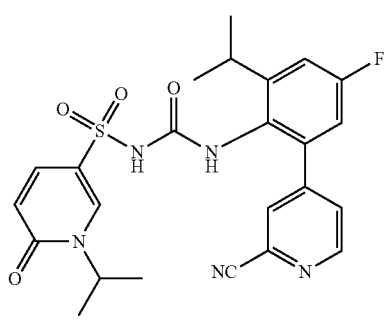
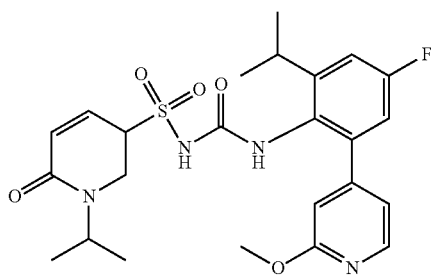
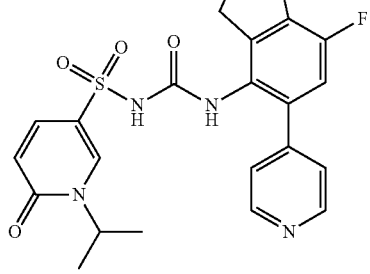
66
-continued
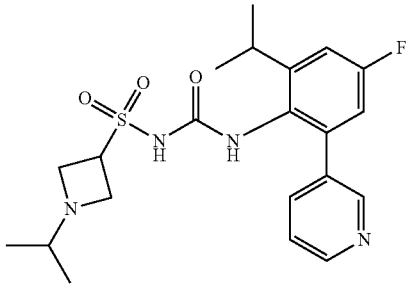
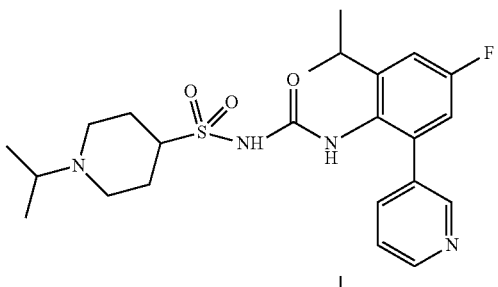
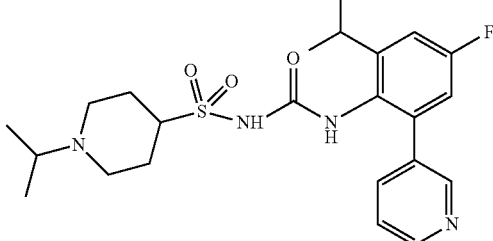
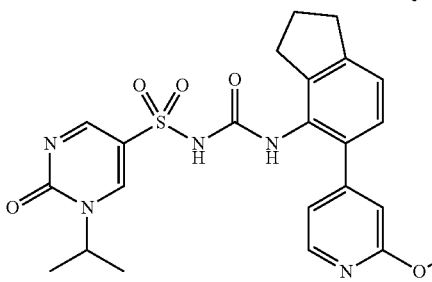
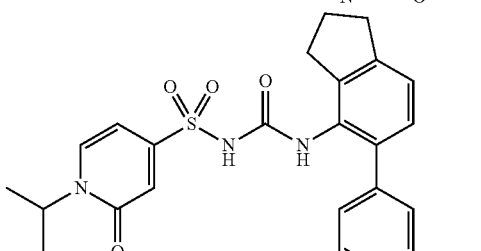
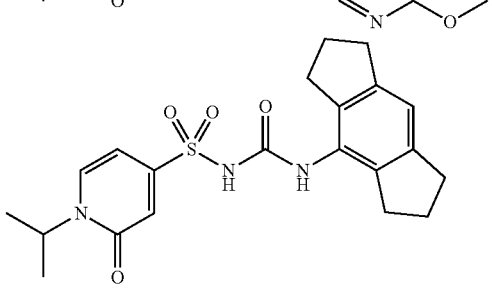

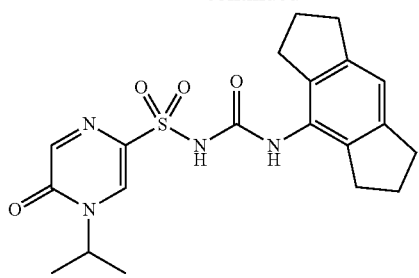
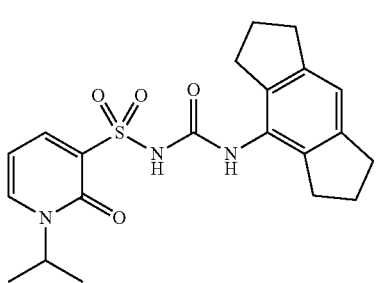
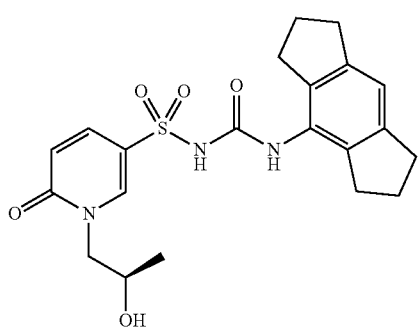
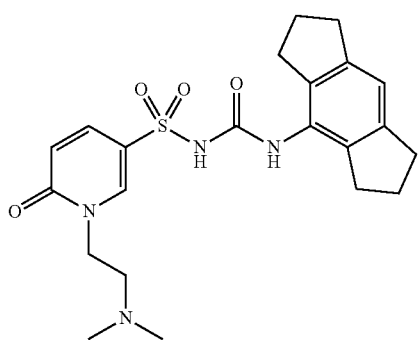
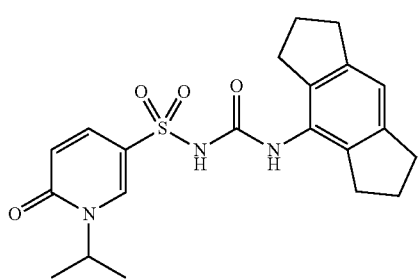
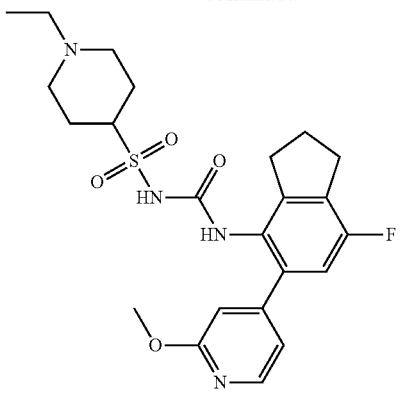
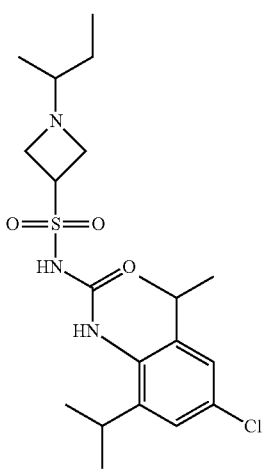
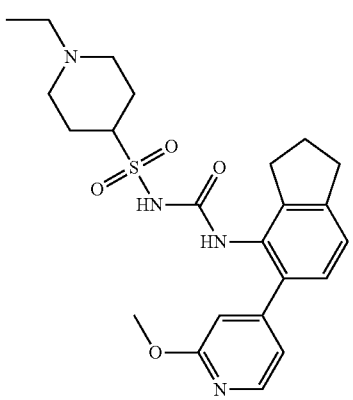
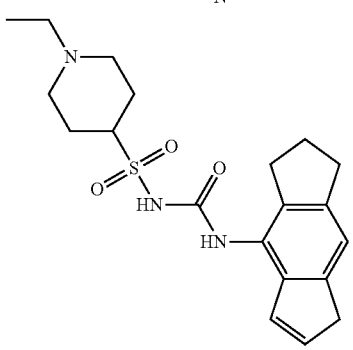

| 69 -continued | 70 -continued |
|---|---|
| 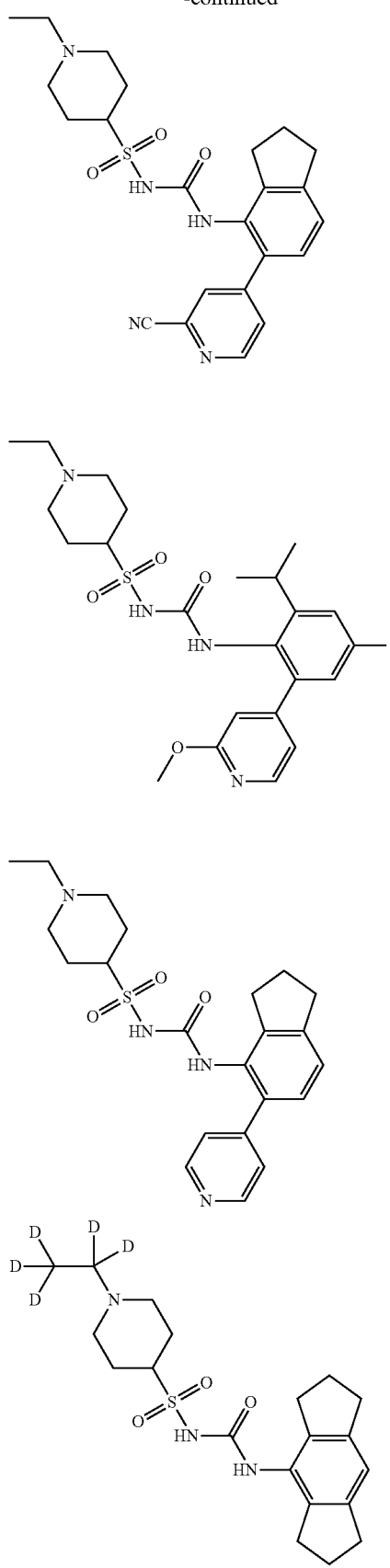 | 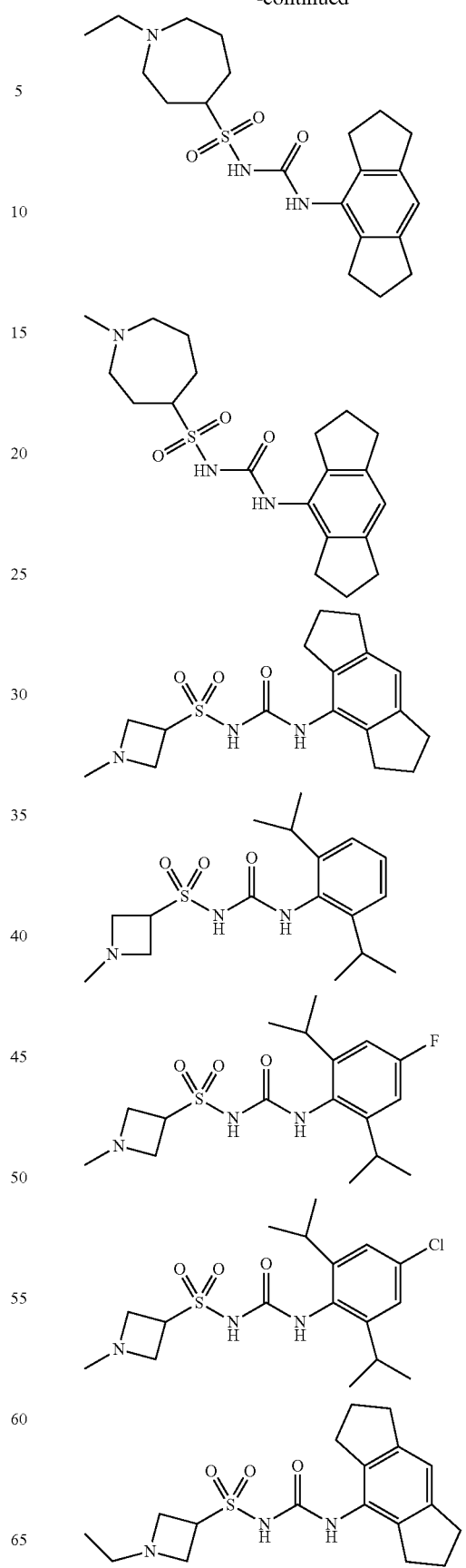 |

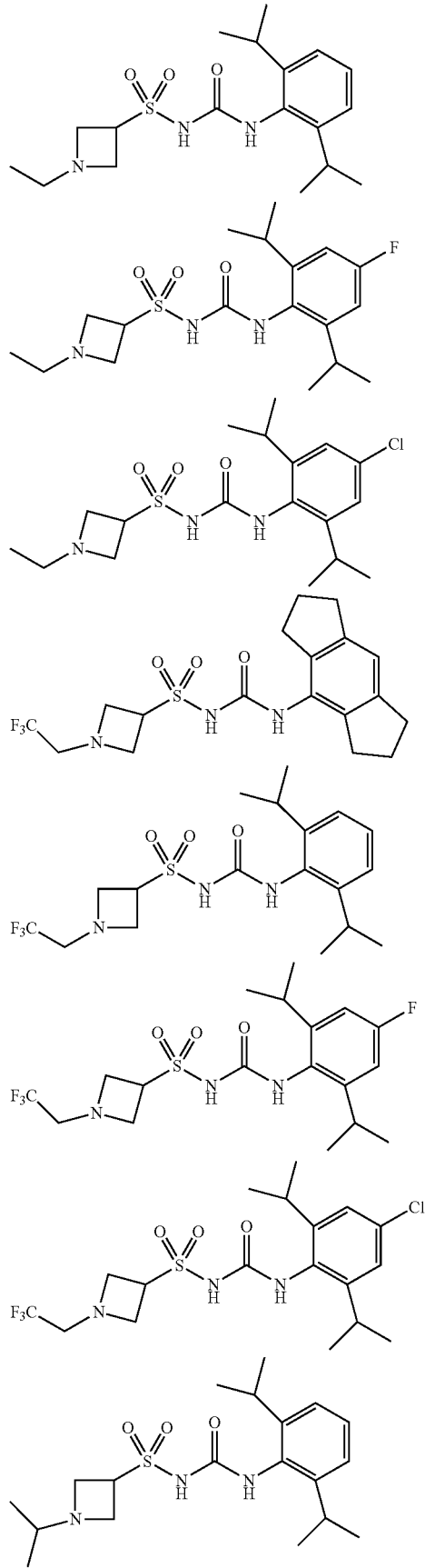
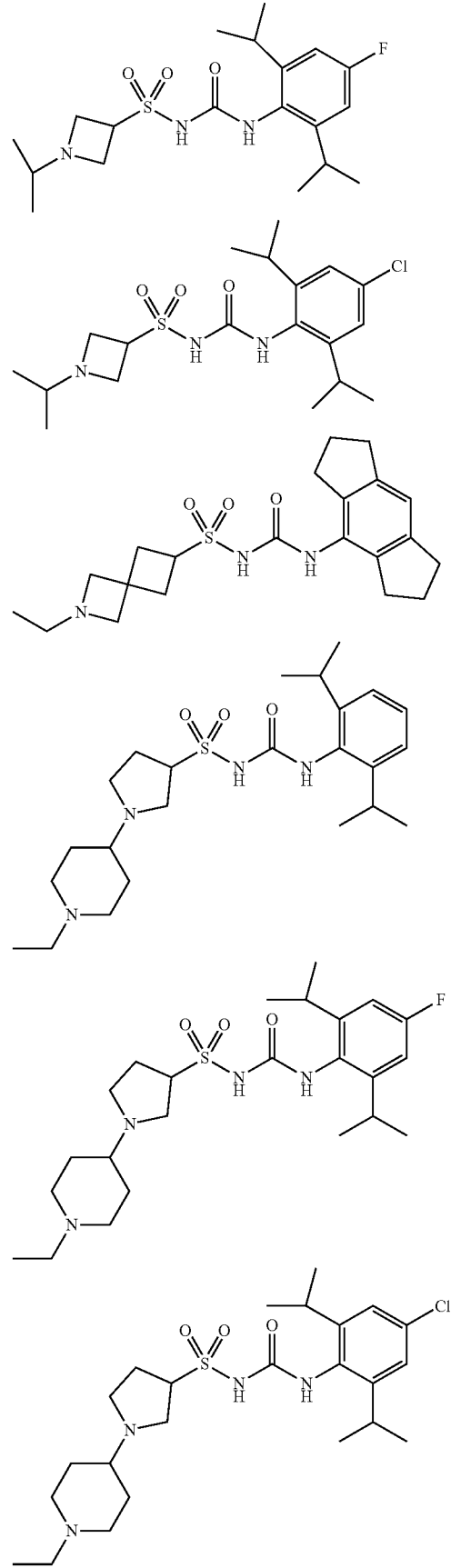

73
-continued
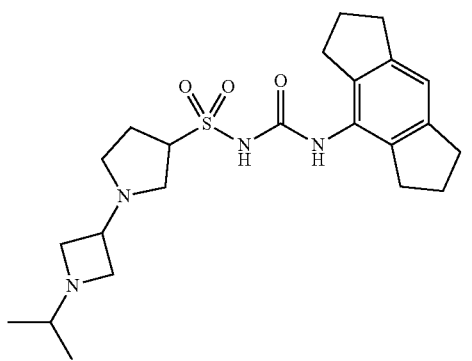
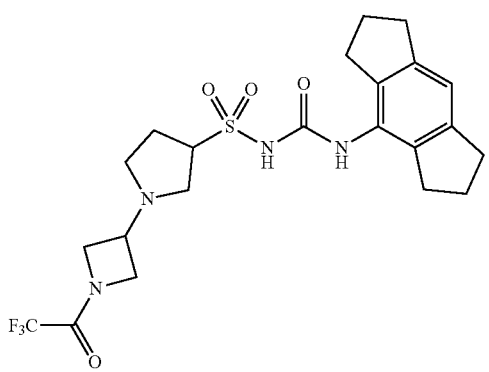
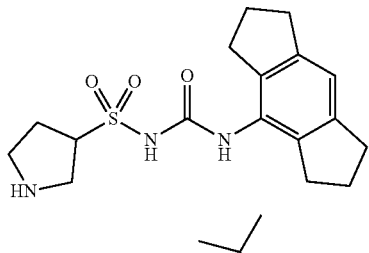
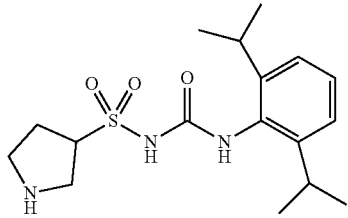
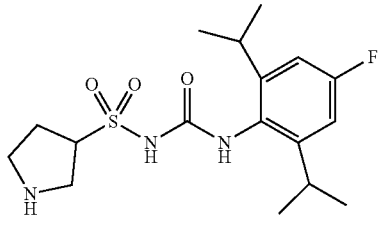
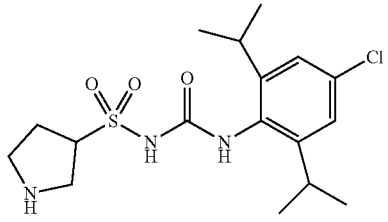
74
-continued
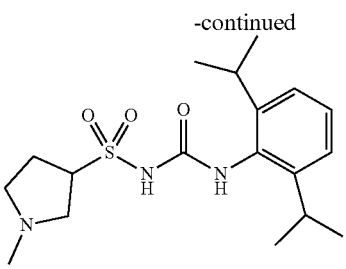
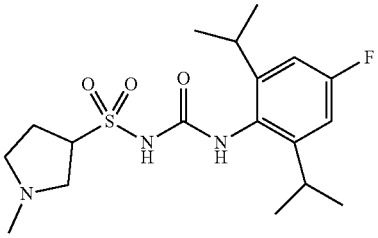
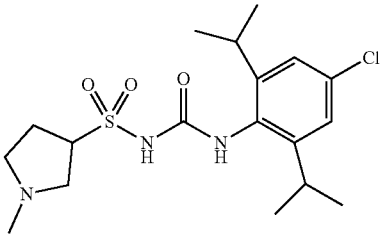
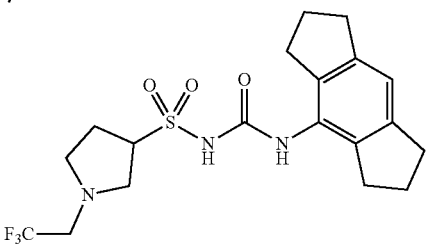
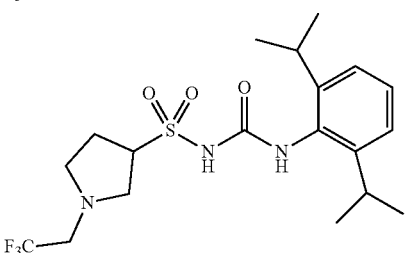
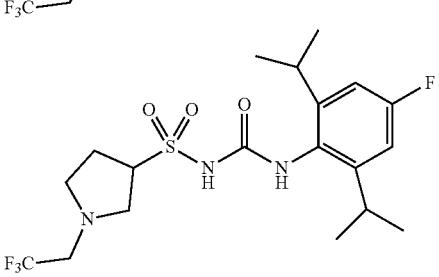
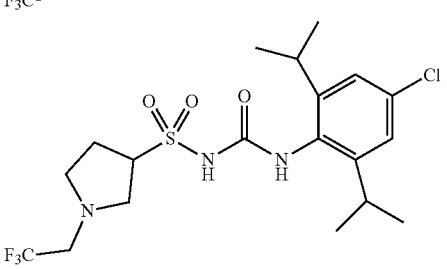

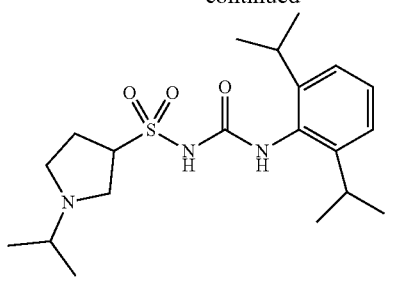
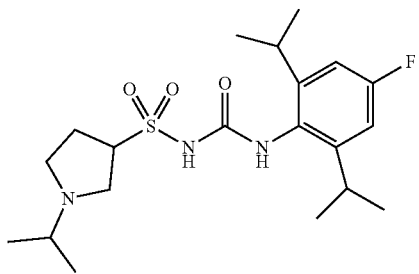
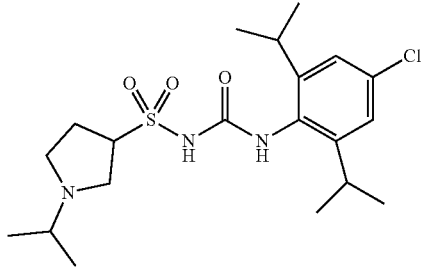
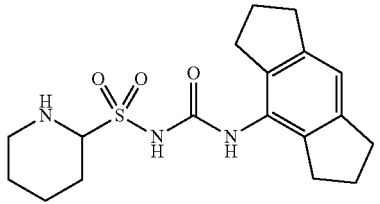
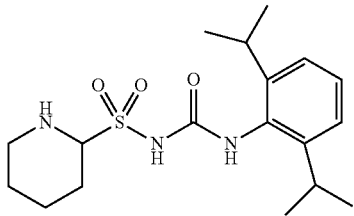
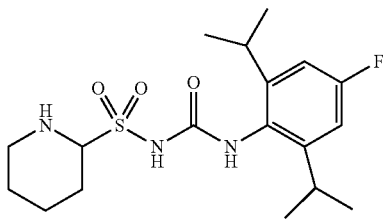
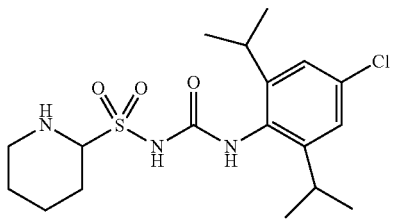
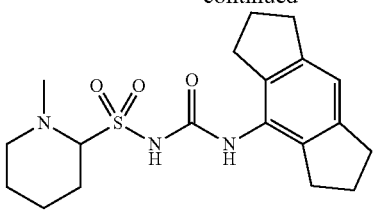
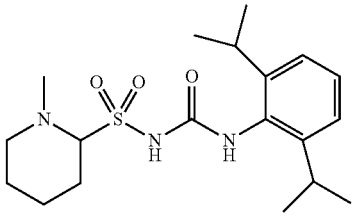
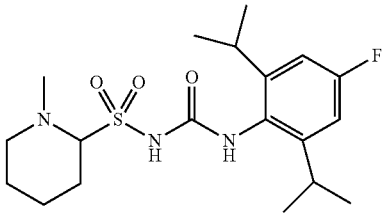
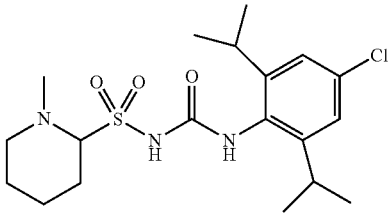
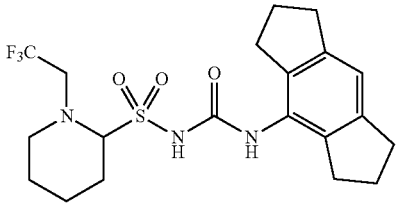
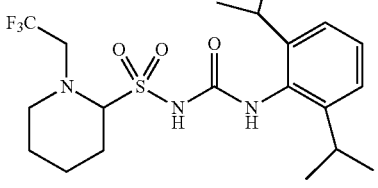
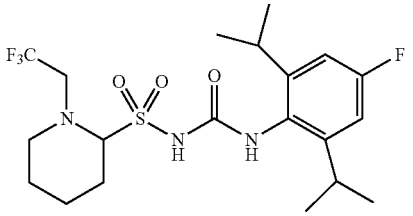

77
-continued
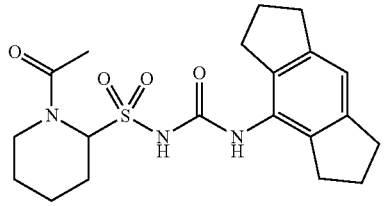
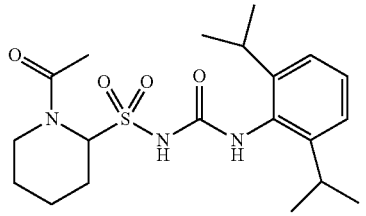
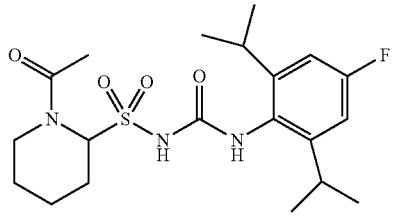
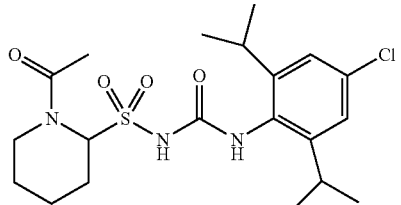
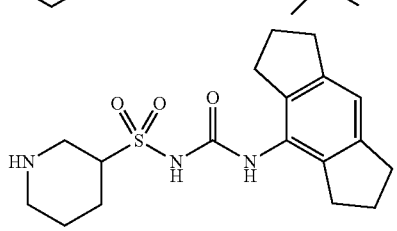
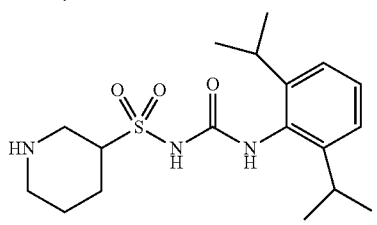
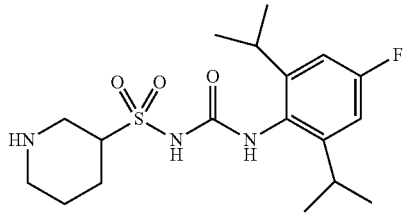
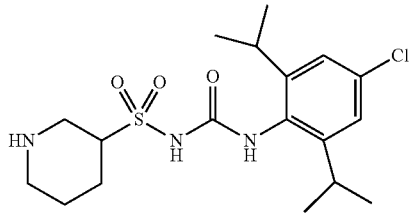
78
-continued
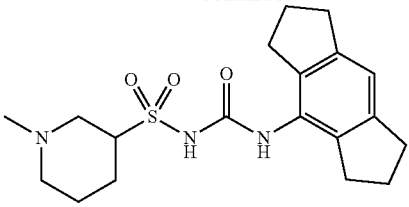
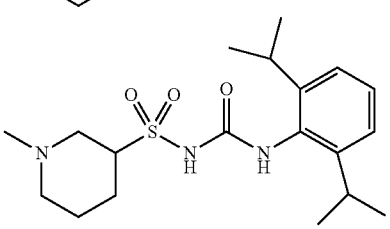
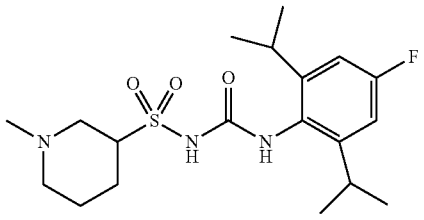
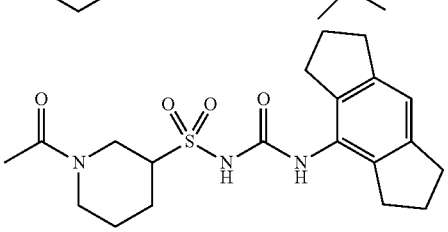
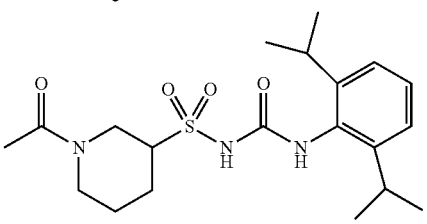
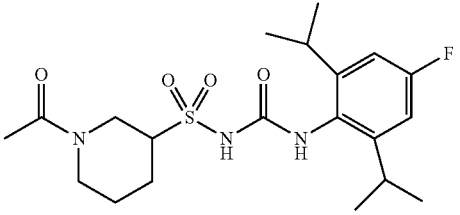
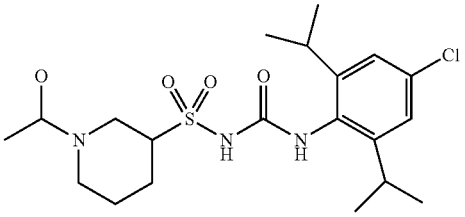

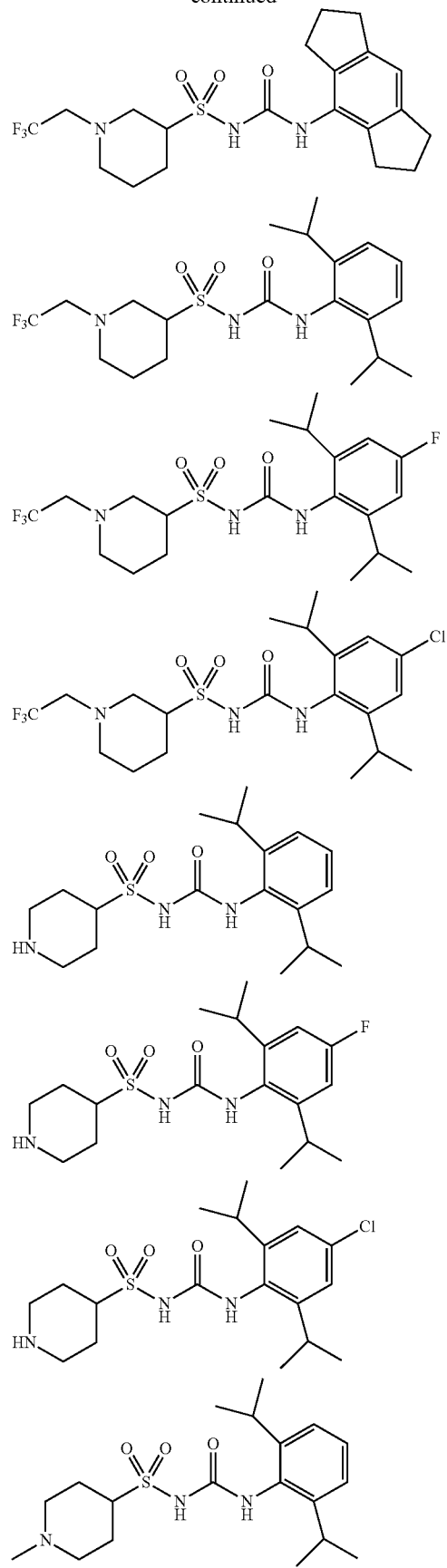
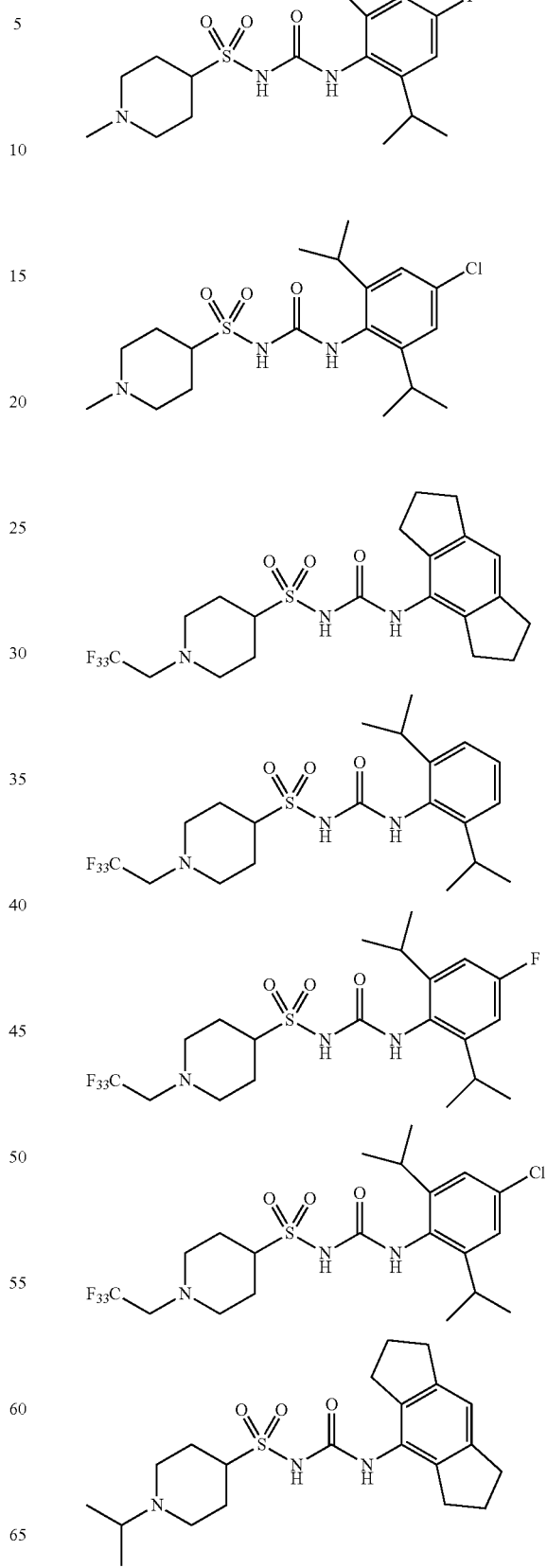

-continued
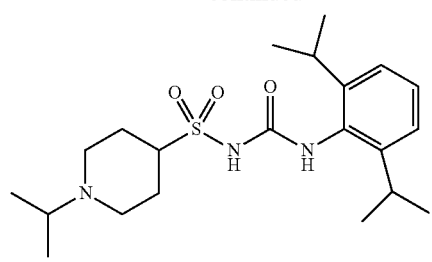
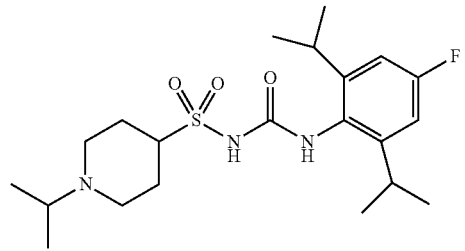
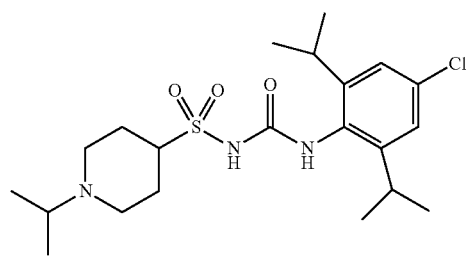
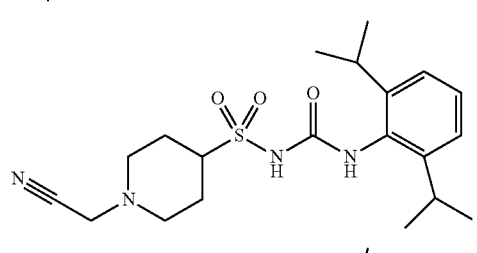
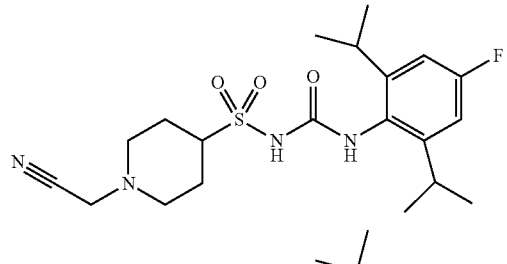
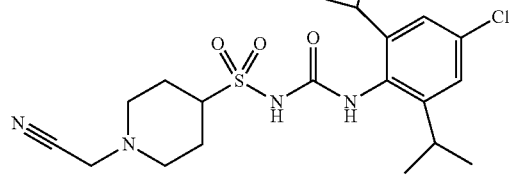
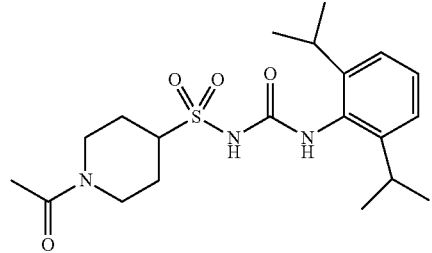
-continued
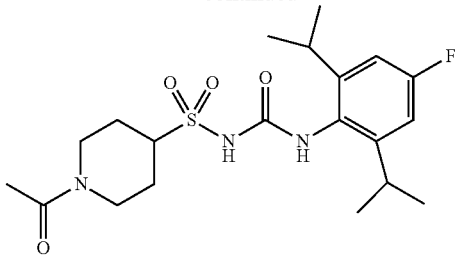
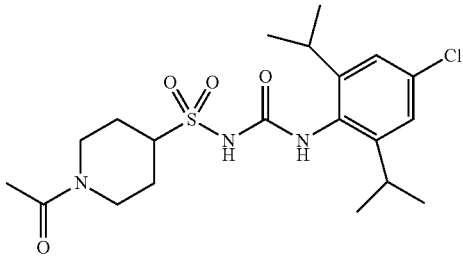
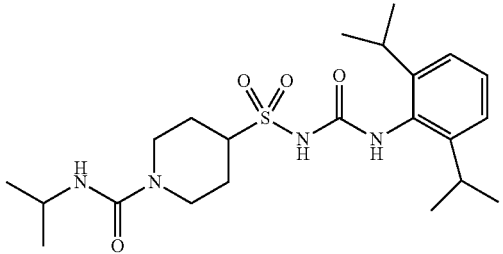
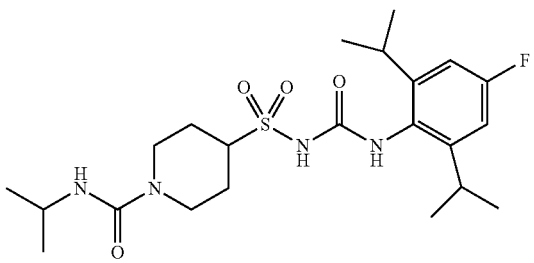
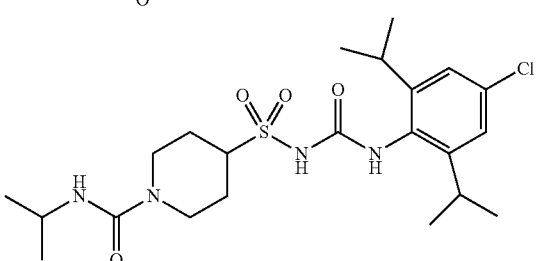
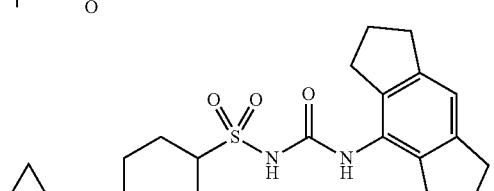
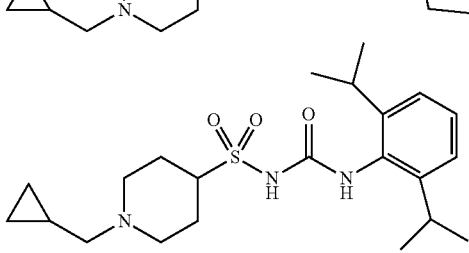

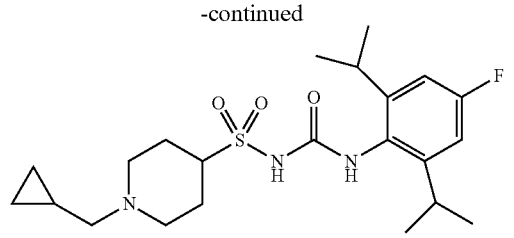
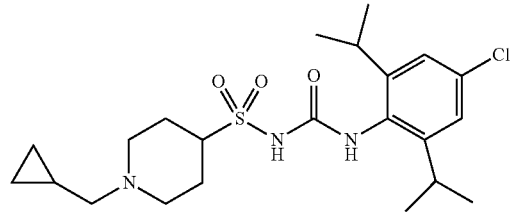
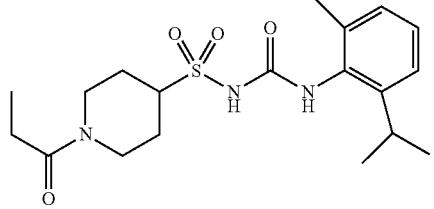
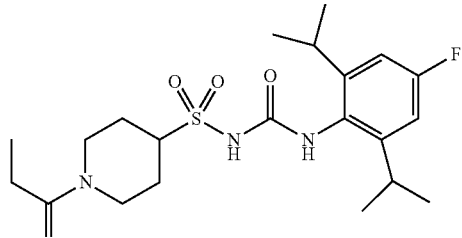
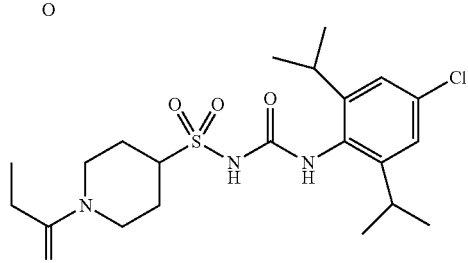
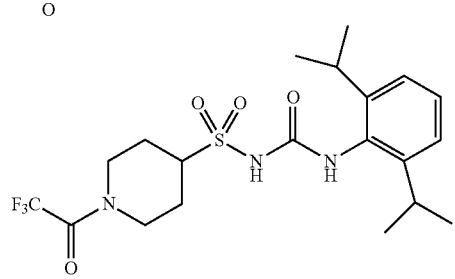
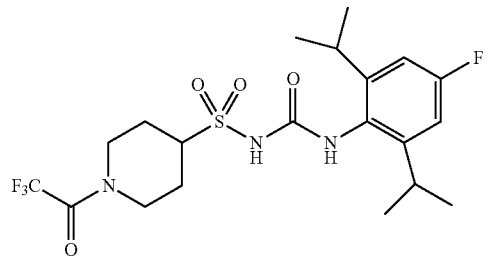
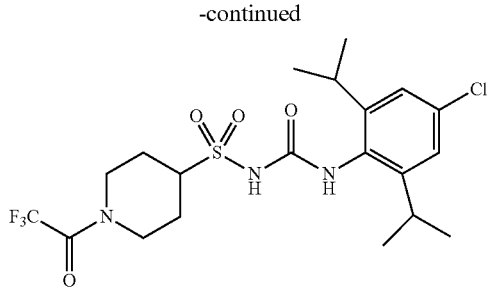
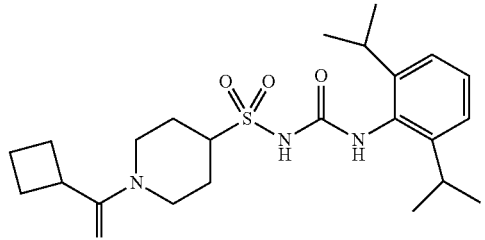
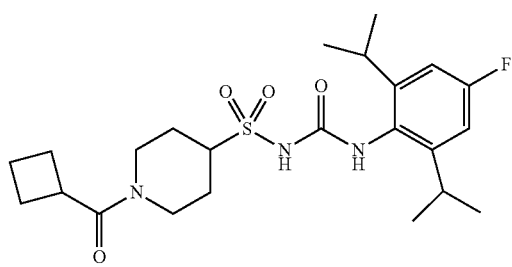
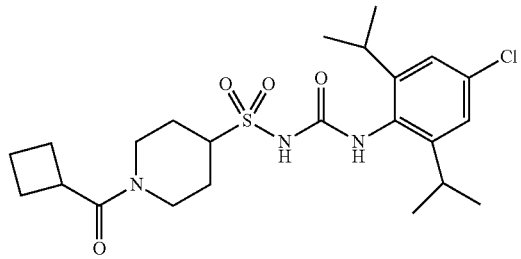
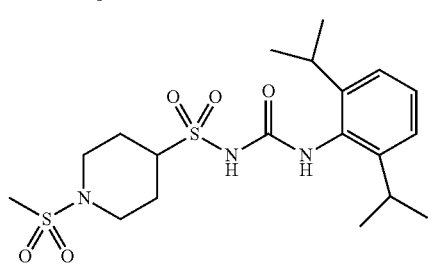
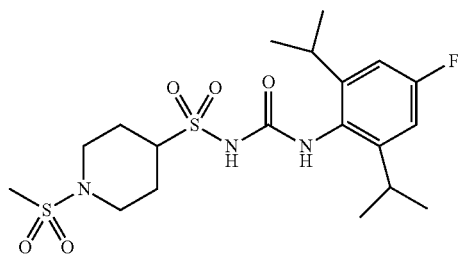

85
-continued
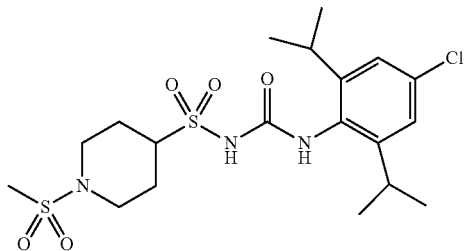
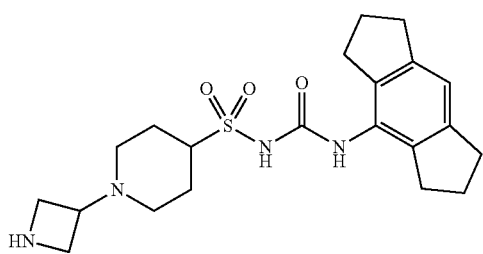
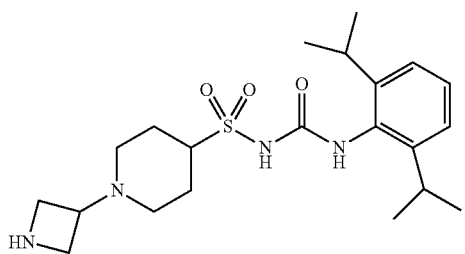
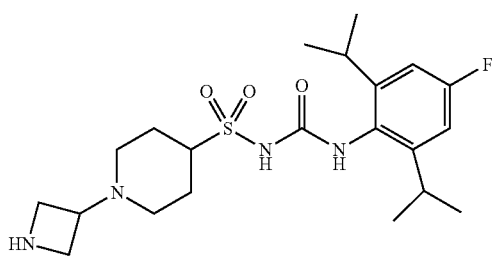
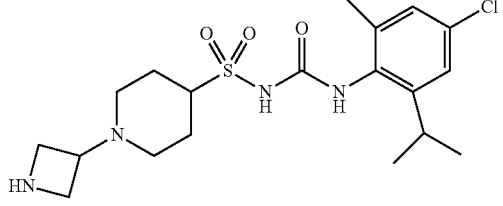
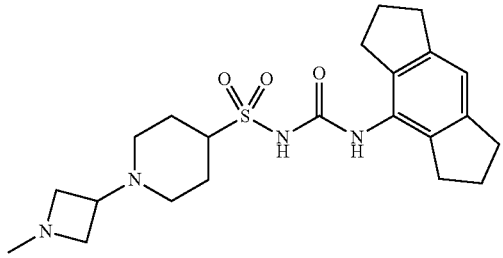
86
-continued
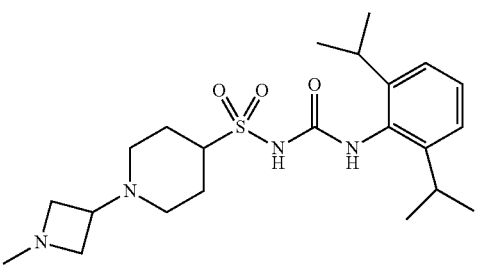
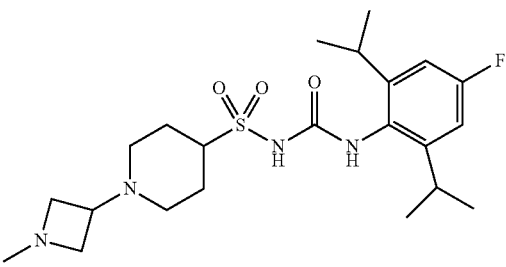
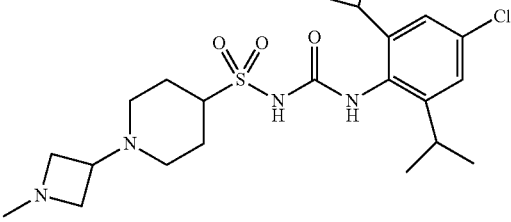
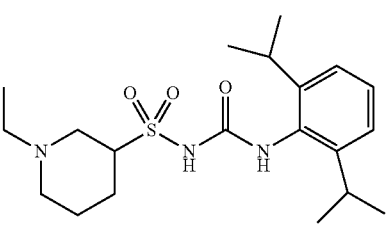
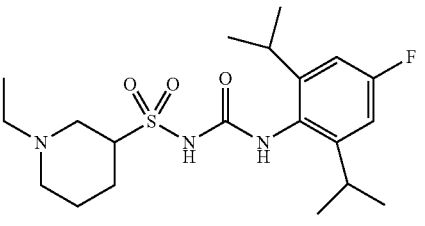
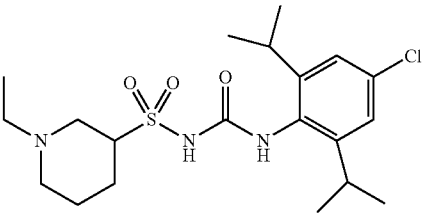
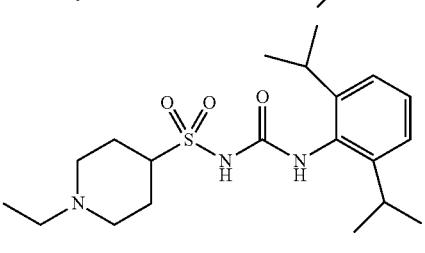

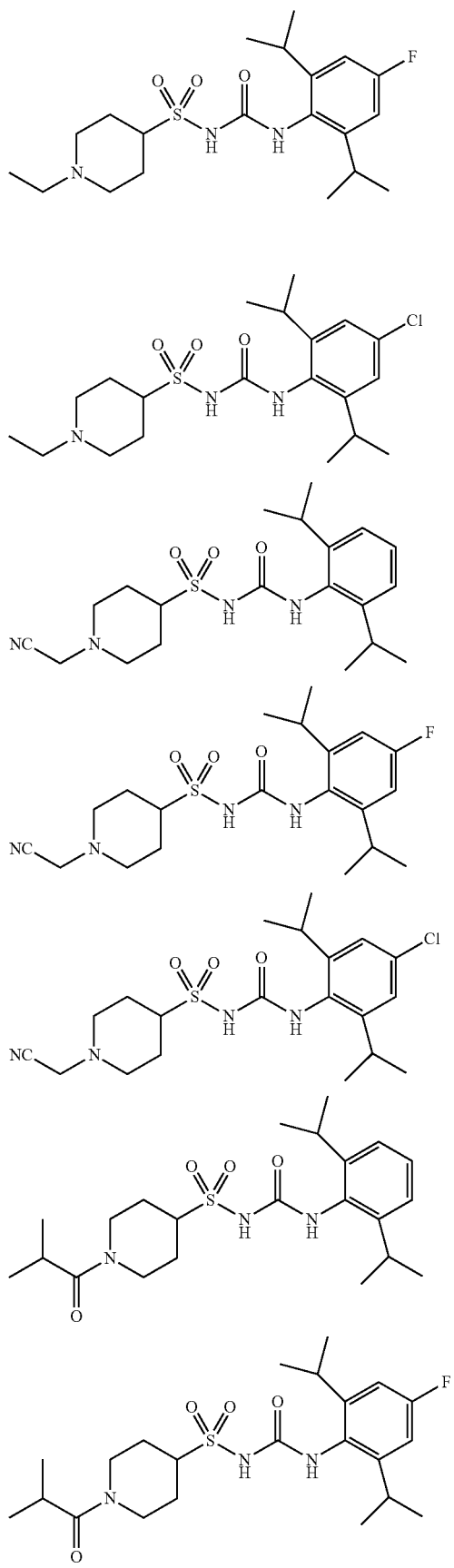
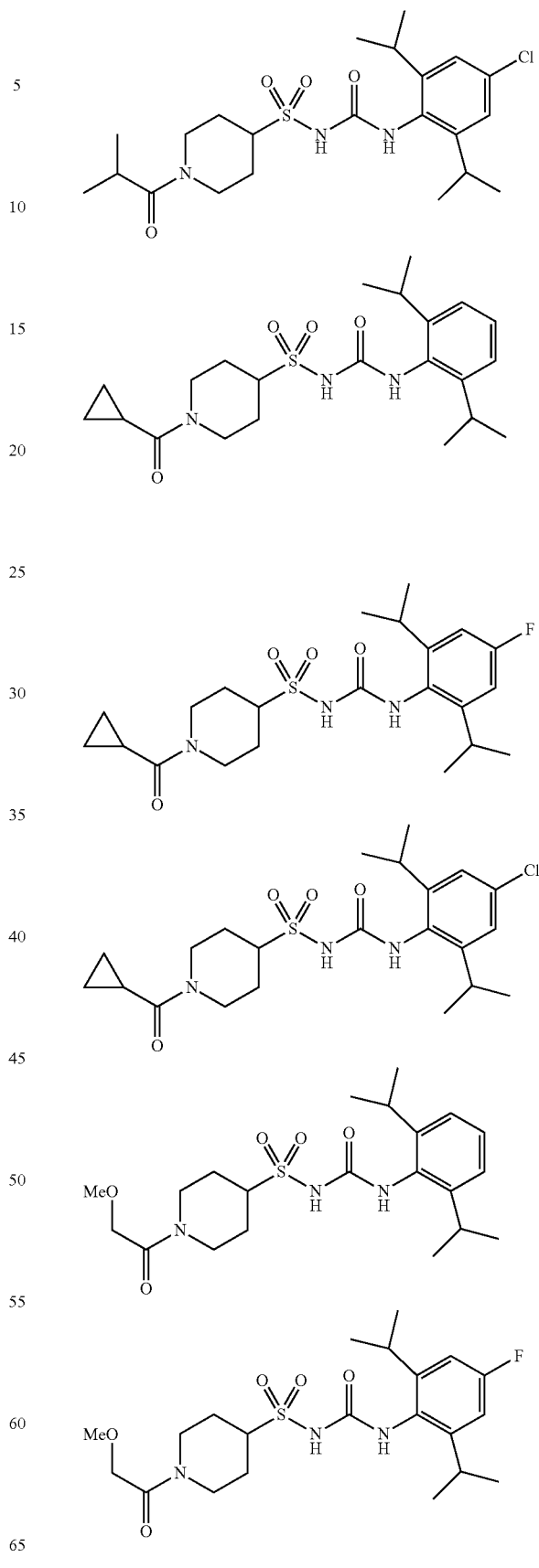

89
-continued
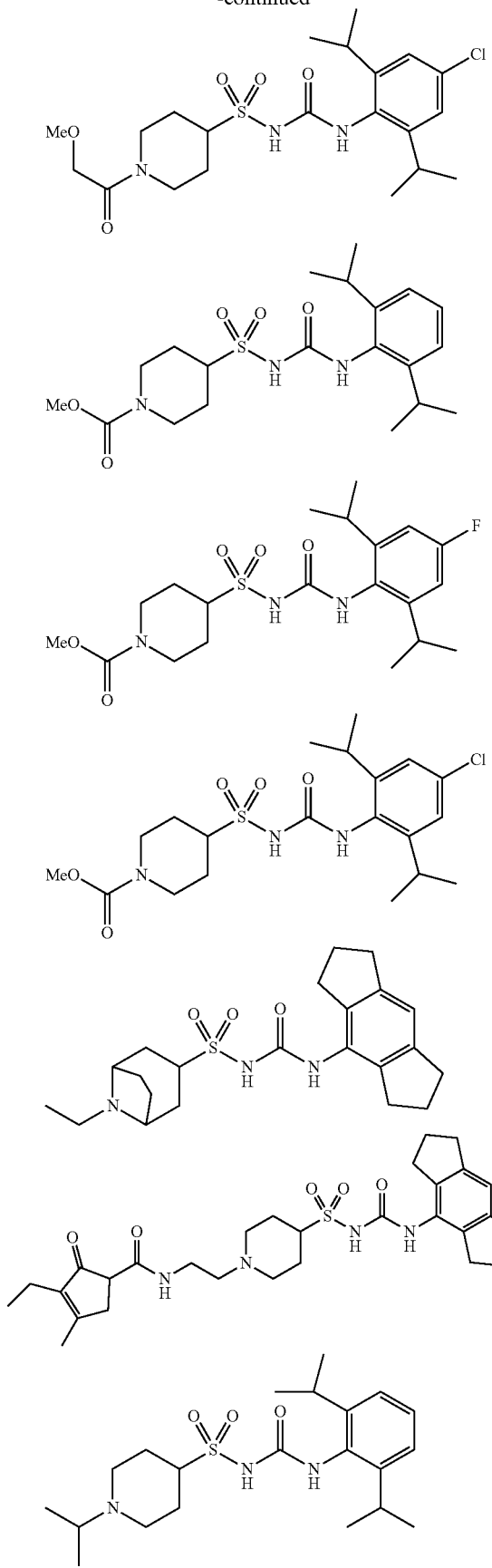
90
-continued
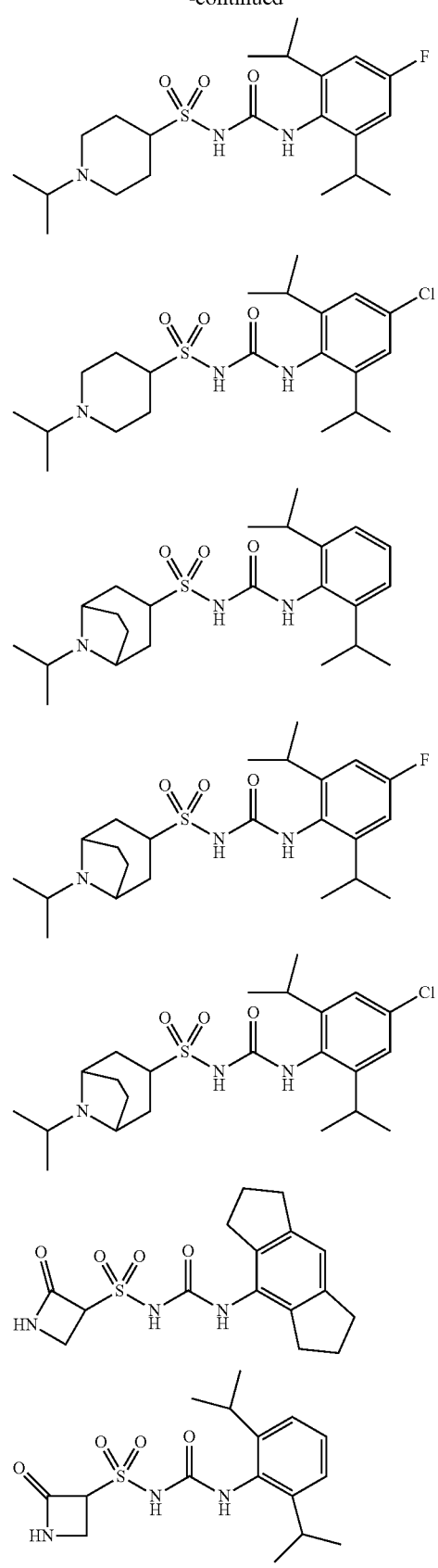

-continued
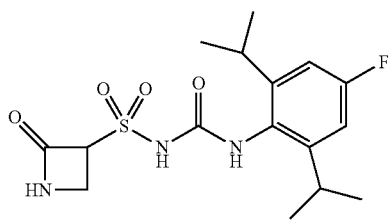
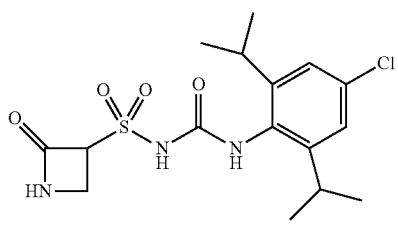
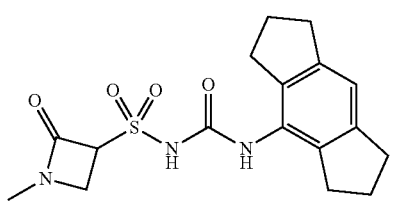
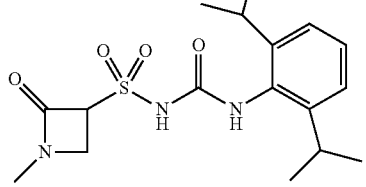
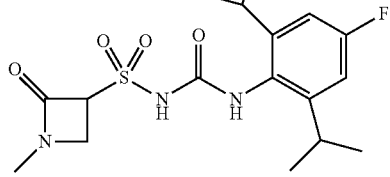
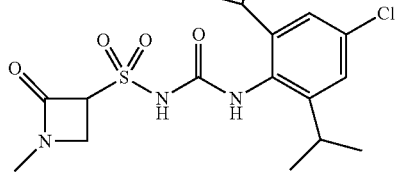
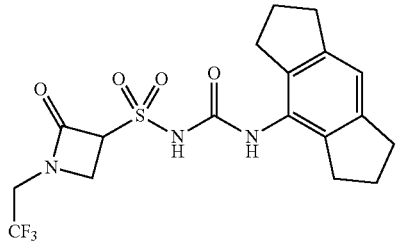
-continued
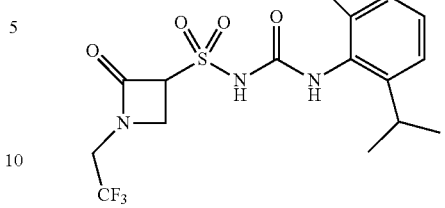
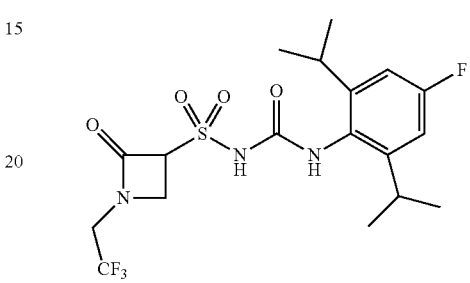
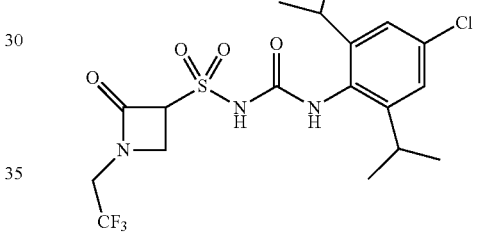
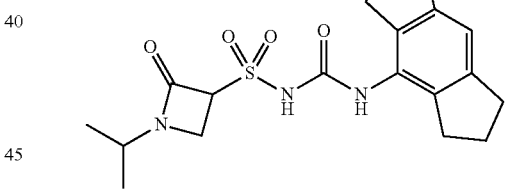
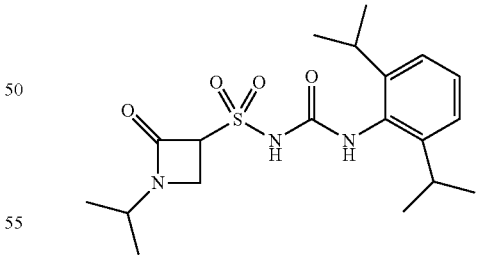
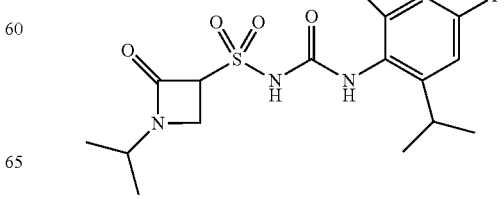

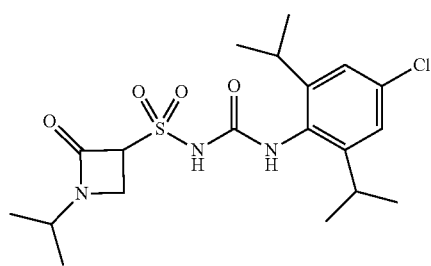
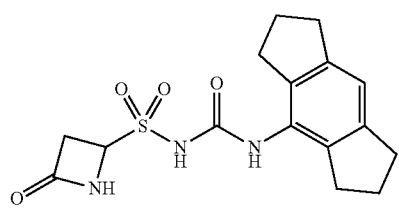
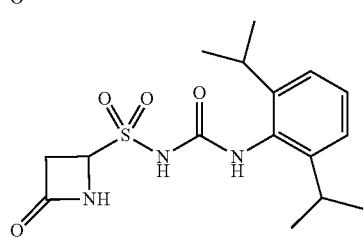
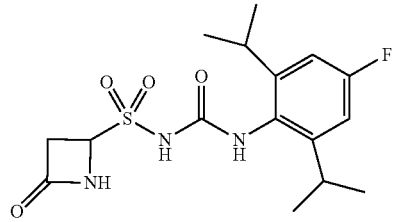
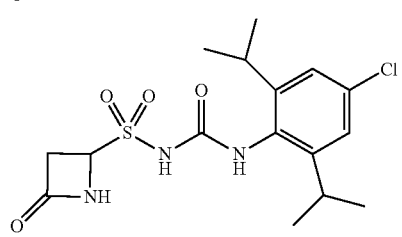
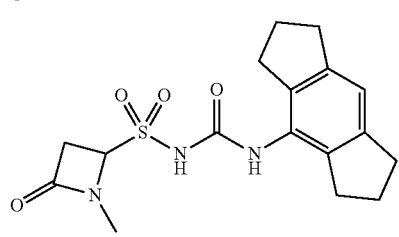
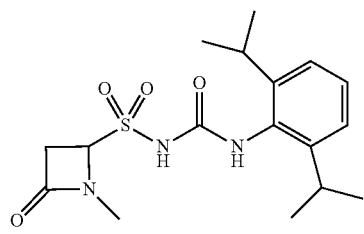
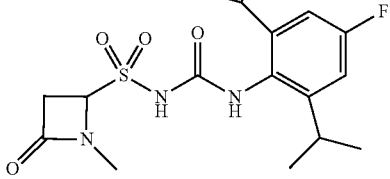
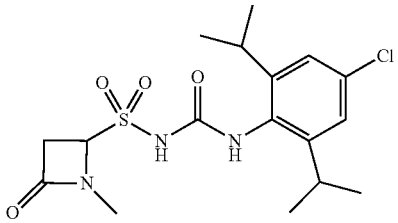
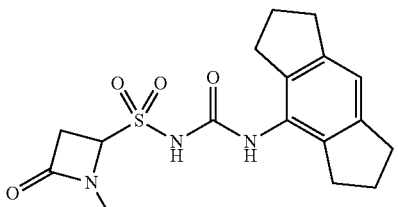
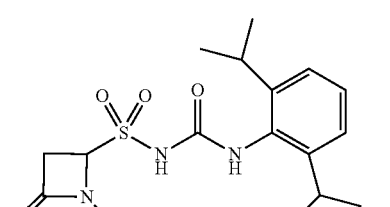
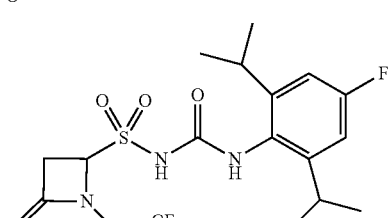
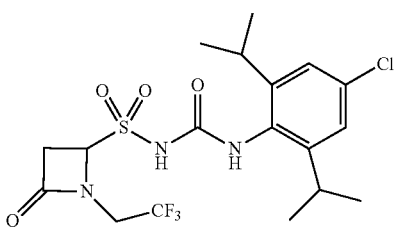
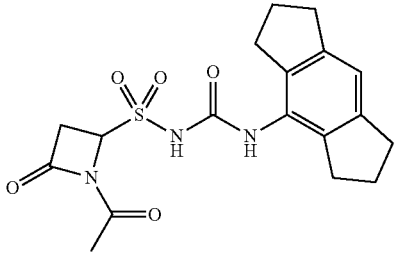

-continued
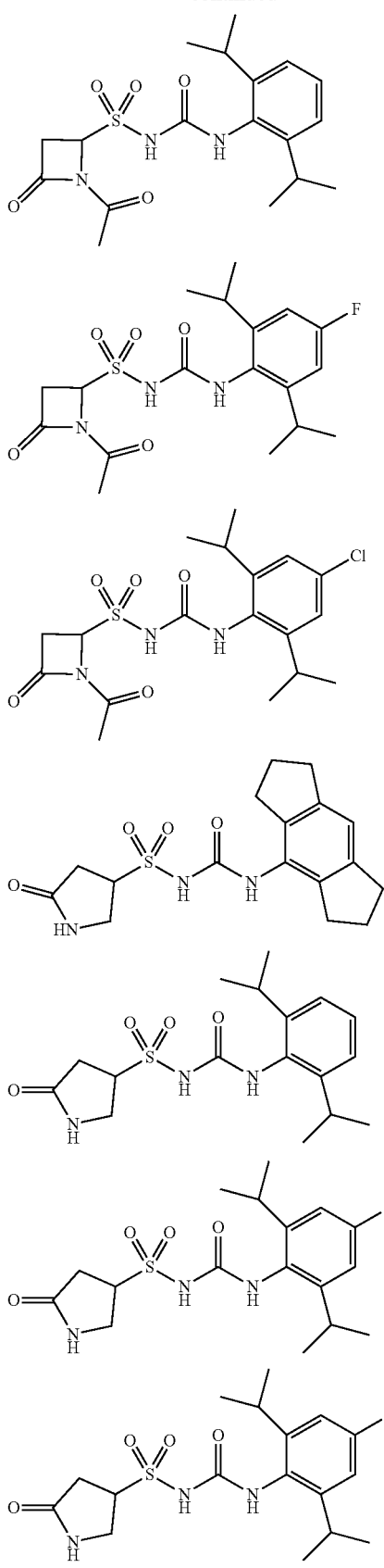
-continued
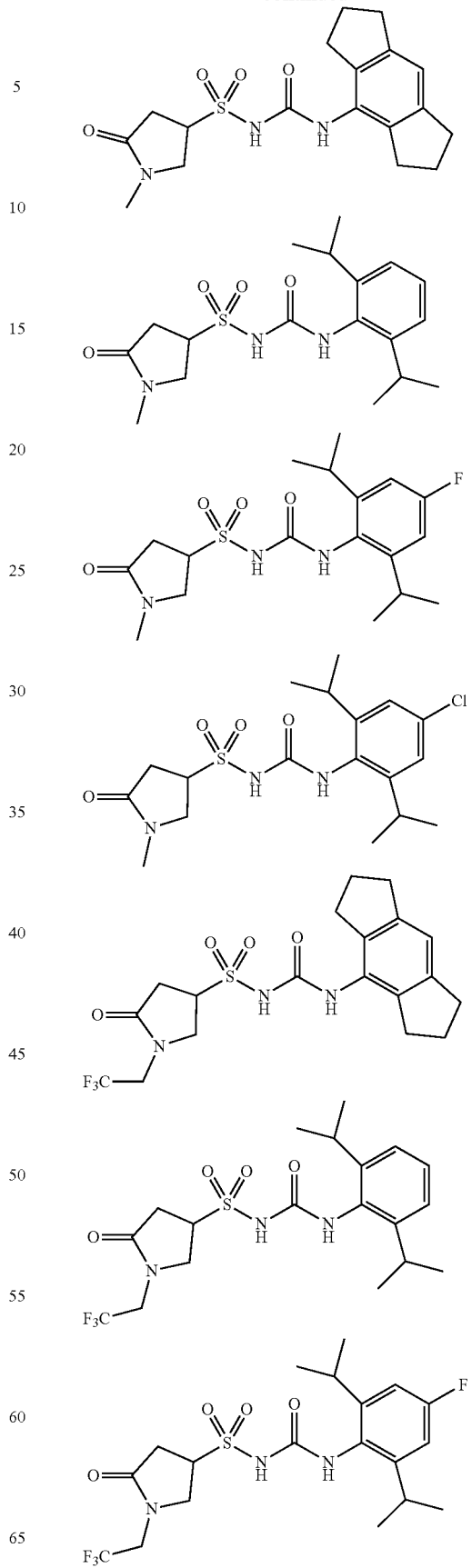

-continued
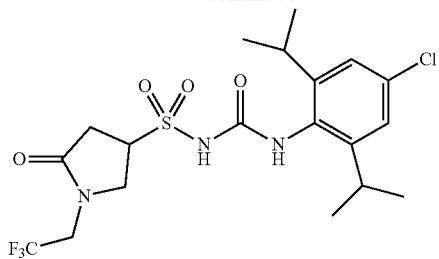
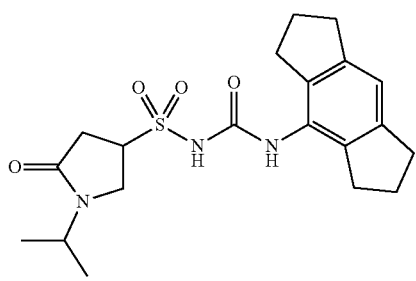
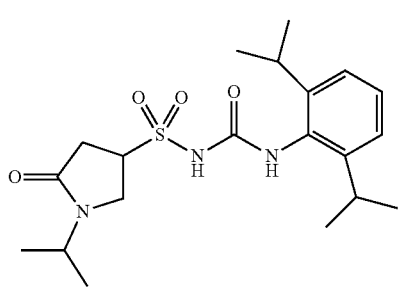
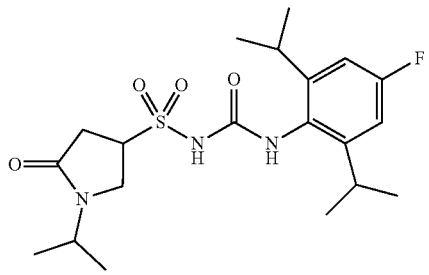
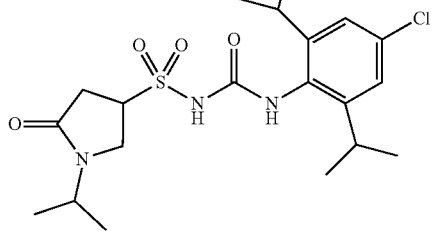
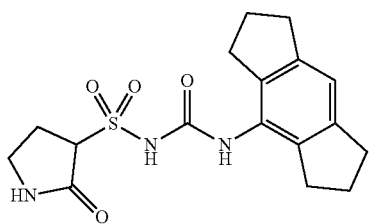
-continued
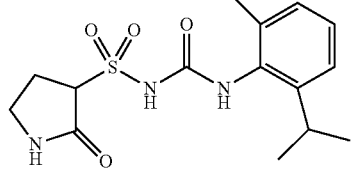
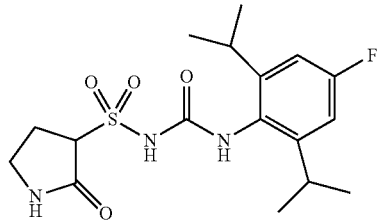
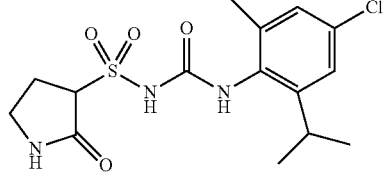
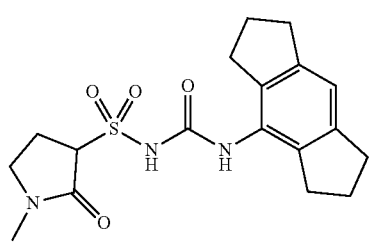
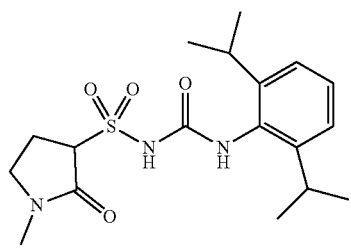
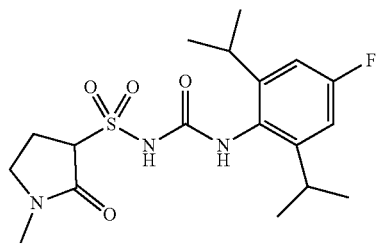
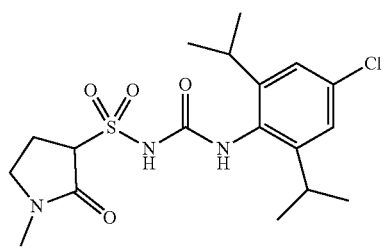

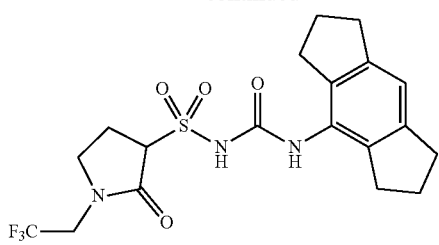
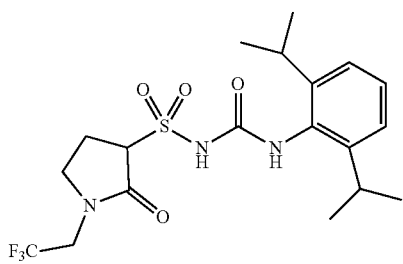
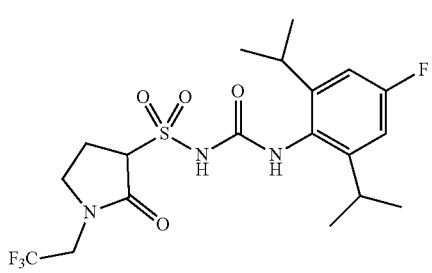
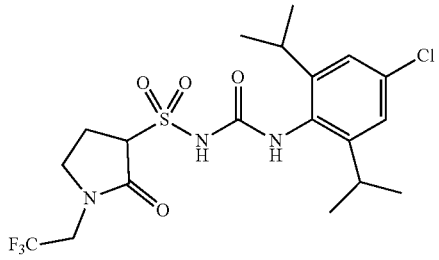
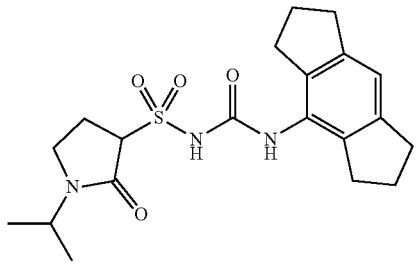
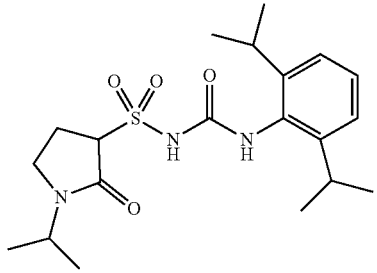
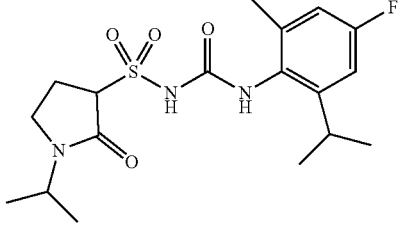
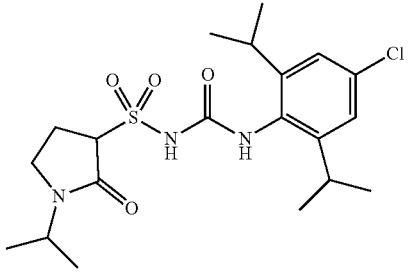
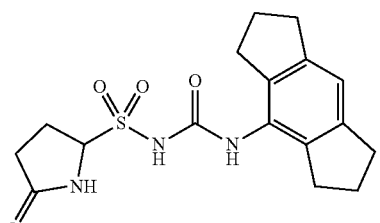
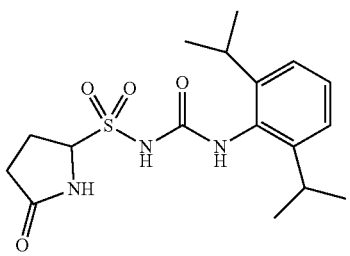
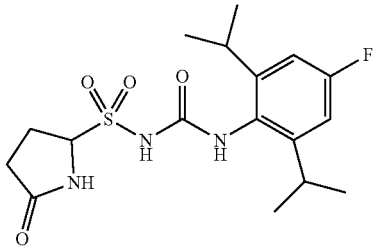
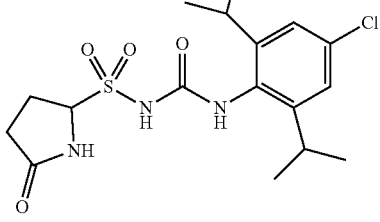

101
-continued
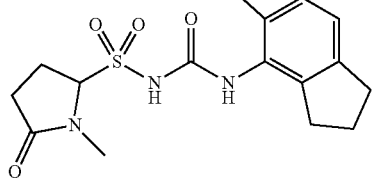
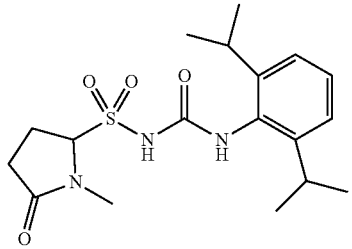
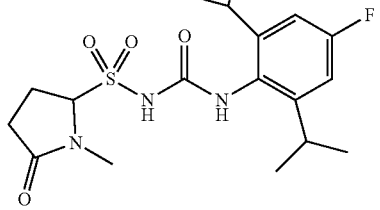
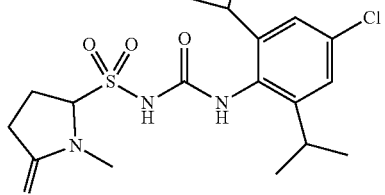
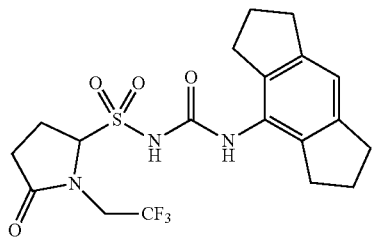
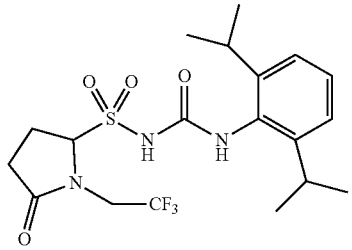
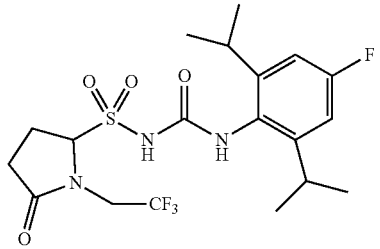
102
-continued
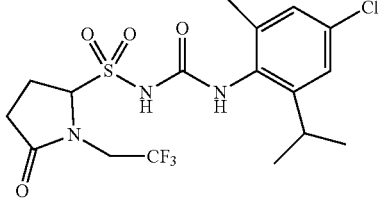
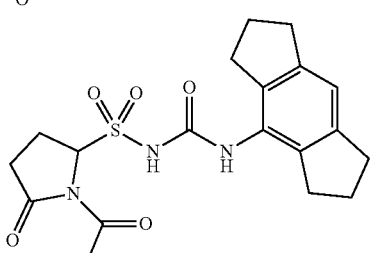
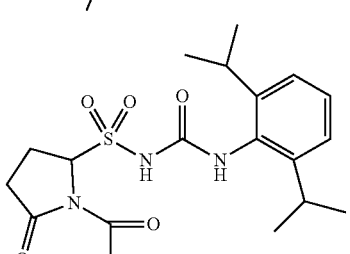
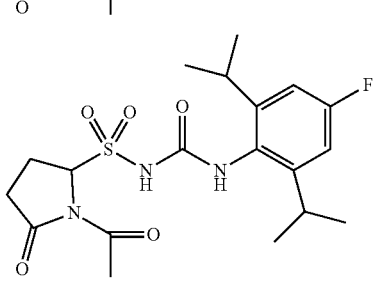
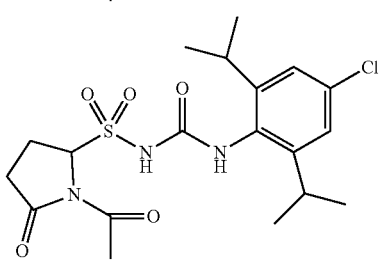
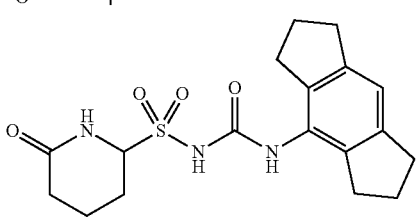
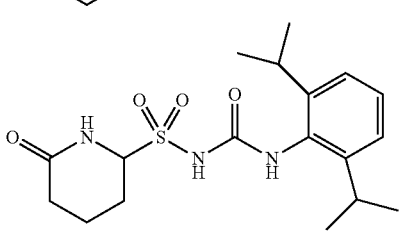

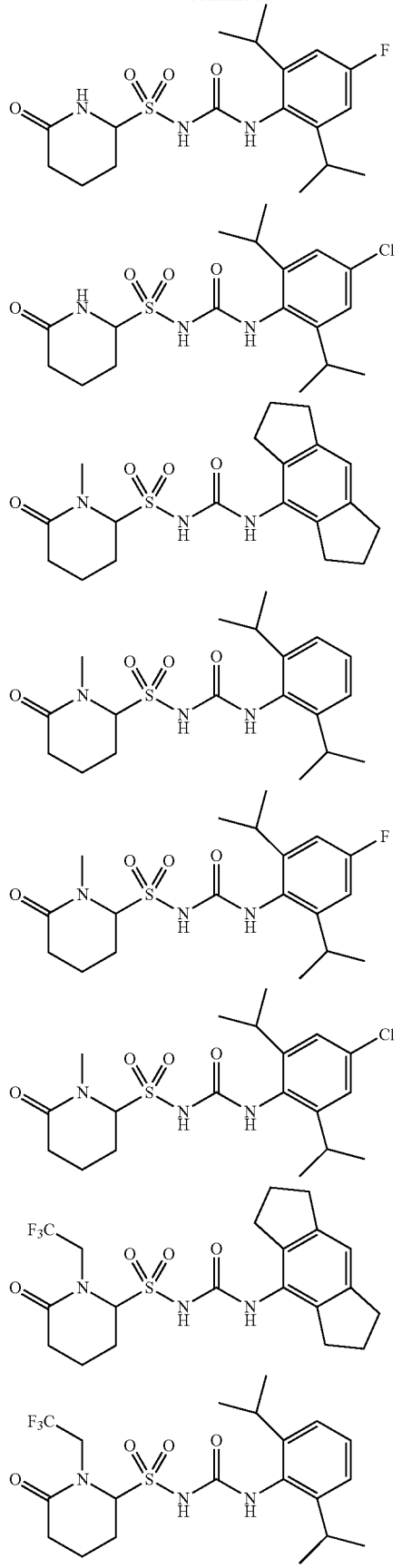
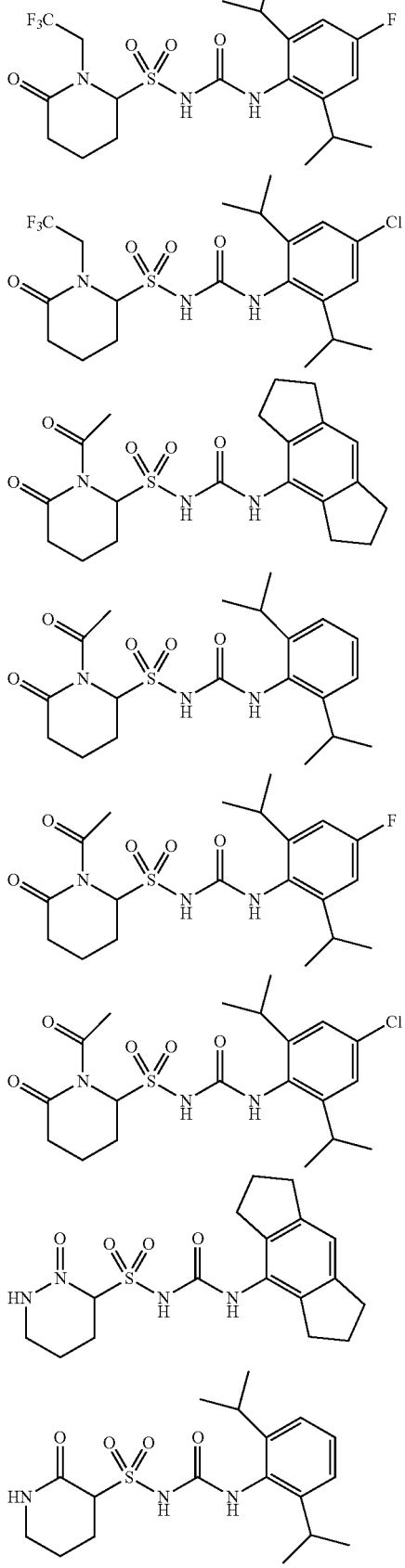

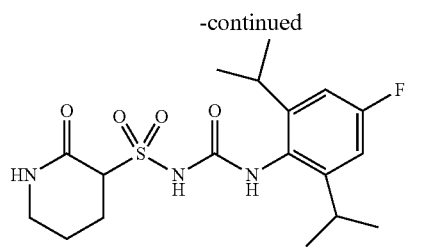
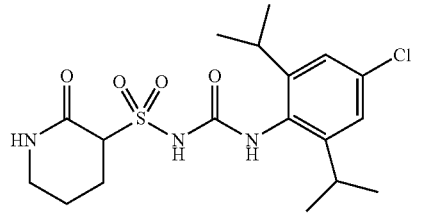
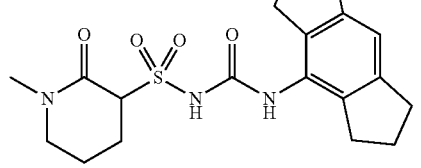
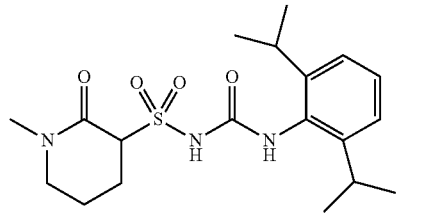
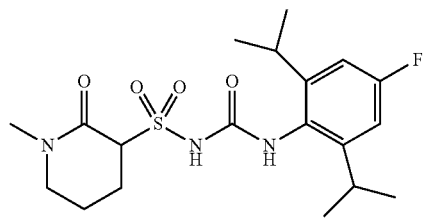
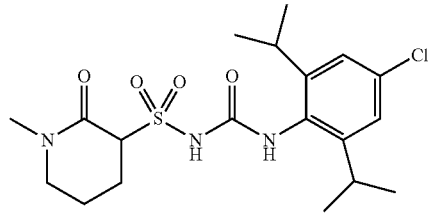
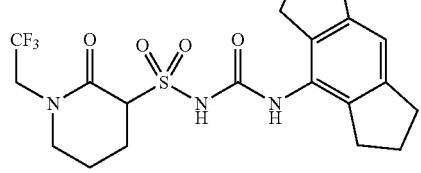
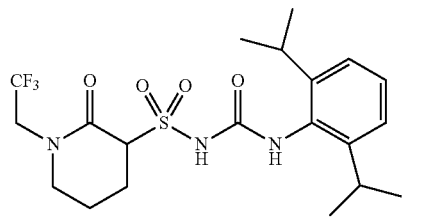
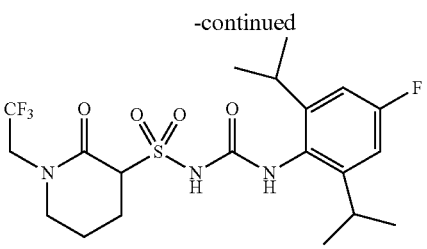
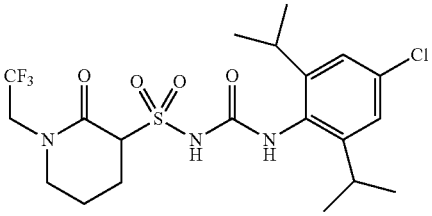
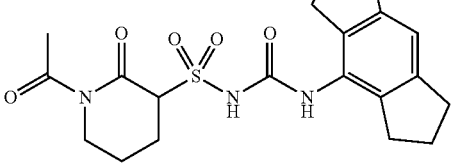
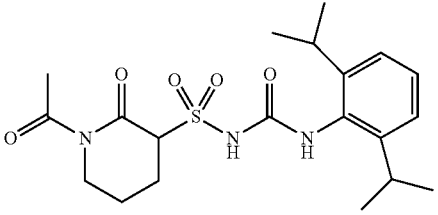
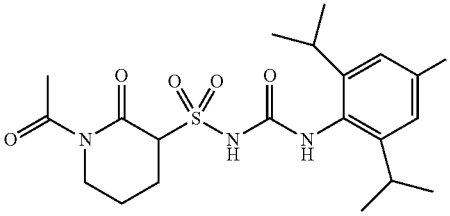
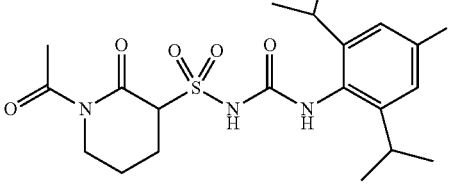
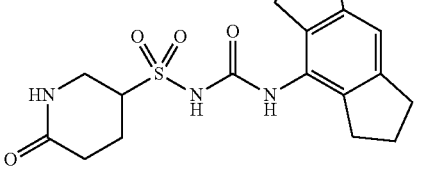
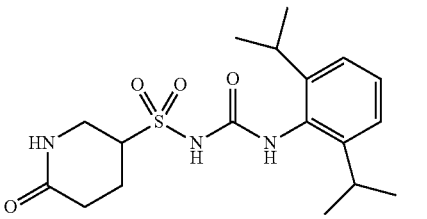

107
-continued
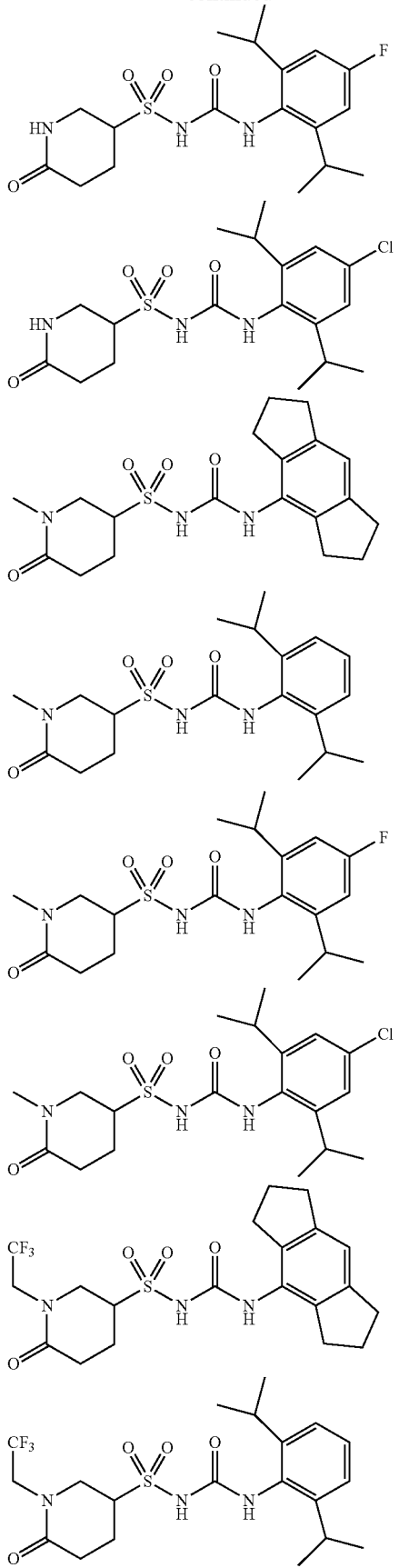
108
-continued
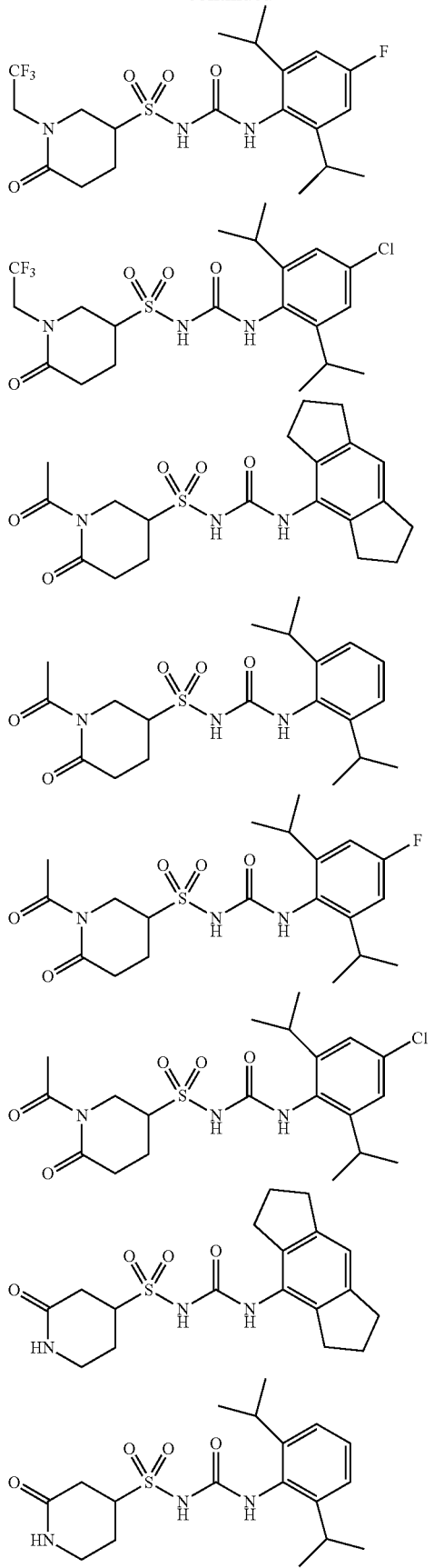

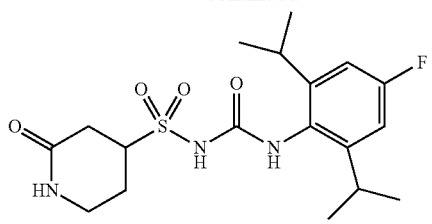
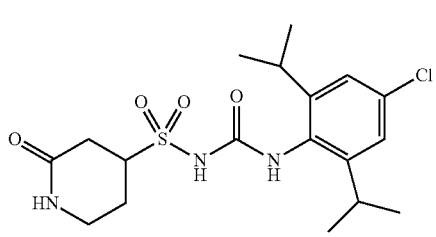
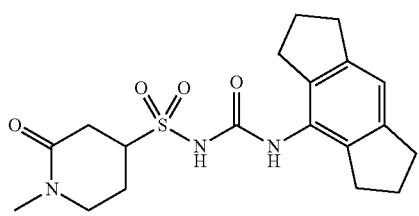
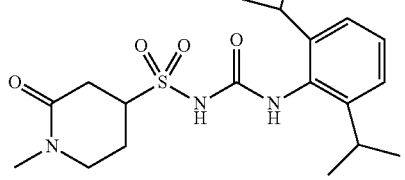
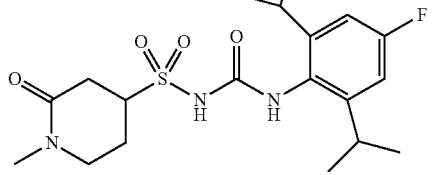
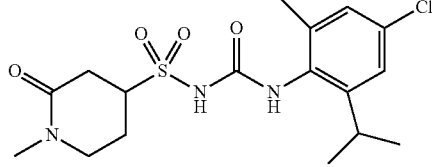
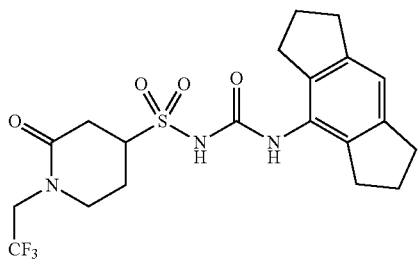
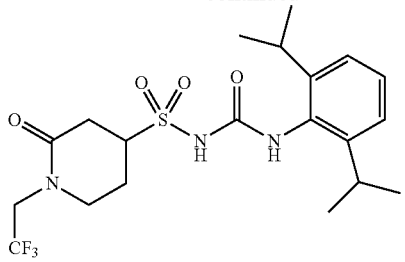
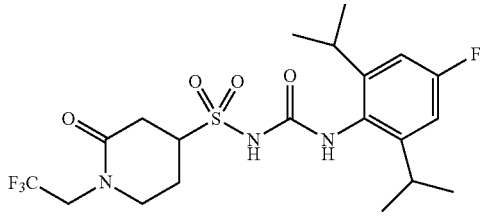
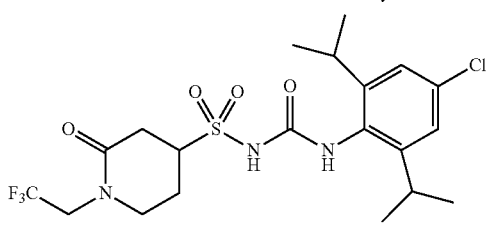
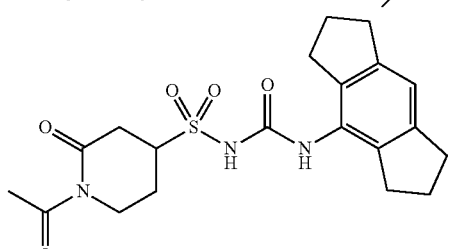
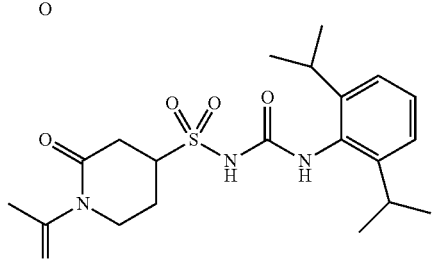
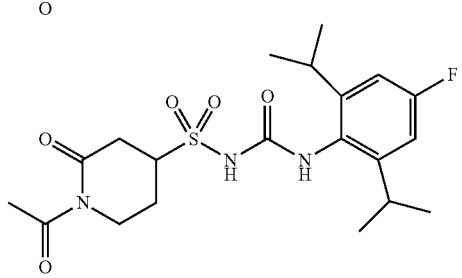
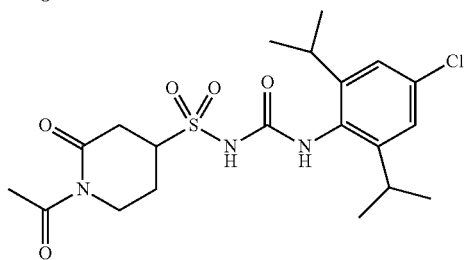

111
-continued
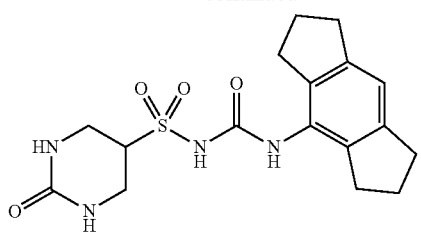
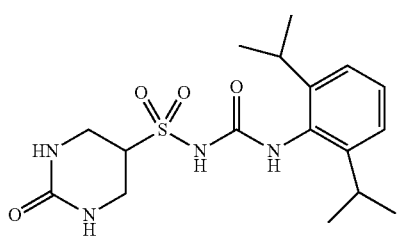
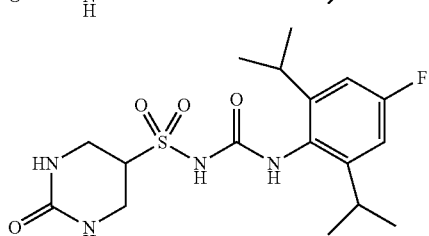
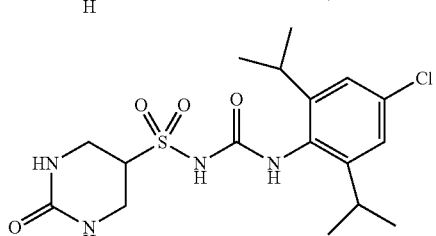
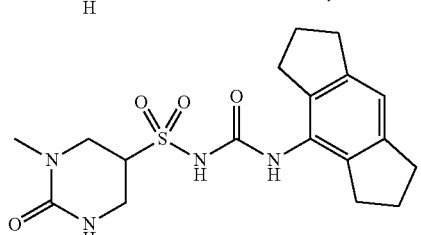
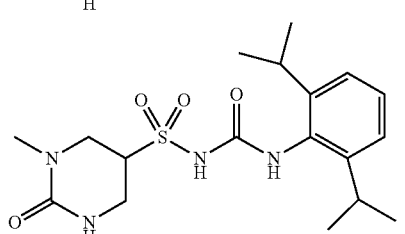
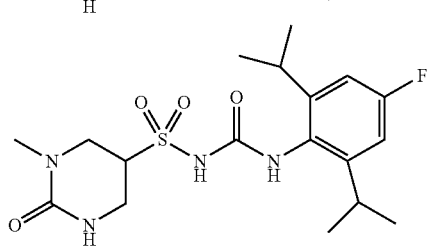
112
-continued
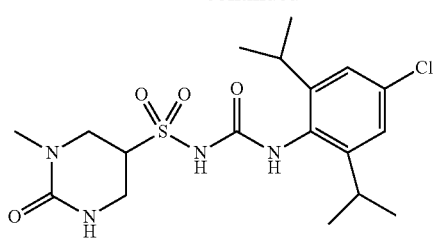
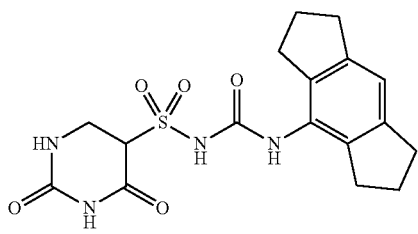
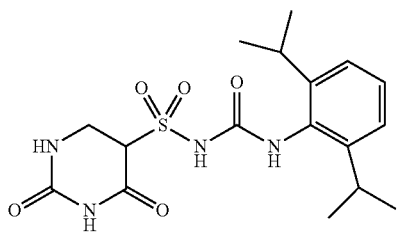
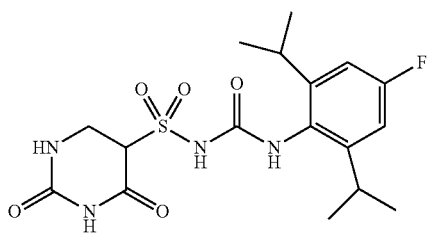
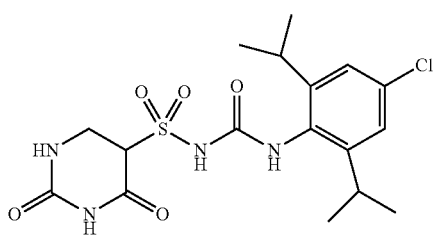
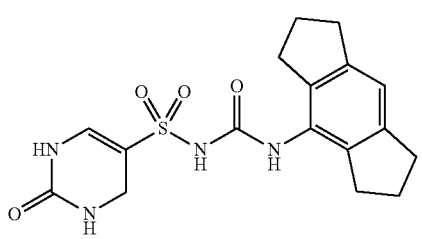
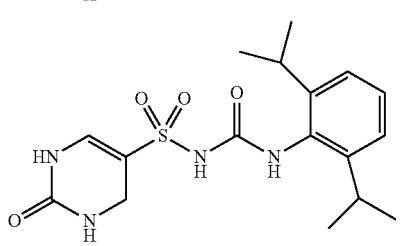

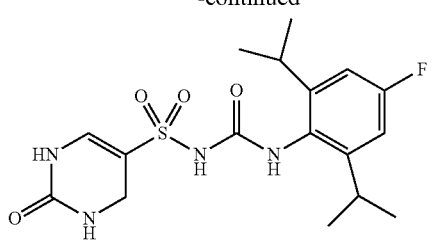
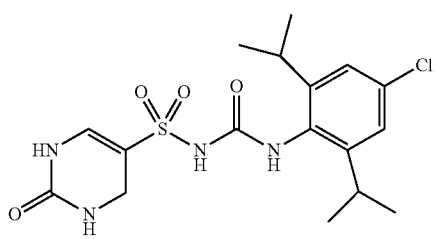
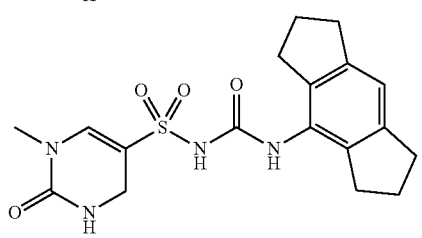
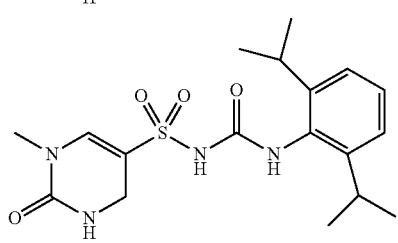
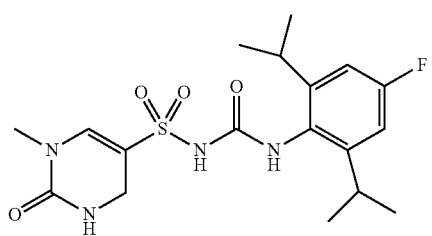
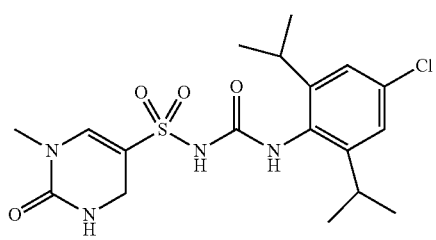
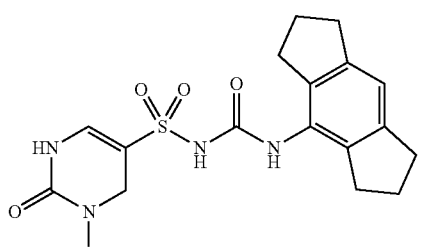
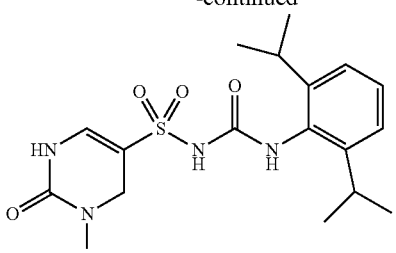
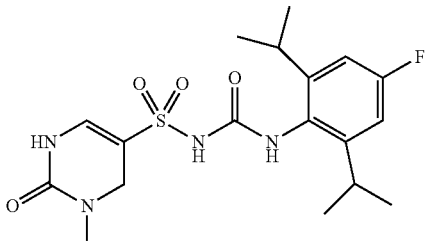
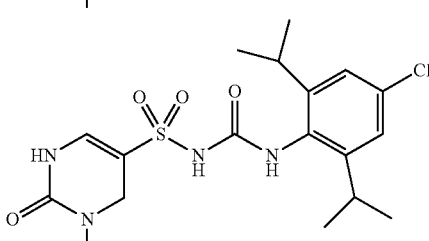
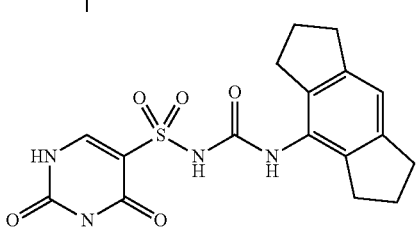
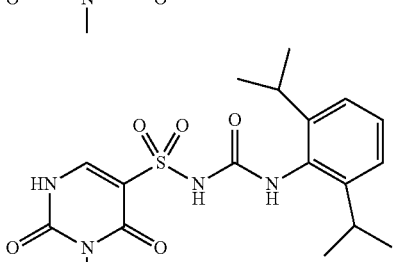
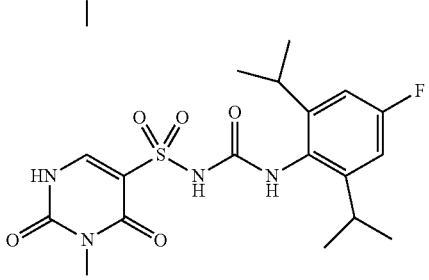
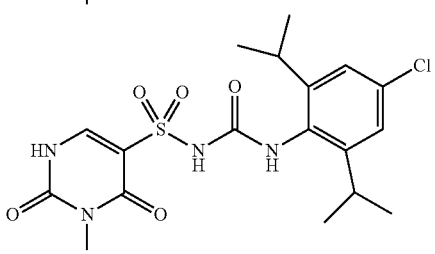

115
-continued
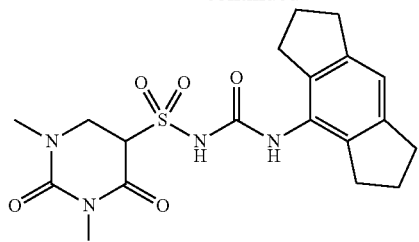
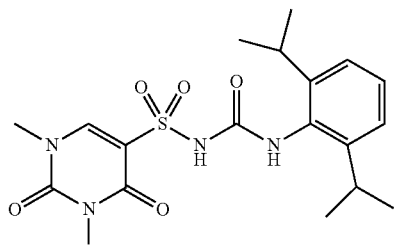
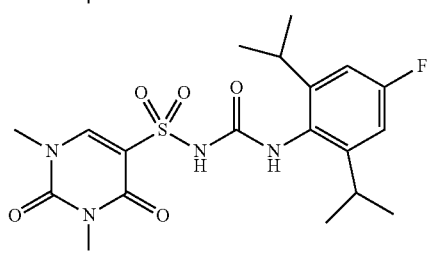
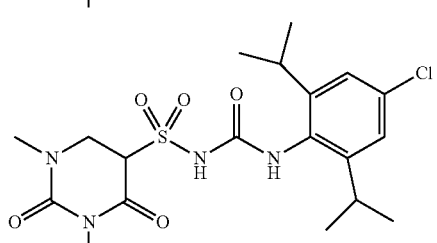
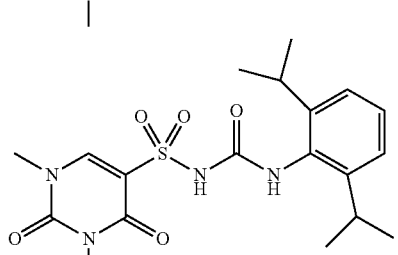
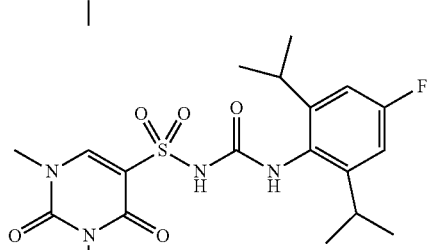
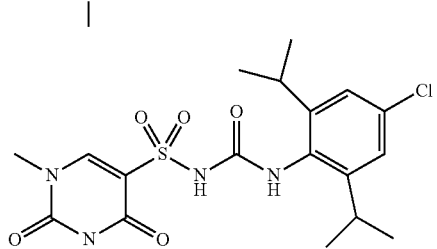
116
-continued
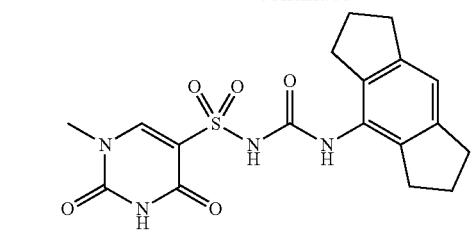
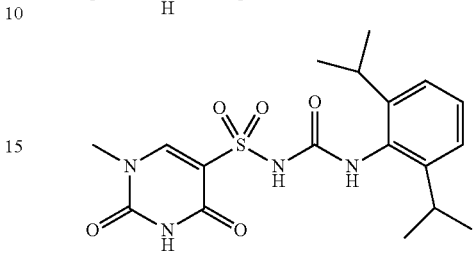
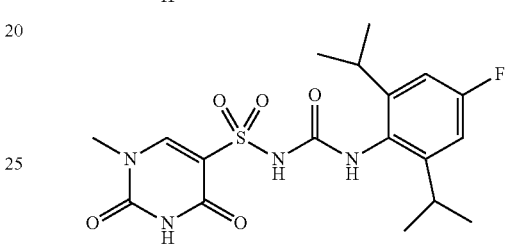
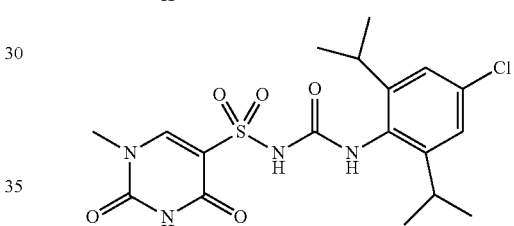
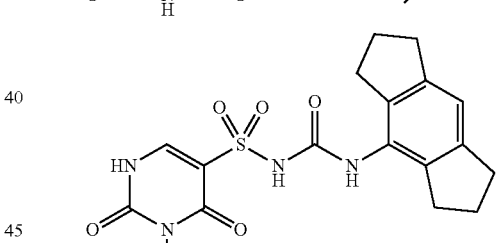
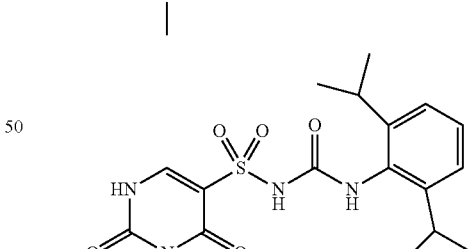
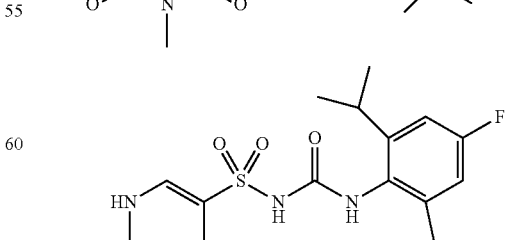

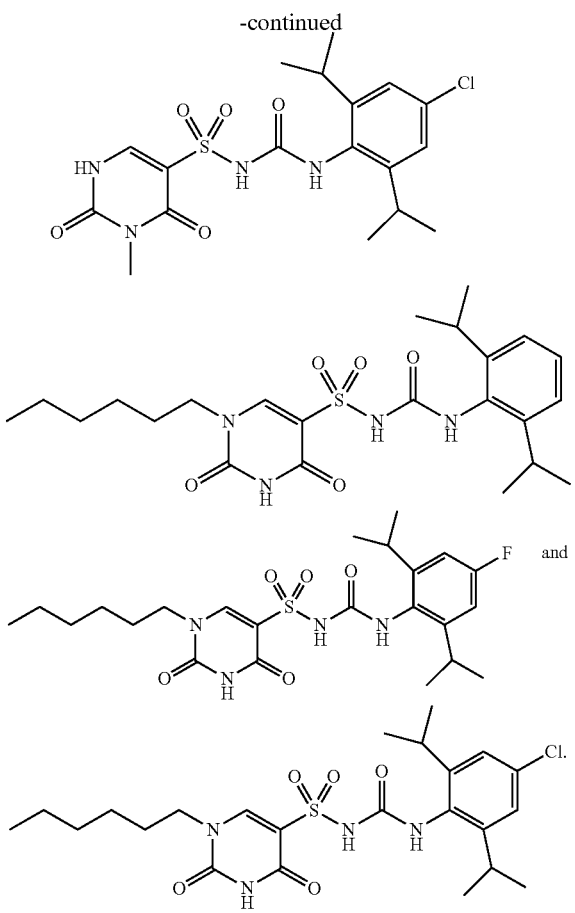

A third aspect of the invention provides a pharmaceutically acceptable salt, solvate or prodrug of any compound of the first or second aspect of the invention.

The compounds of the present invention can be used both in their free base form and their acid addition salt form. For the purposes of this invention, a "salt" of a compound of the present invention includes an acid addition salt. Acid addition salts are preferably pharmaceutically acceptable, non-toxic addition salts with suitable acids, including but not limited to inorganic acids such as hydrohalogenic acids (for example, hydrofluoric, hydrochloric, hydrobromic or hydroiodic acid) or other inorganic acids (for example, nitric, perchloric, sulfuric or phosphoric acid); or organic acids such as organic carboxylic acids (for example, propionic, butyric, glycolic, lactic, mandelic, citric, acetic, benzoic, salicylic, succinic, malic or hydroxysuccinic, tartaric, fumaric, maleic, hydroxymaleic, mucic or galactaric, gluconic, pantothenic or pamoic acid), organic sulfonic acids (for example, methanesulfonic, trifluoromethanesulfonic, ethanesulfonic, 2-hydroxyethanesulfonic, benzenesulfonic, toluene-p-sulfonic, naphthalene-2-sulfonic or camphorsulfonic acid) or amino acids (for example, ornithinic, glutamic or aspartic acid). The acid addition salt may be a mono-, di-, tri- or multi-acid addition salt. A preferred salt is a hydrohalogenic, sulfuric, phosphoric or organic acid addition salt. A preferred salt is a hydrochloric acid addition salt.

Where a compound of the invention includes a quaternary ammonium group, typically the compound is used in its salt form. The counter ion to the quaternary ammonium group may be any pharmaceutically acceptable, non-toxic counter ion. Examples of suitable counter ions include the conjugate bases of the protic acids discussed above in relation to acid-addition salts.

The compounds of the present invention can also be used both, in their free acid form and their salt form. For the purposes of this invention, a "salt" of a compound of the present invention includes one formed between a protic acid functionality (such as a carboxylic acid group) of a compound of the present invention and a suitable cation. Suitable cations include, but are not limited to lithium, sodium, potassium, magnesium, calcium and ammonium. The salt may be a mono-, di-, tri- or multi-salt. Preferably the salt is a mono- or di-lithium, sodium, potassium, magnesium, calcium or ammonium salt. More preferably the salt is a mono- or di-sodium salt or a mono- or di-potassium salt.

Preferably any salt is a pharmaceutically acceptable non-toxic salt. However, in addition to pharmaceutically acceptable salts, other salts are included in the present invention, since they have potential to serve as intermediates in the purification or preparation of other, for example, pharmaceutically acceptable salts, or are useful for identification, characterisation or purification of the free acid or base.

The compounds and/or salts of the present invention may be anhydrous or in the form of a hydrate (e.g. a hemihydrate, monohydrate, dihydrate or trihydrate) or other solvate. Such solvates may be formed with common organic solvents, including but not limited to, alcoholic solvents e.g. methanol, ethanol or isopropanol.

In some embodiments of the present invention, therapeutically inactive prodrugs are provided. Prodrugs are compounds which, when administered to a subject such as a human, are converted in whole or in part to a compound of the invention. In most embodiments, the prodrugs are pharmacologically inert chemical derivatives that can be converted in vivo to the active drug molecules to exert a therapeutic effect. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include, but are not limited to, compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound. The present invention also encompasses salts and solvates of such prodrugs as described above.

The compounds, salts, solvates and prodrugs of the present invention may contain at least one chiral centre. The compounds, salts, solvates and prodrugs may therefore exist in at least two isomeric forms. The present invention encompasses racemic mixtures of the compounds, salts, solvates and prodrugs of the present invention as well as enantiomerically enriched and substantially enantiomerically pure isomers. For the purposes of this invention, a "substantially enantiomerically pure" isomer of a compound comprises less than 5% of other isomers of the same compound, more typically less than 2%, and most typically less than 0.5% by weight.

The compounds, salts, solvates and prodrugs of the present invention may contain any stable isotope including, but not limited to $^{12}C$, $^{13}C$, $^{1}H$, $^{2}H$ (D), $^{14}N$, $^{15}N$, $^{16}O$, $^{17}O$, $^{18}O$, $^{19}F$ and $^{127}I$, and any radioisotope including, but not limited to $^{11}C$, $^{14}C$, $^{3}H$ (T), $^{13}N$, $^{15}O$, $^{18}F$, $^{123}I$, $^{124}I$, $^{125}I$ and $^{131}I$.

The compounds, salts, solvates and prodrugs of the present invention may be in any polymorphic or amorphous form.

A fourth aspect of the invention provides a pharmaceutical composition comprising a compound of the first or second aspect of the invention, or a pharmaceutically acceptable salt, solvate or prodrug of the third aspect of the invention, and a pharmaceutically acceptable excipient.

Conventional procedures for the selection and preparation of suitable pharmaceutical formulations are described in, for example, "Aulton's Pharmaceutics—The Design and Manufacture of Medicines", M. E. Aulton and K. M. G. Taylor, Churchill Livingstone Elsevier, $4^{th}$ Ed., 2013.

Pharmaceutically acceptable excipients including adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins such as human serum albumin, buffer substances such as phosphates, glycerine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinylpyrrolidone, cellulose-based substances, polyethylene glycol, sodium carboxymethylcellulose, polyacrylates, waxes, polyethylene-polyoxypropylene-block polymers, polyethylene glycol and wool fat.

In one embodiment, the pharmaceutical composition of the fourth aspect of the invention additionally comprises one or more further active agents.

In a further embodiment, the pharmaceutical composition of the fourth aspect of the invention may be provided as a part of a kit of parts, wherein the kit of parts comprises the pharmaceutical composition of the fourth aspect of the invention and one or more further pharmaceutical compositions, wherein the one or more further pharmaceutical compositions each comprise a pharmaceutically acceptable excipient and one or more further active agents.

A fifth aspect of the invention provides a compound of the first or second aspect of the invention, or a pharmaceutically acceptable salt, solvate or prodrug of the third aspect of the invention, or a pharmaceutical composition of the fourth aspect of the invention, for use in medicine, and/or for use in the treatment or prevention of a disease, disorder or condition. Typically, the use comprises the administration of the compound, salt, solvate, prodrug or pharmaceutical composition to a subject. In one embodiment, the use comprises the co-administration of one or more further active agents.

The term "treatment" as used herein refers equally to curative therapy, and ameliorating or palliative therapy. The term includes obtaining beneficial or desired physiological results, which may or may not be established clinically. Beneficial or desired clinical results include, but are not limited to, the alleviation of symptoms, the prevention of symptoms, the diminishment of extent of disease, the stabilisation (i.e., not worsening) of a condition, the delay or slowing of progression/worsening of a condition/symptoms, the amelioration or palliation of the condition/symptoms, and remission (whether partial or total), whether detectable or undetectable. The term "palliation", and variations thereof, as used herein, means that the extent and/or undesirable manifestations of a physiological condition or symptom are lessened and/or time course of the progression is slowed or lengthened, as compared to not administering a compound, salt, solvate, prodrug or pharmaceutical composition of the present invention. The term "prevention" as used herein in relation to a disease, disorder or condition, relates to prophylactic or preventative therapy, as well as therapy to reduce the risk of developing the disease, disorder or condition. The term "prevention" includes both the avoidance of occurrence of the disease, disorder or condition, and the delay in onset of the disease, disorder or condition. Any statistically significant ($p \leq 0.05$) avoidance of occurrence, delay in onset or reduction in risk as measured by a controlled clinical trial may be deemed a prevention of the disease, disorder or condition. Subjects amenable to prevention include those at heightened risk of a disease, disorder or condition as identified by genetic or biochemical markers. Typically, the genetic or biochemical markers are appropriate to the disease, disorder or condition under consideration and may include for example, inflammatory biomarkers such as C-reactive protein (CRP) and monocyte chemoattractant protein 1 (MCP-1) in the case of inflammation; total cholesterol, triglycerides, insulin resistance and C-peptide in the case of NAFLD and NASH; and more generally IL1β and IL18 in the case of a disease, disorder or condition responsive to NLRP3 inhibition.

A sixth aspect of the invention provides the use of a compound of the first or second aspect, or a pharmaceutically effective salt, solvate or prodrug of the third aspect, in the manufacture of a medicament for the treatment or prevention of a disease, disorder or condition. Typically, the treatment or prevention comprises the administration of the compound, salt, solvate, prodrug or medicament to a subject. In one embodiment, the treatment or prevention comprises the co-administration of one or more further active agents.

A seventh aspect of the invention provides a method of treatment or prevention of a disease, disorder or condition, the method comprising the step of administering an effective amount of a compound of the first or second aspect, or a pharmaceutically acceptable salt, solvate or prodrug of the third aspect, or a pharmaceutical composition of the fourth aspect, to thereby treat or prevent the disease, disorder or condition. In one embodiment, the method further comprises the step of co-administering an effective amount of one or more further active agents. Typically, the administration is to a subject in need thereof.

An eighth aspect of the invention provides a compound of the first or second aspect of the invention, or a pharmaceutically acceptable salt, solvate or prodrug of the third aspect of the invention, or a pharmaceutical composition of the fourth aspect of the invention, for use in the treatment or prevention of a disease, disorder or condition in an individual, wherein the individual has a germline or somatic non-silent mutation in NLRP3. The mutation may be, for example, a gain-of-function or other mutation resulting in increased NLRP3 activity. Typically, the use comprises the administration of the compound, salt, solvate, prodrug or pharmaceutical composition to the individual. In one embodiment, the use comprises the co-administration of one or more further active agents. The use may also comprise the diagnosis of an individual having a germline or somatic non-silent mutation in NLRP3, wherein the compound, salt, solvate, prodrug or pharmaceutical composition is administered to an individual on the basis of a positive diagnosis for the mutation. Typically, identification of the mutation in NLRP3 in the individual may be by any suitable genetic or biochemical means.

A ninth aspect of the invention provides the use of a compound of the first or second aspect, or a pharmaceutically effective salt, solvate or prodrug of the third aspect, in the manufacture of a medicament for the treatment or prevention of a disease, disorder or condition in an individual, wherein the individual has a germline or somatic non-silent mutation in NLRP3. The mutation may be, for example, a gain-of-function or other mutation resulting in increased NLRP3 activity. Typically, the treatment or prevention comprises the administration of the compound, salt, solvate, prodrug or medicament to the individual. In one embodiment, the treatment or prevention comprises the co-administration of one or more further active agents. The treatment or prevention may also comprise the diagnosis of an individual having a germline or somatic non-silent mutation in NLRP3, wherein the compound, salt, solvate, prodrug or medicament is administered to an individual on the basis of a positive diagnosis for the mutation. Typically, identification of the mutation in NLRP3 in the individual may be by any suitable genetic or biochemical means.

A tenth aspect of the invention provides a method of treatment or prevention of a disease, disorder or condition, the method comprising the steps of diagnosing of an individual having a germline or somatic non-silent mutation in NLRP3, and administering an effective amount of a compound of the first or second aspect, or a pharmaceutically acceptable salt, solvate or prodrug of the third aspect, or a pharmaceutical composition of the fourth aspect, to the positively diagnosed individual, to thereby treat or prevent the disease, disorder or condition. In one embodiment, the method further comprises the step of co-administering an effective amount of one or more further active agents. Typically, the administration is to a subject in need thereof.

In general embodiments, the disease, disorder or condition may be a disease, disorder or condition of the immune system, the cardiovascular system, the endocrine system, the gastrointestinal tract, the renal system, the hepatic system, the metabolic system, the respiratory system, the central nervous system, may be a cancer or other malignancy, and/or may be caused by or associated with a pathogen.

It will be appreciated that these general embodiments defined according to broad categories of diseases, disorders and conditions are not mutually exclusive. In this regard any particular disease, disorder or condition may be categorized according to more than one of the above general embodiments. A non-limiting example is type I diabetes which is an autoimmune disease and a disease of the endocrine system.

In one embodiment of the fifth, sixth, seventh, eighth, ninth or tenth aspect of the present invention, the disease, disorder or condition is responsive to NLRP3 inhibition. As used herein, the term "NLRP3 inhibition" refers to the complete or partial reduction in the level of activity of NLRP3 and includes, for example, the inhibition of active NLRP3 and/or the inhibition of activation of NLRP3.

There is evidence for a role of NLRP3-induced IL-1 and IL-18 in the inflammatory responses occurring in connection with, or as a result of, a multitude of different disorders (Menu et al., Clinical and Experimental Immunology, 166: 1-15, 2011; Strowig et al., Nature, 481:278-286, 2012).

NLRP3 has been implicated in a number of autoinflammatory diseases, including Familial Mediterranean fever (FMF), TNF receptor associated periodic syndrome (TRAPS), hyperimmunoglobulinemia D and periodic fever syndrome (HIDS), pyogenic arthritis, pyoderma gangrenosum and acne (PAPA), Sweet's syndrome, chronic nonbacterial osteomyelitis (CNO), and acne vulgaris (Cook et al., Eur. J. Immunol., 40: 595-653, 2010). In particular, NLRP3 mutations have been found to be responsible for a set of rare autoinflammatory diseases known as CAPS (Ozaki et al., J. Inflammation Research, 8:15-27, 2015; Schroder et al., Cell, 140: 821-832, 2010; and Menu et al., Clinical and Experimental Immunology, 166: 1-15, 2011). CAPS are heritable diseases characterized by recurrent fever and inflammation and are comprised of three autoinflammatory disorders that form a clinical continuum. These diseases, in order of increasing severity, are familial cold autoinflammatory syndrome (FCAS), Muckle-Wells syndrome (MWS), and chronic infantile cutaneous neurological articular syndrome (CINCA; also called neonatal-onset multisystem inflammatory disease, NOMID), and all have been shown to result from gain-of-function mutations in the NLRP3 gene, which leads to increased secretion of IL-1β.

A number of autoimmune diseases have been shown to involve NLRP3 including, in particular, multiple sclerosis, type-1 diabetes (TID), psoriasis, rheumatoid arthritis (RA), Behcet's disease, Schnitzler syndrome, macrophage activation syndrome (Masters Clin. Immunol. 2013; Braddock et al. Nat. Rev. Drug Disc. 2004 3: 1-10; Inoue et al., Immunology 139: 11-18, Coll et al. Nat. Med. 2015 21(3):248-55; and Scott et al. Clin. Exp. Rheumatol 2016 34(1): 88-93), systemic lupus erythematosus (Lu et al. J Immunol. 2017 198(3): 1119-29), and systemic sclerosis (Artlett et al. Arthritis Rheum. 2011; 63(11): 3563-74). NLRP3 has also been shown to play a role in a number of lung diseases including chronic obstructive pulmonary disorder (COPD), asthma (including steroid-resistant asthma), asbestosis, and silicosis (De Nardo et al., Am. J. Pathol., 184: 42-54, 2014 and Kim et al. Am J Respir Crit Care Med. 2017 196(3): 283-97). NLRP3 has also been suggested to have a role in a number of central nervous system conditions, including Parkinson's disease (PD), Alzheimer's disease (AD), dementia, Huntington's disease, cerebral malaria, brain injury from pneumococcal meningitis (Walsh et al., Nature Reviews, 15: 84-97, 2014, and Dempsey et al. Brain. Behav. Immun. 2017 61: 306-316), intracranial aneurysms (Zhang et al. J. Stroke & Cerebrovascular Dis. 2015 24; 5: 972-979), and traumatic brain injury (Ismael et al. J Neurotrauma. 2018 Jan. 2). NRLP3 activity has also been shown to be involved in various metabolic diseases including type 2 diabetes (T2D), atherosclerosis, obesity, gout, pseudo-gout, metabolic syndrome (Wen et al., Nature Immunology, 13: 352-357, 2012; Duewell et al., Nature, 464: 1357-1361, 2010; Strowig et al., Nature, 481: 278-286, 2012), and non-alcoholic steatohepatitis (Mridha et al. J Hepatol. 2017 66(5): 1037-46). A role for NLRP3 via IL-1β has also been suggested in atherosclerosis, myocardial infarction (van Hout et al. Eur. Heart J 2017 38(11): 828-36), heart failure (Sano et al. J AM. Coll. Cardiol. 2018 71(8): 875-66), aortic aneurysm and dissection (Wu et al. Arterioscler. Thromb. Vasc. Biol. 2017 37(4): 694-706), and other cardiovascular events (Ridker et al, N Engl J Med., doi: 10.1056/NEJMoa1707914, 2017). Other diseases in which NLRP3 has been shown to be involved include: ocular diseases such as both wet and dry age-related macular degeneration (Doyle et al., Nature Medicine, 18: 791-798, 2012 and Tarallo et al. Cell 2012 149(4): 847-59), diabetic retinopathy (Loukovaara et al. Acta Ophthalmol. 2017; 95(8): 803-808) and optic nerve damage (Puyang et al. Sci Rep. 2016 Feb. 19; 6:20998); liver diseases including non-alcoholic steatohepatitis (NASH) (Henao-Meija et al., Nature, 482: 179-185, 2012); inflammatory reactions in the lung and skin (Primiano et al. J Immunol. 2016 197(6): 2421-33) including contact hypersensitivity (such as bullous pemphigoid (Fang et al. J Dermatol Sci. 2016; 83(2): 116-23)), atopic dermatitis (Niebuhr et al. Allergy 2014 69(8): 1058-67), Hidradenitis suppurativa (Alikhan et al. 2009 J Am Acad Dermatol 60(4): 539-61), acne vulgaris (Qin et al. J Invest. Dermatol. 2014 134(2): 381-88), and sarcoidosis (Jager et al. Am J Respir Crit Care Med 2015 191: A5816); inflammatory reactions in the joints (Braddock et al., Nat. Rev. Drug Disc., 3: 1-10, 2004); amyotrophic lateral sclerosis (Gugliandolo et al. Inflammation 2018 41(1): 93-103); cystic fibrosis (Iannitti et al. Nat. Commun. 2016 7: 10791); stroke (Walsh et al., Nature Reviews, 15: 84-97, 2014); chronic kidney disease (Granata et al. PLoS One 2015 10(3): e0122272); and inflammatory bowel diseases including ulcerative colitis and Crohn's disease (Braddock et al., Nat. Rev. Drug Disc., 3: 1-10, 2004, Neudecker et al. J Exp. Med. 2017 214(6): 1737-52, and Lazaridis et al. Dig. Dis. Sci. 2017 62(9): 2348-56). The NLRP3 inflammasome has been found to be activated in response to oxidative stress, and UVB irradiation (Schroder et al., Science, 327: 296-300, 2010). NLRP3 has also been shown to be involved in inflammatory hyperalgesia (Dolunay et al., Inflammation, 40: 366-386, 2017).

The inflammasome, and NLRP3 specifically, has also been proposed as a target for modulation by various pathogens including viruses such as DNA viruses (Amsler et al., Future Virol. (2013) 8(4), 357-370).

NLRP3 has also been implicated in the pathogenesis of many cancers (Menu et al., Clinical and Experimental Immunology 166: 1-15, 2011; and Masters Clin. Immunol. 2013). For example, several previous studies have suggested a role for IL-1β in cancer invasiveness, growth and metastasis, and inhibition of IL-1β with canakinumab has been shown to reduce the incidence of lung cancer and total cancer mortality in a randomised, double-blind, placebo-controlled trial (Ridker et al. Lancet, S0140-6736(17)32247-X, 2017). Inhibition of the NLRP3 inflammasome or IL-1β has also been shown to inhibit the proliferation and migration of lung cancer cells in vitro (Wang et al. Oncol Rep. 2016; 35(4): 2053-64). A role for the NLRP3 inflammasome has been suggested in myelodysplastic syndromes (Basiorka et al. Blood. 2016 Dec. 22; 128(25):2960-2975) and also in the carcinogenesis of various other cancers including glioma (Li et al. Am J Cancer Res. 2015; 5(1): 442-449), inflammation-induced tumours (Allen et al. J Exp Med. 2010; 207(5): 1045-56 and Hu et al. PNAS. 2010; 107(50): 21635-40), multiple myeloma (Li et al. Hematology 2016 21(3): 144-51), and squamous cell carcinoma of the head and neck (Huang et al. J Exp Clin Cancer Res. 2017 2; 36(1): 116). Activation of the NLRP3 inflammasome has also been shown to mediate chemoresistance of tumour cells to 5-Fluorouracil (Feng et al. J Exp Clin Cancer Res. 2017 21; 36(1): 81), and activation of NLRP3 inflammasome in peripheral nerve contributes to chemotherapy-induced neuropathic pain (Jia et al. Mol Pain. 2017; 13: 1-11).

NLRP3 has also been shown to be required for the efficient control of viral, bacterial, fungal, and helminth pathogen infections (Strowig et al., Nature, 481:278-286, 2012).

Accordingly, examples of diseases, disorders or conditions which may be responsive to NLRP3 inhibition and which may be treated or prevented in accordance with the fifth, sixth, seventh, eighth, ninth or tenth aspect of the present invention include:

(i) inflammation, including inflammation occurring as a result of an inflammatory disorder, e.g. an autoinflammatory disease, inflammation occurring as a symptom of a non-inflammatory disorder, inflammation occurring as a result of infection, or inflammation secondary to trauma, injury or autoimmunity;

(ii) auto-immune diseases such as acute disseminated encephalitis, Addison's disease, ankylosing spondylitis, antiphospholipid antibody syndrome (APS), anti-synthetase syndrome, aplastic anemia, autoimmune adrenalitis, autoimmune hepatitis, autoimmune oophoritis, autoimmune polyglandular failure, autoimmune thyroiditis, Coeliac disease, Crohn's disease, type 1 diabetes (TID), Goodpasture's syndrome, Graves' disease, Guillain-Barré syndrome (GBS), Hashimoto's disease, idiopathic thrombocytopenic purpura, Kawasaki's disease, lupus erythematosus including systemic lupus erythematosus (SLE), multiple sclerosis (MS) including primary progressive multiple sclerosis (PPMS), secondary progressive multiple sclerosis (SPMS) and relapsing remitting multiple sclerosis (RRMS), myasthenia gravis, opsoclonus myoclonus syndrome (OMS), optic neuritis, Ord's thyroiditis, pemphigus, pernicious anaemia, polyarthritis, primary biliary cirrhosis, rheumatoid arthritis (RA), psoriatic arthritis, juvenile idiopathic arthritis or Still's disease, refractory gouty arthritis, Reiter's syndrome, Sjögren's syndrome, systemic sclerosis a systemic connective tissue disorder, Takayasu's arteritis, temporal arteritis, warm autoimmune hemolytic anemia, Wegener's granulomatosis, alopecia universalis, Behcet's disease, Chagas' disease, dysautonomia, endometriosis, hidradenitis suppurativa (HS), interstitial cystitis, neuromyotonia, psoriasis, sarcoidosis, scleroderma, ulcerative colitis, Schnitzler syndrome, macrophage activation syndrome, Blau syndrome, vitiligo or vulvodynia; (iii) cancer including lung cancer, pancreatic cancer, gastric cancer, myelodysplastic syndrome, leukaemia including acute lymphocytic leukaemia (ALL) and acute myeloid leukaemia (AML), adrenal cancer, anal cancer, basal and squamous cell skin cancer, bile duct cancer, bladder cancer, bone cancer, brain and spinal cord tumours, breast cancer, cervical cancer, chronic lymphocytic leukaemia (CLL), chronic myeloid leukaemia (CML), chronic myelomonocytic leukaemia (CMML), colorectal cancer, endometrial cancer, oesophagus cancer, Ewing family of tumours, eye cancer, gallbladder cancer, gastrointestinal carcinoid tumours, gastrointestinal stromal tumour (GIST), gestational trophoblastic disease, glioma, Hodgkin lymphoma, Kaposi sarcoma, kidney cancer, laryngeal and hypopharyngeal cancer, liver cancer, lung carcinoid tumour, lymphoma including cutaneous T cell lymphoma, malignant mesothelioma, melanoma skin cancer, Merkel cell skin cancer, multiple myeloma, nasal cavity and paranasal sinuses cancer, nasopharyngeal cancer, neuroblastoma, non-Hodgkin lymphoma, non-small cell lung cancer, oral cavity and oropharyngeal cancer, osteosarcoma, ovarian cancer, penile cancer, pituitary tumours, prostate cancer, retinoblastoma, rhabdomyosarcoma, salivary gland cancer, skin cancer, small cell lung cancer, small intestine cancer, soft tissue sarcoma, stomach cancer, testicular cancer, thymus cancer, thyroid cancer including anaplastic thyroid cancer, uterine sarcoma, vaginal cancer, vulvar cancer, Waldenstrom macroglobulinemia, and Wilms tumour; (iv) infections including viral infections (e.g. from influenza virus, human immunodeficiency virus (HIV), alphavirus (such as Chikungunya and Ross River virus), flaviviruses (such as Dengue virus and Zika virus), herpes viruses (such as Epstein Barr Virus, cytomegalovirus, Varicella-zoster virus, and KSHV), poxviruses (such as vaccinia virus (Modified vaccinia virus Ankara) and Myxoma virus), adenoviruses (such as Adenovirus 5), or papillomavirus), bacterial infections (e.g. from *Staphylococcus aureus, Helicobacter pylori, Bacillus anthracis, Bordatella pertussis, Burkholderia pseudomallei, Corynebacterium diptheriae, Clostridium tetani, Clostridium botulinum, Streptococcus pneumoniae, Strepto-*

*coccus pyogenes, Listeria monocytogenes, Hemophilus influenzae, Pasteurella multicida, Shigella dysenteriae, Mycobacterium tuberculosis, Mycobacterium leprae, Mycoplasma pneumoniae, Mycoplasma hominis, Neisseria meningitidis, Neisseria gonorrhoeae, Rickettsia rickettsii, Legionella pneumophila, Klebsiella pneumoniae, Pseudomonas aeruginosa, Propionibacterium acnes, Treponema pallidum, Chlamydia trachomatis, Vibrio cholerae, Salmonella typhimurium, Salmonella typhi, Borrelia burgdorferi* or *Yersinia pestis*), fungal infections (e.g. from *Candida* or *Aspergillus* species), protozoan infections (e.g. from *Plasmodium, Babesia, Giardia, Entamoeba, Leishmania* or Trypanosomes), helminth infections (e.g. from *Schistosoma*, roundworms, tapeworms or flukes) and prion infections;

(v) central nervous system diseases such as Parkinson's disease, Alzheimer's disease, dementia, motor neuron disease, Huntington's disease, cerebral malaria, brain injury from pneumococcal meningitis, intracranial aneurysms, traumatic brain injury, and amyotrophic lateral sclerosis;

(vi) metabolic diseases such as type 2 diabetes (T2D), atherosclerosis, obesity, gout, and pseudo-gout;

(vii) cardiovascular diseases such as hypertension, ischaemia, reperfusion injury including post-MI ischemic reperfusion injury, stroke including ischemic stroke, transient ischemic attack, myocardial infarction including recurrent myocardial infarction, heart failure including congestive heart failure and heart failure with preserved ejection fraction, embolism, aneurysms including abdominal aortic aneurysm, and pericarditis including Dressler's syndrome;

(viii) respiratory diseases including chronic obstructive pulmonary disorder (COPD), asthma such as allergic asthma and steroid-resistant asthma, asbestosis, silicosis, nanoparticle induced inflammation, cystic fibrosis and idiopathic pulmonary fibrosis;

(ix) liver diseases including non-alcoholic fatty liver disease (NAFLD) and non-alcoholic steatohepatitis (NASH) including advanced fibrosis stages F3 and F4, alcoholic fatty liver disease (AFLD), and alcoholic steatohepatitis (ASH);

(x) renal diseases including chronic kidney disease, oxalate nephropathy, nephrocalcinosis, glomerulonephritis, and diabetic nephropathy;

(xi) ocular diseases including those of the ocular epithelium, age-related macular degeneration (AMD) (dry and wet), uveitis, corneal infection, diabetic retinopathy, optic nerve damage, dry eye, and glaucoma;

(xii) skin diseases including dermatitis such as contact dermatitis and atopic dermatitis, contact hypersensitivity, sunburn, skin lesions, hidradenitis suppurativa (HS), other cyst-causing skin diseases, and acne conglobata;

(xiii) lymphatic conditions such as lymphangitis and Castleman's disease;

(xiv) psychological disorders such as depression and psychological stress;

(xv) graft versus host disease;

(xvi) allodynia including mechanical allodynia; and (xvii) any disease where an individual has been determined to carry a germline or somatic non-silent mutation in NLRP3.

In one embodiment, the disease, disorder or condition is selected from:
(i) cancer;
(ii) an infection;
(iii) a central nervous system disease;
(iv) a cardiovascular disease;
(v) a liver disease;
(vi) an ocular diseases; or
(vii) a skin disease.

More typically, the disease, disorder or condition is selected from:
(i) cancer;
(ii) an infection;
(iii) a central nervous system disease; or
(iv) a cardiovascular disease.

In one embodiment, the disease, disorder or condition is selected from:
(i) acne conglobata;
(ii) atopic dermatitis;
(iii) Alzheimer's disease;
(iv) amyotrophic lateral sclerosis;
(v) age-related macular degeneration (AMD);
(vi) anaplastic thyroid cancer;
(vii) cryopyrin-associated periodic syndromes (CAPS);
(viii) contact dermatitis;
(ix) cystic fibrosis;
(x) congestive heart failure;
(xi) chronic kidney disease;
(xii) Crohn's disease;
(xiii) familial cold autoinflammatory syndrome (FCAS);
(xiv) Huntington's disease;
(xv) heart failure;
(xvi) heart failure with preserved ejection fraction;
(xvii) ischemic reperfusion injury;
(xviii) juvenile idiopathic arthritis;
(xix) myocardial infarction;
(xx) macrophage activation syndrome;
(xxi) myelodysplastic syndrome;
(xxii) multiple myeloma;
(xxiii) motor neuron disease;
(xxiv) multiple sclerosis;
(xxv) Muckle-Wells syndrome;
(xxvi) non-alcoholic steatohepatitis (NASH);
(xxvii) neonatal-onset multisystem inflammatory disease (NOMID);
(xxviii) Parkinson's disease;
(xxix) systemic juvenile idiopathic arthritis;
(xxx) systemic lupus erythematosus;
(xxxi) traumatic brain injury;
(xxxii) transient ischemic attack; and
(xxxiii) ulcerative colitis.

In a further typical embodiment of the invention, the disease, disorder or condition is inflammation. Examples of inflammation that may be treated or prevented in accordance with the fifth, sixth, seventh, eighth, ninth or tenth aspect of the present invention include inflammatory responses occurring in connection with, or as a result of:

(i) a skin condition such as contact hypersensitivity, bullous pemphigoid, sunburn, psoriasis, atopical dermatitis, contact dermatitis, allergic contact dermatitis, seborrhoetic dermatitis, lichen planus, scleroderma, pemphigus, epidermolysis bullosa, urticaria, erythemas, or alopecia;

(ii) a joint condition such as osteoarthritis, systemic juvenile idiopathic arthritis, adult-onset Still's disease, relapsing polychondritis, rheumatoid arthritis, juvenile chronic arthritis, gout, or a seronegative spondyloarthropathy (e.g. ankylosing spondylitis, psoriatic arthritis or Reiter's disease);

(iii) a muscular condition such as polymyositis or myasthenia gravis;

(iv) a gastrointestinal tract condition such as inflammatory bowel disease (including Crohn's disease and ulcerative colitis), gastric ulcer, coeliac disease, proctitis, pancreatitis, eosinopilic gastro-enteritis, mastocytosis, antiphospholipid syndrome, or a food-related allergy which may have effects remote from the gut (e.g., migraine, rhinitis or eczema);

(v) a respiratory system condition such as chronic obstructive pulmonary disease (COPD), asthma (including bronchial, allergic, intrinsic, extrinsic or dust asthma, and particularly chronic or inveterate asthma, such as late asthma and airways hyper-responsiveness), bronchitis, rhinitis (including acute rhinitis, allergic rhinitis, atrophic rhinitis, chronic rhinitis, rhinitis caseosa, hypertrophic rhinitis, rhinitis pumlenta, rhinitis sicca, rhinitis medicamentosa, membranous rhinitis, seasonal rhinitis e.g. hay fever, and vasomotor rhinitis), sinusitis, idiopathic pulmonary fibrosis (IPF), sarcoidosis, farmer's lung, silicosis, asbestosis, adult respiratory distress syndrome, hypersensitivity pneumonitis, or idiopathic interstitial pneumonia;

(vi) a vascular condition such as atherosclerosis, Behcet's disease, vasculitides, or wegener's granulomatosis;

(vii) an autoimmune condition such as systemic lupus erythematosus, Sjogren's syndrome, systemic sclerosis, Hashimoto's thyroiditis, type I diabetes, idiopathic thrombocytopenia purpura, or Graves disease;

(viii) an ocular condition such as uveitis, allergic conjunctivitis, or vernal conjunctivitis;

(ix) a nervous condition such as multiple sclerosis or encephalomyelitis;

(x) an infection or infection-related condition, such as Acquired Immunodeficiency Syndrome (AIDS), acute or chronic bacterial infection, acute or chronic parasitic infection, acute or chronic viral infection, acute or chronic fungal infection, meningitis, hepatitis (A, B or C, or other viral hepatitis), peritonitis, pneumonia, epiglottitis, malaria, dengue hemorrhagic fever, leishmaniasis, streptococcal myositis, *Mycobacterium tuberculosis, Mycobacterium avium intracellulare, Pneumocystis carinii* pneumonia, orchitis/epidydimitis, *Legionella*, Lyme disease, influenza A, epstein-barr virus, viral encephalitis/aseptic meningitis, or pelvic inflammatory disease;

(xi) a renal condition such as mesangial proliferative glomerulonephritis, nephrotic syndrome, nephritis, glomerular nephritis, acute renal failure, uremia, or nephritic syndrome;

(xii) a lymphatic condition such as Castleman's disease;

(xiii) a condition of, or involving, the immune system, such as hyper IgE syndrome, lepromatous leprosy, familial hemophagocytic lymphohistiocytosis, or graft versus host disease;

(xiv) a hepatic condition such as chronic active hepatitis, non-alcoholic steatohepatitis (NASH), alcohol-induced hepatitis, non-alcoholic fatty liver disease (NAFLD), alcoholic fatty liver disease (AFLD), alcoholic steatohepatitis (ASH) or primary biliary cirrhosis;

(xv) a cancer, including those cancers listed above;

(xvi) a burn, wound, trauma, haemorrhage or stroke;

(xvii) radiation exposure; and/or (xviii) obesity; and/or (xix) pain such as inflammatory hyperalgesia.

In one embodiment of the fifth, sixth, seventh, eighth, ninth or tenth aspect of the present invention, the disease, disorder or condition is an autoinflammatory disease such as cryopyrin-associated periodic syndromes (CAPS), Muckle-Wells syndrome (MWS), familial cold autoinflammatory syndrome (FCAS), familial Mediterranean fever (FMF), neonatal onset multisystem inflammatory disease (NOMID), Tumour Necrosis Factor (TNF) Receptor-Associated Periodic Syndrome (TRAPS), hyperimmunoglobulinemia D and periodic fever syndrome (HIDS), deficiency of interleukin 1 receptor antagonist (DIRA), Majeed syndrome, pyogenic arthritis, pyoderma gangrenosum and acne syndrome (PAPA), adult-onset Still's disease (AOSD), haploinsufficiency of A20 (HA20), pediatric granulomatous arthritis (PGA), PLCG2-associated antibody deficiency and immune dysregulation (PLAID), PLCG2-associated autoinflammatory, antibody deficiency and immune dysregulation (APLAID), or sideroblastic anaemia with B-cell immunodeficiency, periodic fevers and developmental delay (SIFD).

Examples of diseases, disorders or conditions which may be responsive to NLRP3 inhibition and which may be treated or prevented in accordance with the fifth, sixth, seventh, eighth, ninth or tenth aspect of the present invention are listed above. Some of these diseases, disorders or conditions are substantially or entirely mediated by NLRP3 inflammasome activity, and NLRP3-induced IL-1β and/or IL-18. As a result, such diseases, disorders or conditions may be particularly responsive to NLRP3 inhibition and may be particularly suitable for treatment or prevention in accordance with the fifth, sixth, seventh, eighth, ninth or tenth aspect of the present invention. Examples of such diseases, disorders or conditions include cryopyrin-associated periodic syndromes (CAPS), Muckle-Wells syndrome (MWS), familial cold autoinflammatory syndrome (FCAS), neonatal onset multisystem inflammatory disease (NOMID), familial Mediterranean fever (FMF), pyogenic arthritis, pyoderma gangrenosum and acne syndrome (PAPA), hyperimmunoglobulinemia D and periodic fever syndrome (HIDS), Tumour Necrosis Factor (TNF) Receptor-Associated Periodic Syndrome (TRAPS), systemic juvenile idiopathic arthritis, adult-onset Still's disease (AOSD), relapsing polychondritis, Schnitzler's syndrome, Sweet's syndrome, Behcet's disease, anti-synthetase syndrome, deficiency of interleukin 1 receptor antagonist (DIRA), and haploinsufficiency of A20 (HA20).

Moreover, some of the diseases, disorders or conditions mentioned above arise due to mutations in NLRP3, in particular, resulting in increased NLRP3 activity. As a result, such diseases, disorders or conditions may be particularly responsive to NLRP3 inhibition and may be particularly suitable for treatment or prevention in accordance with the fifth, sixth, seventh, eighth, ninth or tenth aspect of the present invention. Examples of such diseases, disorders or conditions include cryopyrin-associated periodic syndromes (CAPS), Muckle-Wells syndrome (MWS), familial cold autoinflammatory syndrome (FCAS), and neonatal onset multisystem inflammatory disease (NOMID).

In one embodiment of the fifth, sixth, seventh, eighth, ninth or tenth aspect of the present invention, the disease, disorder or condition is not an ocular inflammatory disease or a symptom of an ocular inflammatory disease. In one embodiment of the fifth, sixth or seventh aspect of the present invention, the disease, disorder or condition is not a skin disease. In one embodiment of the fifth, sixth or seventh aspect of the present invention, the disease, disorder or condition is not a disease involving a chemokine receptor. In one embodiment of the fifth, sixth or seventh aspect of the present invention, the disease, disorder or condition is not a dermatic disease. In one embodiment of the fifth, sixth or seventh aspect of the present invention, the disease, disorder or condition is not dermatitis. In one embodiment of the fifth, sixth or seventh aspect of the present invention, the disease, disorder or condition is not a disease involving an increase in eosinophils. In one embodiment of the fifth, sixth or seventh aspect of the present invention, the disease, disorder or condition is not an allergic disease. In one embodiment of the fifth, sixth or seventh aspect of the present invention, the disease, disorder or condition is not a disease susceptible to treatment with a chymase inhibitor. In one embodiment of the fifth, sixth or seventh aspect of the present invention, the disease, disorder or condition is not fibrosis or extracellular matrix dysbolism. In one embodiment of the fifth, sixth or seventh aspect of the present invention, the disease, disorder or condition is not a disease accompanied by abnormal vascular function. In one embodiment of the fifth, sixth or seventh aspect of the present invention, the disease, disorder or condition is not a rheumatic disease. In one embodiment of the fifth, sixth or seventh aspect of the present invention, the disease, disorder or condition is not a cardiac or circulatory system disease. In one embodiment of the fifth, sixth or seventh aspect of the present invention, the disease, disorder or condition is not inflammatory bowel disease. In one embodiment of the fifth, sixth or seventh aspect of the present invention, the disease, disorder or condition is not HCV infection. In one embodiment of the fifth, sixth or seventh aspect of the present invention, the disease, disorder or condition is not cancer. In one embodiment of the fifth, sixth or seventh aspect of the present invention, the disease, disorder or condition is not a disease susceptible to treatment with a hypoglycaemic agent.

An eleventh aspect of the invention provides a method of inhibiting NLRP3, the method comprising the use of a compound of the first or second aspect of the invention, or a pharmaceutically acceptable salt, solvate or prodrug of the third aspect of the invention, or a pharmaceutical composition of the fourth aspect of the invention, to inhibit NLRP3.

In one embodiment of the eleventh aspect of the present invention, the method comprises the use of a compound of the first or second aspect of the invention, or a pharmaceutically acceptable salt, solvate or prodrug of the third aspect of the invention, or a pharmaceutical composition of the fourth aspect of the invention, in combination with one or more further active agents.

In one embodiment of the eleventh aspect of the present invention, the method is performed ex vivo or in vitro, for example in order to analyse the effect on cells of NLRP3 inhibition.

In another embodiment of the eleventh aspect of the present invention, the method is performed in vivo. For example, the method may comprise the step of administering an effective amount of a compound of the first or second aspect, or a pharmaceutically acceptable salt, solvate or prodrug of the third aspect, or a pharmaceutical composition of the fourth aspect, to thereby inhibit NLRP3. In one embodiment, the method further comprises the step of co-administering an effective amount of one or more further active agents. Typically the administration is to a subject in need thereof.

Alternately, the method of the eleventh aspect of the invention may be a method of inhibiting NLRP3 in a non-human animal subject, the method comprising the steps of administering the compound, salt, solvate, prodrug or pharmaceutical composition to the non-human animal subject and optionally subsequently mutilating or sacrificing the non-human animal subject. Typically such a method further comprises the step of analysing one or more tissue or fluid samples from the optionally mutilated or sacrificed non-human animal subject. In one embodiment, the method further comprises the step of co-administering an effective amount of one or more further active agents.

A twelfth aspect of the invention provides a compound of the first or second aspect of the invention, or a pharmaceutically acceptable salt, solvate or prodrug of the third aspect of the invention, or a pharmaceutical composition of the fourth aspect of the invention, for use in the inhibition of NLRP3. Typically the use comprises the administration of the compound, salt, solvate, prodrug or pharmaceutical composition to a subject. In one embodiment, the compound, salt, solvate, prodrug or pharmaceutical composition is co-administered with one or more further active agents.

A thirteenth aspect of the invention provides the use of a compound of the first or second aspect of the invention, or a pharmaceutically effective salt, solvate or prodrug of the third aspect of the invention, in the manufacture of a medicament for the inhibition of NLRP3. Typically, the inhibition comprises the administration of the compound, salt, solvate, prodrug or medicament to a subject. In one embodiment, the compound, salt, solvate, prodrug or medicament is co-administered with one or more further active agents.

In any embodiment of any of the fifth to thirteenth aspects of the present invention that comprises the use or co-administration of one or more further active agents, the one or more further active agents may comprise for example one, two or three different further active agents.

The one or more further active agents may be used or administered prior to, simultaneously with, sequentially with or subsequent to each other and/or to the compound of the first or second aspect of the invention, the pharmaceutically acceptable salt, solvate or prodrug of the third aspect of the invention, or the pharmaceutical composition of the fourth aspect of the invention. Where the one or more further active agents are administered simultaneously with the compound of the first or second aspect of the invention, or the pharmaceutically acceptable salt, solvate or prodrug of the third aspect of the invention, a pharmaceutical composition of the fourth aspect of the invention may be administered wherein the pharmaceutical composition additionally comprises the one or more further active agents.

In one embodiment of any of the fifth to thirteenth aspects of the present invention that comprises the use or co-administration of one or more further active agents, the one or more further active agents are selected from:
 (i) chemotherapeutic agents;
 (ii) antibodies;
 (iii) alkylating agents;
 (iv) anti-metabolites;
 (v) anti-angiogenic agents;
 (vi) plant alkaloids and/or terpenoids;
 (vii) topoisomerase inhibitors;
 (viii) mTOR inhibitors;
 (ix) stilbenoids;
 (x) STING agonists;
 (xi) cancer vaccines;
 (xii) immunomodulatory agents;
 (xiii) antibiotics;
 (xiv) anti-fungal agents;
 (xv) anti-helminthic agents; and/or
 (xvi) other active agents.

It will be appreciated that these general embodiments defined according to broad categories of active agents are not mutually exclusive. In this regard any particular active agent may be categorized according to more than one of the above general embodiments. A non-limiting example is urelumab which is an antibody that is an immunomodulatory agent for the treatment of cancer.

In some embodiments, the one or more chemotherapeutic agents are selected from abiraterone acetate, altretamine, amsacrine, anhydrovinblastine, auristatin, azathioprine, adriamycin, bexarotene, bicalutamide, BMS 184476, bleomycin, N,N-dimethyl-L-valyl-L-valyl-N-methyl-L-valyl-L-prolyl-L-proline-t-butylamide, cisplatin, carboplatin, carboplatin cyclophosphamide, chlorambucil, cachectin, cemadotin, cyclophosphamide, carmustine, cryptophycin, cytarabine, docetaxel, doxetaxel, doxorubicin, dacarbazine (DTIC), dactinomycin, daunorubicin, decitabine, dolastatin, etoposide, etoposide phosphate, enzalutamide (MDV3100), 5-fluorouracil, fludarabine, flutamide, gemcitabine, hydroxyurea and hydroxyureataxanes, idarubicin, ifosfamide, irinotecan, leucovorin, lonidamine, lomustine (CCNU), larotaxel (RPR109881), mechlorethamine, mercaptopurine, methotrexate, mitomycin C, mitoxantrone, melphalan, mivobulin, 3',4'-didehydro-4'-deoxy-8'-norvincaleukoblastine, nilutamide, oxaliplatin, onapristone, prednimustine, procarbazine, paclitaxel, platinum-containing anti-cancer agents, 2,3,4,5,6-pentafluoro-N-(3-fluoro-4-methoxyphenyl)benzene sulphonamide, prednimustine, procarbazine, rhizoxin, sertenef, streptozocin, stramustine phosphate, tretinoin, tasonermin, taxol, topotecan, tamoxifen, teniposide, taxane, tegafur/uracil, vincristine, vinblastine, vinorelbine, vindesine, vindesine sulfate, and/or vinflunine.

Alternatively or in addition, the one or more chemotherapeutic agents may be selected from CD59 complement fragment, fibronectin fragment, gro-beta (CXCL2), heparinases, heparin hexasaccharide fragment, human chorionic gonadotropin (hCG), interferon alpha, interferon beta, interferon gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-β), vasculostatin, vasostatin (calreticulin fragment), and/or cytokines (including interleukins, such as interleukin-2 (IL-2), or IL-10).

In some embodiments, the one or more antibodies may comprise one or more monoclonal antibodies. In some embodiments, the one or more antibodies are selected from abciximab, adalimumab, alemtuzumab, atlizumab, basiliximab, belimumab, bevacizumab, bretuximab vedotin, canakinumab, cetuximab, ceertolizumab pegol, daclizumab, denosumab, eculizumab, efalizumab, gemtuzumab, golimumab, ibritumomab tiuxetan, infliximab, ipilimumab, muromonab-CD3, natalizumab, ofatumumab, omalizumab, palivizumab, panitumuab, ranibizumab, rituximab, tocilizumab, tositomomab, and/or trastuzumab.

In some embodiments, the one or more alkylating agents may comprise an agent capable of alkylating nucleophilic functional groups under conditions present in cells, including, for example, cancer cells. In some embodiments, the one or more alkylating agents are selected from cisplatin, carboplatin, mechlorethamine, cyclophosphamide, chlorambucil, ifosfamide and/or oxaliplatin. In some embodiments, the alkylating agent may function by impairing cell function by forming covalent bonds with amino, carboxyl, sulfhydryl, and/or phosphate groups in biologically important molecules. In some embodiments, the alkylating agent may function by modifying a cell's DNA.

In some embodiments, the one or more anti-metabolites may comprise an agent capable of affecting or preventing RNA or DNA synthesis. In some embodiments, the one or more anti-metabolites are selected from azathioprine and/or mercaptopurine.

In some embodiments, the one or more anti-angiogenic agents are selected from endostatin, angiogenin inhibitors, angiostatin, angioarrestin, angiostatin (plasminogen fragment), basement-membrane collagen-derived anti-angiogenic factors (tumstatin, canstatin, or arrestin), anti-angiogenic antithrombin III, and/or cartilage-derived inhibitor (CDI).

In some embodiments, the one or more plant alkaloids and/or terpenoids may prevent microtubule function. In some embodiments, the one or more plant alkaloids and/or terpenoids are selected from a Vinca alkaloid, a podophyllotoxin and/or a taxane. In some embodiments, the one or more Vinca alkaloids may be derived from the Madagascar periwinkle, Catharanthus roseus (formerly known as Vinca rosea), and may be selected from vincristine, vinblastine, vinorelbine and/or vindesine. In some embodiments, the one or more taxanes are selected from taxol, paclitaxel, docetaxel and/or ortataxel. In some embodiments, the one or more podophyllotoxins are selected from an etoposide and/or teniposide.

In some embodiments, the one or more topoisomerase inhibitors are selected from a type I topoisomerase inhibitor and/or a type II topoisomerase inhibitor, and may interfere with transcription and/or replication of DNA by interfering with DNA supercoiling. In some embodiments, the one or more type I topoisomerase inhibitors may comprise a camptothecin, which may be selected from exatecan, irinotecan, lurtotecan, topotecan, BNP 1350, CKD 602, DB 67 (AR67) and/or ST 1481. In some embodiments, the one or more type II topoisomerase inhibitors may comprise an epipodophyllotoxin, which may be selected from an amsacrine, etoposid, etoposide phosphate and/or teniposide.

In some embodiments, the one or more mTOR (mammalian target of rapamycin, also known as the mechanistic target of rapamycin) inhibitors are selected from rapamycin, everolimus, temsirolimus and/or deforolimus.

In some embodiments, the one or more stilbenoids are selected from resveratrol, piceatannol, pinosylvin, pterostilbene, alpha-viniferin, ampelopsin A, ampelopsin E, diptoindonesin C, diptoindonesin F, epsilon-vinferin, flexuosol A, gnetin H, hemsleyanol D, hopeaphenol, trans-diptoindonesin B, astringin, piceid and/or diptoindonesin A.

In some embodiments, the one or more STING (Stimulator of interferon genes, also known as transmembrane protein (TMEM) 173) agonists may comprise cyclic di-nucleotides, such as cAMP, cGMP, and cGAMP, and/or modified cyclic di-nucleotides that may include one or more of the following modification features: 2'-O/3'-O linkage, phosphorothioate linkage, adenine and/or guanine analogue, and/or 2'-OH modification (e.g. protection of the 2'-OH with a methyl group or replacement of the 2'-OH by —F or —$N_3$).

In some embodiments, the one or more cancer vaccines are selected from an HPV vaccine, a hepatitis B vaccine, Oncophage, and/or Provenge.

In some embodiments, the one or more immunomodulatory agents may comprise an immune checkpoint inhibitor. The immune checkpoint inhibitor may target an immune checkpoint receptor, or combination of receptors comprising, for example, CTLA-4, PD-1, PD-L1, PD-L2, T cell immunoglobulin and mucin 3 (TIM3 or HAVCR2), galectin 9, phosphatidylserine, lymphocyte activation gene 3 protein (LAG3), MHC class I, MHC class II, 4-1BB, 4-1BBL, OX40, OX40L, GITR, GITRL, CD27, CD70, TNFRSF25, TL1A, CD40, CD40L, HVEM, LIGHT, BTLA, CD160, CD80, CD244, CD48, ICOS, ICOSL, B7-H3, B7-H4, VISTA, TMIGD2, HHLA2, TMIGD2, a butyrophilin (including BTNL2), a Siglec family member, TIGIT, PVR, a killer-cell immunoglobulin-like receptor, an ILT, a leukocyte immunoglobulin-like receptor, NKG2D, NKG2A, MICA, MICB, CD28, CD86, SIRPA, CD47, VEGF, neuropilin, CD30, CD39, CD73, CXCR4, and/or CXCL12.

In some embodiments, the immune checkpoint inhibitor is selected from urelumab, PF-05082566, MEDI6469, TRX518, varlilumab, CP-870893, pembrolizumab (PD1), nivolumab (PD1), atezolizumab (formerly MPDL3280A) (PD-L1), MEDI4736 (PD-L1), avelumab (PD-L1), PDR001 (PD1), BMS-986016, MGA271, lirilumab, IPH2201, emactuzumab, INCB0243600, galunisertib, ulocuplumab, BKT140, bavituximab, CC-90002, bevacizumab, and/or MNRP1685A.

In some embodiments, the one or more antibiotics are selected from amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem, cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin, calvulanate, ampicillin, subbactam, tazobactam, ticarcillin, clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethoxazole, sulfanamide, sulfasalazine, sulfisoxazole, trimethoprim-sulfamethoxazole, sulfonamideochrysoidine, demeclocycline, minocycline, oytetracycline, tetracycline, clofaziminine, dapsone, dapreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, daloprisitin, thiamphenicol, tigecycyline, tinidazole, trimethoprim, and/or teixobactin.

In some embodiments, the one or more antibiotics may comprise one or more cytotoxic antibiotics. In some embodiments, the one or more cytotoxic antibiotics are selected from an actinomycin, an anthracenedione, an anthracycline, thalidomide, dichloroacetic acid, nicotinic acid, 2-deoxyglucose, and/or chlofazimine. In some embodiments, the one or more actinomycins are selected from actinomycin D, bacitracin, colistin (polymyxin E) and/or polymyxin B. In some embodiments, the one or more antracenediones are selected from mitoxantrone and/or pixantrone. In some embodiments, the one or more anthracyclines are selected from bleomycin, doxorubicin (Adriamycin), daunorubicin (daunomycin), epirubicin, idarubicin, mitomycin, plicamycin and/or valrubicin.

In some embodiments, the one or more anti-fungal agents are selected from bifonazole, butoconazole, clotrimazole, econazole, ketoconazole, luliconazole, miconazole, omoconazole, oxiconazole, sertaconazole, sulconazole, tioconazole, albaconazole, efinaconazole, epoziconazole, fluconazole, isavuconazole, itraconazole, posaconazole, propiconazole, ravusconazole, terconazole, voriconazole, abafungin, amorolfin, butenafine, naftifine, terbinafine, anidulafungin, caspofungin, micafungin, benzoic acid, ciclopirox, flucytosine, 5-fluorocytosine, griseofulvin, haloprogin, tolnaflate, undecylenic acid, and/or balsam of Peru.

In some embodiments, the one or more anti-helminthic agents are selected from benzimidazoles (including albendazole, mebendazole, thiabendazole, fenbendazole, triclabendazole, and flubendazole), abamectin, diethylcarbamazine, ivermectin, suramin, pyrantel pamoate, levamisole, salicylanilides (including niclosamide and oxyclozanide), and/or nitazoxanide.

In some embodiments, other active agents are selected from growth inhibitory agents, anti-inflammatory agents (including nonsteroidal anti-inflammatory agents), anti-psoriatic agents (including anthralin and its derivatives), vitamins and vitamin-derivatives (including retinoinds, and VDR receptor ligands), corticosteroids, ion channel blockers (including potassium channel blockers), immune system regulators (including cyclosporin, FK 506, and glucocorticoids), lutenizing hormone releasing hormone agonists (such as leuprolidine, goserelin, triptorelin, histrelin, bicalutamide, flutamide and/or nilutamide), and/or hormones (including estrogen).

Unless stated otherwise, in any of the fifth to thirteenth aspects of the invention, the subject may be any human or other animal. Typically, the subject is a mammal, more typically a human or a domesticated mammal such as a cow, pig, lamb, sheep, goat, horse, cat, dog, rabbit, mouse etc. Most typically, the subject is a human.

Any of the medicaments employed in the present invention can be administered by oral, parenteral (including intravenous, subcutaneous, intramuscular, intradermal, intratracheal, intraperitoneal, intraarticular, intracranial and epidural), airway (aerosol), rectal, vaginal or topical (including transdermal, buccal, mucosal and sublingual) administration.

Typically, the mode of administration selected is that most appropriate to the disorder, disease or condition to be treated or prevented. Where one or more further active agents are administered, the mode of administration may be the same as or different to the mode of administration of the compound, salt, solvate, prodrug or pharmaceutical composition of the invention.

For oral administration, the compounds, salts, solvates or prodrugs of the present invention will generally be provided in the form of tablets, capsules, hard or soft gelatine capsules, caplets, troches or lozenges, as a powder or granules, or as an aqueous solution, suspension or dispersion.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose. Corn starch and alginic acid are suitable disintegrating agents. Binding agents may include starch and gelatine. The lubricating agent, if present, may be magnesium stearate, stearic acid or talc. If desired, the tablets may be coated with a material, such as glyceryl monostearate or glyceryl distearate, to delay absorption in the gastrointestinal tract. Tablets may also be effervescent and/or dissolving tablets.

Capsules for oral use include hard gelatine capsules in which the active ingredient is mixed with a solid diluent, and soft gelatine capsules wherein the active ingredient is mixed with water or an oil such as peanut oil, liquid paraffin or olive oil.

Powders or granules for oral use may be provided in sachets or tubs. Aqueous solutions, suspensions or dispersions may be prepared by the addition of water to powders, granules or tablets.

Any form suitable for oral administration may optionally include sweetening agents such as sugar, flavouring agents, colouring agents and/or preservatives.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For parenteral use, the compounds, salts, solvates or prodrugs of the present invention will generally be provided in a sterile aqueous solution or suspension, buffered to an appropriate pH and isotonicity. Suitable aqueous vehicles include Ringer's solution and isotonic sodium chloride or glucose. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate. The compounds of the invention may also be presented as liposome formulations.

For transdermal and other topical administration, the compounds, salts, solvates or prodrugs of the invention will generally be provided in the form of ointments, cataplasms (poultices), pastes, powders, dressings, creams, plasters or patches.

Suitable suspensions and solutions can be used in inhalers for airway (aerosol) administration.

The dose of the compounds, salts, solvates or prodrugs of the present invention will, of course, vary with the disorder, disease or condition to be treated or prevented. In general, a suitable dose will be in the range of 0.01 to 500 mg per kilogram body weight of the recipient per day. The desired dose may be presented at an appropriate interval such as once every other day, once a day, twice a day, three times a day or four times a day. The desired dose may be administered in unit dosage form, for example, containing 1 mg to 50 g of active ingredient per unit dosage form.

For the avoidance of doubt, insofar as is practicable any embodiment of a given aspect of the present invention may occur in combination with any other embodiment of the same aspect of the present invention. In addition, insofar as is practicable it is to be understood that any preferred, typical or optional embodiment of any aspect of the present invention should also be considered as a preferred, typical or optional embodiment of any other aspect of the present invention.

EXAMPLES—COMPOUND SYNTHESIS

All solvents, reagents and compounds were purchased and used without further purification unless stated otherwise.

Abbreviations

2-MeTHF 2-methyltetrahydrofuran
AcOH acetic acid
aq aqueous
Boc tert-butyloxycarbonyl
br broad
Cbz carboxybenzyl
CDI 1,1-carbonyl-diimidazole
cone concentrated
d doublet
DABCO 1,4-diazabicyclo[2.2.2]octane
DCE 1,2-dichloroethane, also called ethylene dichloride
DCM dichloromethane
DIPEA N,N-diisopropylethylamine, also called Hünig's base
DMAP 4-dimethylaminopyridine, also called N,N-dimethylpyridin-4-amine
DME dimethoxyethane
DMF N,N-dimethylformamide
DMSO dimethyl sulfoxide
(ES+) electrospray ionization, positive mode
Et ethyl
EtOAc ethyl acetate
EtOH ethanol
h hour(s)
HATU 1-[bis(dimethylamino)methylene]-1H-1,2,3-triazolo[4,5-b]pyridinium 3-oxid hexafluorophosphate
HPLC high performance liquid chromatography
LC liquid chromatography
m multiplet
m-CPBA 3-chloroperoxybenzoic acid
Me methyl
MeCN acetonitrile
MeOH methanol
(M+H)+ protonated molecular ion
MHz megahertz
min minute(s)
MS mass spectrometry
Ms mesyl, also called methanesulfonyl
MsCl mesyl chloride, also called methanesulfonyl chloride
MTBE methyl tert-butyl ether, also called tert-butyl methyl ether
m/z mass-to-charge ratio
NaO$^t$Bu sodium tert-butoxide
NBS 1-bromopyrrolidine-2,5-dione, also called N-bromosuccinimide
NCS 1-chloropyrrolidine-2,5-dione, also called N-chlorosuccinimide
NMP N-methylpyrrolidine
NMR nuclear magnetic resonance (spectroscopy)
Pd(dba)$_3$ tris(dibenzylideneacetone) dipalladium(0)
Pd(dppf)Cl$_2$ [1,1'-bis(diphenylphosphino)ferrocene] dichloropalladium(II)
PE petroleum ether
Ph phenyl
PMB p-methoxybenzyl
prep-HPLC preparative high performance liquid chromatography
prep-TLC preparative thin layer chromatography
PTSA p-toluenesulfonic acid
q quartet
RP reversed phase
RT room temperature
s singlet
Sept septuplet
sat saturated
SCX solid supported cation exchange (resin)
t triplet
TBME tert-butyl methyl ether, also called methyl tert-butyl ether
TEA triethylamine
TFA 2,2,2-trifluoroacetic acid
THF tetrahydrofuran TLC thin layer chromatography
wt % weight percent or percent by weight Experimental Methods Analytical Methods NMR spectra were recorded at 300 MHz or 400 MHz with chemical shifts reported in parts per million. Spectra were collected using one of the three machines below: —
- An Agilent VNMRS 300 instrument fitted with a 7.05 Tesla magnet from Oxford instruments, indirect detection probe and direct drive console including PFG module.
- An Agilent MercuryPlus 300 instrument fitted with a 7.05 Tesla magnet from Oxford instruments, 4 nuclei auto-switchable probe and Mercury plus console.
- A Bruker 400 MHz spectrometer using ICON-NMR, under TopSpin program control.

HPLC and LC-MS were recorded on an Agilent 1290 series with UV detector and HP 6130 MSD mass detector. Mobile phase A: ammonium acetate (10 mM); water/MeOH/acetonitrile (900:60:40); mobile phase B: ammonium acetate (10 mM); water/MeOH/acetonitrile (100:540:360); column, Waters XBridge BEH C18 XP (2.1×50 mm, 2.5 μm)

| | |
|---|---|
| Pump flow: 0.6 mL/min | UV detection: 215, 238 nm |
| Injection volume: 0.2 μL | Run time: 4.0 min |
| Column temperature: 35° C. | Mass detection: API-ES +ve and −ve |

Pump Program:

| Gradient Time (min) | % A | % B |
|---|---|---|
| 0.0 | 80 | 20 |
| 0.5 | 80 | 20 |
| 2.0 | 0 | 100 |

Alternatively, LC-MS were recorded using SHIMADZU LCMS-2020, Agilent 1200 LC/G1956A MSD and Agilent 1200\G6110A, Agilent 1200 LC & Agilent 6110 MSD. Mobile Phase: A: 0.025% $NH_3 \cdot H_2O$ in water (v/v); B: Acetonitrile. Column: Kinetex EVO C18 2.1×30 mm, 5 m.

Purification Method 1

Automated reversed phase column chromatography was carried out using a Buchi Sepracore® X50 system driven by a C-605 pump module, C-620 Sepracore control package, C-640 UV photometer detection unit and C-660 fraction collector.

Revelis C18 reversed-phase 12 g cartridge

| | |
|---|---|
| Carbon loading | 18% |
| Surface area | 568 m²/g |
| Pore diameter | 65 Angstrom |
| pH (5% slurry) | 5.1 |
| Average particle size | 40 μm |

The column was conditioned before use with MeOH (5 min) then brought to $H_2O$ (in 5 min) and kept 5 min at $H_2O$. Flow rate=30 mL/min.

Separation Runs:

| Time (min) | A: water (%) | B: MeOH (%) |
|---|---|---|
| 0 | 100 | 0 |
| 5 | 100 | 0 |
| 30 | 30 | 70 |
| 30.1 | 0 | 100 |
| 35 | 0 | 100 |

Detection wavelength: 215, 235, 254 and 280 nm. Before each new run, the cartridge was cleaned using the conditioning method.

Purification Method 2

Alternatively, automated reversed phase column chromatography was carried out using a Gilson GX-281 system driven by a Gilson-322 pump module, Gilson-156 UV photometer detection unit and Gilson-281 fraction collector.

Phenomenex Gemini 150 mm×25 mm×10 μm pH (water (0.05% ammonium hydroxide v/v)–acetonitrile)=10

Average particle size=10 μm

The column was conditioned before use with 100% acetonitrile (2 min) then brought to 5% acetonitrile (in 1.5 min). Flow rate=25 mL/min.

Separation Runs:

| Time (min) | A: water (0.05% ammonium hydroxide v/v) | B: acetonitrile (%) |
|---|---|---|
| 0 | 99 | 1 |
| 12 | 85 | 15 |
| 12.2 | 0 | 100 |
| 14.2 | 0 | 100 |
| 14.5 | 95 | 5 |
| 16.0 | 95 | 5 |

Detection wavelength: 220 and 254 nm. Before each new run, the cartridge was cleaned using the conditioning method.

Synthesis of Intermediates

Intermediate A1:
4-Isocyanato-1,2,3,5,6,7-hexahydro-s-indacene

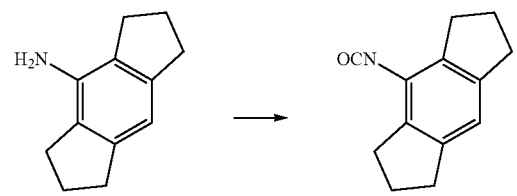

To a solution of phosgene (4.45 mL, 20% weight in toluene, 8.4 mmol) in EtOAc (90 mL) was added drop-wise a solution of 1,2,3,5,6,7-hexahydro-s-indacen-4-amine (589 mg, 3.4 mmol) in EtOAc (45 mL) at ambient temperature. The resulting reaction mixture was then heated to reflux for 3 hours and upon cooling was filtered and concentrated in vacuo to afford the title compound as a brown oil (756 mg, 100% yield). The crude product was used directly in the next step without further purification.

¹H NMR (CDCl₃): δ 6.8 (s, 1H), 2.89 (m, 8H) and 2.09 (m, 4H).

Intermediate A2:
2-Isocyanato-1,3-diisopropylbenzene

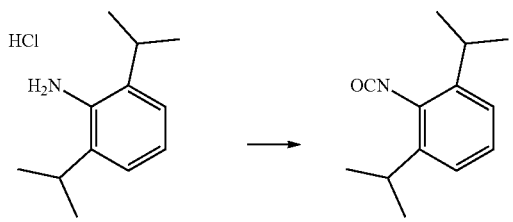

To a suspension of 2,6-diisopropylaniline hydrochloride (1 g, 4.7 mmol) in toluene (50 mL) was added 1 drop of pyridine and the resulting mixture was heated to near reflux whilst a solution of phosgene (7.3 mL, 20 wt % in toluene, 13.8 mmol) was added drop-wise over a period of 10 minutes. The mixture was stirred for an additional 45 minutes at 105° C. and then allowed to partially cool before being concentrated in vacuo to afford the title compound as a mobile yellow oil (1.5 g, >100% yield). The crude product was used directly in the next step without further purification.

¹H NMR (CDCl₃): δ 7.2 (m, 3H), 3.12 (m, 2H) and 1.25 (d, 12H).

Intermediate A3:
5-Fluoro-2-isocyanato-1,3-diisopropylbenzene

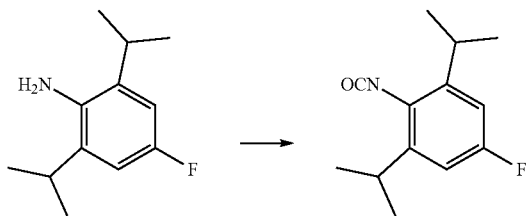

To a solution of 4-fluoro-2,6-diisopropylaniline (0.103 g, 0.527 mmol) in toluene (1.4 mL) was added a phosgene solution (0.69 mL, 20% weight in toluene, 1.3 mmol) and the reaction mixture was refluxed for 1 hour. Upon cooling, the mixture was concentrated in vacuo to afford the title compound as a brown oil (0.110 g, yield 100%). The crude product was used directly in the next step without further purification.

¹H NMR (CDCl₃): δ=6.80 (d, 2H), 3.20 (m, 2H), 1.24 (d, 12H).

Intermediate A4: 5-(2-Methoxypyridin-4-yl)-2,3-dihydro-1H-inden-4-amine

Step A:
N-(5-Bromo-2,3-dihydro-1H-inden-4-yl)pivalamide

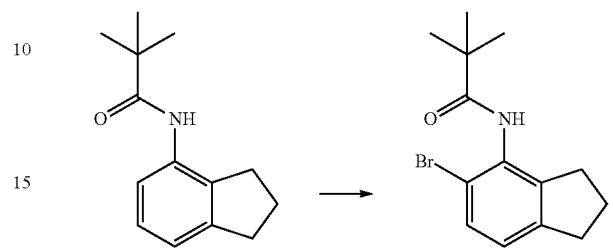

N-(2,3-Dihydro-1H-inden-4-yl)pivalamide (1 g, 4.60 mmol), p-toluenesulfonic acid monohydrate (0.45 g, 2.366 mmol), Pd(OAc)₂ (0.05 g, 0.223 mmol), and NBS (0.9 g, 5.06 mmol) were suspended in toluene (20 mL) and stirred for 16 hours. The dark green mixture was diluted with EtOAc (20 mL), and then washed with saturated aqueous NaHCO₃ (2×10 mL), water (2×10 mL) and brine (10 mL). The organic phase was dried (Na₂SO₄), filtered and concentrated in vacuo to give a dark green amorphous solid. The crude product was purified by chromatography on silica gel (40 g column, 0-% EtOAc/isohexane) to afford the title compound (1.662 g, 100%) as a colourless crystalline solid that was contaminated with a small amount of reaction byproducts.

LCMS: m/z 296.3/298.3 (M+H)⁺ (ES⁺).

Step B: 5-Bromo-2,3-dihydro-1H-inden-4-amine

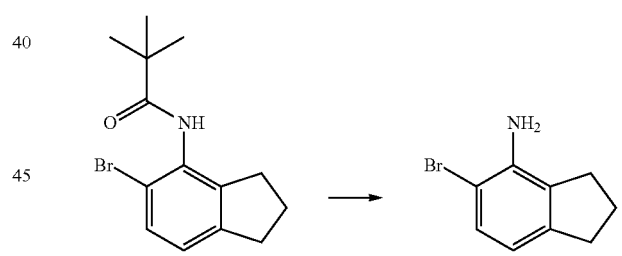

N-(5-Bromo-2,3-dihydro-1H-inden-4-yl)pivalamide (0.632 g, 2.134 mmol) was dissolved in ethanol (5 mL) and stirred at room temperature. H₂SO₄ (95% aqueous) (5 mL, 89 mmol) was slowly added to water (5 mL) and this mixture was then added to the reaction mixture. The slurry was heated to 100° C. (bath temperature) at which point the mixture became homogeneous and it was stirred at this temperature over the weekend. The mixture was cooled to room temperature and then basified with 2 M aqueous NaOH. The mixture was extracted with DCM (3×20 mL). The organic phase was dried by passing through a hydrophobic frit, and then concentrated in vacuo. The crude product was purified by chromatography on silica gel (40 g column, 0-50% EtOAc/isohexane) to afford the title compound (0.14 g, 29%).

¹H NMR (CDCl₃) δ 7.23 (d, J=7.9 Hz, 1H), 6.57 (d, J=8.0 Hz, 1H), 3.92 (s, 2H), 2.89 (t, J=7.6 Hz, 2H), 2.77 (t, J=7.4 Hz, 2H), 2.15 (p, J=7.5 Hz, 2H).

Step C: 5-(2-Methoxypyridin-4-yl)-2,3-dihydro-1H-inden-4-amine

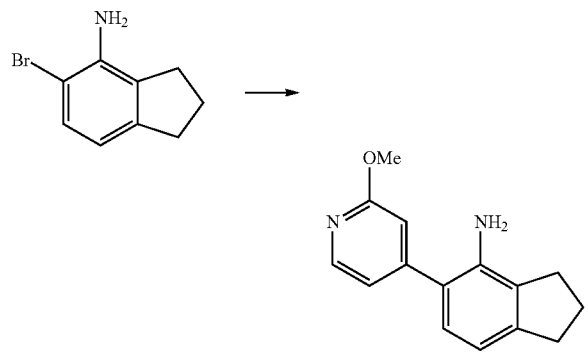

5-Bromo-2,3-dihydro-1H-inden-4-amine (280 mg, 1.320 mmol) was dissolved in dioxane (5 mL). A solution of potassium carbonate (600 mg, 4.34 mmol) in water (1 mL) and (2-methoxypyridin-4-yl)boronic acid (250 mg, 1.635 mmol) were added. The mixture was degassed with nitrogen for 15 minutes before Pd(dppf)Cl$_2$.DCM (60 mg, 0.073 mmol) was added. The reaction mixture was heated to 80° C. (bath temperature) for 2 hours. Then the mixture was cooled to room temperature and partitioned between DCM (30 mL) and water (20 mL). The organic phase was dried by passing through a hydrophobic frit and concentrated in vacuo to give a brown oil. The crude product was purified by chromatography on silica gel (12 g column, 0-50% EtOAc/isohexane) to afford the title compound (0.29 g, 87%) as a pale yellow crystalline solid.

$^1$H NMR (CDCl$_3$) δ 8.26 (d, J=5.4 Hz, 1H), 7.11 (d, J=5.0 Hz, 1H), 7.01 (d, J=7.7 Hz, 1H), 6.97 (s, 1H), 6.80 (d, J=7.6 Hz, 1H), 4.06 (s, 3H), 2.98 (t, J=7.6 Hz, 2H), 2.80 (t, J=7.4 Hz, 2H), 2.19 (p, J=7.5 Hz, 2H). Two exchangeable protons not observed.

LCMS: m/z 241.3 (M+H)$^+$ (ES$^+$).

Intermediate A5: 4-(4-Amino-2,3-dihydro-1H-inden-5-yl)picolinonitrile

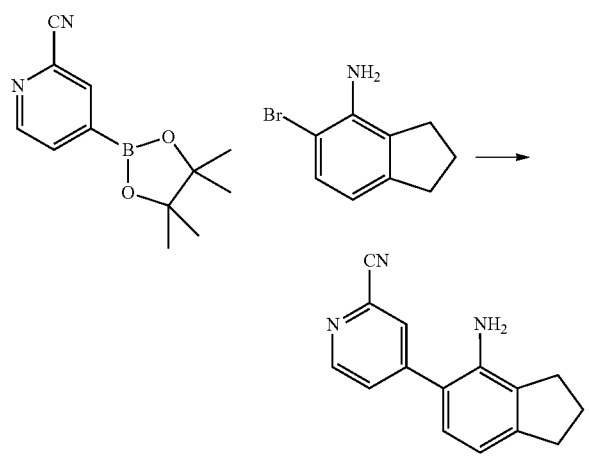

Prepared according to the general procedure of 5-(2-methoxypyridin-4-yl)-2,3-dihydro-1H-inden-4-amine (Intermediate A4, Step C) from 5-bromo-2,3-dihydro-1H-inden-4-amine (Intermediate A4, Step B) and 4-(4,4,5,5-tetramethyl-1,3,2-dioxaborolan-2-yl)picolinonitrile to afford the title compound (215 mg, 61%) as a pale yellow solid.

$^1$H (DMSO-d6) δ 8.72 (dd, J=5.1, 0.8 Hz, 1H), 8.03 (dd, J=1.8, 0.8 Hz, 1H), 7.74 (dd, J=5.1, 1.8 Hz, 1H), 6.91 (d, J=7.7 Hz, 1H), 6.61 (d, J=7.7 Hz, 1H), 4.94 (s, 2H), 2.83 (t, J=7.4 Hz, 2H), 2.71 (t, J=7.4 Hz, 2H), 2.03 (p, J=7.4 Hz, 2H).

LCMS: m/z 236.3 (M+H)$^+$ (ES$^+$).

Intermediate A6: 4-(5-Fluoro-2-isocyanato-3-isopropylphenyl)picolino-nitrile

Step A: 4-Fluoro-2-(prop-1-en-2-yl)aniline

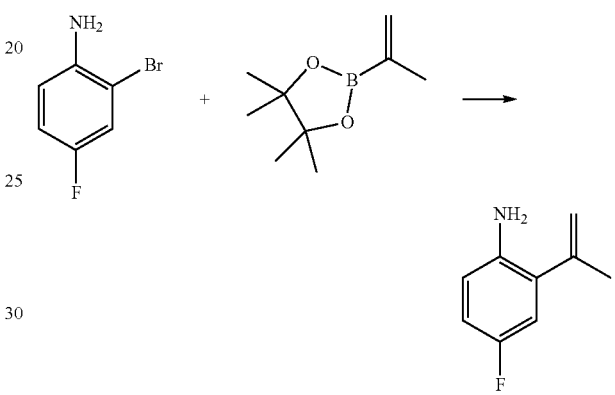

To a mixture of 2-bromo-4-fluoroaniline (39 g, 205.25 mmol, 1 eq), 4,4,5,5-tetramethyl-2-(prop-1-en-2-yl)-1,3,2-dioxaborolane (36.21 g, 215.51 mmol, 1.05 eq) and K$_2$CO$_3$ (70.92 g, 513.12 mmol, 2.5 eq) in dioxane (200 mL) and H$_2$O (40 mL) was added Pd(dppf)Cl$_2$ (7.51 g, 10.26 mmol, 0.05 eq) under a nitrogen atmosphere. Then the reaction mixture was stirred at 80° C. for 5 hours. The reaction mixture was quenched by addition of H$_2$O (600 mL) and extracted with EtOAc (2×500 mL). The combined organic layers were washed with brine (2×600 mL), dried over anhydrous Na$_2$SO$_4$, filtered and concentrated under reduced pressure. The residue was purified by silica gel column chromatography (SiO$_2$, petroleum ether:ethyl acetate 1:0 to 100:1) to give the title compound (27 g, 77% yield, 89% purity on LCMS) as a yellow oil.

$^1$H NMR (CDCl$_3$) δ 6.81-6.76 (m, 2H), 6.66-6.62 (m, 1H), 5.38 (s, 1H), 5.08 (s, 1H), 3.69 (br s, 2H) and 1.25 (s, 3H).

LCMS: m/z 152.2 (M+H)$^+$ (ES$^+$).

Step B: 4-Fluoro-2-isopropylaniline

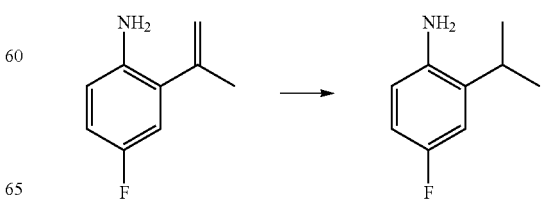

To a solution of 4-fluoro-2-(prop-1-en-2-yl)aniline (21 g, 138.91 mmol, 1 eq) in MeOH (300 mL) was added Pd/C (2.1 g, 178.59 mmol, 10 wt % loading on activated carbon) under a nitrogen atmosphere. The reaction mixture was degassed in vacuo and purged with hydrogen several times. The reaction mixture was stirred at 25° C. for 12 hours under hydrogen (50 psi). The reaction mixture was filtered and the filtrate was concentrated in vacuo to give the title compound (20 g, crude) as a yellow oil.

$^1$H NMR (CDCl$_3$) δ 6.86 (dd, 1H), 6.75-6.72 (m, 1H), 6.63-6.61 (m, 1H), 3.50 (br s, 2H), 2.95-2.84 (m, 1H) and 1.25 (d, 6H).

LCMS: m/z 154.2 (M+H)$^+$ (ES$^+$).

Step C: 2-Bromo-4-fluoro-6-isopropylaniline

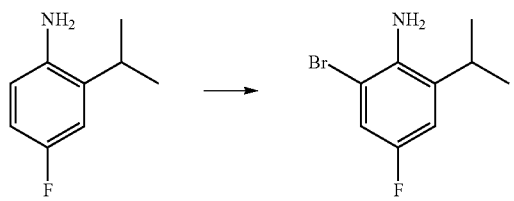

To a solution of 4-fluoro-2-isopropylaniline (20 g, 130.55 mmol, 1 eq) in toluene (250 mL) was added NBS (23.24 g, 130.55 mmol, 1 eq) at 25° C. The reaction mixture was stirred at 25° C. for 10 minutes. The reaction mixture was poured into H$_2$O (300 mL) and extracted with EtOAc (2×250 mL). The combined organic phases were washed with brine (2×400 mL), dried over anhydrous Na$_2$SO$_4$, filtered and concentrated in vacuo. The residue was purified by silica gel column chromatography (SiO$_2$, eluting only by using petroleum ether) to give the title compound (30 g, 99%) as a black brown oil.

$^1$H NMR (CDCl$_3$) δ 6.99 (dd, 1H), 6.78 (dd, 1H), 3.91 (br s, 2H), 2.88-2.71 (m, 1H) and 1.17 (d, 6H).

LCMS: m/z 232.1 (M+H)$^+$ (ES$^+$).

Step D: 4-(2-Amino-5-fluoro-3-isopropylphenyl)picolinonitrile

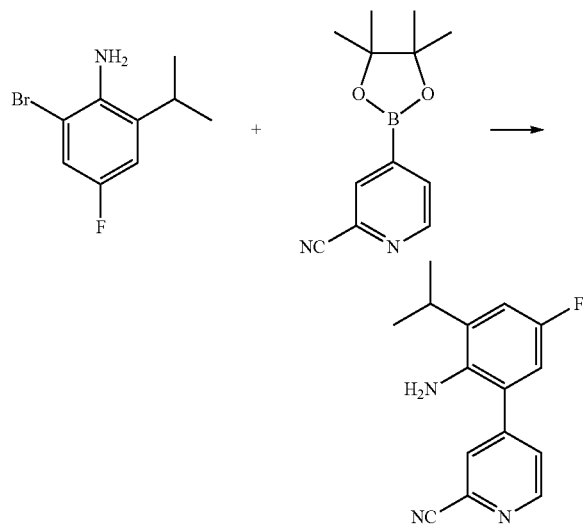

To a solution of 2-bromo-4-fluoro-6-isopropylaniline (3.6 g, 15.51 mmol, 1 eq) and 4-(4,4,5,5-tetramethyl-1,3,2-dioxaborolan-2-yl)picolinonitrile (3.60 g, 15.67 mmol, 1.01 eq) in dioxane (90 mL) and H$_2$O (9 mL) was added Na$_2$CO$_3$ (4.11 g, 38.78 mmol, 2.5 eq). Then Pd(dppf)C$_2$ (1.13 g, 1.55 mmol, 0.1 eq) was added to the mixture under a nitrogen atmosphere. The resulting mixture was stirred at 80° C. for 2 hours under nitrogen. Then the mixture was concentrated in vacuo. The residue was purified by silica gel column chromatography (SiO$_2$, petroleum ether:ethyl acetate, 20:1 to 5:1) and then triturated with petroleum ether (10 mL) to give the title compound (2.65 g, 65% yield, 97% purity on LCMS) as a yellow solid.

$^1$HNMR (CDCl$_3$) δ 8.79 (d, 1H), 7.86 (d, 1H), 7.65 (dd, 1H), 6.99 (dd, 1H), 6.70 (dd, 1H), 3.63 (br s, 2H), 2.98-2.87 (m, 1H) and 1.30 (d, 6H).

LCMS: m/z 256.2 (M+H)$^+$ (ES$^+$).

Step E: 4-(5-Fluoro-2-isocyanato-3-isopropylphenyl)picolinonitrile

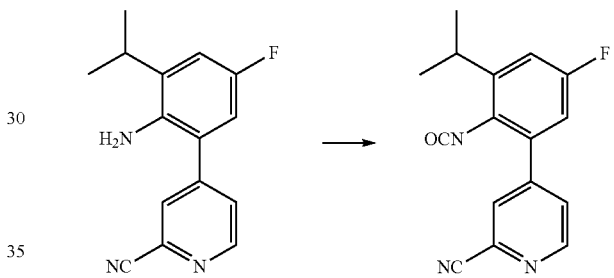

To a solution of 4-(2-amino-5-fluoro-3-isopropylphenyl)picolinonitrile (1 g, 3.92 mmol, 1 eq) in THF (40 mL) was added TEA (793 mg, 7.83 mmol, 2 eq). To the above mixture was added triphosgene (465 mg, 1.57 mmol, 0.4 eq) in portions at 5° C. Then the mixture was stirred at 70° C. for 1 hour. The mixture was diluted with EtOAc (200 mL) and then filtered through silica gel. The filtrate was concentrated in vacuo to give the title compound (1.2 g, crude) as a yellow solid, which was used directly in the next step.

Intermediate A7: 4-(5-Fluoro-2-isocyanato-3-isopropylphenyl)-2-methoxypyridine

Step A: 4-Fluoro-2-isopropyl-6-(2-methoxypyridin-4-yl)aniline

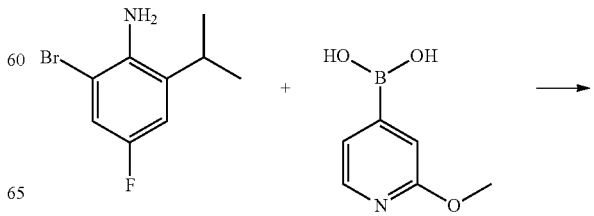

-continued

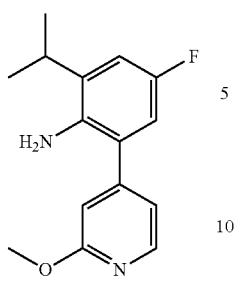

To a solution of 2-bromo-4-fluoro-6-isopropylaniline (12 g, 51.70 mmol, 1 eq) in dioxane (240 mL) and H$_2$O (48 mL) was added (2-methoxypyridin-4-yl)boronic acid (9.49 g, 62.04 mmol, 1.2 eq) and Na$_2$CO$_3$ (13.70 g, 129.26 mmol, 2.5 eq). The reaction mixture was purged with nitrogen three times. Then Pd(dppf)Cl$_2$ (3.78 g, 5.17 mmol, 0.1 eq) was added to the mixture under a nitrogen atmosphere. The resulting mixture was heated at 80° C. for 2 hours. The reaction mixture was quenched with H$_2$O (800 mL) and extracted with EtOAc (2×600 mL). The combined organic layers were washed with brine (2×800 mL), dried over anhydrous Na$_2$SO$_4$, filtered and concentrated under reduced pressure. The residue was purified by silica gel column chromatography (SiO$_2$, petroleum ether:ethyl acetate, 70:1 to 10:1) and then triturated with hexane (100 mL) to give the title compound (10.05 g, 72% yield, 96% purity on LCMS).

$^1$H NMR (CDCl$_3$) δ 8.24 (d, 1H), 6.97 (d, 1H), 6.93 (d, 1H), 6.83 (s, 1H), 6.73-6.70 (m, 1H), 3.99 (s, 3H), 3.66 (br s, 2H), 2.97-2.89 (m, 1H) and 1.29 (dd, 6H).

LCMS: m/z 261.1 (M+H)$^+$ (ES$^+$).

Step B: 4-(5-Fluoro-2-isocyanato-3-isopropylphenyl)-2-methoxypyridine

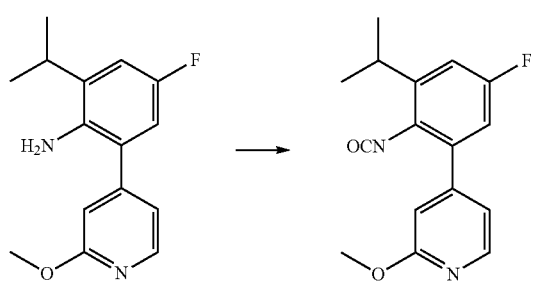

To a solution of 4-fluoro-2-isopropyl-6-(2-methoxypyridin-4-yl)aniline (1 g, 3.84 mmol, 1 eq) in THF (40 mL) was added TEA (777 mg, 7.68 mmol, 2 eq). Then triphosgene (456 mg, 1.54 mmol, 0.4 eq) was added in portions at 5° C. The mixture was stirred at 70° C. for 1 hour. The mixture was diluted with EtOAc (200 mL) and filtered through silica gel. The filtrate was concentrated in vacuo to give the title compound (1.1 g, crude) as a yellow oil, which was used directly in the next step.

Intermediate A8: 4-(4-Isocyanato-2,3-dihydro-1H-inden-5-yl)-2-methoxypyridine

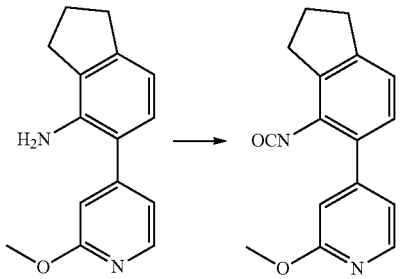

To a solution of 5-(2-methoxypyridin-4-yl)-2,3-dihydro-1H-inden-4-amine (Intermediate A4) (11 g, 45.78 mmol, 1 eq) and TEA (5.10 g, 50.35 mmol, 1.1 eq) in THF (275 mL) was added in portions bis(trichloromethyl) carbonate (4.93 g, 16.61 mmol, 0.36 eq) at 0° C. Then the reaction mixture was stirred at 16° C. for 0.5 hour. The reaction mixture was filtered and the filter cake was washed with THF (2 L). The filtrate was concentrated in vacuo to give the title compound (9.04 g, 74%) as a light yellow solid.

$^1$H NMR (CDCl$_3$) δ 8.28 (d, 1H), 7.20-7.16 (m, 3H), 7.02 (s, 1H), 4.16 (s, 3H), 3.04-2.99 (m, 4H) and 2.23-2.15 (m, 2H).

Intermediate A9: 4-(7-Fluoro-4-isocyanato-2,3-dihydro-1H-inden-5-yl) pyridine

Step A: 7-Fluoro-4-nitro-2,3-dihydro-1H-inden-1-one

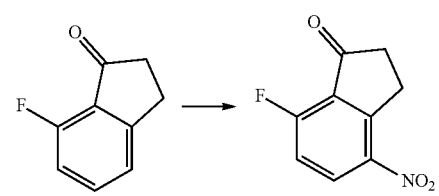 [SMILES: O=C1CCc2cccc(F)c21 ; O=C1CCc2c([N+](=O)[O-])ccc(F)c21]

To a mixture of 7-fluoro-2,3-dihydro-1H-inden-1-one (9.5 g, 63.27 mmol, 1 eq) in concentrated H$_2$SO$_4$ (100 mL) was added dropwise a solution of HNO$_3$ (5.37 mL, 82.25 mmol, 69 wt % in water, 1.3 eq) in concentrated H$_2$SO$_4$ (20 mL) at −15° C. Then the reaction mixture was stirred at 0° C. for 0.5 hour. The mixture was quenched with water (500 mL) at 0° C., and then extracted with EtOAc (3×300 mL). The combined organic phases were dried over anhydrous Na$_2$SO$_4$, filtered and concentrated in vacuo. The residue was purified by silica gel column chromatography (SiO$_2$, petroleum ether:ethyl acetate, 10:1 to 3:1) to give the title compound (11.4 g, 92%) as a yellow solid.

$^1$H NMR (CDCl$_3$) δ 8.51 (dd, 1H), 7.22 (t, 1H), 3.69-3.65 (m, 2H) and 2.88-2.82 (m, 2H).

Step B: 7-Fluoro-4-nitro-2,3-dihydro-1H-inden-1-ol

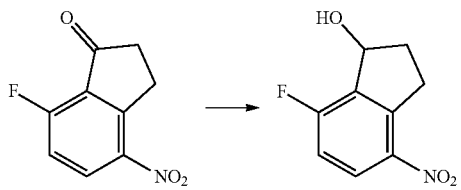 [SMILES: O=C1CCc2c([N+](=O)[O-])ccc(F)c21 ; O=[N+]([O-])c1ccc(F)c2c1CCC2O]

To a mixture of 7-fluoro-4-nitro-2,3-dihydro-1H-inden-1-one (30 g, 153.73 mmol, 1 eq) in EtOH (450 mL) was added NaBH$_4$ (11.63 g, 307.46 mmol, 2 eq) in portions. The reaction mixture was stirred at 15° C. for 1 hour. Then the mixture was poured into water (50 mL) and extracted with DCM (2×200 mL). The combined organic phases were washed with brine (200 mL), dried over anhydrous Na$_2$SO$_4$, filtered and concentrated in vacuo to give the title compound (30 g, crude) as brown oil.

$^1$H NMR (CDCl$_3$) δ 8.21 (dd, 1H), 7.08 (t, 1H), 5.59-5.56 (m, 1H), 3.66-3.59 (m, 1H), 3.44-3.39 (m, 1H), 2.56-2.51 (m, 1H) and 2.22-2.17 (m, 2H).

Step C: 4-Fluoro-7-nitro-2,3-dihydro-1H-indene

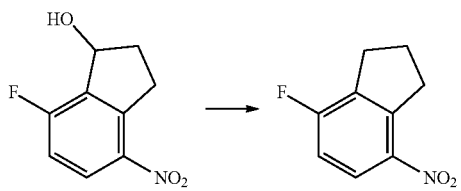 [SMILES: O=[N+]([O-])c1ccc(F)c2c1CCC2O ; O=[N+]([O-])c1ccc(F)c2c1CCC2]

To a mixture of 7-fluoro-4-nitro-2,3-dihydro-1H-inden-1-ol (4.5 g, 22.82 mmol, 1 eq) in TFA (20 mL) was added Et$_3$SiH (7.96 g, 68.47 mmol, 3 eq) in one portion. The reaction mixture was stirred at 25° C. for 12 hours. Then the mixture was quenched with water (100 mL) and extracted with EtOAc (3×100 mL). The combined organic layers were washed with saturated aqueous NaHCO$_3$ solution (2×100 mL), dried over anhydrous Na$_2$SO$_4$, filtered and concentrated in vacuo to give the title compound (5 g, crude) as brown oil.

$^1$H NMR (CDCl$_3$) δ 8.06 (dd, 1H), 7.01 (t, 1H), 3.46 (t, 2H), 3.04 (t, 2H) and 2.25-2.20 (m, 2H).

Step D: 7-Fluoro-2,3-dihydro-1H-inden-4-amine

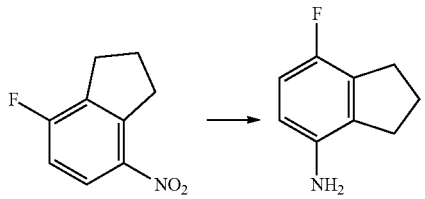 [SMILES: O=[N+]([O-])c1ccc(F)c2c1CCC2 ; Nc1ccc(F)c2c1CCC2]

To a mixture of 4-fluoro-7-nitro-2,3-dihydro-1H-indene (5 g, 27.60 mmol, 1 eq) in MeOH (50 mL) was added Pd/C (0.5 g, 10 wt % loading on activated carbon) at 25° C. under a nitrogen atmosphere. Then the reaction mixture was stirred at 25° C. for 12 hours under hydrogen (15 psi). The mixture was filtered and the filtrate was concentrated in vacuo. The residue was purified by silica gel column chromatography (SiO$_2$, petroleum ether:ethyl acetate, 50:1 to 10:1) to give the title compound (1.8 g, 43%) as a brown solid.

$^1$H NMR (CDCl$_3$) δ 6.69 (t, 1H), 6.44 (dd, 1H), 3.47 (br s, 2H), 2.95 (t, 2H), 2.75 (t, 2H) and 2.19-2.11 (m, 2H).

Step E:
5-Bromo-7-fluoro-2,3-dihydro-1H-inden-4-amine

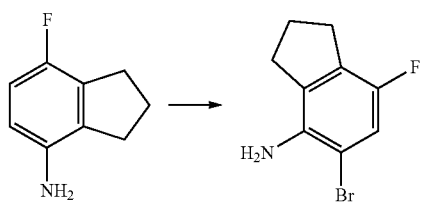 [SMILES: Nc1ccc(F)c2c1CCC2 ; Nc1c(Br)cc(F)c2c1CCC2]

To a solution of 7-fluoro-2,3-dihydro-1H-inden-4-amine (8.3 g, 54.90 mmol, 1 eq) in toluene (100 mL) was added NBS (10.26 g, 57.65 mmol, 1.05 eq) in one portion at 25° C. The reaction mixture turned dark brown immediately and then the mixture was stirred at 25° C. for 30 minutes. The reaction mixture was quenched with saturated aqueous Na$_2$SO$_3$ solution (200 mL) and extracted with EtOAc (2×100 mL). The combined organic phases were washed with brine (100 mL), dried over anhydrous Na$_2$SO$_4$, filtered and concentrated in vacuo. The residue was purified by silica gel column chromatography (SiO$_2$, petroleum ether:ethyl acetate, 1:0 to 20:1) to give the title compound (8.51 g, 67%) as a brown solid.

$^1$H NMR (CDCl$_3$) δ 6.99 (d, 1H), 3.81 (br s, 2H), 2.92 (t, 2H), 2.78 (t, 2H) and 2.21-2.13 (m, 2H).

Step F: 7-Fluoro-5-(pyridin-4-yl)-2,3-dihydro-1H-inden-4-amine

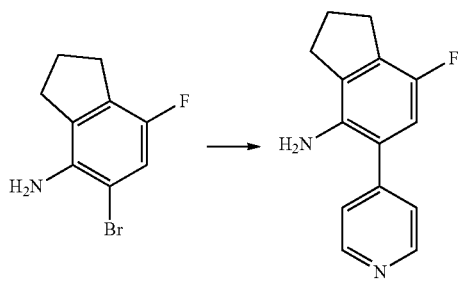 [SMILES: Nc1c(Br)cc(F)c2c1CCC2 ; Nc1c(-c2ccncc2)cc(F)c2c1CCC2]

To a mixture of 5-bromo-7-fluoro-2,3-dihydro-1H-inden-4-amine (3.5 g, 15.21 mmol, 1 eq) and pyridin-4-ylboronic acid (1.96 g, 15.97 mmol, 1.05 eq) in dioxane (50 mL) and H$_2$O (5 mL) was added K$_2$CO$_3$ (6.31 g, 45.64 mmol, 3 eq) and Pd(dppf)Cl$_2$ (1.11 g, 1.52 mmol, 0.1 eq) in one portion under a nitrogen atmosphere. Then the reaction mixture was heated to 80° C. for 12 hours. The reaction mixture was filtered. The filtrate was diluted with water (50 mL) and extracted with EtOAc (3×100 mL). The combined organic phases were washed with brine (100 mL), dried over anhydrous Na$_2$SO$_4$, filtered and concentrated in vacuo. The residue was purified by silica gel column chromatography (SiO$_2$, petroleum ether:ethyl acetate, 10:1 to 2:1) to give the title compound (1.7 g, 45% yield, 90.98% purity on HPLC) as a brown solid.

$^1$H NMR (CDCl$_3$) δ 8.68 (dd, 2H), 7.40 (dd, 2H), 6.72 (d, 1H), 3.76 (br s, 2H), 3.01 (t, 2H), 2.80 (t, 2H) and 2.26-2.18 (m, 2H).

Step G: 4-(7-Fluoro-4-isocyanato-2,3-dihydro-1H-inden-5-yl)pyridine

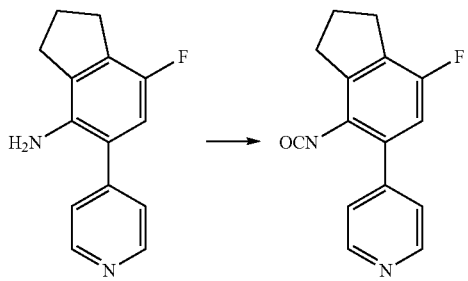

To a solution of 7-fluoro-5-(pyridin-4-yl)-2,3-dihydro-1H-inden-4-amine (400 mg, 1.75 mmol, 1 eq) and TEA (355 mg, 3.50 mmol, 2 eq) in THF (30 mL) was added bis(trichloromethyl) carbonate (208 mg, 700.94 µmol, 0.4 eq) at 0° C. The reaction mixture was stirred at 70° C. for 30 minutes. Then the reaction mixture was filtered through a pad of silica gel and the filter cake was washed with THF (20 mL). The filtrate was concentrated in vacuo to reduce to 10 mL, which was used directly in the next step.

Intermediate A10: 3-(5-Fluoro-2-isocyanato-3-isopropylphenyl)pyridine

Step A: 4-Fluoro-2-isopropyl-6-(pyridin-3-yl)aniline

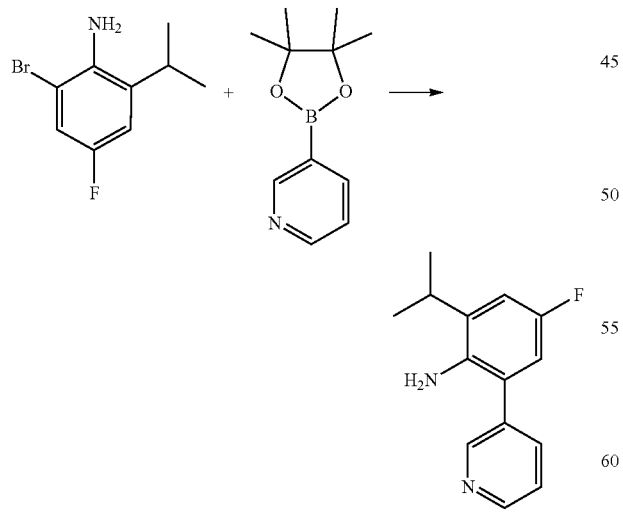

To a solution of 2-bromo-4-fluoro-6-isopropylaniline (21 g, 90.48 mmol, 1 eq) in dioxane (450 mL) and H$_2$O (90 mL) was added 3-(4,4,5,5-tetramethyl-1,3,2-dioxaborolan-2-yl)pyridine (22.26 g, 108.58 mmol, 1.2 eq) and Na$_2$CO$_3$ (23.98 g, 226.20 mmol, 2.5 eq). The reaction mixture was purged with nitrogen three times. Then Pd(dppf)Cl$_2$ (5.10 g, 6.97 mmol, 0.077 eq) was added under a nitrogen atmosphere. The resulting mixture was heated to 80° C. and stirred for 2 hours. The reaction mixture was quenched by addition of H$_2$O (800 mL) and extracted with EtOAc (2×600 mL). The combined organic layers were washed with brine (2×800 mL), dried over anhydrous Na$_2$SO$_4$, filtered and concentrated under reduced pressure. The residue was purified by silica gel column chromatography (SiO$_2$, petroleum ether:ethyl acetate, 50:1 to 1:1) and then triturated with hexane (40 mL) to give the title compound (17 g, 82%) as a grey solid.

$^1$H NMR (CDCl$_3$) δ 8.70 (d, 1H), 8.63 (dd, 1H), 7.79 (dd, 1H), 7.41-7.38 (m, 1H), 6.94 (dd, 1H), 6.71 (dd, 1H), 3.57 (s, 2H), 2.97-2.88 (m, 1H) and 1.30 (d, 6H).

LCMS: m/z 231.2 (M+H)$^+$ (ES$^+$).

Step B: 3-(5-Fluoro-2-isocyanato-3-isopropylphenyl)pyridine

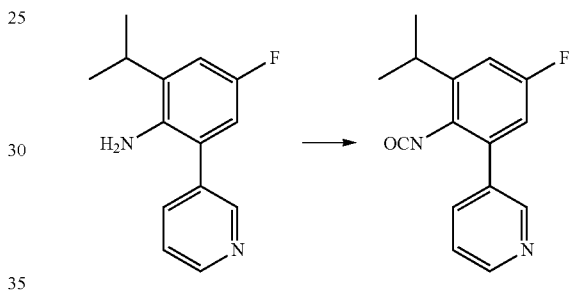

To a solution of 4-fluoro-2-isopropyl-6-(pyridin-3-yl)aniline (0.5 g, 2.17 mmol, 1 eq) and TEA (439 mg, 4.34 mmol, 2 eq) in THF (10 mL) was added triphosgene (257 mg, 868.51 µmol, 0.4 eq) in portions at 5° C. Then the reaction mixture was heated to 70° C. and stirred for 1 hour. The reaction mixture was concentrated in vacuo. The residue was treated with EtOAc (100 mL) and filtered. The filtrate was concentrated in vacuo to give the title compound (0.2 g, crude) as a yellow oil, which was used directly in the next step.

Intermediate A11: 4-(7-Fluoro-4-isocyanato-2,3-dihydro-1H-inden-5-yl)-2-methoxypyridine Step A: 7-Fluoro-5-(2-methoxypyridin-4-yl)-2,3-dihydro-1H-inden-4-amine

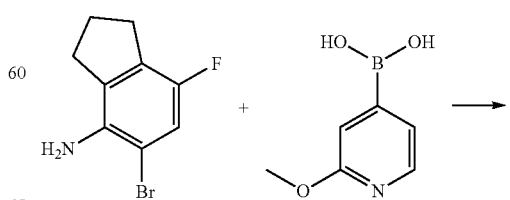

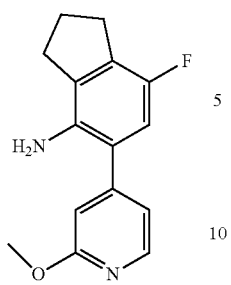

To a mixture of 5-bromo-7-fluoro-2,3-dihydro-1H-inden-4-amine (Intermediate A9, Step E) (8.5 g, 36.94 mmol, 1 eq) and (2-methoxypyridin-4-yl)boronic acid (5.93 g, 38.79 mmol, 1.05 eq) in dioxane (150 mL) and water (15 mL) were added K$_2$CO$_3$ (15.32 g, 110.83 mmol, 3 eq) and Pd(dppf)Cl$_2$ (2.70 g, 3.69 mmol, 0.1 eq) in one portion under nitrogen. Then the reaction mixture was heated to 80° C. and stirred for 12 hours. The reaction mixture was quenched with water (300 mL) and extracted with EtOAc (3×300 mL). The combined organic layers were washed with brine (100 mL), dried with anhydrous Na$_2$SO$_4$, filtered and concentrated in vacuo. The residue was purified by silica gel chromatography (petroleum ether:EtOAc, 1:0 to 10:1) and then purified by trituration with a mixture of TBME and n-hexane (50 mL, 1:20) to give the title compound (5.06 g, 52% yield, 97.44% purity on LCMS) as an off-white solid.

$^1$H NMR (CDCl$_3$) δ 8.23 (d, 1H), 6.99 (dd, 1H), 6.86 (s, 1H), 6.71 (d, 1H), 3.99 (s, 3H), 3.67 (br s, 2H), 3.00 (t, 2H), 2.79 (t, 2H) and 2.25-2.17 (m, 2H).

Step B: 4-(7-Fluoro-4-isocyanato-2,3-dihydro-1H-inden-5-yl)-2-methoxypyridine

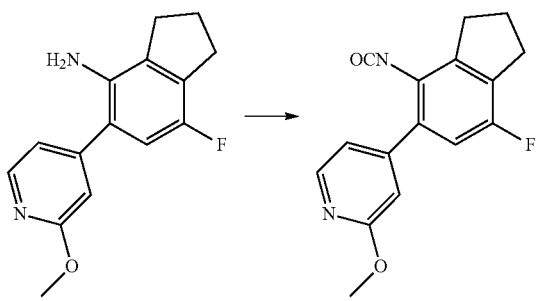

To a solution of phosgene (1.5 mL, 20 wt % in toluene, 2.9 mmol) in toluene (40 mL) was added dropwise a solution of 7-fluoro-5-(2-methoxypyridin-4-yl)-2,3-dihydro-1H-inden-4-amine (300 mg, 1.16 mmol) in toluene (20 mL) at ambient temperature. The resulting reaction mixture was then heated to reflux for 70 minutes and upon cooling was concentrated in vacuo to afford the title compound as a brown oil (325 mg, 98%).
The crude product was used directly in the next step without further purification.

$^1$H NMR (CDCl$_3$) δ 8.24 (d, 1H), 6.95 (dd, 1H), 6.88 (s, 1H), 6.85-6.75 (m, 1H), 4.00 (s, 3H), 3.15-2.95 (m, 4H), 2.32-2.12 (m, 2H).

Intermediate A12:
4-(4-Isocyanato-2,3-dihydro-1H-inden-5-yl) Picolinonitrile

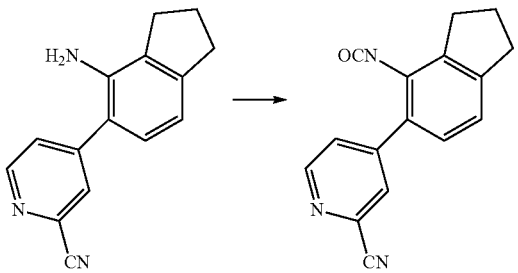

To a solution of phosgene (1.7 mL, 20 wt % in toluene, 3.2 mmol) in toluene (40 mL) was added dropwise a solution of 4-(4-amino-2,3-dihydro-1H-inden-5-yl)picolinonitrile (Intermediate A5) (300 mg, 1.3 mmol) in toluene (20 mL) at ambient temperature. The resulting reaction mixture was then heated to reflux for 70 minutes and upon cooling was concentrated in vacuo to afford the title compound as a brown oil (333 mg, 100%). The crude product was used directly in the next step without further purification.

$^1$H NMR (CDCl$_3$) δ 8.75 (dd, 1H), 7.81 (dd, 1H), 7.63 (dd, 1H), 7.22-7.08 (m, 2H), 3.04 (m, 4H), 2.23 (m, 2H).

Intermediate A13:
4-(4-Isocyanato-2,3-dihydro-1H-inden-5-yl)pyridine

Step A: 5-(Pyridin-4-yl)-2,3-dihydro-1H-inden-4-amine

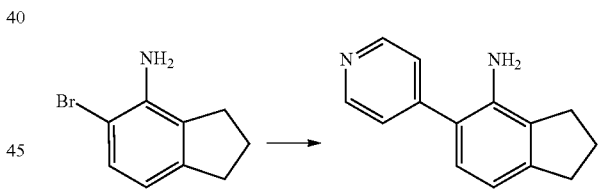

5-Bromo-2,3-dihydro-1H-inden-4-amine (1.2 g, 5.7 mmol) was dissolved in dioxane (25 mL). A solution of potassium carbonate (3.1 g, 23 mmol) in water (6 mL) and pyridin-4-ylboronic acid (0.83 g, 6.8 mmol) were added. The mixture was degassed with nitrogen for 20 minutes before Pd(dppf)Cl$_2$.DCM (0.74 g, 0.91 mmol) was added. The reaction mixture was heated to 77° C. for 2 hours. Then the mixture was cooled to room temperature and filtered over Celite with DCM (100 mL) and water (25 mL). The organic phase was dried (Na$_2$SO$_4$), filtered and concentrated in vacuo to give a brown oil (3.3 g). The crude product was purified by chromatography on silica gel (80 g column, 0-100% EtOAc/heptane) to afford the title compound (0.75 g, 63%) as a pale yellow crystalline solid.

$^1$H NMR (CDCl$_3$) δ 8.72-8.54 (m, 2H), 7.50-7.37 (m, 2H), 6.97 (d, 1H), 6.78 (d, 1H), 3.72 (s, 2H), 2.96 (t, 2H), 2.77 (t, 2H), 2.18 (m, 2H).

Step B:
4-(4-Isocyanato-2,3-dihydro-1H-inden-5-yl)pyridine

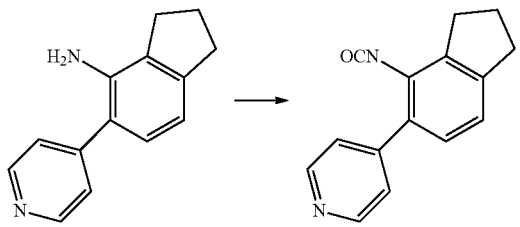

To a solution of phosgene (1.1 mL, 20 wt % in toluene, 2.06 mmol) in toluene (40 mL) was added dropwise a solution of 5-(pyridin-4-yl)-2,3-dihydro-1H-inden-4-amine (175 mg, 0.83 mmol) in toluene (20 mL) at ambient temperature. The resulting reaction mixture was then heated to reflux for 70 minutes and upon cooling to room temperature a yellow precipitate was formed. The solid was filtered and dried in vacuo to afford the title compound as a yellow solid (145 mg, 74%). The crude product was used directly in the next step without further purification.
¹H NMR (CDCl₃) δ 8.76 (d, 2H), 8.04 (d, 2H), 7.26-7.08 (m, 2H), 3.08 (t, 4H), 2.26 (m, 2H).

Intermediate A14:
8-Isocyanato-1,2,3,5-tetrahydro-s-indacene

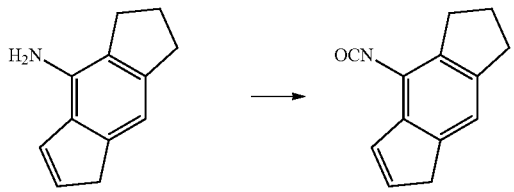

To a solution of phosgene (1.4 mL, 20 wt % in toluene, 2.6 mmol) in toluene (40 mL) was added dropwise a solution of 1,2,3,7-tetrahydro-s-indacen-4-amine (180 mg, 1.05 mmol) in toluene (20 mL) at ambient temperature. The resulting reaction mixture was then heated to reflux for 70 minutes and upon cooling was concentrated in vacuo to afford the title compound as a brown oil (207 mg, 100%). The crude product was used directly in the next step without further purification.
¹H NMR (CDCl₃) (mixture of isomers) δ 7.18, 7.12 (m, 1H), 6.94, 6.80 (m, 1H), 6.52, 6.50 (s, 1H), 3.38, 3.34 (m, 2H), 2.95 (m, 4H), 2.16 (m, 2H).

Intermediate A15:
5-Chloro-2-isocyanato-1,3-diisopropylbenzene

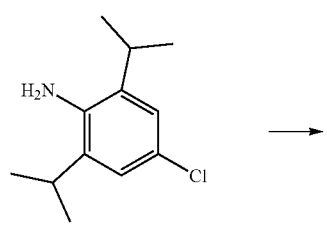

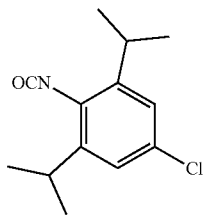

To a solution of 4-chloro-2,6-diisopropylaniline (0.105 g, 0.496 mmol) in toluene (1 mL) was added a phosgene solution (0.65 mL, 20 wt % in toluene, 1.22 mmol) and the reaction mixture was refluxed for 1 hour. Upon cooling, the mixture was concentrated in vacuo to afford the title compound as an orange oil (0.111 g, 94%).
¹H NMR (CDCl₃) δ 7.07 (d, 2H), 3.17 (h, 2H), 1.24 (d, 12H).

Intermediate P3:
1-(Prop-2-yn-1-yl)piperidine-4-sulfonamide

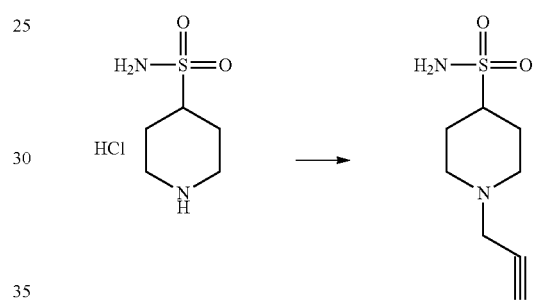

To a mixture of piperidine-4-sulfonamide hydrochloric acid (200 mg, 1.0 mmol, 1.0 equiv.), potassium carbonate (4.0 equiv., 4.0 mmol, 552 mg) and acetonitrile (10 mL) was added propargyl bromide (0.1 mL, 1.0 mmol, 1.0 equiv.). After stirring overnight at room temperature, the reaction mixture was concentrated in vacuo and the crude material was suspended in methanol, coated on Agilent hydromatrix (a high purity, inert diatomaceous earth sorbent) and then submitted to normal phase flash chromatography using dichloromethane and a mixture of ammonia (3.5 M) in methanol to afford the title compound (115 mg, 56%).
¹H NMR (CDCl₃): δ 4.42 (br s, 1H), 3.38 (s, 2H), 3.05 (d, 2H), 2.95 (m, 1H), 2.12 (m, 4H) and 1.95 (m, 2H).

Intermediate P4:
1-(2,2,2-Trifluoroacetyl)piperidine-4-sulfonamide

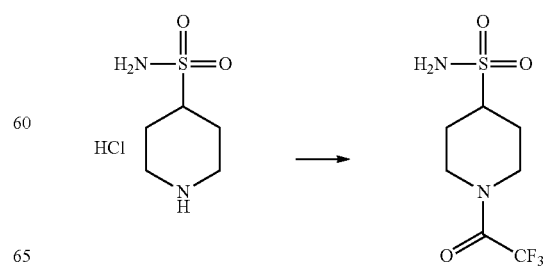

To a suspension of piperidine-4-sulfonamide hydrochloric acid (200 mg, 1.0 mmol, 1.0 equiv.) and triethylamine (0.35 mL, 2.5 mmol, 2.5 equiv.) in acetonitrile (10 mL) was added trifluoroacetic anhydride (0.14 mL, 1.0 mmol, 1.0 equiv.). After stirring overnight at room temperature, the reaction mixture was concentrated in vacuo. The crude product was suspended in methanol, coated on Agilent hydromatrix (a high purity, inert diatomaceous earth sorbent) and submitted to normal phase flash chromatography using dichloromethane and a mixture of trimethylamine-methanol (ratio 1:1) to afford the title compound (61 mg, yield 23%).

$^1$H NMR (CDCl$_3$): δ 4.73 (d, 1H), 4.52 (s, 2H), 4.20 (d, 1H), 3.21 (t, 2H), 2.91 (t, 1H), 2.37 (d, 2H) and 1.95 (m, 2H).

Intermediate P5:
N-iso-Propyl-4-sulfamoylpiperidine-1-carboxamide

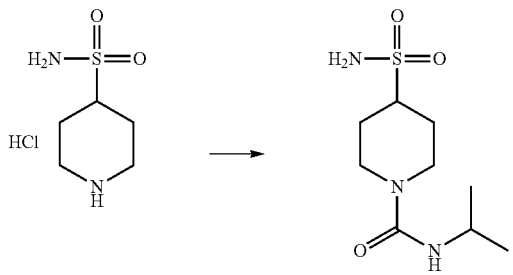 [SMILES: Cl ; NS(=O)(=O)C1CCNCC1 ; CC(C)NC(=O)N1CCC(S(N)(=O)=O)CC1]

To a suspension of piperidine-4-sulfonamide hydrochloric acid (200 mg, 1.0 mmol, 1.0 equiv.), 4-dimethylaminopyrimidine (12 mg, 0.1 mmol, 0.1 equiv.) and triethylamine (0.34 mL, 2.5 mmol, 2.5 equiv.) was added isopropyl isocyanate (0.1 mL, 1.0 mmol, 1.0 equiv.). After stirring overnight at room temperature, the reaction mixture was concentrated in vacuo. The crude product was suspended in methanol, coated on Agilent hydromatrix (a high purity, inert diatomaceous earth sorbent) and then purified by normal phase flash chromatography using dichloromethane and a mixture of trimethylamine-methanol (ratio 1:1) as eluent to afford the title compound (55 mg, yield 22%).

$^1$H NMR (CDCl$_3$): δ 4.45 (br s, 1H), 4.22 (m, 1H), 4.10 (d, 2H), 3.98 (m, 1H), 3.10 (m, 1H), 2.81 (t, 2H), 2.20 (d, 2H), 1.80 (m, 2H) and 1.19 (d, 6H).

Intermediate P6: 1-Ethylpiperidine-4-sulfonamide

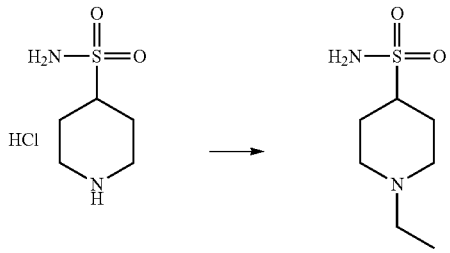

Prepared as described for 1-(prop-2-yn-1-yl)piperidine-4-sulfonamide (Intermediate P3) using ethyliodide instead of propargyl bromide. The crude product was coated on Agilent hydromatrix (a high purity, inert diatomaceous earth sorbent) and was submitted to normal phase flash chromatography using dichloromethane and a mixture of trimethylamine-methanol (ratio 1:1) as eluent to afford the title compound contaminated with triethylamine hydrochloride (50 mg, yield 26%). The crude product was used as such in preparing examples.

$^1$H NMR (CDCl$_3$): δ 5.05 (br s, 2H), 3.10 (m, 2H), 2.95 (m, 1H), 2.45 (m, 2H), 2.20 (d, 2H), 1.95 (m, 4H) and 1.08 (t, 3H).

Intermediate P7: 1-Acetylpiperidine-4-sulfonamide

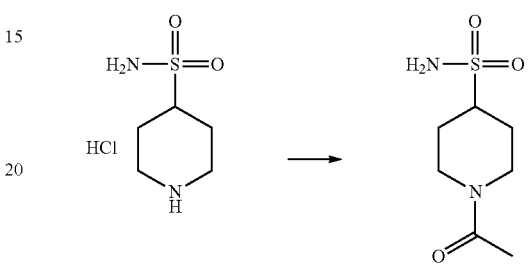

Prepared as described for 1-(2,2,2-trifluoroacetyl)piperidine-4-sulfonamide (Intermediate P4) except that the suspension was cooled to 0° C. and then acetic anhydride was added instead of trifluoroacetic anhydride. The reaction mixture was allowed to warm to room temperature overnight. The crude product was coated on Agilent hydromatrix (a high purity, inert diatomaceous earth sorbent) and was submitted to normal phase flash chromatography using dichloromethane and a mixture of ammonia (3.5 M) in methanol as eluent to afford the title compound as a mixture with triethylamine hydrochloride salt (139 mg, yield 67%). The crude product was used as such in the preparation of examples.

$^1$H NMR (CDCl$_3$): δ 4.90 (m, 3H), 3.99 (d, 1H), 3.10 (m, 2H), 2.60 (t, 1H), 2.10 (t, 2H), 2.05 (s, 3H) and 1.75 (m, 2H).

Intermediate P8:
1-(Cyclopropanecarbonyl)piperidine-4-sulfonamide

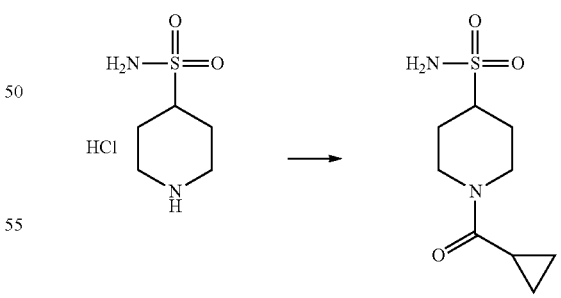

Prepared as described for 1-(2,2,2-trifluoroacetyl)piperidine-4-sulfonamide (Intermediate P4) except that cyclopropanecarbonyl chloride (1.0 equiv.) was used instead of trifluoroacetic anhydride. The crude product was coated on Agilent hydromatrix and was submitted to normal phase flash chromatography using dichloromethane and a mixture of trimethylamine-methanol (ratio 1:1) as eluent to afford the title compound (84 mg, yield 36%).

¹H NMR (CDCl₃): δ 4.80 (br s, 1H), 4.58 (s, 2H), 4.40 (br s, 1H), 3.18 (m, 2H), 2.64 (br s, 1H), 2.25 (br s, 2H), 1.78 (m, 3H), 1.00 (m, 2H) and 0.79 (m, 2H).

Intermediate P9:
1-(Cyanomethyl)piperidine-4-sulfonamide

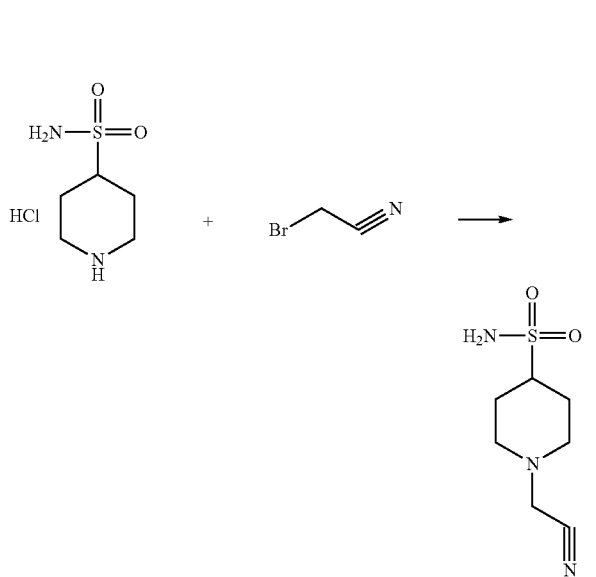

Prepared as described for 1-(prop-2-yn-1-yl)piperidine-4-sulfonamide (Intermediate P3) using bromo acetonitrile instead of propargyl bromide to afford the title compound as a solid (40%).

¹H NMR (DMSO-d6): δ=6.71 (s, 2H), 3.73 (s, 2H), 2.89 (d, 2H), 2.79 (m, 1H), 2.19 (t, 2H), 1.99 (d, 2H) and 1.60 (m, 2H).

Intermediate P10:
1-Propionylpiperidine-4-sulfonamide

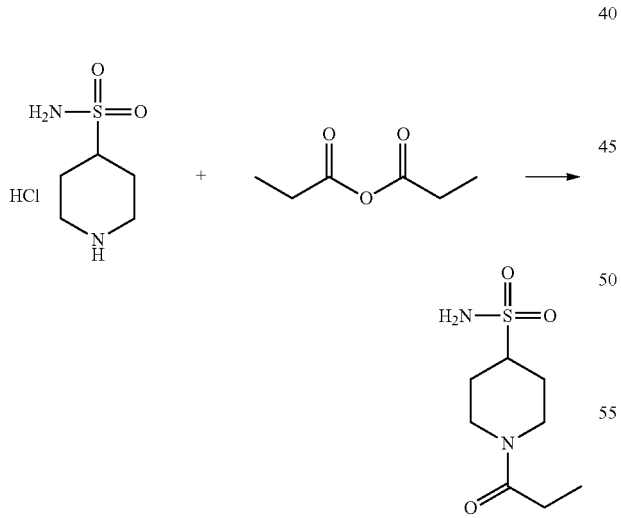

Prepared as described for 1-(2,2,2-trifluoroacetyl)piperidine-4-sulfonamide (Intermediate P4) using propionic anhydride instead of trifluoroacetic anhydride to afford the title compound as a solid (71%).

¹H NMR (CD₃OD): δ=4.67 (d, 1H), 4.05 (d, 1H), 3.17 (m, 2H), 2.65 (t, 1H), 2.42 (q, 2H), 2.18 (t, 2H), 1.65 (m, 2H) and 1.10 (t, 3H).

Intermediate P11:
1-iso-Butyrylpiperidine-4-sulfonamide

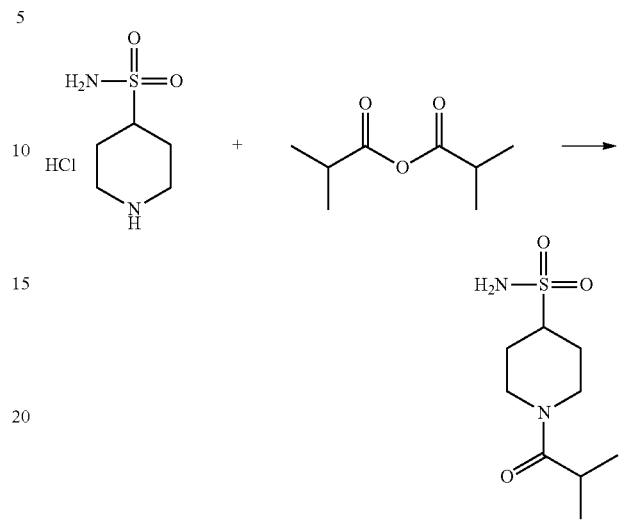

Prepared as described for 1-(2,2,2-trifluoroacetyl)piperidine-4-sulfonamide (Intermediate P4) using iso-butyric anhydride instead of trifluoroacetic anhydride to afford the title compound contaminated with triethylamine hydrochloride (64%).

¹H NMR (CDCl₃): δ=4.83 (d, 1H), 4.63 (s, 2H), 4.10 (d, 1H), 3.10 (m, 2H), 2.79 (m, 1H) 2.60 (t, 1H), 2.14 (m, 2H), 2.76 (m, 2H) and 1.16 (d, 6H).

Intermediate P12:
1-(2-Methoxyacetyl)piperidine-4-sulfonamide

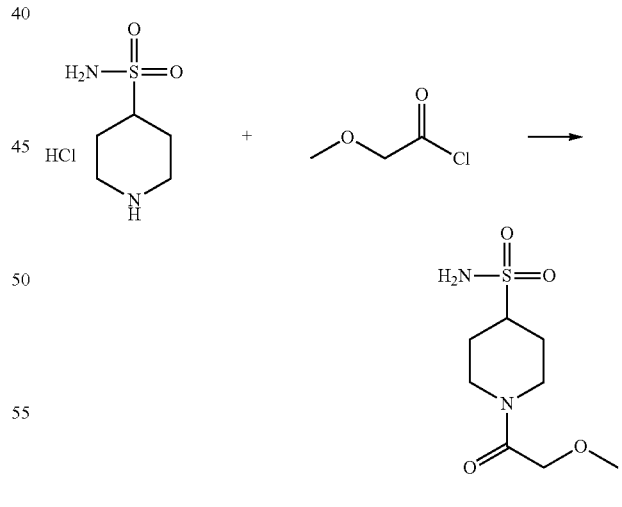

Prepared as described for 1-(2,2,2-trifluoroacetyl)piperidine-4-sulfonamide (Intermediate P4) using 2-methoxyacetyl chloride instead of cyclopropanecarbonyl chloride to afford the title compound contaminated with triethylamine hydrochloride (55%).

¹H NMR (CDCl₃): δ=5.37 (bs, 2H), 4.72 (d, 1H), 4.10 (m, 3H), 3.41 (s, 3H), 3.16 (m, 2H), 2.64 (t, 1H), 2.23 (d, 2H) and 1.79 (m, 2H).

Intermediate P13: Methyl 4-sulfamoylpiperidine-1-carboxylate

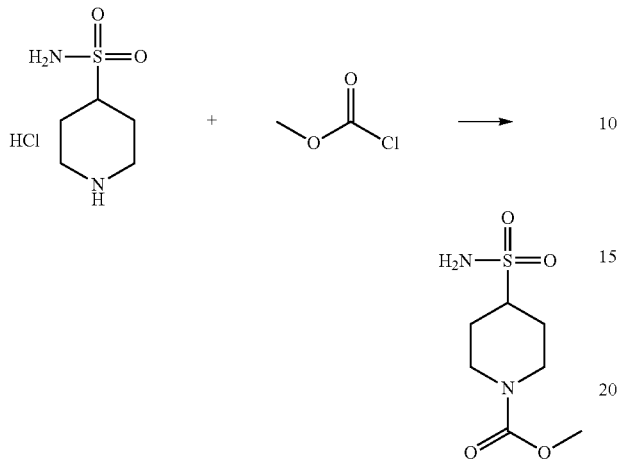

Prepared as described for 1-(2,2,2-trifluoroacetyl)piperidine-4-sulfonamide (Intermediate P4) using methyl chloroformate instead of cyclopropanecarbonyl chloride to afford the tittle compound as a solid (10%).

$^1$H NMR (CDCl$_3$): δ=4.49 (s, 2H), 4.33 (bs, 2H), 3.72 (s, 3H), 3.07 (m, 1H), 2.80 (t, 2H), 2.19 (d, 2H) and 1.77 (m, 2H).

Intermediate P14: 1-Cyclobutylpiperidine-4-sulfonamide

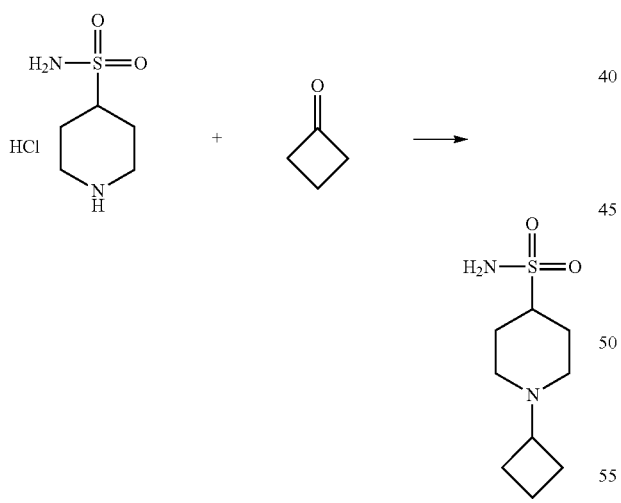

To a suspension of piperidine-4-sulfonamide hydrochloric acid (157 mg, 0.79 mmol, 1.0 equiv.) and triethylamine (0.12 mL, 0.86 mmol, 1.1 equiv.) in acetonitrile (10 mL) was added cyclobutanone (61 μL, 0.82 mmol, 1.05 equiv.) followed by sodium triacetoxyborohydride (207 mg, 0.98 mmol, 1.25 equiv.). After being allowed to stir overnight the reaction mixture was concentrated in vacuo. The crude product was suspended in methanol, coated on hydromatrix and then purified by normal phase flash chromatography using dichloromethane and a mixture of trimethylamine-methanol (1:1) as eluent to afford the title compound contaminated with trimethylamine hydrochloride (110 mg product, yield 64%).

$^1$H NMR (CDCl$_3$): δ=4.76 (bs, 2H), 2.98 (m, 3H), 2.78 (m, 1H), 2.19 (d, 2H), 2.00 (m, 2H), 1.88 (m, 6H) and 1.65 (m, 2H).

Intermediate P15: 1-Ethylpiperidine-3-sulfonamide

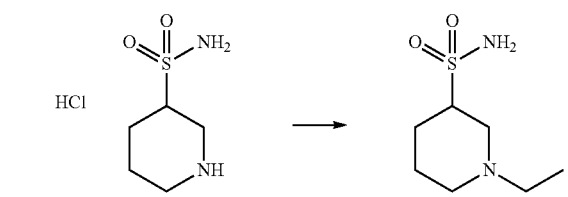

Piperidine-3-sulfonamide hydrochloride (0.5 g, 3.2 mmol) was suspended in acetonitrile (10 mL) and potassium carbonate (1.75 g, 12.6 mmol) was added before the mixture was allowed to stir for 30 minutes. To the resulting slurry was added ethyl bromide (0.24 mL, 0.34 g, 3.2 mmol) and the mixture was allowed to stir for 60 hours at ambient temperature. The reaction was concentrated in vacuo and then purified by column chromatography (40 g Silicycle FLH-R10030B-ISO40 cartridge, 5-25% methanol in DCM) to afford the title compound (0.11 g, 0.57 mmol, yield 18%).

$^1$H NMR (1:1 CD$_3$OD:CDCl$_3$): δ 3.36 (m, 2H), 3.10 (m, 1H), 2.92 (bd, 1H), 2.56 (q, 2H), 2.22 (bd, 1H), 2.11 (t, 1H), 1.88 (m, 2H), 1.58 (m, 2H) and 1.10 (t, 3H).

Intermediate P16: 1-Propylpiperidine-4-sulfonamide

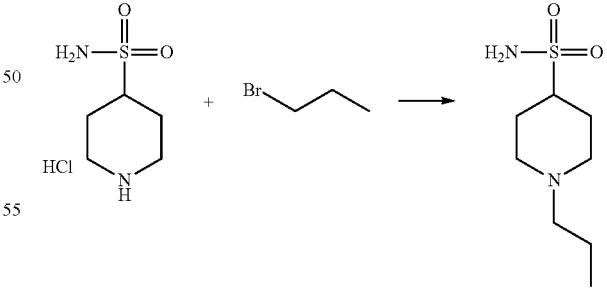

Prepared as described for 1-(prop-2-yn-1-yl)piperidine-4-sulfonamide (Intermediate P3) from 1-bromopropane and piperidine-4-sulfonamide hydrochloric acid. This afforded the title compound impure (44 mg, yield 40%) which was used without purification.

$^1$H NMR (CDCl$_3$): δ=3.10 (m, 3H), 2.38 (m, 2H), 2.20 (m, 2H), 2.00 (m, 4H), 1.25 (m, 2H) and 0.95 (t, 3H).

Intermediate P17: 1-(Oxetan-3-yl)piperidine-4-sulfonamide

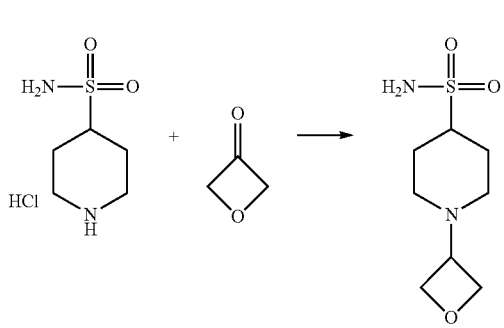 [SMILES: Cl ; NS(=O)(=O)C1CCNCC1 ; O=C1COC1 ; NS(=O)(=O)C1CCN(C2COC2)CC1]

Prepared as described for 1-cyclobutylpiperidine-4-sulfonamide (Intermediate P14) from 3-oxetanone and piperidine-4-sulfonamide hydrochloric acid (130 mg, yield 59%).

$^1$H NMR (DMSO-$d_6$): δ=6.75 (s, 2H), 4.49 (t, 2H), 4.38 (t, 2H), 3.38 (m, 2H), 2.79 (m, 2H), 1.98 (d, 2H), 1.79 (t, 2H) and 1.59 (m, 2H).

Intermediate P18: Methyl 2-(4-sulfamoylpiperidin-1-yl)acetate

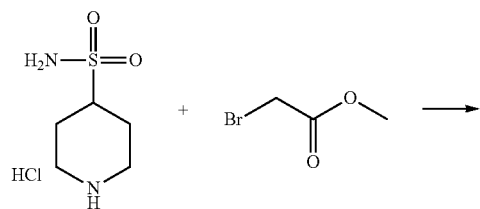

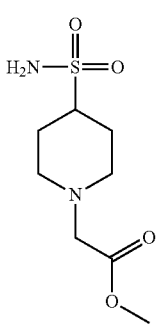

Prepared as described for 1-(prop-2-yn-1-yl)piperidine-4-sulfonamide (Intermediate P3) using methyl bromoacetate instead of propargyl bromide (91 mg, yield 39%).

$^1$H NMR (DMSO-$d_6$): δ=6.70 (s, 2H), 3.60 (s, 3H), 3.19 (s, 2H), 2.93 (d, 2H), 2.76 (m, 1H), 2.18 (t, 2H), 1.93 (d, 2H) and 1.59 (m, 2H).

Intermediate P19: 1-Cyclopropylpiperidine-4-sulfonamide

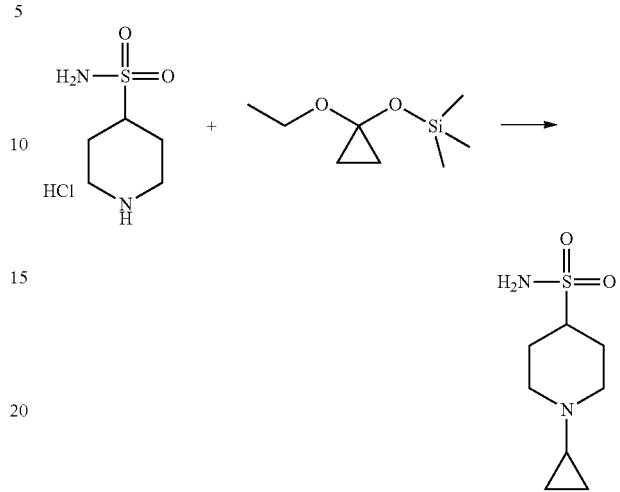

Prepared as described for 1-cyclopropylpyrrolidine-3-sulfonamide (Intermediate P30) from piperidine-4-sulfonamide hydrochloric acid and triethylamine (1.1 equiv.) was added to the suspension. This afforded the title compound (150 mg, yield 73%) which was used as such without further purification.

$^1$H NMR (DMSO-$d_6$): δ=6.67 (s, 2H), 2.98 (m, 2H), 2.77 (m, 1H), 2.15 (t, 2H), 1.92 (m, 2H), 1.52 (m, 3H), 0.23 (m, 2H) and 0.39 (m, 2H).

Intermediate P20: 1-(1-Ethylazetidin-3-yl)piperidine-4-sulfonamide

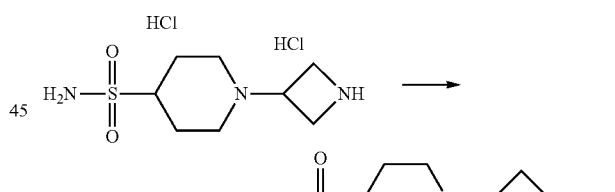

A suspension of 1-(azetidin-3-yl)piperidine-4-sulfonamide dihydrochloride (145 mg, 0.45 mmol) in acetonitrile (5.8 mL) was stirred with triethylamine (0.13 mL, 95 mg, 0.94 mmol) for 30 minutes. To this was added acetaldehyde (0.03 mL, 25 mg, 0.6 mmol) and sodium triacetoxyborohydride (122 mg, 0.56 mmol). The stirring was continued for 20 hours and then the mixture concentrated in vacuo. The residue was dissolved in methanol/dichloromethane (1:1) and purified by chromatography (40 g Silicycle SiO$_2$ cartridge through a syringe filter and eluted with 5-30% 3.5 N ammonia in methanol/dichloromethane) to afford the title compound (73 mg, 0.28 mmol, yield 63%).

$^1$H NMR (DMSO-$d_6$): δ=6.71 (br s, 2H), 3.49 (m, 4H), 2.89 (m, 3H), 2.77 (m, 3H), 1.95 (br d, 2H), 1.77 (m, 2H), 1.57 (dq, 2H) and 0.89 (t, 3H).

Intermediate P21:
1-(Cyclobutanecarbonyl)piperidine-4-sulfonamide

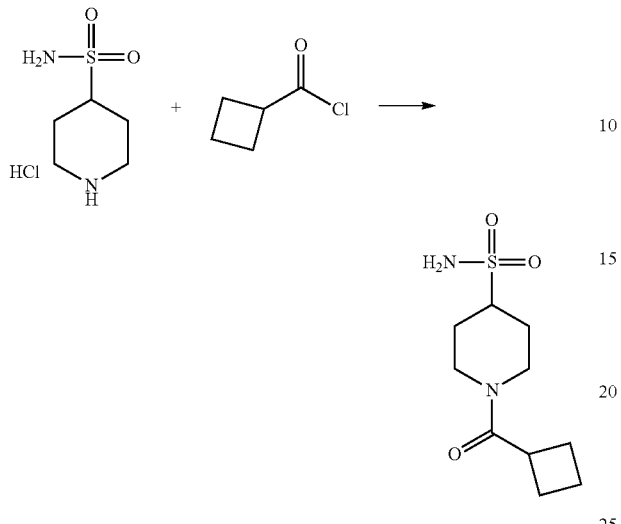

Prepared as described for 1-(2,2,2-trifluoroacetyl)piperidine-4-sulfonamide (Intermediate P4) using cyclobutanecarbonyl chloride instead of trifluoroacetic anhydride to afford the title compound (158 mg, yield 64%).

$^1$H NMR (CDCl$_3$): δ=4.81 (d, 1H), 4.58 (s, 2H), 3.84 (d, 1H), 3.24 (m, 1H), 3.18 (m, 1H), 3.01 (t, 1H), 2.60 (t, 1H), 2.37 (m, 2H), 2.20 (m, 4H), 1.99 (m, 1H), 1.89 (m, 1H) and 1.72 (m, 2H).

Intermediate P22:
N-Ethyl-4-sulfamoylpiperidine-1-carboxamide

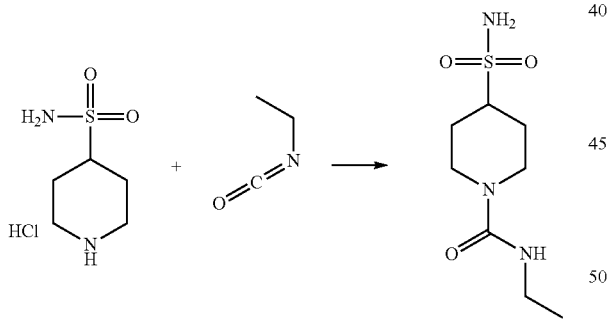

To a suspension of piperidine-4-sulfonamide hydrochloric acid (200 mg, 1.0 mmol, 1.0 equiv.) and triethylamine (0.34 mL, 2.5 mmol, 2.5 equiv.) in acetonitrile (10 mL) was added ethyl isocyanate (79 µL, 1.0 mmol, 1.0 equiv.). The reaction mixture was stirred overnight and then concentrated in vacuo. The crude product was coated on Agilent Hydromatrix and then submitted to normal phase flash chromatography on silica gel using dichloromethane and a mixture of methanol and triethylamine (ratio 1:1) to afford the title compound (141 mg, yield 60%) which was used without any further purification.

$^1$H NMR (DMSO-d$_6$): δ=6.78 (br s, 2H), 4.04 (d, 2H), 2.98 (m, 3H), 2.64 (t, 2H), 1.91 (d, 2H), 1.39 (m, 2H) and 0.98 (t, 3H).

Intermediate P23:
N-Methyl-4-sulfamoylpiperidine-1-carboxamide

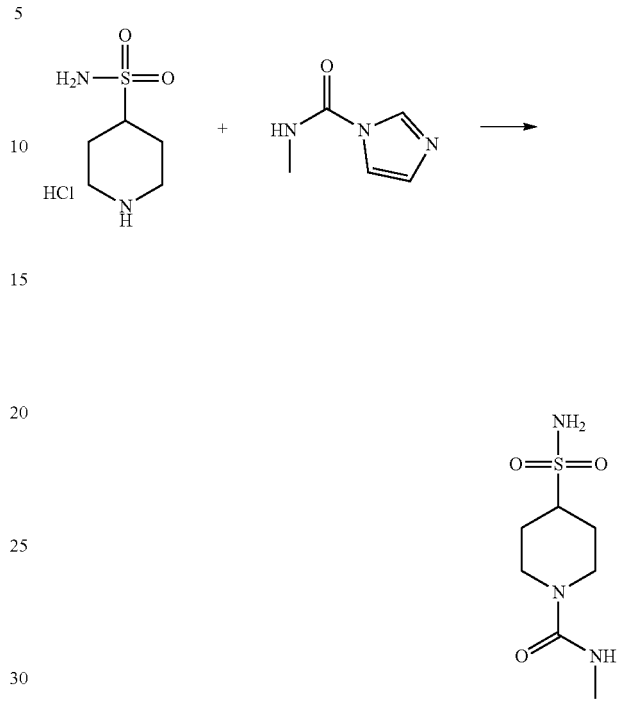

Prepared as described for N-iso-propyl-4-sulfamoylpiperidine-1-carboxamide (Intermediate P5) from piperidine-4-sulfonamide hydrochloric acid and N-methyl-1H-imidazole-1-carboxamide, but no 4-dimethylaminopyrimidine was required. The title compound (12 mg, yield 5%) was used without purification.

$^1$H NMR (CDCl$_3$): δ=4.18 (d, 2H), 3.18 (m, 1H), 2.78 (m, 5H), 2.20 (m, 2H) and 1.75 (m, 2H).

Intermediate P24:
1-(Methylsulfonyl)piperidine-4-sulfonamide

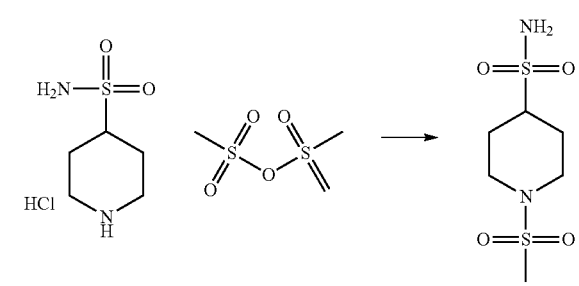

Prepared as described for 1-(2,2,2-trifluoroacetyl)piperidine-4-sulfonamide (Intermediate P4) from piperidine-4-sulfonamide hydrochloric acid and methanesulfonic anhydride. The title compound (18 mg, yield 7%) was used without purification.

$^1$H NMR (CD$_3$OD): δ=3.90 (m, 2H), 3.08 (m, 2H), 2.82 (m, 4H), 2.23 (d, 2H) and 1.83 (m, 2H).

Intermediate P25:
N-Ethyl-3-sulfamoylpyrrolidine-1-carboxamide

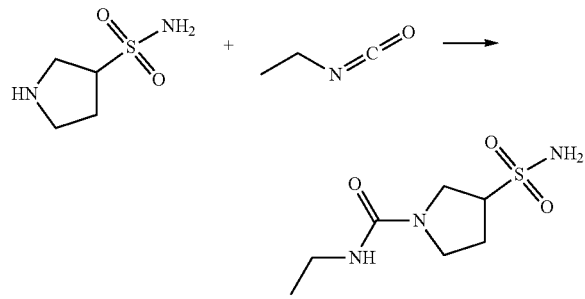

Prepared as described for N-iso-propyl-4-sulfamoylpiperidine-1-carboxamide (Intermediate P5) from ethyl isocyanate and pyrrolidine-3-sulfonamide, but no 4-dimethylaminopyrimidine nor triethylamine were required. The title compound (13 mg, yield 5%) was used crude without purification.

$^1$H NMR (CD$_3$OD): δ=3.81 (m, 1H), 3.57 (m, 1H), 3.39 (m, 1H), 3.19 (m, 4H), 2.38 (m, 2H) and 1.10 (t, 3H).

Intermediate P26:
N-iso-Propyl-3-sulfamoylpiperidine-1-carboxamide

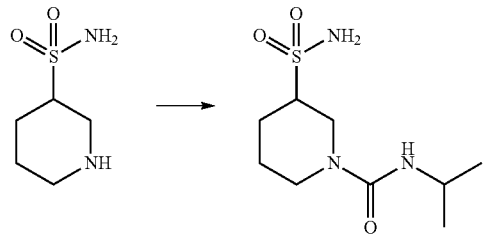 [SMILES: NS(=O)(=O)C1CCCNC1 ; CC(C)NC(=O)N1CCCC(S(N)(=O)=O)C1]

Prepared as described for N-iso-propyl-4-sulfamoylpiperidine-1-carboxamide (Intermediate P5) from isopropyl isocyanate and piperidine-3-sulfonamide hydrochloride to afford the title compound (0.11 g, 0.44 mmol, yield 41%).

$^1$H NMR (CD$_3$OD): δ=3.85 (m, 2H), 2.98 (m, 2H), 2.77 (br t, 1H), 2.25 (br d, 1H), 2.00 (s, 2H), 1.65-1.90 (m, 2H) and 1.13 (d, 6H).

Intermediate P27:
1-Methylpyrrolidine-3-sulfonamide

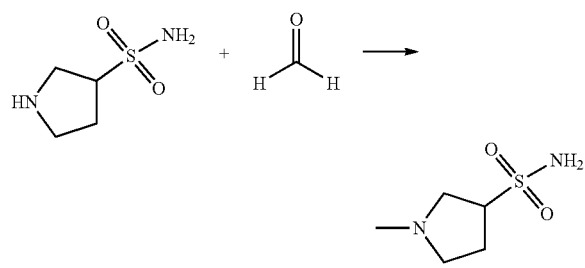

To a suspension of pyrrolidine-3-sulfonamide (150 mg, 1.0 mmol, 1.0 equiv.) and formaldehyde (37% in water stabilized with methanol; 78 μL, 1.05 mmol, 1.05 equiv.) in acetonitrile (10 mL) was added sodium triacetoxyborohydride (265 mg, 1.25 mmol, 1.25 equiv.). The reaction mixture was stirred for 5 days at room temperature and then concentrated in vacuo. The crude material was dissolved in methanol, coated on hydromatrix and then submitted for normal phase flash chromatography using dichloromethane and a mixture of triethylamine:methanol (ratio 1:1) as eluent to afford the title compound impure (80 mg, yield 49%) which was used as such in further reactions.

$^1$H NMR (CD$_3$OD): δ=3.78 (m, 1H), 3.18 (m, 3H), 2.86 (m, 2H), 2.70 (m, 1H) and 2.43 (s, 3H).

Intermediate P28: 1-Ethylpyrrolidine-3-sulfonamide

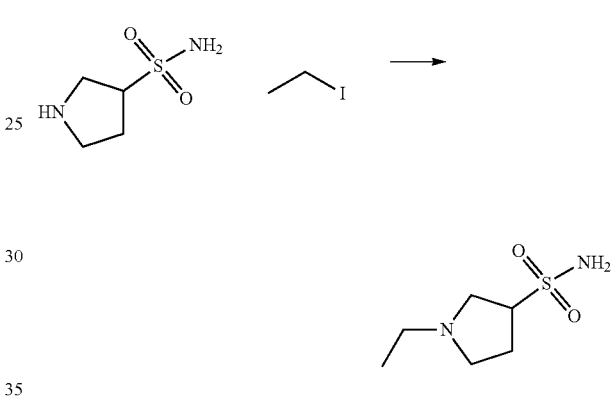

Prepared as described for 1-ethylpiperidine-4-sulfonamide (Intermediate P6) from pyrrolidine-3-sulfonamide and ethyl iodide. The title compound (75 mg, yield 42%) was used without further purification.

$^1$H NMR (CD$_3$OD): δ=3.77 (m, 1H), 3.10 (t, 1H), 2.79 (m, 2H), 2.57 (m, 3H), 2.19 (m, 2H) and 1.16 (t, 3H).

Intermediate P29:
1-Acetylpyrrolidine-3-sulfonamide

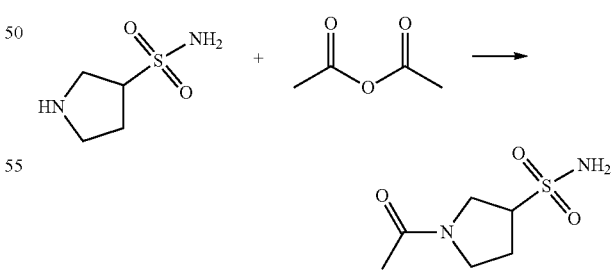

Prepared as described for 1-(2,2,2-trifluoroacetyl)piperidine-4-sulfonamide (Intermediate P4) from acetic anhydride (1.0 equiv.) and pyrrolidine-3-sulfonamide. The title compound (75 mg, yield 39%) was used without purification.

$^1$H NMR (CD$_3$OD): δ=3.89 (m, 2H), 3.78 (m, 2H), 3.62 (m, 1H), 2.41 (m, 2H) and 2.08 (s, 3H).

Intermediate P30:
1-Cyclopropylpyrrolidine-3-sulfonamide

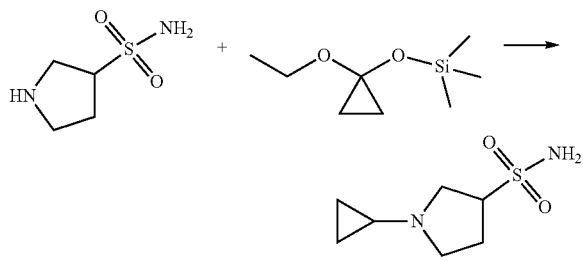

To a suspension of pyrrolidine-3-sulfonamide (150 mg, 1.00 mmol) and 1-(ethoxycyclopropoxy)trimethylsilane (0.4 mL, 2.0 mmol, 2.0 equiv.) in tetrahydrofuran (5 mL) and methanol (5 mL) was added acetic acid (0.12 mL, 2.2 mmol, 2.2 equiv.) followed by sodium cyanoborohydride (94 mg, 1.5 mmol, 1.5 equiv.). The reaction mixture was stirred overnight and then concentrated in vacuo. The crude was dissolved in methanol, coated on hydromatrix and then submitted for normal phase flash chromatography using dichloromethane and a mixture of triethylamine:methanol (ratio 1:1) as eluent to afford the title compound (75 mg, yield 39%).

$^1$H NMR (DMSO-$d_6$): δ=6.79 (s, 2H), 3.57 (m, 1H), 2.98 (t, 1H), 2.80 (t, 1H), 2.71 (m, 1H), 2.58 (q, 1H), 2.01 (q, 2H), 1.64 (m, 1H), 0.28 (m, 2H) and 0.38 (m, 2H).

Intermediate P31:
N,N-Dimethyl-3-sulfamoylpyrrolidine-1-carboxamide

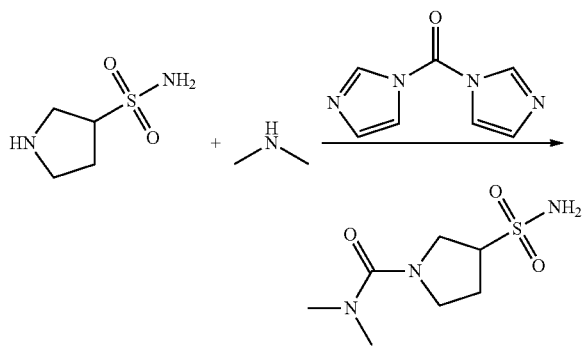

To a solution of carbonyldiimidazole (269 mg, 1.66 mmol) in acetonitrile (10 mL) was added dimethylamine hydrochloride (122 mg, 1.55 mmol, 0.9 equiv.). The resulting solution was allowed to stir for 1.5 hours at room temperature after which triethylamine (0.3 mL, 2.0 mmol, 1.2 equiv.) and pyrrolidine-3-sulfonamide (250 mg, 1.66 mmol) were added. The reaction mixture was stirred for 3 hours before extra triethylamine (0.3 mL, 2.0 mmol, 1.2 equiv.) was added to the suspension. After stirring overnight, more carbonyldiimidazole (269 mg, 1.66 mmol, 1.0 equiv.), and 2 M dimethylamine in tetrahydrofuran (0.83 mL, 1.66 mmol, 1.0 equiv.) were added. The reaction mixture was heated to 50° C. overnight, and then more dimethylamine (2 M in tetrahydrofuran; 0.83 mL, 1.66 mmol, 1.0 equiv.) was added. After heating overnight, more dimethylamine (2 M in tetrahydrofuran; 4.2 mL, 8.3 mmol, 5.0 equiv.) was added. The reaction mixture was again heated overnight. Upon cooling the reaction mixture was concentrated in vacuo. The crude was dissolved in methanol, coated on hydromatrix and then submitted for normal phase flash chromatography on silicagel using dichloromethane and a mixture of 3.5 M ammonia in methanol as eluent to afford the title compound, still not completely pure (35 mg, yield 15%). The product was used as such.

$^1$H NMR (DMSO-$d_6$): δ=7.19 (s, 2H), 3.84 (m, 2H), 3.79 (m, 1H), 3.58 (m, 2H), 2.73 (s, 6H) and 2.02 (m, 2H).

Intermediate P32:
1-iso-Propylpyrrolidine-3-sulfonamide

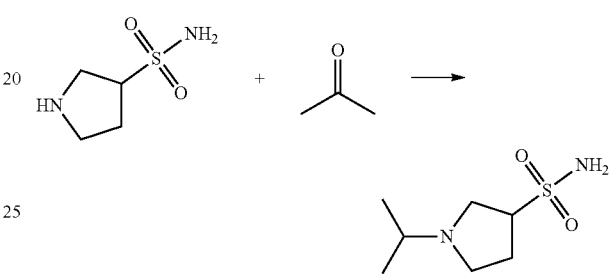

Prepared as described for 1-cyclobutylpiperidine-4-sulfonamide (Intermediate P14) from pyrrolidine-3-sulfonamide and acetone, but no triethylamine was required. The title compound (130 mg, yield 67%) was used without purification.

$^1$H NMR (CD$_3$OD): δ=3.76 (m, 1H), 3.23 (t, 1H), 2.92 (m, 1H), 2.90 (m, 1H), 2.62 (m, 1H), 2.52 (m, 1H), 2.21 (m, 2H) and 1.17 (m, 6H).

Intermediate P33: Azetidine-3-sulfonamide

Step A: Benzyl 3-sulfamoylazetidine-1-carboxylate

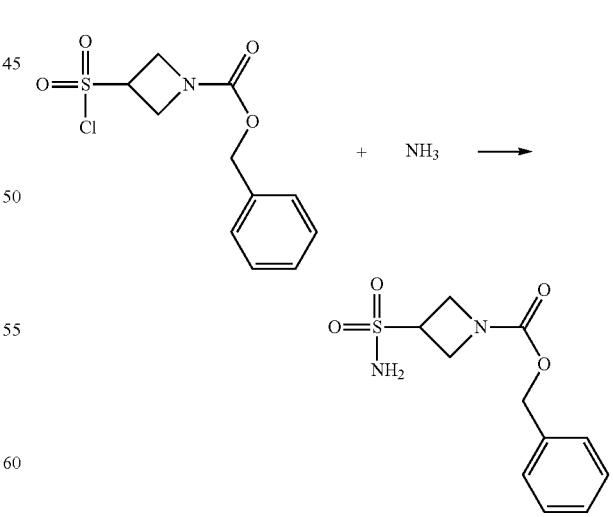

A solution of ammonium hydroxide (25% in water; 22 mL, 73 mmol, 10.0 equiv.) was added to benzyl 3-(chlorosulfonyl)azetidine-1-carboxylate (2.1 g, 7.3 mmol, 1.0 equiv.). The suspension was stirred at room temperature for 20 minutes to afford a clear solution and the reaction mixture was then acidified to pH 8-9, using hydrochloric acid (2 M, aqueous) and extracted into ethyl acetate. The organic layer was washed with brine, dried over sodium sulfate, filtered and then concentrated in vacuo to afford the title compound (1.52 g, 5.62 mmol, yield 77%) which was used without further purification.

$^1$H NMR (CDCl$_3$): δ=7.38 (m, 5H), 5.18 (s, 4H), 4.40 (m, 4H) and 4.00 (m, 1H).

Step B: Azetidine-3-sulfonamide

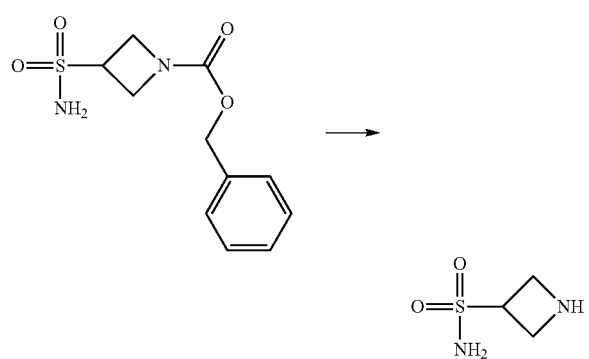

A suspension of benzyl 3-sulfamoylazetidine-1-carboxylate (1.52 g, 5.62 mmol, 1.0 equiv.) in ethyl acetate (30 mL) was flushed with a flow of nitrogen before Pd/C (10 wt % loading, 595 mg, 0.56 mmol, 0.1 equiv.) was added and the flask was then flushed with hydrogen. The reaction mixture was heated to reflux for 20 hours under hydrogen atmosphere (balloon). Upon cooling the suspension was filtered over Celite® 545 and the Celite was washed extensively with methanol. The filtrates were combined and concentrated in vacuo to afford the title compound (541 mg, 3.97 mmol, yield 70%) which was used without further purification.

$^1$H NMR (DMSO-d$_6$): δ=6.91 (br s, 2H), 4.08 (m, 1H), 3.74 (t, 2H) and 3.63 (t, 2H).

Intermediate P34: Quinuclidine-3-sulfonamide

Step A: (Quinuclidin-3-yl) Ethanethioate

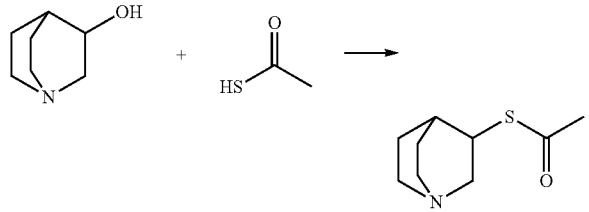

To a solution of triphenylphosphine (4.12 g, 15.7 mmol, 2.0 equiv.) in tetrahydrofuran (64 mL) cooled in an ice-bath was added di-iso-propyl azodicarboxylate (3.1 mL, 15.7 mmol, 2.0 equiv.). The clear yellow solution was stirred for to minutes during which time a precipitate appeared. 3-Quinuclidinol (1.0 g, 7.86 mmol, 1.0 equiv.) was added, followed by thioacetic acid (1.2 mL, 15.7 mmol, 2.0 equiv.) and then the ice-bath was removed and the green solution was stirred for 2.5 hours. The reaction mixture was concentrated in vacuo and the crude material was purified by normal phase flash chromatography using dichloromethane and methanol as eluent to afford the title compound (581 mg, yield 40%).

$^1$H NMR (CDCl$_3$): δ=3.71 (m, 1H), 2.97 (m, 5H), 2.77 (dd, 1H), 2.33 (s, 3H) 1.92 (m, 1H), 1.81 (m, 3H) and 1.57 (m, 1H).

Step B: Quinuclidine-3-sulfonamide

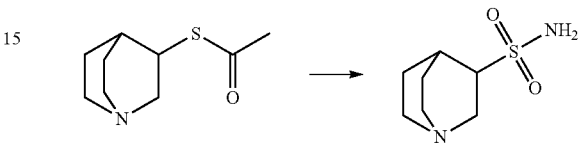

To a suspension of N-chlorosuccinimide (1.7 g, 12.5 mmol, 4.0 equiv.) in acetonitrile (7.0 mL) was added hydrochloric acid (aqueous, 2 M, 1.2 mL, 2.50 mmol, 0.8 equiv.). The solution was cooled in an ice-bath, after which a solution of S-(quinuclidin-3-yl) ethanethioate (581 mg, 3.14 mmol, 1.0 equiv.) in acetonitrile (3.0 mL) was added and the ice-bath was removed. The reaction mixture was stirred for 45 minutes and then added drop-wise to a solution of ammonium hydroxide (25 wt % in water; 25 mL, 160 mmol, 51 equiv.). The mixture was stirred for to minutes and then concentrated in vacuo. The resulting solid was suspended in methanol, filtered and the filtrate was concentrated in vacuo. The crude was purified by reversed phase flash chromatography (see "Experimental Methods", "Purification Method 1") using water and methanol as eluent to afford the title compound impure (43 mg, 0.22 mmol, yield 7%).

$^1$H NMR (DMSO-d$_6$): δ=3.74 (m, 1H), 3.55 (m, 4H), 3.01 (m, 1H), 2.65 (m, 1H), 2.38 (m, 2H), 2.23 (m, 2H) and 2.01 (m, 1H).

Intermediate P35:
1-(1-Ethylpiperidin-4-yl)pyrrolidine-3-sulfonamide

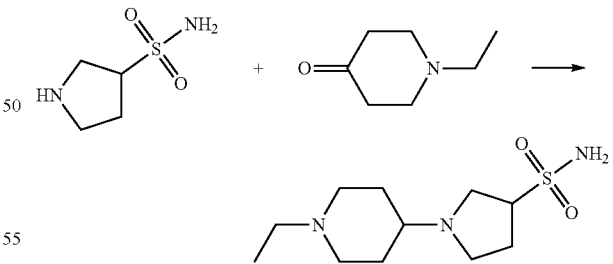

Prepared as described for 1-cyclobutylpiperidine-4-sulfonamide (Intermediate P14) from pyrrolidine-3-sulfonamide and 1-ethyl-4-piperidone, but no triethylamine was required. The crude compound was purified by normal phase flash chromatography using dichloromethane and a mixture of 3.5 M ammonia in methanol as eluent to afford the title compound (217 mg, yield 83%).

$^1$H NMR (DMSO-d$_6$): δ=6.81 (s, 2H), 3.58 (m, 1H), 3.00 (m, 3H), 2.65 (m, 4H), 2.44 (m, 3H), 2.08 (br s, 1H), 2.03 (m, 2H), 1.82 (m, 2H), 1.49 (br s, 2H) and 1.07 (t, 3H).

Intermediate P36: (1R*,3R*,5S*)-8-iso-Propyl-8-azabicyclo[3.2.1]octane-3-sulfonamide Step A: tert-Butyl (1R*,3S*,5S*)-3-((methylsulfonyl)oxy)-8-azabicyclo[3.2.1]octane-8-carboxylate

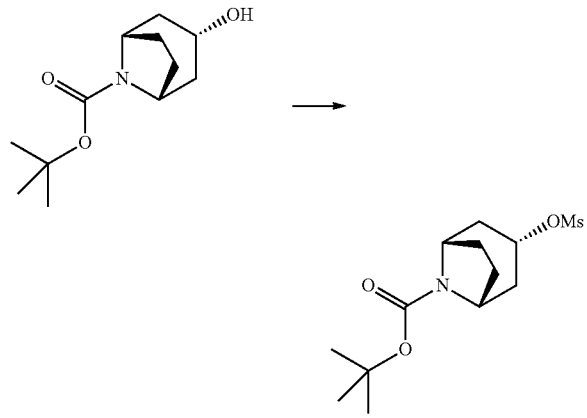

To a mixture of tert-butyl 3-exo-hydroxy-8-azabicyclo[3.2.1]octane-8-carboxylate (3.0 g, 13.2 mmol, 1.0 equiv.) and N,N-diisopropylethylamine (3.0 mL, 17.2 mmol, 1.3 equiv.) in dichloromethane (66 mL) was added methanesulfonyl chloride (1.1 mL, 14.5 mmol, 1.1 equiv.). The reaction mixture was stirred for 2.5 hours at room temperature and then the solution was washed twice with water, once with brine, then dried over sodium sulfate, filtered and concentrated in vacuo to afford the title compound (4.08 g, 13.2 mmol, quantitative yield).

¹H NMR (CDCl₃): δ=5.08 (m, 1H), 4.28 (br s, 2H), 3.00 (s, 3H), 2.10 (br d, 4H), 1.82 (br s, 2H), 1.63 (d, 2H) and 1.44 (s, 9H).

Step B: tert-Butyl (1R*,3R*,5S*)-3-(acetylthio)-8-azabicyclo[3.2.1]octane-8-carboxylate

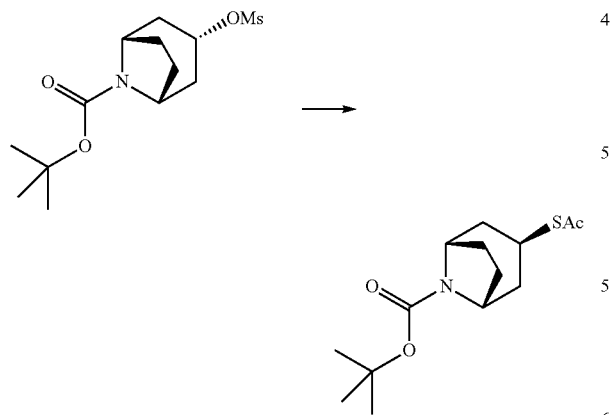

To a solution of tert-butyl (1R*,3S*,5S*)-3-((methylsulfonyl)oxy)-8-azabicyclo[3.2.1]octane-8-carboxylate (4.08 g, 13.2 mmol, 1.0 equiv.) in dimethylformamide (50 mL) and acetonitrile (13 mL) was added potassium thioacetate (4.52 g, 39.6 mmol, 3.0 equiv.). The reaction mixture was heated to reflux for 1 hour and then allowed to cool to room temperature. Brine and ethyl acetate were added to the solution and after thorough mixing the organic layer was separated, washed twice with brine, dried (over sodium sulfate), filtered and concentrated in vacuo. The crude material was purified by normal phase flash chromatography using ethyl acetate and heptane as eluent to afford the title compound (2.95 g, yield 78%).

¹H NMR (CDCl₃): δ=4.20 (br s, 2H), 3.98 (t, 1H), 2.42 (br s, 2H), 2.28 (S, 3H), 1.98 (m, 4H), 1.64 (m, 2H) and 1.44 (s, 9H).

Step C: tert-Butyl (1R*,3R*,5S*)-3-sulfamoyl-8-azabicyclo[3.2.1]octane-8-carboxylate

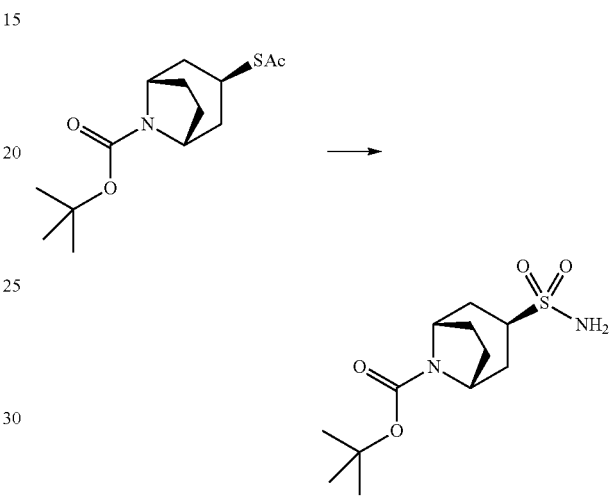

To a solution of tert-butyl (1R*,3R*,5S*)-3-(acetylthio)-8-azabicyclo[3.2.1]octane-8-carboxylate (2.95 g, 10.3 mmol, 1.0 equiv.) in water (10.3 mL) and acetic acid (103 mL) was added N-chlorosuccinimide (4.1 g, 30.9 mmol, 3.0 equiv.). The reaction mixture was stirred at room temperature for 1 hour and then concentrated to about 20-30 mL before the resulting solution was added dropwise to a solution of ammonium hydroxide (25 wt % in water; 400 mL) and after that stirred for to minutes at room temperature. The solution was then acidified with hydrochloric acid (aqueous, 1 M) to pH 7-8 and extracted with ethyl acetate. The organic layer was washed with brine, dried over sodium sulfate, filtered and concentrated in vacuo to afford the title compound impure (387 mg, yield 12%) which was used without further purification.

¹H NMR (CDCl₃): δ=4.33 (br s, 2H), 3.11 (m, 1H), 2.00 (m, 4H), 1.82 (m, 2H), 1.64 (m, 2H) and 1.44 (s, 9H).

Step D: (1R*,3R*,5S*)-8-Azabicyclo[3.2.1]octane-3-sulfonamide Hydrochloride

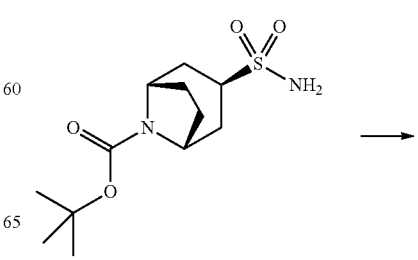

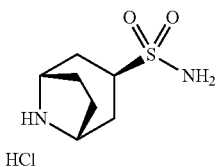

To a solution of tert-butyl (1R*,3R*,5S*)-3-sulfamoyl-8-azabicyclo[3.2.1]octane-8-carboxylate (387 mg, 1.33 mmol, 1.0 equiv.) in dichloromethane (10 mL) was added hydrochloric acid (4 M in dioxane, 3.3 mL, 13.3 mmol, 10.0 equiv.). The solution was stirred at room temperature for 1.5 hours. Then the solvent was decanted and dichloromethane was added and then decanted again. This afforded the title compound impure (200 mg, yield 66%) which was used without purification.

$^1$H NMR (DMSO-d$_6$): δ=9.40 (br s, 1H), 9.20 (br s, 1H), 6.93 (br s, 2H), 4.01 (m, 2H), 3.32 (m, 1H), 2.18 (m, 1H), 1.98 (m, 6H) and 1.79 (m, 1H).

Step E: (1R*,3R*,5S*)-8-iso-Propyl-8-azabicyclo[3.2.1]octane-3-sulfonamide

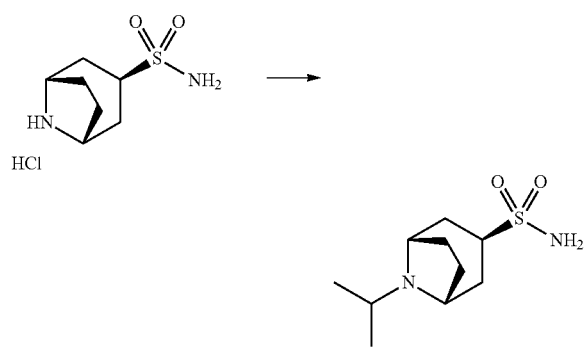

Prepared as described for 1-cyclobutylpiperidine-4-sulfonamide (Intermediate P14) from (1R*,3R*,5S*)-8-azabicyclo[3.2.1]octane-3-sulfonamide hydrochloride and acetone. The crude compound was purified by normal phase flash chromatography using dichloromethane and a mixture of 3.5 M ammonia in methanol as eluent to afford the title compound (22 mg, yield 21%) in a non-homogeneous state, which was used without further purification.

$^1$H NMR (DMSO-d$_6$): δ=6.61 (s, 2H), 3.50 (s, 2H), 3.12 (m, 2H), 1.82 (m, 4H), 1.50 (m, 4H) and 0.97 (d, 6H).

Intermediate P37: 1-iso-Propylazetidine-3-sulfonamide

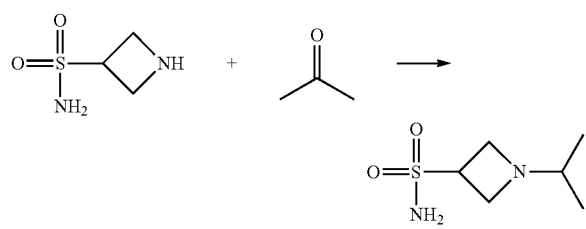

Prepared as described for 1-cyclobutylpiperidine-4-sulfonamide (Intermediate P14) from azetidine-3-sulfonamide (Intermediate P33) and acetone, but no triethylamine was required. The title compound (12 mg, yield 6%) was used without purification.

$^1$H NMR (DMSO-d$_6$): δ=6.87 (br s, 2H), 3.82 (m, 1H), 3.39 (m, 2H), 3.23 (t, 2H), 2.32 (m, 1H) and 0.81 (d, 6H).

Intermediate P38: 1'-Ethyl-[1,4'-bipiperidine]-4-sulfonamide

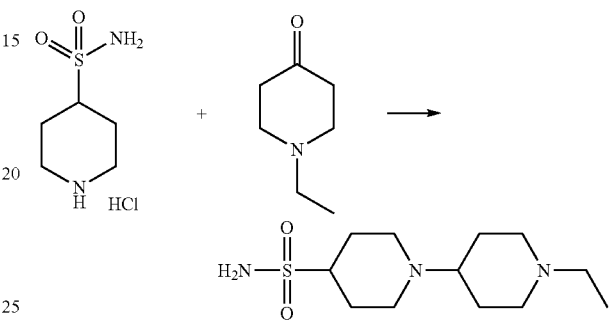

A suspension of 4-piperidine sulfonamide hydrochloric acid (0.35 g, 1.6 mmol) in acetonitrile (14 mL) was stirred with triethylamine (0.17 g, 0.24 mL, 1.7 mmol) for 30 minutes. To this was added 1-ethyl-4-piperidone (0.21 g, 0.23 mL, 1.6 mmol) and sodium triacetoxy-borohydride (0.43 g, 2.0 mmol). The stirring was allowed to continue for 20 hours and then the solution concentrated in vacuo. The crude material was suspended in a few mL of dichloromethane/methanol/7 N ammonia in methanol (1:1:1) and purified by chromatography (40 g Silicycle SiO$_2$ cartridge through a syringe filter eluting with 5-30% 3.5 N ammonia/methanol in dichloromethane) to afford the title compound (290 mg, yield 90%).

$^1$H NMR (CD3OD): δ=3.09 (m, 4H), 2.88 (m, 1H), 2.52 (q, 2H), 2.40 (m, 1H), 2.27 (m, 2H), 2.15 (m, 4H), 1.84 (m, 4H), 1.64 (m, 2H) and 1.13 (t, 3H).

Intermediate P39: 1-Methylazetidine-3-sulfonamide

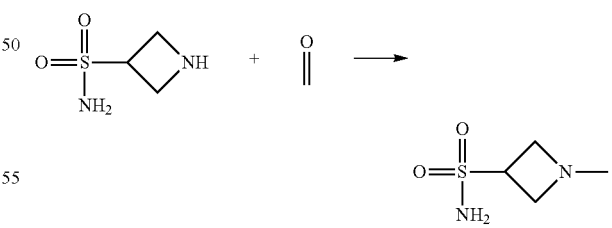

Prepared as described for 1-methylpyrrolidine-3-sulfonamide (Intermediate P27) from azetidine-3-sulfonamide (Intermediate P33) and formaldehyde. The crude compound was purified by normal phase flash chromatography on silicagel using dichloromethane and a mixture of 3.5 M ammonia in methanol as eluent to afford the title compound (24 mg, yield 16%).

$^1$H NMR (CD$_3$OD): δ=4.08 (m, 1H), 3.91 (t, 2H), 3.87 (t, 2H) and 2.54 (s, 3H).

Intermediate P40: 2-Ethyl-2-azaspiro[3.3]heptane-6-sulfonamide

Step A: tert-Butyl 6-((methylsulfonyl)oxy)-2-azaspiro[3.3]heptane-2-carboxylate

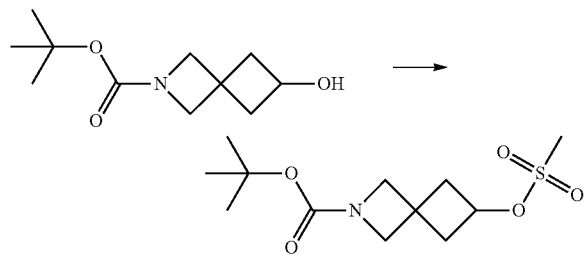

To a solution of tert-butyl 6-hydroxy-2-azaspiro[3.3]heptane-2-carboxylate (2 g, 9.4 mmol) in dichloromethane (25 mL) was added triethylamine (2.6 mL, 18.8 mmol). The solution was cooled to 0° C. and a solution of methanesulfonylchloride (0.8 mL, 10.3 mmol) in dichloromethane (5 mL) was added dropwise. The mixture was stirred for 18 hours at room temperature and then washed with water and brine, dried (sodium sulfate), filtered and evaporated to afford the title compound (2.7 g, yield 100%) as a white solid.

$^1$H NMR (CDCl$_3$): δ=4.89 (m, 1H), 3.94 (s, 4H), 2.99 (s, 3H), 2.70 (m, 2H), 2.48 (m, 2H) and 1.44 (s, 9H).

Step B: tert-Butyl 6-(acetylthio)-2-azaspiro[3.3]heptane-2-carboxylate

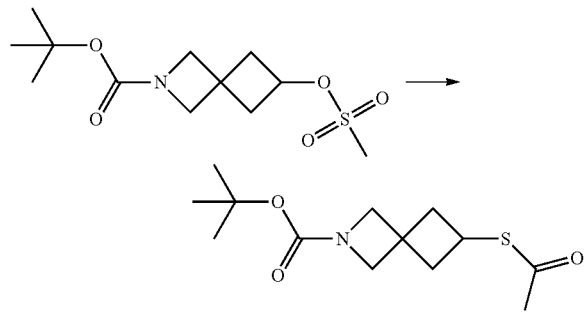

To a solution of tert-butyl 6-((methylsulfonyl)oxy)-2-azaspiro[3.3]heptane-2-carboxylate (1 g, 3.4 mmol) in acetonitrile (10 mL) and dimethylformamide (40 mL) was added potassium thioacetate (1.57 g, 13.7 mmol). The reaction was heated to reflux for 18 hours and upon cooling was poured into water (200 mL) and ethyl acetate (100 mL). The mixture was separated and the water layer was extracted with ethyl acetate. The combined organic layers were washed with water (4x) and brine, before being dried (sodium sulfate), filtered and evaporated in vacuo to afford the title compound (1 g, yield 100%) as a brown oil.

$^1$H NMR (CDCl$_3$): δ=3.96 (s, 2H), 3.90 (m, 1H), 3.86 (s, 2H), 2.65 (m, 2H), 2.27 (s, 3H), 2.18 (m, 2H) and 1.42 (s, 9H).

Step C: tert-Butyl 6-sulfamoyl-2-azaspiro[3.3]heptane-2-carboxylate

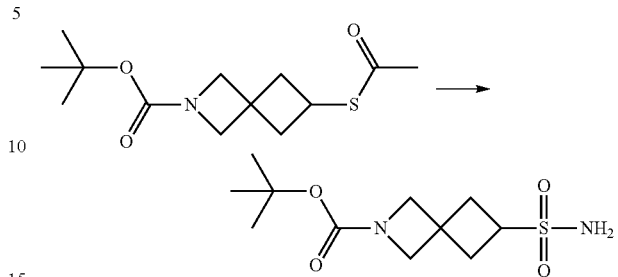

A mixture of tert-butyl 6-(acetylthio)-2-azaspiro[3.3]heptane-2-carboxylate (650 mg, 2.4 mmol), acetic acid (5 mL) and water (1 mL) was cooled in ice/water. N-chloro succinimide (960 mg, 7.8 mmol) was added in portions over a 10 minute period. Then the reaction mixture was stirred at room temperature for 1 hour, before being poured into cold aqueous ammonium hydroxide (50 mL, 25%). The mixture was allowed to stir for 18 hours at room temperature, before the solvents were evaporated in vacuo and the residue was triturated in tetrahydrofuran and decanted. The combined tetrahydrofuran layers were evaporated and the residue was purified over silica, using dichloromethane/methanol (9:1) as the eluent. The title compound was obtained as a white foam (240 mg, yield 36%).

$^1$H NMR (CDCl$_3$): δ=4.87 (br s, 2H), 3.96 (s, 4H), 3.72 (m, 1H), 2.62 (m, 4H) and 1.44 (s, 9H).

Step D: 2-Azaspiro[3.3]heptane-6-sulfonamide

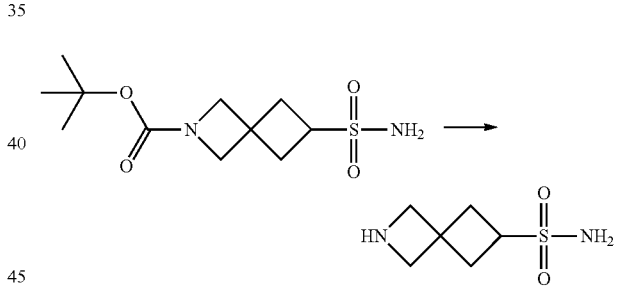

To a solution of tert-butyl 6-sulfamoyl-2-azaspiro[3.3]heptane-2-carboxylate (240 mg, 0.87 mmol) in dichloromethane (10 mL) was added trifluoroacetic acid (0.26 mL, 3.5 mmol). The reaction was stirred for 48 hours and the solvents were evaporated. The residue was dissolved in methanol and purified over Amberlite 410 ion exchange resin, to afford the title compound (100 mg, yield 67%) as a pale yellow oil.

$^1$H NMR (CD$_3$OD): δ=3.93 (s, 4H), 3.66 (m, 1H) and 2.64 (m, 4H).

Step E: 2-Ethyl-2-azaspiro[3.3]heptane-6-sulfonamide

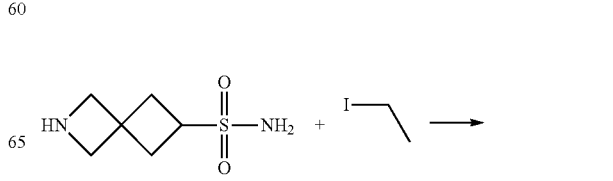

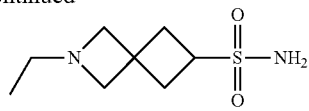

Prepared following the procedure as described for 1-(prop-2-yn-1-yl)piperidine-4-sulfonamide (Intermediate P3) from ethyliodide and 2-azaspiro[3.3]heptane-6-sulfonamide. The crude material was purified by normal phase flash chromatography using ethyl acetate and methanol (9:1) as eluent to afford the product as a mixture with triethylamine salts. The crude product was dissolved in methanol and filtered over Amberlite 410. The solvent was evaporated to afford the title compound (8 mg, yield 15%).

$^1$H NMR (CD$_3$ OD): δ=3.67 (m, 1H), 3.24 (d, 4H), 2.50 (d, 4H), 2.43 (q, 2H) and 0.95 (t, 3H).

Intermediate P41: 1-(1-iso-Propylazetidin-3-yl)pyrrolidine-3-sulfonamide

Step A: 1-(Azetidin-3-yl)pyrrolidine-3-sulfonamide Dihydrochloride

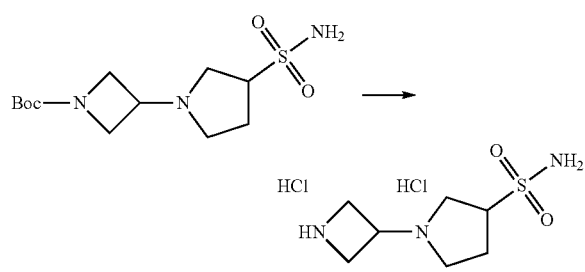

To a solution of tert-butyl 3-(3-sulfamoylpyrrolidin-1-yl)azetidine-1-carboxylate (726 mg, 2.38 mmol, 1.0 equiv.) in dichloromethane (24 mL) was added hydrochloric acid in dioxane (4 M, 6.0 mL, 23.8 mmol, 10.0 equiv.). The reaction mixture was stirred for 1.5 hours and then concentrated in vacuo to afford the title compound as a dihydrochloride salt (774 mg, 2.38 mmol, yield too %) which was used without purification.

$^1$H NMR (DMSO-d$_6$): δ=9.60 (br s, 1H), 9.17 (br s, 1H), 7.24 (s, 2H), 4.34 (m, 4H), 4.11 (m, 3H), 3.91 (m, 2H) and 2.23 (m, 4H).

Step B: 1-(1-iso-Propylazetidin-3-yl)pyrrolidine-3-sulfonamide

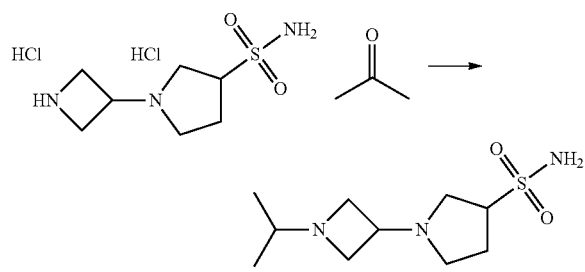

Prepared as described for 1-cyclobutylpiperidine-4-sulfonamide (Intermediate P14) from 1-(azetidin-3-yl)pyrrolidine-3-sulfonamide dihydrochloride and acetone, but 2.5 equivalent of triethylamine was required. The crude compound was purified by normal phase flash chromatography using dichloromethane and a mixture of 3.5 M ammonia in methanol as eluent to afford the title compound (94 mg, yield 38%).

$^1$H NMR (DMSO-d$_6$): δ=6.91 (s, 2H), 3.58 (m, 1H), 3.24 (t, 2H), 2.98 (m, 1H), 2.90 (m, 3H), 2.52 (m, 2H), 2.38 (q, 1H), 2.21 (m, 1H), 2.01 (m, 2H) and 0.81 (d, 6H).

Intermediate P42: (1R*,3R*,5S*)-8-Ethyl-8-azabicyclo[3.2.1]octane-3-sulfonamide

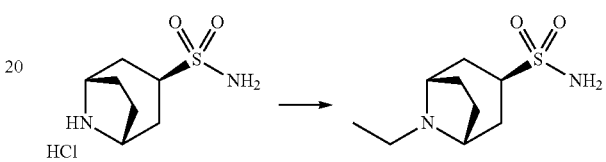

Prepared as described for 1-(prop-2-yn-1-yl)piperidine-4-sulfonamide (Intermediate P3) from iodoethane and (1R,3R,5S)-8-azabicyclo[3.2.1]octane-3-sulfonamide hydrochloride. The title compound (36 mg, yield 41%) was used without further purification.

$^1$H NMR (DMSO-d$_6$): δ=6.63 (br s, 2H), 3.97 (br s, 2H), 3.10 (q, 2H), 2.98 (br s, 1H), 2.58 (m, 2H), 2.30 (m, 2H), 2.11 (m, 4H) and 1.11 (m, 3H).

Intermediate P43: 1-Ethylazetidine-3-sulfonamide

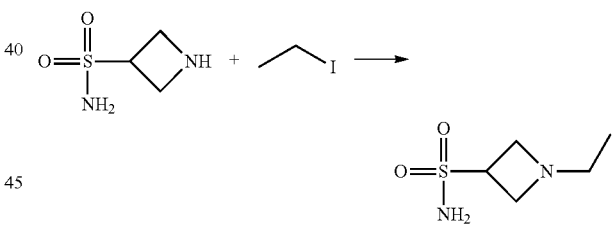

Prepared as described for 1-ethylpiperidine-4-sulfonamide (Intermediate P6) from azetidine-3-sulfonamide (Intermediate P33) and ethyl iodide. This afforded the title compound impure (15 mg, yield 9%) which was used without further purification.

$^1$H NMR (CD$_3$OD): δ=4.11 (m, 1H), 3.81 (t, 2H), 3.62 (t, 2H), 2.74 (q, 2H) and 1.02 (t, 3H).

Intermediate P44: 1-(2,2,2-Trifluoroacetyl)pyrrolidine-3-sulfonamide

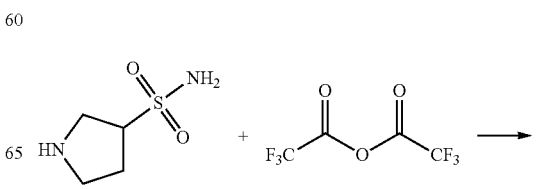

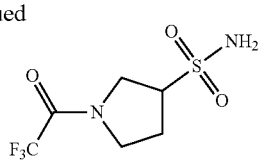

Prepared as described for 1-(2,2,2-trifluoroacetyl)piperidine-4-sulfonamide (Intermediate P4) from pyrrolidine-3-sulfonamide and bis-trifluoroacetic anhydride. This afforded the title compound (72 mg, yield 36%) which was used without purification.

$^1$H NMR (CD$_3$OD): δ=4.08 (m, 1H), 3.91 (m, 3H), 3.63 (m, 1H), 2.45 (m, 1H) and 2.38 (m, 1H).

Intermediate P45:
1-(Cyclopropylmethyl)piperidine-3-sulfonamide

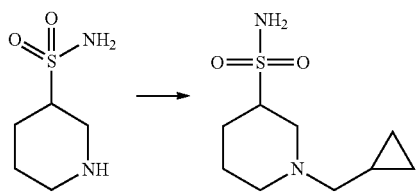 [SMILES: NS(=O)(=O)C1CCCNC1 ; NS(=O)(=O)C1CCCN(CC2CC2)C1]

Prepared as described for 1-ethylpiperidine-3-sulfonamide (Intermediate P15) using piperidine-3-sulfonamide hydrochloride (0.5 g, 3.2 mmol) and iodomethyl-cyclopropane (0.29 mL, 0.58 g, 3.2 mmol) to afford the title compound (0.28 g, 1.26 mmol, yield 40%) after column purification.

$^1$H NMR (CDCl$_3$): δ=3.41 (br d, 1H), 3.31 (m, 1H), 2.96 (br d, 1H), 2.44 (t, 1H), 2.36 (d, 2H), 2.20 (m, 2H), 1.91 (m, 1H), 1.71 (m, 2H), 0.90 (m, 1H), 0.57 (m, 2H) and 0.15 (m, 2H).

Intermediate P46:
1-Methylpiperidine-3-sulfonamide

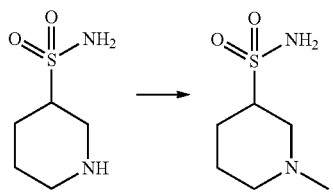

Prepared as described for 1-ethylpiperidine-3-sulfonamide (Intermediate P15) using piperidine-3-sulfonamide hydrochloride (0.5 g, 3.2 mmol) and methyl iodide (0.20 mL, 0.45 g, 3.2 mmol) to give the title compound (0.24 g, 1.35 mmol, yield 43%). The crude product was used without further purification.

$^1$H NMR (CD$_3$OD): δ=3.2-3.4 (m, 3H), 2.97 (br d, 1H), 2.45 (s, 3H), 2.38 (br t, 1H), 2.20 (m, 1H), 1.90 (br d, 1H) and 1.5-1.8 (m, 2H).

Intermediate P47: Benzyl 3-sulfamoylazetidine-1-carboxylate

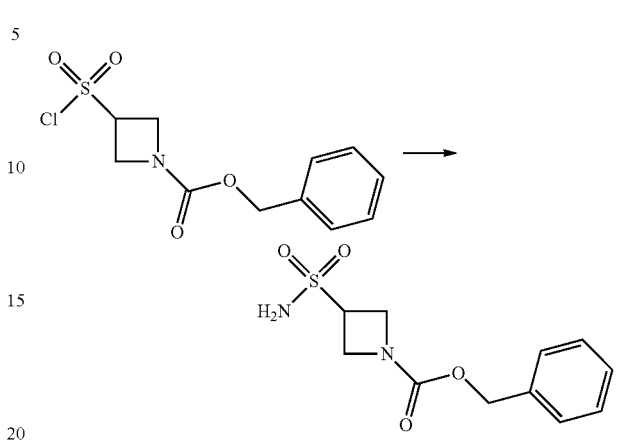

To a stirred solution of benzyl 3-(chlorosulfonyl)azetidine-1-carboxylate (2.0 g, 6.9 mmol) in dichloromethane (30 mL) at 0° C. was added ammonia (7 N in methanol, 30 mL). The resultant mixture was stirred overnight, slowly warming to room temperature and then concentrated to a white solid, triturated with THF and the resulting title compound isolated as a white solid by filtration (yield 95%) and used without further purification.

$^1$H NMR (CD$_3$OD): δ=7.3 (m, 5H), 5.05 (d, 2H), 4.25 (m, 2H), 4.13 (m, 2H) and 2.47 (m, 1H).

Intermediate P48:
N,N-Dimethyl-4-sulfamoylpiperidine-1-carboxamide

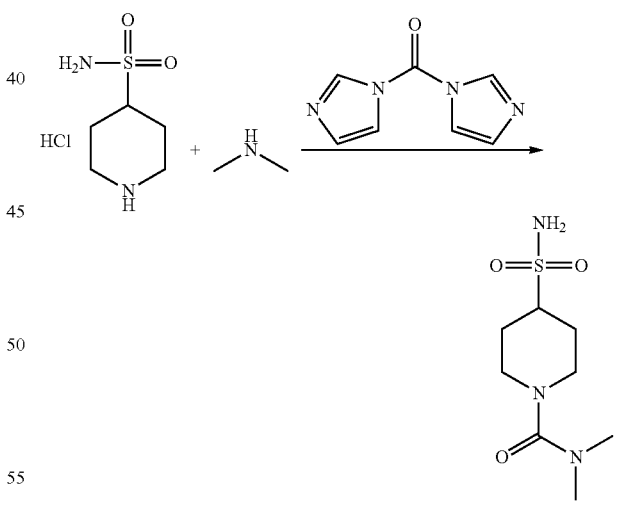

To a solution of carbonyldiimidazole (162 mg, 1.0 mmol) in acetonitrile (10 mL) was added dimethylamine hydrochloride (81 mg, 1.0 mmol) and the solution was stirred overnight at room temperature. Triethylamine (0.42 mL, 3.0 mmol, 3.0 equiv.) and piperidine-4-sulfonamide hydrochloric acid (200 mg, 1.0 mmol) were added to the suspension. The reaction mixture was stirred overnight and additional portions of carbonyldiimidazole (162 mg, 1.0 mmol), triethylamine (0.42 mL, 3.0 mmol, 3.0 equiv.) and 2 M dimethylamine in tetrahydrofuran (0.5 mL, 1.0 mmol) were added. After stirring overnight, extra 2 M dimethylamine in tetrahydrofuran (2 mL, 4.0 mmol, 4.0 equiv.) was added. The reaction mixture was then stirred at room temperature for 3 days, before being transferred to a microwave vial and additional 2 M dimethylamine in tetrahydrofuran (2.0 mL, 4.0 mmol, 4.0 equiv.) added. The vial was heated to 50° C. overnight and then concentrated in vacuo. The crude was dissolved in methanol, coated on hydromatrix and then purified by normal phase flash chromatography using dichloromethane and a mixture of triethylamine and methanol (ratio 1:1) as eluent to afford the title compound (73 mg, yield 31%).

$^1$H NMR (DMSO-d$_6$): δ=6.72 (s, 2H), 3.60 (d, 2H), 2.98 (m, 1H), 2.72 (m, 8H), 1.94 (d, 2H), 1.52 (m, 2H).

Intermediate P49: 1-(1-Isopropyl-azetidin-3-yl)piperidine-4-sulfonamide

Step A: tert-Butyl 3-(4-sulfamoylpiperidin-1-yl)azetidine-1-carboxylate

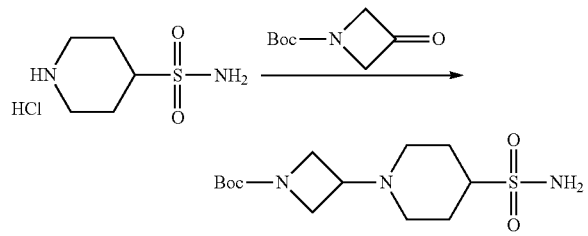

Prepared as described for 1-cyclobutylpiperidine-4-sulfonamide (Intermediate P14) from piperidine-4-sulfonamide hydrochloride salt (0.35 g, 1.6 mmol) and 1-Boc-azetidinone (0.28 g, 1.6 mmol) using 2 equivalents of triethylamine. The crude compound was purified by normal phase flash chromatography using dichloromethane and a mixture of 3.5 M ammonia in methanol as eluent to afford the title compound as a white waxy solid (236 mg, yield 47%).

HPLC-MS: 100% (ELSD), M 319+1 (ACPI pos.)

$^1$H NMR (Methanol-d4): δ=4.37 (s, 2H), 3.94 (dd, J=8.8, 7.2 Hz, 2H), 3.77 (dd, J=9.0, 5.3 Hz, 2H), 3.09 (tt, J=7.1, 5.3 Hz, 1H), 3.00-2.81 (m, 3H), 2.22-2.08 (m, 2H), 1.98-1.70 (m, 4H), 1.41 (s, 9H).

Step B: 1-(Azetidin-3-yl)piperidine-4-sulfonamide Dihydrochloride

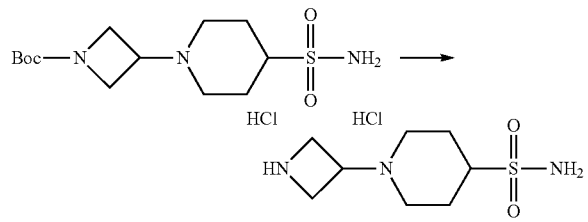

tert-Butyl 3-(4-sulfamoylpiperidin-1-yl)azetidine-1-carboxylate (0.23 g, 0.7 mmol) from step A was suspended in HCl in dioxane (4N, 9 mL, 36 mmol) and stirred for 20 hours at ambient temperature. The solvents were evaporated in vacuo and the residue stripped once with dioxane (25 mL) to afford the crude product (250 mg, quant. yield), which was used as is in the next step.

HPLC-MS: 97% (ELSD), M 291+1 (ACPI pos.)

$^1$H NMR (Methanol-d4): δ=4.72-4.57 (m, 2H), 4.44-4.28 (m, 3H), 3.61 (d, J=11.7 Hz, 2H), 3.26 (dd, J=11.1, 4.2 Hz, 2H), 3.01 (s, 1H), 2.44 (dd, J=14.3, 3.1 Hz, 2H), 2.24 (t, 1H), 1.61 (s, 1H).

Step C: 1-(1-Isopropyl-azetidin-3-yl)piperidine-4-sulfonamide

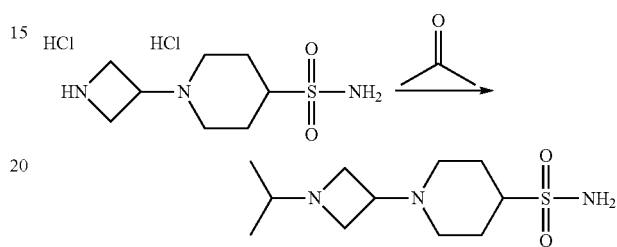

Prepared following the procedure as described for 1-cyclobutylpiperidine-4-sulfonamide (Intermediate P14) from 1-(azetidin-3-yl)piperidine-4-sulfonamide dihydrochloride (100 mg, 0.31 mmol) from step B and acetone (0.03 mL, 22 mg, 0.39 mmol) to yield the title compound as a white solid (70 mg, yield 87%) after column chromatography.

HPLC-MS: 59+40% (ELSD) showed two peaks both have M 262+1 (ACPI pos.) $^1$H NMR (Methanol-d4): δ=3.55 (t, J=6.5 Hz, 2H), 3.02-2.82 (m, 6H), 2.49 (h, J=6.2 Hz, 1H), 2.13 (ddd, J=12.0, 4.2, 2.2 Hz, 2H), 1.88 (dd, J=11.3, 2.1 Hz, 2H), 1.77 (qd, J=12.1, 3.5 Hz, 2H), 0.97 (d, J=6.3 Hz, 6H).

Intermediate P50: 2-Isopropyl-2-azaspiro[3.3]heptane-6-sulfonamide

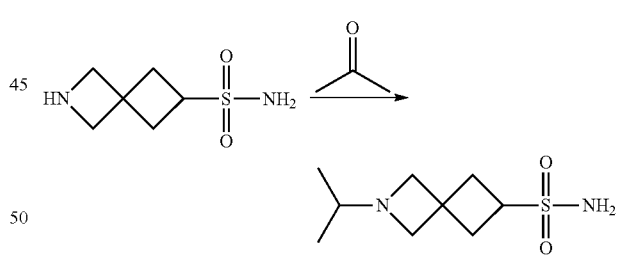

To a solution of 2-azaspiro[3.3]heptane-6-sulfonamide (50 mg, 0.28 mmol) and acetone (25 mg, 0.43 mmol, 1.5 equiv.) in acetonitrile (5 mL) was added sodium triacetoxyborohydride (89 mg, 0.43 mmol, 1.5 equiv.). The reaction mixture was stirred for 18 hours at room temperature and then concentrated in vacuo. The crude material was dissolved in methanol and treated with Amberlite 410 ion exchange resin. The mixture was filtered and the methanol was evaporated. The residue was triturated in THF. The mixture was filtered and the THF was evaporated to afford the title compound (40 mg, yield 65%) which was used as such.

$^1$H NMR (CD3OD): δ=3.71 (m, 1H), 3.25 (m, 4H), 2.53 (m, 4H), 2.33 (m, 1H), 0.93 (d, 6H).

Intermediate P51: 2-Methyl-2-azaspiro[3.3]heptane-6-sulfonamide

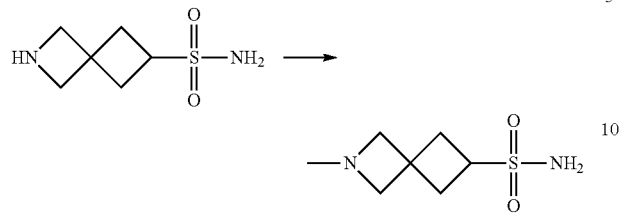

To a solution of 2-azaspiro[3.3]heptane-6-sulfonamide (50 mg, 0.28 mmol) and formaldehyde (32 µL, 37% in water, 0.43 mmol, 1.5 equiv.) in acetonitrile (5 mL) was added sodium triacetoxyborohydride (90 mg, 0.43 mmol, 1.5 equiv.). The reaction mixture was stirred for 18 hours at room temperature and then concentrated in vacuo. The crude material was dissolved in methanol and treated with Amberlite 410 ion exchange resin. The mixture was filtered and the methanol was evaporated. The residue was triturated in THF. The mixture was filtered and the THF was evaporated to afford the title compound (40 mg, yield 74%) which was used as such.

$^1$H NMR (CD$_3$OD): δ=3.71 (m, 1H), 3.37-3.21 (m, 4H), 2.52 (m, 4H), 2.29 (s, 3H).

Intermediate P52: 1-(Pentan-3-yl)azetidine-3-sulfonamide

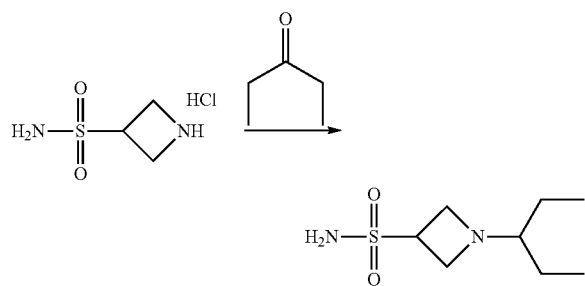

Prepared as described for 1-cyclobutylpiperidine-4-sulfonamide (Intermediate P14) from azetidine-3-sulfonamide hydrochloride and 3-pentanone. The title compound (20 mg, yield 12%) was used without further purification.

$^1$H NMR (DMSO-d6): δ=6.86 (s, 2H), 3.82 (m, 1H), 3.42 (t, 2H), 3.21 (t, 2H), 2.03 (m, 1H), 1.24 (m, 4H), 0.74 (m, 6H).

Intermediate P53: 1-Ethyl-1,2,3,4-tetrahydroquinoline-3-sulfonamide

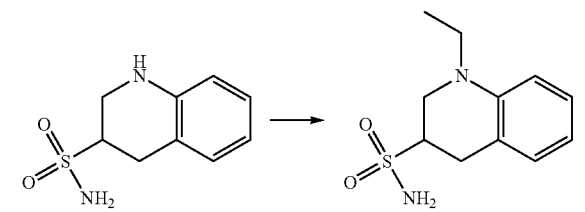 [SMILES: NS(=O)(=O)C1CNc2ccccc2C1 ; CCN1CC(S(N)(=O)=O)Cc2ccccc21]

Prepared as described for 1-cyclobutylpiperidine-4-sulfonamide (Intermediate P14) from 1,2,3,4-tetrahydroquinoline-3-sulfonamide, acetone and acetic acid, but no triethylamine was required. The title compound (27 mg, yield 11%) was used without further purification. The expected iso-propyl analog was not isolated.

$^1$H NMR (CDCl$_3$): δ=7.09 (m, 2H), 6.70 (m, 2H), 4.52 (br s, 2H), 3.60 (m, 3H), 3.44 (m, 2H), 3.26 (m, 2H), 1.17 (t, 3H).

Intermediate P54: 1-(2,2,2-Trifluoroethyl)piperidine-4-sulfonamide

Step A: 1-(2,2,2-Trifluoroacetyl)piperidine-4-sulfonamide

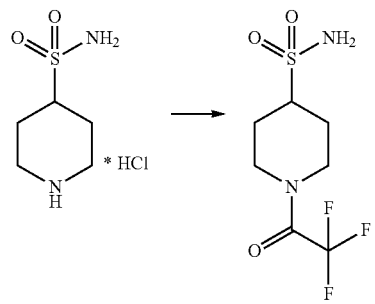 [SMILES: NS(=O)(=O)C1CCNCC1 ; NS(=O)(=O)C1CCN(C(=O)C(F)(F)F)CC1]

A suspension of piperidine-4-sulfonamide hydrochloride salt (600 mg, 2.7 mmol) was stirred with triethylamine (0.75 mL, 0.54 g, 5.4 mmol) in acetonitrile (12 mL) for 30 minutes. To this slurry was added trifluoroacetic anhydride (0.38 mL, 0.57 g, 2.7 mmol) and the stirring continued for 20 hours. The mixture was concentrated in vacuo and the residue dissolved in methanol, then applied to a silica column (40 g) and eluted with 0-30% methanol in DCM to afford 1-(2,2,2-trifluoroacetyl)piperidine-4-sulfonamide (182 mg, yield 26%), contaminated with a bistrifluoroacetylated byproduct. This was used for the next step as such.

HPLC-MS: 76% (ELSD), M 260+1 (ACPI pos.).
HPLC-MS: 23% (ELSD), M 356+1 (ACPI pos.) for the bistrifluoroacetylated byproduct.

$^1$H NMR (Methanol-d4): δ=7.39 (s, 1H), 4.64-4.47 (m, 1H), 4.10 (d, J=13.1 Hz, 1H), 3.51 (tt, J=11.4, 4.0 Hz, 1H), 3.22 (dt, J=12.6, 3.5 Hz, 2H), 2.87 (td, J=13.0, 2.9 Hz, 1H), 2.21 (ddt, J=20.3, 13.9, 3.2 Hz, 2H), 1.78 (ddtt, J=24.0, 16.4, 7.6, 4.4 Hz, 2H).

Step B: 1-(2,2,2-Trifluoroethyl)piperidine-4-sulfonamide

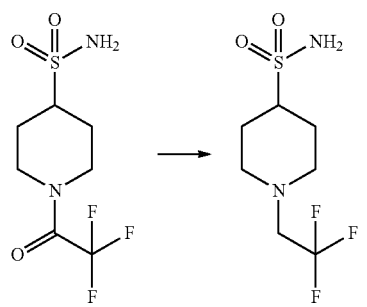 [SMILES: NS(=O)(=O)C1CCN(C(=O)C(F)(F)F)CC1 ; NS(=O)(=O)C1CCN(CC(F)(F)F)CC1]

The 1-(2,2,2-trifluoroacetyl)piperidine-4-sulfonamide from step A (65 mg, 0.22 mmol) was dissolved in THF (3.25 mL) and cooled to 0° C. To this solution was added dropwise borane-DMS-adduct (94%, 9.9M, 0.10 mL, 1.01 mmol) at 0° C. and then the mixture was heated to reflux for 4 hours and subsequently allowed to cool to room temperature over the weekend. This mixture was quenched with MeOH until no gas evolution was visible anymore and then evaporated in vacuo and stripped twice with methanol. Drying in vacuo gave the crude product as a clear oil (with a slight DMS smell), which was purified by ISCO 5-30% MeOH (3.5N NH3) in DCM to afford the title compound (31 mg, yield 56%).

HPLC-MS: 100% (ELSD), M 246+1 (ACPI pos.)

¹H NMR (Methanol-d4): δ=3.16-3.00 (m, 4H), 2.88 (tt, J=12.2, 3.8 Hz, 1H), 2.42 (td, J=12.0, 2.5 Hz, 2H), 2.08 (dt, J=13.1, 2.9 Hz, 2H), 1.80 (qd, J=12.4, 4.1 Hz, 2H), 1.17 (t, J=7.1 Hz, 1H), 1.00-0.81 (m, 1H).

Intermediate P55: (1R*,3S*,5S*)-8-iso-Propyl-8-azabicyclo[3.2.1]octane-3-sulfonamide Step A: tert-Butyl (1R*,3R*,5S*)-3-((methylsulfonyl)oxy)-8-azabicyclo[3.2.1]octane-8-carboxylate

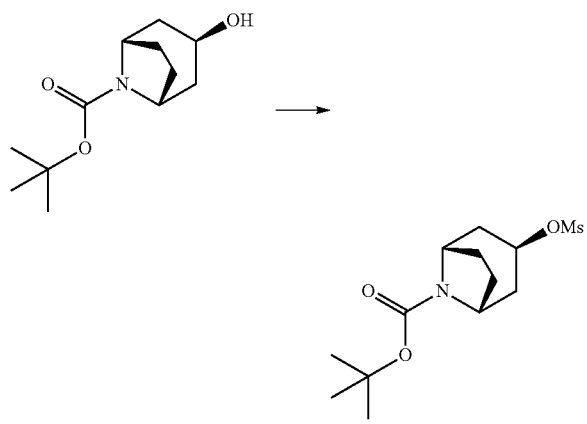

Prepared as described for tert-butyl (1R*,3S*,5S*)-3-((methylsulfonyl)oxy)-8-azabicyclo[3.2.1] octane-8-carboxylate (intermediate P36 step A) from tert-butyl 3-endo-hydroxy-8-azabicyclo[3.2.1]octane-8-carboxylate to afford the title compound (3.3 g, yield 81%).

¹H NMR (CDCl₃): δ=5.02 (t, 1H), 4.21 (br s, 2H), 3.00 (s, 3H), 2.03 (m, 8H), 1.45 (s, 9H).

Step B: tert-Butyl (1R*,3S*,5S*)-3-(acetylthio)-8-azabicyclo[3.2.1]octane-8-carboxylate

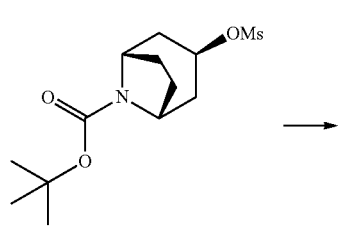

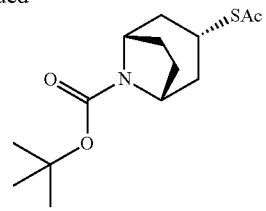

Prepared as described for tert-butyl (1R*,3R*,5S*)-3-(acetylthio)-8-azabicyclo[3.2.1]octane-8-carboxylate (intermediate P36 step B) from tert-butyl (1R*,3R*,5S*)-3-((methylsulfonyl)oxy)-8-azabicyclo[3.2.1]octane-8-carboxylate to afford the title compound (1.65 g, yield 53%).

¹H NMR (CDCl₃): δ=4.19 (br s, 2H), 3.87 (m, 1H), 2.28 (s, 3H), 1.98 (m, 2H), 1.79 (d, 6H), 1.45 (s, 9H).

Step C: tert-Butyl (1R*,3S*,5S*)-3-sulfamoyl-8-azabicyclo[3.2.1]octane-8-carboxylate

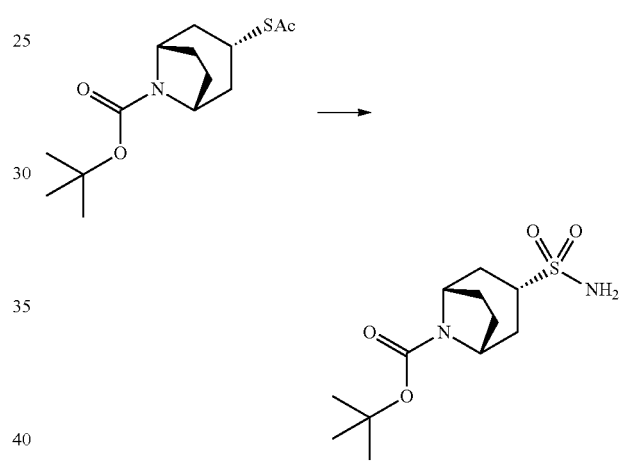

Prepared as described for tert-butyl (1R*,3R*,5S*)-3-sulfamoyl-8-azabicyclo[3.2.1]octane-8-carboxylate (intermediate P36 step C) from tert-butyl (1R*,3S*,5S*)-3-(acetylthio)-8-azabicyclo[3.2.1]octane-8-carboxylate, except that the crude title compound was purified by normal phase flash chromatography using heptane and ethyl acetate to afford the title compound (235 mg, yield 14%).

¹H NMR (CDCl₃): δ=4.50 (m, 2H), 3.11 (m, 1H), 2.03 (m, 4H), 1.68 (m, 4H), 1.46 (s, 9H).

Step D: (1R*,3S*,5S*)-8-Azabicyclo[3.2.1]octane-3-sulfonamide Hydrochloride

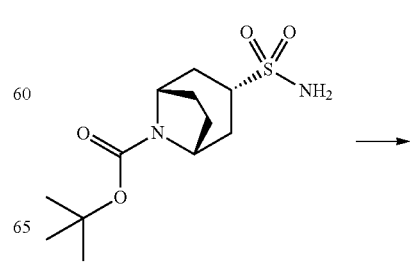

-continued

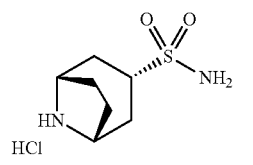

Prepared as described for (1R*,3R*,5S*)-8-azabicyclo[3.2.1]octane-3-sulfonamide hydrochloride (intermediate P36 step D) from tert-butyl (1R*,3S*,5S*)-3-sulfamoyl-8-azabicyclo[3.2.1]octane-8-carboxylate to afford the title compound (203 mg, quantitative yield).

$^1$H NMR (DMSO-d6): δ=9.28 (s, 1H), 9.11 (s, 1H), 6.90 (s, 2H), 4.04 (m, 2H), 3.95 (s, 1H), 2.07 (m, 1H), 1.96 (m, 6H), 1.82 (d, 1H).

Step E: (1R*,3S*,5S*)-8-iso-Propyl-8-azabicyclo[3.2.1]octane-3-sulfonamide

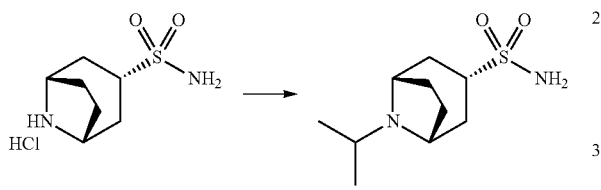

Prepared as described for 1-cyclobutylpiperidine-4-sulfonamide (Intermediate P14) from (1R*,3S*,5S*)-8-azabicyclo[3.2.1]octane-3-sulfonamide hydrochloride, except that the crude compound was purified by normal phase flash chromatography using dichloromethane and a mixture of 7M ammonia in methanol to afford the title compound (15 mg, yield 16%), which was used without further purification.

$^1$H NMR (CD3OD): δ=4.24 (m, 1H), 4.14 (m, 1H), 3.53 (m, 2H), 2.49 (m, 1H), 2.20 (m, 5H), 2.00 (m, 2H), 1.37 (d, 6H).

Intermediate P56: (1R*,3S*,5S*)-8-Ethyl-8-azabicyclo[3.2.1]octane-3-sulfonamide

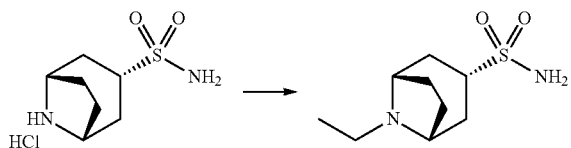

Prepared as described for 1-ethylpiperidine-4-sulfonamide (intermediate P6) from (1R*,3S*,5S*)-8-azabicyclo[3.2.1]octane-3-sulfonamide hydrochloride to afford the title compound (30 mg, yield 34%), which was used without further purification.

$^1$H NMR (CD3OD): δ=4.10 (m, 1H), 4.00 (m, 1H), 3.53 (m, 1H), 3.08 (m, 2H), 2.58 (m, 1H), 2.24 (m, 5H), 2.02 (m, 2H), 1.34 (m, 3H).

Intermediate P57: 1-Benzylazetidine-3-sulfonamide

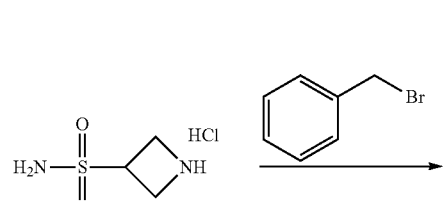

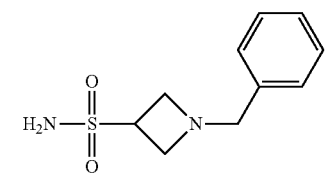

Prepared as described for 1-(prop-2-yn-1-yl)piperidine-4-sulfonamide (intermediate P3) from azetidine-3-sulfonamide hydrochloride and benzyl bromide. The title compound (57 mg, yield 25%) was used without further purification.

$^1$H NMR (DMSO-d6): δ=7.24 (m, 5H), 6.93 (s, 2H), 3.92 (m, 1H), 3.58 (s, 2H), 3.46 (t, 2H), 3.35 (m, 2H).

Intermediate P58: 1-(1-Ethylpiperidin-4-yl)azetidine-3-sulfonamide

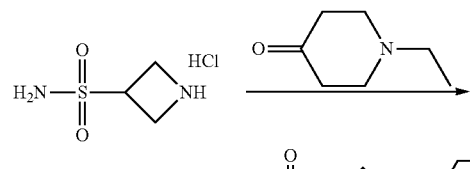

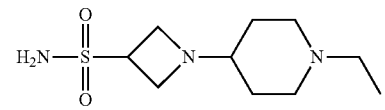

Prepared as described for 1-cyclobutylpiperidine-4-sulfonamide (Intermediate P14) from azetidine-3-sulfonamide hydrochloride and 1-ethyl-4-piperidone. The title compound (111 mg, yield 44%) was used without further purification.

$^1$H NMR (DMSO-d6): δ=6.88 (s, 2H), 3.85 (m, 1H), 3.42 (t, 2H), 3.22 (t, 2H), 2.71 (m, 2H), 2.27 (q, 2H), 2.02 (m, 1H), 1.87 (m, 2H), 1.57 (dd, 2H), 1.09 (m, 2H), 0.95 (t, 3H).

Intermediate P59: 1-Acetylazetidine-3-sulfonamide

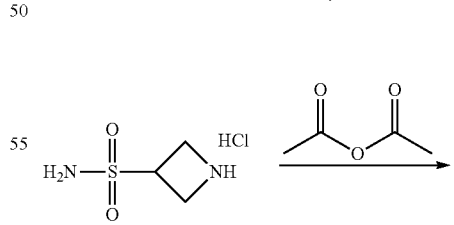

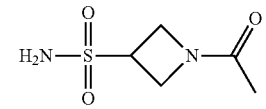

Prepared as described for 1-acetylpiperidine-4-sulfonamide (Intermediate P7) from azetidine-3-sulfonamide hydrochloride. The title compound (31 mg, yield 20%) was used without further purification.

¹H NMR (CD3OD): δ=4.57 (m, 1H), 4.50 (m, 2H), 4.36 (m, 2H), 1.98 (s, 3H).

Intermediate P60: 1-(Tetrahydro-2H-pyran-4-yl)azetidine-3-sulfonamide

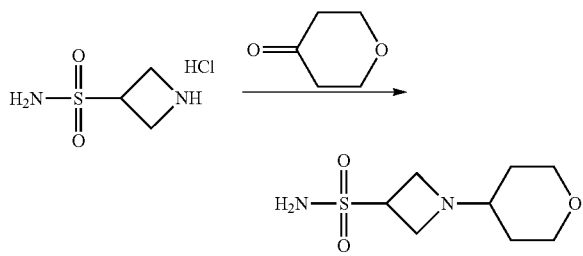

Prepared as described for 1-cyclobutylpiperidine-4-sulfonamide (Intermediate P14) from azetidine-3-sulfonamide hydrochloride and tetrahydro-4H-pyran-4-one. The title compound (112 mg, yield 50%) was used without further purification.

¹H NMR (DMSO-d6): δ=6.89 (s, 2H), 3.86 (m, 1H), 3.77 (dt, 2H), 3.44 (t, 2H), 3.24 (m, 3H), 2.98 (q, 1H), 2.26 (tq, 1H), 1.55 (dd, 2H), 1.11 (m, 2H).

Intermediate P61: 1-Propylazetidine-3-sulfonamide

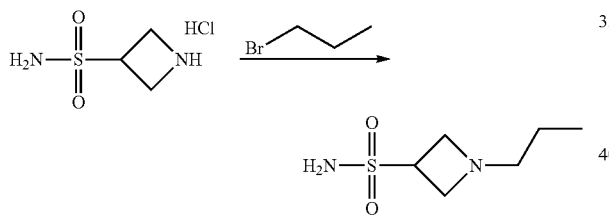

Prepared as described for 1-(prop-2-yn-1-yl)piperidine-4-sulfonamide (Intermediate P3) from azetidine-3-sulfonamide hydrochloride and 1-bromopropane. The title compound (15 mg, yield 8%) was used without further purification.

¹H NMR (DMSO-d6): δ=6.88 (s, 2H), 3.87 (m, 1H), 3.44 (t, 2H), 3.22 (t, 2H), 2.32 (t, 2H), 1.24 (m, 2H), 0.80 (t, 3H).

Intermediate P62: tert-Butyl 3-sulfamoylazetidine-1-carboxylate

Step A: tert-Butyl 3-(acetylthio)azetidine-1-carboxylate

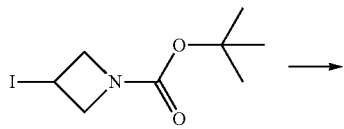

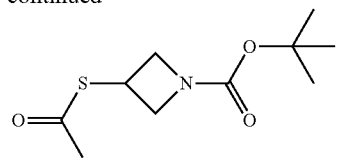

To a solution of tert-butyl 3-iodoazetidine-1-carboxylate (17.2 g, 60.8 mmol, 1.0 equiv.) and thioacetic acid (8.7 mL, 121.6 mmol, 2.0 equiv.) in dimethylformamide (83 mL) was added cesium carbonate (39.6 g, 121.6 mmol, 2.0 equiv.) portionwise. The reaction was exothermic during this addition. Then the reaction mixture was heated to 70° C. for 1 hour to afford complete conversion. The mixture was diluted with water (600 mL) and then extracted with diethyl ether (600 mL). The organic layer was washed twice with water (600 mL), once with brine (500 mL), dried over Na₂SO₄, filtered and concentrated in vacuo. The crude was submitted to normal phase flash chromatography on silica gel using heptane and ethyl acetate as eluent to afford the title compound (8.76 g, yield 62%).

¹H NMR (CDCl₃): δ=4.35 (t, 2H), 4.10 (m, 1H), 3.78 (dd, 2H), 2.28 (s, 3H), 1.39 (s, 9H).

Step B: tert-Butyl 3-(chlorosulfonyl)azetidine-1-carboxylate

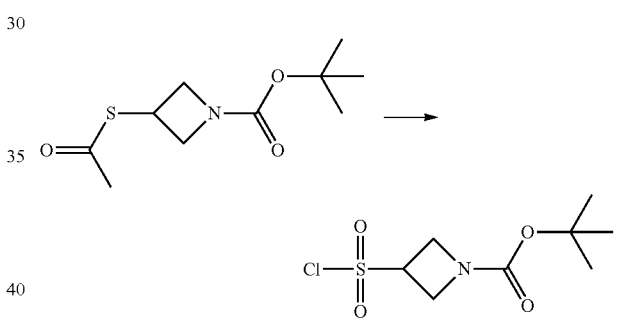

To a solution of tert-butyl 3-(acetylthio)azetidine-1-carboxylate (8.76 g, 37.9 mmol, 1.0 equiv.) in water (38 mL) and acetic acid (380 mL) was added N-chlorosuccinimide (15.2 g, 113.7 mmol, 3.0 equiv.). The suspension was stirred for 20 minutes at room temperature to afford a clear solution and complete conversion. The reaction mixture was diluted with water (600 mL), and then extracted with dichloromethane (600 mL). The organic layer was washed twice with water (600 mL), once with brine (300 mL), dried over Na2SO4, filtered and then used as such for the following reaction without further concentrating the organic layer.

¹H NMR (CDCl₃): δ=4.57 (m, 1H), 4.38 (m, 4H), 1.42 (s, 9H).

Step C: tert-Butyl 3-sulfamoylazetidine-1-carboxylate

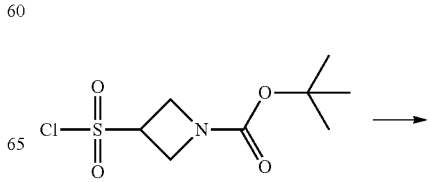

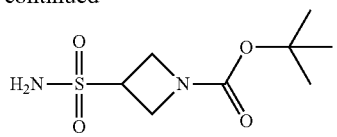

To a solution of tert-butyl 3-(chlorosulfonyl)azetidine-1-carboxylate (max 37.9 mmol) in dichloromethane (600 mL) was added 7M ammonia in methanol (55 mL, 379 mmol, 10 equiv.). The clear solution was stirred for half an hour at room temperature. The suspension was concentrated in vacuo. The crude was dissolved in methanol, coated on hydromatrix and then submitted to normal phase flash chromatography using dichloromethane and a mixture of ammonia (3.5 M) in methanol as eluent to afford the tittle compound (2.67 g, 11.3 mmol, yield over two steps 30%).

$^1$H NMR (DMSO-d6): δ=7.18 (s, 2H), 4.10 (m, 2H), 3.98 (m, 3H), 1.39 (s, 9H).

Intermediate P63: Methyl 2-(3-sulfamoylazetidin-1-yl)acetate

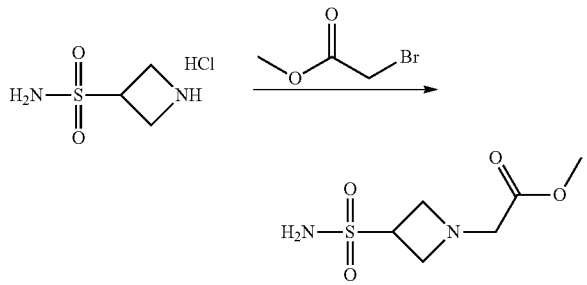

Prepared as described for 1-(prop-2-yn-1-yl)piperidine-4-sulfonamide (Intermediate P3) from azetidine-3-sulfonamide hydrochloride and methyl bromoacetate. The title compound (43 mg, yield 21%) was used without further purification.

$^1$H NMR (DMSO-d6): δ=6.92 (s, 2H), 3.92 (m, 1H), 3.58 (m, 5H), 3.41 (dd, 2H), 3.29 (s, 2H).

Intermediate P64: 1-Isopropyl-2-oxopyrrolidine-3-sulfonamide

Step A: 2-Bromo-4-chlorobutanoyl Chloride

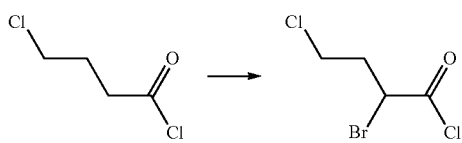 [SMILES: O=C(Cl)CCCCl ; O=C(Cl)C(Br)CCCl]

To a solution of 4-chlorobutanoyl chloride (25 g, 177.31 mmol, 1 eq) in DCM (45 mL) was added NBS (47.34 g, 265.97 mmol, 1.5 eq) and SOCl$_2$ (1.05 g, 8.87 mmol, 643.13 µL, 0.05 eq) followed by HBr (1.33 g, 6.58 mmol, 892.86 µL, 40% purity, 0.037 eq) at 25° C. The mixture was stirred at 50° C. for 1.5 hours. The reaction mixture was diluted with hexane (300 mL) and filtered. The filtrate was concentrated in vacuo to give the title compound (35 g, crude), which was used in the next step without further purification.

$^1$H NMR (CDCl$_3$): δ=4.87-4.80 (m, 1H), 3.76-3.74 (m, 2H) and 2.59-2.44 (m, 2H).

Step B: 2-Bromo-4-chloro-N-isopropylbutanamide

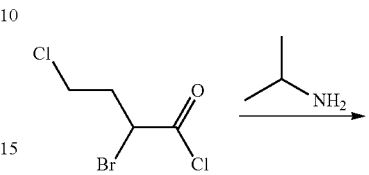

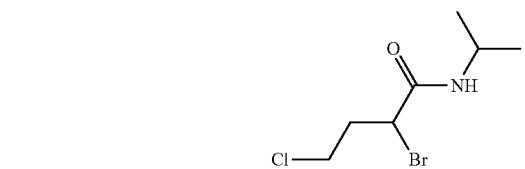

To a solution of 2-bromo-4-chlorobutanoyl chloride (20 g, 90.95 mmol, 1 eq) in DCM (50 mL) was added propan-2-amine (6.45 g, 109.14 mmol, 9.38 mL, 1.2 eq) at 0° C. The mixture was warmed to 25° C. and stirred at 25° C. for another 1 hour. The reaction mixture was diluted with DCM (200 mL) and washed with water (100 mL). The organic layer was dried over Na$_2$SO$_4$, filtered and concentrated in vacuo to give the title compound (19.1 g, 78.75 mmol, yield 87%).

Step C: 3-Bromo-1-isopropylpyrrolidin-2-one

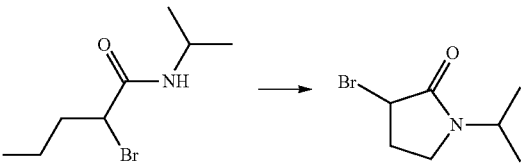

To a solution of 2-bromo-4-chloro-N-isopropylbutanamide (19 g, 78.34 mmol, 1 eq) in THF (200 mL) was added NaH (6.27 g, 156.67 mmol, 60% purity, 2 eq) at 0° C. The mixture was stirred at 25° C. for 1 hour. Then the reaction mixture was quenched with H$_2$O (200 mL) and extracted with ethyl acetate (2×300 mL). The combined organic layers were washed with brine (200 mL), dried over Na$_2$SO$_4$, filtered and concentrated in vacuo. The residue was purified by column chromatography (SiO$_2$, petroleum ether:ethyl acetate=20:1 to 1:1) to give the title compound (11.5 g, 55.80 mmol, yield 71%).

$^1$H NMR (CDCl$_3$): δ=4.41-4.31 (m, 2H), 3.46-3.43 (m, 1H), 3.32-3.29 (m, 1H), 2.55-2.49 (m, 1H), 2.32-2.30 (m, 1H) and 1.16-1.14 (m, 6H).

Step D: Methyl 3-((1-isopropyl-2-oxopyrrolidin-3-yl)sulfonyl)propanoate

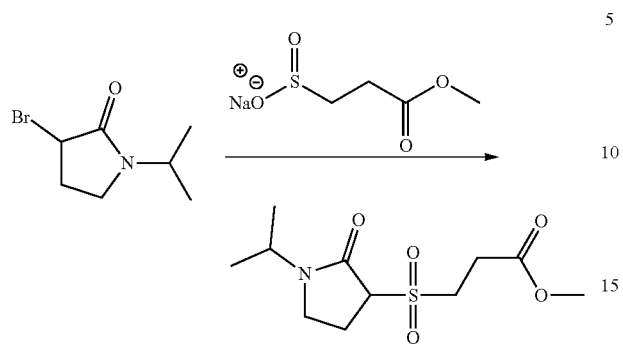

To a solution of 3-bromo-1-isopropylpyrrolidin-2-one (1 g, 4.85 mmol, 1 eq) in DMSO (10 mL) was added sodium 3-methoxy-3-oxo-propane-1-sulfinate (845 mg, 4.85 mmol, 1 eq). The mixture was stirred at 25° C. for 16 hours. The reaction mixture was quenched with water (80 mL) and extracted with ethyl acetate (3×80 mL). The combined organic layers were washed with brine (60 mL), dried over $Na_2SO_4$, filtered and concentrated in vacuo. The residue was purified by column chromatography ($SiO_2$, petroleum ether:ethyl acetate=10:1 to 1:1) to give the title compound (1.1 g, 3.97 mmol, yield 82%).

$^1$H NMR (CDCl$_3$): δ=4.37-4.33 (m, 1H), 3.97-3.93 (m, 1H), 3.82-3.72 (m, 5H), 3.58-3.51 (m, 1H), 3.39-3.38 (m, 1H), 2.94-2.90 (m, 2H), 2.77-2.73 (m, 1H), 2.44-2.34 (m, 1H) and 1.18 (d, 6H).

LCMS: m/z 277.9 (M+H)$^+$ (ES$^+$).

Step E: Sodium 1-isopropyl-2-oxopyrrolidine-3-sulfinate

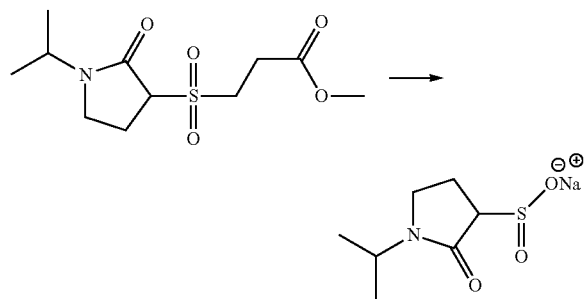

To a solution of methyl 3-((1-isopropyl-2-oxopyrrolidin-3-yl)sulfonyl)propanoate (0.6 g, 2.16 mmol, 1 eq) in a mixture of MeOH (4.8 mL) and THF (4.8 mL) was added a solution of NaOMe in MeOH (6.2 M, 1.05 mL, 3 eq) at 25° C. The mixture was stirred at 25° C. for 3 hours. Then the reaction mixture was concentrated in vacuo to give the title compound (461.3 mg, crude) as a brown solid, which was used in the next step without further purification.

$^1$H NMR (CD$_3$OD): δ=4.34-4.27 (m, 1H), 3.53-3.41 (m, 1H), 3.19-3.15 (m, 2H), 2.54-2.51 (m, 1H), 2.17-2.12 (m, 1H) and 1.19-1.14 (m, 6H).

LCMS: m/z 192.0 (M+H)$^+$ (ES$^+$).

Step F: 1-Isopropyl-2-oxopyrrolidine-3-sulfonamide

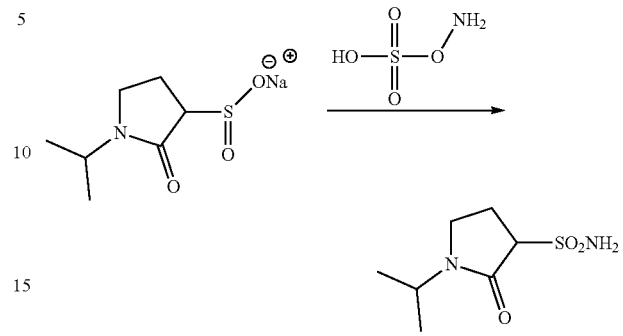

To a solution of sodium 1-isopropyl-2-oxopyrrolidine-3-sulfinate (461 mg, 2.16 mmol, 1 eq) in DMSO (6 mL) was added a solution of (aminooxy)sulfonic acid (1.22 g, 10.82 mmol, 5 eq) and AcONa (709 mg, 8.65 mmol, 4 eq) in H$_2$O (2 mL) at 0° C. The mixture was warmed to 25° C. and stirred at 25° C. for 16 hours. The reaction mixture was filtered and the filter cake was washed with MeOH (10 mL). The filtrate was concentrated in vacuo. The residue was purified by prep-HPLC (see "Experimental Methods", "Purification Method 2") to give the title compound (219.8 mg, 1.07 mmol, yield 49%, 100% purity) as white solid.

$^1$H NMR (DMSO-d$_6$): δ=6.92 (br s, 2H), 4.18-4.15 (m, 1H), 3.91-3.88 (m, 1H), 3.33-3.27 (m, 2H), 2.38-2.30 (m, 2H) and 1.10-1.03 (m, 6H).

LCMS: m/z 206.9 (M+H)$^+$ (ES$^+$).

Intermediate P65: 1-(1-Acetylazetidin-3-yl)piperidine-4-sulfonamide

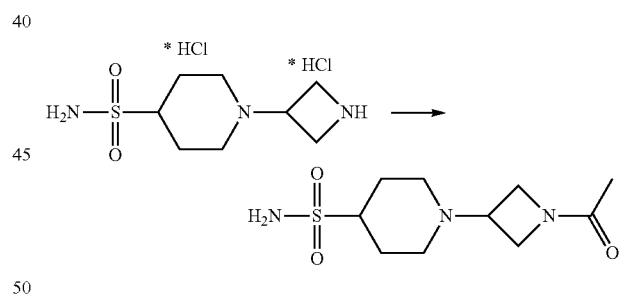

A suspension of 1-(azetidin-3-yl)piperidine-4-sulfonamide dihydrochloride salt (95%, 250 mg, 0.81 mmol) and triethylamine (0.23 mL, 164 mg, 1.63 mmol) in acetonitrile (10 mL) was stirred for 30 minutes. Acetic anhydride (0.08 mL, 87 mg, 0.85 mmol) was added to this slurry and the stirring was continued for 20 hours. The mixture was concentrated in vacuo and the residue dissolved in methanol, then applied to a silica column (40 g) and eluted with 0-30% methanol in DCM to afford the title compound (93 mg, yield 43%).

HPLC-MS: 100% (ELSD), M 261+1 (ACPI pos.)

$^1$H NMR (DMSO-d6): δ=6.72 (s, 2H), 4.08 (t, J=7.8 Hz, 1H), 3.91 (dd, J=8.6, 5.1 Hz, 1H), 3.81 (dd, J=9.7, 7.2 Hz, 1H), 3.61 (dd, J=9.8, 5.1 Hz, 1H), 3.13-2.98 (m, 1H), 2.94-2.72 (m, 3H), 2.04-1.92 (m, 2H), 1.90-1.73 (m, 5H), 1.59 (qt, J=12.9, 3.5 Hz, 2H).

Intermediate P66:
1-(1-Methylazetidin-3-yl)piperidine-4-sulfonamide

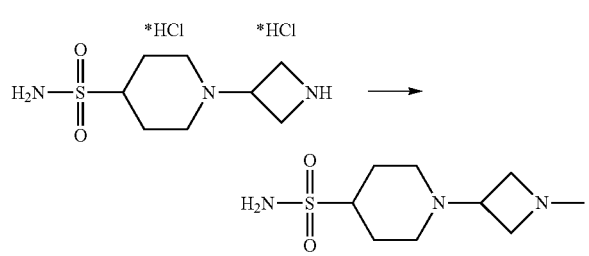

A suspension of 1-(azetidin-3-yl)piperidine-4-sulfonamide dihydrochloride salt (95%, 200 mg, 0.65 mmol) and triethylamine (0.19 mL, 138 mg, 1.36 mmol) in acetonitrile (8 mL) was stirred for 30 minutes. A formalin solution (37% w/w, 15% methanol, 0.09 mL, 0.81 mmol) and sodium triacetoxyborohydride (1.25 eq., 178 mg, 0.81 mmol) were added to the resulting slurry portionwise. The stirring was continued for 20 hours at ambient temperature, then the mixture was concentrated in vacuo. The residue was dissolved in 3.5N ammonia in methanol and applied to a silica cartridge (40 g, silicycle). The title compound (65 mg, yield 38%) was isolated by elution with 0-30% gradient of 3.5N (ammonia/methanol) in DCM.

HPLC-MS: 100% (ELSD), M 233+1 (ACPI pos.)

$^1$H NMR (DMSO-d6): δ=6.70 (s, 2H), 3.44 (s, 2H), 2.89-2.66 (m, 6H), 2.25 (s, 2H), 1.95 (dd, J=13.0, 3.5 Hz, 2H), 1.81-1.67 (m, 3H), 1.56 (qd, J=12.2, 3.9 Hz, 2H).

Intermediate P67:
1-(Pentan-3-yl)pyrrolidine-3-sulfonamide

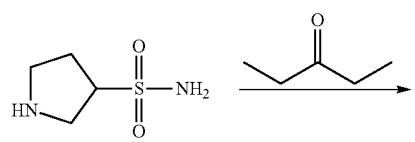

Prepared as described for 1-cyclobutylpiperidine-4-sulfonamide (Intermediate P14) from pyrrolidine-3-sulfonamide and 3-pentanone, but no triethylamine was required. The title compound (143 mg, yield 64%) was used without further purification.

$^1$H NMR (DMSO-d6): δ=6.80 (s, 2H), 3.53 (m, 1H), 2.90 (dd, 1H), 2.65 (m, 2H), 2.48 (m, 1H), 2.01 (m, 3H), 1.40 (m, 4H), 0.79 (m, 6H).

Intermediate P68:
1-(sec-Butyl)pyrrolidine-3-sulfonamide

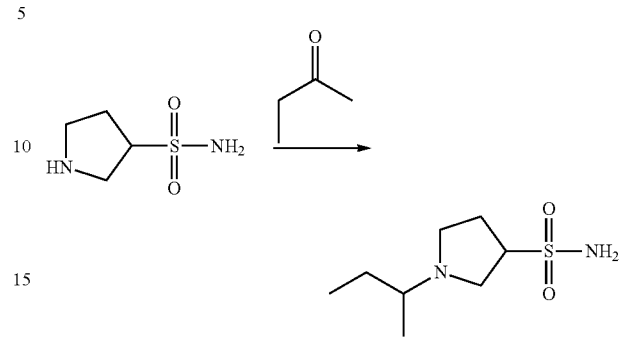

Prepared as described for 1-cyclobutylpiperidine-4-sulfonamide (Intermediate P14) from pyrrolidine-3-sulfonamide and 2-butanone, but no triethylamine was required. The title compound (143 mg, yield 64%) was used without further purification.

$^1$H NMR (CD3OD): δ=3.78 (m, 1H), 3.33 (m, 1H), 2.99 (m, 2H), 2.78 (m, 1H), 2.51 (m, 1H), 2.25 (q, 2H), 1.74 (m, 1H), 1.40 (m, 1H), 1.15 (dd, 3H), 0.93 (t, 3H).

Intermediate P69: 1-Butylazetidine-3-sulfonamide

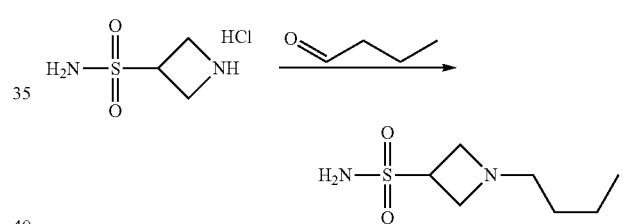

Prepared as described for 1-cyclobutylpiperidine-4-sulfonamide (Intermediate P14) from azetidine-3-sulfonamide hydrochloride and butyraldehyde. The title compound (82 mg, yield 42%) was used without further purification.

$^1$H NMR (DMSO-d6): δ=6.88 (s, 2H), 3.85 (m, 1H), 3.43 (t, 2H), 3.22 (m, 2H), 2.34 (t, 2H), 1.22 (m, 4H), 0.83 (t, 3H).

Intermediate P70: 1-(2-Hydroxy-2-methylpropyl)azetidine-3-sulfonamide

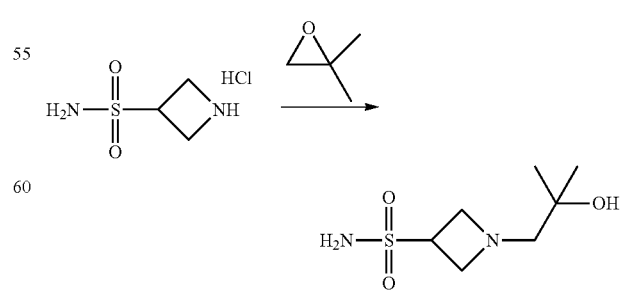

To a solution of azetidine-3-sulfonamide hydrochloride (172 mg, 1.0 mmol, 1.0 equiv.) and potassium carbonate (691 mg, 5.0 mmol, 5.0 equiv.) in water (5 mL) and ethanol (5 mL) in a microwave vial (20 mL) was added 1,2-epoxy-2-methylpropane (88 μL, 1.0 mmol, 1.0 equiv.). The reaction mixture was heated in the microwave at 110° C. for 30 minutes and then concentrated in vacuo. The crude material was suspended in methanol and filtered. The filtrate was coated on Agilent hydromatrix (a high purity, inert diatomaceous earth sorbent) and then submitted to normal phase flash chromatography using dichloromethane and a mixture of ammonia (3.5 M) in methanol to afford the title compound (38 mg, yield 18%), which was used without further purification.

$^1$H NMR (DMSO-d6): δ=6.86 (s, 2H), 4.03 (s, 1H), 3.88 (m, 1H), 3.54 (t, 2H), 3.36 (m, 2H), 2.31 (s, 2H), 1.00 (s, 6H).

Intermediate P71:
1-Cyclopropylazetidine-3-sulfonamide

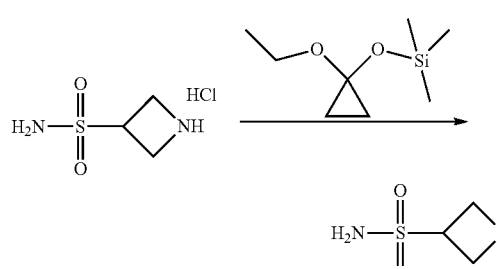

Prepared as described for 1-cyclopropylpyrrolidine-3-sulfonamide (Intermediate P30) from azetidine-3-sulfonamide hydrochloride, except that the reaction was stirred for 3 days at room temperature and another 8 hours at 50° C. The title compound (47 mg, yield 26%) was used without further purification.

$^1$H NMR (DMSO-d6): δ=6.92 (s, 2H), 3.84 (m, 1H), 3.50 (t, 2H), 3.40 (t, 2H), 1.94 (m, 1H), 0.32 (m, 2H), 0.19 (m, 2H).

Intermediate P72:
1-(1,3-Difluoropropan-2-yl)azetidine-3-sulfonamide

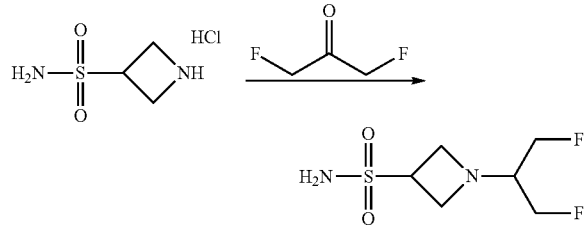

Prepared as described for 1-cyclobutylpiperidine-4-sulfonamide (Intermediate P14) from azetidine-3-sulfonamide hydrochloride and 1,3-difluoroacetone. The title compound (87 mg, yield 40%) was used without further purification.

$^1$H NMR (DMSO-d6): δ=6.93 (s, 2H), 4.47 (m, 2H), 4.32 (m, 2H), 3.94 (m, 1H), 3.59 (t, 2H), 3.48 (t, 2H), 2.80 (m, 1H).

Intermediate P73:
1-(Cyanomethyl)azetidine-3-sulfonamide

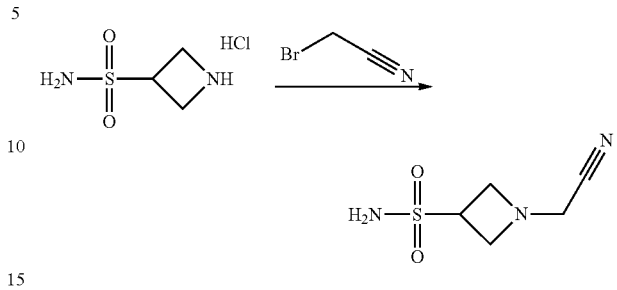

Prepared as described for 1-(prop-2-yn-1-yl)piperidine-4-sulfonamide (Intermediate P3) from azetidine-3-sulfonamide hydrochloride and bromoacetonitrile. The title compound (47 mg, yield 26%) was used without further purification.

$^1$H NMR (DMSO-d6): δ=6.98 (s, 2H), 3.91 (m, 1H), 3.62 (s, 2H), 3.53 (m, 4H).

Intermediate P74:
1-(2-Methoxyethyl)azetidine-3-sulfonamide

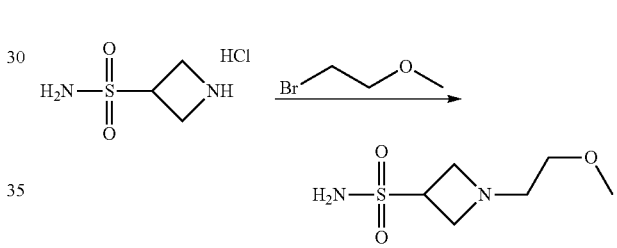

Prepared as described for 1-(prop-2-yn-1-yl)piperidine-4-sulfonamide (Intermediate P3) from azetidine-3-sulfonamide hydrochloride and 2-bromoethyl methyl ether. The title compound (38 mg, yield 20%) was used without further purification.

$^1$H NMR (DMSO-d6): δ=6.89 (s, 2H), 3.87 (m, 1H), 3.47 (t, 2H), 3.32 (m, 2H), 3.25 (m, 2H), 3.18 (s, 3H), 2.54 (m, 2H).

Intermediate P75:
1-(Cyclohexylmethyl)azetidine-3-sulfonamide

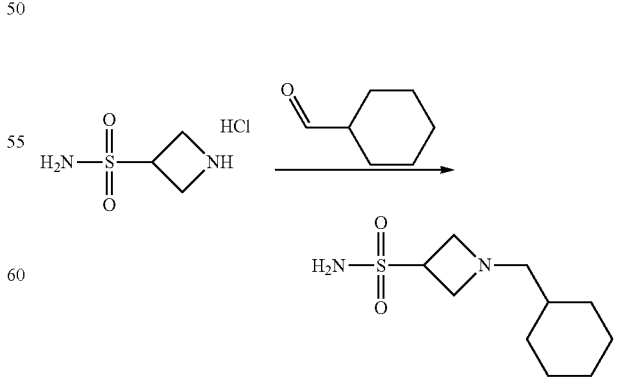

Prepared as described for 1-cyclobutylpiperidine-4-sulfonamide (Intermediate P14) from azetidine-3-sulfonamide hydrochloride and cyclohexanecarboxaldehyde. The title compound (202 mg, yield 86%) was used without further purification.

$^1$H NMR (DMSO-d6): δ=6.87 (s, 2H), 3.86 (m, 1H), 3.44 (t, 2H), 3.22 (t, 2H), 2.21 (d, 2H), 1.63 (m, 5H), 1.14 (m, 4H), 0.81 (m, 2H).

Intermediate P76:
1-(Pyridin-3-ylmethyl)azetidine-3-sulfonamide

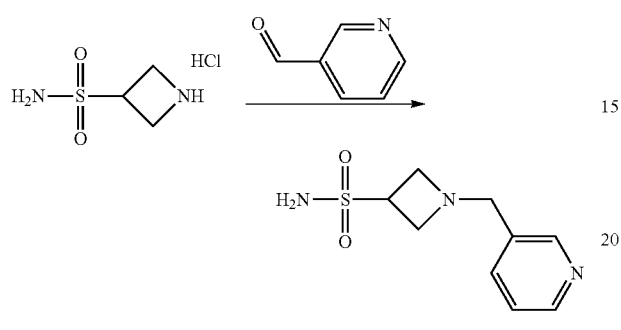

Prepared as described for 1-cyclobutylpiperidine-4-sulfonamide (Intermediate P14) from azetidine-3-sulfonamide hydrochloride and pyridin-3-aldehyde. The title compound (131 mg, yield 58%) was used without further purification.

$^1$H NMR (DMSO-d6): δ=8.44 (m, 2H), 7.65 (dt, 1H), 7.32 (dd, 1H), 6.95 (s, 2H), 3.92 (m, 1H), 3.61 (s, 2H), 3.48 (t, 2H), 3.37 (m, 2H).

Intermediate P77:
N,N-Dimethyl-2-(3-sulfamoylazetidin-1-yl)acetamide

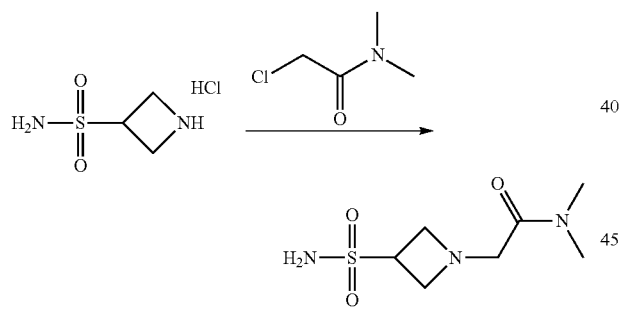

Prepared as described for 1-(prop-2-yn-1-yl)piperidine-4-sulfonamide (Intermediate P3) from azetidine-3-sulfonamide hydrochloride and 2-chloro-N,N-dimethylacetamide, except that potassium iodide (0.5 equiv.) was added to the reaction mixture. The title compound (40 mg, yield 18%) was used without further purification.

$^1$H NMR (DMSO-d6): δ=7.17 (s, 2H), 4.07 (m, 3H), 3.90 (m, 4H), 2.88 (s, 3H), 2.80 (s, 3H).

Intermediate P78:
1-(2-Chloroethyl)azetidine-3-sulfonamide

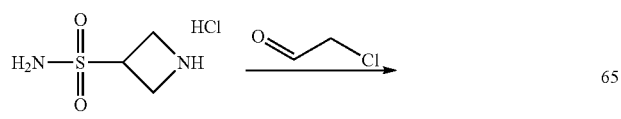

-continued

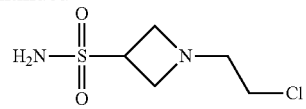

Prepared as described for 1-cyclobutylpiperidine-4-sulfonamide (Intermediate P14) from azetidine-3-sulfonamide hydrochloride and chloroacetaldehyde (~50 wt % in H$_2$O). The title compound (100 mg, yield 50%) was used without further purification.

$^1$H NMR (DMSO-d6): δ=6.91 (s, 2H), 3.92 (m, 1H), 3.53 (m, 4H), 3.36 (t, 2H), 2.73 (t, 2H).

Intermediate P79:
1-Cyclobutylazetidine-3-sulfonamide

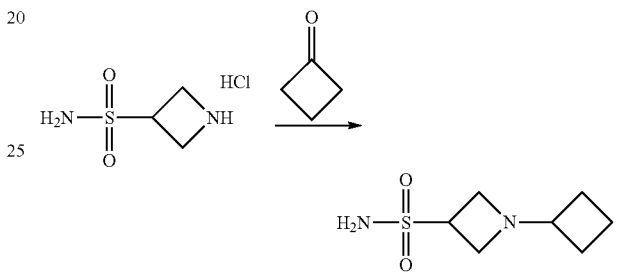

Prepared as described for 1-cyclobutylpiperidine-4-sulfonamide (Intermediate P14) from azetidine-3-sulfonamide hydrochloride and cyclobutanone. The title compound (127 mg, yield 66%) was used without further purification.

$^1$H NMR (DMSO-d6): δ=6.91 (s, 2H), 3.86 (m, 1H), 3.39 (t, 2H), 3.30 (m, 2H), 3.09 (q, 1H), 1.87 (m, 2H), 1.67 (m, 4H).

Intermediate P80: 1-Isopropyl-N,N-dimethyl-4-sulfamoylpyrrolidine-2-carboxamide

Step A: 4-Nitrobenzyl 2-(dimethylcarbamoyl)-4-sulfamoylpyrrolidine-1-carboxylate

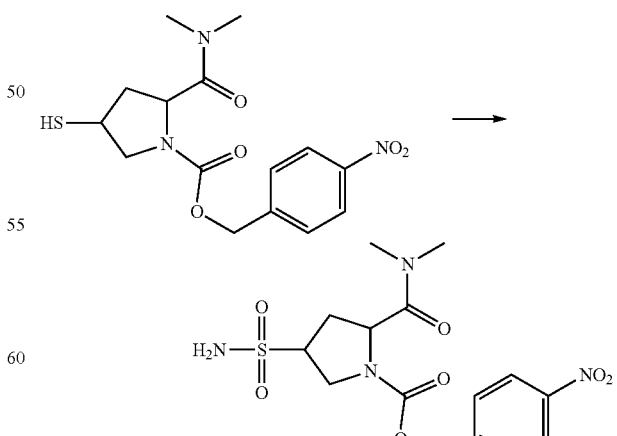

A suspension of 4-nitrobenzyl 2-(dimethylcarbamoyl)-4-mercaptopyrrolidine-1-carboxylate (1 g, 2.83 mmol) in acetic acid (5 mL)/water (1 mL) was cooled in an ice-bath to 0° C. N-Chlorosuccinimide (1.13 g, 8.49 mmol, 3.0 equiv.) was added in portions over a 5 minute period. The mixture was allowed to stir for another hour at room temperature. The reaction was then poured into ammonia (50 mL, 25% solution in water). The resulting solution was stirred for 18 hours at room temperature. The solvents were evaporated and the residue was triturated with ethanol (50 mL). Sodium sulphate (15 g) was added and the mixture was filtered and evaporated. The residue was dissolved in methanol (50 mL) and Amberlite 400 (OH) (20 g) was added. After 18 hours stirring, the mixture was filtered and evaporated to afford the title compound (610 mg, yield 54%) as an oil that crystallized upon standing.

$^1$H NMR (CD$_3$OD): δ=8.20 (m, 2H), 7.62 (d, 1H), 7.53 (d, 1H), 5.26 (d, 2H), 4.08-3.66 (m, 4H), 3.00 (m, 6H), 2.12 (m, 2H).

Step B:
N,N-Dimethyl-4-sulfamoylpyrrolidine-2-carboxamide

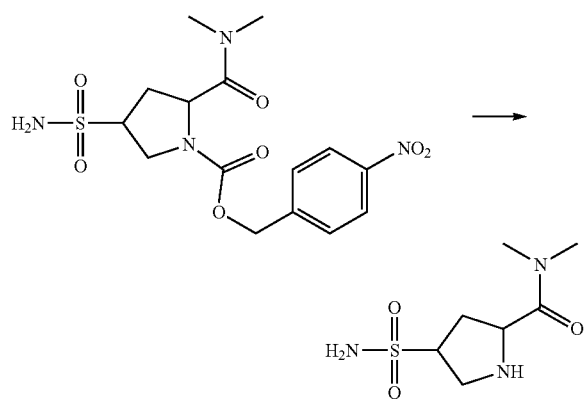

4-Nitrobenzyl 2-(dimethylcarbamoyl)-4-sulfamoylpyrrolidine-1-carboxylate (61 mg, 1.53 mmol) was dissolved in methanol (10 mL). Palladium (47 mg, 10% on charcoal) was added and the mixture was stirred for 18 hours under a hydrogen atmosphere (balloon). The mixture was filtered over Celite and evaporated. The residue was purified by reversed phase silica to yield white solids (0.5 g), which were triturated with THF. The THF layer was decanted and evaporated to afford the title compound (350 mg, yield 100%) as a white solid.

$^1$H NMR (CD$_3$OD): δ=3.79-3.55 (m, 4H), 3.00 (m, 6H), 1.90 (m, 2H).

Step C: 1-Isopropyl-N,N-dimethyl-4-sulfamoylpyrrolidine-2-carboxamide

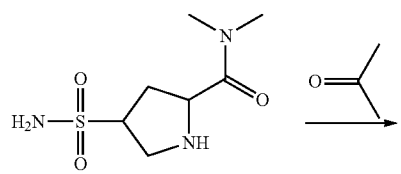

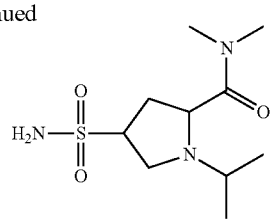

N,N-Dimethyl-4-sulfamoylpyrrolidine-2-carboxamide (84 mg, 0.38 mmol) was dissolved in acetonitrile (10 mL). Acetone (90 mg, 1.5 mmol) was added followed by sodium triacetoxyborohydride. After 18 hours stirring at room temperature, the solvents were evaporated and the residue was purified over silica to afford the title compound (10 mg, yield to %) as an oil.

$^1$H NMR (CD$_3$OD): δ=3.92 (t, 1H), 3.73 (m, 1H), 3.46 (dd, 1H), 3.18 (s, 3H), 3.05 (m, 1H), 2.95 (s, 3H), 2.88 (m, 1H), 2.57 (m, 1H), 2.14 (m, 1H), 1.08 (d, 3H), 1.03 (d, 3H).

Intermediate P81:
1-Ethyl-5-oxopyrrolidine-3-sulfonamide

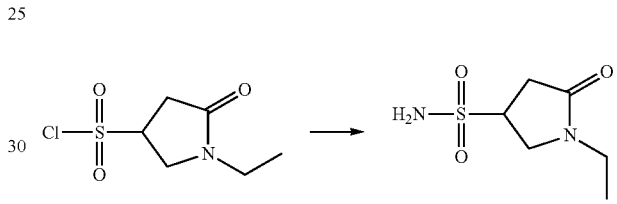

1-Ethyl-5-oxopyrrolidine-3-sulfonyl chloride (15 mg, 0.71 mmol) was dissolved in THF (3 mL) and added dropwise to ammonia (25% solution in water, 5 mL) at 4° C. After 18 hours stirring at room temperature, the solvents were evaporated. The residue was triturated in THF. The THF layer was decanted and evaporated to afford the title compound (30 mg, yield 22%) as a brown oil.

$^1$H NMR (CD$_3$OD): δ=3.80 (m, 2H), 3.34 (m, 3H), 2.78 (m, 2H), 1.13 (t, 3H).

Intermediate P82:
1-(tert-Butyl)azetidine-3-sulfonamide

Step A: 1-(tert-Butyl)azetidin-3-yl Methanesulfonate

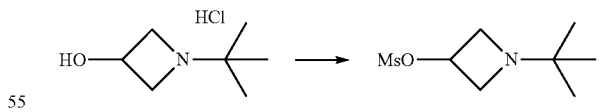

To a suspension of N-tert-butyl-3-hydroxyazetidine hydrochloride (1.0 g, 6.0 mmol) in dichloromethane (30 mL) was added N,N-diisopropylethylamine (2.4 mL, 13.8 mmol, 2.5 equiv.). After stirring for 20 minutes at room temperature, the clear solution was cooled to 0° C. and mesyl chloride (0.5 mL, 6.6 mmol, 1.1 equiv.) was added dropwise.

The reaction mixture was stirred for 1 hour, while allowing to warm up to room temperature. Then the solvent was removed by evaporation in vacuo. The crude product was dissolved in methanol, coated on Agilent hydromatrix (a high purity, inert diatomaceous earth sorbent) and then submitted to normal phase flash chromatography using dichloromethane and a mixture of ammonia (3.5 M) in methanol to afford the title compound (456 mg, yield 37%).

$^1$H NMR (CDCl$_3$): δ=5.10 (m, 1H), 3.74 (m, 2H), 3.47 (m, 2H), 3.02 (s, 3H), 1.04 (s, 9H).

Step B: S-(1-(tert-Butyl)azetidin-3-yl) Ethanethioate

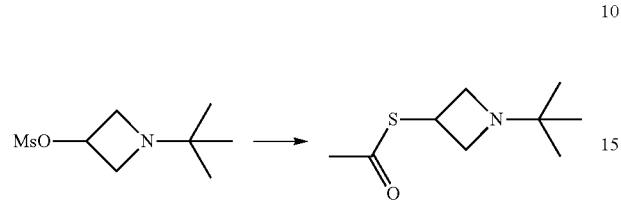

To a solution of 1-(tert-butyl)azetidin-3-yl methanesulfonate (269 mg, 1.3 mmol) in acetonitrile (20 mL) was added potassium thioacetate (447 mg, 3.9 mmol, 3 equiv.). The reaction mixture was stirred overnight at room temperature, and then for another 7 hours at 50° C. The solvent was removed by evaporation in vacuo. The crude product was dissolved in methanol, coated on Agilent hydromatrix (a high purity, inert diatomaceous earth sorbent) and then submitted to normal phase flash chromatography using dichloromethane and a mixture of ammonia (3.5 M) in methanol to afford the title compound (90 mg, yield 37%).

$^1$H NMR (CDCl$_3$): δ=4.15 (m, 1H), 3.80 (m, 2H), 3.30 (m, 2H), 2.31 (s, 3H), 1.03 (s, 9H).

Step C: 1-(tert-Butyl)azetidine-3-sulfonamide

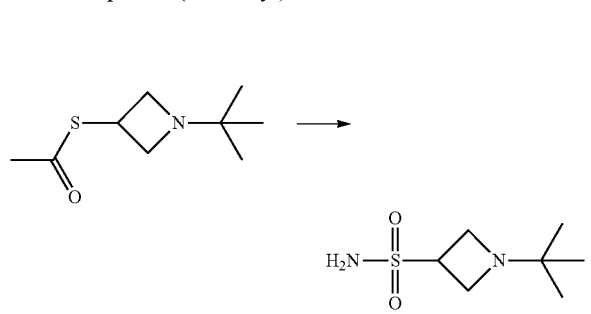

To a suspension of N-chlorosuccinimide (200 mg, 1.5 mmol, 3 equiv.) in acetonitrile (2.0 mL) was added hydrochloric acid (aqueous, 2 M, 0.2 mL, 0.38 mmol, 0.8 equiv.). The solution was cooled in an ice-bath, after which a solution of S-(1-(tert-butyl)azetidin-3-yl) ethanethioate (90 mg, 0.48 mmol, 1.0 equiv.) in acetonitrile (1.0 mL) was added and the ice-bath was removed. The reaction mixture was stirred for 1 hour and then added dropwise to a solution of ammonia in methanol (7 M, 50 mL, 350 mmol, 729 equiv.). The mixture was stirred for 30 minutes and then concentrated in vacuo. The crude product was dissolved in methanol, coated on Agilent hydromatrix (a high purity, inert diatomaceous earth sorbent) and then submitted to normal phase flash chromatography using dichloromethane and a mixture of ammonia (3.5 M) in methanol to afford the title compound (11 mg, yield to %).

$^1$H NMR (CD$_3$OD): δ=3.97 (m, 1H), 3.68 (m, 2H), 3.51 (m, 2H), 1.02 (S, 9H).

Intermediate P83:
1-(Cyclopropylmethyl)azetidine-3-sulfonamide

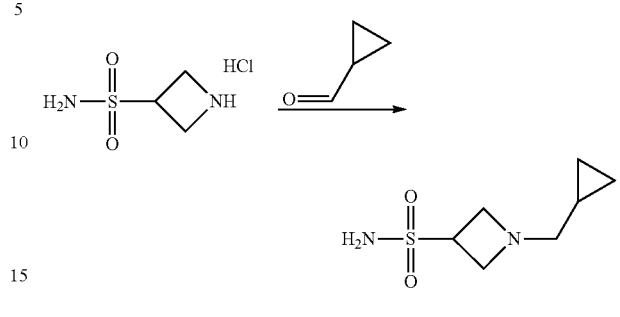

Prepared as described for 1-cyclobutylpiperidine-4-sulfonamide (Intermediate P14) from azetidine-3-sulfonamide hydrochloride and cyclopropane carboxaldehyde. The crude product was dissolved in methanol, coated on Agilent hydromatrix (a high purity, inert diatomaceous earth sorbent) and then submitted to normal phase flash chromatography using dichloromethane and a mixture of ammonia (3.5 M) in methanol to afford the title compound (180 mg, yield 94%) which was used without further purification.

$^1$H NMR (DMSO-d$_6$): δ=6.90 (s, 2H), 3.90 (m, 1H), 3.49 (t, 2H), 3.30 (t, 2H), 2.26 (d, 2H), 0.69 (m, 1H), 0.37 (m, 2H), 0.07 (m, 2H).

Intermediate P84:
1-Isobutylazetidine-3-sulfonamide

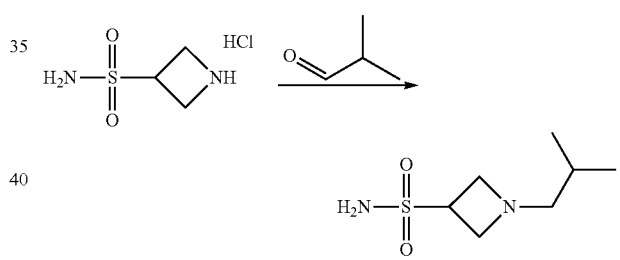

Prepared as described for 1-cyclobutylpiperidine-4-sulfonamide (Intermediate P14) from azetidine-3-sulfonamide hydrochloride and isobutyraldehyde. The title compound (138 mg, yield 71%) was used without further purification.

$^1$H NMR (DMSO-d$_6$): δ=6.88 (s, 2H), 3.88 (m, 1H), 3.46 (t, 2H), 3.23 (m, 2H), 2.18 (d, 2H), 1.47 (m, 1H), 0.80 (d, 6H).

Intermediate P85:
1-(2-Azidoethyl)azetidine-3-sulfonamide

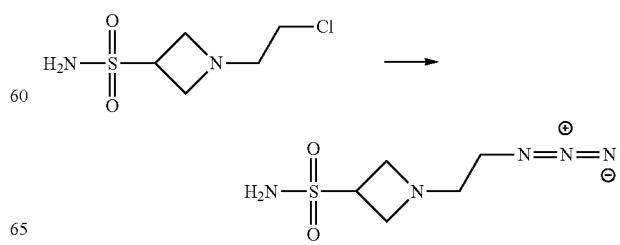

To a solution of 1-(2-chloroethyl)azetidine-3-sulfonamide (45 mg, 0.22 mmol, 1.0 equiv.) in acetonitrile (5 mL) was added sodium azide (14 mg, 0.22 mmol, 1.0 equiv.). The reaction mixture was stirred at room temperature over the weekend. Extra sodium azide (56 mg, 0.88 mmol, 4.0 equiv.) was added and the reaction mixture was heated to 50° C. After stirring overnight, water (0.4 mL) was added and the reaction mixture was stirred for 2 more days. The solution was concentrated in vacuo. The residue was suspended in methanol, filtered and the filtrate was concentrated in vacuo to afford the crude title compound (45 mg, 0.22 mmol, quantitative yield). The crude title compound was used without further purification.

$^1$H NMR (DMSO-d$_6$): δ=6.93 (s, 2H), 3.92 (m, 1H), 3.53 (t, 2H), 3.34 (m, 2H), 3.21 (dd, 2H), 2.59 (dd, 2H).

Intermediate P86: 1-(2,2,2-Trifluoroethyl)azetidine-3-sulfonamide

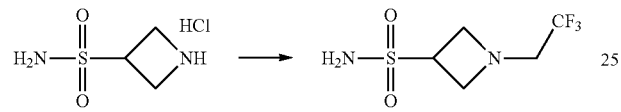

To a suspension of azetidine-3-sulfonamide hydrochloride (333 mg, 1.92 mmol) and triethylamine (0.67 mL, 4.8 mmol, 2.5 equiv.) in acetonitrile (20 mL) was added trifluoroacetic anhydride (0.24 mL, 1.73 mmol, 0.9 equiv.). After stirring for 4 hours at room temperature, the reaction mixture was concentrated in vacuo. The crude intermediate 1-(2,2,2-trifluoroacetyl)azetidine-3-sulfonamide was dissolved in methanol, coated on Agilent hydromatrix (a high purity, inert diatomaceous earth sorbent) and then submitted to normal phase flash chromatography using dichloromethane and a mixture of ammonia (3.5 M) in methanol. The impure intermediate (max 1.92 mmol) was dissolved in tetrahydrofuran (20 mL) and then cooled to 0° C. To this solution, borane dimethyl sulfide (0.85 mL, 9.0 mmol, 4.5 equiv.) was added dropwise. The reaction mixture was refluxed overnight, and then cooled to room temperature. Methanol was added to the reaction mixture until no more gas evolution was observed and then the reaction mixture was concentrated in vacuo. The crude product was dissolved in methanol, coated on Agilent hydromatrix (a high purity, inert diatomaceous earth sorbent) and then submitted to normal phase flash chromatography using dichloromethane and a mixture of ammonia (3.5 M) in methanol to afford the title compound (20 mg, yield 5%). The title compound was used without further purification.

$^1$H NMR (DMSO-d$_6$): δ=7.07 (s, 2H), 4.24-4.08 (m, 1H), 3.65 (t, 2H), 3.52 (dd, 2H), 3.31-3.16 (m, 2H).

Intermediate P87: 1-(2-((tert-Butyldimethylsilyl)oxy)ethyl)azetidine-3-sulfonamide

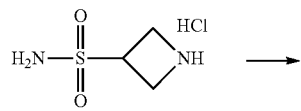

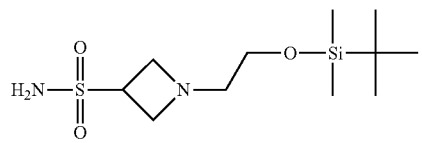

Prepared as described for 1-(prop-2-yn-1-yl)piperidine-4-sulfonamide (intermediate P3) from azetidine-3-sulfonamide hydrochloride and (2-bromoethoxy)-tert-butyldimethylsilane. The title compound (44 mg, yield 16%) was used without further purification.

$^1$H NMR (DMSO-d$_6$): δ=6.89 (s, 2H), 3.88 (q, 1H), 3.50 (m, 4H), 3.31 (m, 2H), 0.84 (s, 9H), 0.01 (s, 6H).

Intermediate P88: 1-Cyclohexylazetidine-3-sulfonamide

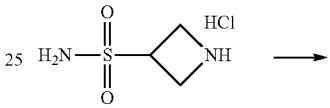

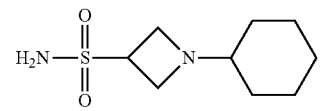

Prepared as described for 1-cyclobutylpiperidine-4-sulfonamide (Intermediate P14) from azetidine-3-sulfonamide hydrochloride and cyclohexanone. The title compound (218 mg, quantitative yield) was used without further purification.

$^1$H NMR (DMSO-d6): δ=6.86 (s, 2H), 3.83 (p, 1H), 3.41 (t, 2H), 3.21 (dd, 2H), 2.00 (m, 1H), 1.59 (m, 6H), 1.15 (q, 2H), 0.93 (m, 2H).

Intermediate P89: 1-Cyclopentylazetidine-3-sulfonamide

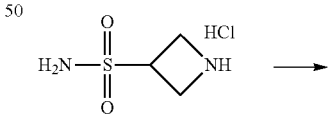

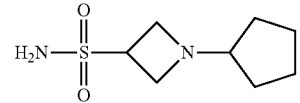

Prepared as described for 1-cyclobutylpiperidine-4-sulfonamide (Intermediate P14) from azetidine-3-sulfonamide hydrochloride and cyclopentanone. The title compound (204 mg, quantitative yield) was used without further purification.

$^1$H NMR (DMSO-d$_6$): δ=6.86 (s, 2H), 3.82 (m, 1H), 3.41 (t, 2H), 3.18 (m, 2H), 2.72 (m, 1H), 1.49 (m, 6H), 1.24 (m, 2H).

Intermediate P90:
1-(1-Iminoethyl)azetidine-3-sulfonamide

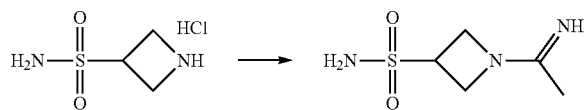

To a suspension of azetidine-3-sulfonamide hydrochloride (172 mg, 1.0 mmol, 1.0 equiv.) and triethylamine (0.49 mL, 3.5 mmol, 3.5 equiv.) in acetonitrile (10 mL) was added ethyl acetimidate hydrochloride (123 mg, 1.0 mmol, 1.0 equiv.). The reaction mixture was stirred overnight at room temperature and then concentrated in vacuo. The crude compound (approx. 300 mg) was dissolved in water/methanol (ratio 1:1) (3 mL). 1 mL of this solution was purified by reversed phase flash chromatography to afford the title compound (30 mg, yield 9%).

$^1$H NMR (DMSO-$d_6$): δ=10.25 (s, 1H), 7.41 (s, 2H), 4.61 (dd, 1H), 4.44 (m, 2H), 4.21 (m, 2H), 2.08 (s, 3H).

Intermediate P91:
1-(Oxetan-3-ylmethyl)azetidine-3-sulfonamide

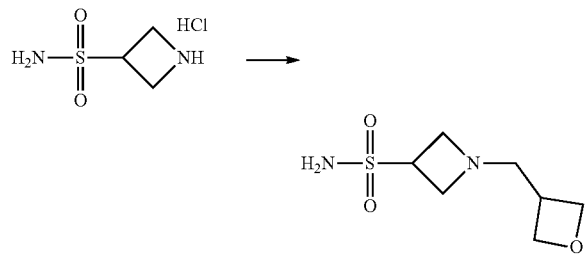

Prepared as described for 1-cyclobutylpiperidine-4-sulfonamide (Intermediate P14) from azetidine-3-sulfonamide hydrochloride and 3-oxetanecarboxaldehyde. The title compound (156 mg, yield 75%) was used without further purification.

$^1$H NMR (DMSO-$d_6$): δ=6.91 (s, 2H), 4.57 (dd, 2H), 4.22 (t, 2H), 3.90 (m, 1H), 3.47 (t, 2H), 3.28 (m, 2H), 2.90 (m, 1H), 2.68 (d, 2H).

Intermediate P92:
1-(2-(Dimethylamino)ethyl)azetidine-3-sulfonamide

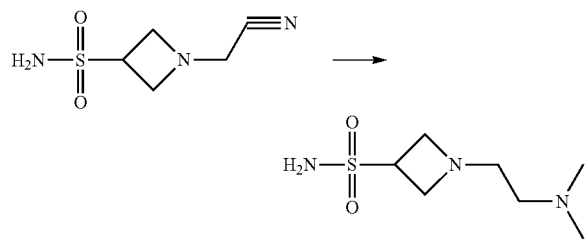

To a solution of 1-(cyanomethyl)azetidine-3-sulfonamide (220 mg, 1.25 mmol) in tetrahydrofuran (15 mL), cooled to 0° C., was added borane dimethyl sulfide (0.16 mL, 1.63 mmol, 1.3 equiv.). The reaction mixture was refluxed overnight, and then quenched with methanol. The solution was concentrated in vacuo. The crude intermediate was suspended in acetonitrile (20 mL) and formaldehyde (37% in water stabilized with methanol, 186 µL, 2.5 mmol, 2.1 equiv.) followed by sodium triacetoxyborohydride (688 mg, 3.25 mmol, 2.6 equiv.) was added. The reaction mixture was stirred overnight at room temperature and then concentrated in vacuo. The crude product was dissolved in methanol, coated on Agilent hydromatrix (a high purity, inert diatomaceous earth sorbent) and then submitted to normal phase flash chromatography using dichloromethane and a mixture of ammonia (3.5 M) in methanol to afford the title compound (28 mg, yield 14%).

$^1$H NMR (CD$_3$OD): δ=4.02 (m, 1H), 3.67 (m, 2H), 3.55 (m, 2H), 2.74 (dt, 4H), 2.56 (s, 6H).

Intermediate P93:
1-(Pyridin-4-ylmethyl)azetidine-3-sulfonamide

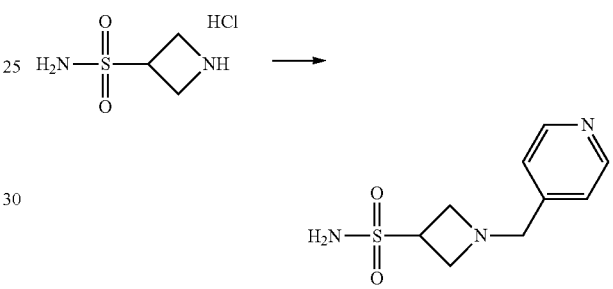

Prepared as described for 1-cyclobutylpiperidine-4-sulfonamide (Intermediate P14) from azetidine-3-sulfonamide hydrochloride and 4-pyridinecarboxaldehyde. The title compound (130 mg, yield 57%) was used without further purification.

$^1$H NMR (DMSO-$d_6$): δ=8.47 (d, 2H), 7.26 (d, 2H), 6.97 (s, 2H), 3.94 (m, 1H), 3.64 (s, 2H), 3.52 (t, 2H), 3.39 (t, 2H).

Intermediate P94:
1-(Pyridin-2-ylmethyl)azetidine-3-sulfonamide

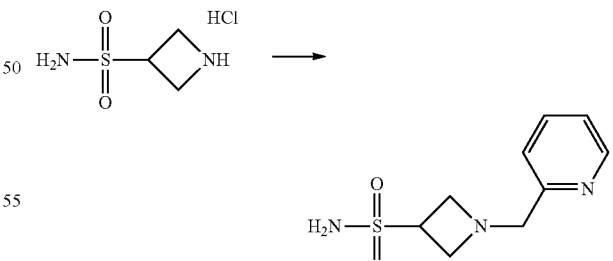

Prepared as described for 1-cyclobutylpiperidine-4-sulfonamide (Intermediate P14) from azetidine-3-sulfonamide hydrochloride and 2-pyridinecarboxaldehyde. The title compound (196 mg, yield 86%) was used without further purification.

$^1$H NMR (DMSO-$d_6$): δ=8.46 (dd, 1H), 7.73 (td, 1H), 7.32 (d, 1H), 7.24 (m, 1H), 6.95 (s, 2H), 3.94 (tt, 1H), 3.70 (s, 2H), 3.55 (t, 2H), 3.44 (t, 2H).

Intermediate P95: 1-((2-Bromopyridin-3-yl)methyl)azetidine-3-sulfonamide

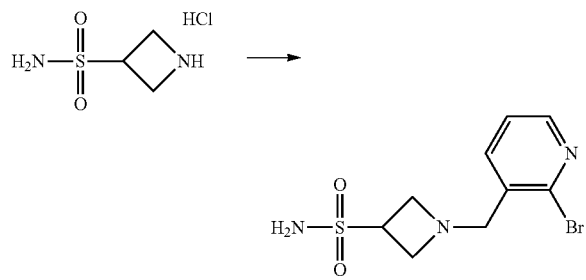

Prepared as described for 1-cyclobutylpiperidine-4-sulfonamide (Intermediate P14) from azetidine-3-sulfonamide hydrochloride and 2-bromo-3-pyridinecarboxaldehyde. The title compound (137 mg, yield 45%) was used without further purification.

$^1$H NMR (DMSO-$d_6$): δ=8.27 (dd, 1H), 7.79 (dd, 1H), 7.44 (dd, 1H), 7.02 (S, 2H), 3.97 (m, 1H), 3.67 (s, 2H), 3.61 (t, 2H), 3.49 (dd, 2H).

Intermediate P96: tert-butyl 3-sulfamoyl-[1,3'-biazetidine]-1'-carboxylate

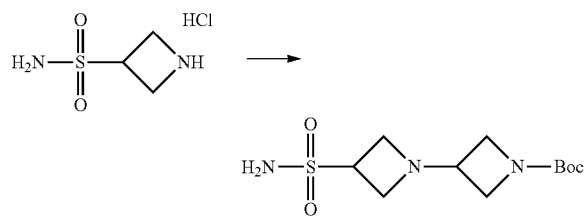

Prepared as described for 1-cyclobutylpiperidine-4-sulfonamide (Intermediate P14) from azetidine-3-sulfonamide hydrochloride and tert-butyl-3-oxoazetidine-1-carboxylate. The title compound (350 mg, yield 24%) was used without further purification.

$^1$H NMR (DMSO-$d_6$): δ=6.95 (s, 2H), 3.92 (m, 1H), 3.80 (t, 2H), 3.57 (d, 2H), 3.48 (t, 2H), 3.36 (m, 3H), 1.35 (s, 9H).

Intermediate P97: 1'-Methyl-[1,3'-biazetidine]-3-sulfonamide

Step A: [1,3'-Biazetidine]-3-sulfonamide Dihydrochloride

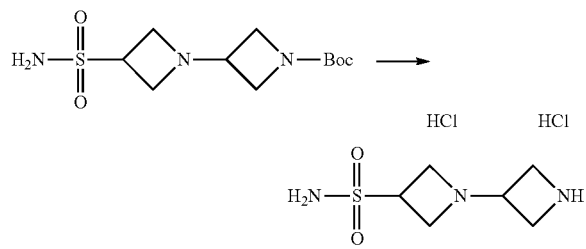

To a solution of tert-butyl 3-sulfamoyl-[1,3'-biazetidine]-1'-carboxylate (intermediate P96; 315 mg, 1.08 mmol) in dichloromethane (10 mL) was added 4M hydrochloric acid in dioxane (2.7 mL, 10.8 mmol). After stirring for 2 hours at room temperature, the reaction mixture was concentrated in vacuo to afford the title compound (285 mg, quantitative yield), which was used without further purification.

$^1$H NMR (DMSO-$d_6$): δ=9.50 (bs, 1H), 9.18 (bs, 1H), 7.42 (s, 2H), 4.57-4.31 (m, 3H), 4.31-4.00 (m, 8H).

Step B: 1'-Methyl-[1,3'-biazetidine]-3-sulfonamide

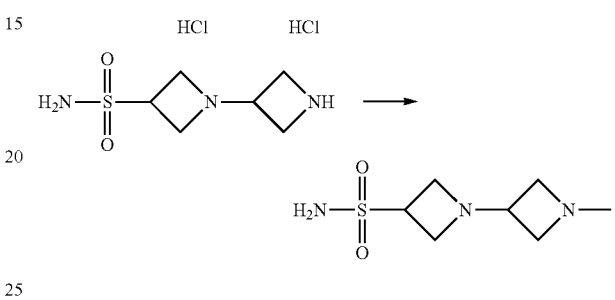

Prepared as described for 1-methylazetidine-3-sulfonamide (intermediate P39) from [1,3'-biazetidine]-3-sulfonamide dihydrochloride. The title compound (63 mg, yield 61%) was used without further purification.

$^1$H NMR (CD$_3$OD): δ=4.10-3.94 (m, 1H), 3.75-3.60 (m, 4H), 3.59-3.51 (m, 2H), 3.51-3.44 (m, 1H), 3.41-3.32 (m, 2H), 2.55 (s, 3H).

Intermediate P98: 1-(2-(Methylthio)ethyl)azetidine-3-sulfonamide

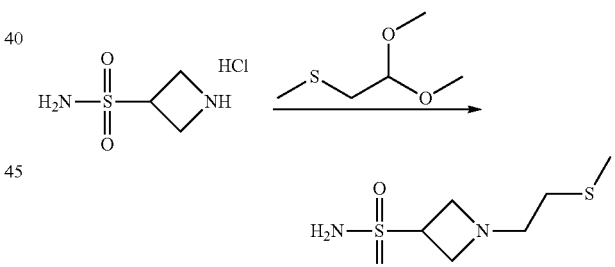

To a solution of 0.5M hydrochloric acid in water (6.0 mL, 3.0 mmol) was added (methylthio)acetaldehyde dimethyl acetal (0.4 mL, 3.0 mmol). After heating the reaction for 1 hour at 50° C., the reaction mixture was cooled to room temperature and then extracted with dichloromethane (10 mL). The organic layer was added to a suspension of azetidine-3-sulfonamide hydrochloride (172 mg, 1.0 mmol) and triethylamine (0.17 mL, 1.2 mmol) in acetonitrile. After that, sodium triacetoxyborohydride (265 mg, 1.25 mmol) was added. The reaction mixture was stirred overnight at room temperature and then concentrated in vacuo. The crude product was dissolved in methanol, coated on Agilent hydromatrix (a high purity, inert diatomaceous earth sorbent) and then submitted to normal phase flash chromatography using dichloromethane and a mixture of ammonia (3.5 M) in methanol to afford the title compound (89 mg, yield 42%).

$^1$H NMR (DMSO-d$_6$): δ=6.91 (s, 2H), 3.89 (p, 1H), 3.49 (t, 2H), 3.33-3.25 (m, 2H), 2.59 (dd, 2H), 2.37 (dd, 2H), 2.03 (s, 3H).

Intermediate P99:
1-(2-Fluoroethyl)azetidine-3-sulfonamide

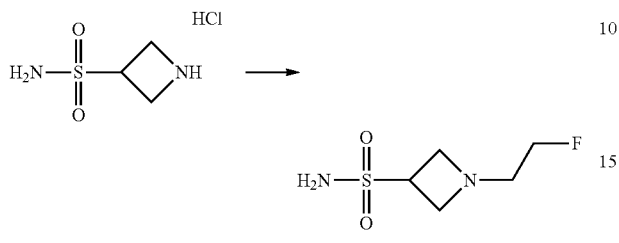

Prepared as described for 1-(prop-2-yn-1-yl)piperidine-4-sulfonamide (Intermediate P3) from azetidine-3-sulfonamide hydrochloride and 1-bromo-2-fluoroethane. The title compound (yield 10%) was used without further purification.

$^1$H NMR (DMSO-d$_6$): δ=6.91 (s, 2H), 4.44 (t, 1H), 4.29 (t, 1H), 3.90 (q, 1H), 3.53 (t, 2H), 3.36 (t, 2H), 2.79-2.69 (m, 1H), 2.64 (t, 1H).

Intermediate P100:
1-(Thietan-3-yl)azetidine-3-sulfonamide

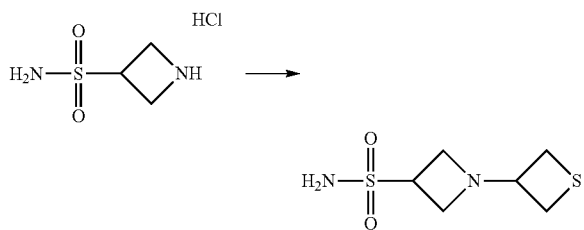

Prepared as described for 1-cyclobutylpiperidine-4-sulfonamide (Intermediate P14) from azetidine-3-sulfonamide hydrochloride and thietan-3-one. The title compound (54 mg, yield 26%) was used without further purification.

$^1$H NMR (DMSO-d$_6$): δ=6.95 (s, 2H), 3.98-3.83 (m, 2H), 3.43 (P, 4H), 3.19 (t, 2H), 2.97 (t, 2H).

Intermediate P101: 1-(2-(3-(But-3-yn-1-yl)-3H-diazirin-3-yl)ethyl)azetidine-3-sulfonamide

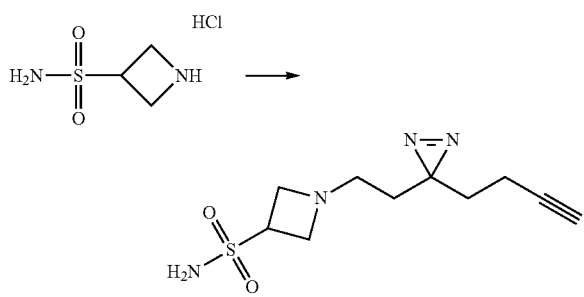

Prepared as described for 1-(prop-2-yn-1-yl)piperidine-4-sulfonamide (Intermediate P3) from azetidine-3-sulfonamide hydrochloride and (3-(but-3-yn-1-yl)-3-(2-iodoethyl)-3H-diazirine (0.8 equiv.) except that a more diluted solution was used (0.02 M solution). The title compound (yield 10%) was used without further purification.

$^1$H NMR (CD$_3$OD): δ=4.09-3.92 (m, 1H), 3.61 (td, 2H), 3.47-3.35 (m, 2H), 2.37 (dd, 2H), 2.27 (t, 1H), 2.02 (td, 2H), 1.60 (t, 2H), 1.51-1.39 (m, 2H).

Intermediate P102: tert-Butyl (Z)-(((tert-butoxycarbonyl)amino)(3-sulfamoylazetidin-1-yl)methylene)carbamate

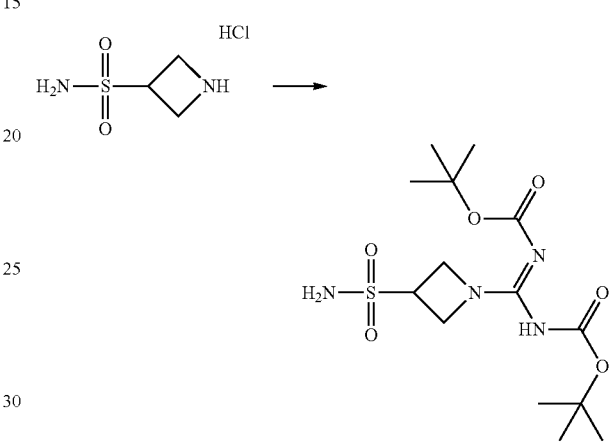

To a suspension of azetidine-3-sulfonamide hydrochloride (172 mg, 1.0 mmol), triethylamine (0.49 mmol, 3.5 mmol) and 1,3-bis(tert-butoxycarbonyl)-2-methyl-2-thiopseudourea (290 mg, 1.0 mmol) in acetonitrile (10 mL) was added mercury dichloride (271 mg, 1.0 mmol). After stirring over the weekend, the reaction mixture was concentrated in vacuo. The crude product was suspended in methanol, coated on Agilent hydromatrix (a high purity, inert diatomaceous earth sorbent) and then submitted to normal phase flash chromatography using dichloromethane and a mixture of ammonia (3.5 M) in methanol to afford the title compound (216 mg, yield 57%).

$^1$H NMR (DMSO-d$_6$): δ=10.24 (s, 1H), 7.16 (s, 2H), 4.41-3.94 (m, 5H), 1.41 (s, 9H), 1.35 (s, 9H).

Intermediate P103:
1-(3-Methylcyclobutyl)azetidine-3-sulfonamide

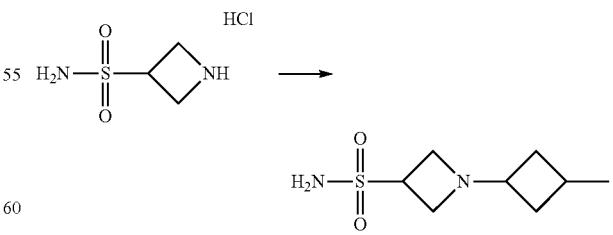

Prepared as described for 1-cyclobutylpiperidine-4-sulfonamide (Intermediate P14) from azetidine-3-sulfonamide hydrochloride and 3-methylcyclobutan-1-one. The title compound (79 mg, yield 39%) was used without further purification.

¹H NMR (DMSO-d₆): δ=6.88 (s, 2H), 3.84 (td, 1H), 3.44-3.18 (m, 4H), 2.92 (m, 1H), 2.10-1.96 (m, 1H), 1.91-1.78 (m, 2H), 1.59-1.45 (m, 1H), 1.39-1.24 (m, 1H), 1.00 (S, 3H).

Intermediate P104:
1-(3,3-Dimethylcyclobutyl)azetidine-3-sulfonamide

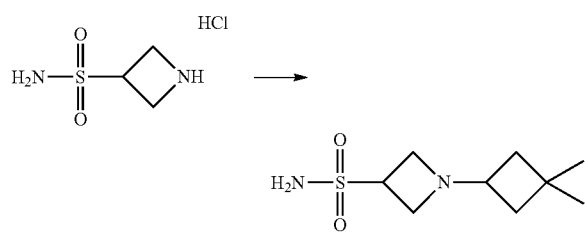

Prepared as described for 1-cyclobutylpiperidine-4-sulfonamide (Intermediate P14) from azetidine-3-sulfonamide hydrochloride and 3,3-dimethylcyclobutan-1-one. The title compound (96 mg, yield 44%) was used without further purification.

¹H NMR (DMSO-d₆): δ=6.88 (s, 2H), 3.84 (m, 1H), 3.34 (t, 2H), 3.29-3.19 (m, 2H), 3.08 (dq, 1H), 1.77-1.62 (m, 2H), 1.58-1.43 (m, 2H), 1.03 (td, 6H).

Intermediate P105:
1-(Pyrimidin-5-ylmethyl)azetidine-3-sulfonamide

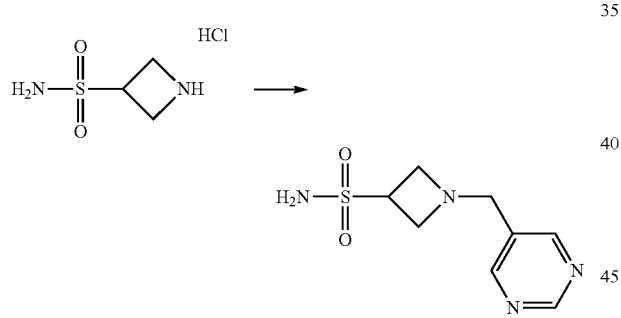

Prepared as described for 1-cyclobutylpiperidine-4-sulfonamide (Intermediate P14) from azetidine-3-sulfonamide hydrochloride and pyrimidine-5-carboxyaldehyde. The title compound (98 mg, yield 43%) was used without further purification.

¹H NMR (DMSO-d₆): δ=9.07 (s, 1H), 8.69 (s, 2H), 6.96 (s, 2H), 3.93 (m, 1H), 3.64 (s, 2H), 3.52 (t, 2H), 3.40 (t, 2H).

Intermediate P106:
1-(Tetrahydrofuran-3-yl)azetidine-3-sulfonamide

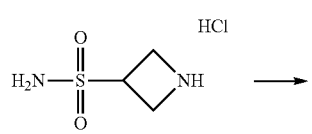

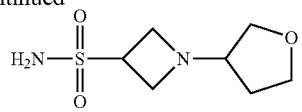

Prepared as described for 1-cyclobutylpiperidine-4-sulfonamide (Intermediate P14) from azetidine-3-sulfonamide hydrochloride and tetrahydrofuran-3-one. The title compound (31 mg, yield 15%) was used without further purification.

¹H NMR (DMSO-d₆): δ=6.90 (s, 2H), 3.86 (m, 1H), 3.70-3.54 (m, 2H), 3.54-3.34 (m, 4H), 3.29-3.19 (m, 2H), 3.08-2.98 (m, 1H), 1.83-1.67 (m, 1H), 1.62-1.49 (m, 1H).

Intermediate P107:
1-(sec-Butyl)azetidine-3-sulfonamide

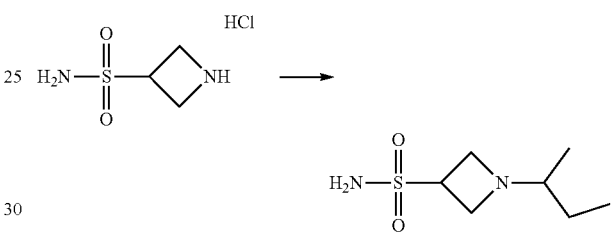

Prepared as described for 1-cyclobutylpiperidine-4-sulfonamide (Intermediate P14) from azetidine-3-sulfonamide hydrochloride and 2-butanone. The title compound (191 mg, yield 85%) was used without further purification.

¹H NMR (DMSO-d₆): δ=6.87 (s, 2H), 3.81 (m, 1H), 3.41 (td, 2H), 3.21 (t, 2H), 2.45-2.34 (m, 1H), 2.18-2.03 (m, 1H), 1.42-1.25 (m, 1H), 1.01 (t, 3H), 0.78 (d, 3H).

Intermediate P108: 1-((1-Methyl-1H-imidazol-2-yl)methyl)azetidine-3-sulfonamide

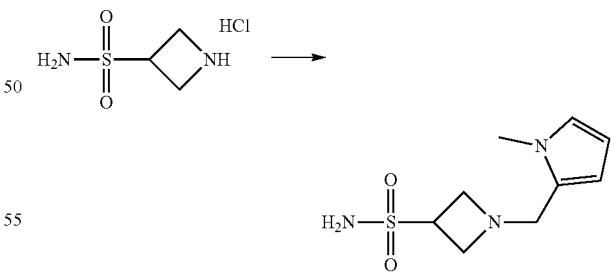

Prepared as described for 1-cyclobutylpiperidine-4-sulfonamide (Intermediate P14) from azetidine-3-sulfonamide hydrochloride and 1-methylimidazole-2-carbaldehyde. The title compound (144 mg, yield 63%) was used without further purification.

¹H NMR (DMSO-d₆): δ=7.03 (d, 1H), 6.91 (s, 2H), 6.71 (d, 1H), 3.96-3.80 (m, 1H), 3.61 (s, 2H), 3.57 (s, 3H), 3.45 (t, 2H), 3.37 (dd, 2H).

Intermediate P109: 1-(2,2-Dimethylcyclobutyl)azetidine-3-sulfonamide

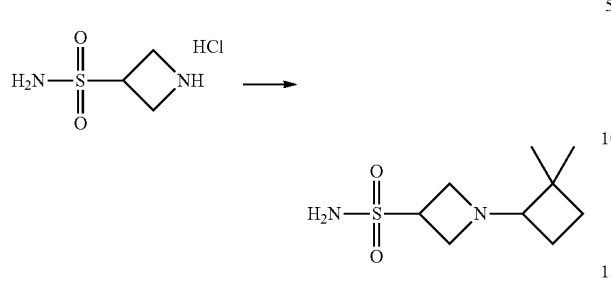

Prepared as described for 1-cyclobutylpiperidine-4-sulfonamide (Intermediate P14) from azetidine-3-sulfonamide hydrochloride and 2,2-dimethylcyclobutanone. The title compound (24 mg, yield 11%) was used without further purification.

$^1$H NMR (DMSO-d$_6$): δ=6.87 (s, 2H), 3.90 (p, 1H), 3.40 (dd, 2H), 3.20 (dt, 2H), 2.57 (d, 1H), 1.86-1.72 (m, 1H), 1.56-1.33 (m, 3H), 1.00 (s, 3H), 0.92 (s, 3H).

Intermediate P110: tert-Butyl (E)-(((tert-butoxycarbonyl)imino)(3-sulfamoylazetidin-1-yl)methyl)(methyl)carbamate

Step A: 1-Methyl-1,3-bis(tert-butoxycarbonyl)-2-methyl-2-thiopseudourea

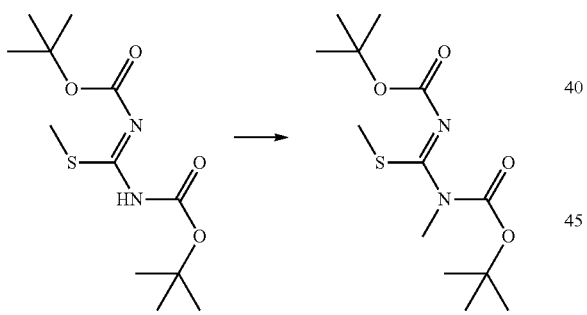

A solution of 1,3-bis(tert-butoxycarbonyl)-2-methyl-2-thiopseudourea (435 mg, 1.5 mmol) in dimethylformamide (5 mL) was cooled to 0° C. in a cooling bath and then sodium hydride (60% dispersion in mineral oil, 72 mg, 1.8 mmol) was added. The cooling bath was removed. After stirring for 1 hour at room temperature, methyl iodide (0.19 mL, 3.0 mmol) was added. After stirring overnight, the reaction mixture was poured into water and then extracted once with dichloromethane and once with ethyl acetate. The organic layers were combined, washed twice with water, once with brine, dried over sodium sulphate, filtered and then concentrated in vacuo to afford the title compound (230 mg, yield 50%), which was used without further purification.

$^1$H NMR (CDCl$_3$): δ=3.12 (s, 3H), 2.39 (s, 3H), 1.51 (s, 9H), 1.48 (s, 9H).

Step B: tert-Butyl (E)-(((tert-butoxycarbonyl)imino)(3-sulfamoylazetidin-1-yl)methyl)(methyl)carbamate

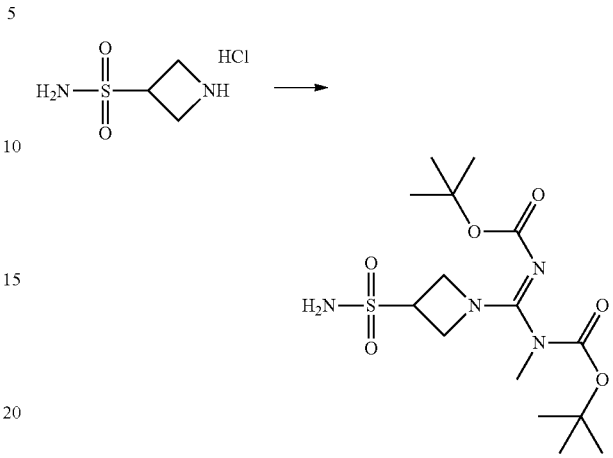

Prepared as described for tert-butyl (Z)-(((tert-butoxycarbonyl)amino)(3-sulfamoylazetidin-1-yl)methylene)carbamate (Intermediate P102) from 1-methyl-1,3-bis(tert-butoxycarbonyl)-2-methyl-2-thiopseudourea, except that after stirring over the weekend, water was added to the reaction mixture. The mixture was extracted three times with dichloromethane. The organic layers were combined, dried over sodium sulfate, filtered and then concentrated in vacuo. The crude product was suspended in methanol, coated on Agilent hydromatrix (a high purity, inert diatomaceous earth sorbent) and then submitted to normal phase flash chromatography using dichloromethane and a mixture of ammonia (3.5 M) in methanol to afford the title compound (48 mg, yield 16%).

$^1$H NMR (DMSO-d$_6$): δ=7.23 (s, 2H), 4.20 (bs, 1H), 4.09 (P, 4H), 2.84 (s, 3H), 1.41 (s, 9H), 1.36 (s, 9H).

Intermediate P111: 1-(Cyclobutylmethyl)azetidine-3-sulfonamide

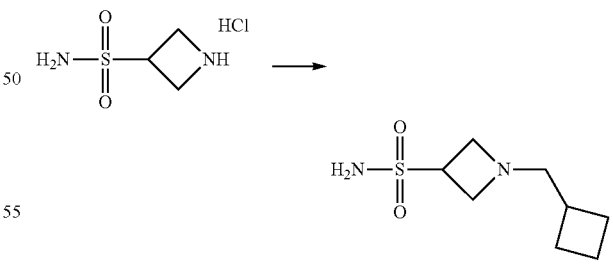

Prepared as described for 1-cyclobutylpiperidine-4-sulfonamide (Intermediate P14) from azetidine-3-sulfonamide hydrochloride and cyclobutane carboxaldehyde. The title compound (145 mg, yield 11%) was used without further purification.

$^1$H NMR (DMSO-d$_6$): δ=6.88 (s, 2H), 3.87 (m, 1H), 3.43 (t, 2H), 3.29-3.18 (m, 2H), 2.39 (d, 2H), 2.22 (dt, 1H), 1.98-1.85 (m, 2H), 1.77 (m, 2H), 1.67-1.49 (m, 2H).

Intermediate P112:
1-(2-(Hydroxyimino)propyl)azetidine-3-sulfonamide

Step A: 1-(2-Oxopropyl)azetidine-3-sulfonamide

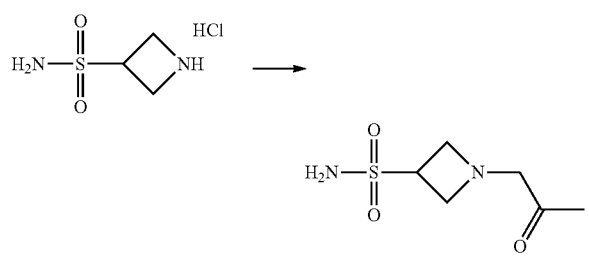

Prepared as described for 1-(prop-2-yn-1-yl)piperidine-4-sulfonamide (Intermediate P3) from azetidine-3-sulfonamide hydrochloride and chloroacetone to afford the title compound (125 mg, yield 21%).

$^1$H NMR (CD$_3$OD): δ=4.06 (m, 1H), 3.75 (td, 2H), 3.60-3.49 (m, 4H), 2.07 (s, 3H).

Step B: 1-(2-(Hydroxyimino)propyl)azetidine-3-sulfonamide

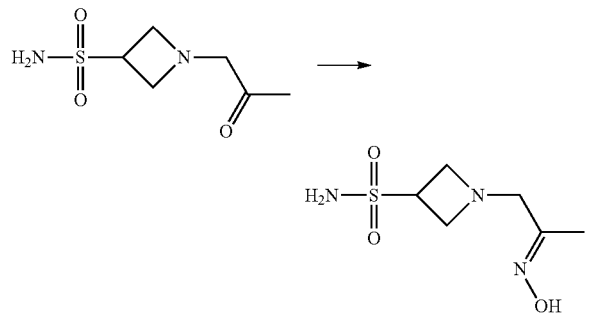

A solution of 1-(2-oxopropyl)azetidine-3-sulfonamide (138 mg, 0.72 mmol) and 7M ammonia in methanol (4.1 mL, 28.7 mmol) was cooled to 0° C. and then hydroxylamine-O-sulfonic acid (81 mg, 0.72 mmol) was added. After stirring for 3 hours, the reaction mixture was filtered over cotton and the residue was washed extensively with methanol. The filtrates were combined and then concentrated in vacuo. The residue was dissolved in methanol (10 mL) and then triethylamine (0.1 mL, 0.72 mmol) was added. The mixture was cooled in an ice bath and iodine (183 mg, 0.72 mmol) was added in small portions. After stirring for 5 minutes, the mixture was concentrated in vacuo. The crude product was suspended in methanol, coated on Agilent hydromatrix (a high purity, inert diatomaceous earth sorbent) and then submitted to normal phase flash chromatography using dichloromethane and a mixture of ammonia (3.5 M) in methanol to afford the title compound (18 mg, yield 12%).

$^1$H NMR (CD$_3$OD): δ=4.16-4.01 (m, 1H), 3.82-3.72 (m, 2H), 3.60 (dd, 2H), 3.33 (p, 2H), 1.85 (s, 3H).

Intermediate P113:
1-(1-Hydroxypropan-2-yl)azetidine-3-sulfonamide

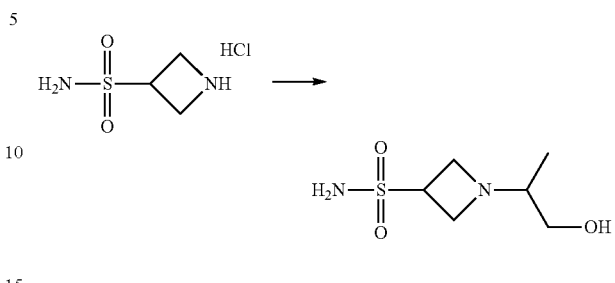

Prepared as described for 1-cyclobutylpiperidine-4-sulfonamide (Intermediate P14) from azetidine-3-sulfonamide hydrochloride and hydroxyacetone. The title compound (36 mg, yield 18%) was used without further purification.

$^1$H NMR (DMSO-d$_6$): δ=6.85 (s, 2H), 4.41 (t, 1H), 3.83 (t, 1H), 3.45 (dt, 2H), 3.27-3.17 (m, 3H), 3.05 (dd, 2H), 0.78 (d, 3H).

Intermediate P114:
1-(1,1-Difluoropropan-2-yl)azetidine-3-sulfonamide

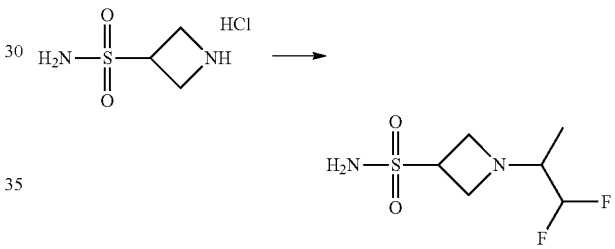

Prepared as described for 1-cyclobutylpiperidine-4-sulfonamide (Intermediate P14) from azetidine-3-sulfonamide hydrochloride and 1,1-difluoroacetone. The title compound (81 mg, yield 38%) was used without further purification.

$^1$H NMR (DMSO-d$_6$): δ=6.93 (s, 2H), 5.73 (td, 1H), 3.90 (m, 1H), 3.55 (q, 2H), 3.44 (dd, J 2H), 2.68-2.57 (m, 1H), 0.90 (d, 3H).

Intermediate P115: 1-Allylazetidine-3-sulfonamide

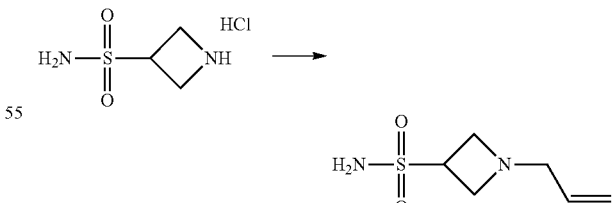

Prepared as described for 1-(prop-2-yn-1-yl)piperidine-4-sulfonamide (Intermediate P3) from azetidine-3-sulfonamide hydrochloride and allylbromide to afford the title compound (56 mg, yield 32%).

$^1$H NMR (DMSO-d$_6$): δ=6.90 (s, 2H), 5.77-5.57 (m, 1H), 5.22-4.96 (m, 2H), 3.96-3.82 (m, 1H), 3.44 (t, 2H), 3.31-3.22 (m, 2H), 3.01 (dt, 2H).

Intermediate P116:
1-(Prop-2-yn-1-yl)azetidine-3-sulfonamide

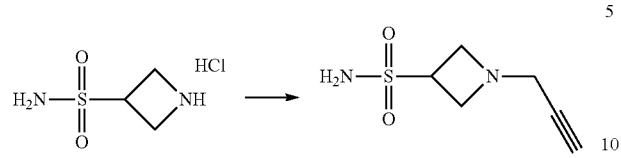

Prepared as described for 1-(prop-2-yn-1-yl)piperidine-4-sulfonamide (Intermediate P3) from azetidine-3-sulfonamide hydrochloride and propargyl bromide (80 wt % in toluene) to afford the title compound (21 mg, yield 15%).

$^1$H NMR (DMSO-d$_6$): δ=6.91 (s, 2H), 3.86 (m, 1H), 3.43 (dt, 4H), 3.20 (d, 2H), 3.16-3.12 (m, 1H).

Intermediate P117:
1-(3-Hydroxypropyl)azetidine-3-sulfonamide

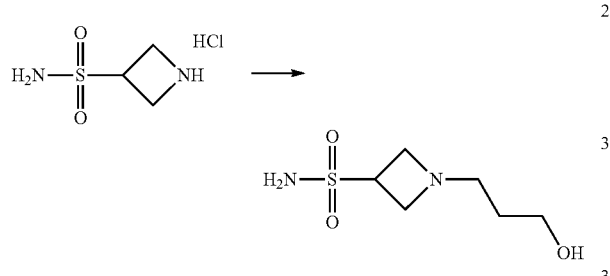

Prepared as described for 1-(prop-2-yn-1-yl)piperidine-4-sulfonamide (Intermediate P3) from azetidine-3-sulfonamide hydrochloride and 3-bromo-1-propanol to afford the title compound (60 mg, yield 38%).

$^1$H NMR (DMSO-d$_6$): δ=6.91 (s, 2H), 3.89 (m, 1H), 3.49 (t, 2H), 3.37 (t, 2H), 3.32-3.24 (m, 2H), 2.47-2.41 (m, 2H), 1.39 (p, 2H).

Intermediate P118:
1-Neopentylazetidine-3-sulfonamide

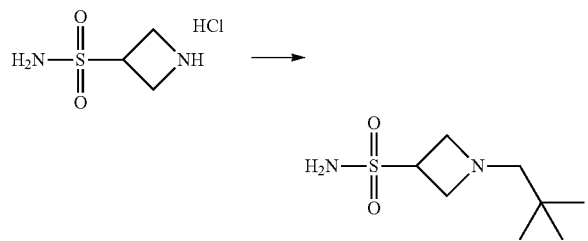

Prepared as described for 1-cyclobutylpiperidine-4-sulfonamide (Intermediate P14) from azetidine-3-sulfonamide hydrochloride and pivalaldehyde. The title compound (71 mg, yield 35%) was used without further purification.

$^1$H NMR (DMSO-d$_6$): δ=6.90 (s, 2H), 3.92 (m, 1H), 3.57 (t, 2H), 3.39-3.29 (m, 2H), 2.20 (s, 2H), 0.80 (s, 9H).

Intermediate P119:
1-((Trimethylsilyl)methyl)azetidine-3-sulfonamide

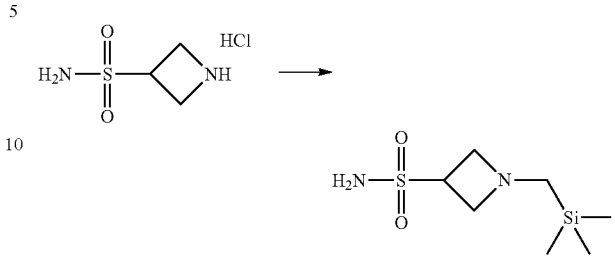

Prepared as described for 1-(prop-2-yn-1-yl)piperidine-4-sulfonamide (Intermediate P3) from azetidine-3-sulfonamide hydrochloride and (iodomethyl)trimethylsilane to afford the title compound (60 mg, yield 33%).

$^1$H NMR (DMSO-d$_6$): δ=6.92 (s, 2H), 3.89 (t, 1H), 3.61 (bs, 2H), 3.31 (bs, 2H), 2.07 (s, 2H), −0.01 (s, 9H).

Intermediate P120:
1-(2-Hydroxypropyl)azetidine-3-sulfonamide

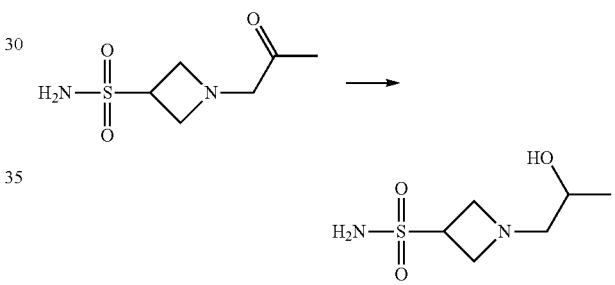

To a solution of 1-(2-oxopropyl)azetidine-3-sulfonamide (Intermediate P112 step A, 125 mg, 0.65 mmol) in methanol (10 mL) was added sodium borohydride (29 mg, 0.78 mmol). After stirring for 4 hours at room temperature, more sodium borohydride (7.4 mg, 0.2 mmol) was added. After stirring overnight, the reaction mixture was quenched with water (1.0 mL) and then concentrated in vacuo. The crude product was suspended in methanol, coated on Agilent hydromatrix (a high purity, inert diatomaceous earth sorbent) and then submitted to normal phase flash chromatography using dichloromethane and a mixture of ammonia (3.5 M) in methanol to afford the title compound (11 mg, yield 8%).

$^1$H NMR (CD$_3$OD): δ=4.09-3.96 (m, 1H), 3.77-3.64 (m, 3H), 3.61-3.48 (m, 2H), 2.55-2.44 (m, 2H), 1.12 (d, 3H).

Intermediate P121:
1-(4-Hydroxybutyl)azetidine-3-sulfonamide

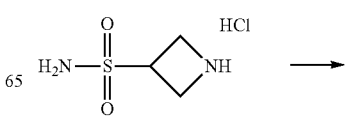

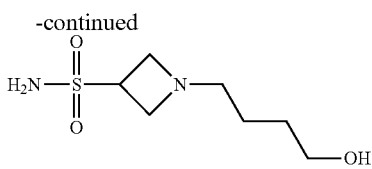

Prepared as described for 1-(prop-2-yn-1-yl)piperidine-4-sulfonamide (Intermediate P3) from azetidine-3-sulfonamide hydrochloride and 4-bromo-1-butanol to afford the title compound (41 mg, yield 20%).

$^1$H NMR (DMSO-$d_6$): δ=6.98 (s, 2H), 3.93 (m, 1H), 3.57 (t, 2H), 3.36 (t, 4H), 3.16 (d, 1H), 2.50-2.42 (m, 2H), 1.47-1.21 (m, 4H).

Intermediate P122: 1-(2-(3-Methyl-3H-diazirin-3-yl)ethyl)azetidine-3-sulfonamide Step A: 2-(3-Methyl-3H-diazirin-3-yl)ethan-1-ol

To cooled liquid ammonia (−78° C., 30 mL) was added 4-hydroxy-2-butanone (5.3 mL, 60.5 mmol). The solution was stirred at −40° C. for 4 hours, and then cooled back to −78° C. To the cooled mixture was added dropwise a solution of hydroxylamine-O-sulfonic acid (7.6 g, 67 mmol) in methanol (60 mL). The cooling bath was removed and the reaction mixture was stirred overnight at room temperature. The suspension was filtered and the residue was washed with methanol extensively. The filtrates were combined and concentrated in vacuo to about 100 mL, and then degassed by passing nitrogen through the filtrates for 20 minutes. The solution was cooled in an ice bath and then triethylamine (7.5 mL, 53.8 mmol) was added followed by iodine (5.0 g, 19.7 mmol). After stirring for 1 hour, another batch of iodine (4.0 g, 15.8 mmol) was added. After 5 minutes, the reaction mixture was concentrated in vacuo to about 100 mL, then brine was added. The aqueous solution was extracted three times with diethyl ether. The organic layers were combined, dried over sodium sulfate, filtered and then concentrated in vacuo. Vacuum distillation (90° C., $10^{-2}$ mbar) provided the title compound as a yellow oil (226 mg, yield 3%).

$^1$H NMR (CDCl$_3$): δ=3.53 (t, 2H), 1.73 (s, 1H), 1.64 (t, 2H), 1.07 (s, 3H).

Step B: 2-(3-Methyl-3H-diazirin-3-yl)ethyl methanesulfonate

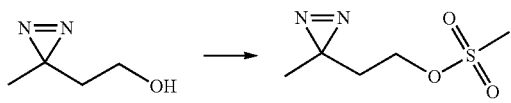

A solution of 2-(3-methyl-3H-diazirin-3-yl)ethan-1-ol (100 mg, 1.0 mmol) and triethylamine (160 μL, 1.15 mmol) in dichloromethane (5 mL) was cooled in an ice bath. To the cooled solution was added methanesulfonyl chloride (93 μL, 1.2 mmol). The reaction mixture was stirred for 1.5 hours in the ice bath, then saturated ammonium chloride was added and the organic layer was separated. The aqueous layer was extracted once with dichloromethane. The organic layers were combined, dried over sodium sulfate, filtered and then concentrated in vacuo to afford the title compound (178 mg, quantitative yield) which was used without further purification.

$^1$H NMR (CDCl$_3$): δ=4.13 (t, 2H), 3.05 (s, 3H), 1.79 (t, 2H), 1.09 (s, 3H).

Step C: 1-(2-(3-Methyl-3H-diazirin-3-yl)ethyl)azetidine-3-sulfonamide

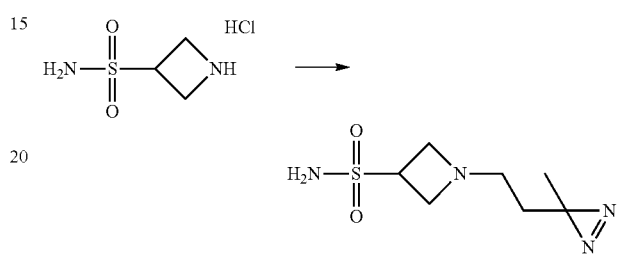

To a solution of 2-(3-methyl-3H-diazirin-3-yl)ethyl methanesulfonate (178 mg, 1.0 mmol) in acetonitrile (20 mL) was added azetidine-3-sulfonamide hydrochloride (344 mg, 2.0 mmol) and then potassium carbonate (1.1 g, 8.0 mmol). The reaction mixture was stirred overnight at 55° C., and then potassium iodide (158 mg, 1.0 mmol) and N,N-dimethylformamide (2 mL) were added. The reaction mixture was stirred for 6 hours at 60° C., then filtered over a glass filter. The residue was washed with methanol. The filtrates were combined and concentrated in vacuo. The crude product was suspended in methanol, coated on Agilent hydromatrix (a high purity, inert diatomaceous earth sorbent) and then submitted to normal phase flash chromatography using dichloromethane and a mixture of ammonia (3.5 M) in methanol to afford the title compound (16 mg, yield 7%).

$^1$H NMR (DMSO-$d_6$): δ=6.90 (s, 2H), 3.92-3.82 (m, 1H), 3.44 (t, 2H), 3.21 (t, 2H), 2.27 (t, 2H), 1.25 (t, 2H), 0.97 (s, 3H).

Intermediate P123: 1-((1-Methyl-6-oxo-1,6-dihydropyridin-3-yl)methyl) azetidine-3-sulfonamide

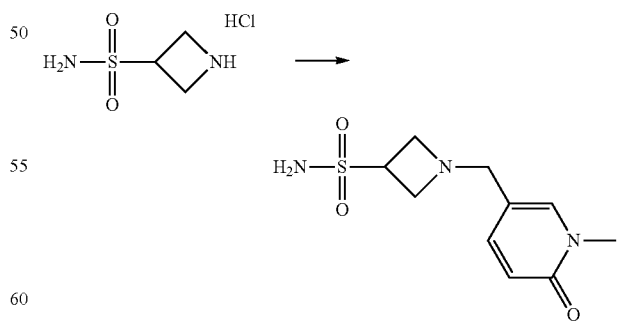

Prepared as described for 1-cyclobutylpiperidine-4-sulfonamide (Intermediate P14) from azetidine-3-sulfonamide hydrochloride and 1-methyl-6-oxo-1,6-dihydropyridine-3-carbaldehyde. The title compound (116 mg, yield 62%) was used without further purification.

¹H NMR (DMSO-d₆): δ=7.54 (s, 1H), 7.29 (d, 1H), 6.93 (s, 2H), 6.32 (d, 1H), 3.97-3.79 (m, 1H), 3.43 (t, 2H), 3.37 (s, 3H), 3.31-3.24 (m, 4H).

Intermediate P124: 1-((1-Methyl-2-oxo-1,2-dihydro-pyridin-4-yl)methyl) azetidine-3-sulfonamide

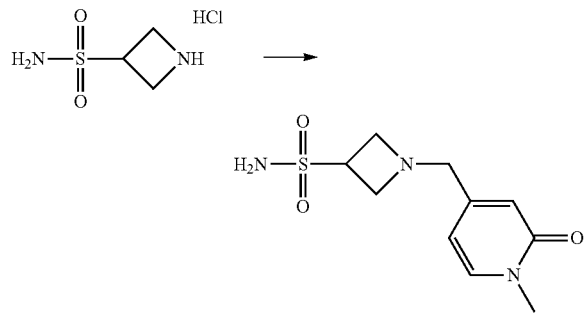

Prepared as described for 1-cyclobutylpiperidine-4-sulfonamide (Intermediate P14) from azetidine-3-sulfonamide hydrochloride and 1-methyl-2-oxo-1,2-dihydropyridine-4-carbaldehyde. The title compound (51 mg, yield 27%) was used without further purification.

¹H NMR (DMSO-d₆): δ=7.57 (d, 1H), 6.98 (s, 2H), 6.23 (s, 1H), 6.07 (d, 1H), 4.00-3.79 (m, 1H), 3.49 (t, 2H), 3.42 (s, 3H), 3.40-3.33 (m, 4H).

Intermediate P125: 1-(2-(Tetrahydrofuran-3-yl)ethyl)azetidine-3-sulfonamide

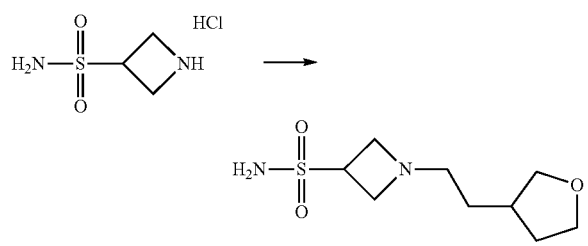

Prepared as described for 1-cyclobutylpiperidine-4-sulfonamide (Intermediate P14) from azetidine-3-sulfonamide hydrochloride and 2-(oxolan-3-yl)acetaldehyde. The title compound (90 mg, yield 27%) was used without further purification.

¹H NMR (DMSO-d₆): δ=6.93 (s, 2H), 3.90 (m, 1H), 3.75 (t, 1H), 3.68 (dt, 1H), 3.59 (q, 1H), 3.47 (t, 2H), 3.26 (t, 3H), 2.45-2.33 (m, 2H), 2.09 (m, 1H), 2.00-1.86 (m, 1H), 1.42 (dt, 1H), 1.30 (q, 2H).

Intermediate P126: 1-((Tetrahydrofuran-3-yl)methyl)azetidine-3-sulfonamide

-continued

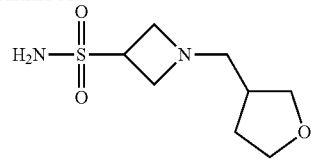

Prepared as described for 1-cyclobutylpiperidine-4-sulfonamide (Intermediate P14) from azetidine-3-sulfonamide hydrochloride and tetrahydrofuran-3-carbaldehyde. The title compound (85 mg, yield 39%) was used without further purification.

¹H NMR (CD₃OD): δ=4.06 (t, 1H), 3.88-3.66 (m, 5H), 3.59 (t, 2H), 3.43 (dd, 1H), 2.66 (d, 2H), 2.35-2.22 (m, 1H), 2.12-1.97 (m, 1H), 1.65-1.52 (m, 1H).

Intermediate P127: 1-((Tetrahydrofuran-2-yl)methyl)azetidine-3-sulfonamide

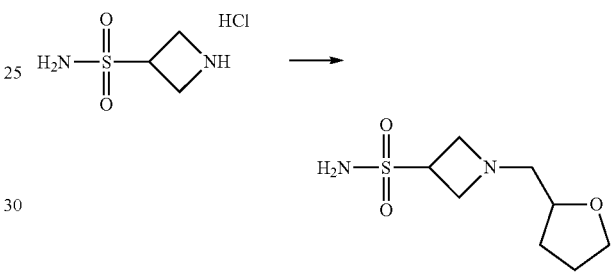

To a solution of (tetrahydrofuran-2-yl)methanol (291 μL, 3.00 mmol) in dichloromethane (30 mL) was added Dess-Martin periodinane (1.40 g, 3.30 mmol). The reaction mixture was stirred at room temperature. After stirring for 1 hour, the solution was washed once with saturated sodium bicarbonate. To the organic solution was added acetonitrile (10 mL), azetidine-3-sulfonamide hydrochloride (172 mg, 1.00 mmol), triethylamine (0.17 mL, 1.20 mmol), and then sodium triacetoxyborohydride (265 mg, 1.25 mmol). The reaction mixture was stirred overnight at room temperature and then concentrated in vacuo. The crude product was suspended in methanol, coated on Agilent hydromatrix (a high purity, inert diatomaceous earth sorbent) and then submitted to normal phase flash chromatography using dichloromethane and a mixture of ammonia (3.5 M) in methanol to afford the title compound (77 mg, yield 35%).

¹H NMR (DMSO-d₆): δ=6.90 (s, 2H), 3.90 (m, 1H), 3.69 (q, 2H), 3.60-3.46 (m, 3H), 3.43-3.33 (m, 2H), 2.44 (d, 2H), 1.89-1.68 (m, 3H), 1.47 (q, 1H).

Intermediate P128: (1R,3R,5S)-8-(1-Methylazetidin-3-yl)-8-azabicyclo[3.2.1] octane-3-sulfonamide Step A: tert-Butyl 3-((1R,3R,5S)-3-sulfamoyl-8-azabicyclo[3.2.1]octan-8-yl)azetidine-1-carboxylate

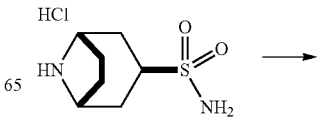

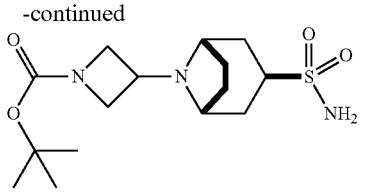

Prepared as described for 1-cyclobutylpiperidine-4-sulfonamide (Intermediate P14) from (1R*,3R*,5S*)-8-azabicyclo[3.2.1]octane-3-sulfonamide hydrochloride and 1-Boc-3-azetidinone. The title compound (286 mg, yield 41%) was used without further purification.

$^1$H NMR (DMSO-$d_6$): δ=6.62 (s, 2H), 3.82 (s, 2H), 3.49 (s, 2H), 3.20-3.04 (m, 4H), 2.36-2.18 (m, 2H), 1.85-1.74 (m, 2H), 1.72-1.64 (m, 2H), 1.58 (dd, 2H), 1.35 (s, 9H).

Step B: (1R,3R,5S)-8-(Azetidin-3-yl)-8-azabicyclo[3.2.1]octane-3-sulfonamide Dihydrochloride

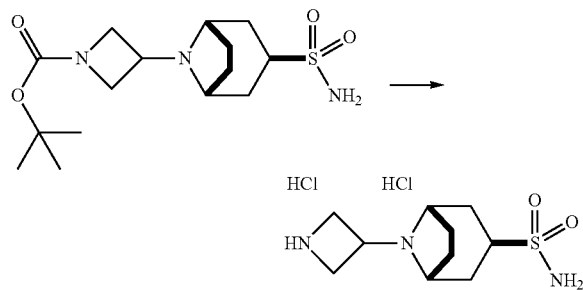

To a solution of tert-butyl 3-((1R,3R,5S)-3-sulfamoyl-8-azabicyclo[3.2.1]octan-8-yl)azetidine-1-carboxylate (286 mg, 0.83 mmol) in dichloromethane (10 mL) was added hydrochloric acid (4 M in dioxane, 2.1 mL, 8.3 mmol). After stirring for 2 hours, the reaction mixture was concentrated in vacuo to afford the tittle compound (237 mg, yield 89%), which was used without further purification.

$^1$H NMR (DMSO-$d_6$): δ=9.86 (bs, 1H), 9.01 (bs, 1H), 6.95 (d, J=6.1 Hz, 2H), 4.46 (bs, 2H), 4.21-3.84 (m, 6H), 3.42-3.25 (m, 1H), 2.83 (bs, 2H), 2.30 (t, 2H), 2.20-1.97 (m, 4H).

Step C: (1R,3R,5S)-8-(1-Methylazetidin-3-yl)-8-azabicyclo[3.2.1]octane-3-sulfonamide

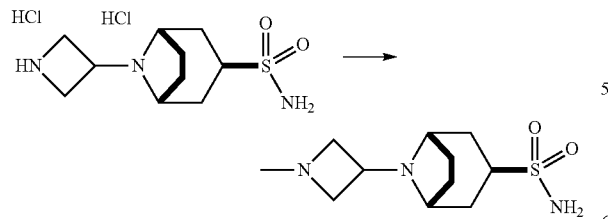

Prepared as described for 1-cyclobutylpiperidine-4-sulfonamide (Intermediate P14) from (1R,3R,5S)-8-(azetidin-3-yl)-8-azabicyclo[3.2.1]octane-3-sulfonamide dihydrochloride and formaldehyde (37 wt % in water). The title compound (37 mg, yield 35%) was used without further purification.

$^1$H NMR (CD$_3$OD): δ=4.15 (bs, 3H), 3.92 (bs, 3H), 2.93 (s, 3H), 2.61-2.39 (m, 2H), 2.03-1.89 (m, 4H), 1.89-1.63 (m, 4H).

Intermediate P129:
4-Methoxy-1-methylpyrrolidine-3-sulfonamide

Step A: Benzyl 3-methoxy-4-sulfamoylpyrrolidine-1-carboxylate

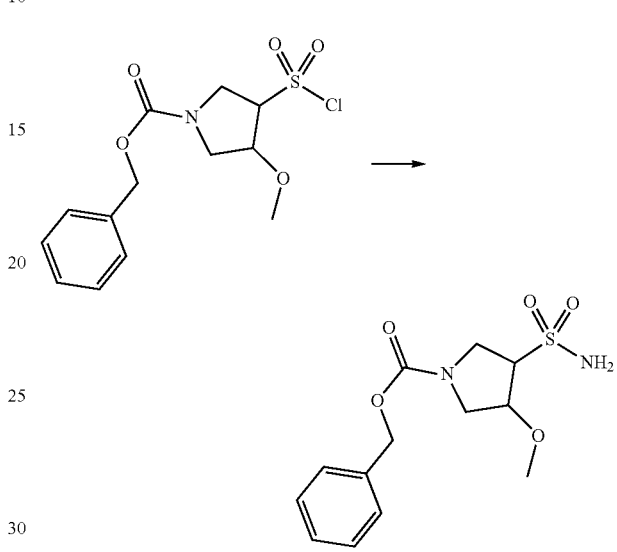

To a solution of ammonia in methanol (7M, 42 mL) was added dropwise a solution of benzyl 3-(chlorosulfonyl)-4-methoxypyrrolidine-1-carboxylate (500 mg, 1.49 mmol) in dichloromethane (10 mL). After stirring for 1.5 hours at room temperature, the reaction mixture was concentrated in vacuo. The residue was diluted with ethyl acetate and then washed with saturated sodium bicarbonate. The organic layer was dried over sodium sulfate and then concentrated in vacuo to afford the title compound (236 mg, yield 50%).

$^1$H NMR (DMSO-$d_6$): δ=7.43-7.28 (m, 5H), 7.21 (S, 2H), 5.08 (s, 2H), 4.24 (bs, 1H), 3.82-3.64 (m, 3H), 3.66-3.55 (m, 1H), 3.46 (d, 1H), 3.29 (s, 3H).

Step B: 4-Methoxypyrrolidine-3-sulfonamide

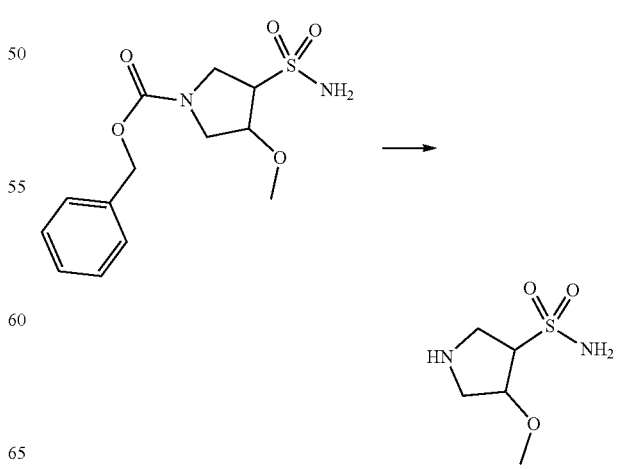

Prepared as described for azetidine-3-sulfonamide (Intermediate P33) from benzyl 3-methoxy-4-sulfamoylpyrrolidine-1-carboxylate to afford the title compound (91 mg, yield 67%) which was used without further purification.

$^1$H NMR (DMSO-d$_6$): δ=6.98 (s, 2H), 4.08 (dt, 1H), 3.76-3.62 (m, 1H), 3.56-3.33 (m, 3H), 3.30-3.15 (m, 3H), 2.99 (dd, 1H), 2.83 (t, 1H).

Step C:
4-Methoxy-1-methylpyrrolidine-3-sulfonamide

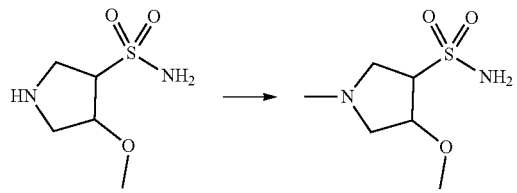

Prepared as described for 1-cyclobutylpiperidine-4-sulfonamide (Intermediate P14) from 4-methoxypyrrolidine-3-sulfonamide and formaldehyde (37 wt % in water). The title compound (mixture of diastereomers, 17 mg, yield 35%) was used without further purification.

$^1$H NMR (CD$_3$OD) of the major diastereomer: δ=4.21-4.11 (m, 1H), 3.65 (td, 1H), 3.40-3.35 (m, 2H), 3.27-3.18 (m, 1H), 2.90 (d, 1H), 2.81 (dd, 1H), 2.70-2.52 (m, 2H), 2.35 (s, 3H).

Intermediate P130:
1-Ethyl-4-methoxypyrrolidine-3-sulfonamide

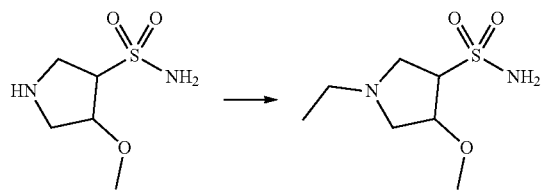

Prepared as described for 1-cyclobutylpiperidine-4-sulfonamide (Intermediate P14) from 4-methoxypyrrolidine-3-sulfonamide and acetaldehyde. The title compound (mixture of diastereomers, 12 mg, yield 23%) was used without further purification.

$^1$H NMR (CD$_3$OD) of the major diastereomer: δ=4.18 (d, 1H), 3.75-3.56 (m, 1H), 3.38 (s, 3H), 3.13-2.94 (m, 2H), 2.72 (dd, 2H), 2.66-2.50 (m, 2H), 1.14 (dd, 3H).

Intermediate P131:
1-(Oxetan-3-yl)azetidine-3-sulfonamide

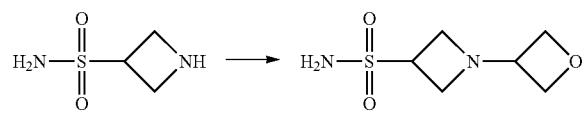 [SMILES: NS(=O)(=O)C1CNC1 ; NS(=O)(=O)C1CN(C2COC2)C1]

To a solution of azetidine-3-sulfonamide (22 mg, 0.16 mmol) in methanol (5 mL) was added oxetan-3-one (23 mg, 0.32 mmol) and 2 drops of acetic acid. Next, sodium cyanoborohydride (20 mg, 0.32 mmol) was added. The reaction mixture was stirred for 18 hours at room temperature. Then the solvents were evaporated to afford the crude title compound (80 mg) as an oil, which was used without further purification.

NMR data of the crude product was very complex. LCMS showed the desired mass.

LCMS: m/z 193 (M+H)$^+$ (ES$^+$); 191 (M–H) (ES$^-$).

Intermediate P132: 1-Isopropyl-6-oxo-1,6-dihydropyridine-3-sulfonamide

Step A: 6-Chloro-N,N-bis(4-methoxybenzyl)pyridine-3-sulfonamide

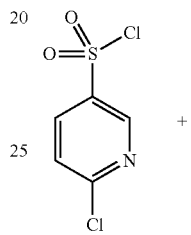

+

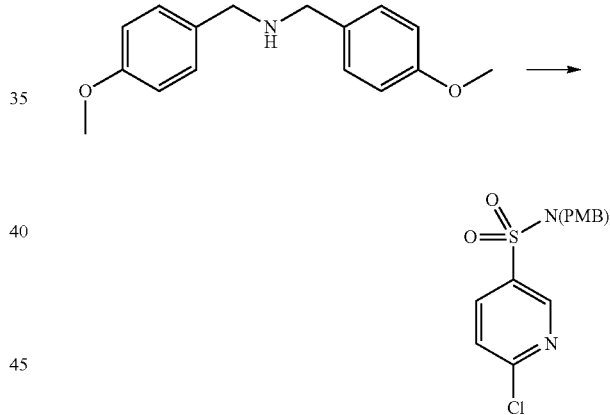

Bis(4-methoxybenzyl)amine (3.71 g, 14.4 mmol) was added to a solution of 2-chloropyridine-5-sulfonyl chloride (3.00 g, 13.7 mmol) and triethylamine (2.49 mL, 17.8 mmol) in DCM (50 mL) at 0° C. The reaction was stirred at 0° C. for 15 minutes and then allowed to warm up to room temperature and stirred for 20 hours. Then the reaction mixture was diluted with DCM (150 mL), washed with a saturated aqueous NH$_4$Cl solution (3×40 mL) and brine (40 mL), dried over MgSO$_4$, filtered, and concentrated in vacuo to give the crude product as a cream solid. The crude product was triturated with TBME (70 mL), filtered and rinsed with TBME (2×40 mL) to afford the title compound (4.97 g, 83%) as an off-white solid.

$^1$H NMR (DMSO-d6) δ 8.76 (dd, J=2.6, 0.7 Hz, 1H), 8.19 (dd, J=8.4, 2.6 Hz, 1H), 7.69 (dd, J=8.4, 0.7 Hz, 1H), 7.08-7.02 (m, 4H), 6.83-6.76 (m, 4H), 4.29 (s, 4H), 3.71 (s, 6H).

LCMS: m/z 433.3 (M+H)$^+$ (ES$^+$).

Step B: 6-Hydroxy-N,N-bis(4-methoxybenzyl)pyridine-3-sulfonamide

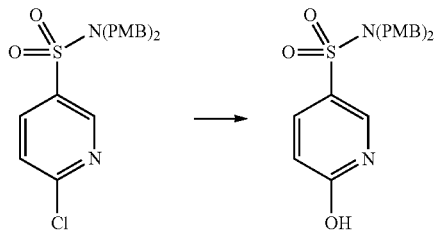

A suspension of 6-chloro-N,N-bis(4-methoxybenzyl)pyridine-3-sulfonamide (0.508 g, 1.17 mmol) in ethane-1,2-diol (10 mL) was treated with 2 M KOH (aq) (2.4 mL, 4.80 mmol). The resultant suspension was stirred at 140° C. for 18 hours. Then the reaction mixture was treated with further 2 M KOH (aq) (0.6 mL, 1.2 mmol, 1 eq) and heated at 140° C. for another 6 hours, and further 2 M KOH (aq) (0.6 mL, 1.2 mmol, 1 eq) and heated at 140° C. for another 18 hours. Then the reaction mixture was diluted with water (40 mL) and DCM (30 mL). Brine (5 mL) was added and the organic layer was collected. The aqueous phase was extracted with DCM (5×30 mL). The combined organic extracts were washed with water (10 mL), dried over MgSO$_4$, filtered and concentrated in vacuo. The residue was dried under reduced pressure at 50° C. overnight to afford the title compound (542 mg, 100%).

$^1$H NMR (DMSO-d6) δ 12.17 (S, 1H), 7.86 (d, J=2.8 Hz, 1H), 7.63 (dd, J=9.6, 2.9 Hz, 1H), 7.11-7.02 (m, 4H), 6.87-6.79 (m, 4H), 6.37 (d, J=9.6 Hz, 1H), 4.21 (s, 4H), 3.72 (s, 6H).

LCMS: m/z 415.4 (M+H)$^+$ (ES$^+$), 413.4 (M−H)$^-$ (ES$^-$).

Step C: 1-Isopropyl-N,N-bis(4-methoxybenzyl)-6-oxo-1,6-dihydropyridine-3-sulfonamide and 6-isopropoxy-N,N-bis(4-methoxybenzyl)pyridine-3-sulfonamide

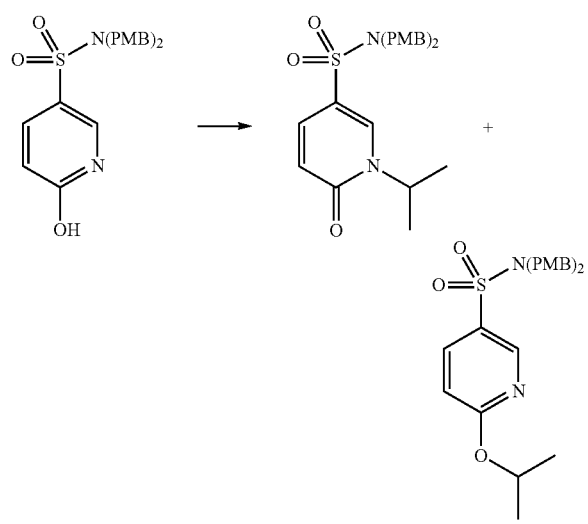

Sodium hydride (60 wt % dispersion in mineral oil) (36 mg, 0.91 mmol) was added to a mixture of 6-hydroxy-N,N-bis(4-methoxybenzyl)pyridine-3-sulfonamide (0.40 g, 0.869 mmol) and lithium bromide (0.154 g, 1.737 mmol) in DME:DMF (5 mL, 4:1) at 0° C.

The mixture was stirred at 0° C. for 10 minutes and then at room temperature for a further 10 minutes. Then 2-iodopropane (0.10 mL, 1.04 mmol) was added and the mixture was stirred at room temperature for 46 hours. The reaction mixture was heated to 65° C. for 17 hours, cooled to room temperature and quenched with saturated aqueous NH$_4$Cl (5 mL) and diluted with EtOAc (100 mL). The organic layer was washed with water (15 mL) and brine (3×15 mL), dried over MgSO$_4$, filtered, and concentrated in vacuo. The crude product was purified by chromatography on silica gel (24 g column, 0-100% EtOAc/isohexane) to afford 1-isopropyl-N,N-bis(4-methoxybenzyl)-6-oxo-1,6-dihydropyridine-3-sulfonamide (0.28 g, 70%) as a white solid and 6-isopropoxy-N,N-bis(4-methoxybenzyl)pyridine-3-sulfonamide (0.11 g, 27%).

1-Isopropyl-N,N-bis(4-methoxybenzyl)-6-oxo-1,6-dihydropyridine-3-sulfonamide $^1$H NMR (CDCl$_3$) δ 7.91 (d, J=2.7 Hz, 1H), 7.41 (dd, J=9.6, 2.6 Hz, 1H), 7.09-7.04 (m, 4H), 6.84-6.79 (m, 4H), 6.54 (dd, J=9.6, 0.5 Hz, 1H), 5.17 (sept, J=6.8 Hz, 1H), 4.26 (s, 4H), 3.79 (s, 6H), 1.34 (d, J=6.8 Hz, 6H).

LCMS: m/z 457.4 (M+H)$^+$ (ES$^+$).

6-Isopropoxy-N,N-bis(4-methoxybenzyl)pyridine-3-sulfonamide $^1$H NMR (CDCl$_3$) δ 8.60-8.55 (m, 1H), 7.84-7.79 (m, 1H), 7.06-6.99 (m, 4H), 6.81-6.75 (m, 4H), 6.72-6.67 (m, 1H), 5.43-5.33 (m, 1H), 4.26 (s, 4H), 3.78 (s, 6H), 1.37 (d, J=6.2 Hz, 6H).

LCMS: m/z 457.4 (M+H)$^+$ (ES$^+$).

Step D: 1-Isopropyl-6-oxo-1,6-dihydropyridine-3-sulfonamide

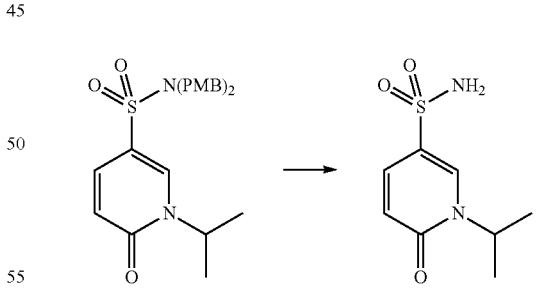

TFA (0.43 ml, 5.64 mmol) was added to a solution of 1-isopropyl-N,N-bis(4-methoxybenzyl)-6-oxo-1,6-dihydropyridine-3-sulfonamide (0.26 g, 0.564 mmol) in DCM (3 mL) at room temperature and the mixture was stirred for 66 hours. Then the reaction was concentrated in vacuo and the residue was redissolved in DCM (5 mL). The product was purified by chromatography on silica gel (12 g column, 0-10% MeOH/DCM) to afford the title compound (60 mg, 49%) as a white solid.

LCMS: m/z 217.3 (M+H)$^+$ (ES$^+$).

Intermediate P133: 4-Isopropyl-5-oxo-4,5-dihydropyrazine-2-sulfonamide

Step A: 2-(Benzylthio)-5-chloropyrazine

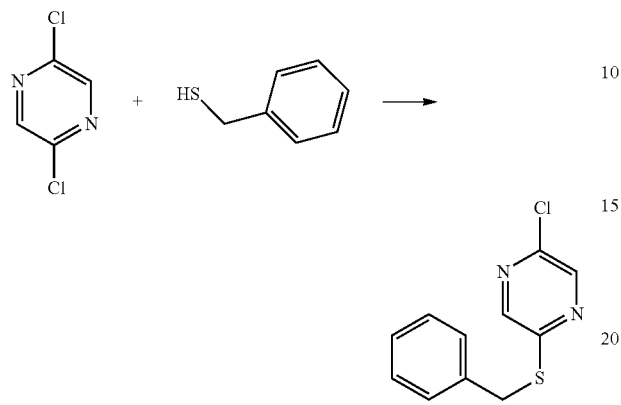

To a solution of NaH (0.755 g, 18.88 mmol) in THF (55 mL) was added benzyl mercaptan (1.5 mL, 12.68 mmol) at 0° C. The reaction mixture was diluted with THF (20 mL) and stirred at 0° C. for 10 minutes. Then a solution of 2,5-dichloropyrazine (1.370 mL, 13.42 mmol) in THF (10 mL) was added dropwise. The reaction mixture was stirred at 0° C. for 1 hour, then warmed to room temperature and stirred for 16 hours. The reaction mixture was cooled to 0° C., MeOH (1 mL) was added carefully and stirred for 5 minutes. Water (20 mL), then DCM (150 mL) was added and the biphasic mixture was passed through a phase separator. The organic phase was concentrated in vacuo. The crude product was purified by chromatography on silica gel (40 g column, 0-3% EtOAc/isohexane) to afford the title compound (2.373 g, 72%) as a clear yellow oil.

$^1$H NMR (DMSO-d6) δ 8.68 (d, J=1.5 Hz, 1H), 8.49 (d, J=1.5 Hz, 1H), 7.43-7.39 (m, 2H), 7.34-7.29 (m, 2H), 7.28-7.23 (m, 1H), 4.46 (s, 2H).

Step B: 5-Chloro-N,N-bis(4-methoxybenzyl)pyrazine-2-sulfonamide

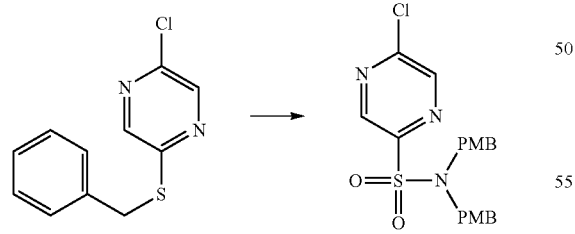

A solution of 2-(benzylthio)-5-chloropyrazine (0.916 g, 3.87 mmol) in DCM (15 mL, 233 mmol) was treated with water (1.5 mL) and the resultant suspension was cooled to between −5 and 0° C. Sulfuryl chloride (2.2 mL, 26.2 mmol) was added and the reaction mixture was stirred for 2 hours maintaining the temperature between −5 and 0° C. A slurry of ice/water (10 mL) was added and the organic phase was collected. The aqueous phase was extracted with DCM (2×10 mL) and the combined organic extracts were dried (MgSO$_4$) and concentrated in vacuo to afford crude intermediate 5-chloropyrazine-2-sulfonyl chloride as a pale yellow liquid (1.198 g).

A suspension of bis(4-methoxybenzyl)amine hydrochloride (1.198 g, 4.08 mmol) and TEA (1.2 mL, 8.61 mmol) in DCM (15 mL) at 0° C. was treated with a solution of 5-chloropyrazine-2-sulfonyl chloride (0.824 g, 3.87 mmol) in DCM (5 mL) dropwise. The resultant solution was stirred at 0° C. for 15 minutes and then allowed to warm to room temperature for 16 hours. A saturated aqueous NH$_4$Cl solution (10 mL) was added and the organic phase was collected. The aqueous phase was extracted with DCM (2×10 mL) and the combined organic extracts were dried (MgSO$_4$) and concentrated in vacuo. The crude product was purified by chromatography on silica gel (24 g column, 0-30% EtOAc/isohexane) to afford the title compound (1.312 g, 77%) as a white solid.

$^1$H NMR (CDCl$_3$) δ 8.78 (d, J=1.4 Hz, 1H), 8.46 (d, J=1.4 Hz, 1H), 7.11-7.07 (m, 4H), 6.79-6.75 (m, 4H), 4.43 (s, 4H), 3.79 (s, 6H).

Step C: N,N-Bis(4-methoxybenzyl)-5-oxo-4,5-dihydropyrazine-2-sulfonamide

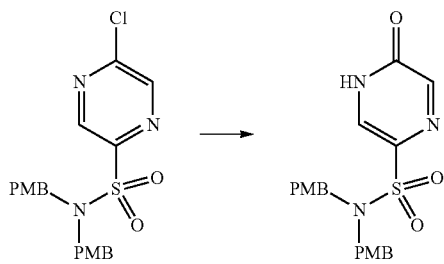

A suspension of 5-chloro-N,N-bis(4-methoxybenzyl)pyrazine-2-sulfonamide (1.31 g, 2.99 mmol) in glycol (15 mL) was treated with 2 M KOH (aq) (7.5 mL, 15 mmol). The resultant suspension was stirred at 140° C. for 18 hours. Then the reaction mixture was allowed to cool to room temperature, diluted with water (100 mL) and neutralised with saturated aqueous NH$_4$Cl solution (30 mL). The white precipitate was collected by filtration, washed with water and dried at 60° C. under vacuum to afford the title compound (1.094 g, 79%) as a pale yellow solid.

$^1$H NMR (DMSO-d6) δ 7.94 (d, J=1.2 Hz, 1H), 7.89 (br s, 1H), 7.10-7.06 (m, 4H), 6.84-6.79 (m, 4H), 4.28 (s, 4H), 3.71 (s, 6H). One exchangeable proton not observed.

LCMS: m/z 438.2 (M+Na)$^+$ (ES$^+$); 414.2 (M−H)$^-$ (ES$^-$).

Step D: 4-Isopropyl-N,N-bis(4-methoxybenzyl)-5-oxo-4,5-dihydropyrazine-2-sulfonamide

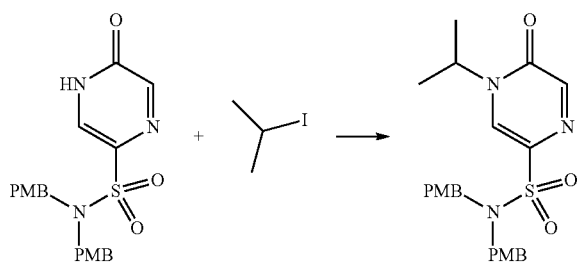

A suspension of N,N-bis(4-methoxybenzyl)-5-oxo-4,5-dihydropyrazine-2-sulfonamide (0.503 g, 1.090 mmol) and lithium bromide (0.192 g, 2.167 mmol) in DME:DMF (6 mL, 4:1) at 0° C. was treated with NaH (0.053 g, 1.325 mmol). The resultant suspension was stirred at 0° C. for 10 minutes, treated with 2-iodopropane (0.218 ml, 2.136 mmol) and then stirred at 65° C. for 64 hours. A saturated aqueous NH$_4$Cl solution (6 mL) and EtOAc (10 mL) were added and the organic layer was collected. The aqueous layer was extracted with EtOAc (2×10 mL) and the combined organic extracts were washed with water (10 mL) and brine (2×10 mL), dried (MgSO$_4$) and concentrated in vacuo. The crude product was purified by chromatography on silica gel (12 g column, 0-100% EtOAc/isohexane) to afford the title compound (0.293 g, 53%) as a clear yellow oil.

$^1$H NMR (DMSO-d6) δ 8.07 (d, J=1.0 Hz, 1H), 7.96 (d, J=0.9 Hz, 1H), 7.13-7.09 (m, 4H), 6.83-6.79 (m, 4H), 4.78 (sept, J=6.5 Hz, 1H), 4.33 (s, 4H), 3.71 (s, 6H), 1.34 (d, J=6.8 Hz, 6H).

LCMS: m/z 480.3 (100, [M+Na]+), 458.5 (9, [M+H]$^+$) (ES$^+$).

Step E: 4-Isopropyl-5-oxo-4,5-dihydropyrazine-2-sulfonamide

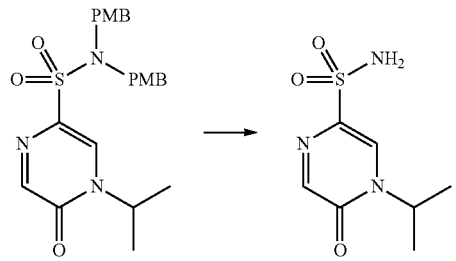

A solution of 4-isopropyl-N,N-bis(4-methoxybenzyl)-5-oxo-4,5-dihydropyrazine-2-sulfonamide (0.287 g, 0.565 mmol) in DCM (1 mL) was treated with TFA (1 mL, 12.98 mmol) at room temperature. The resultant solution was stirred for 28 hours. Then the reaction mixture was concentrated in vacuo and the crude product was purified by chromatography on silica gel (4 g column, 0-10% MeOH/DCM) to afford the title compound (0.116 g, 94%) as a white solid.

$^1$H NMR (DMSO-d6) δ 8.14 (d, J=1.0 Hz, 1H), 8.08 (d, J=1.0 Hz, 1H), 7.40 (s, 2H), 4.88 (sept, J=6.7 Hz, 1H), 1.36 (d, J=6.8 Hz, 6H).

LCMS: 216.1 (M–H)$^-$ (ES$^-$).

Intermediate P134:
1-Isopropylazetidine-3-sulfonamide

Step A: tert-Butyl 3-hydroxyazetidine-1-carboxylate

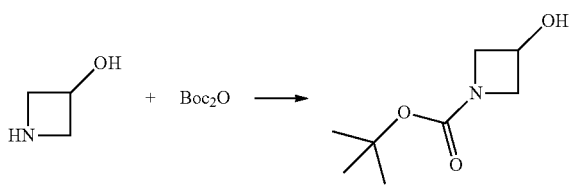

To a solution of azetidin-3-ol hydrochloride (45 g, 410.75 mmol, 1 eq) in MeOH (1.2 L) was added TEA (83.13 g, 821.51 mmol, 2 eq) and di-tert-butyl dicarbonate (89.65 g, 410.75 mmol, 1 eq). The mixture was stirred at 25° C. for 16 hours. Then the reaction mixture was concentrated in vacuo. The residue was re-dissolved in EtOAc (1 L). The mixture was washed with H$_2$O (3×500 mL) and brine (3×500 mL), dried over anhydrous Na$_2$SO$_4$, filtered and concentrated in vacuo to give the title compound (65 g, 91%) as a yellow oil, which was used directly in the next step.

$^1$H NMR (CDCl$_3$) δ 4.59 (s, 1H), 4.19-4.12 (m, 2H), 3.84-3.79 (m, 2H), 1.45 (s, 9H).

Step B: tert-Butyl 3-((methylsulfonyl)oxy)azetidine-1-carboxylate

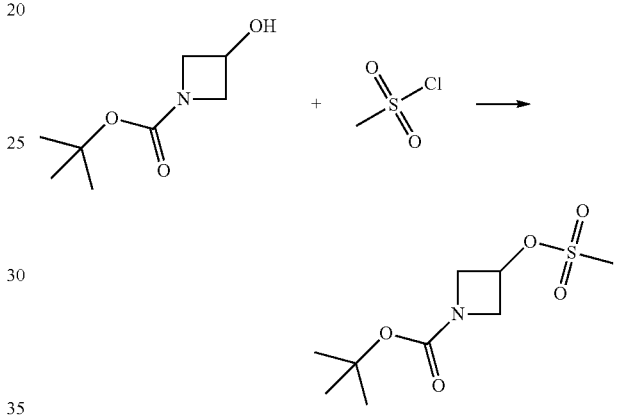

To a solution of tert-butyl 3-hydroxyazetidine-1-carboxylate (65 g, 375.27 mmol, 1 eq) and TEA (113.92 g, 3 eq) in THF (650 mL) was added methanesulfonyl chloride (51.58 g, 450.32 mmol, 1.2 eq) at 0° C. Then the mixture was stirred at 25° C. for 12 hours. The reaction mixture was diluted with EtOAc (2 L), washed with water (3×1.5 L) and brine (3×1.5 L), dried over anhydrous Na$_2$SO$_4$, filtered and concentrated in vacuo to give the title compound (90 g, 95%) as a yellow oil, which was used directly in the next step.

$^1$H NMR (CDCl$_3$) δ 5.25-5.20 (m, 1H), 4.32-4.27 (m, 2H), 4.14-4.10 (m, 2H), 3.08 (s, 3H) and 1.46 (s, 9H).

Step C: tert-Butyl 3-(acetylthio)azetidine-1-carboxylate

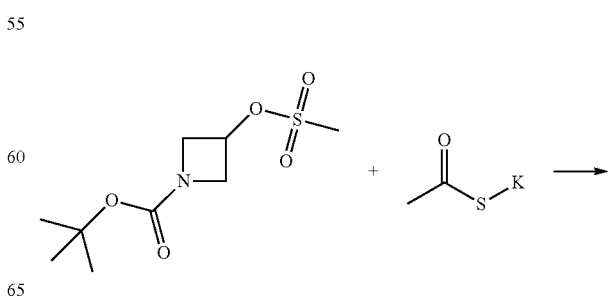

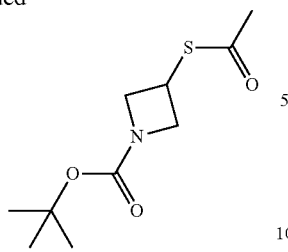

To a solution of tert-butyl 3-((methylsulfonyl)oxy)azetidine-1-carboxylate (90 g, 358.14 mmol, 1 eq) in DMF (1.5 L) was added potassium ethanethioate (49.08 g, 429.77 mmol, 1.2 eq). The mixture was stirred at 80° C. for 12 hours. Then the reaction mixture was diluted with EtOAc (3 L), washed with saturated aqueous NH$_4$Cl solution (3×2 L) and brine (3×2 L), dried over anhydrous Na$_2$SO$_4$, filtered and concentrated in vacuo. The residue was purified by silica gel column chromatography (SiO$_2$, petroleum ether:ethyl acetate, 100:1 to 20:1) to give the title compound (54 g, 65%) as a yellow oil.

$^1$H NMR (CDCl$_3$) δ 4.37 (t, 2H), 4.17-4.14 (m, 1H), 3.82 (dd, 2H), 2.34 (s, 3H) and 1.44 (s, 9H).

Step D: tert-Butyl 3-(chlorosulfonyl)azetidine-1-carboxylate

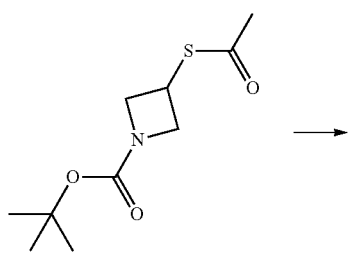

To a solution of tert-butyl 3-(acetylthio)azetidine-1-carboxylate (5 g, 21.62 mmol, 1 eq) in AcOH (200 mL) and H$_2$O (20 mL) was added NCS (8.66 g, 64.85 mmol, 3 eq). The reaction mixture was stirred at 25° C. for 1 hour. Then the reaction mixture was diluted with DCM (300 mL), washed with water (3×300 mL) and brine (3×300 mL), dried over anhydrous Na$_2$SO$_4$ and filtered. The solution was used directly in the next step.

Step E: tert-Butyl 3-sulfamoylazetidine-1-carboxylate

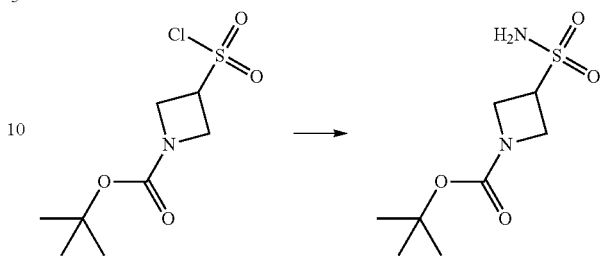

Through a solution of tert-butyl 3-(chlorosulfonyl)azetidine-1-carboxylate (55.28 g, crude) in DCM (1.5 L) was bubbled NH$_3$ for 30 minutes at 0° C. Then the reaction mixture was filtered and the filtrate was concentrated in vacuo. The residue was triturated with a mixture of petroleum ether and EtOAc (21 mL, 20: 1) to give the title compound (27 g, 53%) as a white solid.

$^1$H NMR (DMSO-d$_6$) δ 7.16 (br s, 2H), 4.18-4.03 (m, 2H), 4.03-3.90 (m, 3H) and 1.38 (s, 9H).

Step F: tert-Butyl 3-(N,N-bis(4-methoxybenzyl)sulfamoyl)azetidine-1-carboxylate

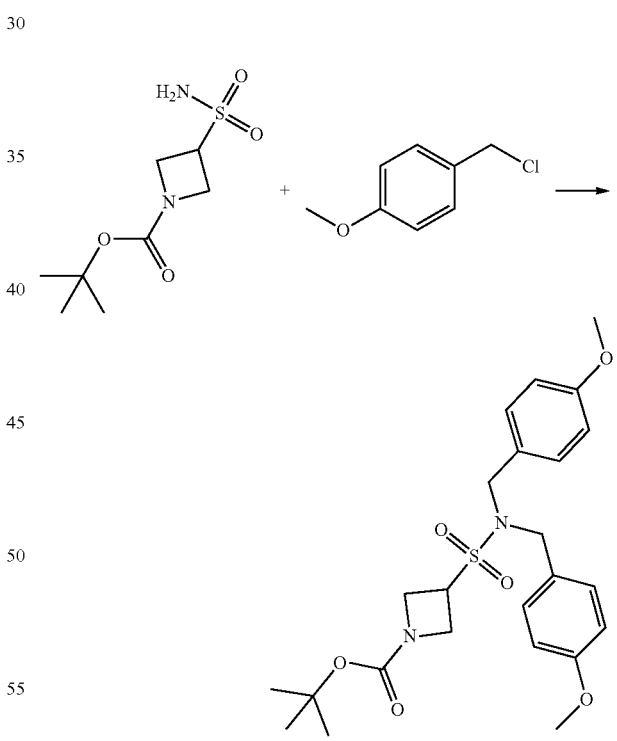

To a solution of tert-butyl 3-sulfamoylazetidine-1-carboxylate (1 g, 4.23 mmol, 1 eq) in DMF (10 mL) was added NaH (507 mg, 12.69 mmol, 60 wt % in mineral oil, 3 eq) at 0° C. The mixture was stirred at 0° C. for 30 minutes. Then 1-(chloromethyl)-4-methoxybenzene (1.99 g, 12.69 mmol, 3 eq) was added. The mixture was stirred at 25° C. for 14 hours. Then the reaction mixture was diluted with EtOAc (50 mL), washed with a saturated aqueous NH$_4$Cl solution (3×30 mL) and brine (3×30 mL), dried over anhydrous Na$_2$SO$_4$, filtered and concentrated in vacuo. The residue was triturated with MeOH (10 mL) to give the title compound (1 g, 50%) as a white solid.

$^1$H NMR (CDCl$_3$) δ 7.17 (d, 4H), 6.91-6.88 (m, 4H), 4.30 (s, 4H), 4.22 (dd, 2H), 4.01 (t, 2H), 3.83 (s, 6H), 3.75-3.62 (m, 1H) and 1.44 (s, 9H).

LCMS: m/z 499.2 (M+Na)$^+$ (ES$^+$).

Step G: N,N-Bis(4-methoxybenzyl)azetidine-3-sulfonamide

Step H: 1-Isopropyl-N,N-bis(4-methoxybenzyl)azetidine-3-sulfonamide

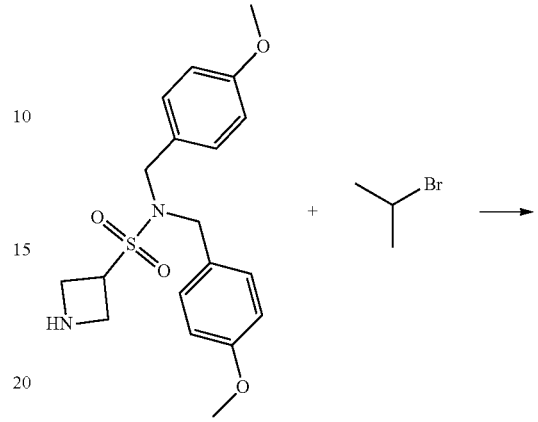

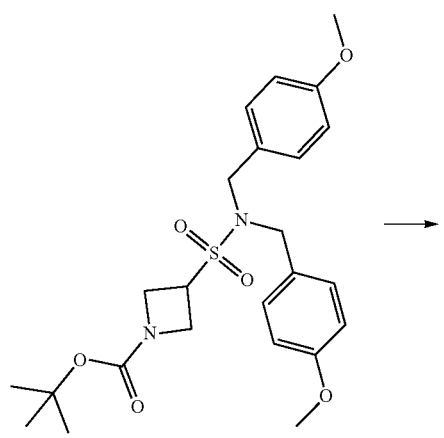

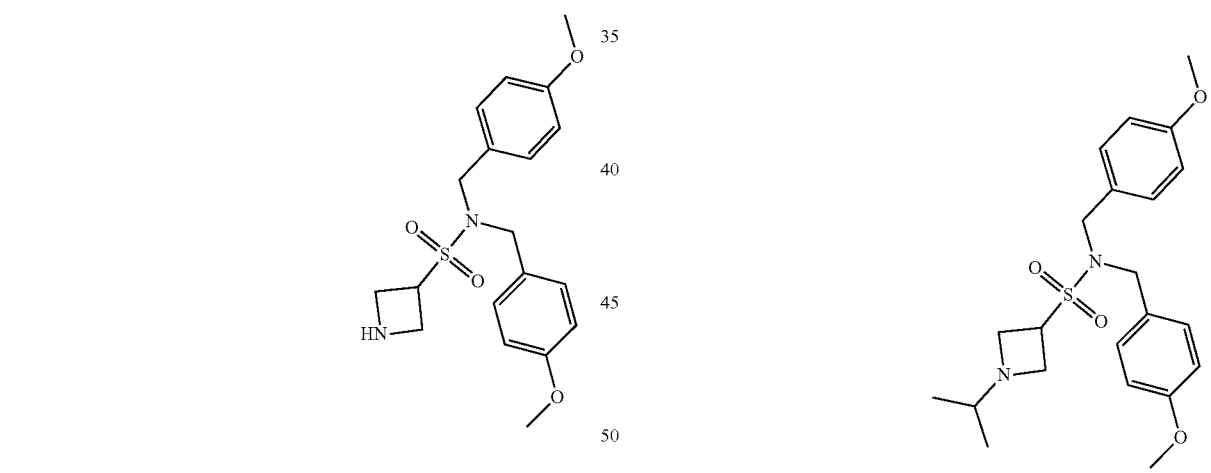

To a solution of tert-butyl 3-(N,N-bis(4-methoxybenzyl)sulfamoyl)azetidine-1-carboxylate (7 g, 14.69 mmol, 1 eq) and 2,6-lutidine (4.72 g, 44.06 mmol, 3 eq) in DCM (80 mL) was added trimethylsilyl trifluoromethanesulfonate (9.79 g, 44.06 mmol, 3 eq) at 0° C. Then the reaction mixture was stirred at 0° C. for 1 hour. The reaction mixture was quenched with a saturated aqueous NH$_4$Cl solution (20 mL) and extracted with DCM (3×50 mL). The combined organic layers were dried over anhydrous Na$_2$SO$_4$, filtered and concentrated in vacuo. The residue was triturated with a mixture of petroleum ether and ethyl acetate (40 mL, 1:1) to give the title compound (4 g, 72%) as a white solid.

$^1$H NMR (CD$_3$OD) δ 7.21 (d, 4H), 6.94-6.85 (m, 4H), 4.35 (s, 4H), 4.28-4.11 (m, 5H) and 3.81 (s, 6H).

LCMS: m/z 377.2 (M+H)$^+$ (ES$^+$).

To a solution of N,N-bis(4-methoxybenzyl)azetidine-3-sulfonamide (2.5 g, 6.64 mmol, 1 eq) and K$_2$CO$_3$ (1.38 g, 9.96 mmol, 1.5 eq) in MeCN (5 mL) was added 2-bromopropane (1.63 g, 13.28 mmol, 2 eq). The mixture was stirred at 70° C. for 12 hours. Then H$_2$O (10 mL) was added and the reaction mixture was extracted with EtOAc (3×30 mL). The combined organic layers were dried over anhydrous Na$_2$SO$_4$, filtered and concentrated in vacuo to give the title compound (2.5 g, 90%).

$^1$H NMR (CDCl$_3$) δ 7.12-7.07 (m, 4H), 6.83-6.76 (m, 4H), 4.16 (s, 4H), 3.74 (s, 6H), 3.68-3.64 (m, 1H), 3.43 (t, 2H), 3.28 (t, 2H), 2.38-2.29 (m, 1H) and 0.82 (d, 6H).

LCMS: m/z 419.2 (M+H)$^+$ (ES$^+$).

Step I: 1-Isopropylazetidine-3-sulfonamide

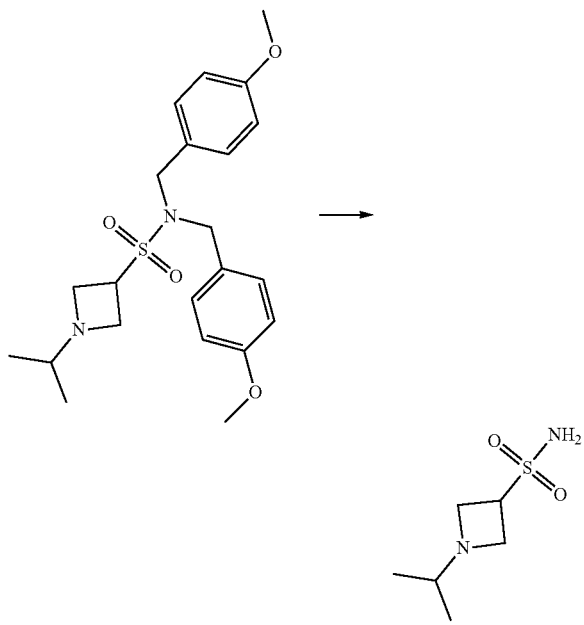

A solution of 1-isopropyl-N,N-bis(4-methoxybenzyl)azetidine-3-sulfonamide (1 g, 2.39 mmol, 1 eq) in TFA (7.70 g, 67.53 mmol, 28.27 eq) was stirred at 25° C. for 12 hours. Then the reaction mixture was concentrated in vacuo. The residue was treated with MeOH (10 mL), filtered and the filtrate was adjusted with $NH_3.H_2O$ (30% of $NH_3.H_2O$ in water) to pH=8-9. The resulting mixture was concentrated in vacuo. The residue was purified by reversed phase flash chromatography (water (0.1% of $NH_3.H_2O$)-MeCN) to give the title compound (220 mg, 52%) as a white solid.

$^1$H NMR (CD$_3$OD) δ 4.05-3.98 (m, 1H), 3.67 (t, 2H), 3.46 (t, 2H), 2.59-2.48 (m, 1H) and 0.97 (d, 6H). Two exchangeable protons not observed.

LCMS: m/z 179.1 (M+H)$^+$ (ES$^+$).

Intermediate P135:
1-Cyclobutylazetidine-3-sulfonamide

Step A: Azetidine-3-sulfonamide

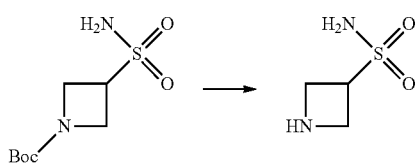 [SMILES: CC(C)(C)OC(=O)N1CC(S(N)(=O)=O)C1 ; NS(=O)(=O)C1CNC1]

To a solution of tert-butyl 3-sulfamoylazetidine-1-carboxylate (3 g, 12.70 mmol, 1 eq, obtained according to Step E of the synthesis of intermediate P134) in DCM (10 mL) was added HCl/EtOAc (12.70 mmol, 20 mL, 1 eq). The mixture was stirred at 25° C. for 1 hour. Then the reaction mixture was concentrated in vacuo. The residue was purified by reversed phase flash chromatography (water (0.05% of $NH_3.H_2O$)-MeCN) to give the title compound (0.8 g, 46%) as a white solid.

$^1$H NMR (DMSO-d$_6$) δ 6.92 (s, 1H), 4.23-4.19 (m, 2H) and 3.77-3.70 (m, 3H). Two exchangeable protons not observed.

LCMS: m/z 137.1 (M+H)$^+$ (ES$^+$).

Step B: 1-Cyclobutylazetidine-3-sulfonamide

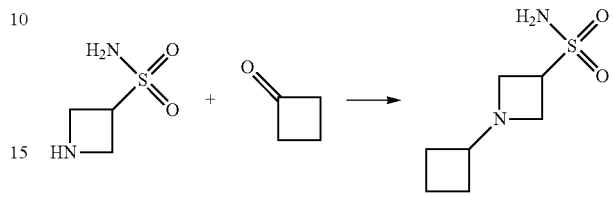

To a solution of azetidine-3-sulfonamide (50 mg, 367.18 µmol, 1 eq) in MeOH (1 mL) was added cyclobutanone (31 mg, 440.62 µmol, 1.2 eq) and NaBH(OAc)$_3$ (97 mg, 458.98 µmol, 1.25 eq). The reaction mixture was stirred at 20° C. for 2 hours. Then the reaction mixture was concentrated in vacuo. The residue was purified by reversed phase flash chromatography (water (0.05% of $NH_3.H_2O$)-MeCN) to give the title compound (12.25 mg, 18%) as a white solid.

$^1$H NMR (DMSO-d$_6$) 6.92 (s, 2H), 3.88-3.85 (m, 1H), 3.41-3.33 (m, 2H), 3.32-3.29 (m, 2H), 3.12-3.09 (m, 1H), 1.89-1.86 (m, 2H) and 1.77-1.60 (m, 4H).

LCMS: m/z 191.1 (M+H)$^+$ (ES$^+$).

Intermediate P136: 1-Ethylazetidine-3-sulfonamide

Step A: 1-Ethyl-N,N-bis(4-methoxybenzyl)azetidine-3-sulfonamide

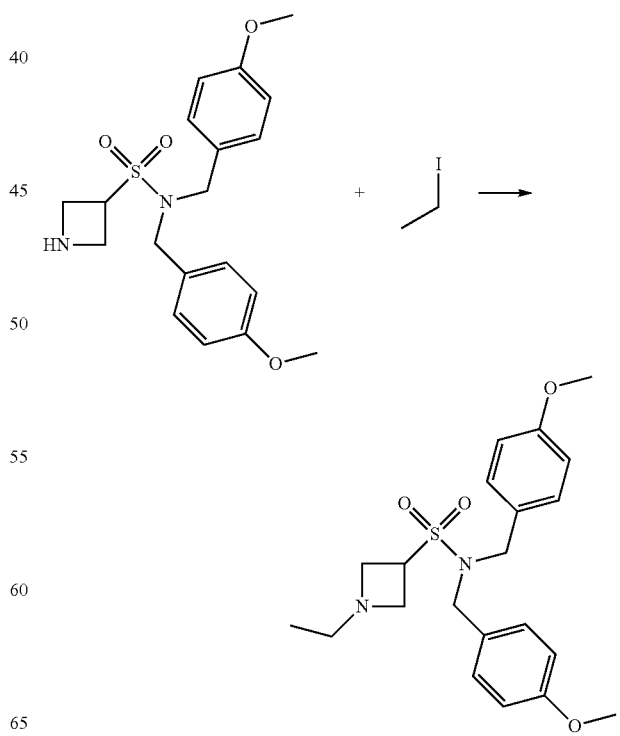

To a solution of N,N-bis(4-methoxybenzyl)azetidine-3-sulfonamide (1 g, 2.66 mmol, 1 eq, obtained according to Step G of the synthesis of intermediate P134) and K₂CO₃ (367 mg, 2.66 mmol, 1 eq) in MeCN (2 mL) was added iodoethane (414 mg, 2.66 mmol, 1 eq). The mixture was stirred at 70° C. for 1 hour. Then the reaction mixture was quenched with water (30 mL) and extracted with EtOAc (3×50 mL). The combined organic layers were dried over anhydrous Na₂SO₄, filtered and concentrated in vacuo. The residue was purified by reversed phase flash chromatography (water (0.1% of NH₃.H₂O)-MeCN) to give the title compound (0.7 g, 22% yield, 100% purity on LCMS) as a white solid.

¹H NMR (CD₃OD) δ 7.20 (d, 4H), 6.90 (d, 4H), 4.28 (S, 4H), 4.00-3.93 (m, 1H), 3.81 (s, 6H), 3.51 (t, 2H), 3.40 (t, 2H), 2.53 (q, 2H) and 0.96 (t, 3H).

LCMS: m/z 405.2 (M+H)⁺ (ES⁺).

Step B: 1-Ethylazetidine-3-sulfonamide

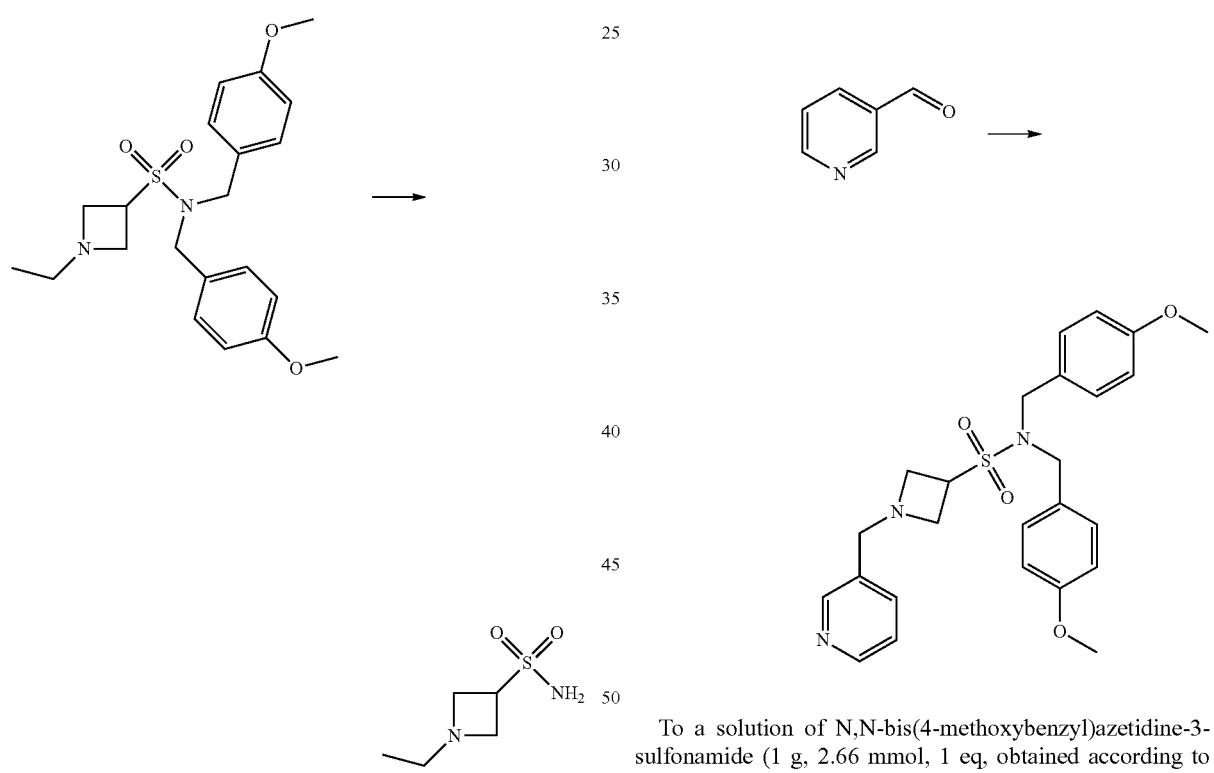

A solution of 1-ethyl-N,N-bis(4-methoxybenzyl)azetidine-3-sulfonamide (800 mg, 1.98 mmol, 1 eq) in TFA (82.13 g, 720.32 mmol, 364 eq) was stirred at 50° C. for 1 hour. Then the reaction mixture was concentrated in vacuo. The residue was purified by reversed phase flash chromatography (water (0.1% of NH₃.H₂O)-MeCN) to give the title compound (160 mg, 47% yield, 95% purity on LCMS) as a white solid.

¹H NMR (DMSO-d₆) δ 6.94 (s, 2H), 3.95-3.86 (m, 1H), 3.47 (t, 2H), 3.31-3.25 (m, 2 H), 2.43 (q, 2H) and 0.86 (t, 3H).

LCMS: m/z 165.1 (M+H)⁺ (ES⁺).

Intermediate P137:
1-(Pyridin-3-ylmethyl)azetidine-3-sulfonamide

Step A: N,N-Bis(4-methoxybenzyl)-1-(pyridin-3-ylmethyl)azetidine-3-sulfonamide

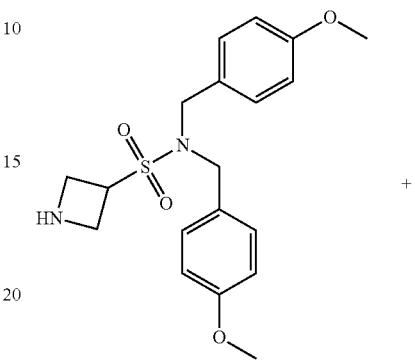

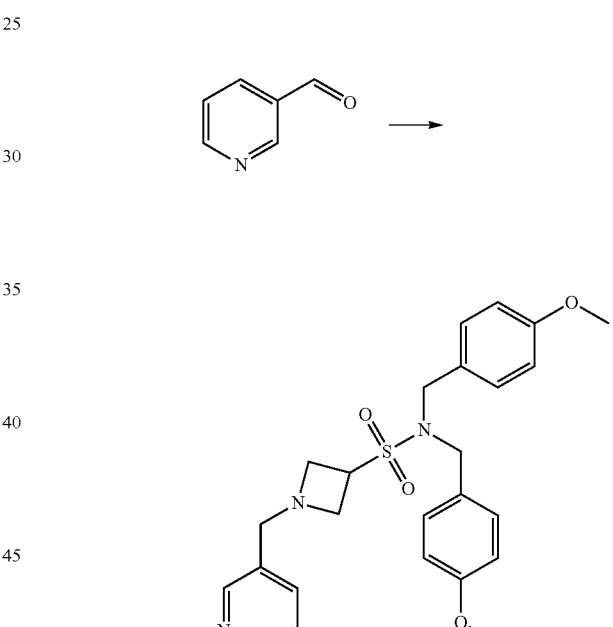

To a solution of N,N-bis(4-methoxybenzyl)azetidine-3-sulfonamide (1 g, 2.66 mmol, 1 eq, obtained according to Step G of the synthesis of intermediate P134) in MeCN (20 mL) was added nicotinaldehyde (341 mg, 3.19 mmol, 1.2 eq) and NaBH(OAc)₃ (1.13 g, 5.31 mmol, 2 eq). The mixture was stirred at 15° C. for 1 hour. Then the reaction mixture was quenched with water (80 mL) and extracted with EtOAc (6×100 mL). The combined organic layers were dried over Na₂SO₄, filtered and concentrated in vacuo. The residue was purified by silica gel column chromatography (SiO₂, petroleum ether:ethyl acetate, 1:1 to 0:1) to give the title compound (1.1 g, 89%) as a yellow oil.

¹H NMR (DMSO-d₆) δ 8.53 (s, 1H), 8.46 (s, 1H), 7.72 (d, 1H), 7.37-7.33 (m, 1H), 7.13 (d, 4H), 6.88 (d, 4H), 4.21-4.17 (m, 5H), 3.73 (s, 6H), 3.61 (s, 2H), 3.47-3.41 (m, 2H) and 3.33-3.31 (m, 2H).

Step B: 1-(Pyridin-3-ylmethyl)azetidine-3-sulfonamide

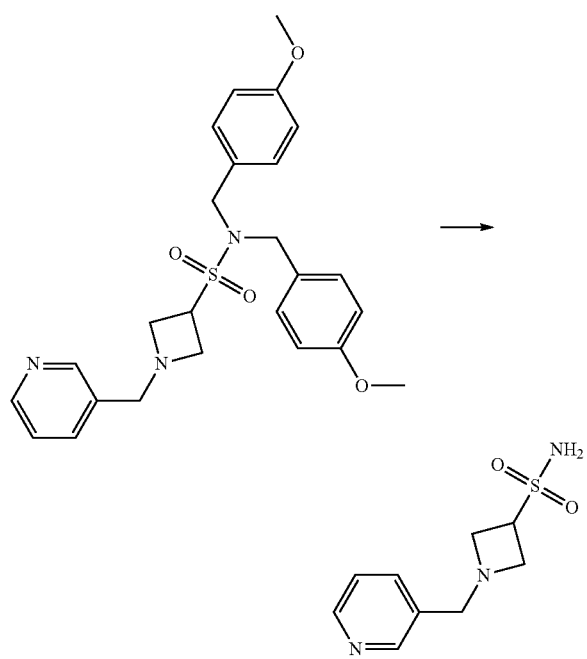

A solution of N,N-bis(4-methoxybenzyl)-1-(pyridin-3-yl-methyl)azetidine-3-sulfonamide (1 g, 2.14 mmol, 1 eq) in TFA (10 mL) was stirred at 10° C. for 36 hours. Then the reaction mixture was concentrated in vacuo. The residue was treated with MeOH (80 mL) and the mixture was stirred for another 1 hour. Then the mixture was filtered and the filtrate was concentrated in vacuo. The residue was purified by reversed phase flash chromatography (water (0.1% of $NH_3 \cdot H_2O$)-MeCN) to give the title compound (240 mg, 49%) as a white solid.

$^1$H NMR (DMSO-$d_6$) δ 8.52-8.45 (m, 2H), 7.67 (d, 1H), 7.35 (dd, 1H), 6.98 (s, 2H), 3.99-3.94 (m, 1H), 3.64 (s, 2H), 3.54-3.49 (m, 2H) and 3.44-3.35 (m, 2H).

LCMS: m/z 228.1 (M+H)$^+$ (ES$^+$).

Intermediate P138: 1-Isopropylpiperidine-4-sulfonamide

Step A: Benzyl 4-hydroxypiperidine-1-carboxylate

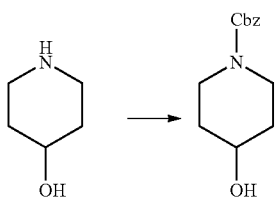 [SMILES: OC1CCNCC1 ; O=C(OCc1ccccc1)N1CCC(O)CC1]

To a solution of piperidin-4-ol (100 g, 988.66 mmol, 1 eq) in DCM (1 L) was added TEA (100.04 g, 988.66 mmol, 1 eq) and benzyl chloroformate (168.66 g, 988.66 mmol, 1 eq) at 0° C. The mixture was warmed to 25° C. and stirred for 12 hours. Then the reaction mixture was diluted with DCM (500 mL), washed with brine (3×500 mL), dried over $Na_2SO_4$, filtered and concentrated under reduced pressure to give the title compound (220 g, 95%) as a yellow oil, which was used in the next step without further purification.

$^1$H NMR (CDCl$_3$) δ 7.36-7.29 (m, 5H), 5.10 (s, 2H), 3.90-3.81 (m, 3H), 3.15-3.08 (m, 2H), 1.83-1.81 (m, 2H) and 1.47-1.45 (m, 2H). One exchangeable proton not observed.

LCMS: m/z 258.1 (M+Na)$^+$ (ES$^+$).

Step B: Benzyl 4-((methylsulfonyl)oxy)piperidine-1-carboxylate

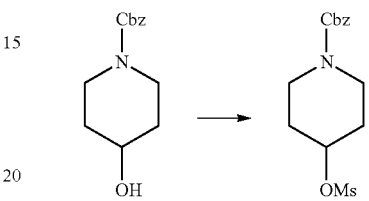

To a solution of benzyl 4-hydroxypiperidine-1-carboxylate (220 g, 935.06 mmol, 1 eq) in DCM (1.7 L) was added TEA (189.24 g, 1.87 mol, 2 eq). Then mesyl chloride (128.54 g, 1.12 mol, 1.2 eq) was added dropwise at 0° C. The solution was heated to 25° C. and stirred for 1 hour. Then the reaction mixture was quenched with saturated aqueous NaHCO$_3$ solution (1.2 L) and the two layers were separated. The organic layer was washed with saturated aqueous NaHCO$_3$ solution (1.2 L) and brine (2×1 L), dried over anhydrous Na$_2$SO$_4$, filtered and concentrated in vacuo to give the title compound (293 g, 100%), which was used directly in the next step.

Step C: Benzyl 4-(acetylthio)piperidine-1-carboxylate

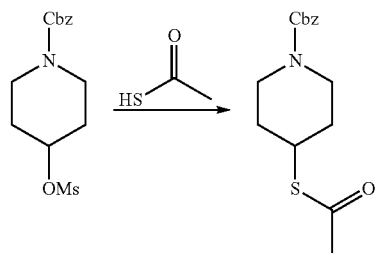

To a solution of benzyl 4-((methylsulfonyl)oxy)piperidine-1-carboxylate (290 g, 925.43 mmol, 1 eq) in DMF (1.4 L) was added Cs$_2$CO$_3$ (331.67 g, 1.02 mol, 1.1 eq) and ethanethioic S-acid (77.49 g, 1.02 mol, 1.1 eq). The mixture was stirred at 80° C. for 12 hours. Some solid was precipitated. The reaction mixture was filtered. The filtrate was concentrated in vacuo to remove most of the DMF. The residue was diluted with EtOAc (1.5 L), washed with H$_2$O (3×1 L) and brine (2×1 L), dried over anhydrous Na$_2$SO$_4$, filtered and concentrated in vacuo. The residue was purified by silica gel column chromatography (SiO$_2$, petroleum ether:ethyl acetate, 50:1 to 40:1) to give the title compound (146 g, crude) as a yellow oil.

$^1$H NMR (CDCl$_3$) δ 7.37-7.35 (m, 5H), 5.13 (s, 2H), 4.07-3.93 (m, 2H), 3.66-3.61 (m, 1H), 3.19-3.12 (m, 2H), 2.33 (s, 3H), 1.94-1.91 (m, 2H) and 1.59-1.56 (m, 2H).

LCMS: m/z 294.1 (M+H)$^+$ (ES$^+$).

Step D: Benzyl 4-(chlorosulfonyl)piperidine-1-carboxylate

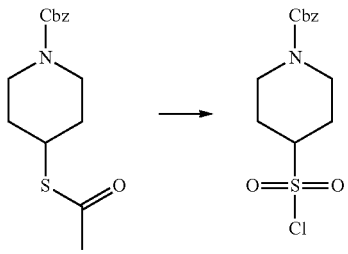 [SMILES: CC(=O)SC1CCN(C(=O)OCc2ccccc2)CC1 ; O=C(OCc1ccccc1)N1CCC(S(=O)(=O)Cl)CC1]

To a solution of benzyl 4-(acetylthio)piperidine-1-carboxylate (30.00 g, 102.26 mmol, 1 eq) in AcOH (1 L) and H$_2$O (100 mL) was added NCS (40.96 g, 306.77 mmol, 3 eq). The reaction mixture was stirred at 25° C. for 40 minutes. Then the reaction mixture was poured into water (1 L) and extracted with DCM (1 L). The organic layer was washed with water (3×1 L) and brine (1 L), dried over Na$_2$SO$_4$, and filtered to give the title compound in DCM (1 L) solution (theoretical amount: 32.4 g, crude), which was used in the next step without further purification.

Step E: Benzyl 4-sulfamoylpiperidine-1-carboxylate

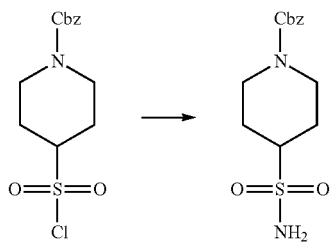 [SMILES: O=C(OCc1ccccc1)N1CCC(S(=O)(=O)Cl)CC1 ; NS(=O)(=O)C1CCN(C(=O)OCc2ccccc2)CC1]

NH$_3$ was bubbled into a solution of benzyl 4-(chlorosulfonyl)piperidine-1-carboxylate (theoretical amount: 30 g, crude) in DCM (1 L) at 0° C. for 20 minutes. Then the reaction mixture was stirred at 25° C. for 40 minutes. The reaction mixture was filtered and the filtrate was concentrated in vacuo. The residue was triturated with a mixture of EtOAc (50 mL) and petroleum ether (40 mL) to give the title compound (21 g, 75%) as a yellow solid.

$^1$H NMR (DMSO-d$_6$) δ 7.38-7.32 (m, 5H), 6.79 (br s, 2H), 5.10 (s, 2H), 4.12-4.01 (m, 2H), 3.09-3.02 (m, 1H), 3.01-2.75 (m, 2H), 2.02-1.96 (m, 2H) and 1.51-1.41 (m, 2H).

Step F: Piperidine-4-sulfonamide

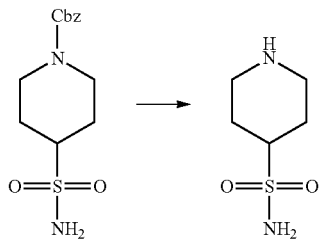

To a solution of benzyl 4-sulfamoylpiperidine-1-carboxylate (21 g, 70.39 mmol, 1 eq) in MeOH (200 mL) was added Pd/C (10 wt % loading on activated carbon, 4 g) under nitrogen. The suspension was degassed in vacuo and purged with hydrogen several times. The mixture was stirred under hydrogen (50 psi) at 25° C. for 30 hours. Then the reaction mixture was filtered and the filtrate was concentrated in vacuo. The residue was triturated with EtOAc (200 mL) to give the title compound (11.2 g, 97% yield, 100% purity on LCMS) as a white solid.

$^1$H NMR (DMSO-d$_6$+D$_2$O) δ 3.06-2.90 (m, 2H), 2.89-2.86 (m, 1H), 2.50-2.46 (m, 2H), 1.95-1.91 (m, 2H) and 1.53-1.46 (m, 2H). Three exchangeable protons not observed.

LCMS: m/z 165.1 (M+H)$^+$ (ES$^+$).

Step G: 1-Isopropylpiperidine-4-sulfonamide

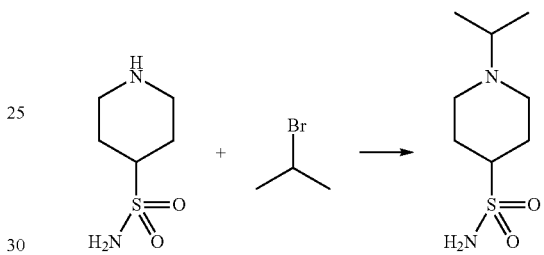

To a solution of piperidine-4-sulfonamide (1.2 g, 7.31 mmol, 1 eq) in acetonitrile (20 mL) was added 2-bromopropane (3.59 g, 29.23 mmol, 4 eq) and NaHCO$_3$ (1.84 g, 21.92 mmol, 3 eq). Then the reaction mixture was stirred at 70° C. for 18 hours. The hot mixture was filtered and the filtrate was concentrated in vacuo to give the title compound (1.05 g, 69% yield, 98.5% purity on LCMS) as a white solid.

$^1$H NMR (DMSO-d$_6$) δ 6.61 (s, 2H), 2.81-2.77 (m, 2H), 2.66-2.61 (m, 2H), 2.05-1.99 (m, 2H), 1.91-1.87 (m, 2H), 1.50-1.45 (m, 2H) and 0.89 (dd, 6H).

LCMS: m/z 207.1 (M+H)$^+$ (ES$^+$).

Intermediate P139: (4-(Dimethylamino)pyridin-1-ium-1-carbonyl)((1-isopropyl-2-oxo-1,2-dihydropyrimidin-5-yl)sulfonyl)amide

Step A: 5-Bromo-1-isopropylpyrimidin-2(1H)-one

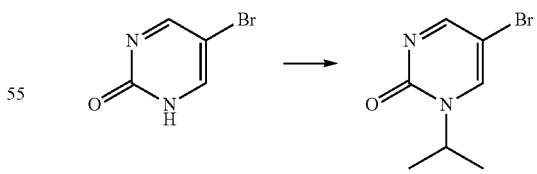

A suspension of 5-bromopyrimidin-2(1H)-one (10.07 g, 57.5 mmol) and K$_2$CO$_3$ (8.35 g, 60.4 mmol) in DMF (200 mL) was treated with 2-iodopropane (6.4 ml, 62.7 mmol) under nitrogen. The resultant suspension was stirred at room temperature for 40 hours, concentrated in vacuo and the residue was partitioned between EtOAc (100 mL) and water (50 mL). The organic layer was collected and the aqueous layer was extracted with EtOAc (3×50 mL). The combined organic extracts were washed with 20% v/v brine (3×50 mL), brine (50 mL), dried (MgSO₄) and concentrated in vacuo to afford crude product as a yellow oil (4.71 g). The crude product was purified by chromatography on silica gel (dry load) (40 g cartridge, 0-5% MeOH/DCM) to afford the title compound (1.34 g, 10%) as a clear yellow oil that solidified on standing.

¹H NMR (CDCl₃) δ 8.52 (dd, J=3.3, 1.6 Hz, 1H), 7.76 (d, J=3.2 Hz, 1H), 4.99 (pd, J=6.8, 1.6 Hz, 1H), 1.40 (dd, J=6.8, 1.0 Hz, 6H).

LCMS: m/z 217.0 (MBr⁷⁹+H)⁺ (ES⁺).

Step B: 5-(Benzylthio)-1-isopropylpyrimidin-2(1H)-one

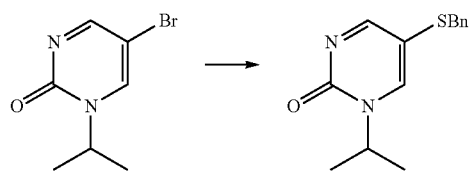

A solution of 5-bromo-1-isopropylpyrimidin-2(1H)-one (1.217 g, 5.05 mmol), DIPEA (1.8 ml, 10.31 mmol) and benzyl mercaptan (0.6 ml, 5.07 mmol) in dioxane (25 mL) was sparged with nitrogen for 15 minutes before Pd₂(dba)₃ (0.233 g, 0.254 mmol) and Xantphos (0.294 g, 0.508 mmol) were added. The reaction mixture was heated at 100° C. for 22 hours and then concentrated in vacuo. The residue was partitioned between EtOAc (30 mL) and saturated aqueous NaHCO₃ (20 mL). The aqueous layer was extracted with EtOAc (3×30 mL) and the combined organic extracts were washed with brine (30 mL), dried (MgSO₄) and concentrated in vacuo to afford crude product as a brown oil (2.3 g). The crude product was purified by chromatography on silica gel (dry load) (40 g cartridge, 0-5% MeOH/DCM) to afford the title compound (1.49 g, 99%) as a brown oil.

¹H NMR (CDCl₃) δ 8.46 (d, J=3.1 Hz, 1H), 7.30-7.22 (m, 3H), 7.15 (d, J=3.2 Hz, 1H), 7.09-7.06 (m, 2H), 4.84 (sept, J=6.8 Hz, 1H), 3.80 (s, 2H), 1.13 (d, J=6.8 Hz, 6H).

LCMS; m/z 261.1 (M+H)⁺ (ES⁺).

Step C: 1-Isopropyl-N,N-bis(4-methoxybenzyl)-2-oxo-1,2-dihydropyrimidine-5-sulfonamide

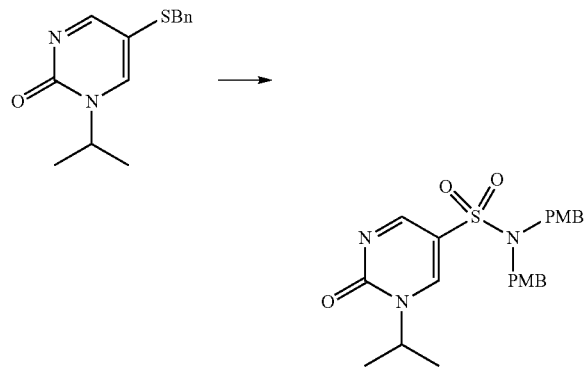

A suspension of 5-(benzylthio)-1-isopropylpyrimidin-2(1H)-one (1.012 g, 3.69 mmol) in DCM (15 mL) and water (1.5 mL) at 0° C. was treated with SO₂Cl₂ (2 ml, 23.86 mmol) dropwise. The resultant yellow suspension was stirred at 0° C. for 1 hour. A slurry of ice/water (20 mL) was added and the organic phase was collected and retained. The aqueous layer was extracted with DCM (2×10 mL) and the combined organic extracts were dried (MgSO₄) and concentrated in vacuo to afford crude sulfonyl chloride intermediate as a pale yellow liquid (1.024 g) which was used without further purification. A solution of bis(4-methoxybenzyl) amine (1.007 g, 3.91 mmol) and Et₃N (0.6 ml, 4.30 mmol) in DCM (20 mL) at 0° C. was treated with a solution of the crude sulfonyl chloride intermediate in DCM (10 mL). The resultant solution was allowed to warm to room temperature, stirred for 1 hour and then diluted with DCM (20 mL) and saturated aqueous NH₄Cl (20 mL). The organic layer was collected and washed with saturated aqueous NH₄Cl (20 mL) and water (20 mL), dried (MgSO₄) and concentrated in vacuo to afford crude product as an orange oil (2.0 g). The crude product was triturated with TBME (30 mL), filtered, rinsing with TBME, and dried in vacuo to afford crude product which was purified by chromatography on silica gel (24 g cartridge, 0-5% MeOH/DCM) to afford the title compound (0.941 g, 44%) as a sticky orange oil.

¹H NMR (CDCl₃) δ 8.65 (d, J=3.3 Hz, 1H), 7.96 (d, J=3.3 Hz, 1H), 7.15-7.10 (m, 4H), 6.85-6.82 (m, 4H), 4.88 (sept, J=6.8 Hz, 1H), 4.32 (s, 4H), 3.79 (s, 6H), 1.34 (d, J=6.8 Hz, 6H).

LCMS: m/z 458.1 (M+H)⁺ (ES⁺).

Step D: 1-Isopropyl-2-oxo-1,2-dihydropyrimidine-5-sulfonamide

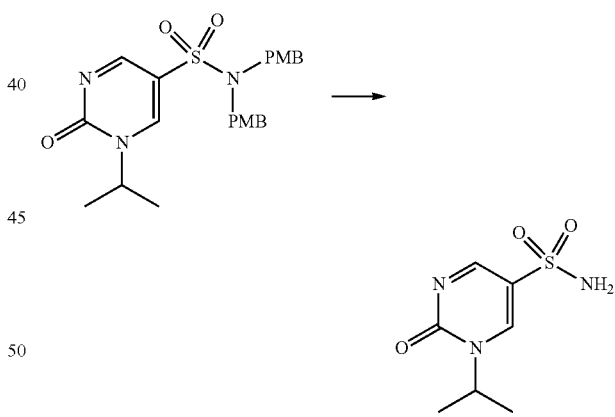

1-Isopropyl-N,N-bis(4-methoxybenzyl)-2-oxo-1,2-dihydropyrimidine-5-sulfonamide (0.941 g, 1.625 mmol) was treated with TFA (15 ml, 195 mmol) and the resultant solution was stirred at room temperature for 64 hours. Then the reaction mixture was concentrated in vacuo and the crude product was purified by chromatography on silica gel (dry load) (12 g cartridge, 0-10% MeOH/DCM) to afford the title compound (0.350 g, 94%) as a tan solid.

¹H NMR (DMSO-d6) δ 8.81 (d, J=3.2 Hz, 1H), 8.51 (d, J=3.3 Hz, 1H), 7.45 (s, 2H), 4.77 (sept, J=6.8 Hz, 1H), 1.37 (d, J=6.8 Hz, 6H).

LCMS; m/z 218.1 (M+H)⁺ (ES⁺); 215.8 (M−H)⁻ (ES⁻).

Step E: (4-(Dimethylamino)pyridin-1-ium-1-carbonyl)((1-isopropyl-2-oxo-1,2-dihydropyrimidin-5-yl)sulfonyl)amide

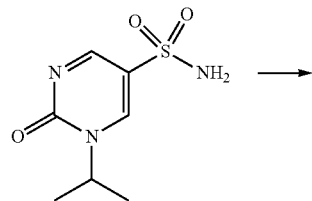

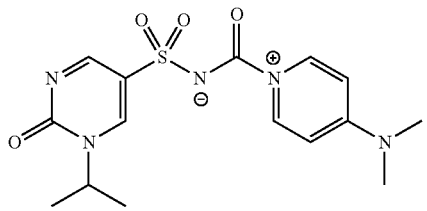

A suspension of 1-isopropyl-2-oxo-1,2-dihydropyrimidine-5-sulfonamide (0.150 g, 0.690 mmol) and DMAP (0.169 g, 1.383 mmol) in dry MeCN (2 mL) was stirred at room temperature for to minutes before diphenyl carbonate (0.163 g, 0.761 mmol) was added in one portion. The reaction was stirred for 18 hours, diluted with TBME (20 mL) and DCM (2 mL), and the precipitate was collected by filtration and used crude in the next step.

Intermediate P140: 1-Isopropyl-2-oxo-1,2-dihydropyridine-4-sulfonamide

Step A: Lithium 2-chloropyridine-4-sulfinate

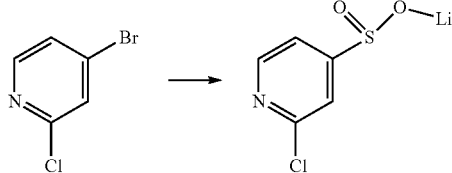

A solution of 4-bromo-2-chloropyridine (5.8 ml, 52.3 mmol) in dry THF (100 mL) at −78° C. was treated with 2.5 M BuLi (in hexanes) (22 ml, 55.0 mmol) dropwise under nitrogen. The resultant solution was stirred at −78° C. for to minutes and then SO$_2$ gas was bubbled through the solution for 20 minutes. The reaction was allowed to warm to room temperature and then concentrated in vacuo. The residue was triturated with TBME (100 mL). The resultant solid was filtered, rinsing with TBME, and dried in vacuo to afford the title compound (8.80 g, 92%) as a dark purple solid that was used crude in the next step.

Step B: 2-Chloro-N,N-bis(4-methoxybenzyl)pyridine-4-sulfonamide

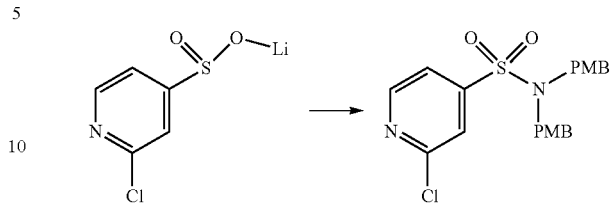

A suspension of lithium 2-chloropyridine-4-sulfinate (6.55 g, 35.7 mmol) in DCM (100 mL) at 0° C. was treated with NCS (4.862 g, 35.7 mmol) in one portion. The resultant suspension was stirred at 0° C. for 2 hours, quenched with water (50 mL) and the organic layer was collected. The aqueous layer was extracted with DCM (2×50 mL) and the combined organic extracts were washed with water (50 mL), dried (MgSO$_4$) and concentrated in vacuo to afford the crude sulfonyl chloride intermediate. A solution of the sulfonyl chloride intermediate in DCM (10 mL) was added dropwise to a suspension of bis(4-methoxybenzyl)amine (9.42 g, 36.6 mmol) and triethylamine (15.92 ml, 114 mmol) in DCM (100 mL) at 0° C. The reaction mixture was allowed to warm to room temperature, stirred for 16 hours and then water (100 mL) was added. The organic layer was collected and the aqueous layer was extracted with DCM (2×50 mL). The combined organic extracts were washed with water (100 mL), 1 M HCl (aq) (2×100 mL), water (100 mL), dried (MgSO$_4$) and concentrated in vacuo to afford crude product which was purified by chromatography on silica gel (dry load) (80 g cartridge, 0-50% EtOAc/isohexane) to afford the title compound (0.677 g, 4%) as an orange solid.
$^1$H NMR (CDCl$_3$) 8.51 (dd, J=4.8, 1.9 Hz, 1H), 8.30 (dd, J=7.8, 1.9 Hz, 1H), 7.30 (dd, J=7.8, 4.8 Hz, 1H), 7.04-6.99 (m, 4H), 6.81-6.75 (m, 4H), 4.38 (s, 4H), 3.78 (s, 6H).
LCMS: m/z 433 (MCl$^{35}$+H)$^+$ (ES$^+$).

Step C: N,N-Bis(4-methoxybenzyl)-2-oxo-1,2-dihydropyridine-4-sulfonamide

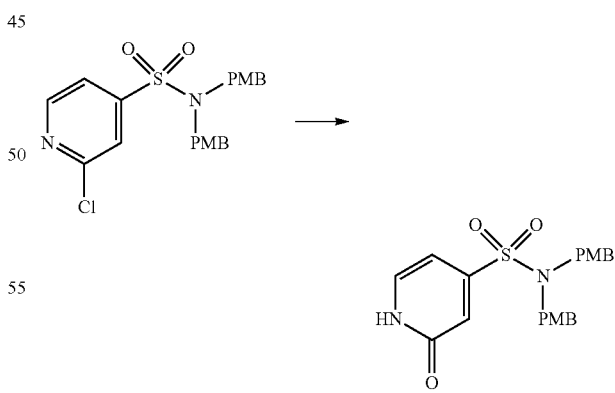

A suspension of 2-chloro-N,N-bis(4-methoxybenzyl)pyridine-4-sulfonamide (0.365 g, 0.759 mmol) in ethane-1,2-diol (5 ml, 0.759 mmol) was treated with 2 M KOH (aq) (1.9 ml, 3.80 mmol). The resultant suspension was stirred at 140° C. for 72 hours, allowed to cool to room temperature and then diluted with saturated aqueous NH$_4$Cl (30 mL) and EtOAc (20 mL). The organic layer was collected and the aqueous layer was extracted with EtOAc (2×20 mL). The combined organic extracts were dried (MgSO₄) and concentrated in vacuo to afford crude product as a yellow solid (510 mg). The crude product was purified by chromatography on silica gel (dry load) (12 g cartridge, 0-100% EtOAc/isohexane) to afford the title compound (0.437 g, 68%) as a pale yellow solid.

LCMS: m/z 437.3 (M+Na)⁺ (ES⁺); 413.1 (M−H)⁻ (ES⁻).

Step D: 1-Isopropyl-N,N-bis(4-methoxybenzyl)-2-oxo-1,2-dihydropyridine-4-sulfonamide

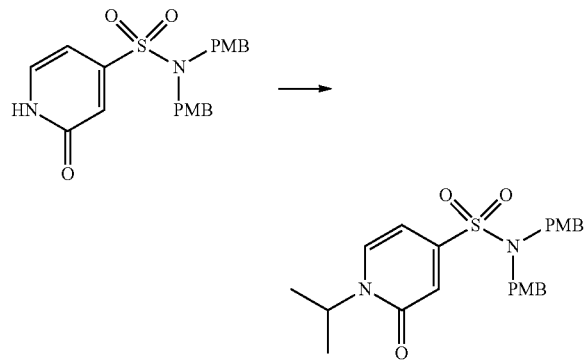

A suspension of N,N-bis(4-methoxybenzyl)-2-oxo-1,2-dihydropyridine-4-sulfonamide (0.437 g, 0.949 mmol) and lithium bromide (0.171 g, 1.930 mmol) in DME:DMF (7.5 mL, 4:1) at 0° C. was treated with NaH in one portion. The resultant suspension was stirred at 0° C. for 15 minutes, treated with 2-iodopropane (0.194 ml, 1.898 mmol) and heated to 65° C. for 65 hours. Further lithium bromide (0.171 g, 1.930 mmol) followed by NaH (0.053 g, 1.328 mmol) were added and the reaction mixture was stirred at 65° C. for 10 minutes. Then further 2-iodopropane (0.194 ml, 1.898 mmol) was added and the reaction mixture was stirred at 65° C. for 18 hours. EtOAc (10 mL) and saturated aqueous NH₄Cl (5 mL) were added and the organic layer was collected. The aqueous layer was extracted with EtOAc (2×10 mL) and the combined organic extracts were washed with 20% v/v brine (3×10 mL) and brine (10 mL), dried (MgSO₄) and concentrated in vacuo to afford crude product as a yellow oil. The crude product was purified by chromatography on silica gel (dry load) (12 g cartridge, 0-100% EtOAc/isohexane) to afford the title compound (0.385 g, 77%) as a pale yellow oil.

¹H NMR (DMSO-d6) δ 8.06 (dd, J=6.8, 2.1 Hz, 1H), 7.99 (dd, J=7.2, 2.0 Hz, 1H), 7.07-7.03 (m, 4H), 6.82-6.78 (m, 4H), 6.39 (t, J=7.0 Hz, 1H), 4.99 (sept, J=6.8 Hz, 1H), 4.34 (s, 4H), 3.71 (s, 6H), 1.28 (d, J=6.8 Hz, 6H).

LCMS; m/z 479.3 (M+Na)⁺ (ES⁺).

Step E: 1-Isopropyl-2-oxo-1,2-dihydropyridine-4-sulfonamide

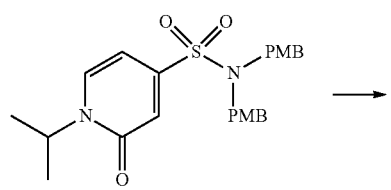

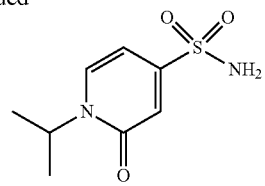

1-Isopropyl-N,N-bis(4-methoxybenzyl)-2-oxo-1,2-dihydropyridine-4-sulfonamide (0.375 g, 0.715 mmol) was treated with TFA (2 ml, 26.0 mmol) and the resultant red solution was stirred at room temperature for 17 hours. The reaction mixture was concentrated in vacuo, azeotroped with DCM (2×5 mL) and the crude product was purified by chromatography on silica gel (dry load) (4 g cartridge, 0-10% MeOH/DCM) to afford the title compound (0.160 g, 100%) as a white solid.

¹H NMR (CDCl₃) δ 8.09 (dd, J=7.1, 2.1 Hz, 1H), 7.61 (dd, J=6.9, 2.1 Hz, 1H), 6.42 (t, J=7.0 Hz, 1H), 5.38 (br s, 2H), 5.32 (sept, J=7.0 Hz, 1H), 1.41 (d, J=6.8 Hz, 6H).

LCMS: m/z 217.3 (M+H)⁺ (ES⁺); 215.1 (M−H)⁻ (ES⁻).

Intermediate P141: 1-Isopropyl-2-oxo-1,2-dihydropyridine-3-sulfonamide

Step A: 2-Chloro-N,N-bis(4-methoxybenzyl)pyridine-3-sulfonamide

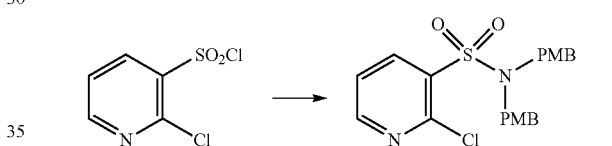

Bis(4-methoxybenzyl)amine (3.78 g, 14.41 mmol) and triethylamine (2.49 ml, 17.8 mmol) in anhydrous DCM (15 mL) were added to a solution of 2-chloropyridine-3-sulfonyl chloride (3.00 g, 13.72 mmol) in anhydrous DCM (35 mL) at 0° C. The mixture was stirred at 0° C. for 0.5 hour, then warmed to room temperature. After 19 hours the reaction mixture was diluted with a further portion of DCM (150 mL), washed with saturated aqueous NH₄Cl (2×50 mL), water (50 mL), and brine (50 mL), dried over MgSO₄, filtered, and concentrated in vacuo to give crude product as a pale orange solid. The crude product was triturated with TBME (50 mL), filtered, rinsing with TBME (2×40 mL), to afford the title compound (5.10 g, 80%) as a cream coloured solid.

¹H NMR (DMSO-d6) δ 8.61 (dd, J=4.8, 1.8 Hz, 1H), 8.27 (dd, J=7.8, 1.8 Hz, 1H), 7.55 (dd, J=7.8, 4.8 Hz, 1H), 7.05-6.98 (m, 4H), 6.86-6.78 (m, 4H), 4.37 (s, 4H), 3.72 (s, 6H).

LCMS: m/z 433.3 (M+H)⁺ (ES⁺).

Step B: 2-Hydroxy-N,N-bis(4-methoxybenzyl)pyridine-3-sulfonamide

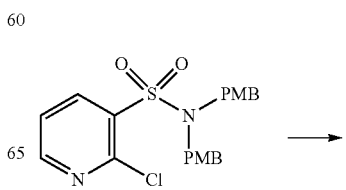

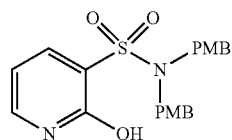

2 M KOH (aq) (2.15 ml, 4.30 mmol) was added to a suspension of 2-chloro-N,N-bis(4-methoxybenzyl)pyridine-3-sulfonamide (0.50 g, 1.074 mmol) in ethane-1,2-diol (10 mL). The reaction mixture was stirred at 140° C. for 66 hours, cooled to room temperature and neutralised with saturated aqueous NH$_4$Cl (10 mL). The mixture was then extracted with DCM (5×40 mL) and the combined organics were washed with brine (20 mL), dried over MgSO$_4$, filtered and concentrated in vacuo to give a cream solid, which was triturated with TBME (15 mL) to afford the title compound (0.38 g, 84%) as a pale cream solid.

$^1$H NMR (DMSO-d6) δ 12.29 (br s, 1H), 8.03 (dd, J=7.2, 2.2, 1H), 7.70 (dd, J=6.3, 2.2, 1H), 7.07-7.02 (m, 4H), 6.82-6.77 (m, 4H), 6.29 (dd, J=7.2, 6.3, 1H), 4.32 (s, 4H), 3.71 (s, 6H).

LCMS: m/z 437.4 (M+Na)$^+$ (ES$^+$).

Step C: 1-Isopropyl-N,N-bis(4-methoxybenzyl)-2-oxo-1,2-dihydropyridine-3-sulfonamide

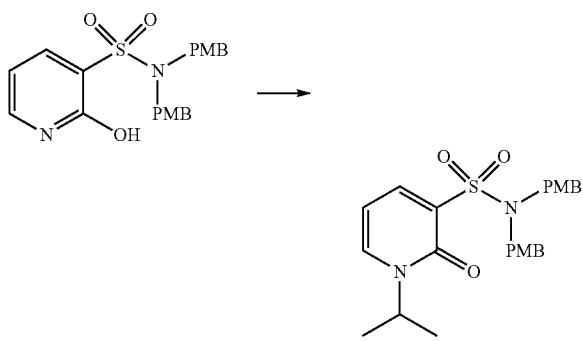

Sodium hydride (60% dispersion in mineral oil) (0.026 g, 0.645 mmol) was added at 0° C. to a mixture of 2-hydroxy-N,N-bis(4-methoxybenzyl)pyridine-3-sulfonamide (0.26 g, 0.615 mmol) and lithium bromide (0.109 g, 1.230 mmol) in a mixture of anhydrous DME/anhydrous DMF (3 mL, 4:1). The reaction mixture was stirred at room temperature for 15 minutes before 2-iodopropane (0.07 ml, 0.74 mmol) was added and the reaction mixture was stirred at 60° C. for 27 hours. The reaction was quenched with saturated aqueous NH$_4$Cl (5 mL) and diluted with EtOAc (100 mL). The organic layer was washed with water (15 mL) and brine (3×15 mL), dried over MgSO$_4$, filtered, and concentrated in vacuo to give crude product as a yellow oil. The crude product was purified by chromatography on silica gel (24 g cartridge, 0-100% EtOAc/isohexane) to afford the title compound (0.25 g, 88%) as a colourless oil.

$^1$H NMR (CDCl$_3$) δ 8.06 (dd, J=7.2, 2.1 Hz, 1H), 7.50 (dd, J=6.8, 2.1 Hz, 1H), 7.11-7.06 (m, 4H), 6.77-6.72 (m, 4H), 6.26 (t, J=7.0 Hz, 1H), 5.21 (sept, J=6.8 Hz, 1H), 4.47 (s, 4H), 3.76 (s, 6H), 1.34 (d, J=6.8 Hz, 6H).

LCMS: m/z 479.4 (M+Na)$^+$ (ES$^+$).

Step D: 1-Isopropyl-2-oxo-1,2-dihydropyridine-3-sulfonamide

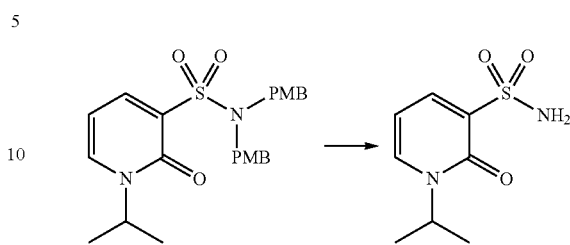

TFA (0.43 ml, 5.64 mmol) was added to a solution of 1-isopropyl-N,N-bis(4-methoxybenzyl)-2-oxo-1,2-dihydropyridine-3-sulfonamide (0.27 g, 0.591 mmol) in anhydrous DCM (3 mL) at room temperature. The reaction mixture was stirred for 66 hours, concentrated in vacuo, then redissolved in DCM (5 mL), pre-adsorbed onto silica and purified by chromatography on silica gel (12 g cartridge, 0-10% MeOH/DCM) to afford the title compound (0.11 g, 82%) as a pale brown solid.

LCMS: m/z 217.1 (M+H)$^+$ (ES$^+$).

Intermediate P142: (R)-1-(2-Hydroxypropyl)-6-oxo-1,6-dihydropyridine-3-sulfonamide Step A: 6-Chloro-N,N-bis(4-methoxybenzyl)pyridine-3-sulfonamide

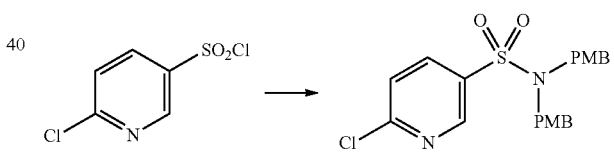

Bis(4-methoxybenzyl)amine (3.71 g, 14.41 mmol) was added to a solution of 2-chloropyridine-5-sulfonyl chloride (3.00 g, 13.72 mmol) and triethylamine (2.49 ml, 17.8 mmol) in anhydrous DCM (50 mL) at 0° C. The reaction mixture was stirred at 0° C. for 15 minutes, then at room temperature for 20 hours. The reaction mixture was diluted with a further portion of DCM (150 mL), washed with saturated aqueous NH$_4$Cl (3×40 mL) and brine (40 mL), dried over MgSO$_4$, filtered, and concentrated in vacuo to give crude product as a cream solid. Trituration with TBME (70 mL) and collection of the solid by filtration followed by rinsing with TBME (2×40 mL) gave the title compound (4.97 g, 83%) as an off-white solid.

$^1$H NMR (DMSO-d6) δ 8.76 (dd, J=2.6, 0.7 Hz, 1H), 8.19 (dd, J=8.4, 2.6 Hz, 1H), 7.69 (dd, J=8.4, 0.7 Hz, 1H), 7.08-7.02 (m, 4H), 6.83-6.76 (m, 4H), 4.29 (s, 4H), 3.71 (s, 6H).

LCMS: m/z 433.3 (M+H)$^+$ (ES$^+$).

Step B: N,N-Bis(4-methoxybenzyl)-6-oxo-1,6-dihydropyridine-3-sulfonamide

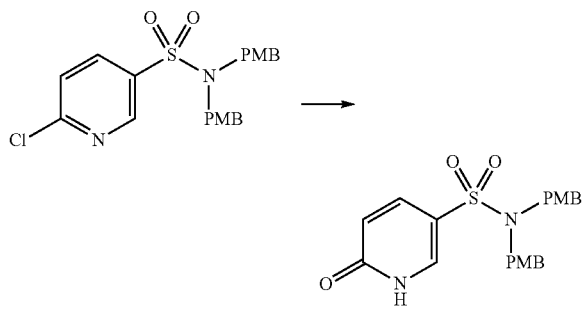

A suspension of 6-chloro-N,N-bis(4-methoxybenzyl)pyridine-3-sulfonamide (4.07 g, 9.40 mmol) in ethane-1,2-diol (90 ml, 9.40 mmol) was treated with 2 M KOH (aq) (23.50 ml, 47.0 mmol) and the resultant suspension was stirred at 140° C. for 42 hours. Then the reaction mixture was diluted with water (200 mL) and DCM (300 mL). Brine (5 mL) was added and the organic layer was collected. The aqueous layer was extracted with DCM (5×100 mL) and the combined organic extracts were washed with water (100 mL), dried (MgSO$_4$) and concentrated in vacuo to afford the title compound (2.764 g, 61%) as a white solid.

$^1$H NMR (DMSO-d6) δ 7.87 (d, J=2.8 Hz, 1H), 7.60 (dd, J=9.6, 2.9 Hz, 1H), 7.09-7.03 (m, 4H), 6.84-6.79 (m, 4H), 6.34 (d, J=9.6 Hz, 1H), 4.19 (s, 4H), 3.71 (s, 6H).

One exchangeable proton not observed.

LCMS: m/z 415.4 (M+H)$^+$ (ES$^+$); 413.3 (M−H)$^−$ (ES$^−$).

Step C: (R)-1-(2-Hydroxypropyl)-N,N-bis(4-methoxybenzyl)-6-oxo-1,6-dihydropyridine-3-sulfonamide

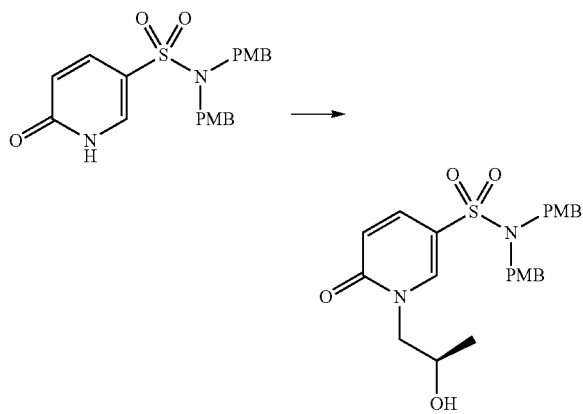

A mixture of N,N-bis(4-methoxybenzyl)-6-oxo-1,6-dihydropyridine-3-sulfonamide (0.206 g, 0.427 mmol) and lithium bromide (0.076 g, 0.855 mmol) in a mixture of DME:DMF (2 mL, 4:1) at 0° C. was treated with NaH (0.026 g, 0.641 mmol). The reaction mixture was stirred at 0° C. for to minutes, then at room temperature for to minutes. (R$^β$)-2-methyloxirane (0.3 ml, 4.24 mmol) was added, and the reaction mixture was heated to 30° C. and stirred for 16 hours. A further portion of (R$^β$)-2-methyloxirane (0.3 ml, 4.24 mmol) was added and the reaction was stirred at 30° C. for 6 hours. Further lithium bromide (0.076 g, 0.855 mmol) followed by NaH (0.026 g, 0.641 mmol) were added and the reaction mixture was stirred at 30° C. for 5 minutes.

Further (R$^β$)-2-methyloxirane (0.3 ml, 4.24 mmol) was added and the reaction mixture was stirred at 30° C. for 16 hours. Saturated aqueous NH$_4$Cl (4 mL) was added, followed by EtOAc (10 mL). The organic layer was collected and the aqueous layer was extracted with EtOAc (2×5 mL). The combined organic extracts were washed with water (2×5 mL), brine (2×5 mL), dried (MgSO$_4$), filtered and concentrated in vacuo to afford crude product which was purified by chromatography on silica gel (dry load) (4 g cartridge, 50-100% EtOAc/isohexane) to afford the title compound (0.189 g, 89%) as a white solid.

$^1$H NMR (CDCl$_3$) δ 7.86 (d, J=2.6 Hz, 1H), 7.47 (dd, J=9.6, 2.7 Hz, 1H), 7.09-7.06 (m, 4H), 6.83-6.80 (m, 4H), 6.55 (d, J=9.7 Hz, 1H), 4.26 (s, 4H), 4.17-4.07 (m, 2H), 3.79 (s, 6H), 3.62 (dd, J=13.3, 8.1 Hz, 1H), 1.25 (d, J=6.3 Hz, 3H). One exchangeable proton not observed.

LCMS: m/z 473.4 (M+H)$^+$ (ES$^+$); 471.3 (M−H)$^−$ (ES$^−$).

Step D: (R)-1-(2-Hydroxypropyl)-6-oxo-1,6-dihydropyridine-3-sulfonamide

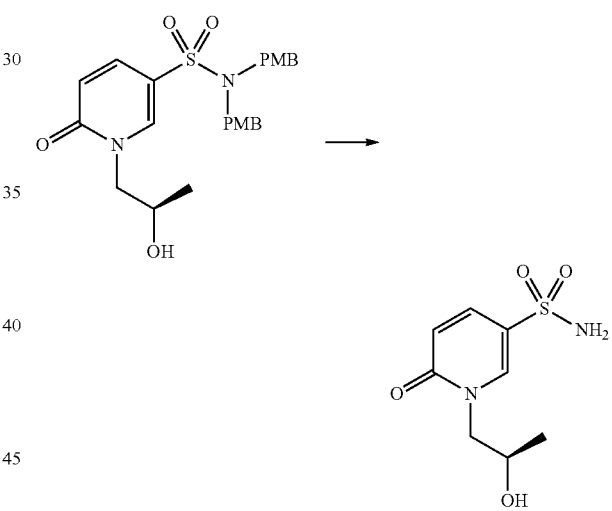

(R)-1-(2-Hydroxypropyl)-N,N-bis(4-methoxybenzyl)-6-oxo-1,6-dihydropyridine-3-sulfonamide (0.182 g, 0.366 mmol) was suspended in DCM (1 ml, 15.54 mmol) and then treated with TFA (1 ml, 12.98 mmol). The resultant solution was stirred at room temperature for 24 hours. The DCM was evaporated and the reaction mixture was stirred at room temperature for 24 hours, then at 40° C. for 21 hours. The reaction mixture was concentrated in vacuo and azeotroped with DCM (3×5 mL) to afford crude product as a brown foam (0.241 g). The crude product was purified by chromatography on silica gel (dry load) (12 g cartridge, 0-10% MeOH/DCM) to afford the title compound (0.049 g, 56%) as a white solid.

$^1$H NMR (DMSO-d6) δ 8.10 (d, J=2.7 Hz, 1H), 7.69 (dd, J=9.6, 2.7 Hz, 1H), 7.33 (s, 2H), 6.53 (d, J=9.5 Hz, 1H), 4.92 (d, J=5.5 Hz, 1H), 4.07 (dd, J=13.0, 3.3 Hz, 1H), 3.91-3.81 (m, 1H), 3.62 (dd, J=13.0, 8.4 Hz, 1H), 1.08 (d, J=6.3 Hz, 3H).

LCMS: m/z 233.0 (M+H)$^+$ (ES$^+$); 230.9 (M−H)$^−$ (ES$^−$).

Intermediate P143: 1-(2-(Dimethylamino)ethyl)-6-oxo-1,6-dihydropyridine-3-sulfonamide Step A: 1-(2-Hydroxyethyl)-N,N-bis(4-methoxybenzyl)-6-oxo-1,6-dihydropyridine-3-sulfonamide

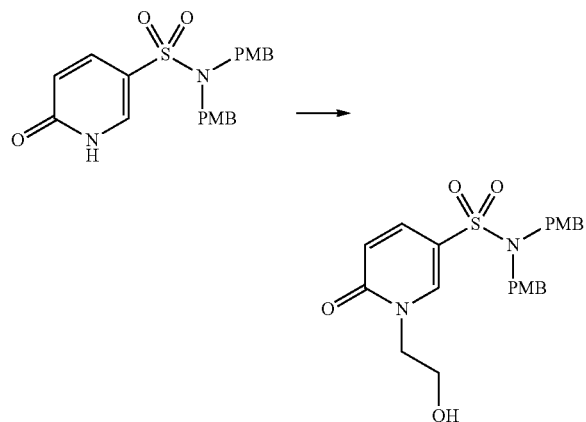

A mixture of N,N-bis(4-methoxybenzyl)-6-oxo-1,6-dihydropyridine-3-sulfonamide (Intermediate P142, Step B) (0.15 g, 0.355 mmol) and lithium bromide (0.063 g, 0.709 mmol) in DME:DMF (2 mL, 4:1) at room temperature was treated with sodium hydride (0.021 g, 0.532 mmol). The reaction mixture was stirred for 10 minutes, treated with 2-bromoethanol (0.030 ml, 0.426 mmol) and then stirred at 50° C. for 69 hours. The reaction was quenched with saturated aqueous NH$_4$Cl (2 mL) and diluted with EtOAc (10 mL). The organic layer was collected, washed with water (2×5 mL) and brine (2×5 mL), dried (MgSO$_4$), filtered and concentrated in vacuo to afford crude product which was purified by chromatography on silica gel (dry load) (4 g cartridge, 50-100% EtOAc/isohexane) to afford the title compound (0.124 g, 75%) as a white solid.

$^1$H NMR (DMSO-d6) δ 8.16 (d, J=2.7 Hz, 1H), 7.63 (dd, J=9.6, 2.8 Hz, 1H), 7.10-7.05 (m, 4H), 6.84-6.80 (m, 4H), 6.44 (d, J=9.6 Hz, 1H), 4.95 (t, J=5.4 Hz, 1H), 4.21 (s, 4H), 3.99 (t, J=5.2 Hz, 2H), 3.71 (s, 6H), 3.62 (app. q, J=5.3 Hz, 2H).

LCMS: m/z 459.4 (M+H)$^+$ (ES$^+$).

Step B: N,N-Bis(4-methoxybenzyl)-6-oxo-1-(2-oxoethyl)-1,6-dihydropyridine-3-sulfonamide

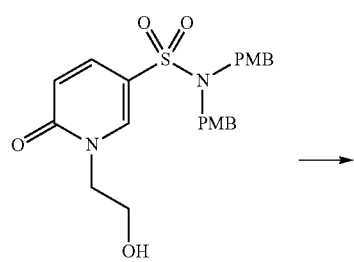

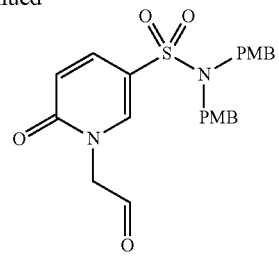

A solution of 1-(2-hydroxyethyl)-N,N-bis(4-methoxybenzyl)-6-oxo-1,6-dihydropyridine-3-sulfonamide (0.177 g, 0.363 mmol) in DCM (5 mL) was treated with Dess-Martin periodinane (0.18 g, 0.424 mmol) and stirred at room temperature for 1 hour. Further Dess-Martin periodinane (0.09 g, 0.212 mmol) was added and the reaction mixture stirred for 0.5 hour. Saturated aqueous NaHCO$_3$ (5 mL) and DCM (5 mL) were added and the reaction mixture was stirred vigorously for 10 minutes. The organic layer was collected and the aqueous layer was extracted with DCM (10 mL). The combined organic extracts were washed with saturated aqueous sodium thiosulfate (10 mL) and water (10 mL), dried (MgSO$_4$), filtered and concentrated in vacuo to afford the title compound as a yellow oil (183 mg, 94%).

$^1$H NMR (CDCl$_3$) δ 9.65 (s, 1H), 7.61-7.58 (m, 1H), 7.47 (dd, J=9.7, 2.6 Hz, 1H), 7.13-7.09 (m, 4H), 6.86-6.82 (m, 4H), 6.57 (d, J=9.7 Hz, 1H), 4.67 (s, 2H), 4.29 (s, 4H), 3.80 (s, 6H).

Step C: 1-(2-(Dimethylamino)ethyl)-N,N-bis(4-methoxybenzyl)-6-oxo-1,6-dihydropyridine-3-sulfonamide

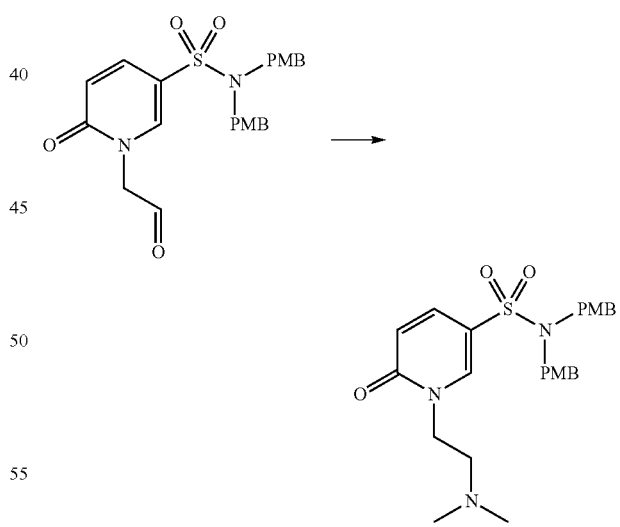

A solution of N,N-bis(4-methoxybenzyl)-6-oxo-1-(2-oxoethyl)-1,6-dihydropyridine-3-sulfonamide (0.183 g, 0.341 mmol) in 1,2-dichloroethane (3 ml, 38.1 mmol) was treated with 2M dimethylamine (in THF) (0.35 ml, 0.700 mmol). The resultant yellow/green solution was stirred for 30 minutes, before sodium triacetoxyborohydride (0.15 g, 0.708 mmol) was added in one portion. The reaction mixture was stirred at room temperature for 16 hours, then saturated aqueous NaHCO$_3$ (5 mL) was added and the organic layer was collected. The aqueous layer was extracted with DCM (2×5 mL) and the combined organic extracts were washed with water (5 mL), dried (MgSO₄), filtered and concentrated in vacuo to afford crude product as a yellow oil (196 mg). The crude product was loaded onto a column of SCX (1.8 g) in MeOH. The column was washed with MeOH and then the product was eluted with 0.7 M ammonia in MeOH. The resultant mixture was concentrated in vacuo to afford the title compound (0.162 g, 96%) as a clear yellow oil.

$^1$H NMR (DMSO-d6) δ 8.23 (d, J=2.7 Hz, 1H), 7.61 (dd, J=9.6, 2.8 Hz, 1H), 7.08-7.03 (m, 4H), 6.85-6.79 (m, 4H), 6.43 (d, J=9.6 Hz, 1H), 4.21 (s, 4H), 4.03 (t, J=6.0 Hz, 2H), 3.71 (s, 6H), 2.51-2.45 (m, 2H), 2.15 (s, 6H). Multiplet at 2.51-2.45 is obscured by the DMSO-d6 solvent signal.

Step D: 1-(2-(Dimethylamino)ethyl)-6-oxo-1,6-dihydropyridine-3-sulfonamide

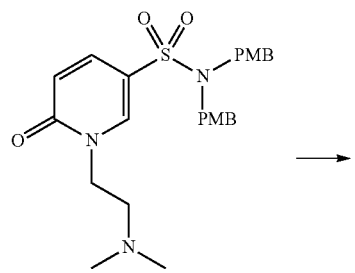

A solution of 1-(2-(dimethylamino)ethyl)-N,N-bis(4-methoxybenzyl)-6-oxo-1,6-dihydropyridine-3-sulfonamide (0.159 g, 0.321 mmol) in DCM (3 ml, 46.6 mmol) was treated with TFA (0.25 ml, 3.24 mmol) dropwise at room temperature and the reaction mixture was stirred for 16 hours. Further TFA (0.25 ml, 3.24 mmol) was added. The reaction mixture was stirred for 2 hours and then concentrated in vacuo. The residue was dissolved in DCM (0.5 mL) and TFA (0.5 mL). The reaction mixture was stirred for 4 hours and then concentrated in vacuo. The residue was treated with TFA (2 mL) and water (0.2 mL). The reaction mixture was stirred for 24 hours at room temperature and then heated to 40° C. for 18 hours. The reaction mixture was concentrated in vacuo and the crude product was loaded onto a column of SCX (1.9 g) in DCM. The column was washed with DCM and then the product was eluted with 0.7 M ammonia in MeOH/DCM (1:1). The resultant mixture was concentrated in vacuo to afford the title compound (0.038 g, 35%) as a pale brown solid.

LCMS: m/z 246.1 (M+H)⁺ (ES⁺); 244.0 (M−H)⁻ (ES⁻).

Intermediate P144: 1-Ethylazepane-4-sulfonamide

Step A: tert-Butyl 4-((methylsulfonyl)oxy)azepane-1-carboxylate

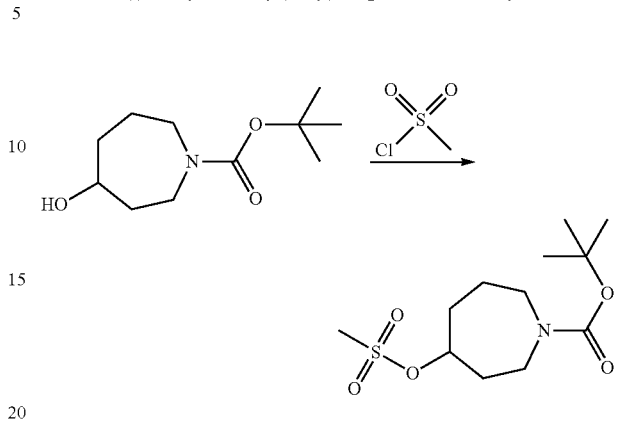

To a solution of tert-butyl 4-hydroxyazepane-1-carboxylate (3.0 g, 14.0 mmol, 1.0 equiv.) and N,N-diisopropylethylamine (3.2 mL, 18.0 mmol, 1.3 equiv.) in dichloromethane (70 mL) was added methanesulfonyl chloride (1.2 mL, 15.0 mmol, 1.1 equiv.). The reaction mixture was stirred at room temperature for 1 hour and then water was added. The organic layer was separated and then washed twice with water, once with brine, dried over sodium sulfate, filtered and concentrated in vacuo to give the title compound (3.87 g, 95%).

$^1$H NMR (CDCl₃) δ 4.97-4.76 (m, 1H), 3.62-3.24 (m, 4H), 3.00 (s, 3H), 2.14-1.83 (m, 4H), 1.68 (q, 2H), 1.45 (s, 9H).

Step B: tert-Butyl 4-(acetylthio)azepane-1-carboxylate

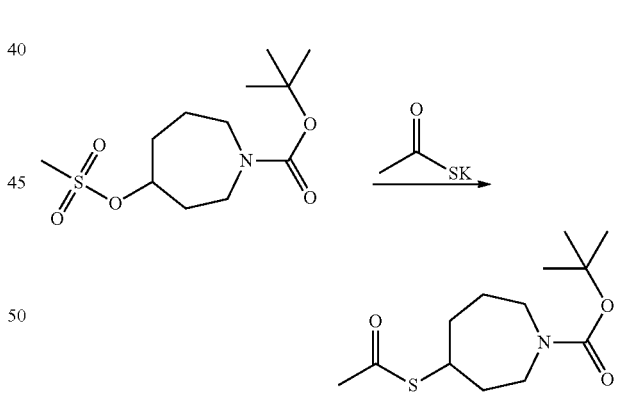

To a solution of tert-butyl 4-((methylsulfonyl)oxy) azepane-1-carboxylate (3.87 g, 13.2 mmol, 1.0 equiv.) in dimethylformamide (50 mL) and acetonitrile (13 mL) was added potassium thioacetate (4.52 g, 39.6 mmol, 3.0 equiv.). The reaction mixture was heated to 90° C. for 50 minutes and then cooled to room temperature. To the suspension was added brine and ethyl acetate. The organic layer was separated, then washed three times with brine, dried over sodium sulfate, filtered and concentrated in vacuo. The crude product was submitted for normal phase flash column chromatography using heptane and ethyl acetate as eluent to give the title compound (2.3 g, 64%).

LC-MS: m/z 174.4 (M+H−C₅H₉O₂)⁺ (ES⁺).

Step C: tert-Butyl 4-sulfamoylazepane-1-carboxylate

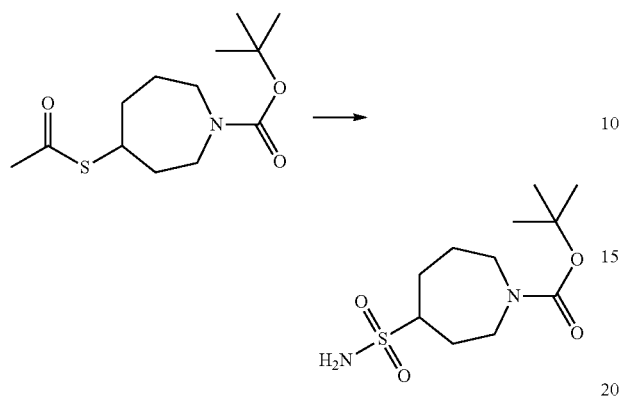

To a solution of tert-butyl 4-(acetylthio)azepane-1-carboxylate (2.2 g, 8.0 mmol, 1.0 equiv.) in water (8.0 ml) and acetic acid (80 mL) was added N-chlorosuccinimide (3.2 g, 24.1 mmol, 3.0 equiv.). The reaction mixture was stirred at room temperature for one hour and then added dropwise to a solution of ammonia in water (25 wt %, 500 mL) cooled in an ice bath. The mixture was adjusted to pH 9 by adding concentrated hydrochloric acid and then extracted twice with ethyl acetate. The organic layers were combined, dried over sodium sulfate, filtered and then concentrated in vacuo. The crude product was submitted for normal phase flash column chromatography using dichloromethane and methanol as eluent to give the title compound (250 mg, 11%).

$^1$H NMR (CDCl$_3$) δ 4.47 (s, 2H), 3.71-3.46 (m, 2H), 3.48-3.35 (m, 1H), 3.36-3.16 (m, 1H), 2.97 (dt, 1H), 2.55-2.36 (m, 2H), 2.07-1.96 (m, 1H), 1.94-1.80 (m, 1H), 1.70-1.60 (m, 2H), 1.46 (s, 9H).

Step D: Azepane-4-sulfonamide Hydrochloride

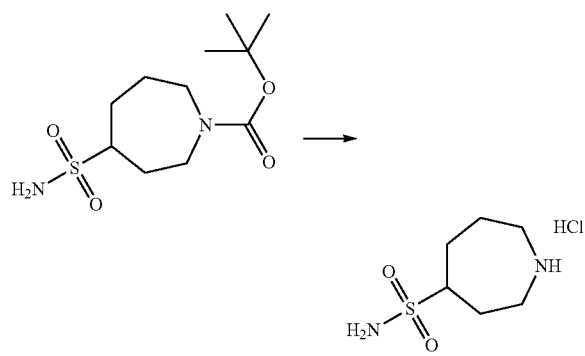

To a solution of tert-butyl 4-sulfamoylazepane-1-carboxylate (252 mg, 0.9 mmol, 1.0 equiv.) in dichloromethane (10 mL) was added 4M hydrochloric acid in dioxane (5.0 mL, 18.1 mmol, 20.0 equiv.). The reaction mixture was stirred overnight at room temperature and then concentrated in vacuo to give the title compound (194 mg, quantitative yield).

$^1$H NMR (CD$_3$OD) δ 3.47 (ddd, 1H), 3.29-3.16 (m, 4H), 2.57-2.34 (m, 2H), 2.31-2.08 (m, 2H), 2.06-1.80 (m, 2H).

Step E: 1-Ethylazepane-4-sulfonamide

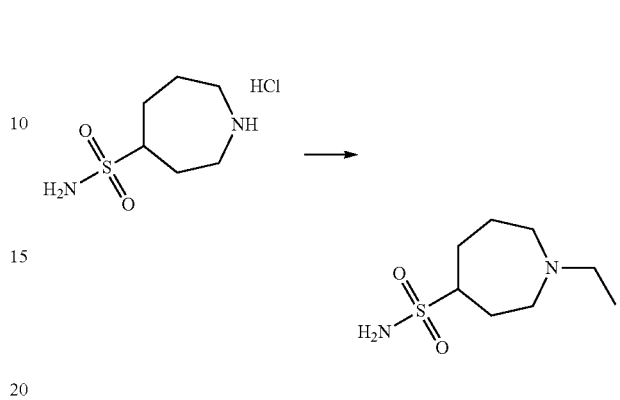

To a suspension of azepane-4-sulfonamide hydrochloride (97 mg, 0.45 mmol, 1.0 equiv.) in acetonitrile (10 mL) was added acetaldehyde (28 μL, 0.5 mmol, 1.1 equiv.), triethylamine (69 μL, 0.5 mmol, 1.1 equiv.) and then sodium triacetoxyborohydride (120 mg, 0.56 mmol, 1.25 equiv.). The suspension was stirred overnight at room temperature and then concentrated in vacuo. The crude product was dissolved in methanol, coated on Agilient hydromatrix (a high purity, inert diatomaceous earth sorbent) and then submitted for normal phase flash column chromatography to give the title compound (29 mg, 31%).

$^1$H NMR (DMSO-d$_6$) δ 6.69 (s, 2H), 3.07-2.93 (m, 1H), 2.81-2.51 (m, 4H), 2.22-2.00 (m, 2H), 1.91-1.42 (m, 6H), 1.00 (t, J=7.1 Hz, 3H).

Intermediate P145:
1-(Ethyl-d5)piperidine-4-sulfonamide

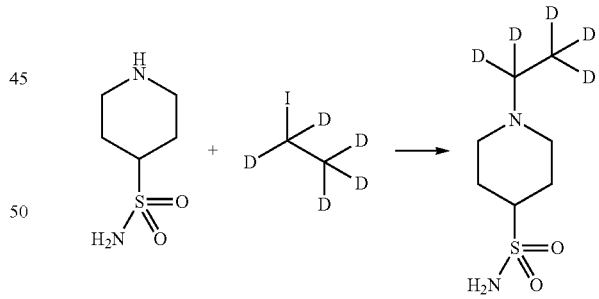

To a solution of piperidine-4-sulfonamide hydrochloride (733 mg, 3.65 mmol, 1 eq) and K$_2$CO$_3$ (2.02 g, 14.6 mmol, 4 eq) in acetonitrile (30 mL) was added 1-iodoethane-1,1,2,2,2-d5 (588 mg, 3.65 mmol, 1 eq) and the reaction mixture was stirred at room temperature for 18 hours. The mixture was concentrated in vacuo. The residue was suspended in methanol, coated on Agilient hydromatrix (a high purity, inert diatomaceous earth sorbent) and then submitted to normal phase flash chromatography using dichloromethane and a mixture of ammonia (3.5 M) in methanol to give the title compound (63 mg, 9%) as an off-white solid.

LCMS: m/z 198 (M+H)$^+$ (ES$^+$).

PREPARATION OF EXAMPLES

Example 1: N-((1,2,3,5,6,7-Hexahydro-s-indacen-4-yl)carbamoyl)-1-methylpiperidine-4-sulfonamide, Potassium Salt

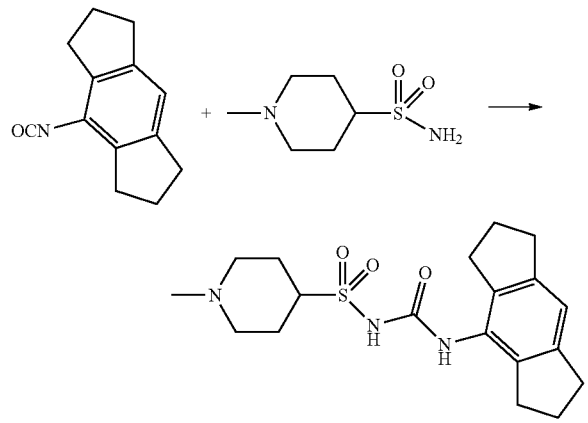

To a cooled (0° C.) solution of 1-methylpiperidine-4-sulfonamide (55 mg, 0.31 mmol) in THF (2 mL) was added potassium tert-butoxide (38 mg, 0.34 mmol). The reaction mixture was stirred and allowed to warm to room temperature over 40 minutes and then a solution of 4-isocyanato-1,2,3,5,6,7-hexahydro-s-indacene (Intermediate A1; 68 mg, 0.34 mmol) in THF (1 mL) was added. The mixture was stirred overnight at room temperature and the resulting precipitate was isolated by filtration and washed with THF (1 mL). The solid was triturated with EtOAc (2 mL) for 1 hour, filtered and dried in vacuo to afford the title compound (17 mg; 13%) as a white solid.

$^1$H NMR (CD$_3$OD) δ 6.83 (s, 1H), 4.58 (br s, 2H), 3.2 (m, 1H), 3.02 (m, 2H), 2.82 (m, 8H), 2.3 (s, 3H) and 1.82-2.1 (m, 10H).

LCMS: m/z 378 (M+H)$^+$ (ES$^+$); 376 (M-H)$^-$ (ES$^-$).

Example 2: N-((1,2,3,5,6,7-Hexahydro-s-indacen-4-yl)carbamoyl)-1-(prop-2-yn-1-yl)piperidine-4-sulfonamide, Potassium Salt

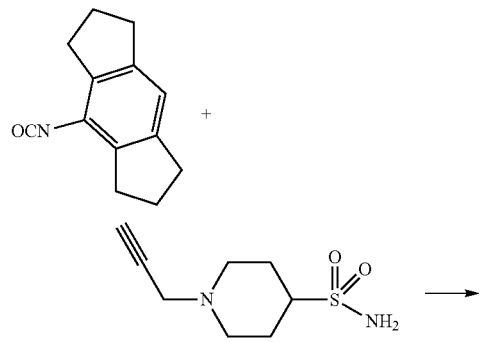

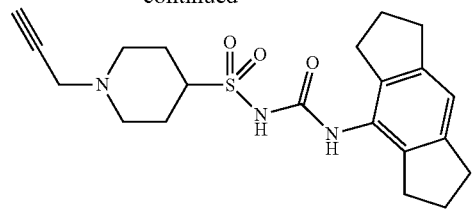

To a cooled (0° C.) solution of 1-(prop-2-yn-1-yl)piperidine-4-sulfonamide (Intermediate P3; 64 mg, 0.31 mmol) in THF (3 mL) was added potassium tert-butoxide (39 mg, 0.35 mmol). The ice bath was removed and the reaction mixture was stirred whilst being allowed to warm to room temperature over 40 minutes. A solution of 4-isocyanato-1,2,3,5,6,7-hexahydro-s-indacene (Intermediate A1; 69 mg, 0.35 mmol) in THF (1 mL) was added and the mixture was stirred overnight at room temperature. The reaction mixture was concentrated in vacuo and water (2 mL) was added. The suspension was filtered over cotton wool and subsequently submitted for purification by reversed phase column chromatography (see "Experimental Methods", "Purification Method 1") to afford the title compound (95 mg; 75%) as a white solid.

$^1$H NMR (CD$_3$OD) δ 6.83 (s, 1H), 3.38 (m, 1H), 3.02 (m, 2H), 2.82 (m, 10H), 2.63 (s, 1H), 2.27 (m, 2H), 2.16 (m, 2H), 2.02 (m, 4H) and 1.88 (m, 2H).

LCMS: m/z 402 (M+H)$^+$ (ES$^+$); 400 (M-H)$^-$ (ES$^-$).

Example 3: 1-Acetyl-N-((1,2,3,5,6,7-hexahydro-s-indacen-4-yl)carbamoyl) piperidine-4-sulfonamide, Potassium Salt

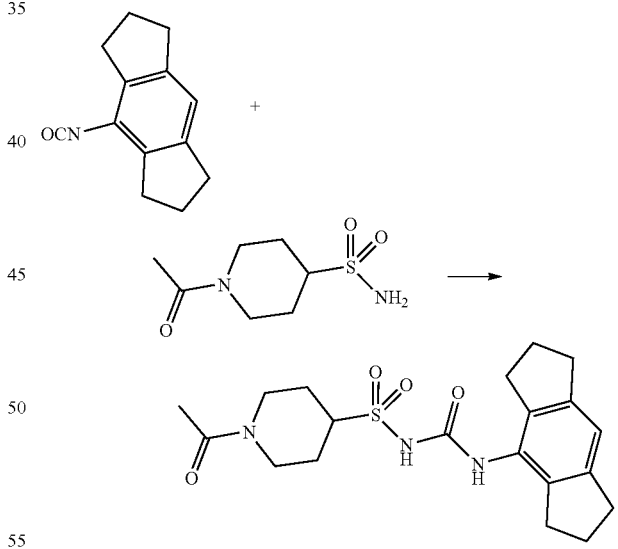

Prepared as described for N-((1,2,3,5,6,7-hexahydro-s-indacen-4-yl)carbamoyl)-1-(prop-2-yn-1-yl)piperidine-4-sulfonamide, potassium salt (example 2) from 4-isocyanato-1,2,3,5,6,7-hexahydro-s-indacene (Intermediate A1) and 1-acetylpiperidine-4-sulfonamide (Intermediate P7) to afford the title compound (73%) as a white solid.

$^1$H NMR (CD$_3$OD) δ 6.84 (s, 1H), 4.6 (m, 2H), 4.02 (m, 1H), 3.62 (m, 1H), 3.15 (m, 1H), 2.82 (m, 8H), 2.64 (m, 1H), 2.17 (m, 1H), 2.09 (s, 3H), 2.02 (m, 4H) and 1.6-1.85 (m, 2H).

LCMS: m/z 406 (M+H)$^+$ (ES$^+$); 404 (M-H)$^-$ (ES$^-$).

Example 4: N-((1,2,3,5,6,7-Hexahydro-s-indacen-4-yl)carbamoyl)-piperidine-4-sulfonamide, Potassium Salt

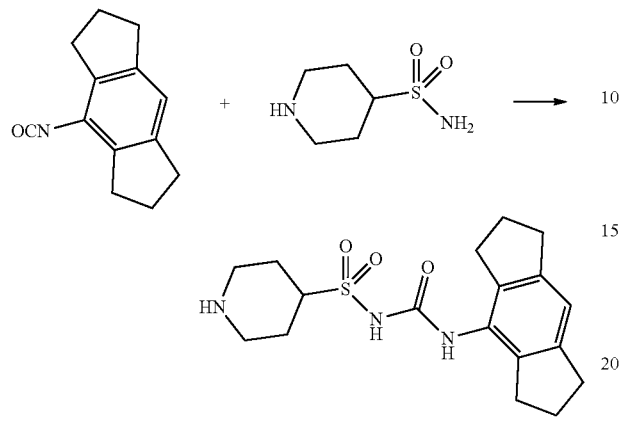

Prepared as described for N-((1,2,3,5,6,7-hexahydro-s-indacen-4-yl)carbamoyl)-1-(prop-2-yn-1-yl)piperidine-4-sulfonamide, potassium salt (example 2) from 4-isocyanato-1,2,3,5,6,7-hexahydro-s-indacene (Intermediate A1) and 1-(2,2,2-trifluoroacetyl)piperidine-4-sulfonamide (Intermediate P4) to afford the deprotected title compound (11%) as a white solid.

¹H NMR (CD₃OD) δ 6.83 (s, 1H), 4.6 (br s, 1H), 3.6 (m, 1H), 2.82 (m, 10H), 2.21 (m, 2H), 2.02 (m, 4H) and 1.86 (m, 4H).

LCMS: m/z 364 (M+H)⁺ (ES⁺); 362 (M−H)⁻ (ES⁻).

Example 5: 4-(N-((1,2,3,5,6,7-Hexahydro-s-indacen-4-yl)carbamoyl)sulfamoyl)-N-isopropylpiperidine-1-carboxamide, Potassium Salt

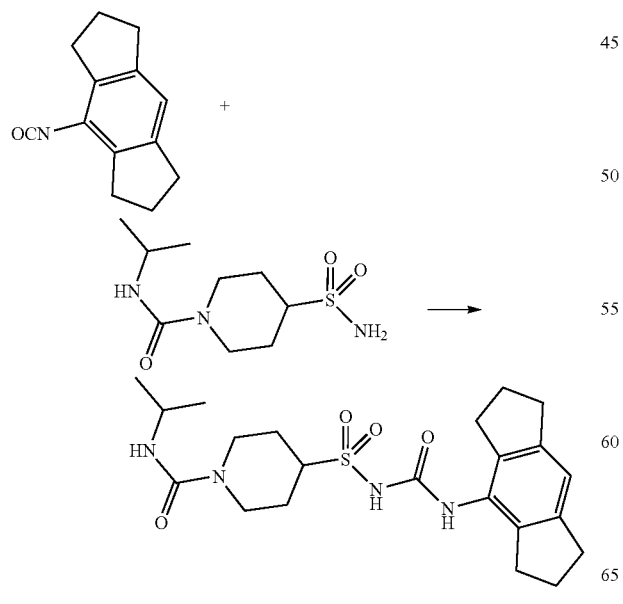

Prepared as described for N-((1,2,3,5,6,7-hexahydro-s-indacen-4-yl)-1-(prop-2-yn-1-yl)piperidine-4-sulfonamide, potassium salt (example 2) from 4-isocyanato-1,2,3,5,6,7-hexahydro-s-indacene (Intermediate A1) and N-iso-propyl-4-sulfamoylpiperidine-1-carboxamide (Intermediate P5) to afford the title compound (39%) as a white solid.

¹H NMR (CD₃OD) δ 6.84 (s, 1H), 4.14 (m, 2H), 3.85 (m, 1H), 3.53 (m, 1H), 2.82 (m, 10H), 2.05 (m, 6H), 1.7 (m, 2H) and 1.12 (d, 6H).

LCMS: m/z 449 (M+H)⁺ (ES⁺); 447 (M−H)⁻ (ES⁻).

Example 6: 1-Ethyl-N-((1,2,3,5,6,7-hexahydro-s-indacen-4-yl)carbamoyl)piperidine-4-sulfonamide, Potassium Salt

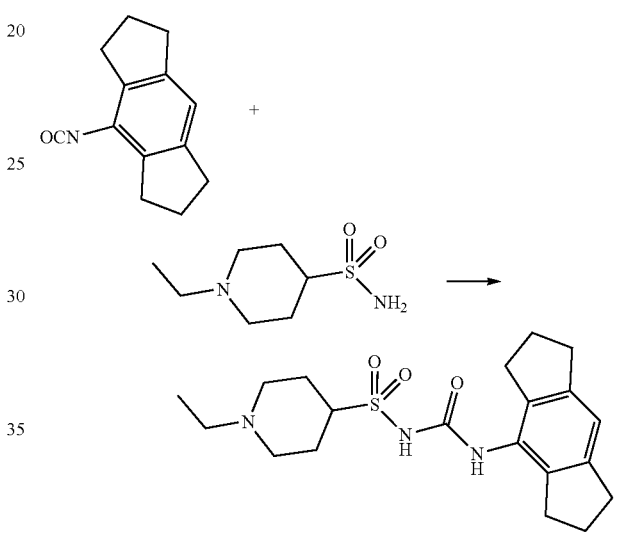

Prepared as described for N-((1,2,3,5,6,7-hexahydro-s-indacen-4-yl)carbamoyl)-1-(prop-2-yn-1-yl)piperidine-4-sulfonamide, potassium salt (example 2) from 4-isocyanato-1,2,3,5,6,7-hexahydro-s-indacene (Intermediate A1) and 1-ethylpiperidine-4-sulfonamide (Intermediate P6) to afford the title compound (14%) as a white solid.

¹H NMR (CD₃OD) δ 6.83 (s, 1H), 4.6 (br s, 1H), 3.18 (m, 2H), 2.82 (m, 8H), 2.55 (q, 2H), 2.17 (m, 4H), 1.85-2.08 (m, 6H) and 1.16 (t, 3H).

LCMS: m/z 392 (M+H)⁺ (ES⁺); 390 (M−H)⁻ (ES⁻).

Example 7: 1-(Cyclopropanecarbonyl)-N-((1,2,3,5,6,7-hexahydro-s-indacen-4-yl)carbamoyl)piperidine-4-sulfonamide, Potassium Salt

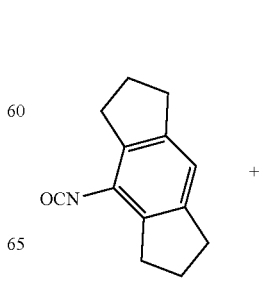

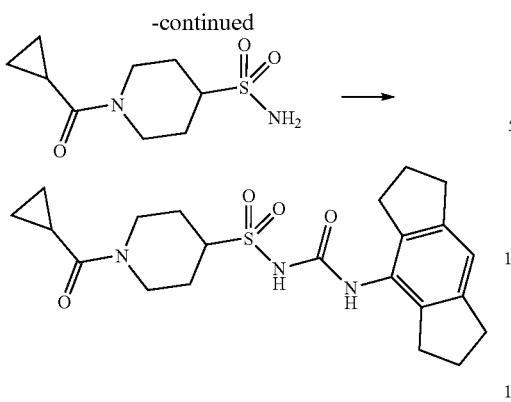

Prepared as described for N-((1,2,3,5,6,7-hexahydro-s-indacen-4-yl)carbamoyl)-1-(prop-2-yn-1-yl)piperidine-4-sulfonamide, potassium salt (example 2) from 4-isocyanato-1,2,3,5,6,7-hexahydro-s-indacene (Intermediate A1) and 1-(cyclopropanecarbonyl)piperidine-4-sulfonamide (Intermediate P8) to afford the title compound (72%) as a white solid.

$^1$H NMR (CD$_3$OD) δ 6.84 (s, 1H), 4.58 (m, 1H), 4.42 (m, 1H), 3.6 (m, 1H), 3.18 (m, 1H), 2.82 (m, 8H), 2.64 (m, 1H), 2.08 (m, 1H), 2.02 (m, 6H), 1.8-1.94 (m, 2H) and 0.92 (m, 4H).

LCMS: m/z 432 (M+H)$^+$ (ES$^+$); 430 (M–H)$^-$ (ES$^-$).

Example 8: N-((1,2,3,5,6,7-Hexahydro-s-indacen-4-yl)carbamoyl)-1-(2,2,2-trifluoroacetyl)piperidine-4-sulfonamide, Potassium Salt

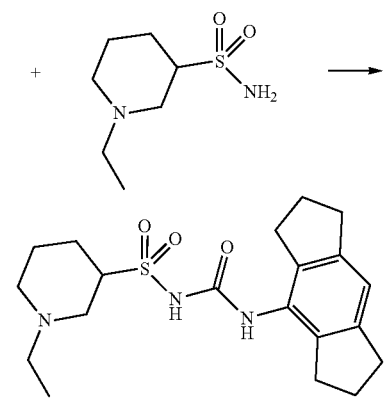

Prepared as described for N-((1,2,3,5,6,7-hexahydro-s-indacen-4-yl)carbamoyl)-1-(prop-2-yn-1-yl)piperidine-4-sulfonamide, potassium salt (example 2) from 4-isocyanato-1,2,3,5,6,7-hexahydro-s-indacene (Intermediate A1) and 1-(2,2,2-trifluoroacetyl)piperidine-4-sulfonamide (Intermediate P4) to afford the title compound (19%) as a white solid.

$^1$H NMR (CD$_3$OD) δ 6.84 (s, 1H), 4.51 (m, 2H), 4.09 (m, 1H), 3.7 (m, 1H), 2.92 (m, 1H), 2.82 (m, 8H), 2.12 (m, 2H), 2.02 (m, 4H) and 1.8 (m, 2H).

LCMS: m/z 460 (M+H)$^+$ (ES$^+$); 458 (M–H)$^-$ (ES$^-$).

Example 9: 1-Ethyl-N-((1,2,3,5,6,7-hexahydro-s-indacen-4-yl)carbamoyl)-piperidine-3-sulfonamide, Potassium Salt

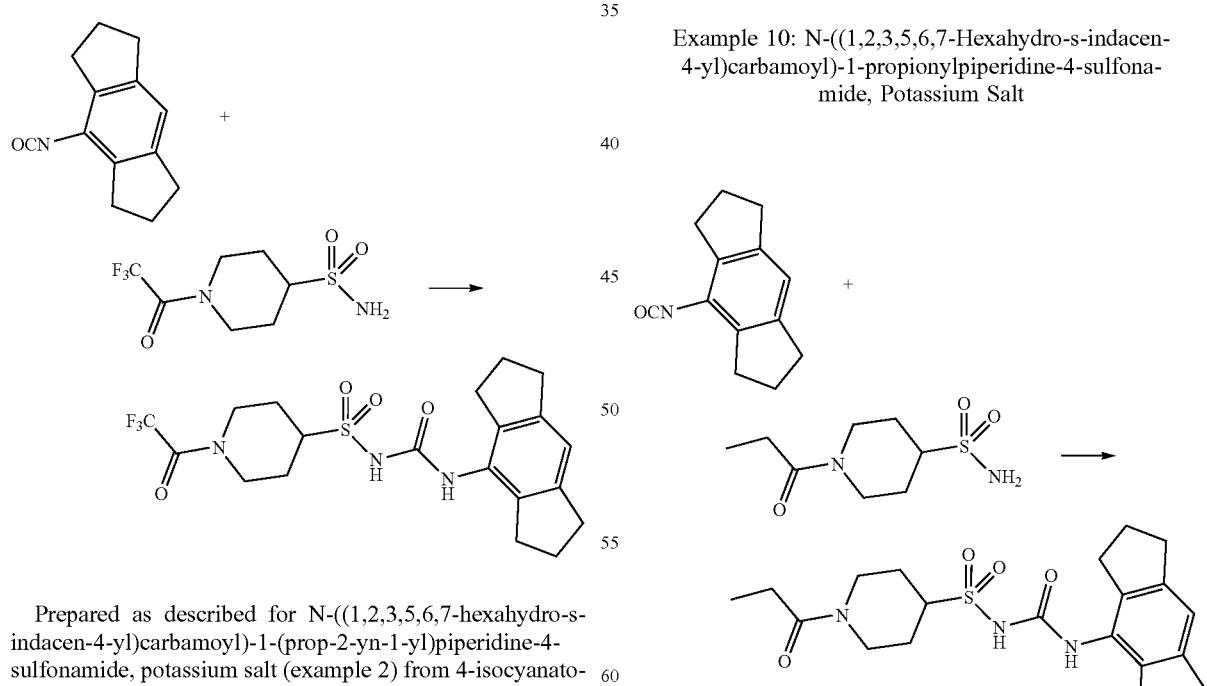

Prepared as described for N-((1,2,3,5,6,7-hexahydro-s-indacen-4-yl)carbamoyl)-1-(prop-2-yn-1-yl)piperidine-4-sulfonamide, potassium salt (example 2) from 4-isocyanato-1,2,3,5,6,7-hexahydro-s-indacene (Intermediate A1) and 1-ethylpiperidine-3-sulfonamide (Intermediate P15) to afford the afford the title compound (23%) as a white solid.

$^1$H NMR (CD$_3$OD) δ 6.83 (s, 1H), 3.61 (m, 1H), 3.45 (m, 1H), 2.94 (m, 1H), 2.82 (m, 8 H), 2.55 (q, 2H), 2.23 (m, 2H), 2.03 (m, 6H), 1.83 (m, 1H), 1.63 (m, 2H) and 1.16 (t, 3H).

LCMS: m/z 392 (M+H)$^+$ (ES$^+$); 390 (M–H)$^-$ (ES$^-$).

Example 10: N-((1,2,3,5,6,7-Hexahydro-s-indacen-4-yl)carbamoyl)-1-propionylpiperidine-4-sulfonamide, Potassium Salt Prepared as described for 1-ethyl-N-((1,2,3,5,6,7-hexahydro-s-indacen-4-yl)carbamoyl)-piperidine-3-sulfonamide, potassium salt (example 9) from 4-isocyanato-1,2,3,5,6,7-hexahydro-s-indacene (Intermediate A1) and 1-propionylpiperidine-4-sulfonamide (Intermediate P10) to afford the title compound (32%) as a white solid.

¹H NMR (CD₃OD) δ 6.83 (s, 1H), 4.62 (m, 1H), 4.04 (m, 1H), 3.61 (m, 1H), 3.09 (m, 1H), 2.82 (m, 8H), 2.65 (m, 1H), 2.42 (q, 2H), 2.17 (m, 2H), 2.02 (m, 4H), 1.7 (m, 2H) and 1.12 (t, 3H).

LCMS: m/z 420 (M+H)⁺ (ES⁺); 418 (M−H)⁻ (ES⁻).

Example 11: N-((1,2,3,5,6,7-Hexahydro-s-indacen-4-yl)carbamoyl)-1-isobutyrylpiperidine-4-sulfonamide, Potassium Salt

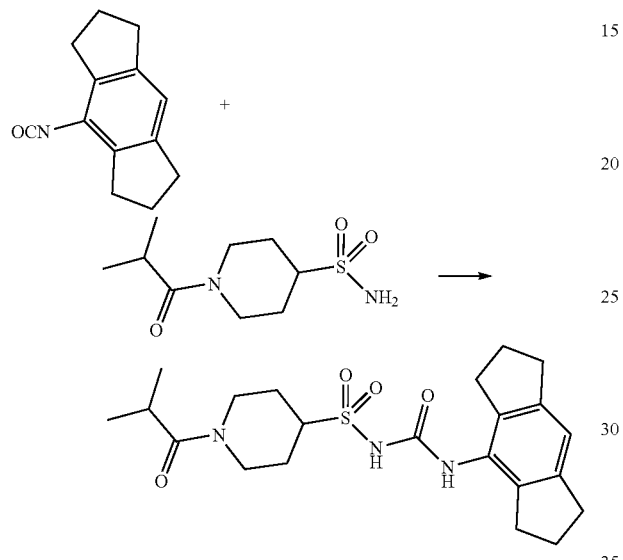

Prepared as described for 1-ethyl-N-((1,2,3,5,6,7-hexahydro-s-indacen-4-yl)carbamoyl)-piperidine-3-sulfonamide, potassium salt (example 9) from 4-isocyanato-1,2,3,5,6,7-hexahydro-s-indacene (Intermediate A1) and 1-isobutyrylpiperidine-4-sulfonamide (Intermediate P11) to afford the title compound (9%) as a white solid.

¹H NMR (CD₃OD) δ 6.83 (s, 1H), 4.62 (m, 1H), 4.18 (m, 1H), 3.65 (m, 1H), 3.07 (m, 1H), 2.96 (m, 1H), 2.82 (m, 8H), 2.65 (m, 1H), 2.17 (m, 2H), 2.02 (m, 4H), 1.7 (m, 2H) and 1.09 (t, 6H).

LCMS: m/z 434 (M+H)⁺ (ES⁺).

Example 12: N-((1,2,3,5,6,7-Hexahydro-s-indacen-4-yl)carbamoyl)-1-(2-methoxyacetyl)piperidine-4-sulfonamide, Potassium Salt

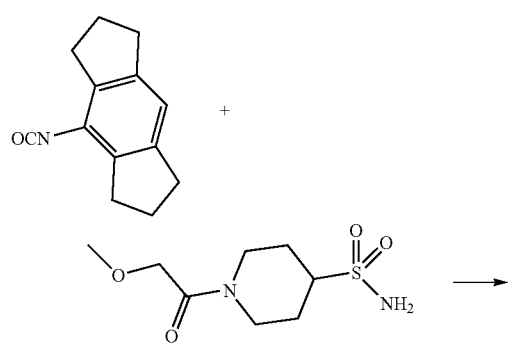

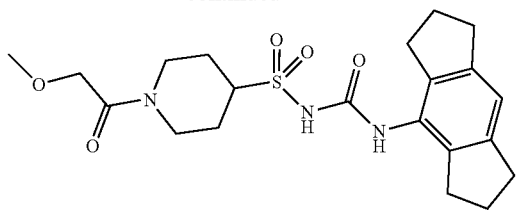

Prepared as described for 1-ethyl-N-((1,2,3,5,6,7-hexahydro-s-indacen-4-yl)carbamoyl)-piperidine-3-sulfonamide, potassium salt (example 9) from 4-isocyanato-1,2,3,5,6,7-hexahydro-s-indacene (Intermediate A1) and 1-(2-methoxyacetyl)piperidine-4-sulfonamide (Intermediate P12) to afford the title compound (5%) as a white solid.

¹H NMR (CD₃OD) δ 6.91 (s, 1H), 4.19 (q, 2H), 4.0 (m, 1H), 3.7 (m, 1H), 3.41 (s, 3H), 3.23-3.03 (m, 2H), 2.82 (m, 8H), 2.7 (m, 1H), 2.19 (m, 2H), 2.02 (m, 4H) and 1.77 (m, 2H).

LCMS: m/z 436 (M+H)⁺ (ES⁺).

Example 13: Methyl 4-(N-((1,2,3,5,6,7-hexahydro-s-indacen-4-yl)carbamoyl)sulfamoyl)piperidine-1-carboxylate, Potassium Salt

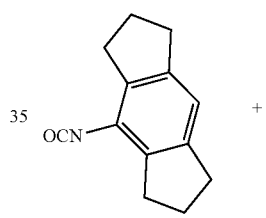

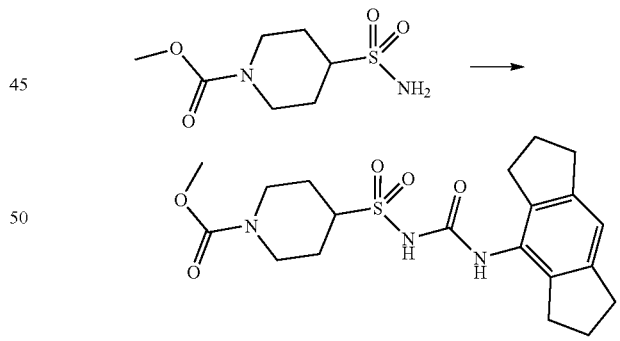

Prepared as described for 1-ethyl-N-((1,2,3,5,6,7-hexahydro-s-indacen-4-yl)carbamoyl)-piperidine-3-sulfonamide, potassium salt (example 9) from 4-isocyanato-1,2,3,5,6,7-hexahydro-s-indacene (Intermediate A1) and methyl 4-sulfamoylpiperidine-1-carboxylate (Intermediate P13) to afford the title compound (32%) as a white solid.

¹H NMR (CD₃OD) δ 6.85 (s, 1H), 4.2 (m, 2H), 3.68 (s, 3H), 3.55 (m, 1H), 2.82 (m, 10H), 2.03 (m, 6H) and 1.7 (m, 2H).

LCMS: m/z 422 (M+H)⁺ (ES⁺); 420 (M−H)⁻ (ES⁻).

Example 14: 1-(Cyanomethyl)-N-((1,2,3,5,6,7-hexahydro-s-indacen-4-yl)carbamoyl)piperidine-4-sulfonamide, Potassium Salt

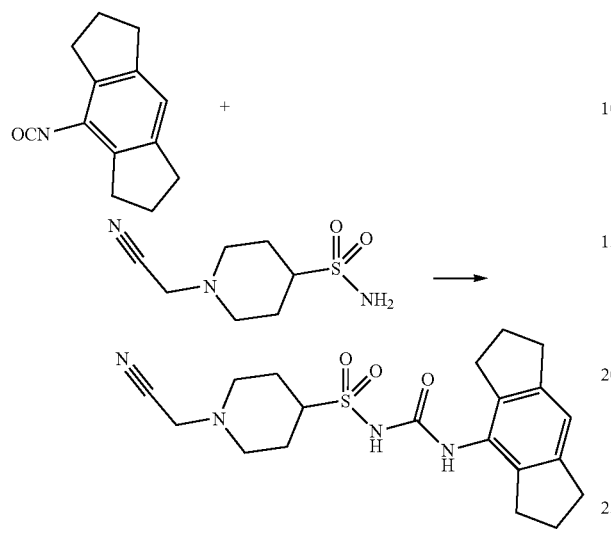

Prepared as described for 1-ethyl-N-((1,2,3,5,6,7-hexahydro-s-indacen-4-yl)carbamoyl)-piperidine-3-sulfonamide, potassium salt (example 9) from 4-isocyanato-1,2,3,5,6,7-hexahydro-s-indacene (Intermediate A1) and 1-(cyanomethyl)piperidine-4-sulfonamide_(Intermediate P9) to afford the title compound (51%) as a white solid.

$^1$H NMR (CD$_3$OD) δ 6.87 (s, 1H), 3.64 (s, 2H), 3.38 (m, 1H), 2.96 (m, 2H), 2.82 (m, 8H), 2.3 (m, 2H), 2.18 (m, 2H), 2.02 (m, 5H) and 1.88 (m, 2H).

LCMS: m/z 403 (M+H)$^+$ (ES$^+$); 401 (M–H)$^-$ (ES$^-$).

Example 15: 1-Cyclobutyl-N-((1,2,3,5,6,7-hexahydro-s-indacen-4-yl)carbamoyl)piperidine-4-sulfonamide, Potassium Salt

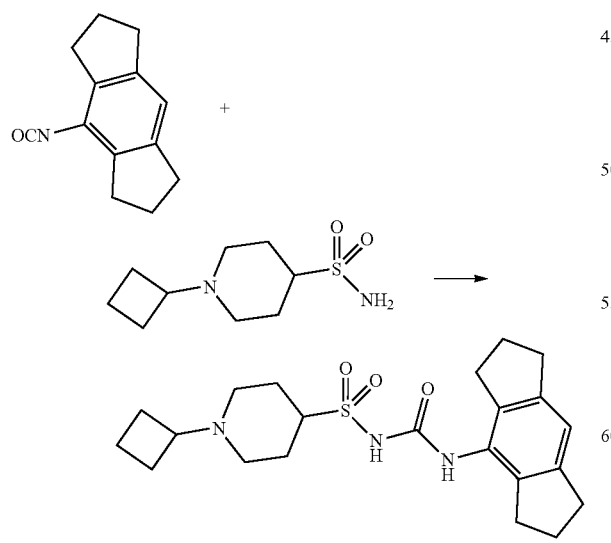

Prepared as described for 1-ethyl-N-((1,2,3,5,6,7-hexahydro-s-indacen-4-yl)carbamoyl)-piperidine-3-sulfonamide, potassium salt (example 9) from 4-isocyanato-1,2,3,5,6,7-hexahydro-s-indacene (Intermediate A1) and 1-cyclobutylpiperidine-4-sulfonamide (Intermediate P14) to afford the title compound (20%) as a white solid.

$^1$H NMR (CD$_3$OD) δ 6.87 (s, 1H), 5.2 (S, 1H), 3.47 (q, 2H), 3.02 (m, 2H), 2.82 (m, 8H), 2.18-1.97 (m, 6H), 1.97-1.82 (m, 4H), 1.72 (m, 2H) and 1.35 (m, 4H).

LCMS: m/z 418 (M+H)$^+$ (ES$^+$); 416 (M–H)$^-$ (ES$^-$).

Example 16: N-((1,2,3,5,6,7-Hexahydro-s-indacen-4-yl)carbamoyl)-1,3-dimethyl-2,4-dioxo-1,2,3,4-tetrahydropyrimidine-5-sulfonamide, Potassium Salt

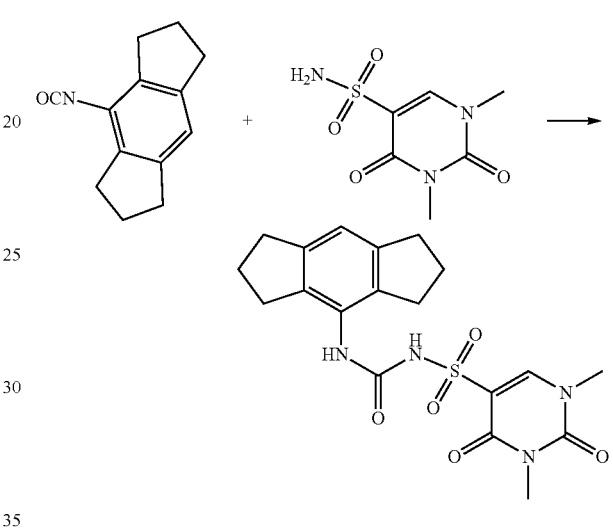

Prepared as described for 1-ethyl-N-((1,2,3,5,6,7-hexahydro-s-indacen-4-yl)carbamoyl)-piperidine-3-sulfonamide, potassium salt (example 9) from 4-isocyanato-1,2,3,5,6,7-hexahydro-s-indacene (Intermediate A1) and 1,2,3,4-tetrahydro-1,3-dimethyl-2,4-dioxo-pyrimidine-5-sulfonate to afford the title compound (50%) as a white solid.

$^1$H NMR (CD$_3$OD) δ 8.22 (s, 1H), 6.83 (s, 1H), 3.43 (s, 3H), 3.35 (s, 3H), 2.8 (t, 4H), 2.75 (t, 4H) and 2.0 (m, 4H).

LCMS: m/z 419 (M+H)$^+$ (ES$^+$); 417 (M–H)$^-$ (ES$^-$).

Example 17: N-((1,2,3,5,6,7-Hexahydro-s-indacen-4-yl)carbamoyl)-1-hexyl-2,4-dioxo-1,2,3,4-tetrahydropyrimidine-5-sulfonamide, Potassium Salt

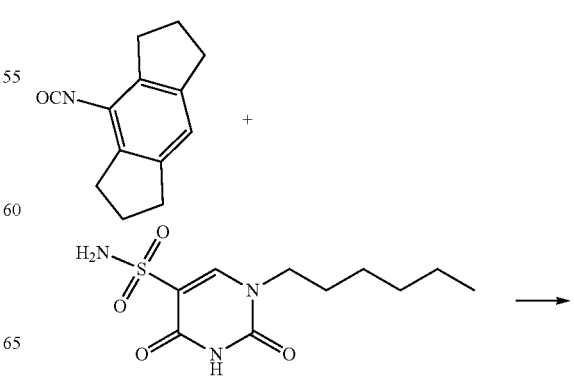

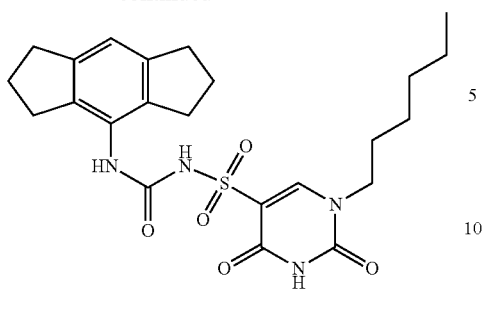

Prepared as described for 1-ethyl-N-((1,2,3,5,6,7-hexahydro-s-indacen-4-yl)carbamoyl)-piperidine-3-sulfonamide, potassium salt (example 9) from 4-isocyanato-1,2,3,5,6,7-hexahydro-s-indacene (Intermediate A1) and 1-hexyl-1,2,3,4-tetrahydro-2,4-dioxo-pyrimidine-5-sulfonamide to afford the title compound (30%) as a white solid.

$^1$H NMR (CD$_3$OD) δ 8.19 (s, 1H), 6.83 (s, 1H), 3.78 (t, 2H), 2.8 (t, 4H), 2.7 (t, 4H), 1.98 (m, 4H), 1.67 (m, 2H), 1.29 (m, 6H) and 0.88 (t, 3H) LCMS: m/z 475 (M+H)$^+$ (ES$^+$); 473 (M−H)$^−$ (ES$^−$).

Example 18: 1-Cyclobutyl-N-((1,2,3,5,6,7-hexahydro-s-indacen-4-yl) carbamoyl)azetidine-3-sulfonamide, Potassium Salt

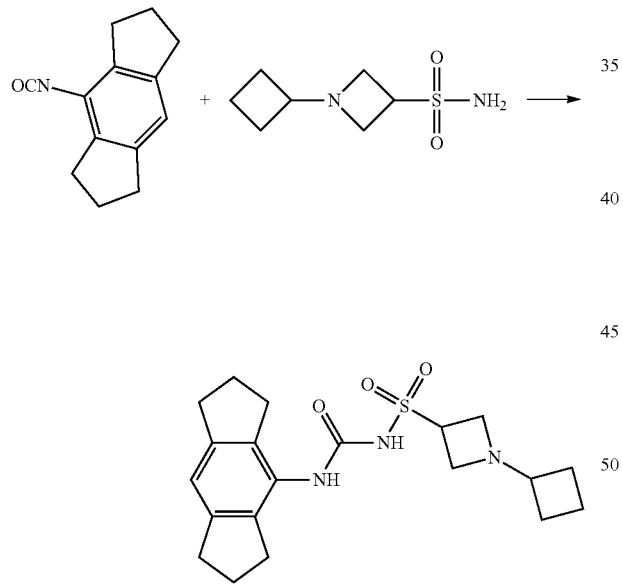

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-cyclobutylazetidine-3-sulfonamide (Intermediate P79) to afford the title compound (25%) as a white solid.

$^1$H NMR (CD$_3$OD): δ=6.86 (s, 1H), 4.34 (t, 1H), 3.63 (dd, 4H), 2.81 (m, 11H), 2.02 (m, 4H), 1.95-1.82 (m, 2H), 1.82-1.65 (m, 2H).

LCMS: m/z 390 (M+H)$^+$ (ES$^+$); 388 (M−H)$^−$ (ES$^−$).

Example 19: N-((1,2,3,5,6,7-Hexahydro-s-indacen-4-yl)carbamoyl)-1-propyl piperidine-4-sulfonamide, Potassium Salt

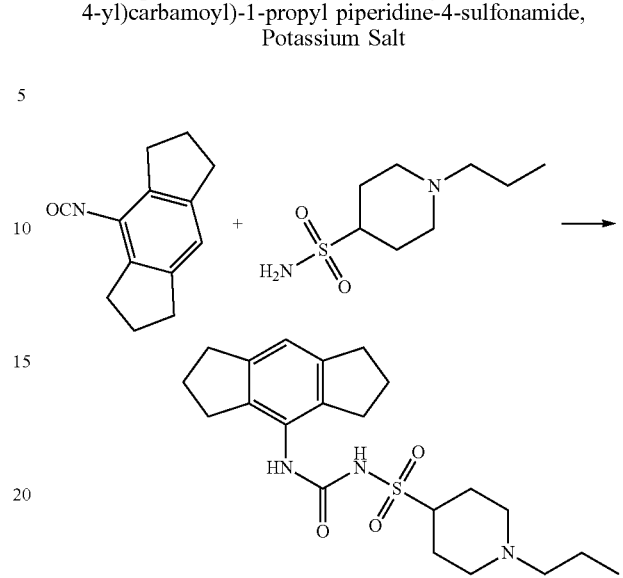

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-propylpiperidine-4-sulfonamide (Intermediate P16) to afford the title compound (2%) as a white solid.

LCMS: m/z 406 (M+H)$^+$ (ES$^+$); 404 (M−H)$^−$ (ES$^−$).

Example 20: N-((1,2,3,5,6,7-Hexahydro-s-indacen-4-yl)carbamoyl)-1-(oxetan-3-yl)piperidine-4-sulfonamide, Potassium Salt

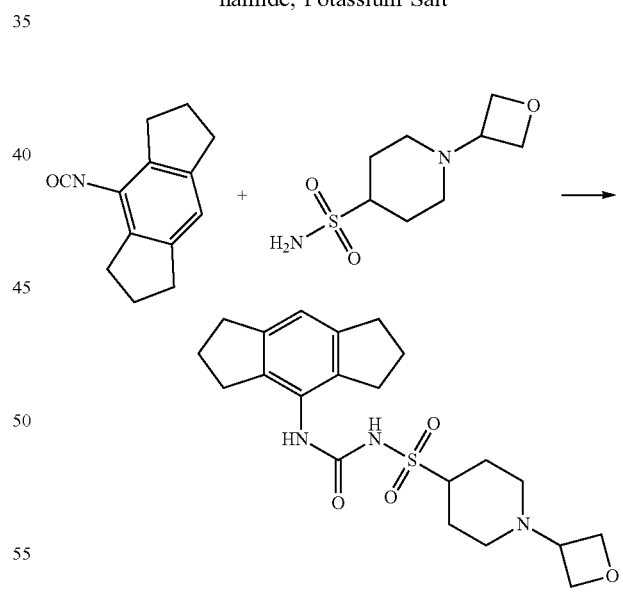

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(oxetan-3-yl)piperidine-4-sulfonamide (Intermediate P17) to afford the title compound (12%) as a white solid.

$^1$H NMR (CD$_3$OD) δ 6.86 (s, 1H), 4.62 (m, 4H), 3.47 (m, 1H), 3.4 (m, 1H), 2.82 (m, 10H), 2.18 (m, 2H), 2.02 (m, 4H) and 1.87 (m, 4H).

LCMS: m/z 420 (M+H)$^+$ (ES$^+$); 418 (M−H)$^−$ (ES$^−$).

Example 21: Methyl 2-(4-(N-((1,2,3,5,6,7-Hexahydro-s-indacen-4-yl) carbamoyl)sulfamoyl)piperidin-1-yl)acetate, Potassium Salt

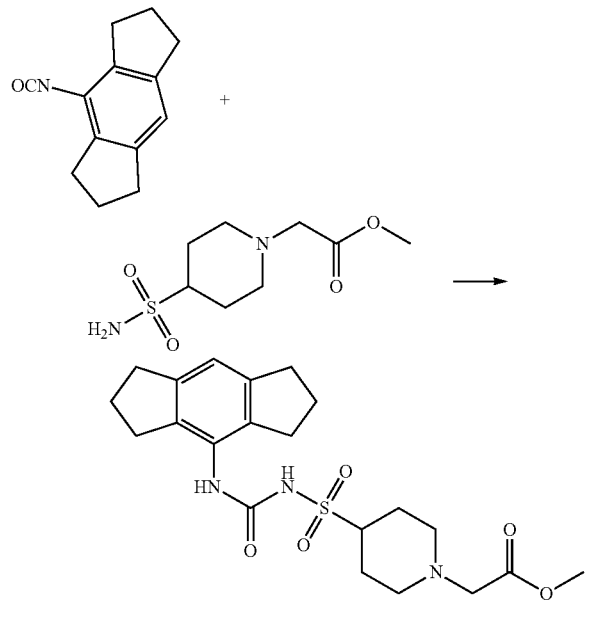

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and methyl 2-(4-sulfamoylpiperidin-1-yl)acetate (Intermediate P18) to afford the title compound (46%) as a white solid.

$^1$H NMR (CD$_3$OD) δ 6.86 (s, 1H), 3.69 (s, 3H), 3.3 (m, 2H), 3.24 (s, 2H), 3.03 (m, 2H), 2.82 (m, 8H), 2.22 (m, 2H) and 2.03 (m, 8H).

LCMS: m/z 436 (M+H)$^+$ (ES$^+$); 434 (M–H)$^-$ (ES$^-$).

Example 22: 1-(2-Fluoroethyl)-N-((1,2,3,5,6,7-hexahydro-s-indacen-4-yl)carbamoyl)piperidine-4-sulfonamide, Potassium Salt

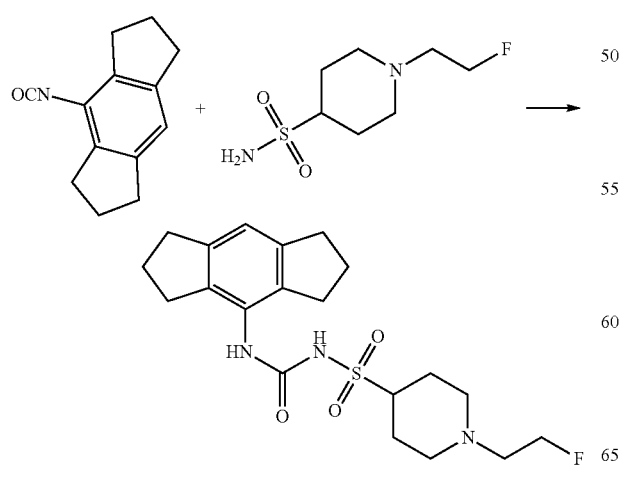

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(2-fluoroethyl)piperidine-4-sulfonamide to afford the title compound (14%) as a white solid.

$^1$H NMR (CD$_3$OD) δ 6.86 (s, 1H), 4.65 (m, 1H), 4.48 (m, 1H), 3.4 (m, 1H), 3.08 (m, 2H), 2.82 (m, 8H), 2.74 (m, 1H), 2.64 (m, 1H), 2.13 (m, 4H), 2.02 (m, 4H) and 1.9 (m, 2H).

LCMS: m/z 410 (M+H)$^+$ (ES$^+$).

Example 23: 1-Cyclopropyl-N-((1,2,3,5,6,7-hexahydro-s-indacen-4-yl)carbamoyl)piperidine-4-sulfonamide, Potassium Salt

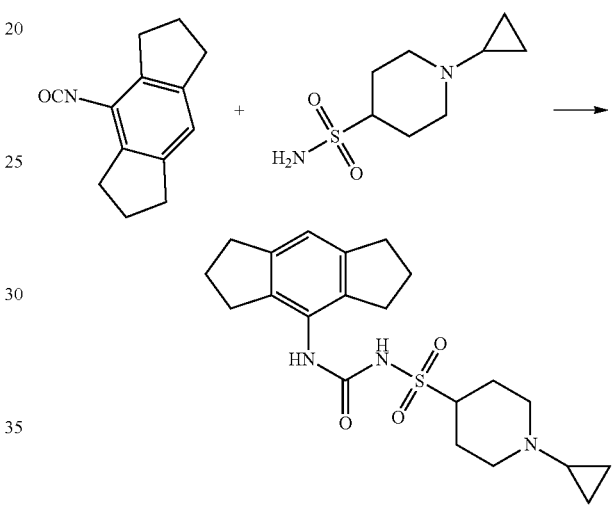

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-cyclopropylpiperidine-4-sulfonamide (Intermediate P19) to afford the title compound (17%) as a white solid.

$^1$H NMR (CD$_3$OD) δ 6.86 (s, 1H), 3.43 (m, 1H), 3.15 (m, 2H), 2.82 (m, 8H), 2.25 (m, 2H), 2.04 (m, 6H), 1.82 (m, 2H), 1.64 (m, 1H) and 0.44 (m, 4H).

LCMS: m/z 404 (M+H)$^+$ (ES$^+$); 402 (M–H)$^-$ (ES$^-$).

Example 24: 1-(1-Ethylazetidin-3-yl)-N-((1,2,3,5,6,7-hexahydro-s-indacen-4-yl)carbamoyl)piperidine-4-sulfonamide, Potassium Salt

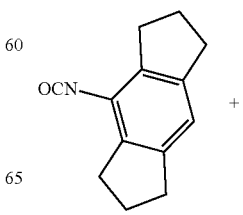

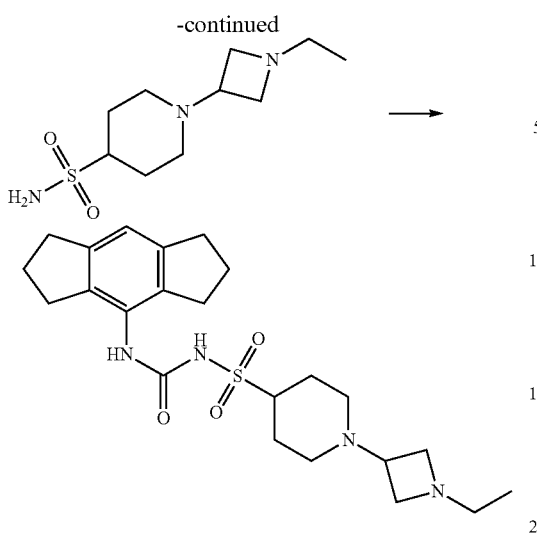

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(1-ethylazetidin-3-yl)piperidine-4-sulfonamide (Intermediate P20) to afford the title compound (34%) as a white solid.

$^1$H NMR (CD$_3$OD) δ 6.86 (s, 1H), 3.65 (m, 2H), 3.33 (m, 1H), 3.05 (m, 3), 2.82 (m, 10H), 2.63 (m, 2H), 2.14 (m, 2H), 2.02 (m, 4H), 1.83 (m, 4H), and 1.01 (t, 3H).

LCMS: m/z 447 (M+H)$^+$ (ES$^+$); 445 (M−H)$^−$ (ES$^−$).

Example 25: 1-(Cyclobutanecarbonyl)-N-((1,2,3,5,6,7-hexahydro-s-indacen-4-yl)carbamoyl)piperidine-4-sulfonamide, Potassium Salt

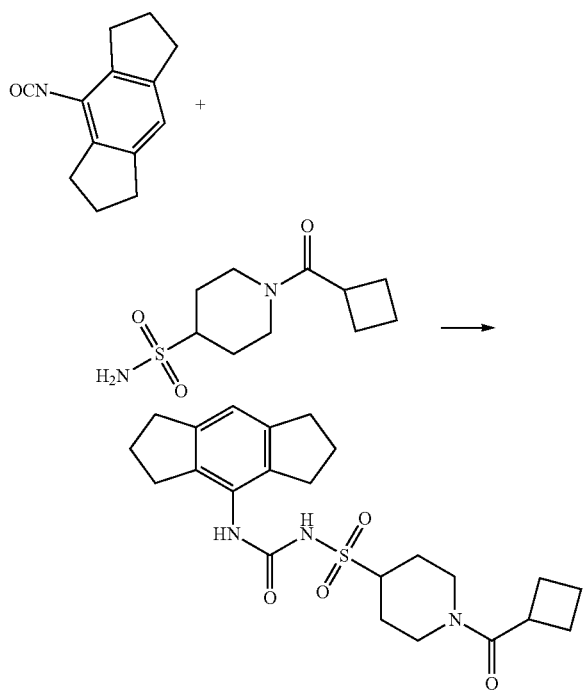

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(cyclobutanecarbonyl)piperidine-4-sulfonamide (Intermediate P21) to afford the title compound (29%) as a white solid.

$^1$H NMR (CD$_3$OD) δ 6.86 (s, 1H), 4.58 (m, 1H), 3.91 (m, 1H), 3.40 (m, 1H), 3.02 (m, 1H), 2.82 (m, 8H), 2.63 (m, 1H), 2.2 (m, 6H), 2.02 (m, 6H), 1.83 (m, 1H) and 1.67 (m, 2H).

LCMS: m/z 446 (M+H)$^+$ (ES$^+$); 444 (M−H)$^−$ (ES$^−$).

Example 26: N-Ethyl-4-(N-((1,2,3,5,6,7-hexahydro-s-indacen-4-yl) carbamoyl)sulfamoyl)piperidine-1-carboxamide, Potassium Salt

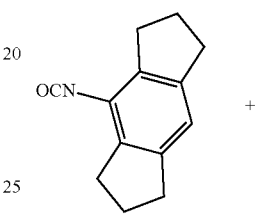

+

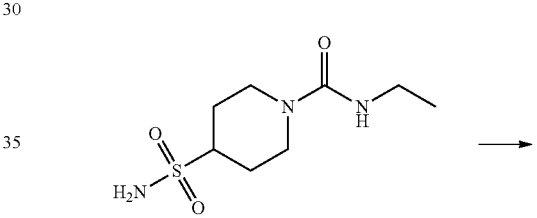

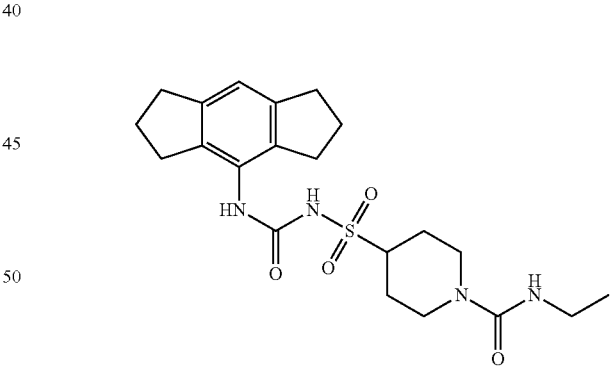

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and N-ethyl-4-sulfamoylpiperidine-1-carboxamide (Intermediate P22) to afford the title compound (5%) as a white solid.

$^1$H NMR (CD$_3$OD) δ 6.86 (s, 1H), 4.13 (m, 2H), 3.56 (m, 1H), 3.18 (m, 2H), 2.82 (m, 10H), 2.02 (m, 6H), 1.7 (m, 2H) and 1.1 (t, 3H).

LCMS: m/z 435 (M+H)$^+$ (ES$^+$).

Example 27: N-Cyclobutyl-3-(N-((1,2,3,5,6,7-hexahydro-s-indacen-4-yl)carbamoyl)sulfamoyl)piperidine-1-carboxamide, Potassium Salt

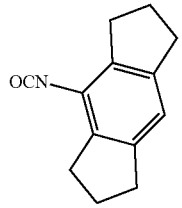
+
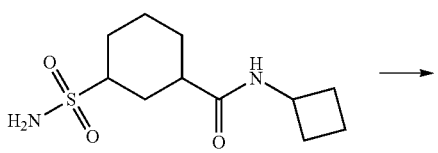
→
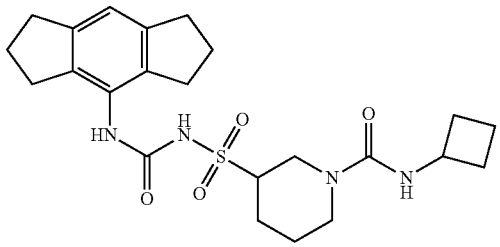

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and N-cyclobutyl-3-sulfamoylpiperidine-1-carboxamide to afford the title compound (11%) as a white solid.

$^1$H NMR (CD$_3$OD) δ 6.86 (s, 1H), 4.3 (m, 2H), 4.03 (m, 2H), 3.46 (m, 1H), 2.99 (m, 2H), 2.82 (m, 8H), 2.65 (m, 2H), 2.27 (m, 1H), 2.02 (m, 4H), 1.8 (m, 4H), 1.6 (m, 2H), 1.44 (m, 1H).

LCMS: m/z 461 (M+H)$^+$ (ES$^+$).

Example 28: 4-(N-((1,2,3,5,6,7-Hexahydro-s-indacen-4-yl)carbamoyl) sulfamoyl)-N-methylpiperidine-1-carboxamide, Potassium Salt

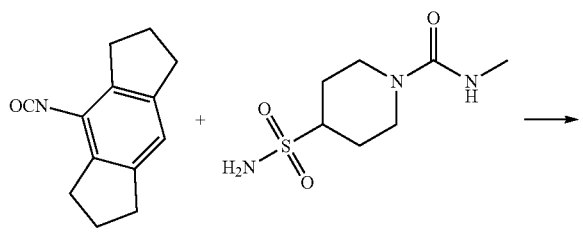
→
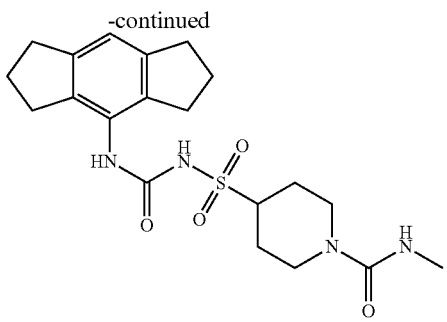

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and N-methyl-4-sulfamoylpiperidine-1-carboxamide (Intermediate P23) to afford the title compound (9%) as a white solid.

$^1$H NMR (CD$_3$OD) δ 6.86 (s, 1H), 4.11 (m, 2H), 3.55 (m, 1H), 3.02 (m, 1H), 2.82 (m, 9H), 2.73 (m, 1H), 2.7 (s, 3H), 2.02 (m, 6H) and 1.7 (m, 2H).

LCMS: m/z 421 (M+H)$^+$ (ES$^+$).

Example 29: N-((1,2,3,5,6,7-Hexahydro-s-indacen-4-yl)carbamoyl)-1-(methylsulfonyl)piperidine-4-sulfonamide, Potassium Salt

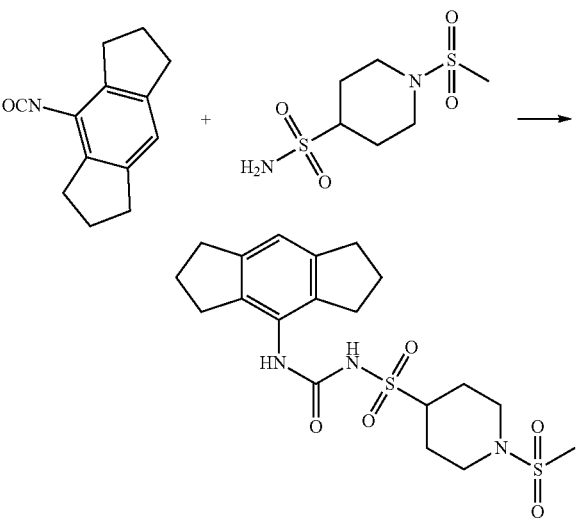

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(methylsulfonyl)piperidine-4-sulfonamide (Intermediate P24) to afford the title compound (33%) as a white solid.

$^1$H NMR (CD$_3$OD) rotamer mixture δ 6.86 (s, 1H), 3.92 (m, 2H, rotamer a), 3.82 (m, 2H, rotamer b), 3.55 (m, 1H), 3.0 (m, 1H) 2.82 (m, 12H), 2.22 (m, 2H), 2.02 (m, 4H), 1.87 (m, 2H).

LCMS: m/z 442 (M+H)$^+$ (ES$^+$).

Example 30: N-Ethyl-3-(N-((1,2,3,5,6,7-hexahydro-s-indacen-4-yl) carbamoyl)sulfamoyl)pyrrolidine-1-carboxamide, Potassium Salt

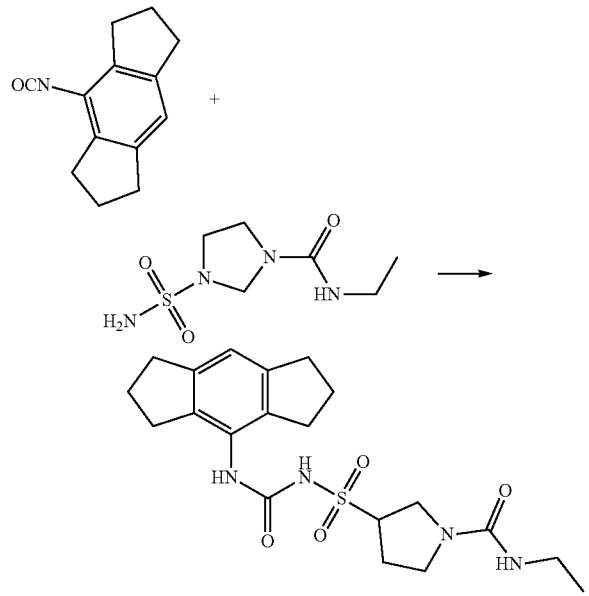

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and N-ethyl-3-sulfamoylpyrrolidine-1-carboxamide (Intermediate P25) to afford the title compound (48%) as a white solid.

$^1$H NMR (CD$_3$OD) δ 6.86 (s, 1H), 4.25 (m, 1H), 3.63 (m, 3H), 3.18 (m, 2H), 2.82 (m, 10H), 2.39 (m, 1H), 2.23 (m, 1H), 2.02 (m, 4H) and 1.08 (t, 3H).

LCMS: m/z 421 (M+H)$^+$ (ES$^+$); 419 (M−H)$^-$ (ES$^-$).

Example 31: N-((1,2,3,5,6,7-Hexahydro-s-indacen-4-yl)carbamoyl)-1-iso-propyl-piperidine-3-sulfonamide, Potassium Salt

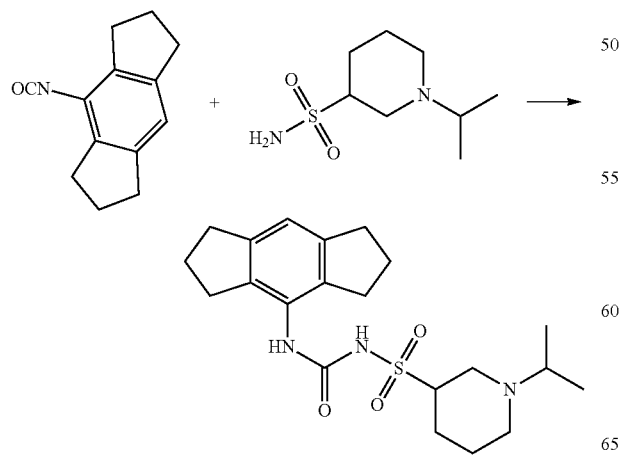

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-isopropylpiperidine-3-sulfonamide to afford the title compound (18%) as a white solid.

$^1$H NMR (CD$_3$OD) δ 6.89 (s, 1H), 3.78 (m, 1H), 3.5 (m, 1H), 3.05 (m, 1H), 2.8 (m, 8H), 2.7 (m, 2H), 2.45 (m, 1H), 2.21 (m, 1H), 2.02 (m, 4H), 1.86 (m, 1H), 1.67 (m, 2H) and 1.17 (d, 6H).

LCMS: m/z 406 (M+H)$^+$ (ES$^+$).

Example 32: N-((1,2,3,5,6,7-Hexahydro-s-indacen-4-yl)carbamoyl)-1-propionylpiperidine-3-sulfonamide, Potassium Salt

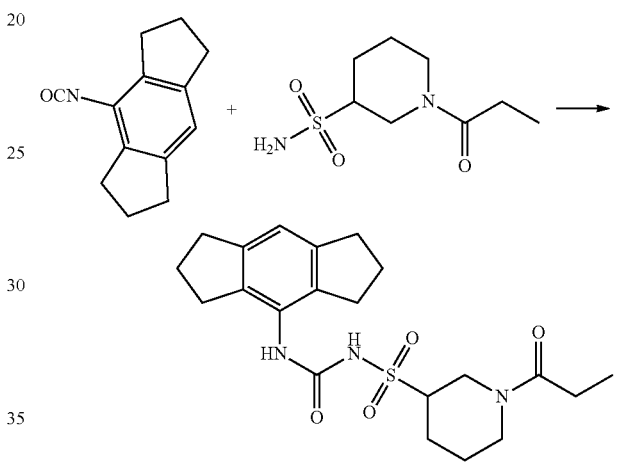

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-propionylpiperidine-3-sulfonamide to afford the title compound (2.7%) as a white solid.

$^1$H NMR (CD$_3$OD) rotamer mixture δ 6.87 (s, 1H), 4.96 (m, 1H, rotamer a), 4.4 (m, 1H, rotamer b), 4.28 (m, 1H, rotamer a), 3.87 (m, 1H, rotamer b), 3.52 (m, 1H), 3.01 (m, 1H), 2.82 (m, 8H), 2.64 (m, 1H), 2.42 (m, 2H), 2.28 (m, 1H), 2.02 (m, 4H), 1.85 (m, 2H), 1.5 (m, 1H) and 1.1 (t, 3H).

LCMS: m/z 420 (M+H)$^+$ (ES$^+$); 418 (M−H)$^-$ (ES$^-$).

Example 33: 3-(N-((1,2,3,5,6,7-Hexahydro-s-indacen-4-yl)carbamoyl) sulfamoyl)-N-iso-propylpiperidine-1-carboxamide, Potassium Salt

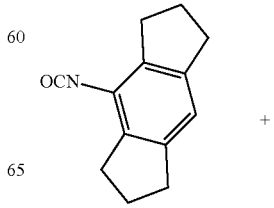

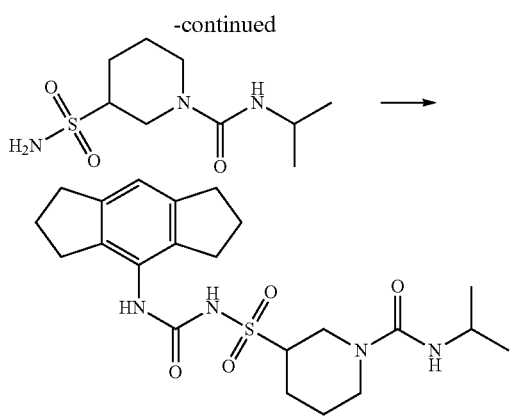

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and N-isopropyl-3-sulfamoylpiperidine-1-carboxamide (Intermediate P26) to afford the title compound (55%) as a white solid.

$^{1}$H NMR (CD$_{3}$OD) δ 6.86 (s, 1H), 4.35 (m, 1H), 4.0 (m, 1H), 3.85 (m, 1H), 3.42 (m, 1H), 2.82 (m, 9H), 2.68 (m, 2H), 2.28 (m, 1H), 2.02 (m, 4H), 1.79 (m, 2H), 1.45 (m, 1H) and 1.1 (d, 6H).

LCMS: m/z 449 (M+H)$^{+}$ (ES$^{+}$); 447 (M−H)$^{−}$ (ES$^{−}$).

Example 34: 1-(2-Fluoroethyl)-N-((1,2,3,5,6,7-hexahydro-s-indacen-4-yl)carbamoyl)piperidine-3-sulfonamide, Potassium Salt

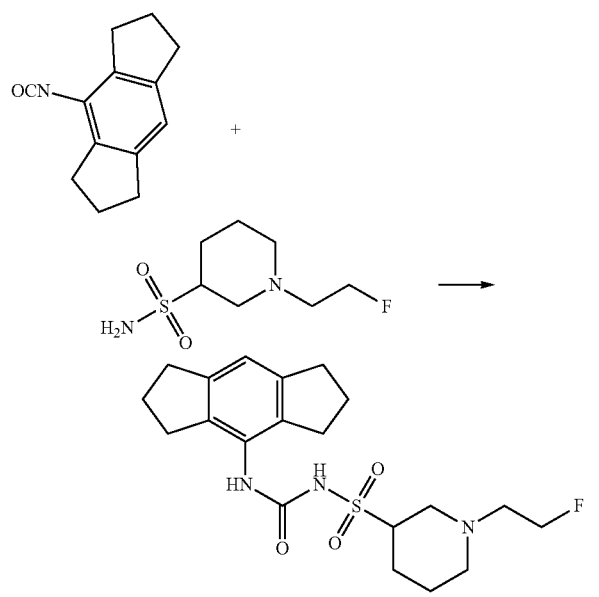

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(2-fluoroethyl)piperidine-3-sulfonamide to afford the title compound (2%) as a white solid.

$^{1}$H NMR (CD$_{3}$OD) δ 6.86 (s, 1H), 4.84 (m, 1H), 4.64 (m, 1H), 3.61 (m, 1H), 3.41 (m, 1H), 2.91 (m, 1H), 2.82 (m, 8H), 2.69 (m, 2H), 2.31 (m, 1H), 2.21 (m, 1H), 2.02 (m, 5H), 1.79 (m, 1H) and 1.61 (m, 2H).

LCMS: m/z 410 (M+H)$^{+}$ (ES$^{+}$); 408 (M−H)$^{−}$ (ES$^{−}$).

Example 35: N-((1,2,3,5,6,7-Hexahydro-s-indacen-4-yl)carbamoyl)-1,2,3,4-tetrahydroquinoline-3-sulfonamide, Potassium Salt

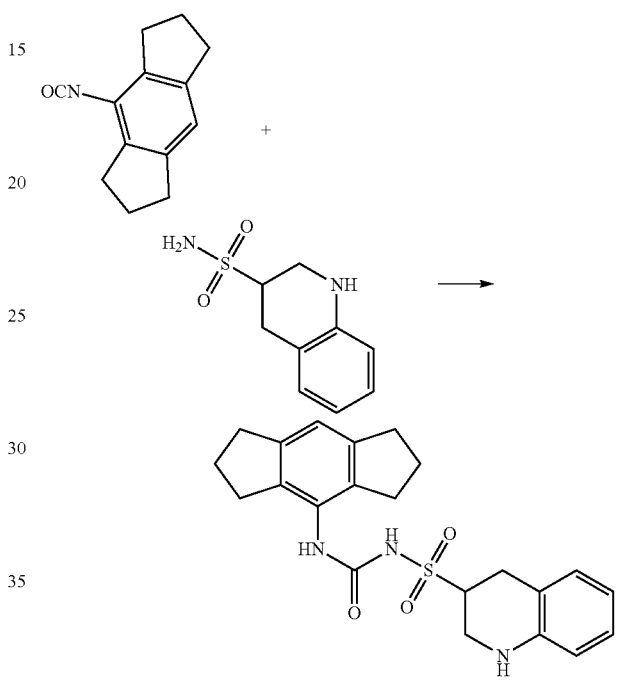

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1,2,3,4-tetrahydroquinoline-3-sulfonamide to afford the title compound (13%) as a white solid.

$^{1}$H NMR (CD$_{3}$OD) δ 6.92 (m, 3H), 6.58 (m, 2H), 3.92 (m, 2H), 3.73 (m, 2H), 3.11 (m, 2H), 2.82 (m, 8H) and 2.02 (m, 4H).

LCMS: m/z 412 (M+H)$^{+}$ (ES$^{+}$).

Example 36: N-((1,2,3,5,6,7-Hexahydro-s-indacen-4-yl)carbamoyl)-1-methylpyrrolidine-3-sulfonamide, Potassium Salt

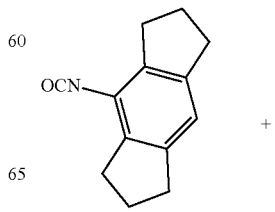

285

-continued

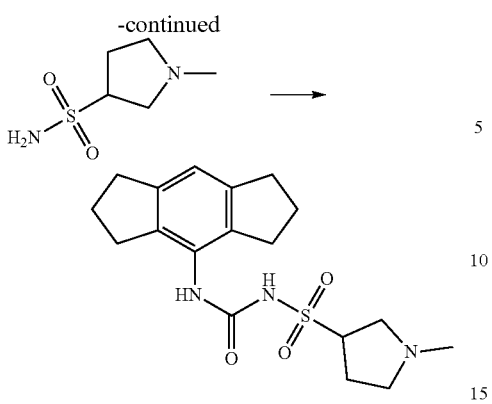

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-methyl-pyrrolidine-3-sulfonamide (Intermediate P27) to afford the title compound (19%) as a white solid.

$^1$H NMR (CD$_3$OD) δ 6.86 (s, 1H), 4.21 (m, 1H), 3.1 (m, 1H), 2.9 (m, 1H), 2.82 (m, 9H), 2.62 (m, 1H), 2.42 (s, 3H), 2.33 (m, 1H), 2.19 (m, 1H) and 2.02 (m, 4H).

LCMS: m/z 364 (M+H)$^+$ (ES$^+$); 362 (M−H)$^−$ (ES$^−$).

Example 37: 1-Ethyl-N-((1,2,3,5,6,7-hexahydro-s-indacen-4-yl)carbamoyl) pyrrolidine-3-sulfonamide, Potassium Salt

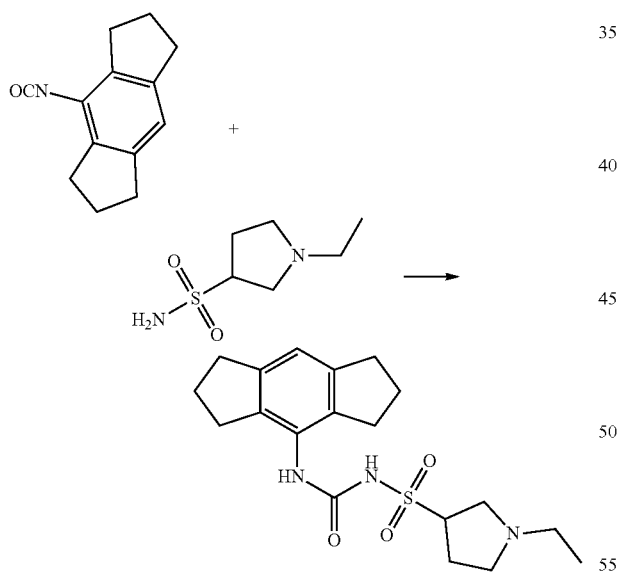

Prepared as described for N-((1,2,3,5,6,7-hexahydro-s-indacen-4-yl)carbamoyl)-1-(prop-2-yn-1-yl)piperidine-4-sulfonamide, potassium salt (example 2) using 4-isocyanato-1,2,3,5,6,7-hexahydro-s-indacene (Intermediate A1) and 1-ethyl-pyrrolidine-3-sulfonamide (Intermediate P28) to afford the title compound (30%) as a white solid.

$^1$H NMR (CD$_3$OD) δ 6.86 (s, 1H), 4.21 (m, 1H), 3.0 (m, 2H), 2.82 (m, 10H), 2.7 (m, 2H), 2.38 (m, 1H), 2.22 (m, 1H), 2.02 (m, 4H) and 1.18 (t, 3H).

LCMS: m/z 378 (M+H)$^+$ (ES$^+$); 376 (M−H)$^−$ (ES$^−$).

286

Example 38: 1-Acetyl-N-((1,2,3,5,6,7-hexahydro-s-indacen-4-yl)carbamoyl) pyrrolidine-3-sulfonamide, Potassium Salt

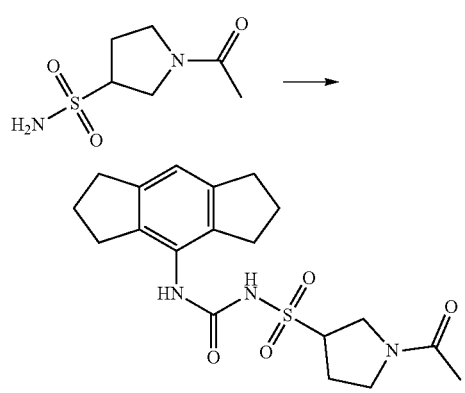

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-acetyl-pyrrolidine-3-sulfonamide (Intermediate P29) to afford the title compound (21%) as a white solid.

$^1$H NMR (CD$_3$OD) δ 6.86 (s, 1H), 4.24 (m, 1H), 3.9 (m, 1H), 3.75 (m, 1H), 3.57 (m, 1H), 3.45 (m, 1H), 2.82 (m, 8H), 2.38 (m, 2H) and 2.02 (m, 7H).

LCMS: m/z 392 (M+H)$^+$ (ES$^+$); 390 (M−H)$^−$ (ES$^−$).

Example 39: 1-Cyclopropyl-N-((1,2,3,5,6,7-hexahydro-s-indacen-4-yl) carbamoyl)pyrrolidine-3-sulfonamide, Potassium Salt

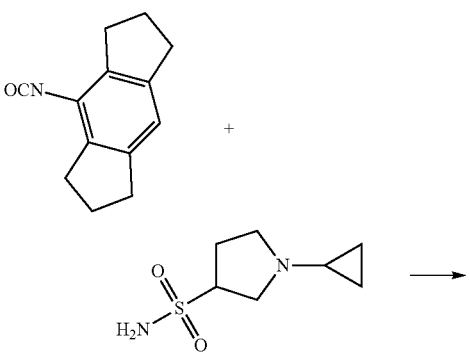

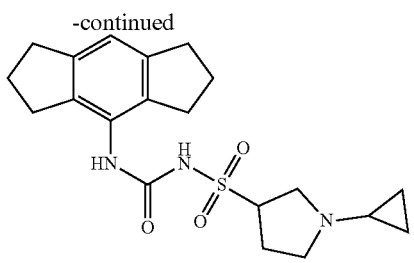

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-cyclopropyl-pyrrolidine-3-sulfonamide (Intermediate P30) to afford the title compound (30%) as a white solid.

$^1$H NMR (CD$_3$OD) δ 6.86 (s, 1H), 4.18 (m, 1H), 3.22 (m, 1H), 3.02 (m, 1H), 2.82 (m, 10H), 2.29 (m, 1H), 2.16 (m, 1H), 2.02 (m, 4H), 1.81 (m, 1H) and 1.45 (m, 4H).

LCMS: m/z 390 (M+H)$^+$ (ES$^+$); 388 (M–H)$^-$ (ES$^-$).

Example 40: 3-(N-((1,2,3,5,6,7-Hexahydro-s-indacen-4-yl) carbamoyl) sulfamoyl)-N,N-dimethylpyrrolidine-1-carboxamide

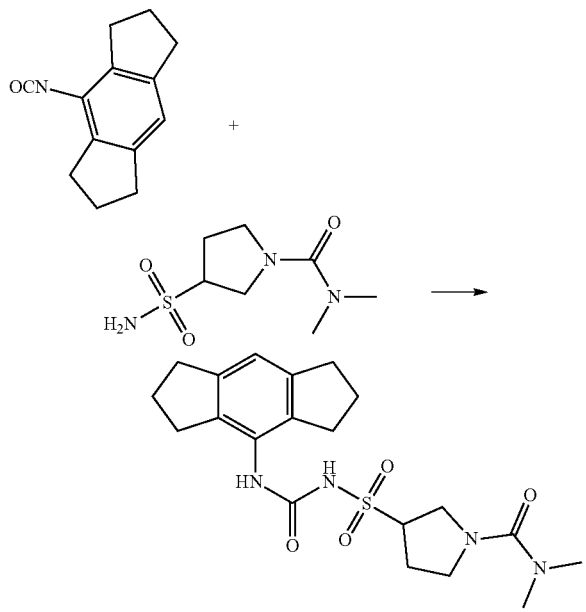

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and N,N-dimethyl-3-sulfamoylpyrrolidine-1-carboxamide (Intermediate P31) to afford the title compound as a white solid.

$^1$H NMR (CD$_3$OD) δ 6.86 (s, 1H), 4.18 (m, 1H), 3.82 (m, 1H), 3.64 (m, 2H), 3.44 (m, 1H), 2.86 (s, 6H), 2.82 (m, 8H), 2.34 (m, 1H), 2.19 (m, 1H) and 2.02 (m, 4H).

LCMS: m/z 421 (M+H)$^+$ (ES$^+$); 419 (M–H)$^-$ (ES$^-$).

Example 41: N-((1,2,3,5,6,7-Hexahydro-s-indacen-4-yl)carbamoyl)-1-iso-propylpyrrolidine-3-sulfonamide, Potassium Salt

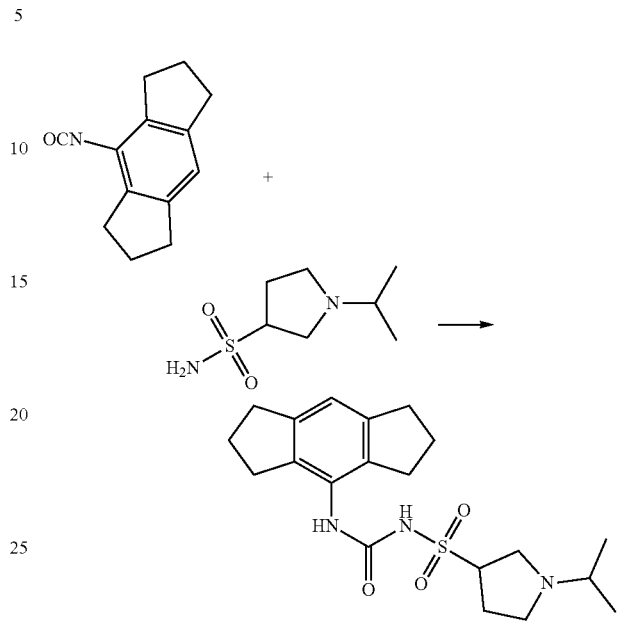

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-isopropylpyrrolidine-3-sulfonamide (Intermediate P32) to afford the title compound (36%) as a white solid.

$^1$H NMR (CD$_3$OD) δ 6.86 (s, 1H), 4.21 (m, 1H), 3.38 (m, 1H), 3.04 (m, 2H), 2.82 (m, 8H), 2.72 (m, 2H), 2.38 (m, 1H), 2.2 (m, 1H), 2.02 (m, 4H) and 1.19 (d, 6H).

LCMS: m/z 392 (M+H)$^+$ (ES$^+$); 390 (M–H)$^-$ (ES$^-$).

Example 42: N-((1,2,3,5,6,7-Hexahydro-s-indacen-4-yl)carbamoyl) azetidine-3-sulfonamide

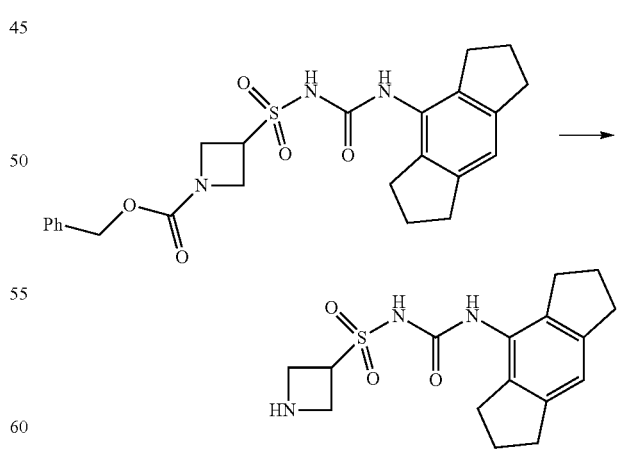

To a solution of benzyl 3-(N-((1,2,3,5,6,7-hexahydro-s-indacen-4-yl)carbamoyl) sulfamoyl)azetidine-1-carboxylate, potassium salt (Example 71) in methanol was added Pd/C and the reaction was heated to 65° C. under an atmosphere of hydrogen. Upon cooling, the mixture was filtered and purified by reversed phase chromatography (see "Experimental Methods", "Purification Method 1") to afford the title compound (28%) as a white solid.

$^{1}$H NMR (CD$_{3}$OD) 6.84 (s, 1H), 4.8 (s, 1H), 4.58 (m, 1H), 4.04 (m, 1H), 3.7 (m, 1H), 3.3 (m, 1H), 2.8 (m, 8H) and 2.02 (m, 4H).

LCMS: m/z 337 (M+H)$^{+}$ (ES$^{+}$).

Example 43: N-((1,2,3,5,6,7-Hexahydro-s-indacen-4-yl)carbamoyl) quinuclidine-3-sulfonamide, Potassium Salt

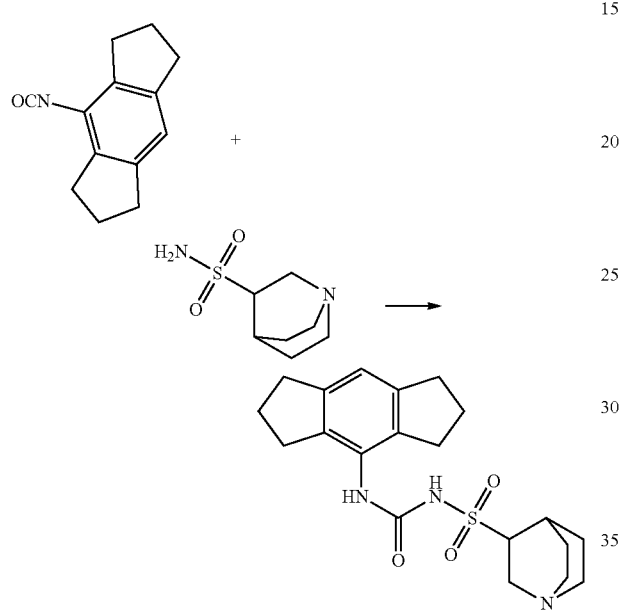

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and quinuclidine-3-sulfonamide (Intermediate P34) to afford the title compound (7%) as a white solid.

$^{1}$H NMR (300 MHz, CD$_{3}$OD) δ 6.86 (s, 1H), 4.18 (m, 1H), 3.97 (m, 1H), 3.82 (m, 1H), 3.62 (m, 1H), 3.58 (m, 2H), 3.08 (m, 1H), 2.82 (m, 8H), 2.41 (m, 2H), 2.02 (m, 4H), 1.77 (m, 2H) and 1.48 (m, 1H).

LCMS: m/z 390 (M+H)$^{+}$ (ES$^{+}$); 388 (M−H)$^{-}$ (ES$^{-}$).

Example 44: 1-(1-Ethylpiperidin-4-yl)-N-((1,2,3,5,6,7-hexahydro-s-indacen-4-yl)carbamoyl)pyrrolidine-3-sulfonamide, Potassium Salt

-continued

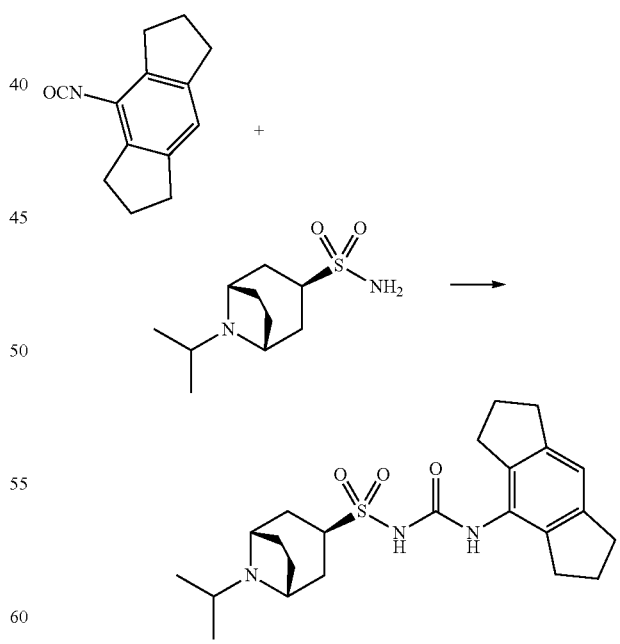

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(1-ethylpiperidin-4-yl)pyrrolidine-3-sulfonamide (Intermediate P35) to afford the title compound (29%) as a white solid.

$^{1}$H NMR (CD$_{3}$OD) δ 6.86 (s, 1H), 4.18 (m, 1H), 3.72 (m, 1H), 3.2 (m, 2H), 3.08 (m, 2H), 2.93 (m, 1H), 2.82 (m, 8H), 2.71 (m, 2H), 2.6 (m, 2H), 2.48 (m, 1H), 2.23 (m, 4H), 2.02 (m, 4H), 1.65 (m, 2H) and 1.18 (t, 3H).

LCMS: m/z 461 (M+H)$^{+}$ (ES$^{+}$); 459 (M−H)$^{-}$ (ES$^{-}$).

Example 45: (1R*,3R*,5S*)—N-((1,2,3,5,6,7-Hexahydro-s-indacen-4-yl)carbamoyl)-8-isopropyl-8-azabicyclo[3.2.1]octane-3-sulfonamide, Potassium Salt Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and (1R*,3R*,5S*)-8-isopropyl-8-azabicyclo[3.2.1]octane- 3-sulfonamide (Intermediate P36) to afford the title compound (12%) as a white solid.

$^1$H NMR (CD3OD) δ 6.86 (s, 1H), 4.02 (m, 1H), 2.82 (m, 8H), 2.68 (m, 1H), 2.22 (m, 10H), 2.02 (m, 4H) and 1.38 (d, 6H).

LCMS: m/z 432 (M+H)$^+$ (ES$^+$); 430 (M–H)$^-$ (ES$^-$).

Example 46: N-((1,2,3,5,6,7-Hexahydro-s-indacen-4-yl)carbamoyl)-1-iso-propylazetidine-3-sulfonamide, Potassium Salt

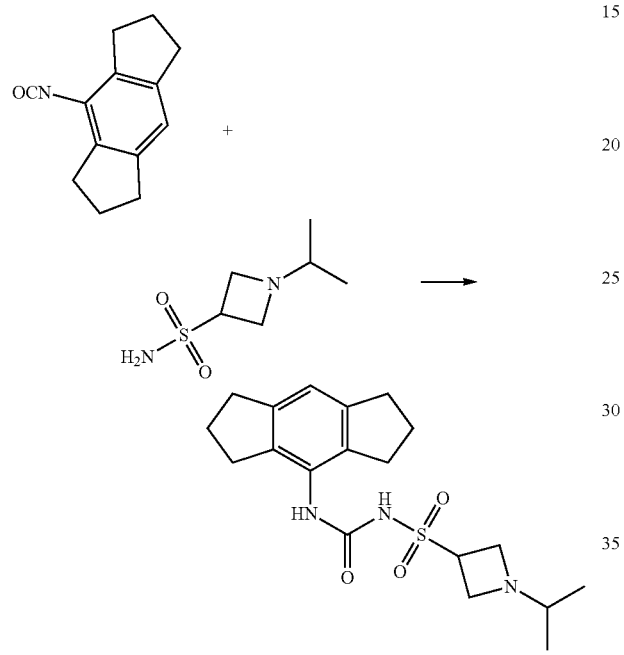

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-iso-propylazetidine-3-sulfonamide (Intermediate P37) to afford the title compound (57%) as a white solid.

$^1$H NMR (CD$_3$OD) δ 6.86 (s, 1H), 4.33 (m, 1H), 3.88 (m, 4H), 2.82 (m, 9H), 2.02 (m, 4H), and 1.03 (d, 6H).

LCMS: m/z 378 (M+H)$^+$ (ES$^+$); 376 (M–H)$^-$ (ES$^-$).

Example 47: N-((1,2,3,5,6,7-Hexahydro-s-indacen-4-yl)carbamoyl)-1-iso-propylpiperidine-4-sulfonamide, Potassium Salt

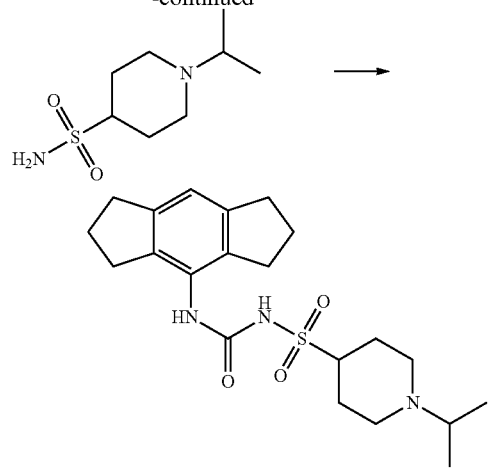

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-isopropylpiperidine-4-sulfonamide (Intermediate P138) to afford the title compound (59%) as a white solid.

$^1$H NMR (CD$_3$OD) δ 6.86 (s, 1H), 3.03 (m, 2H), 2.82 (m, 8H), 2.72 (m, 1H), 2.18 (m, 5H), 2.02 (m, 4H), 1.88 (m, 2H) and 1.07 (d, 6H).

LCMS: m/z 406 (M+H)$^+$ (ES$^+$); 404 (M–H)$^-$ (ES$^-$).

Example 48: 1'-Ethyl-N-((1,2,3,5,6,7-hexahydro-s-indacen-4-yl)carbamoyl)-[1,4'-bipiperidine]-4-sulfonamide, Potassium Salt

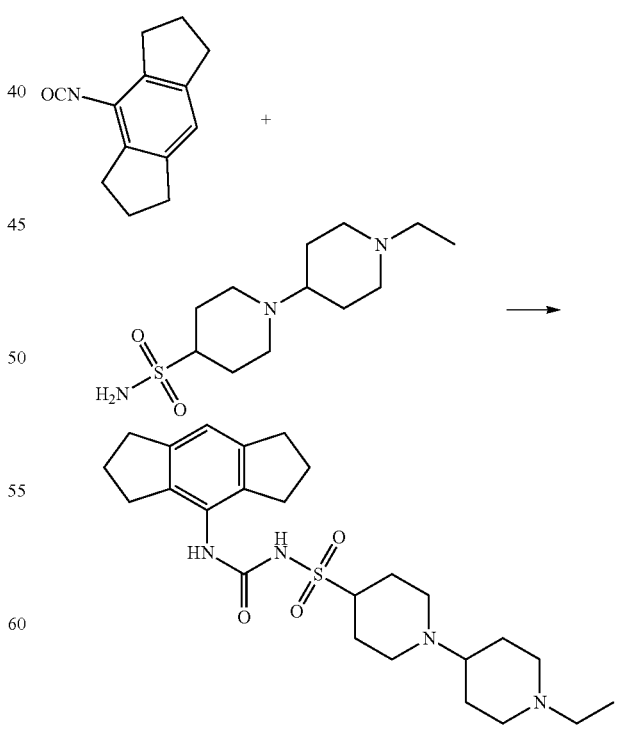

Prepared as described for N-((1,2,3,5,6,7-hexahydro-s-indacen-4-yl)carbamoyl)-1-(prop-2-yn-1-yl)piperidine-4- sulfonamide, potassium salt (Example 2) using 4-isocyanato-1,2,3,5,6,7-hexahydro-s-indacene (Intermediate A1) and 1'-ethyl-[1,4'-bipiperidine]-4-sulfonamide (Intermediate P38) to afford the title compound (22%) as a white solid.

¹H NMR (CD₃OD) δ 6.86 (s, 1H), 3.4 (m, 1H), 3.19 (m, 4H), 2.82 (m, 8H), 2.7 (m, 2H), 2.58 (m, 1H), 2.38 (m, 4H), 2.18 (m, 2H), 2.02 (m, 4H), 1.93 (m, 4H), 1.7 (m, 2H) and 1.18 (t, 3H).

LCMS: m/z 475 (M+H)⁺ (ES⁺); 473 (M−H)⁻ (ES⁻).

Example 49: N-((1,2,3,5,6,7-Hexahydro-s-indacen-4-yl)carbamoyl)-1-methylazetidine-3-sulfonamide, Potassium Salt

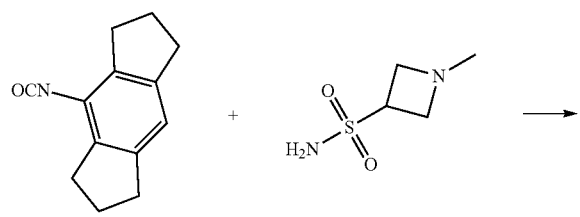

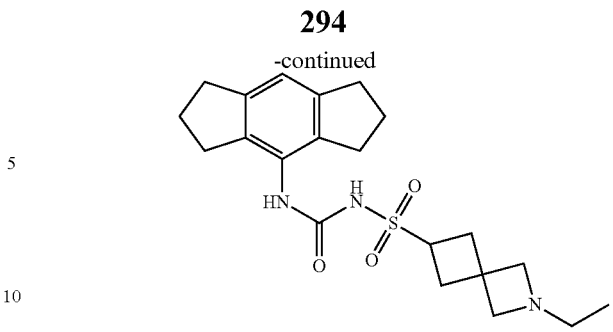

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-methylazetidine-3-sulfonamide (Intermediate P39) to afford the title compound (13%) as a white solid.

¹H NMR (CD₃OD) δ 6.86 (s, 1H), 4.35 (m, 1H), 4.18 (m, 4H), 2.82 (m, 8H), 2.77 (s, 3H) and 2.02 (m, 4H).

LCMS: m/z 350 (M+H)⁺ (ES⁺); 348 (M−H)⁻ (ES⁻).

Example 50: 2-Ethyl-N-((1,2,3,5,6,7-hexahydro-s-indacen-4-yl)carbamoyl)-2-azaspiro[3.3]heptane-6-sulfonamide, Potassium Salt

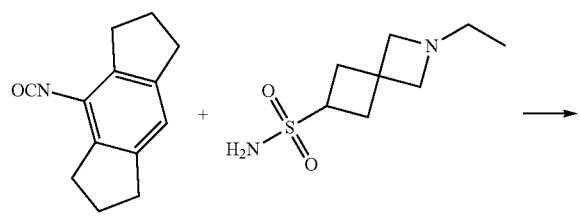

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 2-ethyl-2-azaspiro[3.3]heptane-6-sulfonamide (Intermediate P40) to afford the title compound (35%) as a white solid.

¹H NMR (CD₃OD) δ 6.86 (s, 1H), 4.05 (m, 1H), 3.61 (m, 4H), 2.82 (m, 8H), 2.73 (m, 2H), 2.64 (m, 2H), 2.53 (m, 2H), 2.02 (m, 4H) and 1.03 (t, 3H).

LCMS: m/z 404 (M+H)⁺ (ES⁺); 402 (M−H)⁻ (ES⁻).

Example 51: N-((1,2,3,5,6,7-Hexahydro-s-indacen-4-yl)carbamoyl)-1-(1-isopropylazetidin-3-yl)pyrrolidine-3-sulfonamide, Potassium Salt

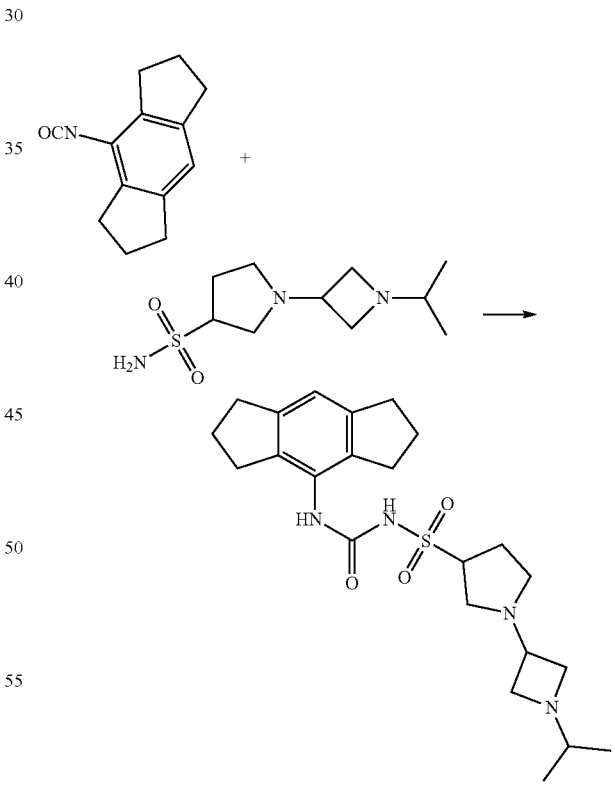

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(1-isopropyl-azetidin-3-yl)pyrrolidine-3-sulfonamide (Intermediate P41) to afford the title compound (21%) as a white solid.

¹H NMR (CD₃OD) δ 6.86 (s, 1H), 4.19 (m, 1H), 3.72 (m, 2H), 3.35 (m, 1H), 3.21 (m, 1H), 2.97 (m, 1H), 2.82 (m, 10H), 2.8 (m, 1H), 2.63 (m, 2H), 2.33 (m, 1H), 2.17 (m, 1H), 2.02 (m, 4H) and 1.03 (d, 6H).
LCMS: m/z 447 (M+H)⁺ (ES⁺).

Example 52: (1R*,3R*,5S*)-8-Ethyl-N-((1,2,3,5,6,7-hexahydro-s-indacen-4-yl)carbamoyl)-8-azabicyclo[3.2.1]octane-3-sulfonamide, Potassium Salt

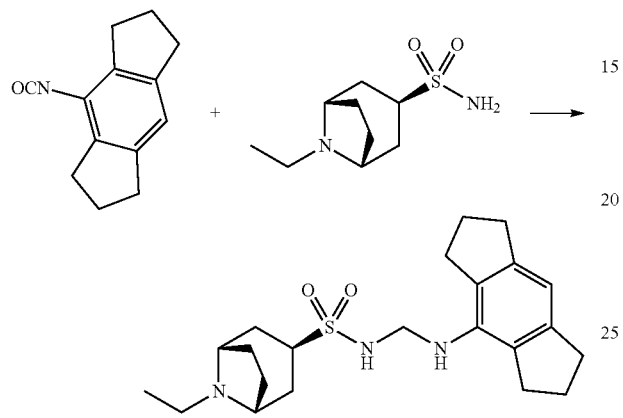

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and (1R*,3R*,5S*)-8-ethyl-8-azabicyclo[3.2.1]octane-3-sulfonamide (Intermediate P42) to afford the title compound (12%) as a white solid.
¹H NMR (CD₃OD) δ 6.86 (s, 1H), 3.91 (m, 1H), 3.64 (m, 2H), 2.82 (m, 10H), 2.5 (m, 3H), 2.29 (m, 3H), 2.02 (m, 6H) and 1.12 (t, 3H).
LCMS: m/z 418 (M+H)⁺ (ES⁺); 416 (M–H)⁻ (ES⁻).

Example 53: 1-Ethyl-N-((1,2,3,5,6,7-hexahydro-s-indacen-4-yl)carbamoyl) azetidine-3-sulfonamide, Potassium Salt

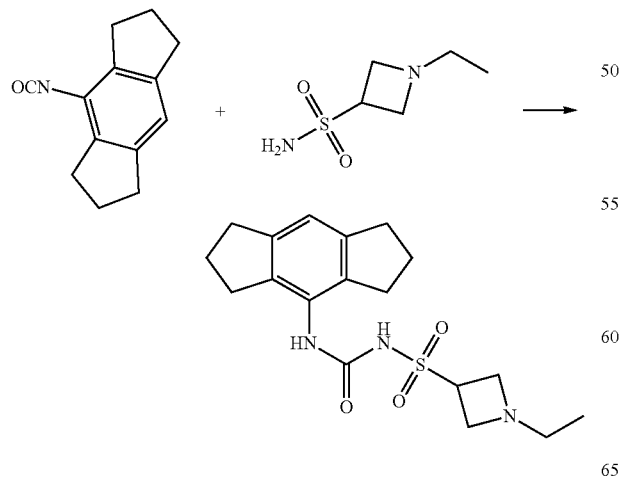

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-ethylazetidine-3-sulfonamide (Intermediate P43) to afford the title compound (18%) as a white solid.
¹H NMR (CD₃OD) δ 6.86 (s, 1H), 4.35 (m, 1H), 3.78 (m, 2H), 3.63 (m, 2H), 2.82 (m, 8H), 2.68 (m, 2H), 2.02 (m, 4H) and 1.01 (t, 3H).
LCMS: m/z 364 (M+H)⁺ (ES⁺); 362 (M–H)⁻ (ES⁻).

Example 54: N-((1,2,3,5,6,7-Hexahydro-s-indacen-4-yl)carbamoyl)-1-(2,2,2-trifluoroacetyl)pyrrolidine-3-sulfonamide, Potassium Salt

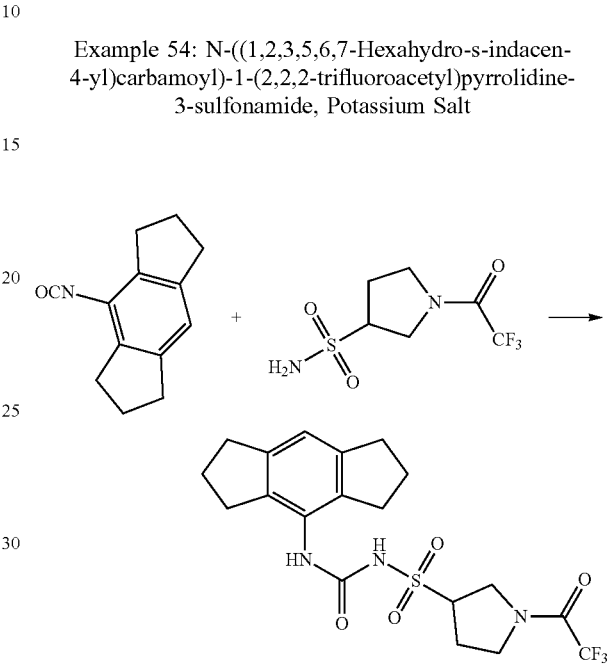

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(2,2,2-trifluoroacetyl)pyrrolidine-3-sulfonamide (Intermediate P44) to afford the title compound (15%) as a white solid.
¹H NMR (CD₃OD) δ 6.96 (s, 1H), 4.42 (m, 1H), 4.14 (m, 1H), 3.85 (m, 2H), 3.58 (m, 1H), 2.8 (m, 8H), 2.5 (m, 2H) and 2.04 (m, 4H).
LCMS: m/z 446 (M+H)⁺ (ES⁺); 444 (M–H)⁻ (ES⁻).

Example 55: N-((1,2,3,5,6,7-Hexahydro-s-indacen-4-yl)carbamoyl pyrrolidine-3-sulfonamide, Potassium Salt

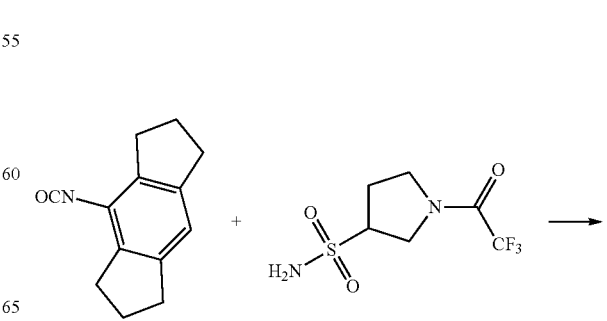

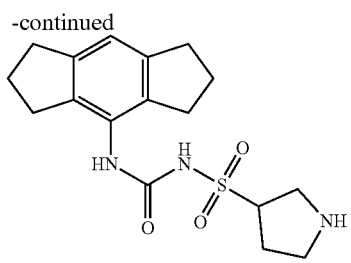

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(2,2,2-trifluoroacetyl)pyrrolidine-3-sulfonamide (Intermediate P44) to afford the deprotected title compound (5%) as a white solid.

$^1$H NMR (CD$_3$OD) δ 6.86 (s, 1H), 4.58 (m, 1H), 4.22 (m, 1H), 3.65 (m, 1H), 3.38 (m, 1H), 3.19 (m, 1H), 2.82 (m, 8H), 2.45 (m, 1H), 2.29 (m, 1H), and 2.02 (m, 4H).

LCMS: m/z 350 (M+H)$^+$ (ES$^+$); 348 (M−H)$^−$ (ES$^−$).

Example 56: 1-Acetyl-N-((1,2,3,5,6,7-hexahydro-s-indacen-4-yl)carbamoyl) piperidine-3-sulfonamide, Potassium Salt

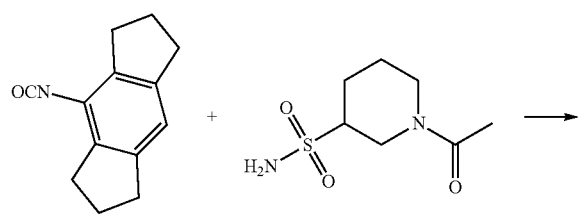

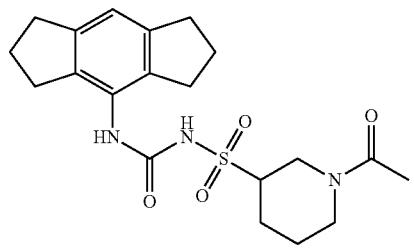

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-acetyl-piperidine-3-sulfonamide to afford the title compound (33%) as a white solid.

$^1$H NMR (CD$_3$OD) rotamer mixture δ 6.87 (s, 1H), 4.96 (m, 1H, rotamer), 4.32 (m, 1H, rotamer), 4.25 (m, 1H, rotamer), 3.85 (m, 1H, rotamer), 3.55 (m, 1H), 3.05 (m, 1H), 2.82 (m, 8H), 2.69 (m, 1H), 2.27 (m, 1H), 2.17 (s, 3H, rotamer), 2.09 (s, 3H, rotamer), 2.02 (m, 4H), 1.85 (m, 2H), 1.5 (m, 1H).

LCMS: m/z 406 (M+H)$^+$ (ES$^+$); 404 (M−H)$^−$ (ES$^−$).

Example 57: 1-(Cyclopropylmethyl)-N-((1,2,3,5,6,7-hexahydro-s-indacen-4-yl)carbamoyl)piperidine-3-sulfonamide, Potassium Salt

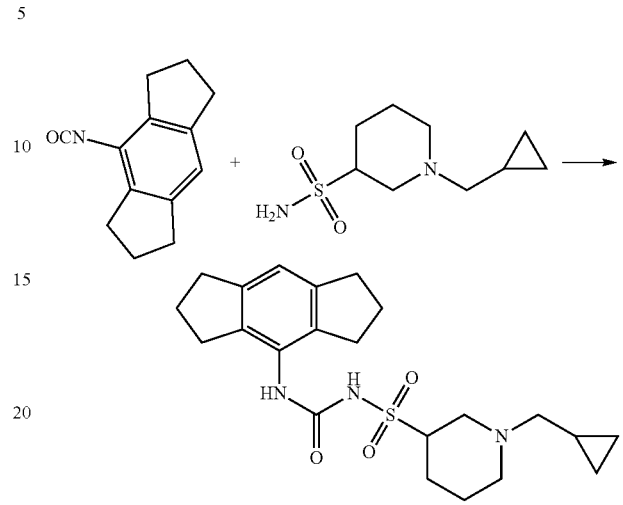

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(cyclopropylmethyl)piperidine-3-sulfonamide (Intermediate P45) to afford the title compound (21%) as a white solid.

$^1$H NMR (CD$_3$OD) δ 6.86 (s, 1H), 3.72 (m, 2H), 3.06 (m, 1H), 2.8 (m, 8H), 2.5 (m, 3H), 2.22 (m, 2H), 2.02 (m, 4H), 1.85 (m, 2H), 1.65 (m, 2H), 0.6 (m, 2H) and 0.21 (m, 2H).

LCMS: m/z 418 (M+H)$^+$ (ES$^+$); 416 (M−H)$^−$ (ES$^−$).

Example 58: 1-(Cyanomethyl)-N-((1,2,3,5,6,7-hexahydro-s-indacen-4-yl)carbamoyl)piperidine-3-sulfonamide, Potassium Salt

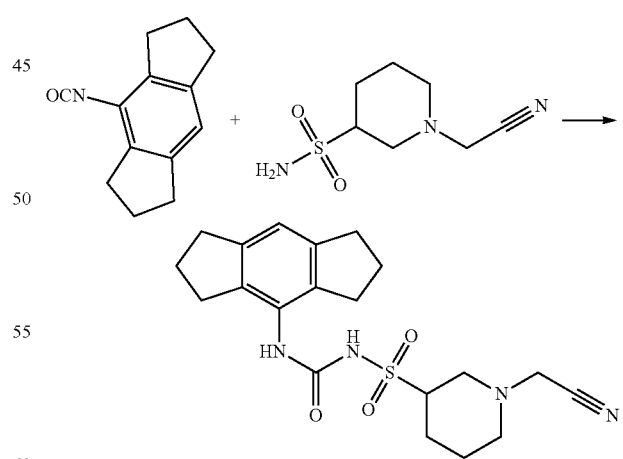

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(cyanomethyl) piperidine-3-sulfonamide to afford the title compound (41%) as a white solid.

¹H NMR (CD₃OD) δ 6.86 (s, 1H), 3.67 (s, 2H), 3.6 (m, 1H), 3.29 (m, 2H), 2.82 (m, 8H), 2.47 (t, 1H), 2.21 (m, 2H), 2.02 (m, 4H), 1.84 (m, 1H) and 1.58 (m, 2H).
LCMS: m/z 403 (M+H)⁺ (ES⁺); 401 (M−H)⁻ (ES⁻).

Example 59: N-((1,2,3,5,6,7-Hexahydro-s-indacen-4-yl)carbamoyl)-1-(prop-2-yn-1-yl)piperidine-3-sulfonamide, Potassium Salt

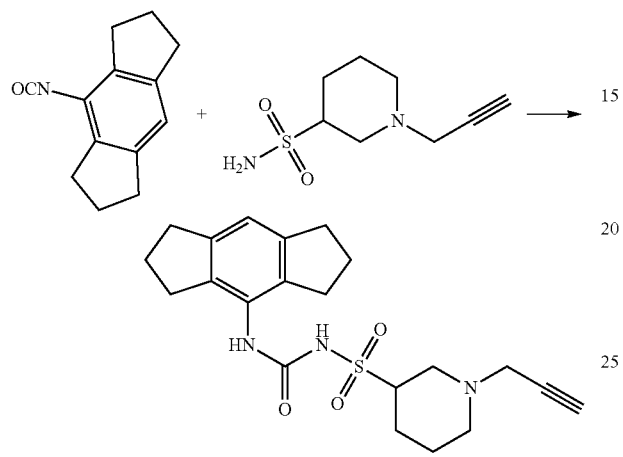

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(prop-2-yn-1-yl)piperidine-3-sulfonamide to afford the title compound (44%) as a white solid.
¹H NMR (CD₃OD) δ 6.86 (s, 1H), 3.57 (m, 1H), 3.33 (m, 4H), 2.82 (m, 8H), 2.65 (m, 1H), 2.42 (t, 1H), 2.2 (m, 2H), 2.02 (m, 4H), 1.82 (m, 1H) and 1.58 (m, 2H).
LCMS: m/z 402 (M+H)⁺ (ES⁺); 400 (M−H)⁻ (ES⁻).

Example 60: N-((1,2,3,5,6,7-Hexahydro-s-indacen-4-yl)carbamoyl)-1-methylpiperidine-3-sulfonamide, Potassium Salt

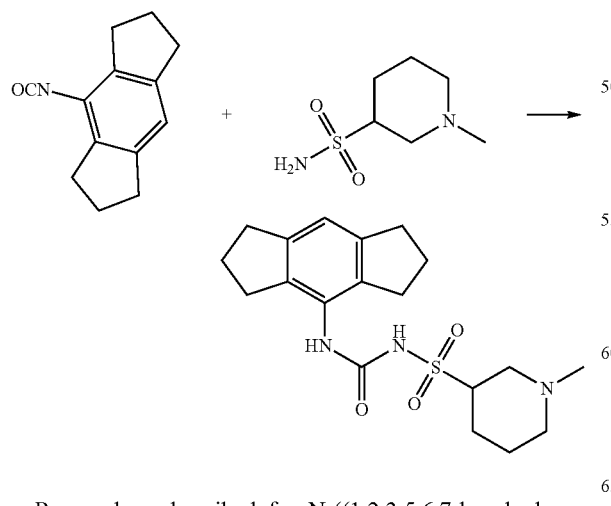

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-methylpiperidine-3-sulfonamide (Intermediate P46) to afford the title compound (11%) as a white solid.
¹H NMR (CD₃OD) δ 6.88 (s, 1H), 3.68 (m, 1H), 3.4 (m, 1H), 2.82 (m, 9H), 2.43 (m, 1H), 2.42 (s, 3H), 2.2 (m, 2H), 2.02 (m, 4H), 1.9 (m, 1H), and 1.64 (m, 2H).
LCMS: m/z 378 (M+H)⁺ (ES⁺).

Example 61: 4-(N-((1,2,3,5,6,7-Hexahydro-s-indacen-4-yl)carbamoyl) sulfamoyl)-N,N-dimethylpiperidine-1-carboxamide

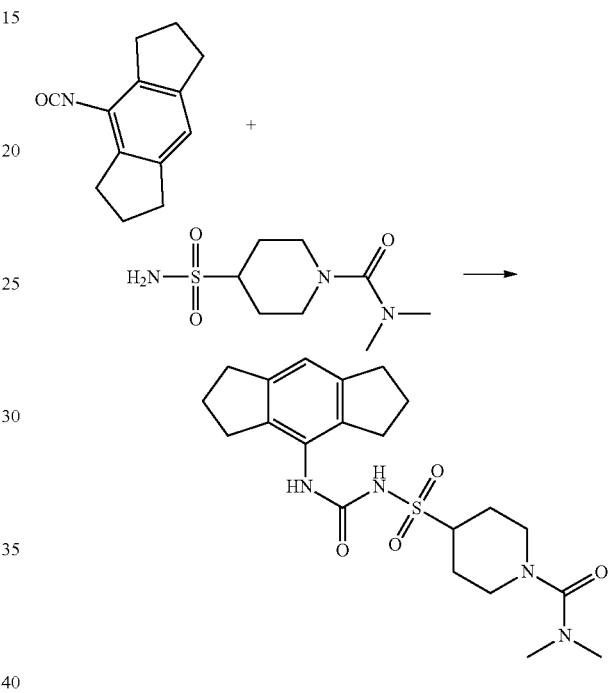

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and N,N-dimethyl-4-sulfamoylpiperidine-1-carboxamide (Intermediate P48) to afford the title compound (46%) as a white solid.
¹H NMR (CD₃OD) δ 6.86 (s, 1H), 3.78 (m, 2H), 3.50 (m, 1H), 2.82 (m, 10H), 2.80 (s, 6H), 2.05 (m, 6H) and 1.8 (m, 2H).
LCMS: m/z 435 (M+H)⁺ (ES⁺); 433 (M−H)⁻ (ES⁻).

Example 62: N-((1,2,3,5,6,7-Hexahydro-s-indacen-4-yl)carbamoyl)-1-(1-isopropylazetidin-3-yl)piperidine-4-sulfonamide, Potassium Salt

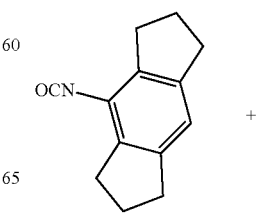

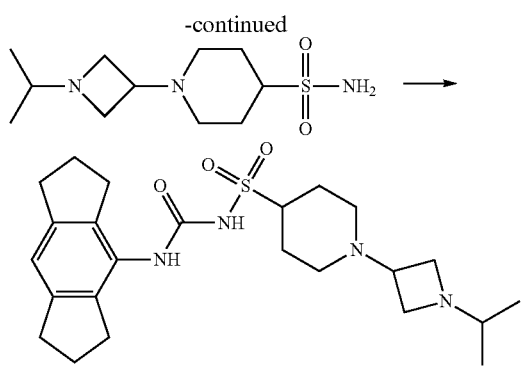

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(1-isopropylazetidin-3-yl)piperidine-4-sulfonamide (Intermediate P49) to afford the title compound (37%) as a white solid.

$^1$H NMR (CD$_3$OD): δ=6.88 (s, 1H), 4.59 (s, 1H), 3.75 (t, 2H), 3.02 (d, 2H), 2.99-2.69 (m, 12H), 2.13 (d, 2H), 2.02 (m, 4H), 1.95-1.76 (m, 4H), 1.05 (d, 6H).

LCMS: m/z 461 (M+H)$^+$ (ES$^+$); 459 (M–H)$^-$ (ES$^-$).

Example 63: N-((1,2,3,5,6,7-Hexahydro-s-indacen-4-yl)carbamoyl)-2-isopropyl-2-azaspiro[3.3]heptane-6-sulfonamide, Potassium Salt

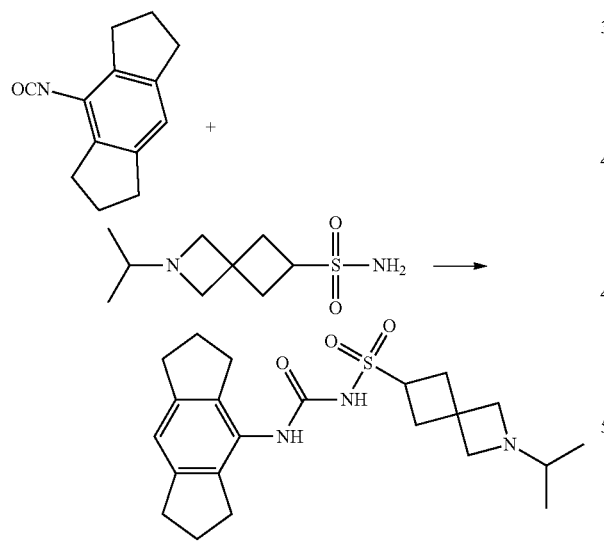

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 2-isopropyl-2-azaspiro[3.3]heptane-6-sulfonamide (Intermediate P50) to afford the title compound (41%) as a white solid.

$^1$H NMR (CD$_3$OD): δ=6.89 (s, 1H), 4.28-3.80 (m, 5H), 3.26-3.12 (m, 1H), 2.81 (dt, 8H), 2.73-2.55 (m, 4H), 2.04 (q, 4H), 1.14 (d, 6H).

LCMS: m/z 418 (M+H)$^+$ (ES$^+$); 416 (M–H)$^-$ (ES$^-$).

Example 64: N-((1,2,3,5,6,7-Hexahydro-s-indacen-4-yl)carbamoyl)-2-methyl-2-azaspiro[3.3]heptane-6-sulfonamide, Potassium Salt

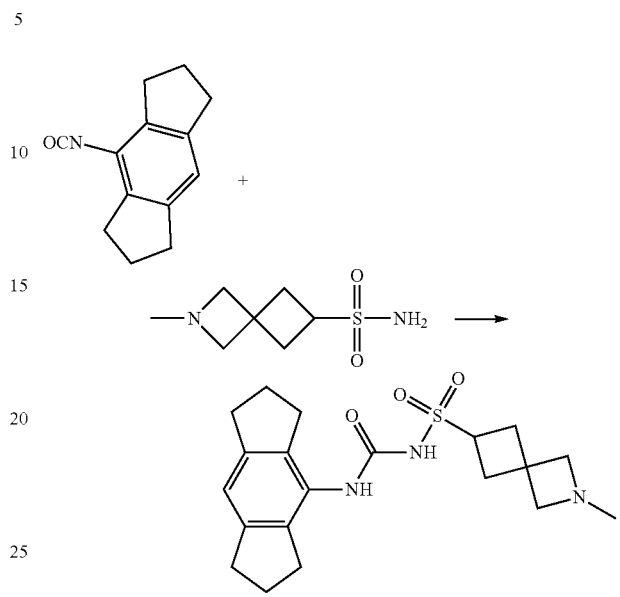

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 2-methyl-2-azaspiro[3.3]heptane-6-sulfonamide (Intermediate P51) to afford the title compound (14%) as a white solid.

$^1$H NMR (CD$_3$OD): δ=6.88 (s, 1H), 4.04 (m, 5H), 2.96-2.72 (m, 11H), 2.72-2.55 (m, 4H), 2.02 (m, 4H).

LCMS: m/z 390 (M+H)$^+$ (ES$^+$); 388 (M–H)$^-$ (ES$^-$).

Example 65: N-((1,2,3,5,6,7-Hexahydro-s-indacen-4-yl)carbamoyl)-1-(pentan-3-yl)azetidine-3-sulfonamide, Potassium Salt

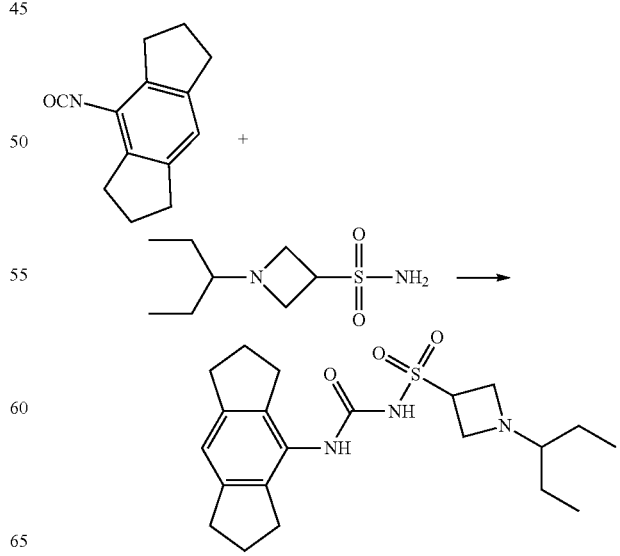

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(pentan-3-yl)azetidine-3-sulfonamide (Intermediate P52) to afford the title compound (31%) as a white solid.

¹H NMR (CD₃OD): δ=6.86 (s, 1H), 4.31 (m, 1H), 4.16 (m, 4H), 2.82 (m, 9H), 2.04 (q, 4H), 1.78-1.41 (m, 4H), 0.92 (t, 6H).

LCMS: m/z 406 (M+H)⁺ (ES⁺); 404 (M−H)⁻ (ES⁻).

Example 66: 1-Ethyl-N-((1,2,3,5,6,7-hexahydro-s-indacen-4-yl)carbamoyl)-1,2,3,4-tetrahydroquinoline-3-sulfonamide, Potassium Salt

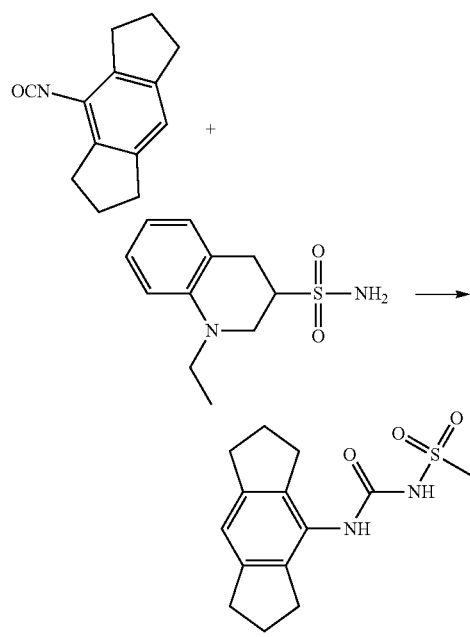

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-ethyl-1,2,3,4-tetrahydroquinoline-3-sulfonamide (Intermediate P53) to afford the title compound (33%) as a white solid.

¹H NMR (CD₃OD): δ=6.95 (m, 3H), 6.81-6.51 (m, 2H), 3.76-3.41 (m, 2H), 3.21-3.01 (m, 2H), 2.83 (m, 10H), 2.29-1.91 (m, 5H), 1.15 (t, 3H).

LCMS: m/z 440 (M+H)⁺ (ES⁺); 438 (M−H)⁻ (ES⁻).

Example 67: N-((1,2,3,5,6,7-Hexahydro-s-indacen-4-yl)carbamoyl)-1-(2,2,2-trifluoroethyl)piperidine-4-sulfonamide, Potassium Salt

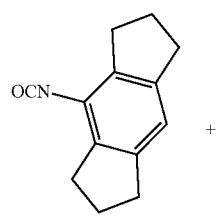

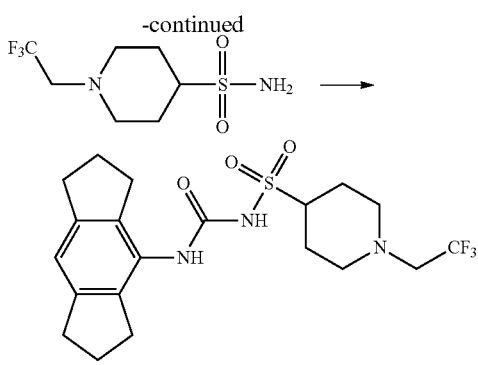

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(2,2,2-trifluoroethyl)piperidine-4-sulfonamide (Intermediate P54) to afford the title compound (49%) as a white solid.

¹H NMR (CD₃OD): δ=6.96 (s, 1H), 3.66-3.39 (m, 1H), 3.09 (dt, 5H), 2.82 (dt, 9H), 2.44 (t, 2H), 2.05 (m, 4H), 1.90 (dd, 2H).

LCMS: m/z 446 (M+H)⁺ (ES⁺); 444 (M−H)⁻ (ES⁻).

Example 68: N-((1,2,3,5,6,7-Hexahydro-s-indacen-4-yl)carbamoyl)-1-isopropyl-2-oxopyrrolidine-3-sulfonamide, Potassium Salt

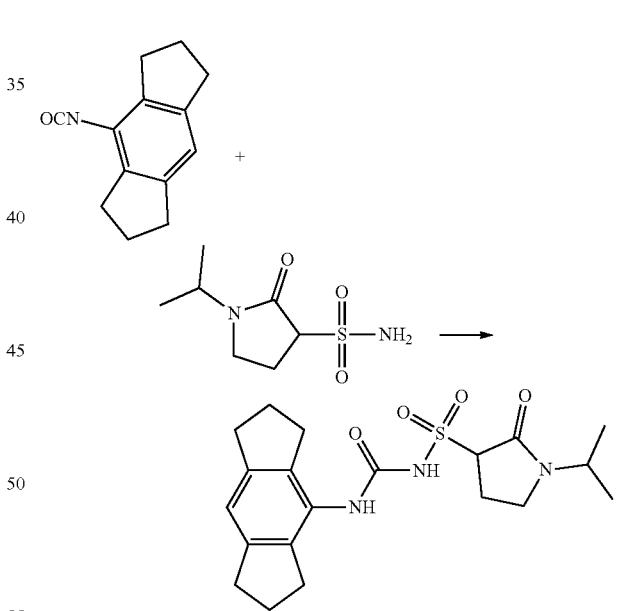

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-isopropyl-2-oxopyrrolidine-3-sulfonamide (Intermediate P64) to afford the title compound (64%) as a white solid.

¹H NMR (CD₃OD): δ=6.88 (s, 1H), 4.47-4.13 (m, 2H), 3.52 (dt, 1H) 3.32 (dt, 1H), 2.82 (q, 8H), 2.68-2.46 (m, 1H), 2.46-2.25 (m, 1H), 2.15-1.89 (m, 4H), 1.15 (d, 6H).

LCMS: m/z 406 (M+H)⁺ (ES⁺); 404 (M−H)⁻ (ES⁻).

Example 69: N-((1,2,3,5,6,7-Hexahydro-s-indacen-4-yl)carbamoyl)-8-isopropyl-8-azabicyclo[3.2.1]octane-3-sulfonamide Exo-Isomer, Potassium Salt

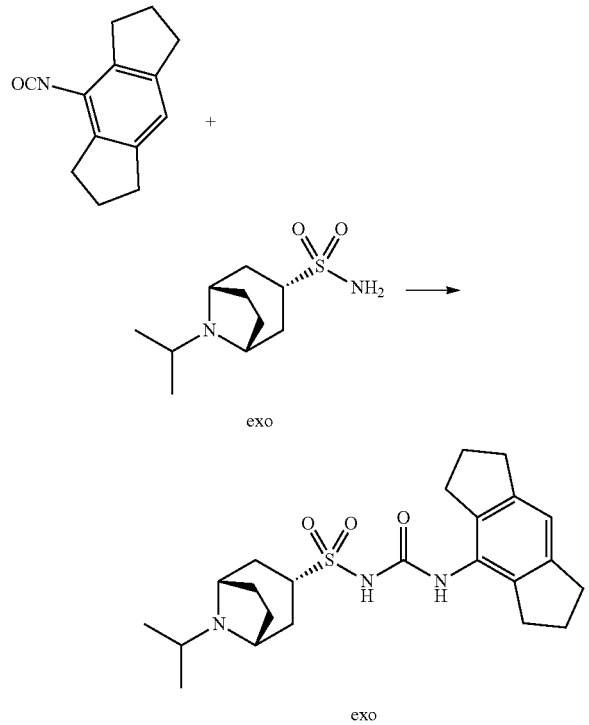

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and (1R*,3S*,5S*)-8-iso-propyl-8-azabicyclo[3.2.1]octane-3-sulfonamide (Intermediate P55) to afford the title compound (40%) as a white solid.

$^{1}$H NMR (CD$_3$OD): δ=6.95 (s, 1H), 4.57 (s, 1H), 4.34 (s, 1H), 4.12 (s, 1H), 2.85 (dt, 9H), 2.59 (s, 1H), 2.47-2.16 (m, 5H), 2.06 (m, 6H), 1.41 (d, 6H).

LCMS: m/z 432 (M+H)$^+$ (ES$^+$); 430 (M−H)$^-$ (ES$^-$).

Example 70: N-((1,2,3,5,6,7-Hexahydro-s-indacen-4-yl)carbamoyl)-8-ethyl-8-azabicyclo[3.2.1]octane-3-sulfonamide Exo Isomers, Potassium Salt

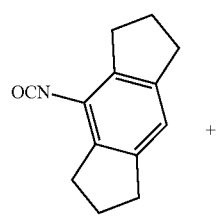

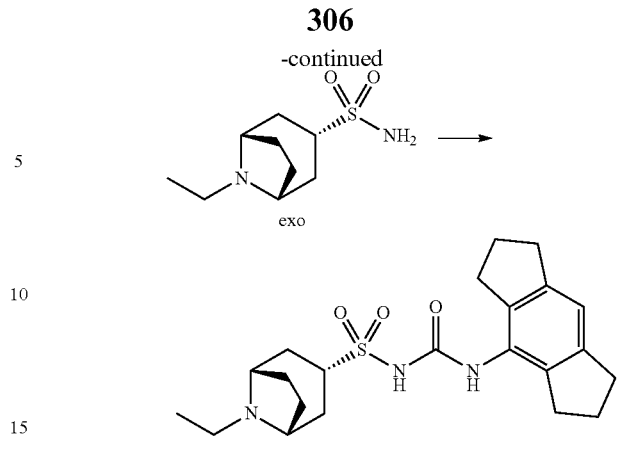

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and (1R*,3S*,5S*)-8-ethyl-8-azabicyclo[3.2.1]octane-3-sulfonamide (Intermediate P56) to afford the title compound (23%) as a white solid.

$^{1}$H NMR (CD$_3$OD): δ=6.91 (s, 1H), 4.57 (s, 1H), 3.99 (d, 3H), 3.84-3.64 (m, 1H), 3.47 (dt, 2H), 3.04 (q, 2H), 2.85 (q, 9H), 2.65-2.40 (m, 1H), 2.40-1.65 (m, 9H).

LCMS: m/z 418 (M+H)$^+$ (ES$^+$); 416 (M−H)$^-$ (ES$^-$).

Example 71: Benzyl 3-(N-((1,2,3,5,6,7-hexahydro-s-indacen-4-yl)carbamoyl)sulfamoyl)azetidine-1-carboxylate, Potassium Salt

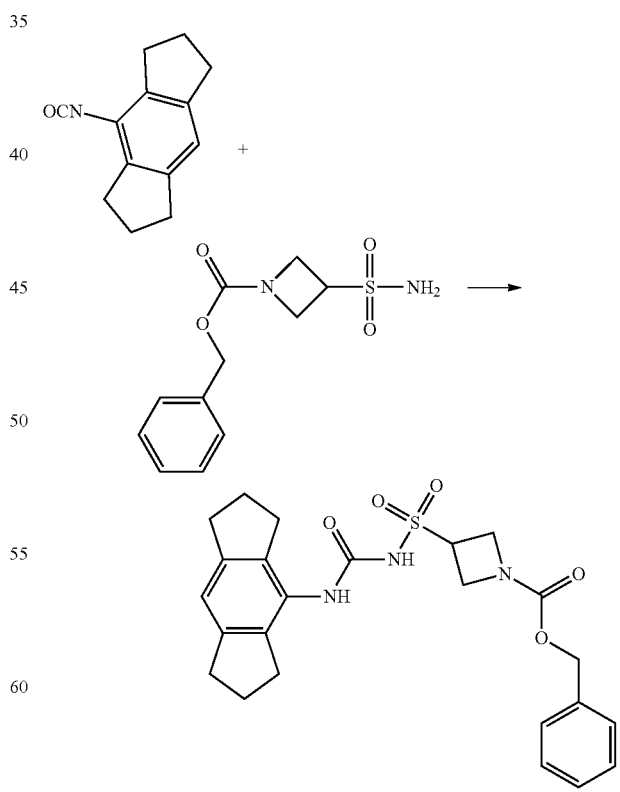

Prepared as described for N-((1,2,3,5,6,7-hexahydro-s-indacen-4-yl)carbamoyl)-1-(prop-2-yn-1-yl)piperidine-4- sulfonamide, potassium salt (Example 2) using 4-isocyanato-1,2,3,5,6,7-hexahydro-s-indacene (Intermediate A1) and benzyl 3-sulfamoylazetidine-1-carboxylate (Intermediate P47) to afford the title compound (41%) as a white solid.

¹H NMR (CD₃OD): δ=7.51-7.15 (m, 5H), 6.93 (s, 1H), 5.09 (s, 2H), 4.31 (m, 4H), 2.80 (dt, 9H), 2.03 (m, 4H).

LCMS: m/z 470 (M+H)⁺ (ES⁺); 468 (M−H)⁻ (ES⁻).

Example 72: 1-Benzyl-N-((1,2,3,5,6,7-hexahydro-s-indacen-4-yl)carbamoyl) azetidine-3-sulfonamide, Potassium Salt

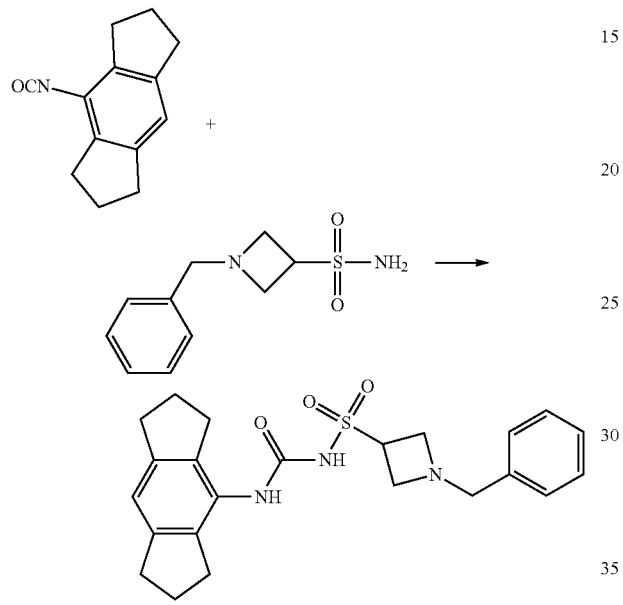

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-benzylazetidine-3-sulfonamide (Intermediate P57) to afford the title compound (47%) as white solid.

¹H NMR (CD₃OD): δ=7.41-7.15 (m, 5H), 6.86 (s, 1H), 4.33 (t, 1H), 3.69 (s, 2H), 3.60 (d, 4H), 2.80 (dt, 8H), 2.02 (q, 4H).

LCMS: m/z 426 (M+H)⁺ (ES⁺); 424 (M−H)⁻ (ES⁻).

Example 73: 1-(1-Ethylpiperidin-4-yl)-N-((1,2,3,5,6,7-hexahydro-s-indacen-4-yl)carbamoyl)azetidine-3-sulfonamide, Potassium Salt

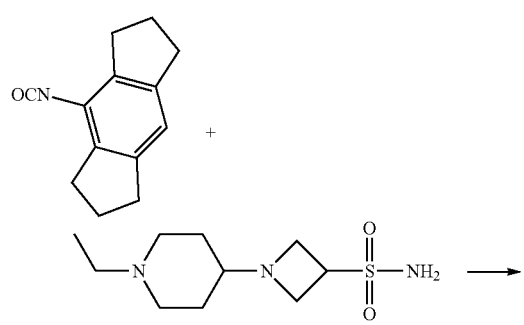

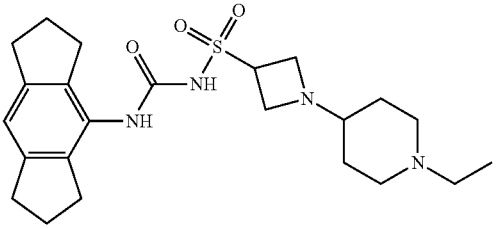

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(1-ethylpiperidin-4-yl)azetidine-3-sulfonamide (Intermediate P58) to afford the title compound (59%) as a white solid.

¹H NMR (CD₃OD): δ=6.88 (s, 1H), 4.31 (q, 1H), 3.65 (t, 2H), 3.54 (t, 2H), 3.00 (d, 2H), 2.83 (q, 9H), 2.51 (q, 2H), 2.25-1.93 (m, 6H), 1.81 (d, 2H), 1.34 (q, 2H), 1.12 (t, 3H).

LCMS: m/z 447 (M+H)⁺ (ES⁺); 445 (M−H)⁻ (ES⁻).

Example 74: 1-Acetyl-N-((1,2,3,5,6,7-hexahydro-s-indacen-4-yl)carbamoyl) azetidine-3-sulfonamide, Potassium Salt

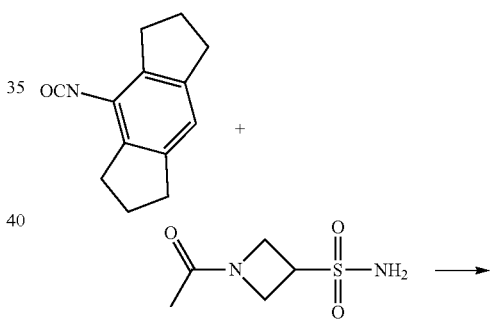

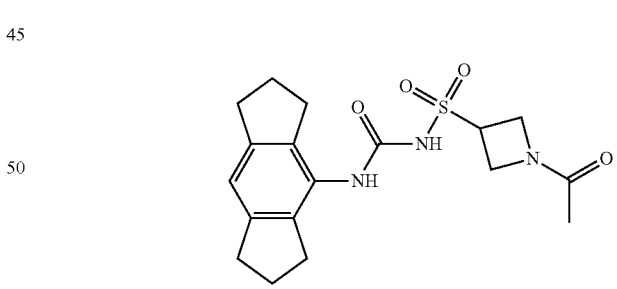

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-acetylazetidine-3-sulfonamide (Intermediate P59) to afford the title compound (5%) as a white solid.

¹H NMR (CD₃OD): δ=6.87 (s, 1H), 4.54-4.32 (m, 2H), 4.32-4.07 (m, 2H), 3.55 (m, 1H), 2.82 (m, 8H), 2.02 (m, 4H), 1.87 (d, 3H).

LCMS: m/z 378 (M+H)⁺ (ES⁺); 376 (M−H)⁻ (ES⁻).

Example 75: N-((1,2,3,5,6,7-Hexahydro-s-indacen-4-yl)carbamoyl)-1-(tetrahydro-2H-pyran-4-yl)azetidine-3-sulfonamide, Potassium Salt

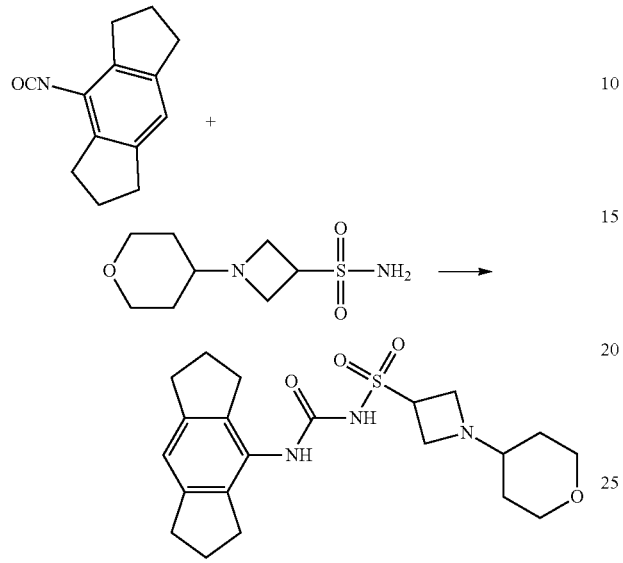

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(tetrahydro-2H-pyran-4-yl)azetidine-3-sulfonamide (Intermediate P60) to afford the title compound (29%) as a white solid.

$^1$H NMR (CD$_3$OD): δ=6.87 (s, 1H), 4.32 (m, 1H), 3.92 (ddd, 2H), 3.74-3.48 (m, 4H), 3.48-3.33 (m, 2H), 2.82 (m, 8H), 2.45 (dt, 1H), 2.02 (m, 4H), 1.70 (dt, 2H), 1.24 (dd, 2H).

LCMS: m/z 420 (M+H)$^+$ (ES$^+$); 418 (M–H)$^-$ (ES$^-$).

Example 76: N-((1,2,3,5,6,7-Hexahydro-s-indacen-4-yl)carbamoyl)-1-propylazetidine-3-sulfonamide, Potassium Salt

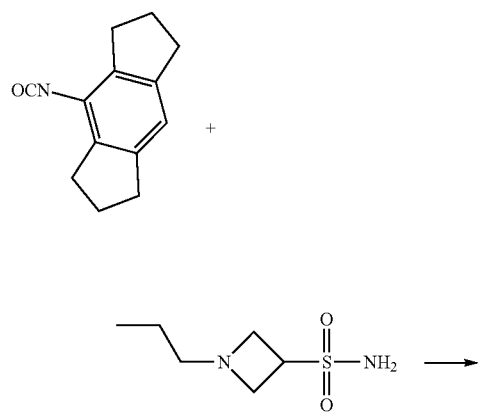

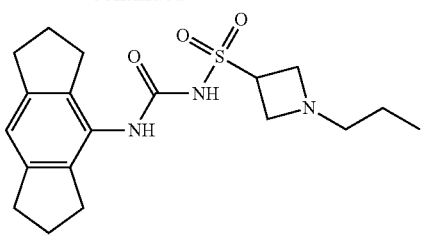

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-propylazetidine-3-sulfonamide (Intermediate P61) to afford the title compound (30%) as a white solid.

$^1$H NMR (CD$_3$OD): δ=6.91 (s, 1H), 4.39 (m, 1H), 4.29 (d, 4H), 3.17-3.01 (m, 2H), 2.83 (m, 8H), 2.04 (m, 4H), 1.57 (m, 2H), 0.99 (t, 3H).

LCMS: m/z 378 (M+H)$^+$ (ES$^+$); 376 (M–H)$^-$ (ES$^-$).

Example 77: tert-Butyl 3-(N-((1,2,3,5,6,7-hexahydro-s-indacen-4-yl)carbamoyl)sulfamoyl)azetidine-1-carboxylate, Potassium Salt

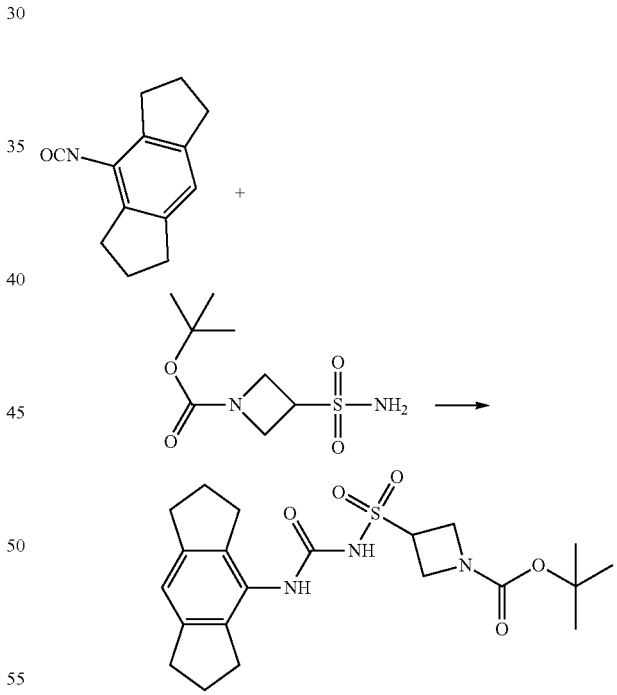

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and tert-butyl 3-sulfamoylazetidine-1-carboxylate (Intermediate P62) to afford the title compound (9%) as a white solid.

$^1$H NMR (CD$_3$OD): δ=6.93 (s, 1H), 4.43 (d, 1H), 4.33-4.03 (m, 4H), 2.82 (m, 8H), 2.04 (m, 4H), 1.44 (s, 9H).

LCMS: m/z 434 (M–H)$^-$ (ES$^-$).

Example 78: Methyl 2-(3-(N-((1,2,3,5,6,7-hexahydro-s-indacen-4-yl) carbamoyl)sulfamoyl)azetidin-1-yl)acetate, Potassium Salt

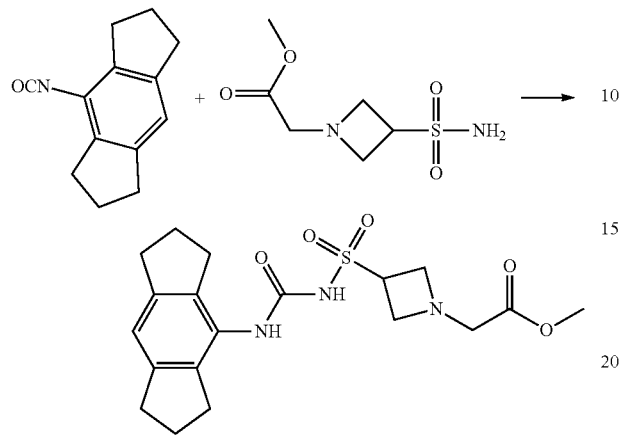

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and methyl 2-(3-sulfamoylazetidin-1-yl)acetate (Intermediate P63) to afford the title compound (43%) as a white solid.

$^1$H NMR (CD$_3$OD): δ=6.87 (s, 1H), 4.36 (m, 1H), 3.87-3.74 (m, 2H), 3.69 (s, 3H), 3.61 (dd, 2H), 3.39 (s, 2H), 2.81 (m, 8H), 2.03 (m, 4H).

LCMS: m/z 408 (M+H)$^+$ (ES$^+$); 406 (M–H)$^-$ (ES$^-$).

Example 79: 1-(1-Acetylazetidin-3-yl)-N-((1,2,3,5,6,7-hexahydro-s-indacen-4-yl)carbamoyl)piperidine-4-sulfonamide, Potassium Salt

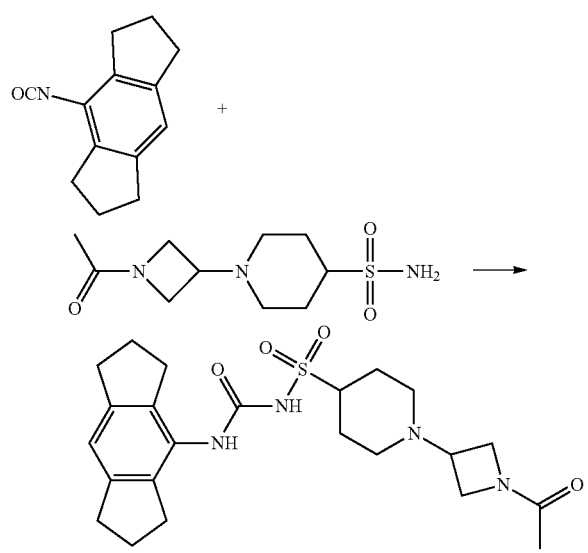

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(1-acetylazetidin-3-yl)piperidine-4-sulfonamide (Intermediate P65) to afford the title compound (20%) as a white solid.

$^1$H NMR (CD$_3$OD): δ=6.88 (s, 1H), 4.23 (m, 1H), 4.03 (m, 2H), 3.82 (dd, 1H), 3.45 (s, 1H), 3.20 (q, 1H), 2.99 (s, 2H), 2.84 (m, 10H), 2.17 (d, 2H), 2.04 (m, 5H), 1.97-1.78 (m, 4H).

LCMS: m/z 461 (M+H)$^+$ (ES$^+$); 459 (M–H)$^-$ (ES$^-$).

Example 80: N-((1,2,3,5,6,7-Hexahydro-s-indacen-4-yl)carbamoyl)-1-(1-methylazetidin-3-yl)piperidine-4-sulfonamide, Potassium Salt

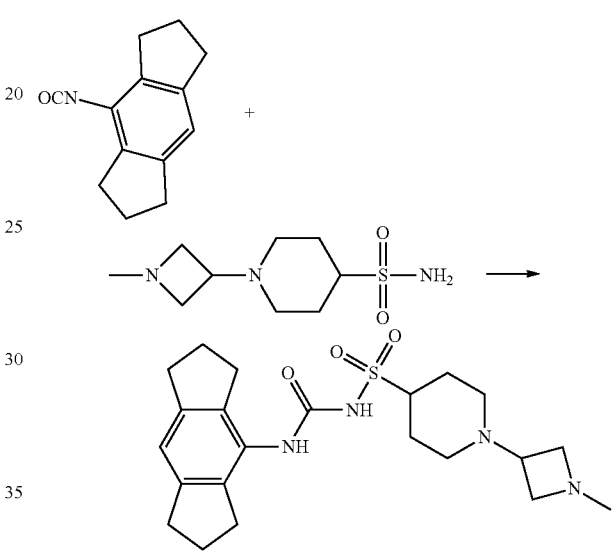

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(1-methylazetidin-3-yl)piperidine-4-sulfonamide (Intermediate P66) to afford the title compound (29%) as a white solid.

$^1$H NMR (CD$_3$OD): δ=6.88 (s, 1H), 3.59 (m, 2H), 3.40 (m, 2H), 3.00 (dq, 3H), 2.83 (m, 11H), 2.40 (s, 3H), 2.04 (m, 4H), 1.89 (q, 4H).

LCMS: m/z 433 (M+H)$^+$ (ES$^+$); 431 (M–H)$^-$ (ES$^-$).

Example 81: N-((1,2,3,5,6,7-Hexahydro-s-indacen-4-yl)carbamoyl)-1-(pentan-3-yl)pyrrolidine-3-sulfonamide, Potassium Salt

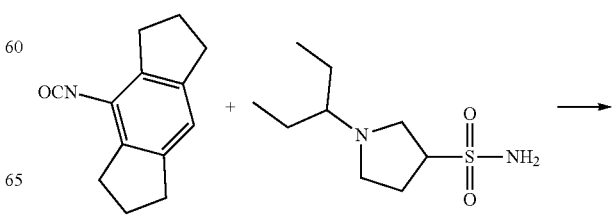

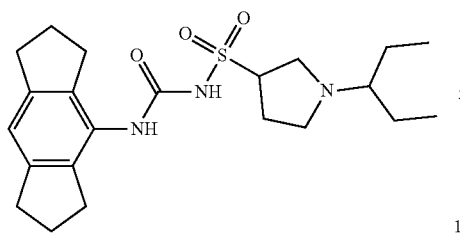

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(pentan-3-yl)pyrrolidine-3-sulfonamide (Intermediate P67) to afford the title compound (33%) as a white solid.

$^1$H NMR (CD$_3$OD): δ=6.88 (s, 1H), 4.22 (S, 1H), 3.07 (m, 2H), 2.82 (m, 8H), 2.62-2.18 (m, 5H), 2.03 (m, 4H), 1.86-1.48 (m, 4H), 0.94 (td, 6H).

LCMS: m/z 420 (M+H)$^+$ (ES$^+$); 418 (M−H)$^−$ (ES$^−$).

Example 82: 1-(sec-Butyl)-N-((1,2,3,5,6,7-hexahydro-s-indacen-4-yl) carbamoyl)pyrrolidine-3-sulfonamide, Potassium Salt

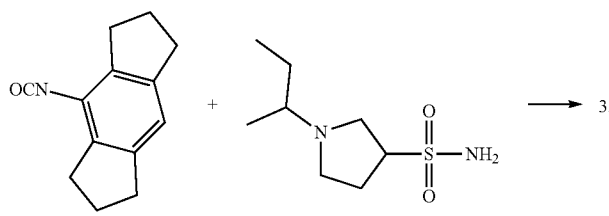

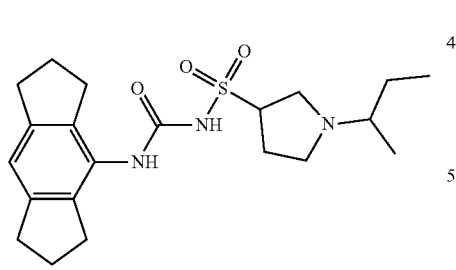

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(sec-butyl)pyrrolidine-3-sulfonamide (Intermediate P68) to afford the title compound (34%) as a white solid.

$^1$H NMR (CD$_3$OD): δ=6.90 (s, 1H), 4.21 (d, 1H), 3.62-3.40 (m, 1H), 3.23-3.07 (m, 1H), 2.98 (s, 1H), 2.84 (q, 10H), 2.35 (dd, 2H), 2.04 (m, 4H), 1.85 (d, 1H), 1.45 (s, 1H), 1.21 (s, 3H), 1.10-0.82 (m, 3H).

LCMS: m/z 406 (M+H)$^+$ (ES$^+$); 404 (M−H)$^−$ (ES$^−$).

Example 83: 1-Butyl-N-((1,2,3,5,6,7-hexahydro-s-indacen-4-yl)carbamoyl) azetidine-3-sulfonamide, Potassium Salt

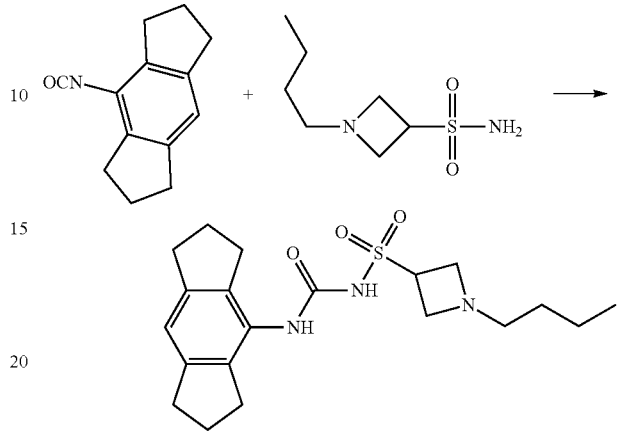

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-butylazetidine-3-sulfonamide (Intermediate P69) to afford the title compound (43%) as a white solid.

$^1$H NMR (CD$_3$OD): δ=6.87 (s, 1H), 4.36 (m, 1H), 3.93-3.59 (m, 4H), 2.81 (q, 8H), 2.66 (t, 2H), 2.02 (m, 4H), 1.48-1.16 (m, 4H), 0.93 (t, 3H).

LCMS: m/z 392 (M+H)$^+$ (ES$^+$); 390 (M−H)$^−$ (ES$^−$).

Example 84: N-((1,2,3,5,6,7-Hexahydro-s-indacen-4-yl)carbamoyl)-1-(2-hydroxy-2-methylpropyl)azetidine-3-sulfonamide, Potassium Salt

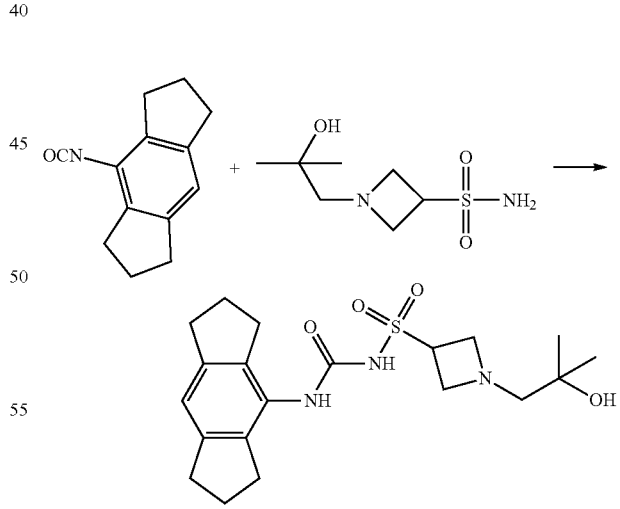

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(2-hydroxy-2-methylpropyl)azetidine-3-sulfonamide (Intermediate P70) to afford the title compound (54%) as a white solid.

¹H NMR (CD₃OD): δ=6.88 (s, 1H), 4.37 (m, 1H), 3.77 (m, 2H), 3.68 (m, 2H), 2.83 (m, 8H), 2.57 (s, 2H), 2.04 (m, 4H), 1.15 (s, 6H).
LCMS: m/z 408 (M+H)⁺ (ES⁺); 406 (M−H)⁻ (ES⁻).

Example 85: 1-Cyclopropyl-N-((1,2,3,5,6,7-hexahydro-s-indacen-4-yl) carbamoyl)azetidine-3-sulfonamide, Potassium Salt

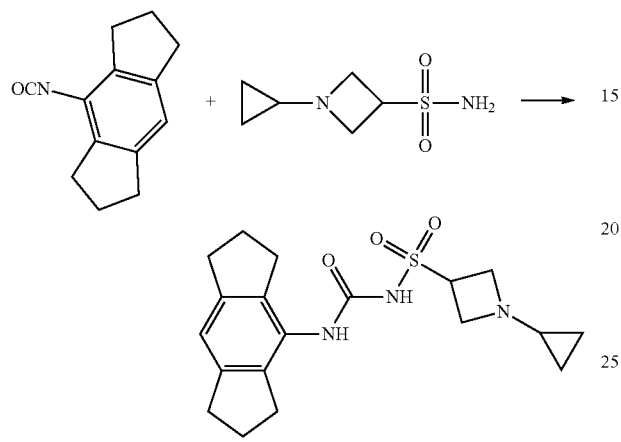

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-cyclopropylazetidine-3-sulfonamide (Intermediate P71) to afford the title compound (27%) as a white solid.
¹H NMR (CD₃OD): δ=6.86 (s, 1H), 4.35 (m, 1H), 3.67 (m, 4H), 2.81 (m, 8H), 2.02 (m, 5H), 0.43 (m, 2H), 0.33 (m, 2H).
LCMS: m/z 376 (M+H)⁺ (ES⁺); 374 (M−H)⁻ (ES⁻).

Example 86: 1-(1,3-Difluoropropan-2-yl)-N-((1,2,3,5,6,7-hexahydro-s-indacen-4-yl)carbamoyl)azetidine-3-sulfonamide, Potassium Salt

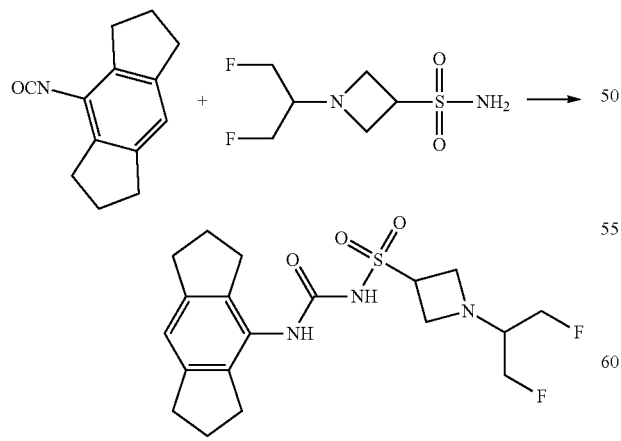

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(1,3-difluoropropan-2-yl)azetidine-3-sulfonamide (Intermediate P72) to afford the title compound (91%) as a white solid.
¹H NMR (CD₃OD): δ=6.86 (s, 1H), 4.52 (m, 2H), 4.37 (m, 3H), 3.72 (d, 4H), 3.30 (m, 1H), 2.81 (m, 8H), 2.03 (m, 4H).
LCMS: m/z 414 (M+H)⁺ (ES⁺); 412 (M−H)⁻ (ES⁻).

Example 87: 1-(Cyanomethyl)-N-((1,2,3,5,6,7-hexahydro-s-indacen-4-yl) carbamoyl)azetidine-3-sulfonamide, Potassium Salt

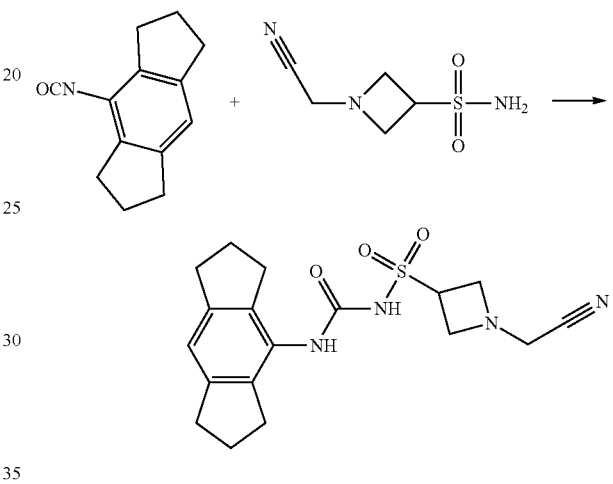

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(cyanomethyl)azetidine-3-sulfonamide (Intermediate P73) to afford the title compound (57%) as a white solid.
¹H NMR (CD₃OD): δ=6.86 (s, 1H), 4.32 (m, 1H), 3.85-3.62 (m, 4H), 3.56 (s, 2H), 2.81 (m, 8H), 2.02 (m, 4H).
LCMS: m/z 375 (M+H)⁺ (ES⁺); 373 (M−H)⁻ (ES⁻).

Example 88: N-((1,2,3,5,6,7-Hexahydro-s-indacen-4-yl)carbamoyl)-1-(2-methoxyethyl)azetidine-3-sulfonamide, Potassium Salt

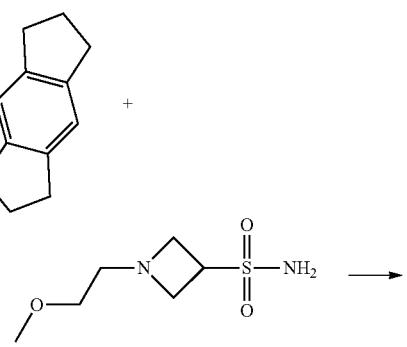

-continued

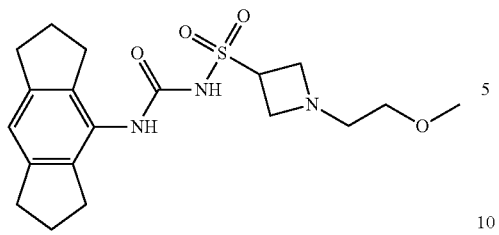

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(2-methoxyethyl)azetidine-3-sulfonamide (Intermediate P74) to afford the title compound (35%) as a white solid.

$^1$H NMR (CD$_3$OD): δ=6.86 (s, 1H), 4.36 (m, 1H), 3.82-3.58 (m, 4H), 3.41 (t, 2H), 3.3 (s, 3H), 2.81 (m, 10H), 2.13-1.92 (m, 4H).

LCMS: m/z 394 (M+H)$^+$ (ES$^+$).

Example 89: 1-(Cyclohexylmethyl)-N-((1,2,3,5,6,7-hexahydro-s-indacen-4-yl)carbamoyl)azetidine-3-sulfonamide, Potassium Salt

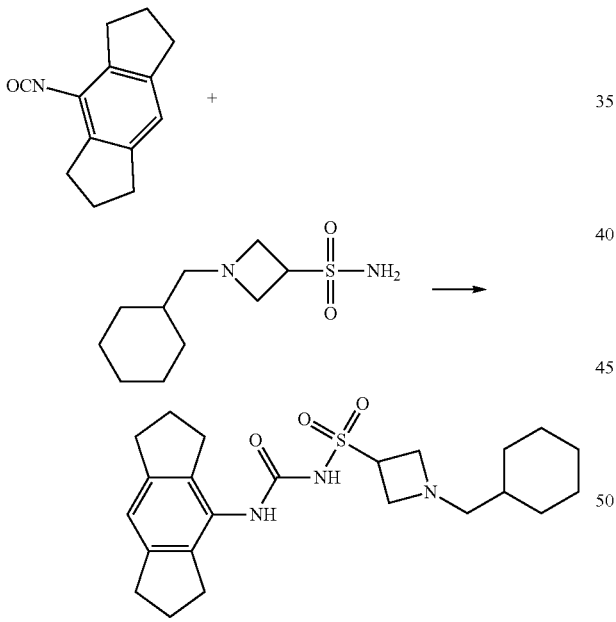

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(cyclohexylmethyl)azetidine-3-sulfonamide (Intermediate P75) to afford the title compound (7%) as a white solid.

$^1$H NMR (CD$_3$OD): δ=6.89 (s, 1H), 4.37 (t, 1H), 3.93-3.67 (m, 4H), 2.83 (m, 9H), 2.61 (m, 1H), 2.12-1.95 (m, 4H), 1.73 (d, 5H), 1.27 (d, 4H), 0.95 (d, 2H).

LCMS: m/z 432 (M+H)$^+$ (ES$^+$); 430 (M−H)$^−$ (ES$^−$).

Example 90: N-((1,2,3,5,6,7-Hexahydro-s-indacen-4-yl)carbamoyl)-1-(pyridin-3-ylmethyl)azetidine-3-sulfonamide, Potassium Salt

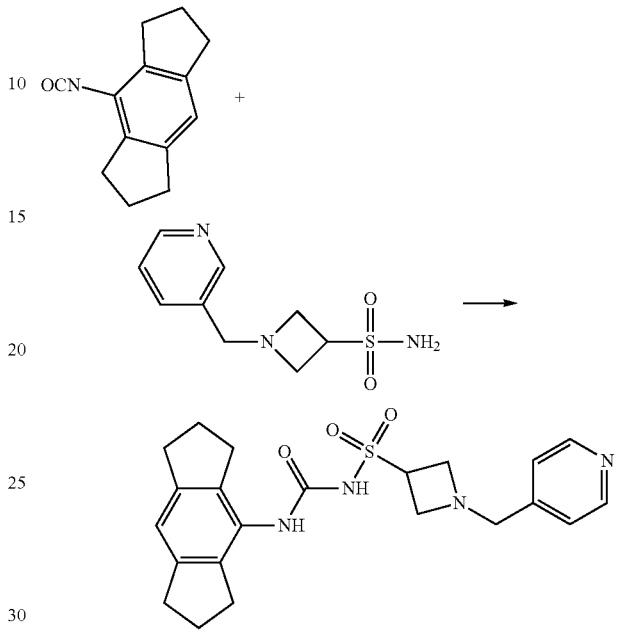

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(pyridin-3-ylmethyl)azetidine-3-sulfonamide (Intermediate P76) to afford the title compound (51%) as a white solid.

$^1$H NMR (CD$_3$OD): δ=8.57-8.37 (m, 2H), 7.82 (d, 1H), 7.41 (dd, 1H), 6.87 (s, 1H), 4.36 (q, 1H), 3.76 (s, 2H), 3.70-3.51 (m, 4H), 2.96-2.70 (m, 8H), 2.03 (m, 4H).

LCMS: m/z 427 (M+H)$^+$ (ES$^+$); 425 (M−H)$^−$ (ES$^−$).

Example 91: 2-(3-(N-((1,2,3,5,6,7-Hexahydro-s-indacen-4-yl)carbamoyl) sulfamoyl)azetidin-1-yl)-N,N-dimethylacetamide, potassium salt

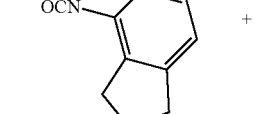

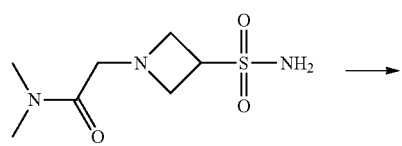

319

-continued

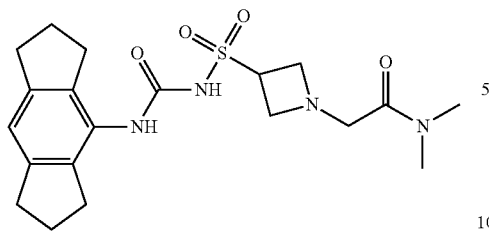

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and N,N-dimethyl-2-(3-sulfamoylazetidin-1-yl)acetamide (Intermediate P77) to afford the title compound (15%) as a white solid.

$^1$H NMR (CD$_3$OD): δ=6.86 (s, 1H), 4.39 (m, 1H), 3.82 (t, 2H), 3.59 (t, 2H), 3.50 (s, 2H), 2.97 (s, 3H), 2.89 (s, 3H), 2.81 (m, 8H), 2.11-1.92 (m, 4H).

LCMS: m/z 421 (M+H)$^+$ (ES$^+$); 419 (M−H)$^−$ (ES$^−$).

Example 92: 1-(2-Chloroethyl)-N-((1,2,3,5,6,7-hexahydro-s-indacen-4-yl) carbamoyl)azetidine-3-sulfonamide, Potassium Salt

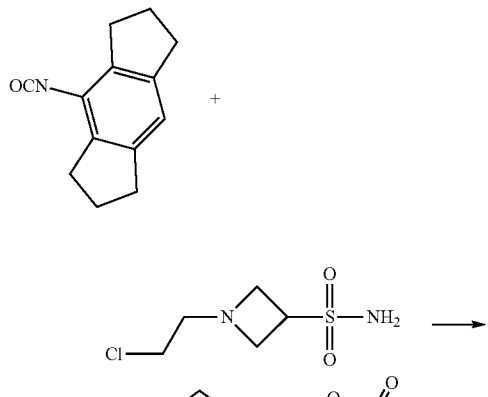

Prepared as described for N-((1,2,3,5,6,7-hexahydro-s-indacen-4-yl)carbamoyl)-1-(prop-2-yn-1-yl)piperidine-4-sulfonamide, potassium salt (Example 2) using 4-isocyanato-1,2,3,5,6,7-hexahydro-s-indacene (Intermediate A1) and 1-(2-chloroethyl)azetidine-3-sulfonamide (Intermediate P78) to afford the title compound (55%) as a white solid.

$^1$H NMR (CD$_3$OD): δ=6.87 (s, 1H), 4.35 (t, 1H), 3.72 (t, 2H), 3.61 (t, 2H), 3.52 (t, 2H), 2.98-2.69 (m, 10H), 2.02 (m, 4H).

LCMS: m/z 398 (M+H)$^+$ (ES$^+$); 396 (M−H)$^−$ (ES$^−$).

320

Example 93: 1-(tert-Butyl)-N-((1,2,3,5,6,7-hexahydro-s-indacen-4-yl) carbamoyl)azetidine-3-sulfonamide, Potassium Salt

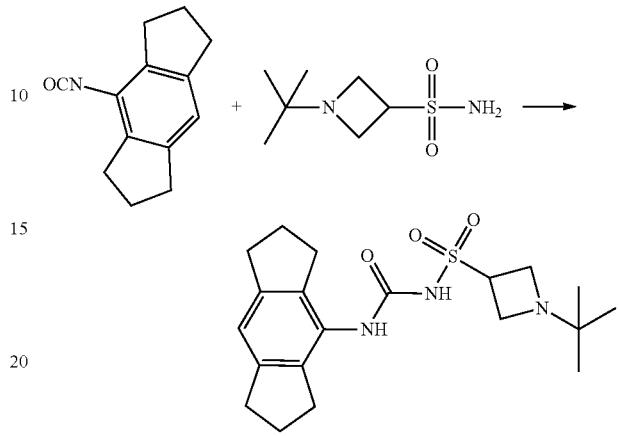

To a solution of 1-(tert-butyl)azetidine-3-sulfonamide (Intermediate P82; 10 mg, 0.052 mmol) in THF (3 mL) was added potassium tert-butoxide (6 mg, 0.052 mmol). The mixture was stirred at room temperature for 40 minutes. A solution of 4-isocyanato-1,2,3,5,6,7-hexahydro-s-indacene (Intermediate A1; 10 mg, 0.052 mmol) in THF (1 mL) was added and the mixture was stirred overnight at room temperature. The reaction mixture was concentrated in vacuo and DMSO (0.5-1 mL) was added. The mixture (filtered over cotton wool when solids were present) was submitted for purification by reversed phase column chromatography (see "Experimental Methods", "Purification Method 1") to afford the title compound (5 mg, 25%) as a white solid.

$^1$H NMR (CD$_3$OD): δ=6.86 (s, 1H), 4.28 (m, 1H), 3.76 (t, 2H), 3.41 (t, 2H), 2.81 (m, 8H), 2.02 (m, 4H), 1.01 (s, 9H).

LCMS: m/z 392 (M+H)$^+$ (ES$^+$); 390 (M−H)$^−$ (ES$^−$).

Example 94: 1-(Cyclopropylmethyl)-N-((1,2,3,5,6,7-hexahydro-s-indacen-4-yl)carbamoyl)azetidine-3-sulfonamide, Potassium Salt

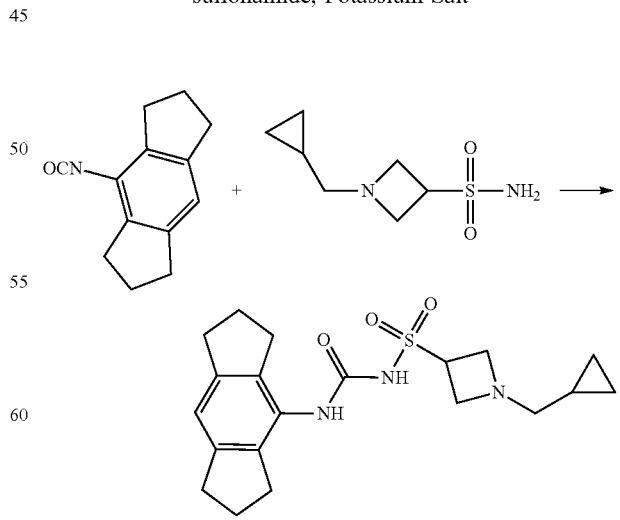

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(cyclopropylmethyl)azetidine-3-sulfonamide (Intermediate P83) to afford the title compound (34%) as a white solid.

¹H NMR (CD₃OD): δ=6.88 (s, 1H), 4.38 (t, 1H), 4.09 (q, 4H), 2.83 (m, 10H), 2.02 (m, 4H), 0.89 (d, 1H), 0.58 (q, 2H), 0.28 (q, 2H).

LCMS: m/z 390 (M+H)⁺ (ES⁺); 388 (M−H)⁻ (ES⁻).

Example 95: 1-(2-Azidoethyl)-N-((1,2,3,5,6,7-hexahydro-s-indacen-4-yl) carbamoyl)azetidine-3-sulfonamide, Potassium Salt

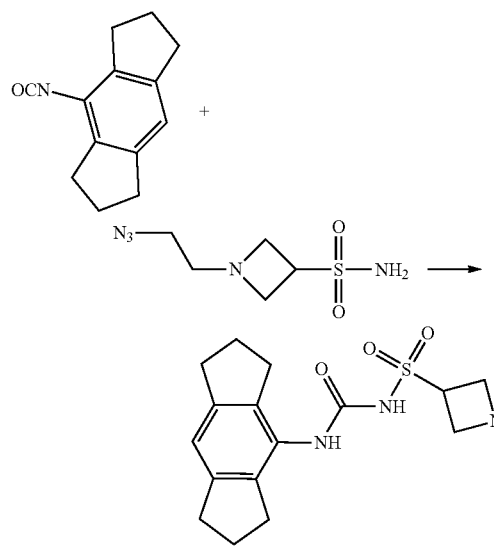

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(2-azidoethyl)azetidine-3-sulfonamide (Intermediate P85) to afford the title compound (33%) as a white solid.

¹H NMR (CD₃OD): δ=6.87 (s, 1H), 4.36 (p, 1H), 3.71 (td, 2H), 3.58 (dd, 2H), 2.81 (m, 10H), 2.77-2.63 (m, 2H), 2.03 (m, 4H).

LCMS: m/z 405 (M+H)⁺ (ES⁺); 403 (M−H)⁻ (ES⁻).

Example 96: N-((1,2,3,5,6,7-Hexahydro-s-indacen-4-yl)carbamoyl)-1-(2,2,2-trifluoroethyl)azetidine-3-sulfonamide, Potassium Salt

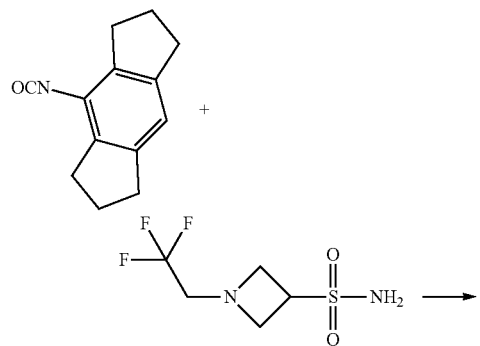

-continued

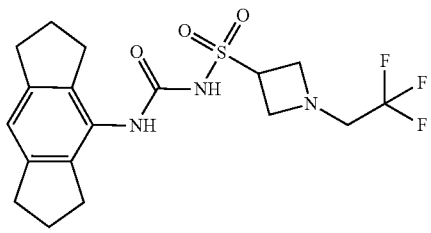

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(2,2,2-trifluoroethyl)azetidine-3-sulfonamide (Intermediate P86) to afford the title compound (11%) as a white solid.

¹H NMR (CD₃OD): δ=6.87 (s, 1H), 4.35 (t, 1H), 3.73 (dt, 4H), 3.16 (q, 2H), 2.81 (m, 8H), 2.02 (m, 4H).

LCMS: m/z 418 (M+H)⁺ (ES⁺); 416 (M−H)⁻ (ES⁻).

Example 97: N-((1,2,3,5,6,7-Hexahydro-s-indacen-4-yl)carbamoyl)-1-isobutylazetidine-3-sulfonamide, Potassium Salt

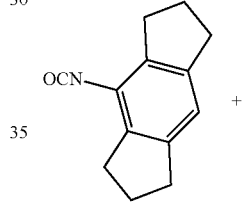

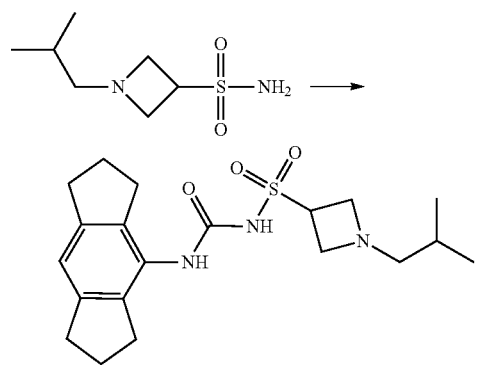

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-isobutylazetidine-3-sulfonamide (Intermediate P84) to afford the title compound (19%) as a white solid.

¹H NMR (CD₃OD): δ=6.88 (s, 1H), 4.36 (p, 1H), 3.92 (dt, 4H), 2.92-2.74 (m, 8H), 2.67 (d, 2H), 2.02 (m, 4H), 1.77 (dt, 1H), 0.92 (dd, 6H).

LCMS: m/z 392 (M+H)⁺ (ES⁺); 390 (M−H)⁻ (ES⁻).

Example 98: 1-Cyclohexyl-N-((1,2,3,5,6,7-hexahydro-s-indacen-4-yl) carbamoyl)azetidine-3-sulfonamide, Potassium Salt

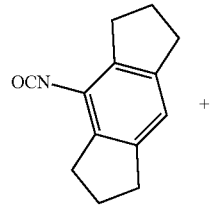

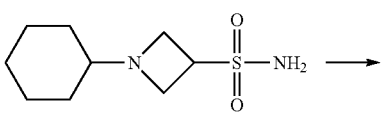

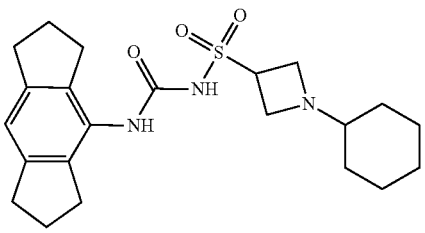

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-cyclohexylazetidine-3-sulfonamide (Intermediate P88) to afford the title compound (9%) as a white solid.

$^1$H NMR (CD$_3$OD): δ=6.87 (s, 1H), 4.32 (p, 1H), 3.79 (dt, 4H), 2.82 (m, 8H), 2.44 (s, 1H), 2.02 (m, 4H), 1.94-1.54 (m, 5H), 1.41-0.84 (m, 5H).

LCMS: m/z 418 (M+H)$^+$ (ES$^+$); 416 (M−H)$^-$ (ES$^-$).

Example 99: 1-Cyclopentyl-N-((1,2,3,5,6,7-hexahydro-s-indacen-4-yl) carbamoyl)azetidine-3-sulfonamide, Potassium Salt

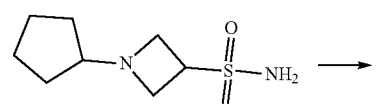

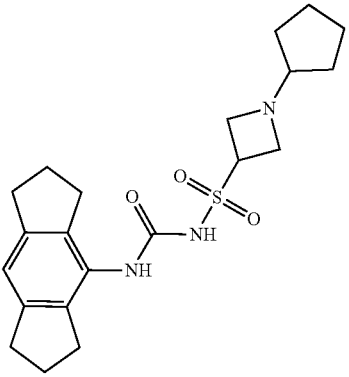

Prepared as described for 1-(tert-butyl)-N-((1,2,3,5,6,7-hexahydro-s-indacen-4-yl) carbamoyl) azetidine-3-sulfonamide, potassium salt (Example 93) using 4-isocyanato-1,2,3,5,6,7-hexahydro-s-indacene (Intermediate A1) and 1-cyclopentylazetidine-3-sulfonamide (Intermediate P89) to afford the title compound (10%) as a white solid.

$^1$H NMR (CD$_3$OD): δ=6.87 (s, 1H), 4.32 (q, 1H), 3.78 (dt, 4H), 2.82 (m, 9H), 2.02 (m, 4H), 1.94-1.49 (m, 6H), 1.48-1.24 (m, 2H).

LCMS: m/z 404 (M+H)$^+$ (ES$^+$); 402 (M−H)$^-$ (ES$^-$).

Example 100: N-((1,2,3,5,6,7-Hexahydro-s-indacen-4-yl)carbamoyl)-1-(1-iminoethyl)azetidine-3-sulfonamide, Potassium Salt

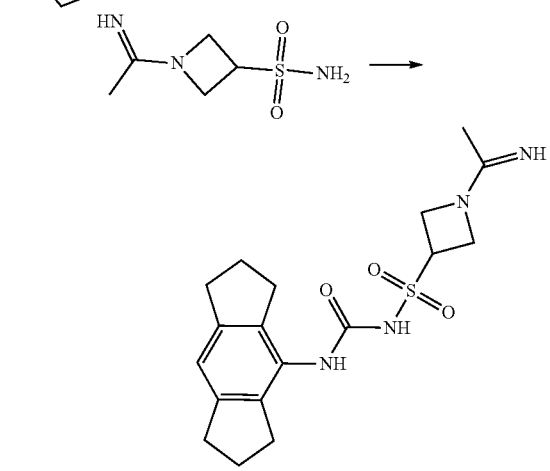

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1), potassium tert-butoxide (2 equiv.) and 1-(1-iminoethyl)azetidine-3-sulfonamide (Intermediate P90) to afford the title compound (8%) as a white solid.

¹H NMR (CD₃OD) (tautomeric mixture): δ=6.89 (s, 1H), 4.60 (q, 2H), 4.53-4.31 (m, 2H), 3.68-3.43 (m, 1H), 2.82 (m, 8H), 2.13 (s, 3H), 2.02 (m, 4H).
LCMS: m/z 377 (M+H)⁺ (ES⁺); 375 (M−H)⁻ (ES⁻).

Example 101: N-((1,2,3,5,6,7-Hexahydro-s-indacen-4-yl)carbamoyl)-1-(oxetan-3-ylmethyl)azetidine-3-sulfonamide, Potassium Salt

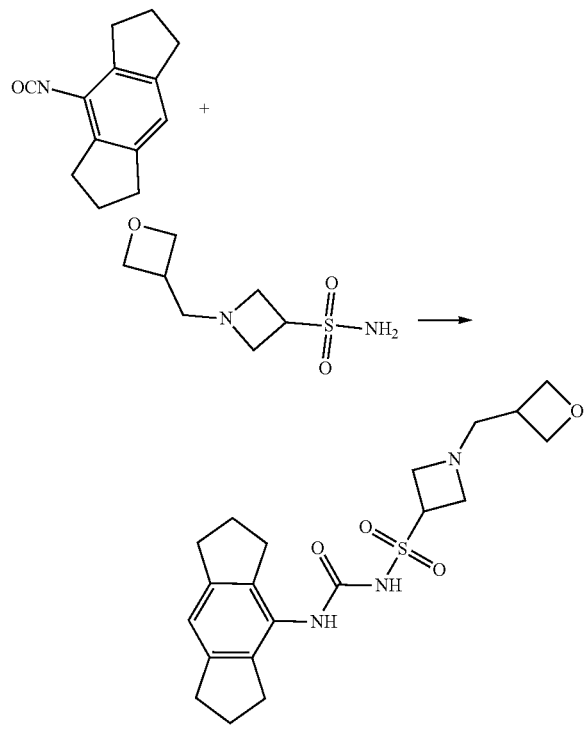

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(oxetan-3-ylmethyl)azetidine-3-sulfonamide (Intermediate P91) to afford the title compound (53%) as a white solid.

¹H NMR (CD₃OD): δ=6.87 (s, 1H), 4.75 (dd, 2H), 4.39 (t, 2H), 4.31 (d, 1H), 3.73-3.59 (m, 2H), 3.52 (t, 2H), 3.05 (dt, 1H), 2.82 (m, 10H), 2.02 (m, 4H).
LCMS: m/z 406 (M+H)⁺ (ES⁺); 404 (M−H)⁻ (ES⁻).

Example 102: 1-(2-(Dimethylamino)ethyl)-N-((1,2,3,5,6,7-hexahydro-s-indacen-4-yl)carbamoyl)azetidine-3-sulfonamide, Potassium Salt

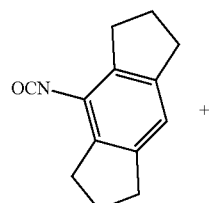 +

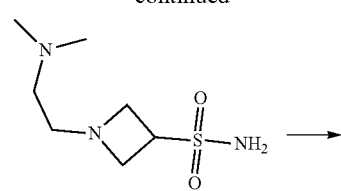 →

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(2-(dimethylamino)ethyl) azetidine-3-sulfonamide (Intermediate P92) to afford the title compound (20%) as a white solid.

¹H NMR (D₂O): δ=6.94 (s, 1H), 4.20 (t, 1H), 3.55 (t, 2H), 3.41 (t, 2H), 2.72 (m, 8H), 2.60 (t, 5H), 2.54 (s, 6H), 2.05-1.81 (m, 3H).
LCMS: m/z 407 (M+H)⁺ (ES⁺); 405 (M−H)⁻ (ES⁻).

Example 103: N-((1,2,3,5,6,7-Hexahydro-s-indacen-4-yl)carbamoyl)-1-(pyridin-4-ylmethyl)azetidine-3-sulfonamide, Potassium Salt

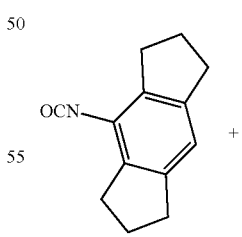 →

-continued

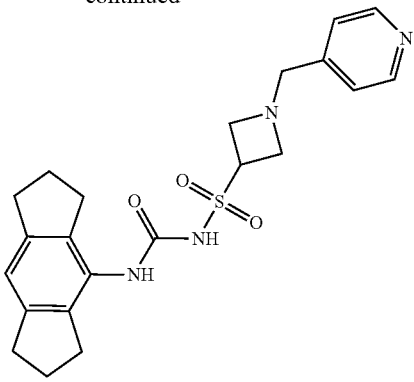

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(pyridin-4-ylmethyl) azetidine-3-sulfonamide (Intermediate P93) to afford the title compound (60%) as a white solid.

$^1$H NMR (D$_2$O): δ=8.38 (d, 2H), 7.24 (d, 2H), 6.96 (s, 1H), 4.25 (t, 1H), 3.69 (s, 2H), 3.61 (t, 2H), 3.50 (t, 2H), 2.75 (t, 4H), 2.63 (t, 4H), 1.91 (m, 4H).

LCMS: m/z 427 (M+H)$^+$ (ES$^+$); 425 (M−H)$^−$ (ES$^−$).

Example 104: N-((1,2,3,5,6,7-Hexahydro-s-indacen-4-yl)carbamoyl)-1-(pyridin-2-ylmethyl)azetidine-3-sulfonamide, Potassium Salt

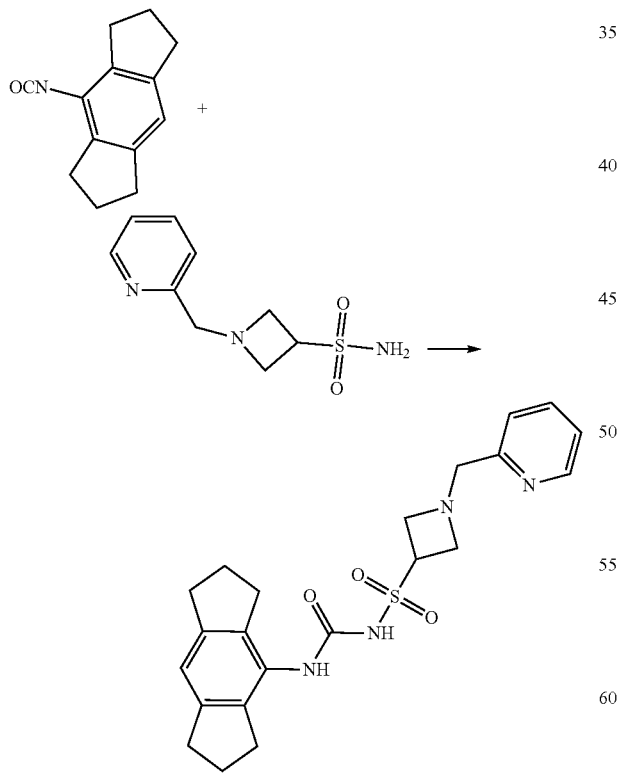

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(pyridin-2-ylmethyl) azetidine-3-sulfonamide (Intermediate P94) to afford the title compound (47%) as a white solid.

$^1$H NMR (D$_2$O): δ=8.32 (d, 1H), 7.71 (t, 1H), 7.23 (d, 2H), 6.93 (s, 1H), 4.20 (t, 1H), 3.69 (s, 2H), 3.53 (dt, 4H), 2.71 (t, 4H), 2.59 (t, 4H), 1.87 (p, 4H).

LCMS: m/z 427 (M+H)$^+$ (ES$^+$); 425 (M−H)$^−$ (ES$^−$).

Example 105: 1-((2-Bromopyridin-3-yl)methyl)-N-((1,2,3,5,6,7-hexahydro-s-indacen-4-yl)carbamoyl)azetidine-3-sulfonamide, Potassium Salt

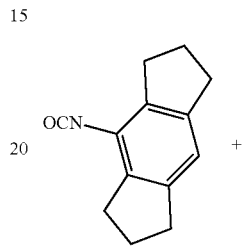

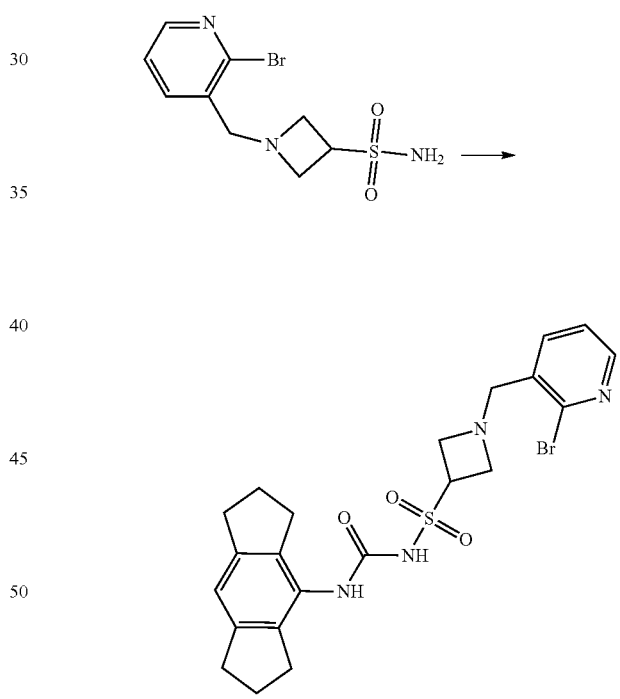

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-((2-bromopyridin-3-yl) methyl)azetidine-3-sulfonamide (Intermediate P95) to afford the title compound (46%) as a white solid.

$^1$H NMR (D$_2$O): δ=8.14 (dd, 1H), 7.64 (dd, 1H), 7.35 (dd, 1H), 6.96 (s, 1H), 4.25 (p, 1H), 3.76 (s, 2H), 3.62 (dt, 4H), 2.75 (t, 4H), 2.64 (t, 4H), 1.91 (m, 4H).

LCMS: m/z 505 (M+H)$^+$ (ES$^+$); 503 (M−H)$^−$ (ES$^−$).

329

Example 106: tert-Butyl 3-(N-((1,2,3,5,6,7-hexa-hydro-s-indacen-4-yl) carbamoyl)sulfamoyl)-[1,3'-biazetidine]-1'-carboxylate, Potassium Salt

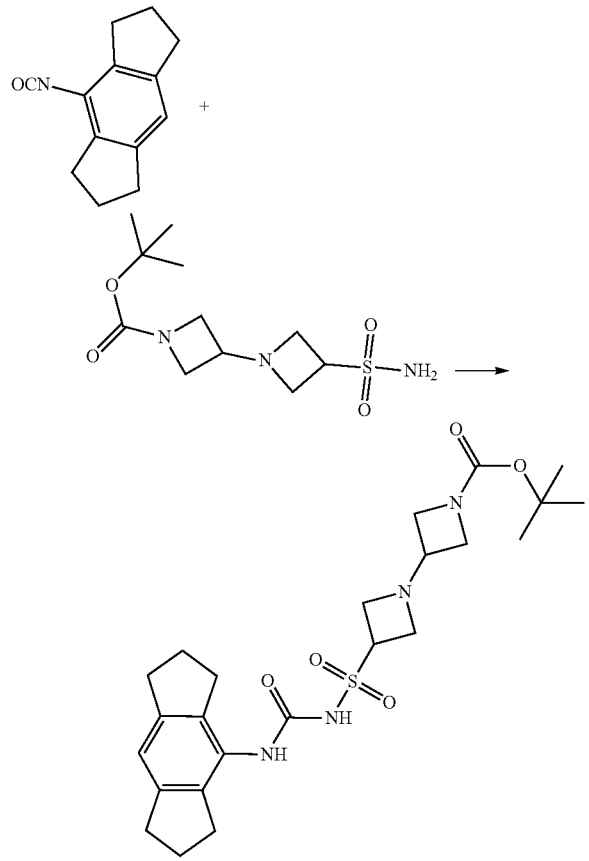

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and tert-butyl 3-sulfamoyl-[1,3'-biazetidine]-1'-carboxylate (Intermediate P96) to afford the title compound (33%) as a white solid.

$^1$H NMR (D$_2$O): δ=6.94 (s, 1H), 4.19 (t, 1H), 3.86 (d, 2H), 3.64-3.48 (m, 4H), 3.40 (m, 3H), 2.72 (t, 4H), 2.60 (t, 4H), 1.89 (m, 4H), 1.27 (d, 9H).

LCMS: m/z 491 (M+H)$^+$ (ES$^+$); 489 (M−H)$^−$ (ES$^−$).

Example 107: N-((1,2,3,5,6,7-Hexahydro-s-indacen-4-yl)carbamoyl)-1-(2-(methylthio)ethyl)azetidine-3-sulfonamide, Potassium Salt

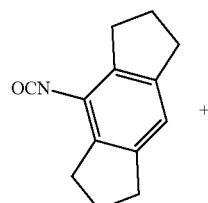

330

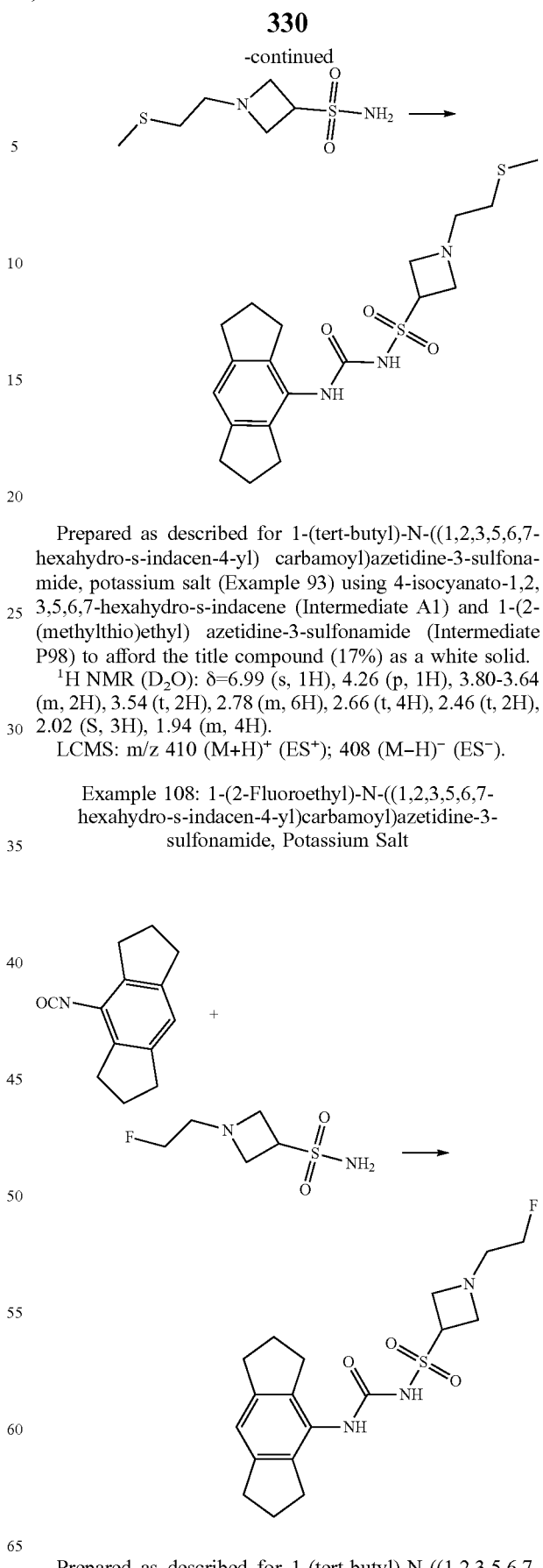

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(2-(methylthio)ethyl) azetidine-3-sulfonamide (Intermediate P98) to afford the title compound (17%) as a white solid.

$^1$H NMR (D$_2$O): δ=6.99 (s, 1H), 4.26 (p, 1H), 3.80-3.64 (m, 2H), 3.54 (t, 2H), 2.78 (m, 6H), 2.66 (t, 4H), 2.46 (t, 2H), 2.02 (S, 3H), 1.94 (m, 4H).

LCMS: m/z 410 (M+H)$^+$ (ES$^+$); 408 (M−H)$^−$ (ES$^−$).

Example 108: 1-(2-Fluoroethyl)-N-((1,2,3,5,6,7-hexahydro-s-indacen-4-yl)carbamoyl)azetidine-3-sulfonamide, Potassium Salt Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(2-fluoroethyl)azetidine-3-sulfonamide (Intermediate P99) to afford the title compound (61%) as a white solid.

$^1$H NMR (D$_2$O): δ=6.94 (s, 1H), 4.42 (t, 1H), 4.26 (t, 1H), 4.20 (d, 1H), 3.58 (t, 2H), 3.40 (t, 2H), 2.84-2.67 (m, 6H), 2.67-2.52 (m, 4H), 1.88 (m, 4H).

LCMS: m/z 382 (M+H)$^+$ (ES$^+$); 380 (M−H)$^−$ (ES$^−$).

Example 109: N-((1,2,3,5,6,7-Hexahydro-s-indacen-4-yl)carbamoyl)-1-(thietan-3-yl)azetidine-3-sulfonamide, Potassium Salt

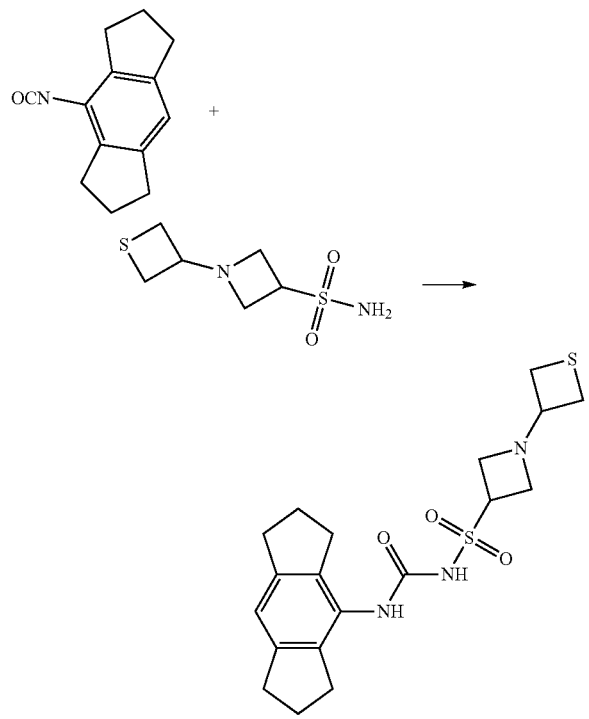

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(thietan-3-yl)azetidine-3-sulfonamide (Intermediate P100) to afford the title compound (16%) as a white solid.

$^1$H NMR (D$_2$O): δ=6.94 (s, 1H), 4.17 (p, 1H), 3.89 (t, 1H), 3.44 (P, 4H), 3.09 (t, 2H), 2.97 (t, 2H), 2.72 (t, 4H), 2.60 (t, 4H), 1.89 (m, 4H).

LCMS: m/z 408 (M+H)$^+$ (ES$^+$); 406 (M−H)$^−$ (ES$^−$).

Example 110: N-((1,2,3,5,6,7-Hexahydro-s-indacen-4-yl)carbamoyl)-1'-methyl-[1,3'-biazetidine]-3-sulfonamide, Potassium Salt

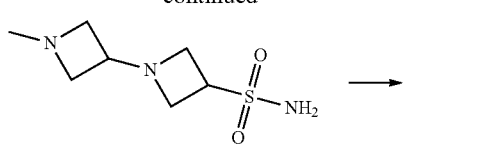

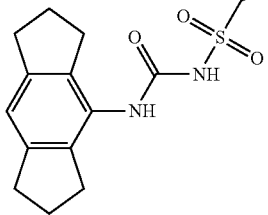

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1'-methyl-[1,3'-biazetidine]-3-sulfonamide (Intermediate P97) to afford the title compound (13%) as a white solid.

$^1$H NMR (D$_2$O): δ=6.95 (s, 1H), 4.20 (p, 1H), 3.84-3.67 (m, 2H), 3.66-3.36 (m, 7H), 2.72 (t, 4H), 2.61 (t, 4H), 2.50 (s, 3H), 1.89 (m, 4H).

LCMS: m/z 405 (M+H)$^+$ (ES$^+$); 403 (M−H)$^−$ (ES$^−$).

Example 111: 1-(2-(3-(But-3-yn-1-yl)-3H-diazirin-3-yl)ethyl)-N-((1,2,3,5,6,7-hexahydro-s-indacen-4-yl)carbamoyl)azetidine-3-sulfonamide, Potassium Salt

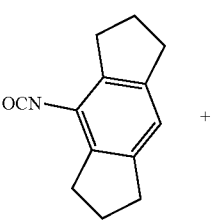

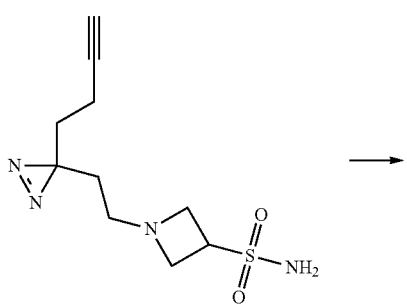

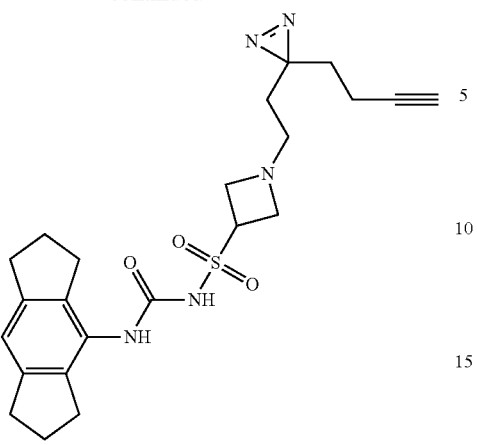

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(2-(3-(but-3-yn-1-yl)-3H-diazirin-3-yl)ethyl) azetidine-3-sulfonamide (Intermediate P101) to afford the title compound (58%) as a white solid (light sensitive).

$^1$H NMR (CD$_3$OD): δ=6.87 (s, 1H), 4.30 (t, 1H), 3.61 (t, 2H), 3.55-3.40 (m, 2H), 2.81 (m, 8H), 2.38 (t, 2H), 2.28 (t, 1H), 2.01 (m, 6H), 1.59 (t, 2H), 1.44 (t, 2H).

LCMS: m/z 456 (M+H)$^+$ (ES$^+$); 454 (M−H)$^−$ (ES$^−$).

Example 112: tert-Butyl-(((tert-butoxycarbonyl)imino)(3-(N-((1,2,3,5,6,7-hexahydro-s-indacen-4-yl)carbamoyl)sulfamoyl)azetidin-1-yl)methyl) Carbamate, Potassium Salt

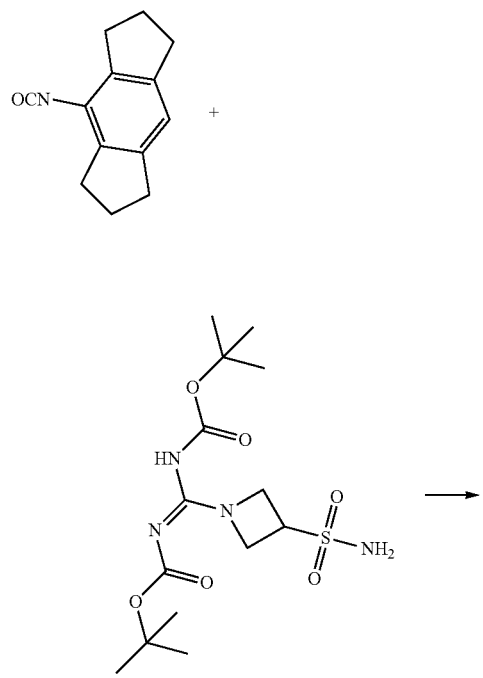

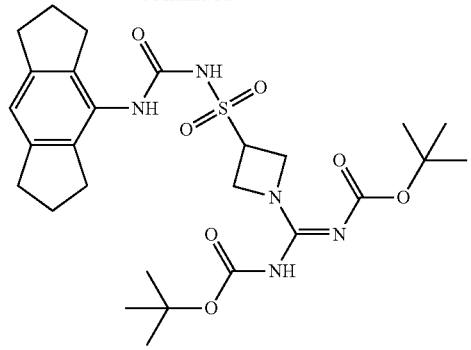

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and tert-butyl (Z)-(((tert-butoxycarbonyl)amino)(3-sulfamoylazetidin-1-yl)methylene)carbamate (Intermediate P102) to afford the title compound (31%) as a white solid.

$^1$H NMR (CDCl$_3$): δ=6.85 (s, 1H), 6.68 (s, 1H), 4.62-4.08 (m, 5H), 2.90-2.56 (m, 8H), 1.96 (m, 4H), 1.41 (d, 18H).

LCMS: m/z 578 (M+H)$^+$ (ES$^+$); 576 (M−H)$^−$ (ES$^−$).

Example 113: 3-(N-((1,2,3,5,6,7-Hexahydro-s-indacen-4-yl)carbamoyl) sulfamoyl)azetidine-1-carboximidamide, TFA Salt

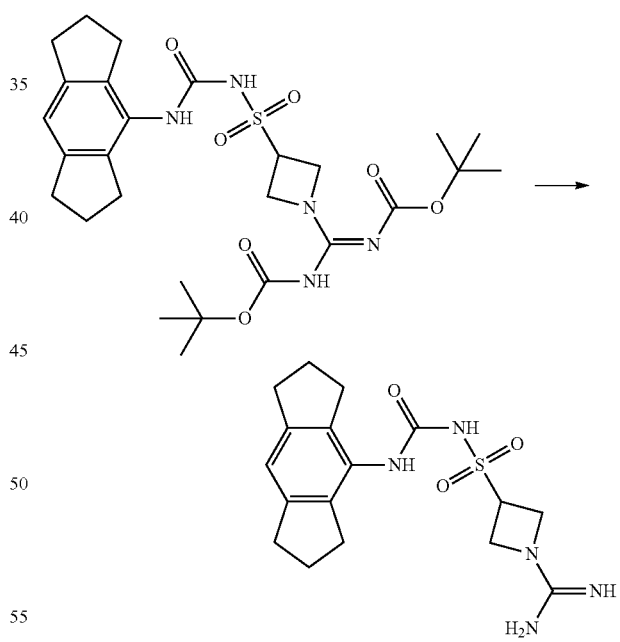

tert-Butyl-(((tert-butoxycarbonyl)imino) (3-(N-((1,2,3,5,6,7-hexahydro-s-indacen-4-yl)carbamoyl)sulfamoyl)azetidin-1-yl)methyl)carbamate, potassium salt (Example 112; 100 mg, 0.17 mmol) in DCM (0.5 mL) was treated with trifluoroacetic acid (0.5 mL) and stirred for 2 hours. Then the reaction mixture was concentrated in vacuo and DMSO (0.5-1 mL) was added. The mixture was submitted for purification by reversed phase column chromatography (see "Experimental Methods", "Purification Method 1") to afford the title compound (28%) as a white solid.

¹H NMR (CD₃OD): δ=6.88 (s, 1H), 4.49-4.24 (m, 5H), 2.82 (m, 8H), 2.02 (m, 4H). ¹⁹F-NMR indicated the presence of TFA.

LCMS: m/z 378 (M+H)⁺ (ES⁺); 376 (M−H)⁻ (ES⁻).

Example 114: N-((1,2,3,5,6,7-Hexahydro-s-indacen-4-yl)carbamoyl)-[1,3'-biazetidine]-3-sulfonamide, TFA Salt

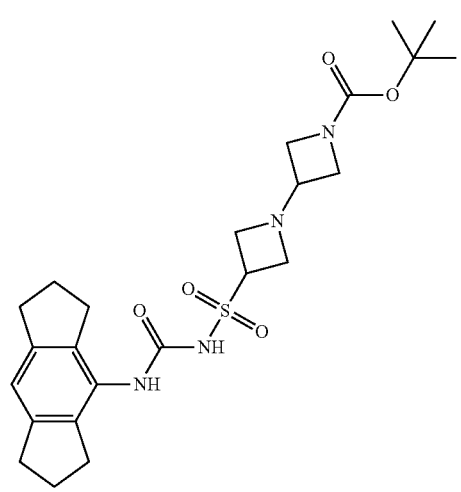

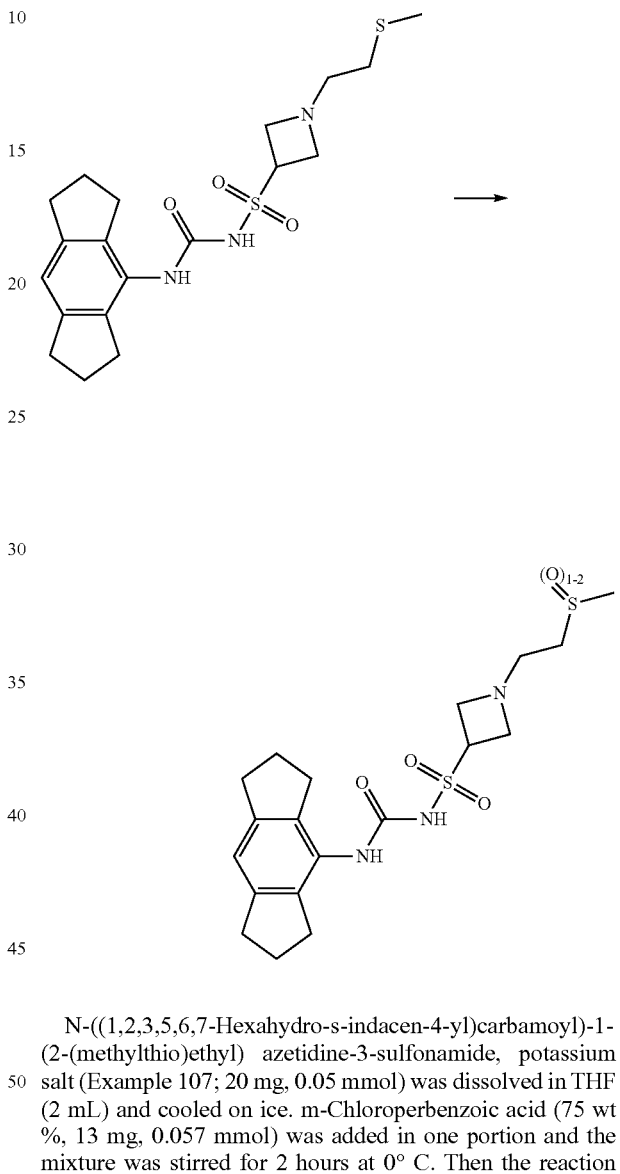

Prepared as described for 3-(N-((1,2,3,5,6,7-hexahydro-s-indacen-4-yl)carbamoyl) sulfamoyl)azetidine-1-carboximidamide, TFA salt (Example 113) from tert-butyl 3-(N-((1,2,3,5,6,7-hexahydro-s-indacen-4-yl)carbamoyl) sulfamoyl)-[1,3'-biazetidine]-1'-carboxylate, potassium salt (Example 106) to afford the title compound (24%) as a white solid.

¹H NMR (D₂O): δ=6.96 (s, 1H), 4.32-4.15 (m, 1H), 4.09-3.91 (m, 2H), 3.91-3.67 (m, 3H), 3.54 (m, 4H), 2.73 (t, 4H), 2.62 (t, 4H), 1.91 (m, 4H).

LCMS: m/z 391 (M+H)⁺ (ES⁺); 389 (M−H)⁻ (ES⁻).

Example 115: N-((1,2,3,5,6,7-Hexahydro-s-indacen-4-yl)carbamoyl)-1-(2-(methylsulfonyl)ethyl)azetidine-3-sulfonamide, Potassium Salt and N-((1,2,3,5,6,7-hexahydro-s-indacen-4-yl)carbamoyl)-1-(2-(methylsulfinyl) ethyl)azetidine-3-sulfonamide, Potassium Salt N-((1,2,3,5,6,7-Hexahydro-s-indacen-4-yl)carbamoyl)-1-(2-(methylthio)ethyl) azetidine-3-sulfonamide, potassium salt (Example 107; 20 mg, 0.05 mmol) was dissolved in THF (2 mL) and cooled on ice. m-Chloroperbenzoic acid (75 wt %, 13 mg, 0.057 mmol) was added in one portion and the mixture was stirred for 2 hours at 0° C. Then the reaction mixture was concentrated in vacuo and DMSO (0.5-1 mL) was added. The mixture was submitted for purification by reversed phase column chromatography (see "Experimental Methods", "Purification Method 1") to afford the title compounds (38%) as a white solid.

¹H NMR (CD₃OD) (mixture of sulfonyl/sulfinyl, ratio 2/1): δ=7.01 (sulfonyl) 6.95 (sulfinyl) (s, 1H), 4.36 (m, 1H), 3.94-3.58 (m, 4H), 3.19-2.97 (m, 4H), 2.97-2.73 (m, 8H), 2.73-2.59 (m, 3H), 2.23-1.97 (m, 4H).

LCMS: m/z 442 (M+H)⁺ (ES⁺); 440 (M−H)⁻ (ES⁻), sulfonyl.

LCMS: m/z 426 (M+H)⁺ (ES⁺); 424 (M−H)⁻ (ES⁻), sulfinyl.

Example 116: N-((1,2,3,5,6,7-Hexahydro-s-indacen-4-yl)carbamoyl)-1-(oxetan-3-yl)azetidine-3-sulfonamide, Potassium Salt

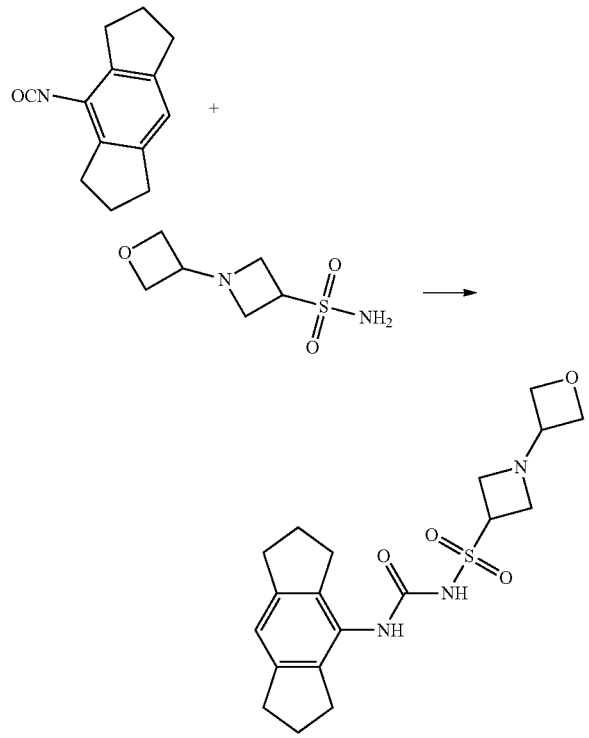

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(oxetan-3-yl)azetidine-3-sulfonamide (Intermediate P131) to afford the title compound (1%) as a white solid.

LCMS: m/z 392 (M+H)$^+$ (ES$^+$); 390 (M–H)$^-$ (ES$^-$).

Example 117: N-((1,2,3,5,6,7-Hexahydro-s-indacen-4-yl)carbamoyl)-1-(1-oxidothietan-3-yl)azetidine-3-sulfonamide, Potassium Salt

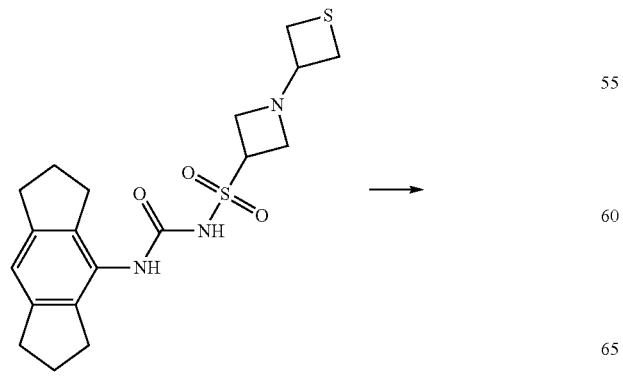

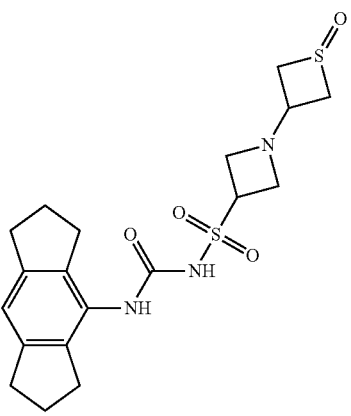

N-((1,2,3,5,6,7-Hexahydro-s-indacen-4-yl)carbamoyl)-1-(thietan-3-yl) azetidine-3-sulfonamide, potassium salt (Example 109; 25 mg, 0.06 mmol) was dissolved in THF (2 mL) and cooled on ice. m-Chloroperbenzoic acid (75 wt %, 17 mg, 0.74 mmol) was added in one portion and the mixture was stirred for 2 hours at 0° C. Then the reaction mixture was concentrated in vacuo and DMSO (0.5-1 mL) was added. The mixture was submitted for purification by reversed phase column chromatography (see "Experimental Methods", "Purification Method 1") to afford the title compounds (15%) as a white solid.

$^1$H NMR (CD$_3$OD): δ=7.00 (s, 1H), 4.69 (s, 1H), 4.14 (t, 1H), 3.61 (t, 1H), 3.49 (d, 1H), 3.03 (dt, 3H), 2.95-2.78 (m, 8H), 2.78-2.66 (m, 3H), 2.06 (m, 4H).

LCMS: m/z 424 (M+H)$^+$ (ES$^+$); 422 (M–H)$^-$ (ES$^-$).

Example 118: N-((1,2,3,5,6,7-Hexahydro-s-indacen-4-yl)carbamoyl)-1-(3-methylcyclobutyl)azetidine-3-sulfonamide, Potassium Salt

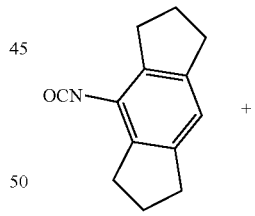

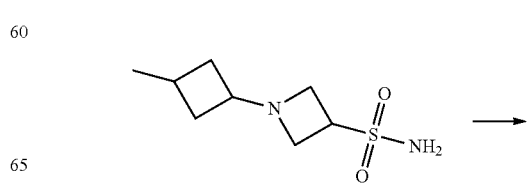

-continued

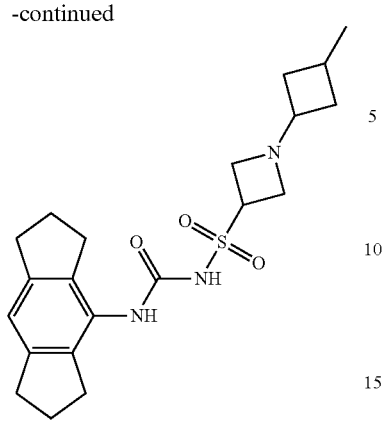

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(3-methylcyclobutyl) azetidine-3-sulfonamide (Intermediate P103) to afford the title compound (22%) as a white solid.

$^1$H NMR (CD$_3$OD): δ=6.87 (s, 1H), 4.31 (qd, 1H), 3.73-3.53 (m, 4H), 2.93-2.71 (m, 8H), 2.37 (d, 1H), 2.20 (td, 1H), 2.02 (m, 6H), 1.79-1.62 (m, 1H), 1.47 (dt, 1H), 1.08 (dd, 3H).

LCMS: m/z 404 (M+H)$^+$ (ES$^+$); 402 (M−H)$^-$ (ES$^-$).

Example 119: 1-(3,3-Dimethylcyclobutyl)-N-((1,2,3,5,6,7-hexahydro-s-indacen-4-yl)carbamoyl)azetidine-3-sulfonamide, Potassium Salt

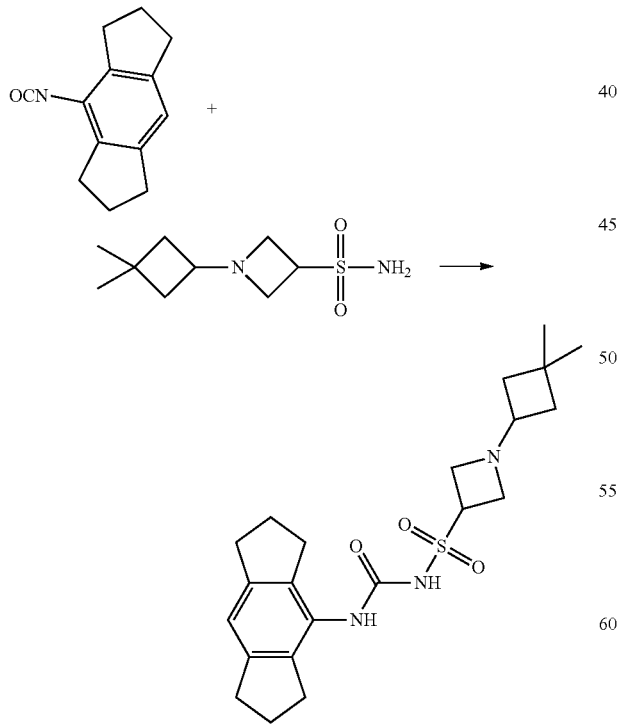

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(3,3-dimethylcyclobutyl) azetidine-3-sulfonamide (Intermediate P104) to afford the title compound (9%) as a white solid.

$^1$H NMR (CD$_3$OD): δ=6.89 (s, 1H), 4.34 (t, 1H), 4.25-3.94 (m, 4H), 3.94-3.69 (m, 1H), 2.81 (m, 8H), 2.04 (m, 6H), 1.82 (t, 2H), 1.15 (d, 6H).

LCMS: m/z 418 (M+H)$^+$ (ES$^+$); 416 (M−H)$^-$ (ES$^-$).

Example 120: 1-(1,1-Dioxidothietan-3-yl)-N-((1,2,3,5,6,7-hexahydro-s-indacen-4-yl)carbamoyl)azetidine-3-sulfonamide, Potassium Salt

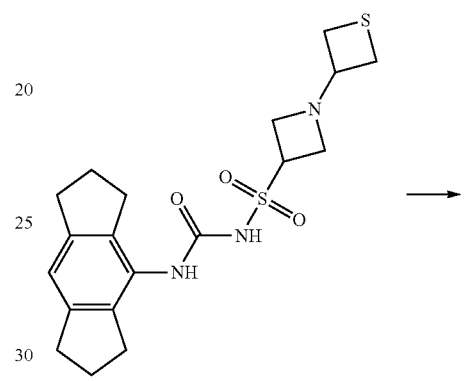

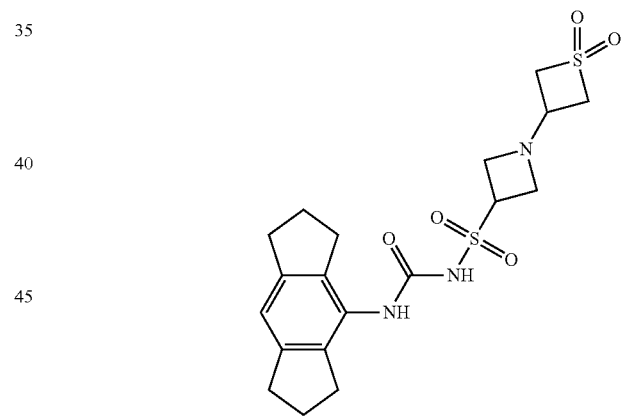

N-((1,2,3,5,6,7-Hexahydro-s-indacen-4-yl)carbamoyl)-1-(thietan-3-yl) azetidine-3-sulfonamide, potassium salt (Example 109; 18 mg, 0.044 mmol) was dissolved in THF (2 mL) and cooled on ice. m-Chloroperbenzoic acid (75 wt %, 18 mg, 0.078 mmol) was added in one portion and the mixture was stirred for 2 hours at 0° C. Then the reaction mixture was concentrated in vacuo and DMSO (0.5-1 mL) was added. The mixture was submitted for purification by reversed phase column chromatography (see "Experimental Methods", "Purification Method 1") to afford the title compounds (47%) as a white solid.

$^1$H NMR (CD$_3$OD): δ=7.00 (s, 1H), 4.21 (m, 1H), 3.88 (s, 2H), 3.65 (m, 2H), 3.13 (dd, 1H), 2.83 (m, 12H), 2.07 (m, 4H).

LCMS: m/z 440 (M+H)$^+$ (ES$^+$); 438 (M−H)$^-$ (ES$^-$).

Example 121: N-((1,2,3,5,6,7-Hexahydro-s-indacen-4-yl)carbamoyl)-1-(tetrahydrofuran-3-yl)azetidine-3-sulfonamide, Potassium Salt

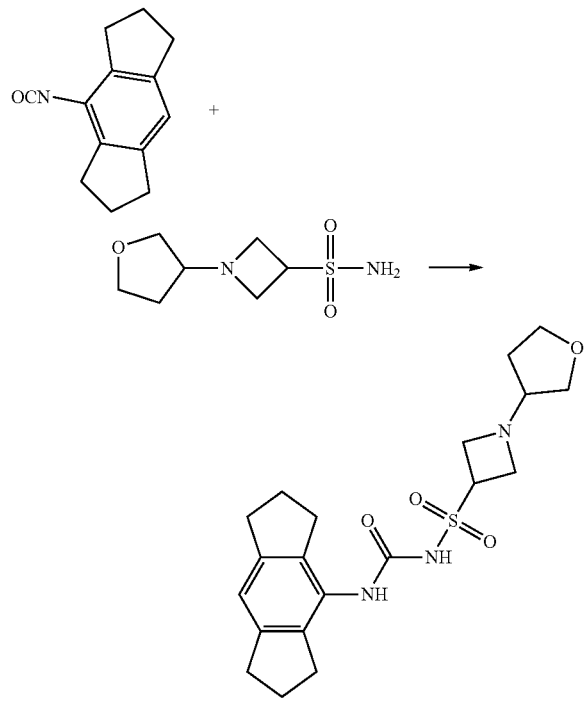

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(tetrahydrofuran-3-yl) azetidine-3-sulfonamide (Intermediate P106) to afford the title compound (27%) as a white solid.

$^1$H NMR (CD$_3$OD): δ=6.87 (s, 1H), 4.31 (p, 1H), 3.87 (q, 1H), 3.79-3.43 (m, 7H), 2.81 (m, 9H), 2.03 (m, 4H), 1.98-1.84 (m, 1H), 1.82-1.62 (m, 1H).

LCMS: m/z 405 (M+H)$^+$ (ES$^+$); 403 (M−H)$^−$ (ES$^−$).

Example 122: 1-(sec-Butyl)-N-((1,2,3,5,6,7-hexahydro-s-indacen-4-yl)carbamoyl)azetidine-3-sulfonamide, Potassium Salt

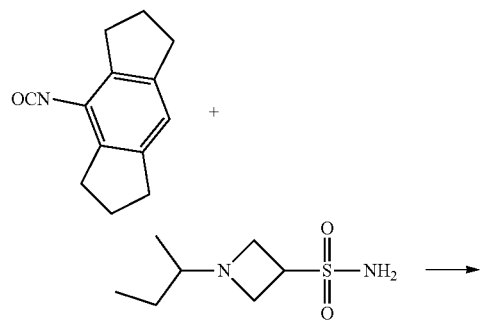

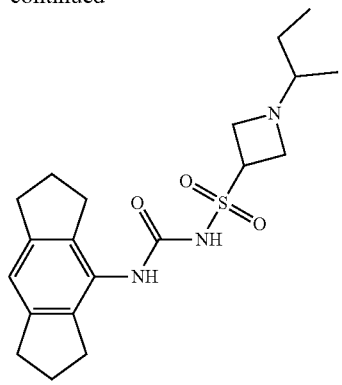

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(sec-butyl)azetidine-3-sulfonamide (Intermediate P107) to afford the title compound (43%) as a white solid.

$^1$H NMR (CD$_3$OD): δ=6.87 (s, 1H), 4.29 (p, 1H), 3.70 (t, 2H), 3.63-3.45 (m, 2H), 2.82 (m, 8H), 2.38 (m, 1H), 2.02 (m, 4H), 1.65-1.45 (m, 1H), 1.21-1.02 (m, 1H), 1.02-0.82 (m, 6H).

LCMS: m/z 392 (M+H)$^+$ (ES$^+$); 390 (M−H)$^−$ (ES$^−$).

Example 123: N-((1,2,3,5,6,7-Hexahydro-s-indacen-4-yl)carbamoyl)-1-((1-methyl-1H-imidazol-2-yl)methyl)azetidine-3-sulfonamide, Potassium Salt Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-((1-methyl-1H-imidazol-2-yl)methyl)azetidine-3-sulfonamide (Intermediate P108) to afford the title compound (49%) as a white solid.

¹H NMR (CD₃OD): δ=7.00 (s, 1H), 6.84 (d, 2H), 4.34 (p, 1H), 3.74 (s, 2H), 3.70 (s, 3H), 3.68-3.52 (m, 4H), 2.80 (m, 8H), 2.01 (m, 4H).
LCMS: m/z 430 (M+H)⁺ (ES⁺); 428 (M−H)⁻ (ES⁻).

Example 124: 1-(2,2-Dimethylcyclobutyl)-N-((1,2,3,5,6,7-hexahydro-s-indacen-4-yl)carbamoyl)azetidine-3-sulfonamide, Potassium Salt

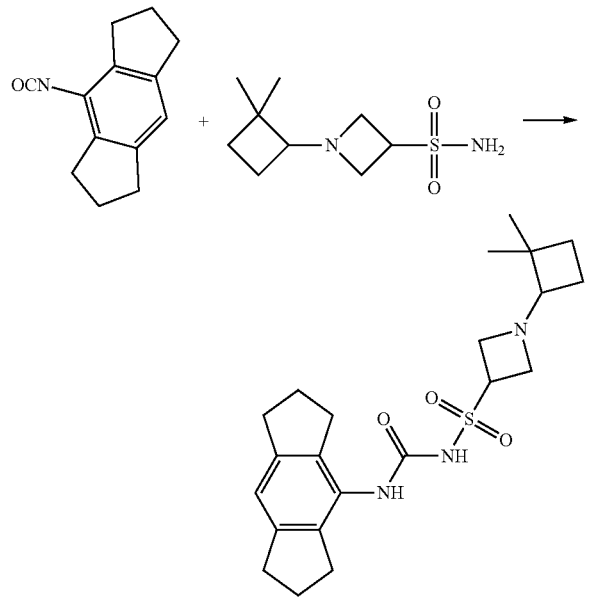

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(2,2-dimethylcyclobutyl) azetidine-3-sulfonamide (Intermediate P109) to afford the title compound (16%) as a white solid.
¹H NMR (CD₃OD): δ=6.89 (s, 1H), 4.40 (t, 1H), 3.73 (dq, 4H), 3.02 (t, 1H), 2.83 (m, 8H), 2.04 (m, 4H), 1.79-1.63 (m, 2H), 1.63-1.46 (m, 2H), 1.10 (d, 6H).
LCMS: m/z 418 (M+H)⁺ (ES⁺); 416 (M−H)⁻ (ES⁻).

Example 125: N-((1,2,3,5,6,7-Hexahydro-s-indacen-4-yl)carbamoyl)-1-(pyrimidin-5-ylmethyl)azetidine-3-sulfonamide, Potassium Salt

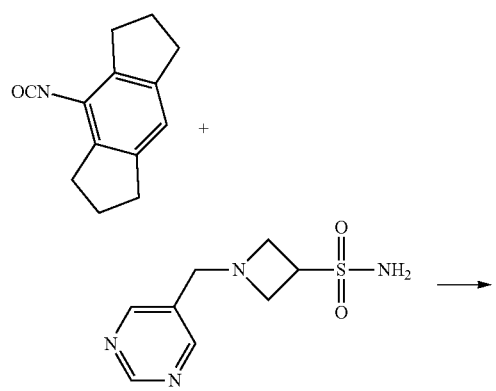

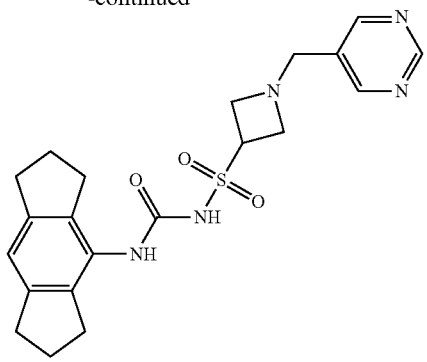

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(pyrimidin-5-ylmethyl)azetidine-3-sulfonamide (Intermediate P105) to afford the title compound (8%) as a white solid.
¹H NMR (CD₃OD): δ=9.06 (s, 1H), 8.76 (s, 2H), 6.88 (s, 1H), 4.38 (t, 1H), 3.77 (s, 2H), 3.74-3.59 (m, 4H), 2.96-2.73 (m, 8H), 2.03 (m, 4H).
LCMS: m/z 428 (M+H)⁺ (ES⁺); 426 (M−H)⁻ (ES⁻).

Example 126: 1-(Cyclobutylmethyl)-N-((1,2,3,5,6,7-hexahydro-s-indacen-4-yl)carbamoyl)azetidine-3-sulfonamide, Potassium Salt

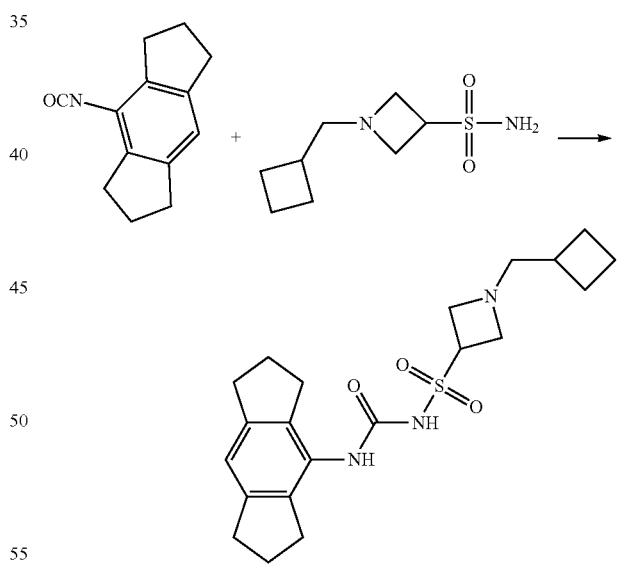

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(cyclobutylmethyl) azetidine-3-sulfonamide (Intermediate P111) to afford the title compound (14%) as a white solid.
¹H NMR (CD₃OD): δ=6.87 (s, 1H), 4.34 (p, 1H), 3.72 (dd, 2H), 3.62 (dd, 2H), 2.81 (m, 8H), 2.65 (d, 2H), 2.40 (p, 1H), 2.02 (m, 6H), 1.95-1.64 (m, 4H).
LCMS: m/z 404 (M+H)⁺ (ES⁺); 402 (M−H)⁻ (ES⁻).

Example 127: tert-Butyl-(((tert-butoxycarbonyl)imino)(3-(N-((1,2,3,5,6,7-hexahydro-s-indacen-4-yl)carbamoyl) sulfamoyl)azetidin-1-yl)methyl) (methyl)carbamate, Potassium Salt

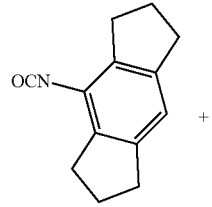

+

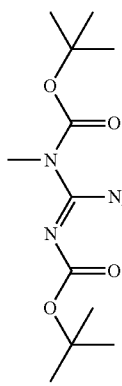

→

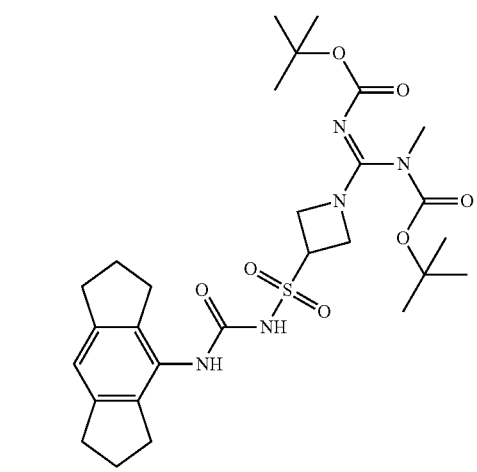

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and tert-butyl-(E)-(((tert-butoxycarbonyl)imino)(3-sulfamoylazetidin-1-yl)methyl) (methyl) carbamate (Intermediate P110) to afford the title compound (49%) as a white solid.

$^1$H NMR (CDCl$_3$): δ=6.83 (s, 1H), 6.81 (s, 1H), 4.51 (d, 1H), 4.24 (dd, 4H), 2.91 (s, 3H), 2.75 (m, 8H), 1.95 (m, 4H), 1.41 (d, 18H).

LCMS: m/z 592 (M+H)$^+$ (ES$^+$); 590 (M−H)$^−$ (ES$^−$).

Example 128: N-((1,2,3,5,6,7-Hexahydro-s-indacen-4-yl)carbamoyl)-1-(2-(hydroxyimino)propyl)azetidine-3-sulfonamide, Potassium Salt

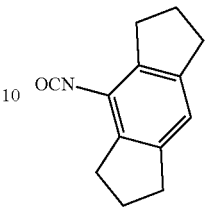 + 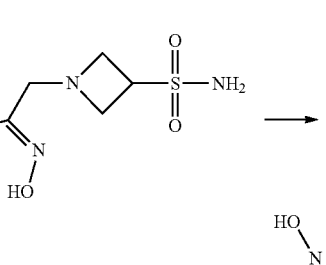 →

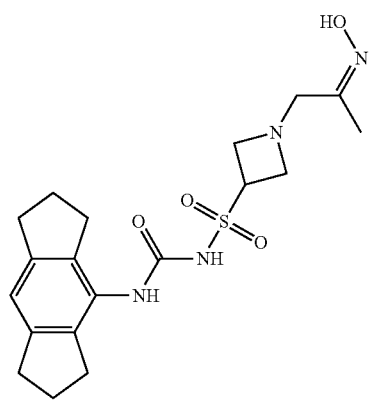

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1), potassium tert-butoxide (2 equiv.) and 1-(2-(hydroxyimino)propyl)azetidine-3-sulfonamide (Intermediate P112) to afford the title compound (6%) as a white solid.

$^1$H NMR (CD$_3$OD): δ=6.86 (s, 1H), 4.47-4.26 (m, 1H), 3.59 (dt, 4H), 3.19 (s, 2H), 2.81 (m, 8H), 2.02 (m, 4H), 1.81 (s, 3H).

LCMS: m/z 407 (M+H)$^+$ (ES$^+$); 405 (M−H)$^−$ (ES$^−$).

Example 129: 3-(N-((1,2,3,5,6,7-Hexahydro-s-indacen-4-yl)carbamoyl) sulfamoyl)-N-methylazetidine-1-carboximidamide, TFA Salt

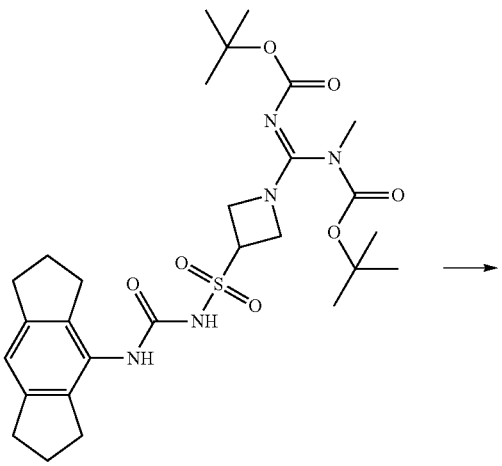 →

-continued

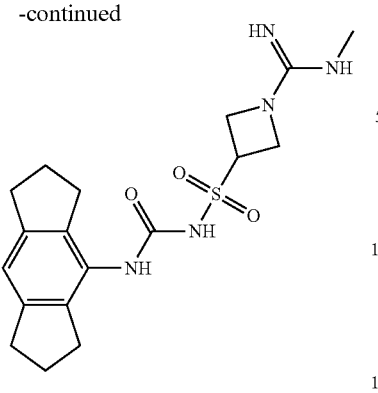

Prepared as described for 3-(N-((1,2,3,5,6,7-hexahydro-s-indacen-4-yl)carbamoyl) sulfamoyl)azetidine-1-carboximidamide, TFA salt (Example 113) from tert-butyl-(((tert-butoxycarbonyl)imino)(3-(N-((1,2,3,5,6,7-hexahydro-s-indacen-4-yl) carbamoyl)sulfamoyl)azetidin-1-yl)methyl)(methyl)carbamate, potassium salt (Example 127) to afford the title compound (48%) as a white solid.

$^1$H NMR (CD$_3$OD): δ=6.88 (s, 1H), 4.46-4.35 (m, 2H), 4.35-4.23 (m, 2H), 2.93-2.71 (m, 11H), 2.71-2.50 (m, 1H), 2.02 (m, 4H).

LCMS: m/z 392 (M+H)$^+$ (ES$^+$).

Example 130: N-((1,2,3,5,6,7-Hexahydro-s-indacen-4-yl)carbamoyl)-1-(1-hydroxypropan-2-yl)azetidine-3-sulfonamide, Potassium Salt

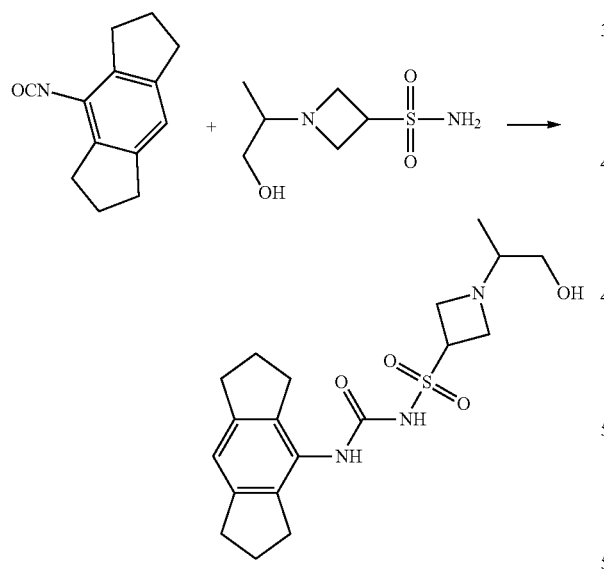

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1), potassium tert-butoxide (2 equiv.) and 1-(1-hydroxypropan-2-yl)azetidine-3-sulfonamide (Intermediate P113) to afford the title compound (12%) as a white solid.

$^1$H NMR (CD$_3$OD): δ=6.86 (s, 1H), 4.33 (p, 1H), 3.63 (tt, 4H), 3.43 (dd, 1H), 2.81 (m, 9H), 2.52 (q, 1H), 2.03 (m, 4H), 0.94 (d, 3H).

LCMS: m/z 394 (M+H)$^+$ (ES$^+$); 392 (M−H)$^-$ (ES$^-$).

Example 131: 1-(1,1-Difluoropropan-2-yl)-N-((1,2,3,5,6,7-hexahydro-s-indacen-4-yl)carbamoyl)azetidine-3-sulfonamide, Potassium Salt

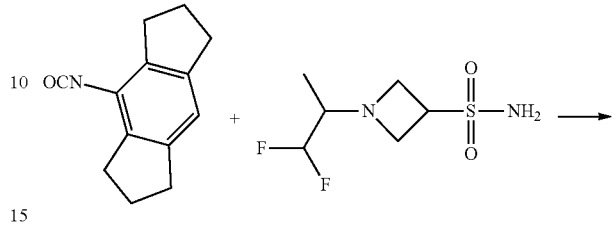

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(1,1-difluoropropan-2-yl)azetidine-3-sulfonamide (Intermediate P114) to afford the title compound (46%) as a white solid.

$^1$H NMR (CD$_3$OD): δ=6.87 (s, 1H), 5.58 (td, 1H), 4.30 (p, 1H), 3.82-3.51 (m, 4H), 2.81 (m, 8H), 2.69 (ddd, 1H), 2.02 (m, 4H), 1.00 (d, 3H).

LCMS: m/z 414 (M+H)$^+$ (ES$^+$); 412 (M−H)$^-$ (ES$^-$).

Example 132: 1-Allyl-N-((1,2,3,5,6,7-hexahydro-s-indacen-4-yl)carbamoyl) azetidine-3-sulfonamide, Potassium Salt

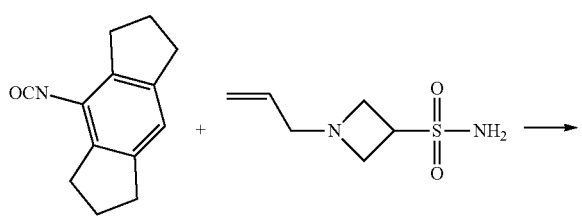

349
-continued

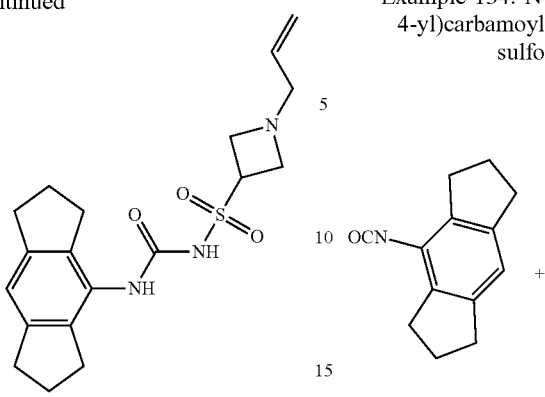

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-allylazetidine-3-sulfonamide (Intermediate P115) to afford the title compound (15%) as a white solid.

$^1$H NMR (CD$_3$OD): δ=6.89 (s, 1H), 5.77 (ddt, 1H), 5.54-5.30 (m, 2H), 4.36 (q, 1H), 4.20-3.97 (m, 4H), 3.55 (d, 2H), 2.81 (m, 8H), 2.17-1.93 (m, 4H).

LCMS: m/z 376 (M+H)$^+$ (ES$^+$); 374 (M−H)$^−$ (ES$^−$).

Example 133: N-((1,2,3,5,6,7-Hexahydro-s-indacen-4-yl)carbamoyl)-1-(prop-2-yn-1-yl)azetidine-3-sulfonamide, Potassium Salt

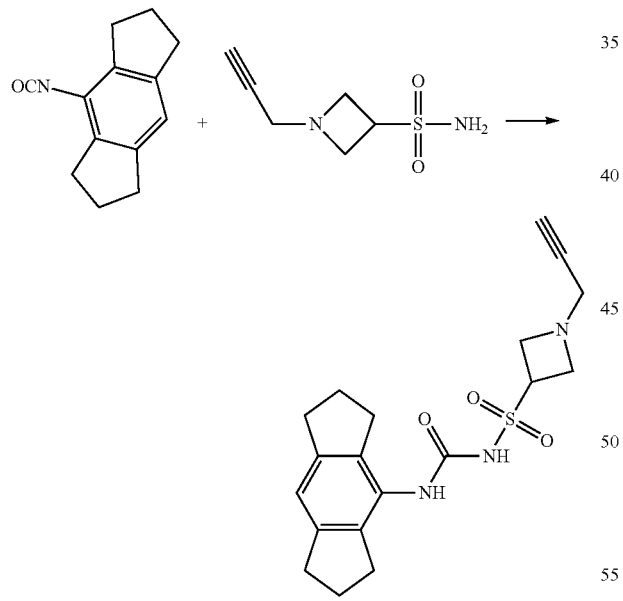

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(prop-2-yn-1-yl)azetidine-3-sulfonamide (Intermediate P116) to afford the title compound (14%) as a white solid.

$^1$H NMR (CD$_3$OD): δ=6.86 (s, 1H), 4.31 (q, 1H), 3.66 (d, 4H), 3.31 (s, 2H), 2.81 (q, 8H), 2.71-2.57 (m, 1H), 2.02 (m, 4H).

LCMS: m/z 374 (M+H)$^+$ (ES$^+$); 372 (M−H)$^−$ (ES$^−$).

Example 134: N-((1,2,3,5,6,7-Hexahydro-s-indacen-4-yl)carbamoyl)-1-(3-hydroxypropyl)azetidine-3-sulfonamide, Potassium Salt

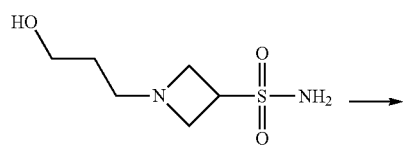

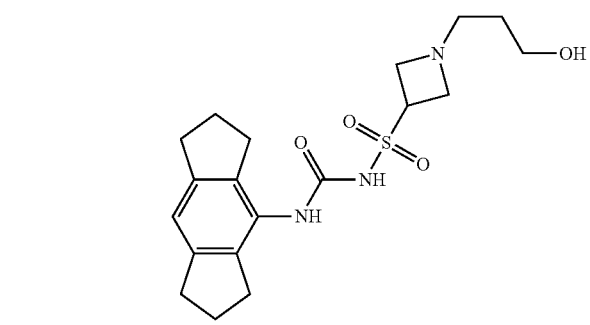

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1), potassium tert-butoxide (2 equiv.) and 1-(3-hydroxypropyl)azetidine-3-sulfonamide (Intermediate P117) to afford the title compound (3%) as a white solid.

LCMS: m/z 394 (M+H)$^+$ (ES$^+$); 392 (M−H)$^−$ (ES$^−$).

Example 135: N-((1,2,3,5,6,7-Hexahydro-s-indacen-4-yl)carbamoyl)-1-neopentylazetidine-3-sulfonamide, Potassium Salt

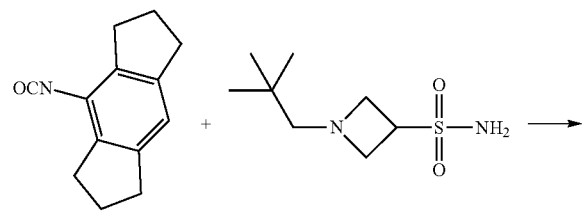

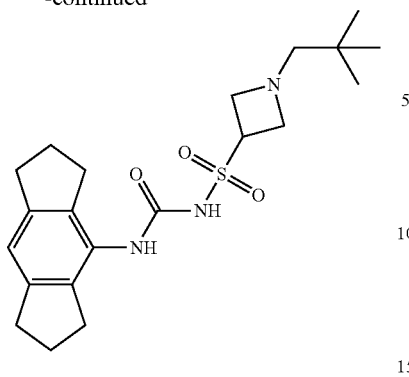

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-neopentylazetidine-3-sulfonamide (Intermediate P118) to afford the title compound (12%) as a white solid.

$^1$H NMR (CD$_3$OD): δ=6.92 (s, 1H), 4.54-4.29 (m, 5H), 3.06 (s, 2H), 2.79 (m, 8H), 2.16-1.93 (m, 4H), 1.00 (s, 9H).

LCMS: m/z 406 (M+H)$^+$ (ES$^+$); 404 (M–H)$^−$ (ES$^−$).

Example 136: N-((1,2,3,5,6,7-Hexahydro-s-indacen-4-yl)carbamoyl)-1-((trimethylsilyl)methyl)azetidine-3-sulfonamide, Potassium Salt

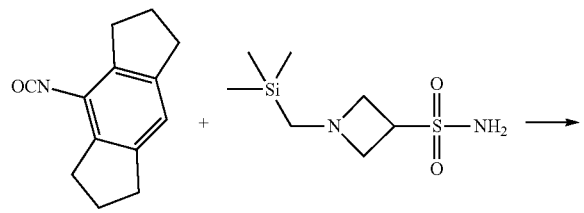

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-((trimethylsilyl)methyl) azetidine-3-sulfonamide (Intermediate P119) to afford the title compound (32%) as a white solid.

$^1$H NMR (CD$_3$OD): δ=6.87 (s, 1H), 4.32 (t, 1H), 3.89 (t, 2H), 3.70 (t, 2H), 2.81 (m, 8H), 2.33 (s, 2H), 2.02 (m, 4H), 0.08 (s, 9H).

LCMS: m/z 422 (M+H)$^+$ (ES$^+$); 420 (M–H)$^−$ (ES$^−$).

Example 137: N-((1,2,3,5,6,7-Hexahydro-s-indacen-4-yl)carbamoyl)-1-(2-hydroxypropyl)azetidine-3-sulfonamide, Potassium Salt

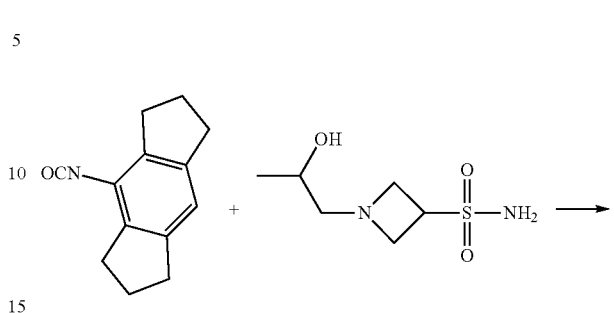

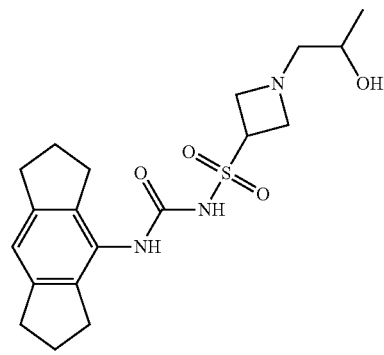

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1), potassium tert-butoxide (2 equiv.) and 1-(2-hydroxypropyl)azetidine-3-sulfonamide (Intermediate P120) to afford the title compound (14%) as a white solid.

$^1$H NMR (CD$_3$OD): δ=6.86 (s, 1H), 4.37 (p, 1H), 3.84-3.47 (m, 4H), 2.81 (m, 9H), 2.50 (d, 2H), 2.13-1.93 (m, 4H), 1.10 (d, 3H).

LCMS: m/z 394 (M+H)$^+$ (ES$^+$); 392 (M–H)$^−$ (ES$^−$).

Example 118: N-((1,2,3,5,6,7-Hexahydro-s-indacen-4-yl)carbamoyl)-1-(4-hydroxybutyl)azetidine-3-sulfonamide, Potassium Salt


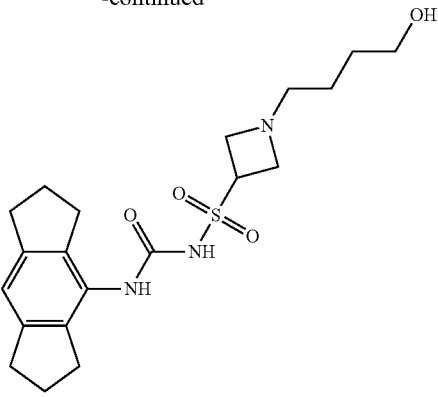

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1), potassium tert-butoxide (2 equiv.) and 1-(4-hydroxybutyl)azetidine-3-sulfonamide (Intermediate P121) to afford the title compound (4%) as a white solid.

$^1$H NMR (CD$_3$OD): δ=6.87 (s, 1H), 4.41-4.23 (m, 1H), 3.67 (t, 2H), 3.61-3.45 (m, 4H), 2.82 (m, 8H), 2.57 (t, 2H), 2.15-1.91 (m, 4H), 1.50 (m, 4H).

LCMS: m/z 408 (M+H)$^+$ (ES$^+$); 406 (M–H)$^-$ (ES$^-$).

Example 139: N-((1,2,3,5,6,7-Hexahydro-s-indacen-4-yl)carbamoyl)-1-(2-(3-methyl-3H-diazirin-3-yl)ethyl)azetidine-3-sulfonamide, Potassium Salt

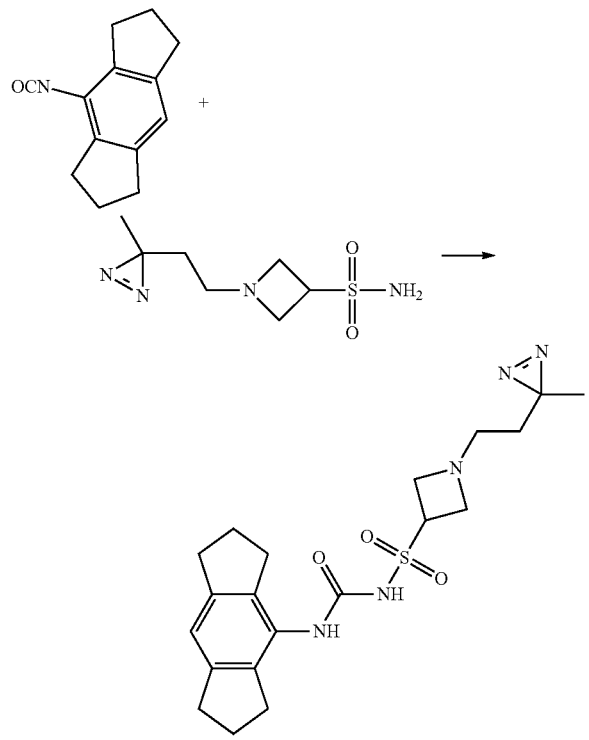

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(2-(3-methyl-3H-diazirin-3-yl)ethyl)azetidine-3-sulfonamide (Intermediate P122) to afford the title compound (3%) as a white solid.

$^1$H NMR (CD$_3$OD): δ=6.87 (s, 1H), 4.33 (p, 1H), 3.64 (t, 2H), 3.49 (q, 2H), 2.82 (m, 8H), 2.46 (t, 2H), 2.03 (m, 4H), 1.35 (t, 2H), 1.00 (s, 3H).

LCMS: m/z 418 (M+H)$^+$ (ES$^+$); 416 (M–H)$^-$ (ES$^-$).

Example 140: N-((1,2,3,5,6,7-Hexahydro-s-indacen-4-yl)carbamoyl)-1-((i-methyl-6-oxo-1,6-dihydropyridin-3-yl)methyl) azetidine-3-sulfonamide, Potassium Salt

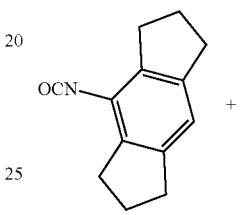

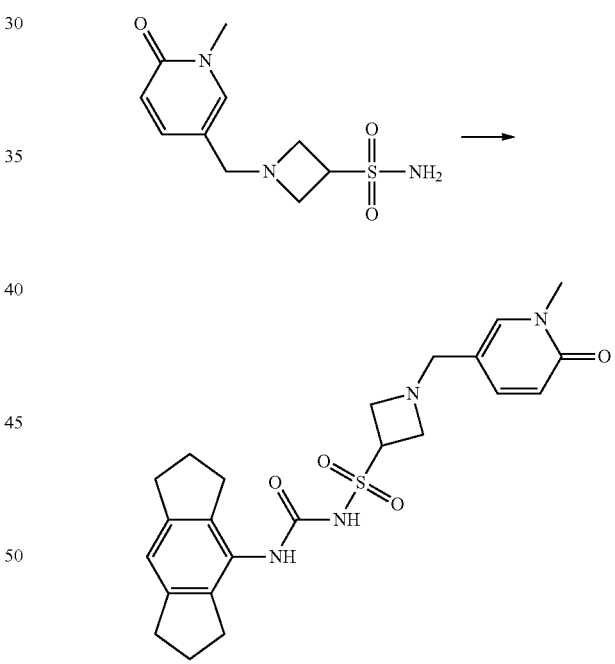

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-((1-methyl-6-oxo-1,6-dihydropyridin-3-yl)methyl)azetidine-3-sulfonamide (Intermediate P123) to afford the title compound (16%) as a white solid.

$^1$H NMR (CD$_3$OD): δ=7.59 (d, 1H), 7.50 (dd, 1H), 6.87 (s, 1H), 6.51 (d, 1H), 4.32 (p, 1H), 3.71-3.57 (m, 3H), 3.53 (d, 4H), 3.47 (s, 2H), 2.80 (m, 8H), 2.01 (m, 4H).

LCMS: m/z 457 (M+H)$^+$ (ES$^+$); 455 (M–H)$^-$ (ES$^-$).

Example 141: N-((1,2,3,5,6,7-Hexahydro-s-indacen-4-yl)carbamoyl)-1-((1-methyl-2-oxo-1,2-dihydropyridin-4-yl)methyl)azetidine-3-sulfonamide, Potassium Salt

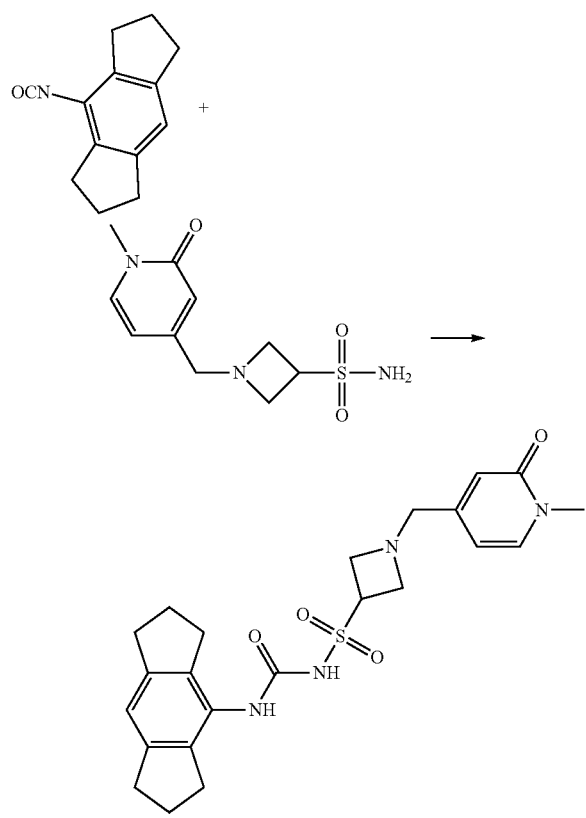

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-((1-methyl-2-oxo-1,2-dihydropyridin-4-yl)methyl)azetidine-3-sulfonamide (Intermediate P124) to afford the title compound (13%) as a white solid.

$^1$H NMR (CD$_3$OD): δ=7.56 (d, 1H), 6.86 (s, 1H), 6.55-6.42 (m, 1H), 6.34 (dd, 1H), 4.37 (p, 1H), 3.68 (t, 2H), 3.59 (t, 4H), 3.52 (s, 3H), 2.93-2.73 (m, 8H), 2.01 (m, 4H).

LCMS: m/z 457 (M+H)$^+$ (ES$^+$); 455 (M–H)$^-$ (ES$^-$).

Example 142: N-((1,2,3,5,6,7-Hexahydro-s-indacen-4-yl)carbamoyl)-1-(2-(tetrahydrofuran-3-yl)ethyl)azetidine-3-sulfonamide, Potassium Salt

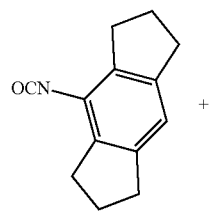

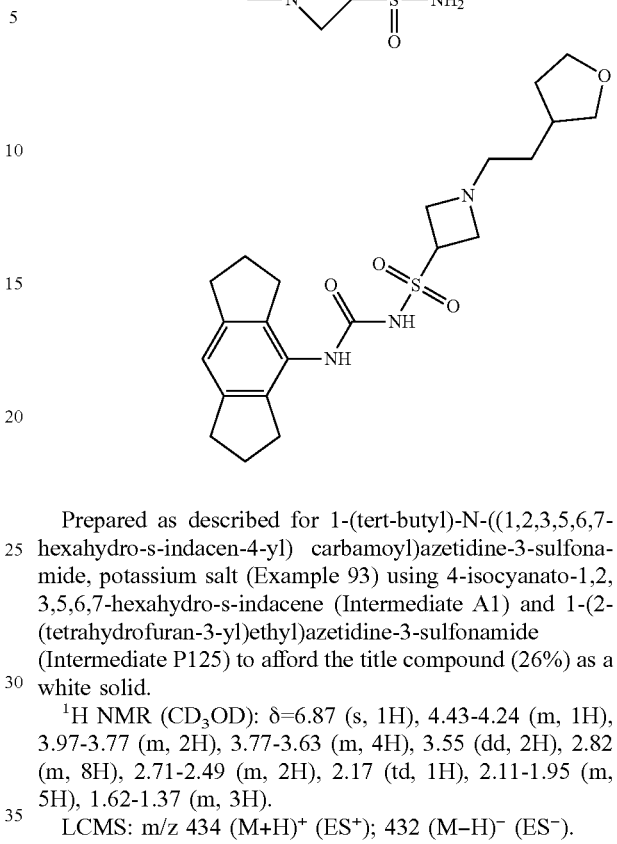

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(2-(tetrahydrofuran-3-yl)ethyl)azetidine-3-sulfonamide (Intermediate P125) to afford the title compound (26%) as a white solid.

$^1$H NMR (CD$_3$OD): δ=6.87 (s, 1H), 4.43-4.24 (m, 1H), 3.97-3.77 (m, 2H), 3.77-3.63 (m, 4H), 3.55 (dd, 2H), 2.82 (m, 8H), 2.71-2.49 (m, 2H), 2.17 (td, 1H), 2.11-1.95 (m, 5H), 1.62-1.37 (m, 3H).

LCMS: m/z 434 (M+H)$^+$ (ES$^+$); 432 (M–H)$^-$ (ES$^-$).

Example 143: 1-(sec-Butyl)-N-((4-fluoro-2,6-diisopropylphenyl)carbamoyl) azetidine-3-sulfonamide

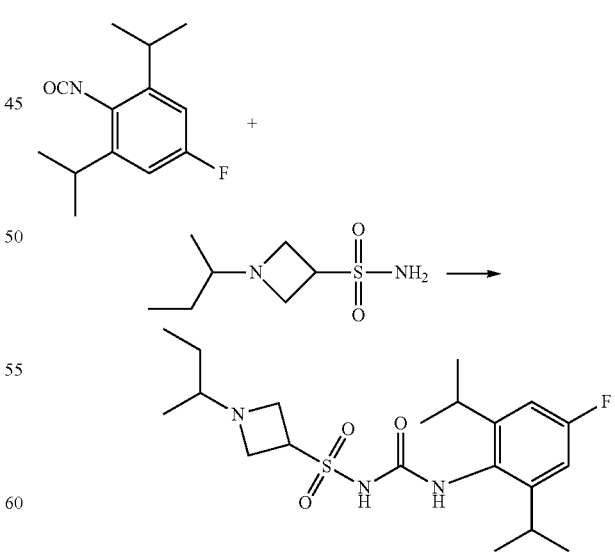

Prepared as described for 1-(tert-butyl)-N-((1,2,3,5,6,7-hexahydro-s-indacen-4-yl) carbamoyl)azetidine-3-sulfonamide, potassium salt (Example 93) using 5-fluoro-2-isocyanato-1,3-diisopropylbenzene (Intermediate A3) and 1-(sec-butyl)azetidine-3-sulfonamide (Intermediate P107) to afford the title compound (26%) as white solid.

¹H NMR (CD₃OD): δ=6.82 (d, 2H), 4.27 (p, 1H), 3.89 (P, 4H), 3.22 (q, 2H), 2.70 (m, 1H), 1.61 (m, 1H), 1.18 (d, 14H), 1.03 (d, 3H), 0.92 (t, 3H).

Example 144: N-((1,2,3,5,6,7-Hexahydro-s-indacen-4-yl)carbamoyl)-1-((tetrahydrofuran-3-yl)methyl)azetidine-3-sulfonamide, Potassium Salt

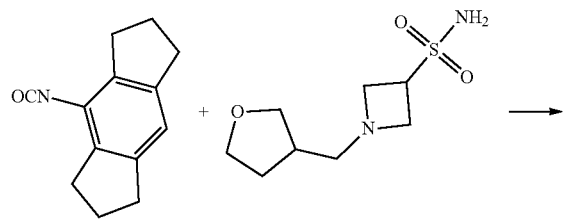

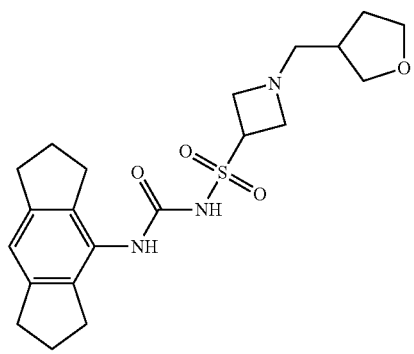

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-((tetrahydrofuran-3-yl)methyl)azetidine-3-sulfonamide (Intermediate P126) to afford the title compound (51%) as a white solid.

¹H NMR (CD₃OD): δ=6.87 (s, 1H), 4.34 (p, 1H), 3.82 (ddd, 2H), 3.77-3.61 (m, 2H), 3.51 (td, 2H), 3.39 (dd, 2H), 2.82 (m, 8H), 2.56 (dd, 2H), 2.39-2.18 (m, 1H), 2.02 (m, 5H), 1.57 (dq, 1H).

LCMS: m/z 420 (M+H)⁺ (ES⁺); 418 (M−H)⁻ (ES⁻).

Example 145: N-((1,2,3,5,6,7-Hexahydro-s-indacen-4-yl)carbamoyl)-1-((tetrahydrofuran-2-yl)methyl)azetidine-3-sulfonamide, Potassium Salt

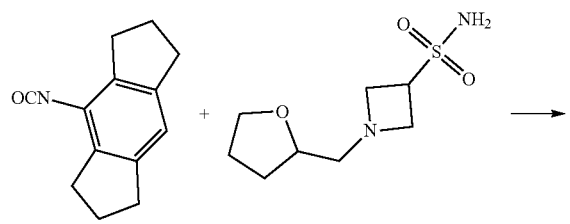

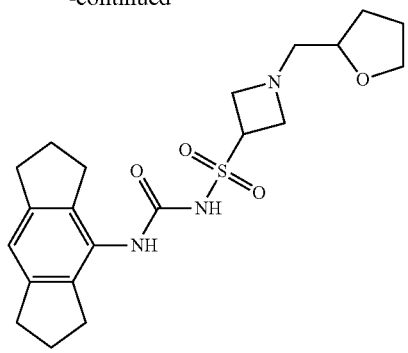

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-((tetrahydrofuran-2-yl)methyl)azetidine-3-sulfonamide (Intermediate P127) to afford the title compound (22%) as a white solid.

¹H NMR (CD₃OD): δ=6.87 (s, 1H), 4.34 (p, 1H), 3.98-3.78 (m, 2H), 3.68 (m, 5H), 2.81 (m, 8H), 2.73-2.56 (m, 2H), 2.02 (m, 5H), 1.87 (dt, 2H), 1.50 (dd, 1H).

LCMS: m/z 420 (M+H)⁺ (ES⁺); 418 (M−H)⁻ (ES⁻).

Example 146: (1R*,3R*,5S*)—N-((1,2,3,5,6,7-Hexahydro-s-indacen-4-yl) carbamoyl)-8-(1-methyl-azetidin-3-yl)-8-azabicyclo[3.2.1]octane-3-sulfonamide, Potassium Salt

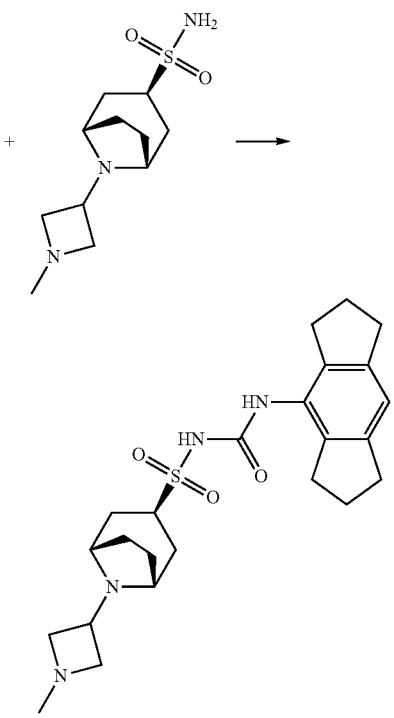

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and (1R, 3R,5S)-8-(1-methylazetidin-3-yl)-8-azabicyclo[3.2.1]
octane-3-sulfonamide (Intermediate P128) to afford the title
compound (8%) as a white solid.

¹H NMR (CD₃OD): δ=6.89 (s, 1H), 3.96 (m, 4H), 3.61 (m, 2H), 2.97-2.66 (m, 11H), 2.43 (m, 2H), 2.03 (m, 4H), 1.91 (m, 4H), 1.67 (m, 2H), 1.32 (m, 2H).

LCMS: m/z 459 (M+H)⁺ (ES⁺); 457 (M−H)⁻ (ES⁻).

Example 147: 1-Ethyl-N-((1,2,3,5,6,7-hexahydro-s-indacen-4-yl)carbamoyl)-5-oxopyrrolidine-3-sulfonamide, Potassium Salt

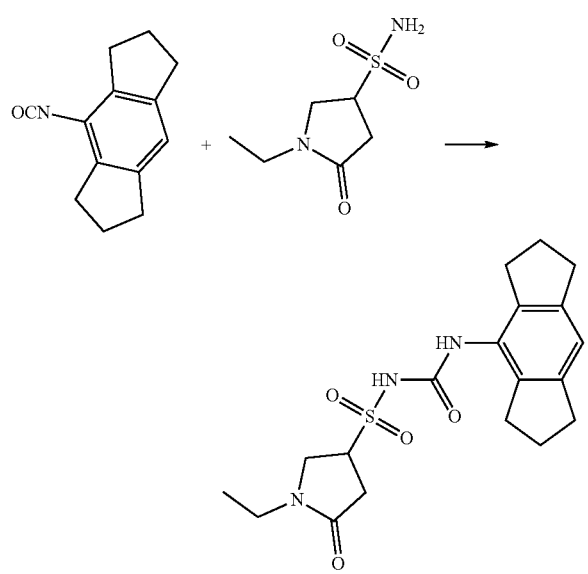

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-ethyl-5-oxopyrrolidine-3-sulfonamide (Intermediate P81) to afford the title compound (62%) as a white solid.

¹H NMR (CD₃OD): δ=6.87 (s, 1H), 4.43-4.24 (m, 1H), 3.86 (dd, 1H), 3.74 (dd, 1H), 3.33 (m, 2H), 2.95-2.70 (m, 10H), 2.15-1.94 (m, 4H), 1.13 (t, 3H).

LCMS: m/z 392 (M+H)⁺ (ES⁺); 390 (M−H)⁻ (ES⁻).

Example 148: 4-(N-((1,2,3,5,6,7-Hexahydro-s-indacen-4-yl)carbamoyl) sulfamoyl)-1-isopropyl-N,N-dimethylpyrrolidine-2-carboxamide, Potassium Salt

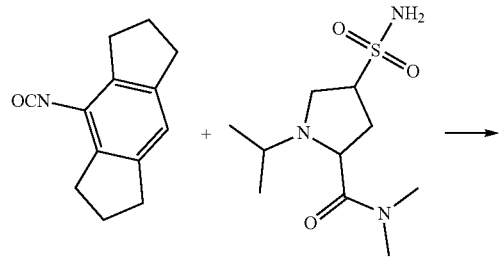

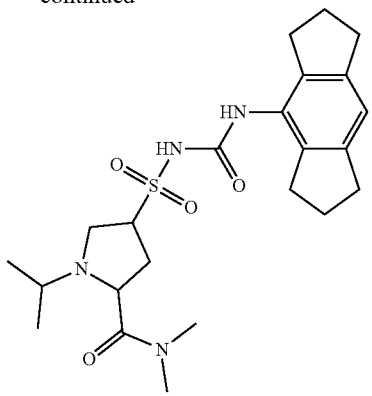

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-isopropyl-N,N-dimethyl-4-sulfamoylpyrrolidine-2-carboxamide (Intermediate P80) to afford the title compound (25%) as a white solid.

¹H NMR (D₂O): δ=6.96 (s, 1H), 4.07 (m, 2H), 3.36 (m, 1H), 3.18 (m, 1H), 3.02 (d, 6H), 2.68 (m, 8H), 2.46 (m, 1H), 1.90 (m, 4H), 1.75 (m, 2H), 1.01-0.83 (m, 6H).

LCMS: m/z 463 (M+H)⁺ (ES⁺); 461 (M−H)⁻ (ES⁻).

Example 149: N-((1,2,3,5,6,7-Hexahydro-s-indacen-4-yl)carbamoyl)-4-methoxy-1-methylpyrrolidine-3-sulfonamide, Potassium Salt

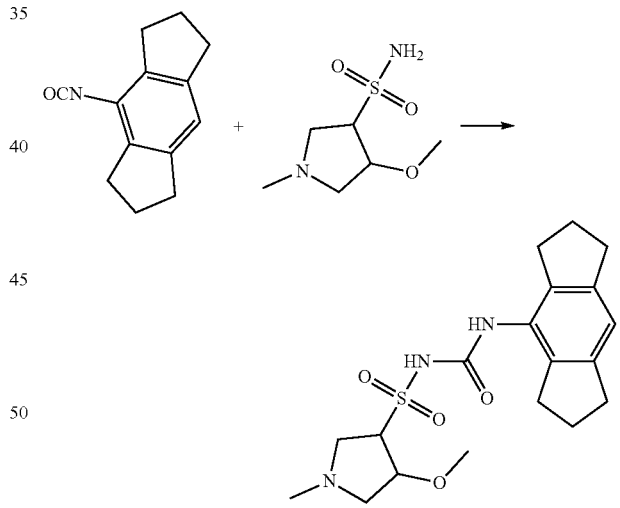

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 4-methoxy-1-methylpyrrolidine-3-sulfonamide (Intermediate P129) to afford the title compound (53%) as a white solid.

¹H NMR (CD₃OD) (mixture of isomers, ratio 2.5:1): δ=6.90 (s, 1H), 4.50 (minor), 4.57-4.19 (major) (m, 2H), 3.67 (dt, 1H), 3.45 (minor), 3.40 (major) (s, 3H), 3.14 (dd, 2H), 3.10-2.96 (m, 1H), 2.83 (m, 8H), 2.74 (minor), 2.70 (major) (s, 3H), 2.04 (m, 4H).

LCMS: m/z 394 (M+H)⁺ (ES⁺); 392 (M−H)⁻ (ES⁻).

Example 150: 1-Ethyl-N-((1,2,3,5,6,7-hexahydro-s-indacen-4-yl)carbamoyl)-4-methoxypyrrolidine-3-sulfonamide, Potassium Salt

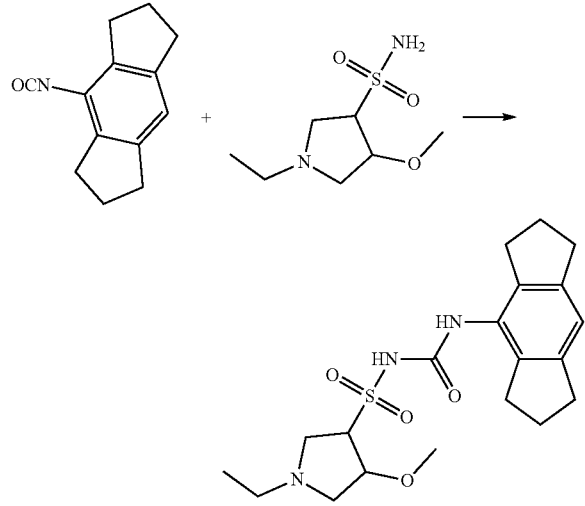

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-ethyl-4-methoxypyrrolidine-3-sulfonamide (Intermediate P130) to afford the title compound (26%) as a white solid.

¹H NMR (CD₃OD) (mixture of isomers, ratio 6:1): δ=6.85 (s, 1H), 4.27 (m, 2H), 3.54 (m, 1H), 3.42 (minor), 3.39 (major) (s, 3H), 3.16-2.89 (m, 2H), 2.82 (m, 11H), 2.04 (m, 4H), 1.18 (t, 3H).

LCMS: m/z 408 (M+H)⁺ (ES⁺); 406 (M−H)⁻ (ES⁻).

Example 151: 1-(2-((tert-Butyldimethylsilyl)oxy)ethyl)-N-((1,2,3,5,6,7-hexahydro-s-indacen-4-yl)carbamoyl)azetidine-3-sulfonamide, Potassium Salt

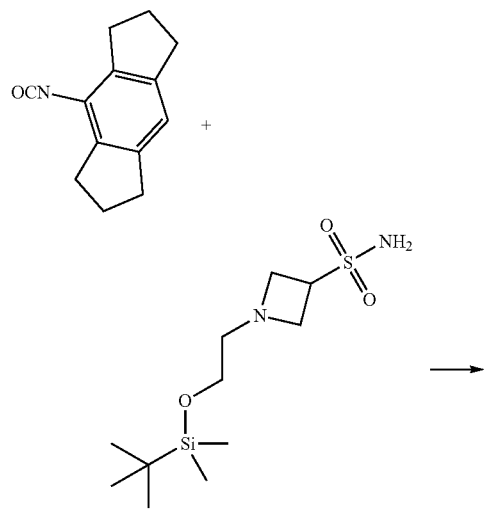

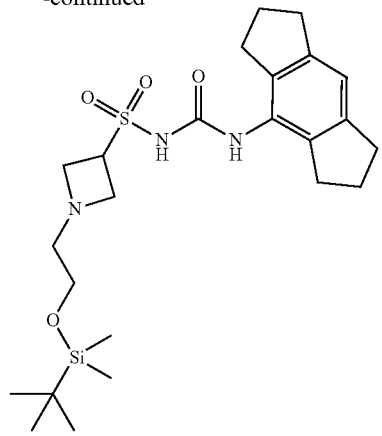

Prepared as described for 1-(tert-butyl)-N-((1,2,3,5,6,7-hexahydro-s-indacen-4-yl) carbamoyl)azetidine-3-sulfonamide, potassium salt (Example 93) using 4-isocyanato-1,2,3,5,6,7-hexahydro-s-indacene (Intermediate A1) and 1-(2-((tert-butyldimethylsilyl) oxy)ethyl)azetidine-3-sulfonamide (Intermediate P87) to afford the title compound (50%) as a white solid.

¹H NMR (CD₃OD): δ=6.88 (s, 1H), 4.40 (m, 1H), 3.88 (t, 2H), 3.68 (m, 2H), 3.55 (m, 2H), 3.13 (m, 2H), 2.84 (m, 8H), 2.00 (m, 4H), 1.18 (s, 9H), 0.1 (s, 6H).

LCMS: m/z 494 (M+H)⁺ (ES⁺); 492 (M−H)⁻ (ES⁻).

Example 152: 1-(2-Hydroxyethyl)-N-((1,2,3,5,6,7-hexahydro-s-indacen-4-yl)carbamoyl)azetidine-3-sulfonamide, Potassium Salt

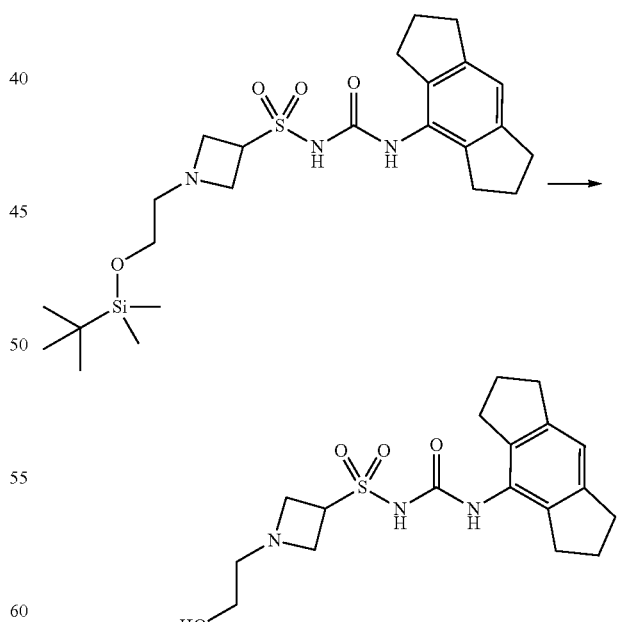

Upon reversed phase purification of 1-(2-((tert-butyldimethylsilyl)oxy)ethyl)-N-((1,2,3,5,6,7-hexahydro-s-indacen-4-yl)carbamoyl) azetidine-3-sulfonamide, potassium salt (Example 151), the deprotected product was also isolated (o1%) as a white solid.

¹H NMR (CD₃OD): δ=6.88 (s, 1H), 4.40 (s, 1H), 3.73 (t, 2H), 3.66 (t, 2H) (3.55 (t, 2H), 3.23 (m, 2H), 2.83 (m, 8H), 2.70 (t, 2H), 2.04 (m, 4H).
LCMS: m/z 380 (M+H)⁺ (ES).

Example 153: 1-Isopropyl-N-((5-(2-methoxypyridin-4-yl)-2,3-dihydro-1H-inden-4-yl)carbamoyl)-6-oxo-1,6-dihydropyridine-3-sulfonamide

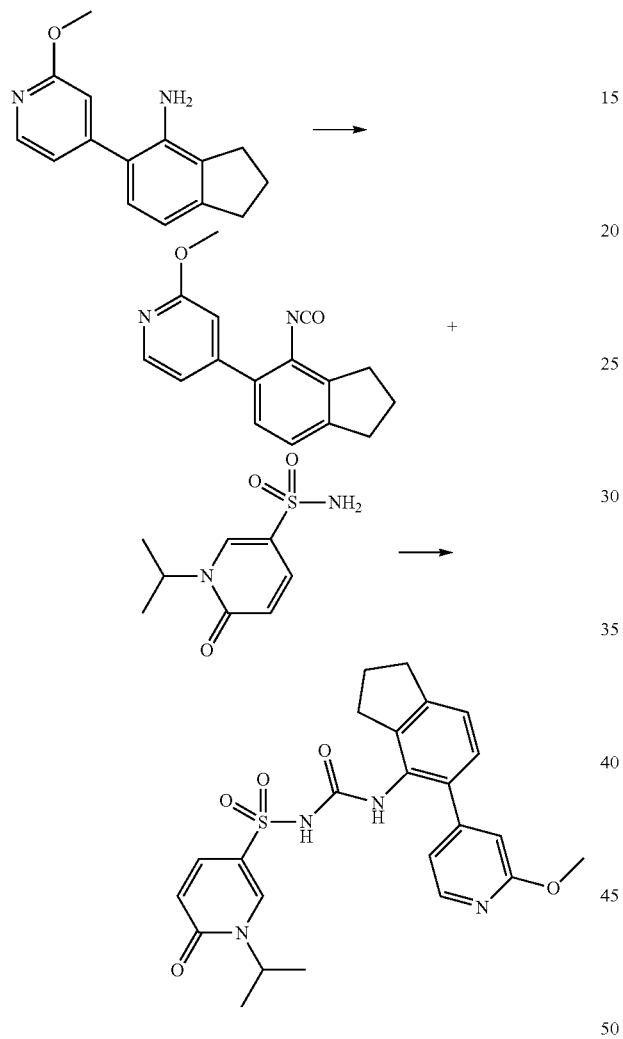

5-(2-Methoxypyridin-4-yl)-2,3-dihydro-1H-inden-4-amine (Intermediate A4) (0.30 g, 1.25 mmol) was dissolved in THF (10 mL). TEA (0.20 mL, 1.43 mmol) was added, followed by a solution of bis(trichloromethyl) carbonate (0.35 g, 1.18 mmol) in THF (2 mL). The mixture was stirred at room temperature for 1 hour, then concentrated in vacuo and dried for 30 minutes to afford the intermediate 4-(4-isocyanato-2,3-dihydro-1H-inden-5-yl)-2-methoxypyridine as a pale yellow solid which was used without further purification.

1-Isopropyl-6-oxo-1,6-dihydropyridine-3-sulfonamide (Intermediate P132) (45 mg, 0.21 mmol) was dissolved in dry THF (2 mL). NaOᵗBu (2 M in THF) (0.125 ml, 0.250 mmol) was added and the mixture was stirred at room temperature for 1 hour. A solution of 4-(4-isocyanato-2,3-dihydro-1H-inden-5-yl)-2-methoxypyridine (prepared above) (55 mg) in THF (2 mL) was added and the mixture was stirred at room temperature overnight. The solvent was removed in vacuo and the residue was dissolved in DMSO (2 mL) and purified by basic prep-HPLC to afford the title compound (41 mg, 40%) as a colourless powder.

¹H NMR (DMSO-d6) δ 10.76 (s, 1H), 8.13 (d, J=2.6 Hz, 1H), 8.03 (dd, J=5.3, 0.7 Hz, 1H), 7.91 (s, 1H), 7.60 (dd, J=9.5, 2.6 Hz, 1H), 7.20 (d, J=7.7 Hz, 1H), 7.10 (d, J=7.6 Hz, 1H), 6.83 (dd, J=5.3, 1.5 Hz, 1H), 6.65 (s, 1H), 6.47 (d, J=9.6 Hz, 1H), 4.99 (sept, J=6.8 Hz, 1H), 3.84 (s, 3H), 2.91 (t, J=7.5 Hz, 2H), 2.67 (t, J=7.5 Hz, 2H), 1.98 (p, J=7.4 Hz, 2H), 1.29 (d, J=6.8 Hz, 6H).
LCMS: m/z 483.3 (M+H)⁺ (ES⁺); 481.5 (M−H)⁻ (ES⁻).

Example 154: N-((5-(2-Cyanopyridin-4-yl)-2,3-dihydro-H-inden-4-yl) carbamoyl)-1-isopropyl-6-oxo-1,6-dihydropyridine-3-sulfonamide, Sodium Salt Step A: N-((5-(2-Cyanopyridin-4-yl)-2,3-dihydro-1H-inden-4-yl) carbamoyl)-1-isopropyl-6-oxo-1,6-dihydropyridine-3-sulfonamide

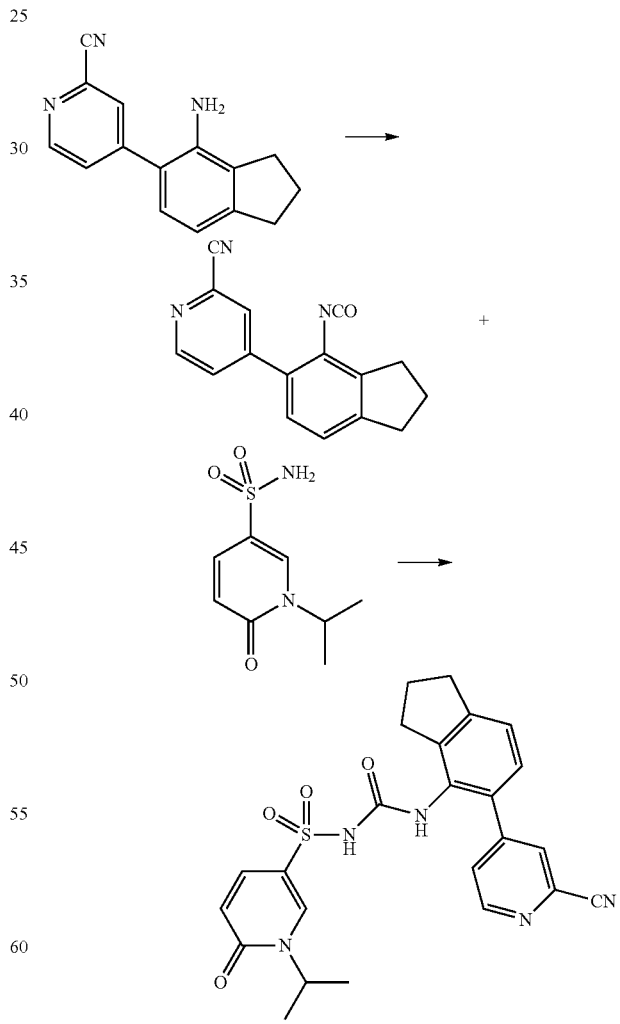

Prepared according to the general procedure of 1-isopropyl-N-((5-(2-methoxypyridin-4-yl)-2,3-dihydro-1H-inden-4-yl)carbamoyl)-6-oxo-1,6-dihydropyridine-3-sulfonamide (Example 153) from 4-(4-amino-2,3-dihydro-1H-inden-5-yl)picolinonitrile (Intermediate A5) (0.03 g, 0.123 mmol) and 1-isopropyl-6-oxo-1,6-dihydropyridine-3-sulfonamide (Intermediate P132) (0.027 g, 0.123 mmol) and purified by reversed phase flash C18 chromatography (12 g column, 0-60% MeCN/10 mM ammonium bicarbonate) to afford the title compound (35 mg, 30%) as a flocculent white solid.

$^1$H NMR (DMSO-d6) δ 8.56 (d, J=5.1 Hz, 1H), 7.93 (d, J=2.6 Hz, 1H), 7.89 (d, J=1.6 Hz, 1H), 7.75 (br s, 1H), 7.59 (dd, J=5.1, 1.8 Hz, 1H), 7.51 (dd, J=9.5, 2.5 Hz, 1H), 7.17-7.12 (m, 2H), 6.32 (d, J=9.4 Hz, 1H), 4.96 (sept, J=6.7 Hz, 1H), 2.91 (t, J=7.5 Hz, 2H), 2.74 (t, J=7.4 Hz, 2H), 1.98 (p, J=7.5 Hz, 2H), 1.25 (d, J=6.8 Hz, 6H). One exchangeable proton not observed.

LCMS: m/z 478.3 (M+H)$^+$ (ES$^+$); 476.2 (M–H)$^-$ (ES$^-$).

Step B: N-((5-(2-Cyanopyridin-4-yl)-2,3-dihydro-1H-inden-4-yl) carbamoyl)-1-isopropyl-6-oxo-1,6-dihydropyridine-3-sulfonamide, Sodium Salt

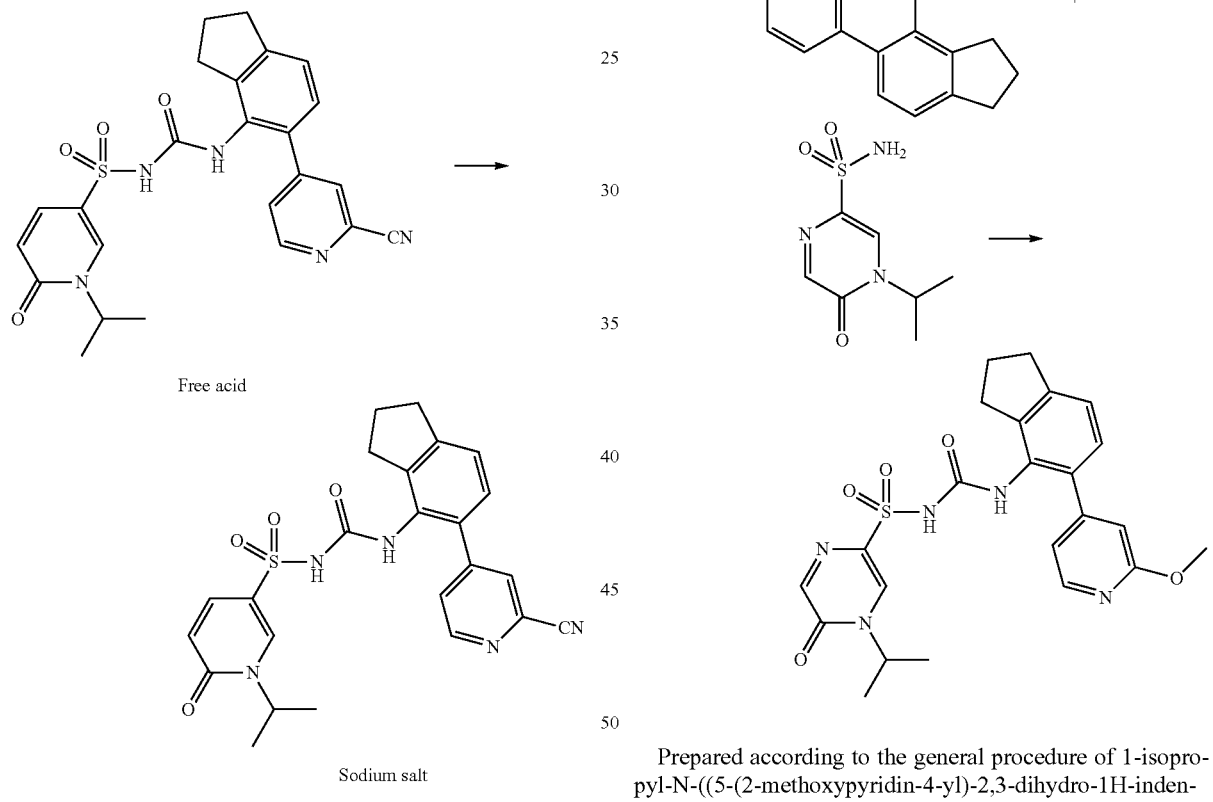

Free acid

Sodium salt

N-((5-(2-Cyanopyridin-4-yl)-2,3-dihydro-1H-inden-4-yl) carbamoyl)-1-isopropyl-6-oxo-1,6-dihydropyridine-3-sulfonamide (0.025 g, 0.052 mmol) was treated with 0.1 M NaOH solution (520 μL) and the resultant solution was freeze-dried to afford the title compound (26 mg, 99%) as a white solid.

$^1$H NMR (DMSO-d6) δ 8.54 (dd, J=5.1, 0.8 Hz, 1H), 7.91-7.89 (m, 1H), 7.87 (d, J=2.5 Hz, 1H), 7.60 (dd, J=5.1, 1.8 Hz, 1H), 7.54-7.46 (m, 2H), 7.13-7.09 (m, 2H), 6.27 (d, J=9.4 Hz, 1H), 4.97 (sept, J=6.7 Hz, 1H), 2.89 (t, J=7.5 Hz, 2H), 2.75 (t, J=7.4 Hz, 2H), 1.96 (p, J=7.5 Hz, 2H), 1.25 (d, J=6.8 Hz, 6H).

LCMS: m/z 478.3 (M+H)$^+$ (ES$^+$); 476.2 (M–H)$^-$ (ES$^-$).

Example 155: N-((5-(2-Cyanopyridin-4-yl)-2,3-dihydro-1H-inden-4-yl) carbamoyl)-4-isopropyl-5-oxo-4,5-dihydropyrazine-2-sulfonamide, Sodium Salt Step A: N-((5-(2-Cyanopyridin-4-yl)-2,3-dihydro-1H-inden-4-yl) carbamoyl)-4-isopropyl-5-oxo-4,5-dihydropyrazine-2-sulfonamide

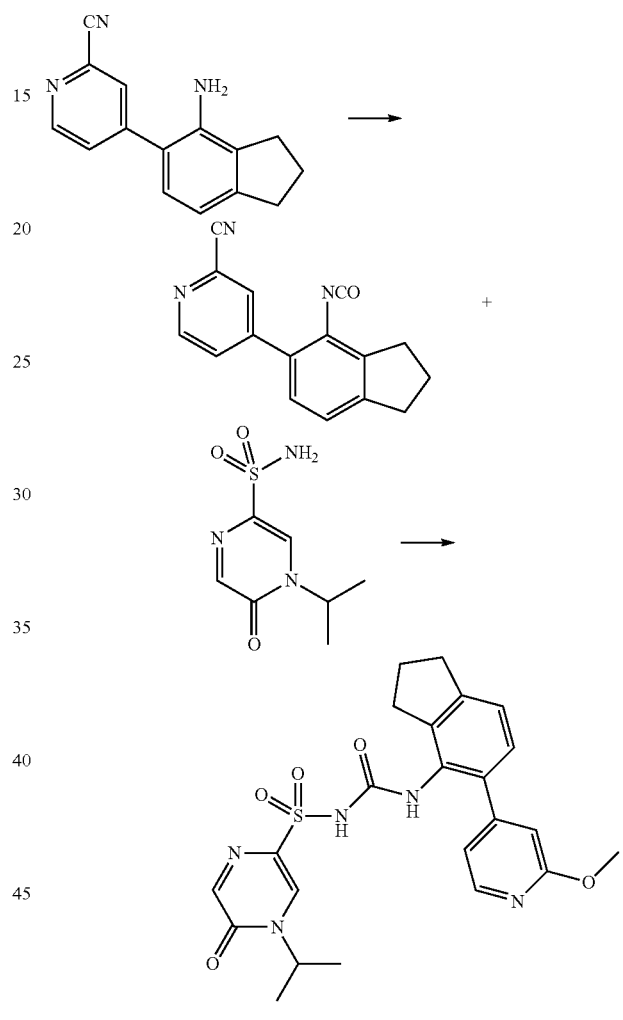

Prepared according to the general procedure of 1-isopropyl-N-((5-(2-methoxypyridin-4-yl)-2,3-dihydro-1H-inden-4-yl)carbamoyl)-6-oxo-1,6-dihydropyridine-3-sulfonamide (Example 153) from 4-(4-amino-2,3-dihydro-1H-inden-5-yl)picolinonitrile (Intermediate A5) (0.03 g, 0.123 mmol) and 4-isopropyl-5-oxo-4,5-dihydropyrazine-2-sulfonamide (Intermediate P133) (0.027 g, 0.123 mmol) and purified by reversed phase flash C18 chromatography (12 g column, 0-60% MeCN/10 mM ammonium bicarbonate) to afford the title compound (0.023 g, 19%) as a flocculent yellow solid.

$^1$H NMR (DMSO-d6) δ 8.58 (d, J=5.1 Hz, 1H), 7.93 (s, 2H), 7.89 (d, J=1.7 Hz, 1H), 7.76 (br s, 1H), 7.59 (dd, J=5.2, 1.7 Hz, 1H), 7.19-7.12 (m, 2H), 4.84 (p, J=6.8 Hz, 1H), 2.91 (t, J=7.5 Hz, 2H), 2.75 (t, J=7.4 Hz, 2H), 1.99 (p, J=7.5 Hz, 2H), 1.28 (d, J=6.8 Hz, 6H).

LCMS: m/z 479.3 (M+H)$^+$ (ES$^+$); 477.2 (M–H)$^-$ (ES$^-$).

Step B: N-((5-(2-Cyanopyridin-4-yl)-2,3-dihydro-1H-inden-4-yl) carbamoyl)-4-isopropyl-5-oxo-4,5-dihydropyrazine-2-sulfonamide, Sodium Salt

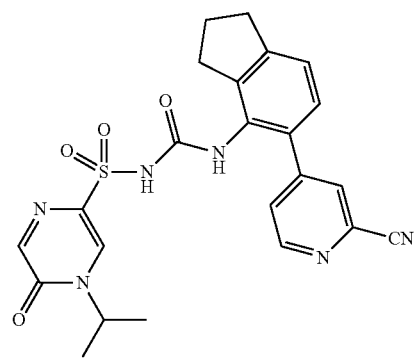

Free acid

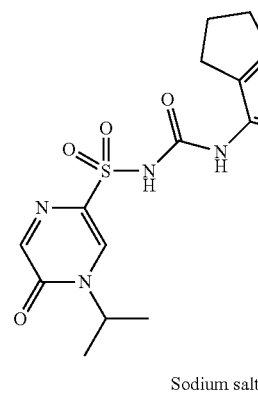

Sodium salt

N-((5-(2-Cyanopyridin-4-yl)-2,3-dihydro-1H-inden-4-yl) carbamoyl)-4-isopropyl-5-oxo-4,5-dihydropyrazine-2-sulfonamide (0.015 g, 0.031 mmol) was treated with 0.1 M NaOH solution (310 µL) and the resultant solution was freeze-dried to afford the title compound (16 mg, quant. yield) as a yellow solid.

¹H NMR (DMSO-d6) δ 8.56 (d, J=5.1 Hz, 1H), 7.89 (t, J=1.6 Hz, 2H), 7.84 (d, J=1.1 Hz, 1H), 7.67-7.56 (m, 2H), 7.13-7.09 (m, 2H), 4.85 (sept, J=6.8 Hz, 1H), 2.90 (t, J=7.5 Hz, 2H), 2.77 (t, J=7.3 Hz, 2H), 1.98 (p, J=7.5 Hz, 2H), 1.28 (d, J=6.8 Hz, 6H).

LCMS: m/z 479.3 (M+H)⁺ (ES⁺); 477.1 (M−H)⁻ (ES⁻).

Example 156: 4-Isopropyl-N-((5-(2-methoxypyridin-4-yl)-2,3-dihydro-1H-inden-4-yl) carbamoyl)-5-oxo-4,5-dihydropyrazine-2-sulfonamide

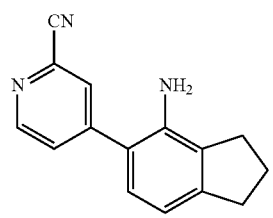

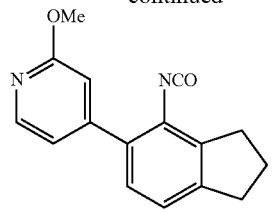

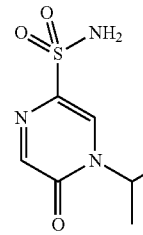

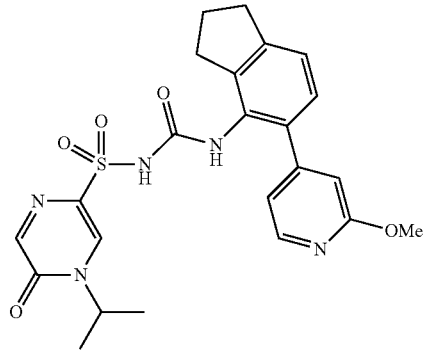

Prepared according to the general procedure of 1-isopropyl-N-((5-(2-methoxypyridin-4-yl)-2,3-dihydro-1H-inden-4-yl)carbamoyl)-6-oxo-1,6-dihydropyridine-3-sulfonamide (Example 153) from 4-isopropyl-5-oxo-4,5-dihydropyrazine-2-sulfonamide (Intermediate P133) (26 mg, 0.12 mmol) and 5-(2-methoxypyridin-4-yl)-2,3-dihydro-1H-inden-4-amine (Intermediate A4) (50 mg, 0.21 mmol) to afford the title compound (13.2 mg, 23%).

¹H NMR (DMSO-d6) δ 8.09 (s, 1H), 8.05 (d, J=5.3 Hz, 1H), 7.98 (s, 1H), 7.71 (s, 1H), 7.16 (d, J=7.7 Hz, 1H), 7.07 (d, J=7.6 Hz, 1H), 6.86 (d, J=5.3 Hz, 1H), 6.65 (s, 1H), 4.86 (sept, J=7.2, 6.7 Hz, 1H), 3.86 (s, 3H), 2.90 (t, J=7.4 Hz, 2H), 2.69 (t, J=7.5 Hz, 2H), 1.98 (p, J=7.4 Hz, 2H), 1.30 (d, J=6.7 Hz, 6H). Partial ammonium salt.

LCMS: m/z 484.3 (M+H)⁺ (ES⁺).

Example 157: N-((2-(2-Cyanopyridin-4-yl)-4-fluoro-6-isopropylphenyl)carbamoyl)-1-isopropylazetidine-3-sulfonamide

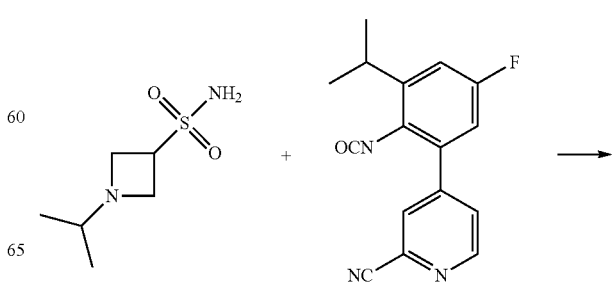

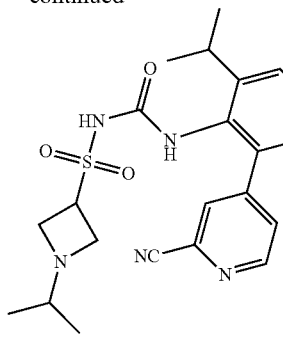

To a solution of 1-isopropylazetidine-3-sulfonamide (Intermediate P134) (70 mg, 392.70 μmol, 1 eq) in THF (2 mL) was added t-BuONa (37 mg, 392.70 μmol, 1 eq). The mixture was stirred at 25° C. for 30 minutes. Then 4-(5-fluoro-2-isocyanato-3-isopropylphenyl)picolinonitrile (Intermediate A6) (110 mg, 392.70 μmol, 1 eq) was added. The reaction mixture was stirred at 70° C. for 30 minutes. Then the reaction mixture was concentrated in vacuo. The residue was purified by prep-HPLC (column: Waters Xbridge C18, 150 mm*25 mm*5 m; mobile phase: [A: water (0.05% ammonia hydroxide v/v); B: MeCN]; B %: 12%-42%, 11.5 min) to give the title compound (80.02 mg, 43% yield, 96% purity on LCMS) as a white solid.

$^1$H NMR (DMSO-d$_6$) δ 8.75 (d, 1H), 8.06 (s, 1H), 7.77-7.66 (m, 2H), 7.21 (dd, 1H), 7.12 (dd, 1H), 3.78-3.49 (m, 4H), 3.26-3.22 (d, 2H), 2.83-2.79 (m, 1H), 1.15 (d, 6H) and 0.95 (d, 6H). One exchangeable proton not observed.

LCMS: m/z 460.2 (M+H)$^+$ (ES$^+$).

Example 158: N-((4-Fluoro-2-isopropyl-6-(2-methoxypyridin-4-yl)phenyl) carbamoyl)-1-isopropylazetidine-3-sulfonamide

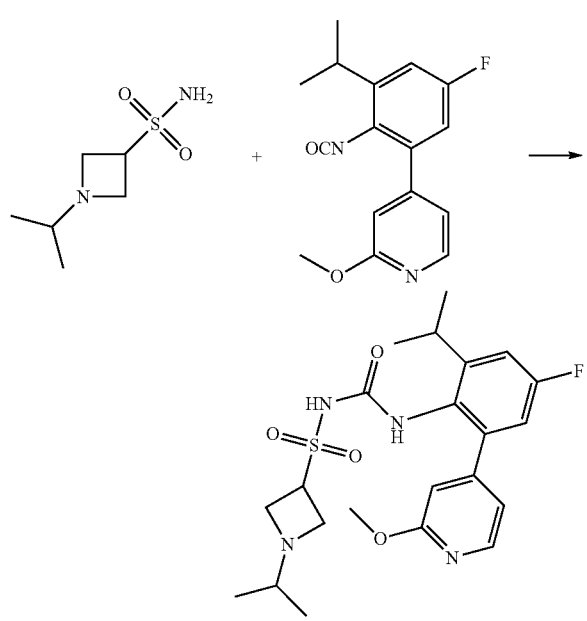

To a solution of 1-isopropylazetidine-3-sulfonamide (Intermediate P134) (70 mg, 392.70 μmol, 1 eq) in THF (2 mL) was added t-BuONa (38 mg, 392.70 μmol, 1 eq). The mixture was stirred at 25° C. for 30 minutes. Then 4-(5-fluoro-2-isocyanato-3-isopropylphenyl)-2-methoxypyridine (Intermediate A7) (112 mg, 392.70 μmol, 1 eq) was added. The mixture was stirred at 70° C. for 30 minutes. Then the reaction mixture was concentrated in vacuo. The residue was purified by prep-HPLC (column: Waters Xbridge C18, 150 mm*25 mm*5 μm; mobile phase: [A: water (0.05% ammonia hydroxide v/v); B: MeCN]; B %: 12%-42%, 11.5 min) to give the title compound (87.88 mg, 48% yield, 99% purity on LCMS) as a white solid.

$^1$H NMR (DMSO-d$_6$) δ 8.11 (d, 1H), 7.17 (br s, 1H), 7.11 (d, 1H), 7.01 (s, 1H), 6.93 (d, 1H), 6.85 (s, 1H), 3.86 (s, 3H), 3.81-3.77 (m, 1H), 3.26-3.22 (m, 1H), 3.18-3.15 (m, 2H), 3.03-3.00 (m, 2H), 2.22-1.98 (m, 1H), 1.16-1.12 (m, 6H) and 0.80 (d, 6H). One exchangeable proton not observed.

LCMS: m/z 465.2 (M+H)$^+$ (ES$^+$).

Example 159: 1-Isopropyl-N-((5-(2-methoxypyridin-4-yl)-2,3-dihydro-1H-inden-4-yl)carbamoyl)azetidine-3-sulfonamide

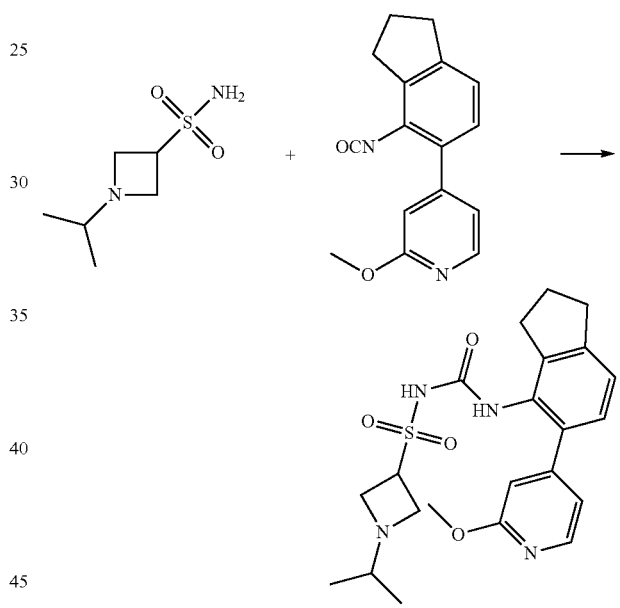

To a solution of 1-isopropylazetidine-3-sulfonamide (Intermediate P134) (70 mg, 392.70 μmol, 1 eq) in THF (2 mL) was added t-BuONa (38 mg, 392.70 μmol, 1 eq). The mixture was stirred at 25° C. for 30 minutes. Then 4-(4-isocyanato-2,3-dihydro-1H-inden-5-yl)-2-methoxypyridine (Intermediate A8) (104 mg, 392.70 μmol, 1 eq) was added. The mixture was stirred at 70° C. for 30 minutes. Then the reaction mixture was concentrated in vacuo. The residue was purified by prep-HPLC (column: Waters Xbridge C18, 150 mm*25 mm*5 μm; mobile phase: [A: water (0.05% ammonia hydroxide v/v); B: MeCN]; B %: 8%-38%, 11.5 min) to give the title compound (56.2 mg, 32% yield, 100% purity on LCMS) as a white solid.

$^1$H NMR (DMSO-d$_6$) δ 8.13 (d, 1H), 7.49 (br s, 1H), 7.12 (d, 1H), 7.07 (d, 1H), 6.98 (d, 1H), 6.79 (s, 1H), 4.00-3.94 (m, 1H), 3.87 (s, 3H), 3.70-3.64 (m, 2H), 3.58-3.54 (m, 2H), 2.91 (t, 2H), 2.83 (t, 2H), 2.76-2.73 (m, 1H), 2.04-1-97 (m, 2H) and 0.94 (d, 6H).

One exchangeable proton not observed.

LCMS: m/z 445.2 (M+H)$^+$ (ES$^+$).

Example 160: N-((7-Fluoro-5-(pyridin-4-yl)-2,3-dihydro-1H-inden-4-yl)carbamoyl)-1-isopropylazetidine-3-sulfonamide

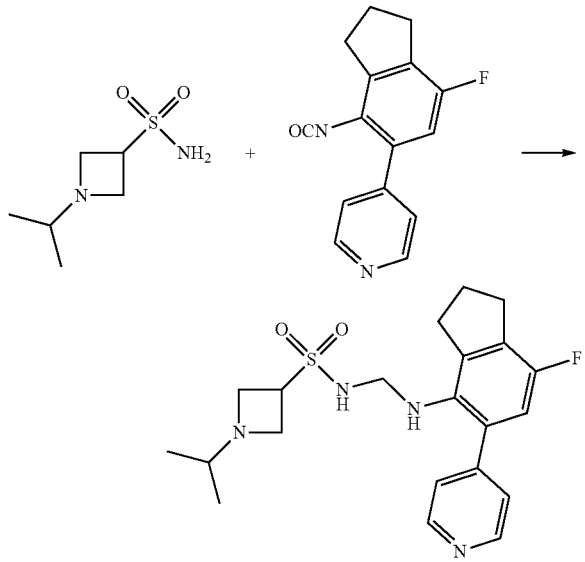

A mixture of 1-isopropylazetidine-3-sulfonamide (Intermediate P134) (50 mg, 280.50 μmol, 1 eq) and t-BuONa (27 mg, 280.50 μmol, 1 eq) in THF (2 mL) was stirred at 25° C. for 10 minutes. 4-(7-Fluoro-4-isocyanato-2,3-dihydro-1H-inden-5-yl)pyridine (Intermediate A9) (71 mg, 280.50 μmol, 1 eq) was added and the resulting mixture was stirred at 70° C. for 30 minutes. Then the reaction mixture was concentrated in vacuo. The residue was purified by prep-HPLC (column: Waters Xbridge C18, 150 mm*25 mm*5 μm; mobile phase: [A: water (0.05% ammonia hydroxide v/v); B: MeCN]; B %: 12%-42%, 10 min) to give the title compound (7.96 mg, 7% yield, 100% purity on LCMS) as a white solid.

$^1$H NMR (DMSO-$d_6$) δ 8.55 (d, 2H), 7.41-7.38 (m, 3H), 6.95 (d, 1H), 3.94-3.88 (m, 1H), 3.70-3.67 (m, 2H), 3.61-3.58 (m, 2H), 2.95 (t, 2H), 2.86 (t, 2H), 2.82-2.75 (m, 1H), 2.10-2.02 (m, 2H) and 0.96 (d, 6H). One exchangeable proton not observed.

LCMS: m/z 433.2 (M+H)$^+$ (ES$^+$).

Example 161: N-((2-(2-Cyanopyridin-4-yl)-4-fluoro-6-isopropylphenyl)carbamoyl)-1-cyclobutylazetidine-3-sulfonamide

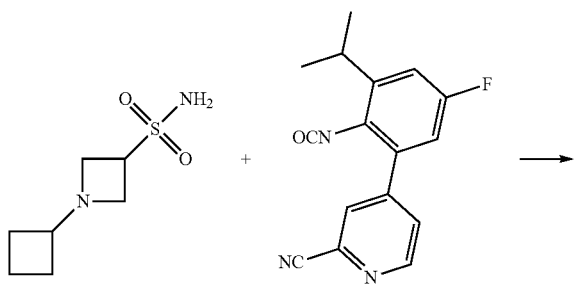

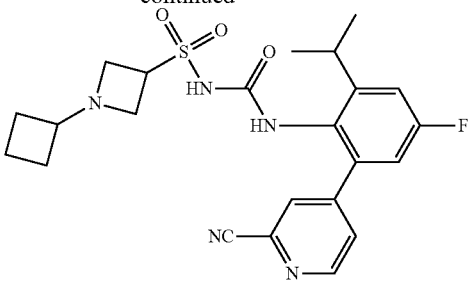

A solution of 1-cyclobutylazetidine-3-sulfonamide (Intermediate P135) (30 mg, 157.68 μmol, 1 eq) and t-BuONa (15 mg, 157.68 μmol, 1 eq) in THF (1 mL) was stirred at 25° C. for 10 minutes. 4-(5-Fluoro-2-isocyanato-3-isopropylphenyl)picolinonitrile (Intermediate A6) (44 mg, 157.68 μmol, 1 eq) was added and the resulting mixture was stirred at 25° C. for 10 minutes. Then the reaction mixture was concentrated in vacuo. The residue was purified by prep-HPLC (Column: Waters Xbridge C18, 150 mm*25 mm*5 μm; mobile phase: [A: water (0.05% ammonia hydroxide v/v); B: MeCN]; B %: 5%-35%, 10 min) to give the title compound (6.35 mg, 8% yield, 97% purity on LCMS) as a white solid.

$^1$H NMR (DMSO-$d_6$) δ 8.75 (d, 1H), 8.05 (s, 1H), 7.77-7.75 (m, 1H), 7.67-7.65 (m, 1H), 7.23-7.18 (m, 1H), 7.12 (d, 1H), 3.95-3.68 (m, 2H), 3.67-3.56 (m, 2H), 3.55-3.42 (m, 2H), 3.25-3.21 (m, 1H), 1.99-1.97 (m, 2H), 1.86-1.84 (m, 2H), 1.71-1.62 (m, 2H) and 1.16 (d, 6H). One exchangeable proton not observed.

LCMS: m/z 472.2 (M+H)$^+$ (ES$^+$).

Example 162: 1-Cyclobutyl-N-((4-fluoro-2-isopropyl-6-(2-methoxypyridin-4-yl) phenyl) carbamoyl) azetidine-3-sulfonamide

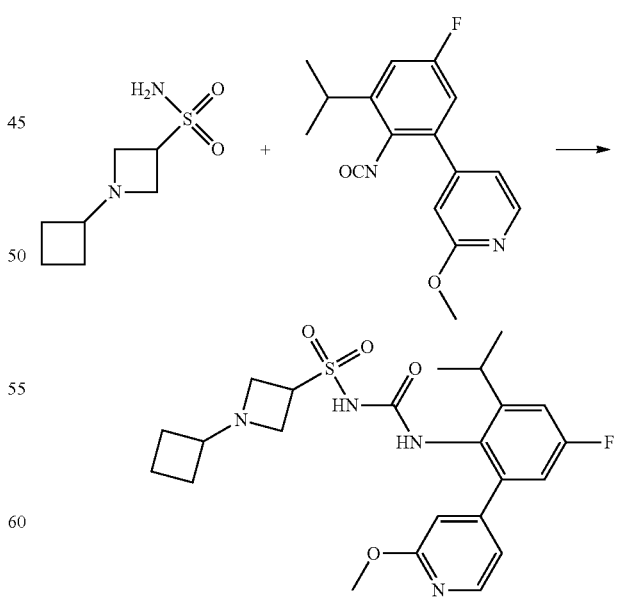

To a solution of 1-cyclobutylazetidine-3-sulfonamide (Intermediate P135) (25 mg, 131.40 μmol, 1 eq) in THF (1 mL) was added t-BuONa (13 mg, 131.40 μmol, 1 eq). The reaction mixture was stirred at 20° C. for 10 minutes. Then 4-(5-fluoro-2-isocyanato-3-isopropylphenyl)-2-methoxypyridine (Intermediate A7) (38 mg, 131.40 µmol, 1 eq) was added and the resulting mixture was stirred at 20° C. for 20 minutes. Then the reaction mixture was concentrated in vacuo. The residue was purified by prep-HPLC (column: Phenomenex Gemini C18, 150 mm*25 mm*10 µm; mobile phase: [A: water (10 mM NH₄HCO₃); B: MeCN]; B %: 15%-45%, 10 min) to give the title compound (41.16 mg, 66% yield, 100% purity on LCMS) as a white solid.

¹H NMR (DMSO-d₆) δ 8.16 (d, 1H), 7.61 (br s, 1H), 7.16 (d, 1H), 7.03-6.96 (m, 2H), 6.83 (s, 1H), 4.02-3.92 (m, 1H), 3.88 (s, 3H), 3.75-3.48 (m, 4H), 3.22-3.02 (m, 2H), 2.15-1.95 (m, 2H), 1.94-1.76 (m, 2H), 1.74-1.56 (m, 2H) and 1.14 (d, 6H). One exchangeable proton not observed.

LCMS: m/z 477.2 (M+H)⁺ (ES⁺).

Example 163: 1-Cyclobutyl-N-((5-(2-methoxypyridin-4-yl)-2,3-dihydro-1H-inden-4-yl)carbamoyl)azetidine-3-sulfonamide

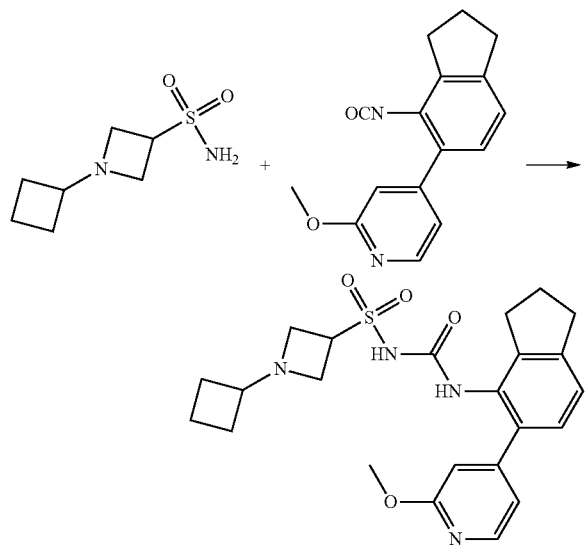

A mixture of 1-cyclobutylazetidine-3-sulfonamide (Intermediate P135) (40 mg, 210.24 µmol, 1 eq) and t-BuONa (20 mg, 210.24 µmol, 1 eq) in THF (2 mL) was stirred at 25° C. for 10 minutes. Then 4-(4-isocyanato-2,3-dihydro-1H-inden-5-yl)-2-methoxypyridine (Intermediate A8) (56 mg, 210.24 µmol, 1 eq) was added and the resulting mixture was stirred at 70° C. for 30 minutes. Then the reaction mixture was concentrated in vacuo. The residue was purified by prep-HPLC (column: Waters Xbridge C18, 150 mm*25 mm*5 µm; mobile phase: [A: water (0.05% ammonia hydroxide v/v); B: MeCN]; B %: 10%-40%, 10 min) to give the title compound (20.06 mg, 21% yield, 100% purity on LCMS) as a white solid.

¹H NMR (DMSO-d₆) δ 8.13 (d, 1H), 7.40 (br s, 1H), 7.12 (d, 1H), 7.06 (d, 1H), 6.96 (d, 1H), 6.77 (s, 1H), 4.06-3.98 (m, 1H), 3.87 (s, 3H), 3.49-3.44 (m, 3H), 3.38-3.35 (m, 2H), 2.91 (t, 2H), 2.82 (t, 2H), 2.03-1.99 (m, 2H), 1.98-1.94 (m, 2H), 1.85-1.81 (m, 2H) and 1.71-1.62 (m, 2H). One exchangeable proton not observed.

LCMS: m/z 457.3 (M+H)⁺ (ES⁺).

Example 164: 1-Cyclobutyl-N-((7-fluoro-5-(pyridin-4-yl)-2,3-dihydro-1H-inden-4-yl)carbamoyl)azetidine-3-sulfonamide

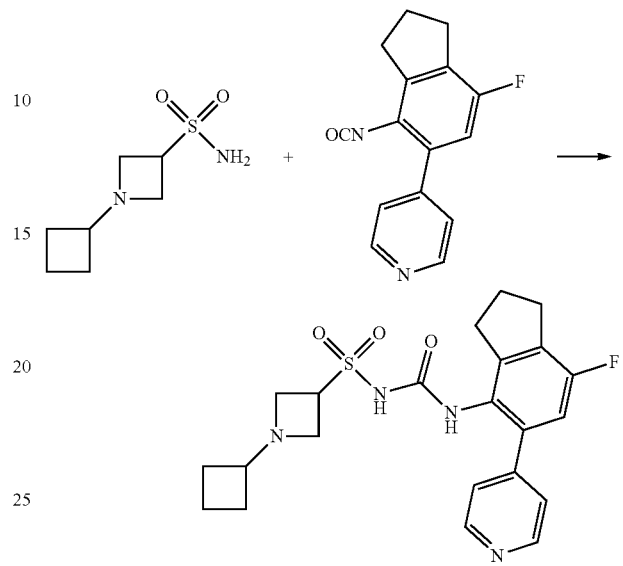

A mixture of 1-cyclobutylazetidine-3-sulfonamide (Intermediate P135) (37 mg, 194.47 µmol, 1 eq) and t-BuONa (19 mg, 194.47 µmol, 1 eq) in THF (2 mL) was stirred at 25° C. for 10 minutes. Then 4-(7-fluoro-4-isocyanato-2,3-dihydro-1H-inden-5-yl)pyridine (Intermediate A9) (49 mg, 194.47 µmol, 1 eq) was added and the resulting mixture was stirred at 25° C. for 10 minutes. Then the reaction mixture was concentrated in vacuo. The residue was purified by prep-HPLC (column: Xtimate C18, 250 mm*50 mm*10 µm; mobile phase: [A: water (0.05% ammonia hydroxide v/v); B: MeCN]; B %: 0%-30%, 10 min) to give the title compound (18.09 mg, 20% yield, 97% purity on LCMS) as a yellow solid.

¹H NMR (DMSO-d₆) δ 8.57 (d, 2H), 7.57 (br s, 1H), 7.39 (d, 2H), 6.97 (d, 1H), 4.02-3.95 (m, 1H), 3.70-3.66 (m, 3H), 3.57-3.54 (m, 1H), 3.37-3.27 (m, 1H), 2.96 (t, 2H), 2.86 (t, 2H), 2.11-2.00 (m, 4H), 1.92-1.87 (m, 2H) and 1.72-1.65 (m, 2H). One exchangeable proton not observed.

LCMS: m/z 445.2 (M+H)⁺ (ES⁺).

Example 165: N-((2-(2-Cyanopyridin-4-yl)-4-fluoro-6-isopropylphenyl)carbamoyl)-1-ethylazetidine-3-sulfonamide

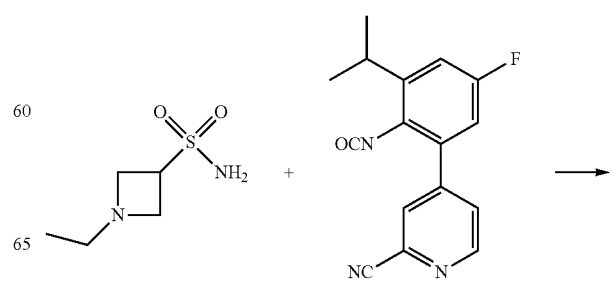

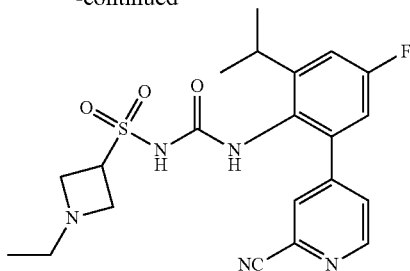

To a solution of 1-ethylazetidine-3-sulfonamide (Intermediate P136) (40 mg, 243.57 μmol, 1 eq) in THF (1 mL) was added t-BuONa (23 mg, 243.57 μmol, 1 eq). The mixture was stirred at 25° C. for 10 minutes. Then 4-(5-fluoro-2-isocyanato-3-isopropylphenyl)-picolinonitrile (Intermediate A6) (68 mg, 243.57 μmol, 1 eq) was added and the mixture was stirred at 70° C. for 10 minutes. Then the reaction mixture was concentrated in vacuo. The residue was purified by prep-HPLC (column: Waters Xbridge C18, 150 mm*50 mm*10 μm; mobile phase: [A: water (0.05% ammonia hydroxide v/v); B: MeCN]; B %: 8%-38%, 11.5 min) to give the title compound (48.97 mg, 45% yield, 100% purity on LCMS) as a white solid.

$^1$H NMR (DMSO-d$_6$) δ 8.75 (d, 1H), 8.05 (s, 1H), 7.76 (s, 1H), 7.66 (s, 1H), 7.22-7.18 (m, 1H), 7.12-7.09 (m, 1H), 3.83-3.76 (m, 5H), 3.24-3.20 (m, 1H), 2.93-2.88 (m, 2H), 1.16 (d, 6H) and 0.99 (t, 3H). One exchangeable proton not observed.

LCMS: m/z 446.2 (M+H)$^+$ (ES$^+$).

Example 166: 1-Ethyl-N-((4-fluoro-2-isopropyl-6-(2-methoxypyridin-4-yl)phenyl) carbamoyl) azetidine-3-sulfonamide

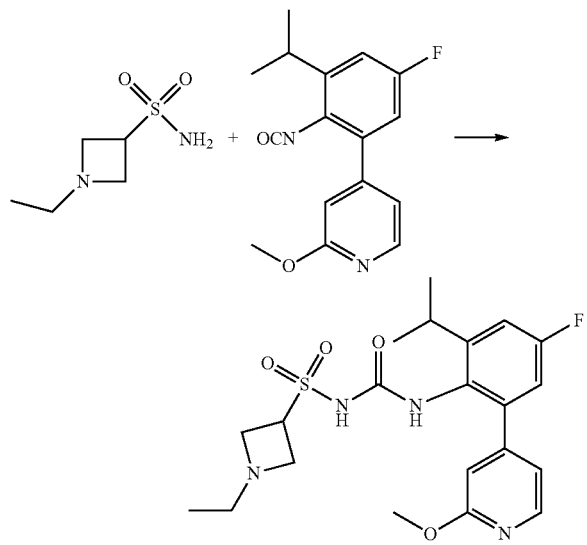

To a solution of 1-ethylazetidine-3-sulfonamide (Intermediate P136) (40 mg, 243.57 μmol, 1 eq) in THF (1 mL) was added t-BuONa (23 mg, 243.57 μmol, 1 eq). The mixture was stirred at 25° C. for 10 minutes. Then 4-(5-fluoro-2-isocyanato-3-isopropylphenyl)-2-methoxypyridine (Intermediate A7) (69 mg, 243.57 μmol, 1 eq) was added and the mixture was stirred at 75° C. for another 10 minutes. Then the reaction mixture was concentrated in vacuo. The residue was purified by prep-HPLC (column: Waters Xbridge C18, 150 mm*50 mm*10 μm; mobile phase: [A: water (0.05% ammonia hydroxide v/v); B: MeCN]; B %: 8%-38%, 11.5 min) to give the title compound (46.05 mg, 42% yield, 100% purity on LCMS) as a white solid.

$^1$H NMR (DMSO-d$_6$) δ 8.15 (d, 1H), 7.48 (s, 1H), 7.17-7.12 (m, 1H), 7.03-6.94 (m, 2H), 6.84 (s, 1H), 3.99-3.77 (m, 8H), 3.24-3.20 (m, 1H), 2.95-2.92 (m, 2H), 1.15 (d, 6H) and 1.00 (t, 3H). One exchangeable proton not observed.

LCMS: m/z 451.2 (M+H)$^+$ (ES$^+$).

Example 167: 1-Ethyl-N-((5-(2-methoxypyridin-4-yl)-2,3-dihydro-1H-inden-4-yl) carbamoyl) azetidine-3-sulfonamide

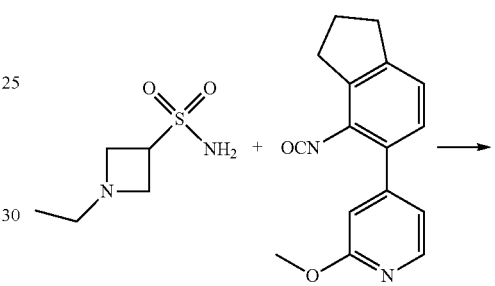

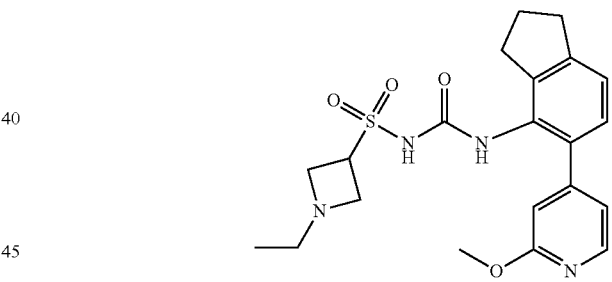

To a solution of 1-ethylazetidine-3-sulfonamide (Intermediate P136) (40 mg, 243.57 μmol, 1 eq) in THF (1 mL) was added t-BuONa (23 mg, 243.57 μmol, 1 eq). The mixture was stirred at 25° C. for 10 minutes. Then 4-(4-isocyanato-2,3-dihydro-1H-inden-5-yl)-2-methoxypyridine (Intermediate A8) (64 mg, 243.57 μmol, 1 eq) was added and the mixture was stirred at 70° C. for 10 minutes. Then the reaction mixture was concentrated in vacuo. The residue was purified by prep-HPLC (column: Waters Xbridge C18, 150 mm*50 mm*10 μm; mobile phase: [A: water (0.05% ammonia hydroxide v/v); B: MeCN]; B %: 8%-38%, 11.5 min) to give the title compound (52.99 mg, 51% yield, 100% purity on LCMS) as a white solid.

$^1$H NMR (DMSO-d$_6$) δ 8.13 (d, 1H), 7.43 (br s, 1H), 7.12 (d, 1H), 7.06 (d, 1H), 6.97 (dd, 1H), 6.79 (s, 1H), 4.08-4.00 (m, 1H), 3.88 (s, 3H), 3.85-3.80 (m, 2H), 3.77-3.72 (m, 2H), 2.91 (t, 2H), 2.87-2.80 (m, 4H), 2.04-1.96 (m, 2H) and 0.98 (t, 3H). One exchangeable proton not observed.

LCMS: m/z 431.2 (M+H)$^+$ (ES$^+$).

Example 168: 1-Ethyl-N-((7-fluoro-5-(pyridin-4-yl)-2,3-dihydro-1H-inden-4-yl) carbamoyl) azetidine-3-sulfonamide

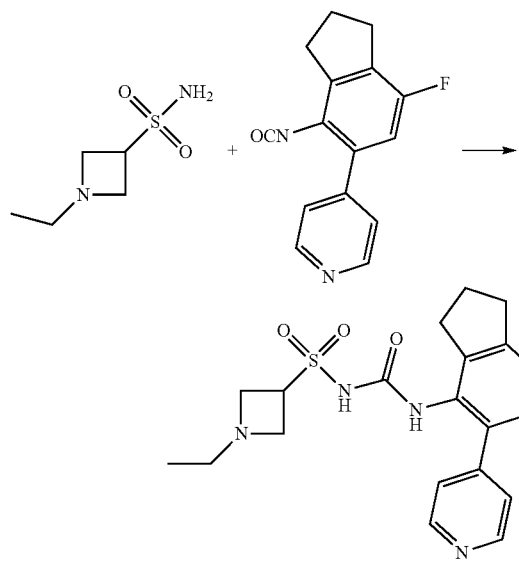

A solution of 1-ethylazetidine-3-sulfonamide (Intermediate P136) (50 mg, 304.46 mol, 1 eq) and t-BuONa (29 mg, 304.46 μmol, 1 eq) in THF (1 mL) was stirred at 25° C. for 10 minutes. Then a solution of 4-(7-fluoro-4-isocyanato-2,3-dihydro-1H-inden-5-yl) pyridine (Intermediate A9) (77 mg, 304.46 μmol, 1 eq) in THF (2 mL) was added and the reaction mixture was stirred at 25° C. for 10 minutes. Then the reaction mixture was concentrated in vacuo. The residue was purified by prep-HPLC (column: Waters Xbridge C18, 150 mm*25 mm*5 μm; mobile phase: [A: water (0.05% ammonia hydroxide v/v); B:MeCN]; B %: 5%-35%, 10 min) to give the title compound (9.59 mg, 8% yield, 100% purity on LCMS) as a white solid.

$^1$H NMR (DMSO-d$_6$) δ 8.57 (d, 2H), 7.43 (br s, 1H), 7.40 (d, 2H), 6.96 (d, 1H), 4.01-3.88 (m, 5H), 2.98-2.93 (m, 4H), 2.86 (t, 2H), 2.11-2.03 (m, 2H) and 1.01 (t, 3H).

One exchangeable proton not observed.

LCMS: m/z 419.2 (M+H)$^+$ (ES$^+$).

Example 169: N-((2-(2-Cyanopyridin-4-yl)-4-fluoro-6-isopropylphenyl)carbamoyl)-1-(pyridin-3-ylmethyl) azetidine-3-sulfonamide

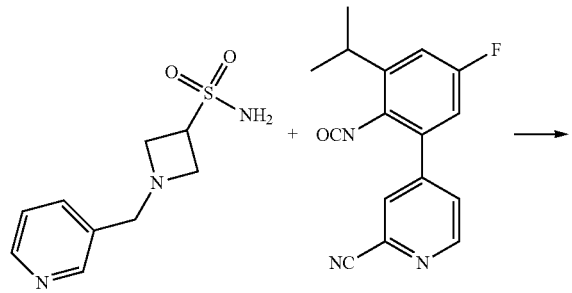

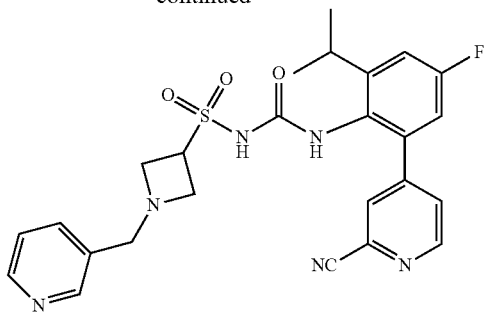

A solution of 1-(pyridin-3-ylmethyl)azetidine-3-sulfonamide (Intermediate P137) (50 mg, 219.99 μmol, 1 eq), 4-(5-fluoro-2-isocyanato-3-isopropylphenyl)picolinonitrile (Intermediate A6) (68 mg, 241.99 μmol, 1.1 eq) and t-BuONa (25 mg, 263.99 μmol, 1.2 eq) in THF (1.5 mL) was stirred at 16° C. for 0.5 hour. Then the reaction mixture was concentrated in vacuo. The residue was purified by prep-HPLC (column: Phenomenex Gemini C18, 150 mm*25 mm*10 μm; mobile phase: [A: water (0.05% NH$_4$HCO$_3$ v/v); B: MeCN]; B %: 15%-45%, 12 min) to give the title compound (10 mg, 9%) as a white solid.

$^1$H NMR (DMSO-d$_6$) δ 8.74 (d, 1H), 8.50-8.47 (m, 2H), 8.05 (s, 1H), 8.00 (br s, 1H), 7.73 (d, 1H), 7.68 (d, 1H), 7.39-7.35 (m, 1H), 7.29-7.25 (m, 1H), 7.16 (d, 1H), 4.03-3.97 (m, 1H), 3.73-3.68 (m, 2H), 3.45-3.38 (m, 4H), 3.19-3.15 (m, 1H) and 1.14 (d, 6H). One exchangeable proton not observed.

LCMS: m/z 509.3 (M+H)$^+$ (ES$^+$).

Example 170: N-((5-(2-Methoxypyridin-4-yl)-2,3-dihydro-1H-inden-4-yl) carbamoyl)-1-(pyridin-3-ylmethyl)azetidine-3-sulfonamide

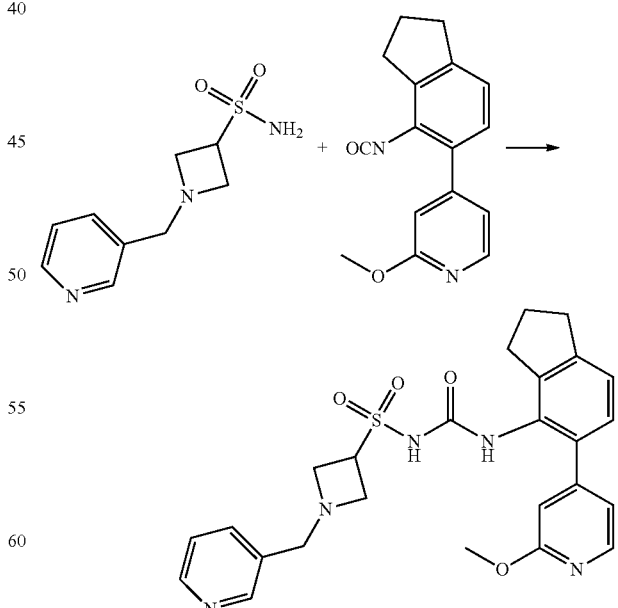

A solution of 1-(pyridin-3-ylmethyl)azetidine-3-sulfonamide (Intermediate P137) (50 mg, 219.99 μmol, 1 eq), 4-(4-isocyanato-2,3-dihydro-1H-inden-5-yl)-2-methoxypyridine (Intermediate A8) (64 mg, 241.99 µmol, 1.1 eq) and t-BuONa (25 mg, 263.99 µmol, 1.2 eq) in THF (1.5 mL) was stirred at 16° C. for 0.5 hour. Then the reaction mixture was concentrated in vacuo. The residue was purified by prep-HPLC (column: Phenomenex Gemini C18, 150 mm*25 mm*10 m; mobile phase: [A: water (0.05% NH₄HCO₃ v/v); B: MeCN]; B %: 15%-45%, 12 min) to give the title compound (37 mg, 34%) as a white solid.

¹H NMR (DMSO-d₆) δ 8.49-8.45 (m, 2H), 8.12 (d, 1H), 7.79 (br s, 1H), 7.67 (d, 1H), 7.38-7.33 (m, 1H), 7.18 (d, 1H), 7.09 (d, 1H), 6.92 (d, 1H), 6.73 (s, 1H), 4.19-4.15 (m, 1H), 3.80 (s, 3H), 3.66 (s, 2H), 3.50-3.43 (m, 2H), 3.38-3.34 (m, 2H), 2.91 (t, 2H), 2.78 (t, 2H) and 2.04-1.98 (m, 2H). One exchangeable proton not observed.

LCMS: m/z 494.2 (M+H)⁺ (ES⁺).

Example 171: N-((7-Fluoro-5-(pyridin-4-yl)-2,3-dihydro-1H-inden-4-yl)carbamoyl)-1-(pyridin-3-ylmethyl) azetidine-3-sulfonamide

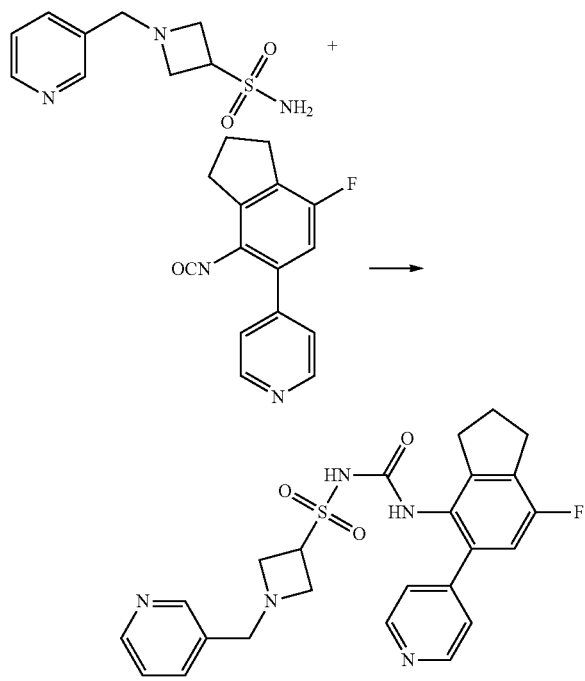

To a solution of 1-(pyridin-3-ylmethyl)azetidine-3-sulfonamide (Intermediate P137) (54 mg, 235.98 µmol, 1 eq) in THF (5 mL) was added t-BuONa (27 mg, 283.18 µmol, 1.2 eq) and a solution of 4-(7-fluoro-4-isocyanato-2,3-dihydro-1H-inden-5-yl)pyridine (Intermediate A9) (60 mg, 235.98 µmol, 1 eq) in THF (5 mL) and DCM (5 mL). The reaction mixture was stirred at 16° C. for 0.5 hour. Then the reaction mixture was concentrated in vacuo. The residue was purified by prep-HPLC (column: Phenomenex Gemini C18, 150 mm*25 mm*10 µm; mobile phase: [A: water (0.05% NH₄HCO₃ v/v); B: MeCN]; B %: 5%-50%, 10 min) to give the title compound (35.53 mg, 31% yield, 99.4% purity on LCMS) as a white solid.

¹H NMR (DMSO-d₆) δ 8.56-8.54 (m, 2H), 8.49-8.47 (m, 2H), 7.76 (br s, 1H), 7.68 (d, 1H), 7.36 (dd, 3H), 7.00 (d, 1H), 4.17-4.12 (m, 1H), 3.68 (s, 2H), 3.47 (t, 2H), 3.40 (t, 2H), 2.96 (t, 2H), 2.84 (t, 2H) and 2.11-2.03 (m, 2H). One exchangeable proton not observed.

LCMS: m/z 482.2 (M+H)⁺ (ES⁺).

Example 172: N-((2-(2-cyanopyridin-4-yl)-4-fluoro-6-isopropylphenyl)carbamoyl)-1-isopropyl-6-oxo-1,6-dihydropyridine-3-sulfonamide

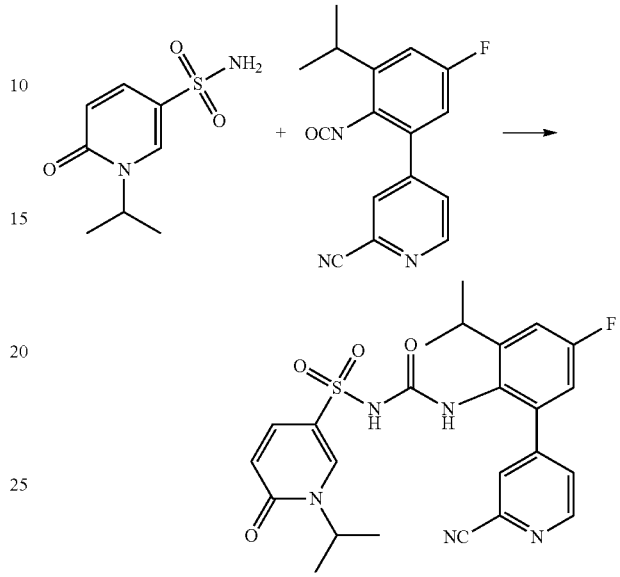

A solution of 1-isopropyl-6-oxo-1,6-dihydropyridine-3-sulfonamide (Intermediate P132) (60 mg, 225.09 µmol, 1 eq), 4-(5-fluoro-2-isocyanato-3-isopropylphenyl)-picolinonitrile (Intermediate A6) (70 mg, 247.60 µmol, 1.1 eq) and t-BuONa (26 mg, 270.11 µmol, 1.2 eq) in THF (1.5 mL) was stirred at 16° C. for 0.5 hour. Then the reaction mixture was concentrated in vacuo. The residue was purified by prep-HPLC (column: Phenomenex Gemini C18, 150 mm*25 mm*10 µm; mobile phase: [A: water (0.05% NH₄HCO₃ v/v); B: MeCN]; B %: 15%-45%, 12 min) to give the title compound (30 mg, 26%) as a white solid.

¹H NMR (DMSO-d₆) δ 8.57 (d, 1H), 7.99-7.92 (m, 3H), 7.64-7.62 (m, 1H), 7.47-7.45 (m, 1H), 7.25-7.22 (m, 1H), 7.14-7.11 (m, 1H), 6.36 (d, 1H), 4.99-4.91 (m, 1H), 3.10-3.05 (m, 1H), 1.25 (d, 6H) and 1.09 (d, 6H). One exchangeable proton not observed.

LCMS: m/z 498.3 (M+H)⁺ (ES⁺).

Example 173: N-((4-Fluoro-2-isopropyl-6-(2-methoxypyridin-4-yl)phenyl) carbamoyl)-1-isopropyl-6-oxo-1,6-dihydropyridine-3-sulfonamide

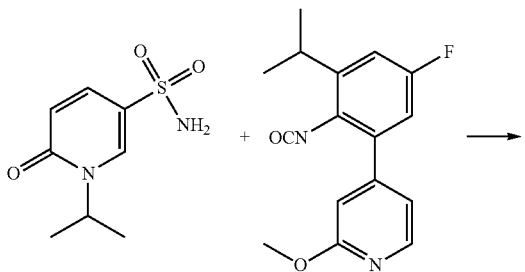

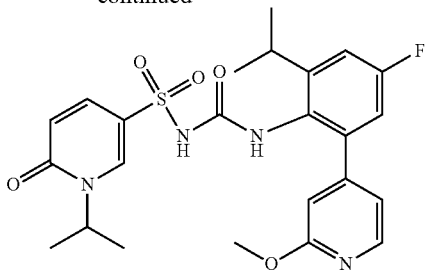

A solution of 1-isopropyl-6-oxo-1,6-dihydropyridine-3-sulfonamide (Intermediate P132) (60 mg, 225.09 μmol, 1 eq), 4-(5-fluoro-2-isocyanato-3-isopropylphenyl)-2-methoxypyridine (Intermediate A7) (71 mg, 247.60 μmol, 1.1 eq) and t-BuONa (26 mg, 270.11 μmol, 1.2 eq) in THF (1.5 mL) was stirred at 16° C. for 0.5 hour. Then the reaction mixture was concentrated in vacuo. The residue was purified by prep-HPLC (column: Xtimate C18, 250 mm*50 mm*10 μm; mobile phase: [A: water (0.05% ammonia hydroxide v/v); B: MeCN]; B %: 2%-32%, 10 min) to give the title compound (61 mg, 54%) as a white solid.

$^1$H NMR (DMSO-d$_6$) δ 7.97 (d, 2H), 7.51 (d, 2H), 7.13 (dd, 1H), 6.96-6.89 (m, 2H), 6.73 (s, 1H), 6.35 (d, 1H), 5.00-4.95 (m, 1H), 3.83 (s, 3H), 3.09-3.04 (m, 1H), 1.25 (d, 6H) and 1.05 (d, 6H). One exchangeable proton not observed.

LCMS: m/z 503.2 (M+H)$^+$ (ES$^+$).

Example 174: N-((7-Fluoro-5-(pyridin-4-yl)-2,3-dihydro-1H-inden-4-yl)carbamoyl)-1-isopropyl-6-oxo-1,6-dihydropyridine-3-sulfonamide

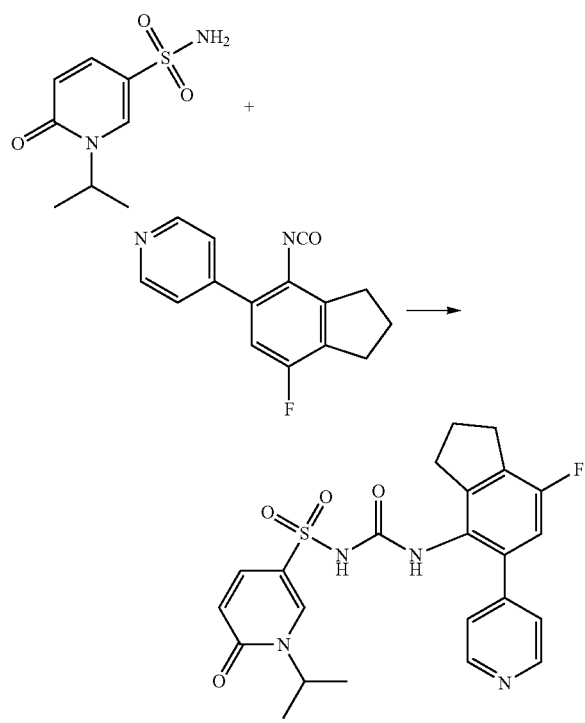

A solution of 1-isopropyl-6-oxo-1,6-dihydropyridine-3-sulfonamide (Intermediate P132) (50 mg, 187-58 μmol, 1 eq), 4-(7-fluoro-4-isocyanato-2,3-dihydro-1H-inden-5-yl)pyridine (Intermediate A9) (52 mg, 206.34 μmol, 1.1 eq) and t-BuONa (22 mg, 225.10 μmol, 1.2 eq) in THF (1.5 mL) was stirred at 16° C. for 0.5 hour. Then the reaction mixture was concentrated in vacuo. The residue was purified by prep-HPLC (column: Phenomenex Gemini C18, 150 mm*25 mm*10 μm; mobile phase: [A: water (0.05% NH$_4$HCO$_3$ v/v); B: MeCN]; B %:12%-42%, 12 min) to give the title compound (6 mg, 7% yield, 99.17% purity on LCMS) as a white solid.

$^1$H NMR (DMSO-d$_6$) δ 8.46 (d, 2H), 8.08 (s, 1H), 7.83 (br s, 1H), 7.58 (dd, 1H), 7.26 (d, 2H), 6.99 (d, 1H), 6.45 (d, 1H), 5.02-4.94 (m, 1H), 2.94 (t, 2H), 2.71 (t, 2H), 2.07-2.01 (m, 2H) and 1.28 (d, 6H). One exchangeable proton not observed.

LCMS: m/z 471.2 (M+H)$^+$ (ES$^+$).

Example 175: N-((4-Fluoro-2-isopropyl-6-(pyridin-3-yl)phenyl)carbamoyl)-1-isopropylazetidine-3-sulfonamide

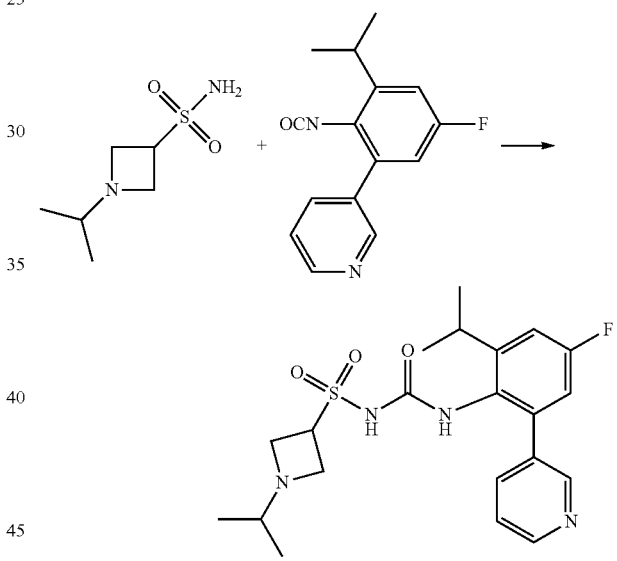

To a solution of 1-isopropylazetidine-3-sulfonamide (Intermediate P134) (200 mg, 1.12 mmol, 1 eq) in THF (5 mL) was added MeONa (60 mg, 1.12 mmol, 1 eq). The reaction mixture was stirred at 25° C. for 30 minutes. Then 3-(5-fluoro-2-isocyanato-3-isopropylphenyl)pyridine (Intermediate A10) (431 mg, 1.68 mmol, 1.5 eq) was added and the resulting mixture was stirred at 70° C. for 30 minutes. Then the reaction mixture was concentrated in vacuo. The residue was purified by reversed phase flash chromatography (column: Welch Ultimate XB_C18, 35 mm*235 mm*20/35 μm, mobile phase: [A: water (0.05% ammonia hydroxide); B: MeCN]; B %: 0%-40%, 10 min) to give the title compound (33 mg, 7% yield, 100% purity on LCMS) as a white solid.

$^1$H NMR (DMSO-d$_6$) δ 8.60-8.51 (m, 2H), 7.92-7.77 (m, 1H), 7.57 (s, 1H), 7.44-7.40 (m, 1H), 7.14 (d, 1H), 7.00 (d, 1H), 3.92-3.74 (m, 3H), 3.29-2.95 (m, 4H), 1.26-1.10 (m, 6H) and 1.02 (d, 6H). One exchangeable proton not observed.

LCMS: m/z 435.2 (M+H)$^+$ (ES$^+$).

Example 176: N-((4-Fluoro-2-isopropyl-6-(pyridin-3-yl)phenyl)carbamoyl)-1-isopropylpiperidine-4-sulfonamide

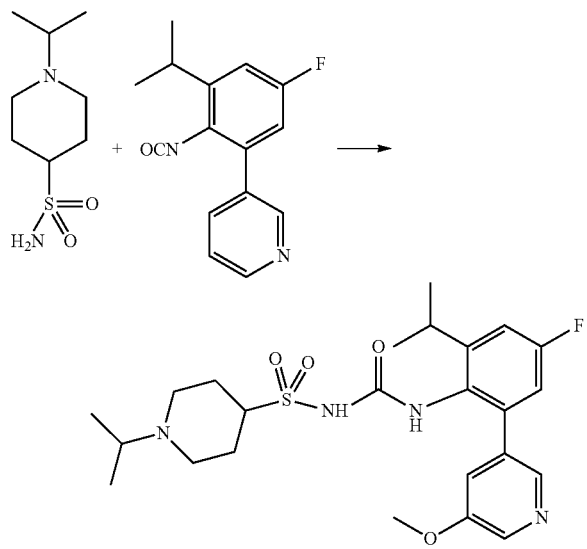

To a solution of 1-isopropylpiperidine-4-sulfonamide (Intermediate P138) (720 mg, 3.49 mmol, 1 eq) in THF (10 mL) was added NaOMe (226 mg, 4.19 mmol, 1.2 eq) and 3-(5-fluoro-2-isocyanato-3-isopropylphenyl)pyridine (Intermediate A10) (805 mg, 3.14 mmol, 0.9 eq). Then the reaction mixture was stirred at 70° C. for 20 minutes. The reaction mixture was concentrated in vacuo. The residue was purified by prep-HPLC (column: Phenomenex Gemini C18, 250 mm*50 mm*10 μm; mobile phase: [A: water (10 mM NH$_4$HCO$_3$); B: MeCN]; B %: 15%-45%, 10 min) to give the title compound (69.36 mg, 4% yield, 100% purity on LCMS) as a white solid.

$^1$H NMR (DMSO-d$_6$) δ 8.57 (s, 1H), 8.48 (d, 1H), 7.87-7.80 (m, 1H), 7.36-7.32 (m, 1H), 7.25 (s, 1H), 7.10 (d, 1H), 6.95 (d, 1H), 6.09 (s, 1H), 2.95-2.85 (m, 1H), 2.79-2.76 (m, 2H), 2.70-2.63 (m, 2H), 1.98-1.85 (m, 2H), 1.65-1.61 (m, 2H), 1.42-1.38 (m, 2H), 1.14 (d, 6H) and 0.94 (d, 6H). One exchangeable proton not observed.

LCMS: m/z 463.4 (M+H)$^+$ (ES$^+$).

Example 177: N-((4-Fluoro-2-isopropyl-6-(2-methoxypyridin-4-yl)phenyl) carbamoyl)-1-(pyridin-3-ylmethyl) azetidine-3-sulfonamide

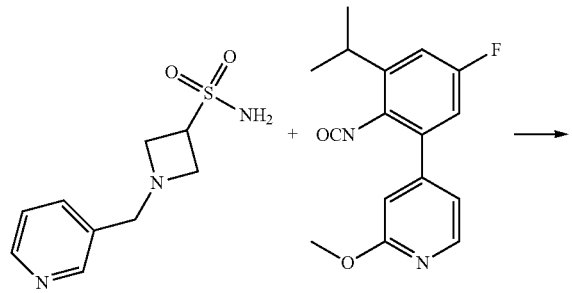

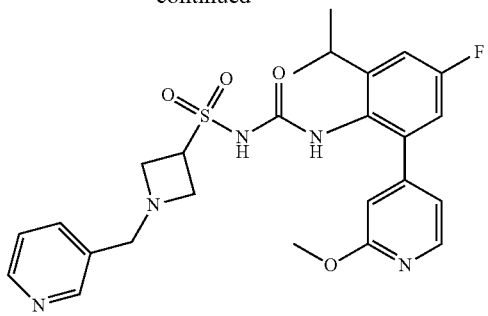

A solution of 1-(pyridin-3-ylmethyl)azetidine-3-sulfonamide (Intermediate P137) (50 mg, 219.99 μmol, 1 eq), 4-(5-fluoro-2-isocyanato-3-isopropylphenyl)-2-methoxypyridine (Intermediate A7) (69 mg, 241.99 μmol, 1.1 eq) and t-BuONa (25 mg, 263.99 μmol, 1.2 eq) in THF (1.5 mL) was stirred at 16° C. for 0.5 hour. Then the reaction mixture was concentrated in vacuo. The residue was purified by prep-HPLC (column: Waters Xbridge C18, 150 mm*50 mm*10 μm, mobile phase: [A: water (0.05% ammonia hydroxide v/v); B: MeCN]; B %: 8%-38%, 11.5 min) to give the title compound (44 mg, 38%) as a white solid.

$^1$H NMR (DMSO-d$_6$) δ 8.47 (s, 2H), 8.12 (d, 1H), 7.67 (d, 2H), 7.35 (dd, 1H), 7.19 (d, 1H), 7.01-6.95 (m, 2H), 6.80 (s, 1H), 4.04-3.98 (m, 1H), 3.78 (s, 3H), 3.64 (s, 2H), 3.43-3.36 (m, 4H), 3.16-3.12 (m, 1H) and 1.12 (d, 6H). One exchangeable proton not observed.

LCMS: m/z 514.3 (M+H)$^+$ (ES$^+$).

Example 178: 1-Isopropyl-N-((5-(2-methoxypyridin-4-yl)-2,3-dihydro-1H-inden-4-yl) carbamoyl)-2-oxo-1,2-dihydropyrimidine-5-sulfonamide, Sodium Salt

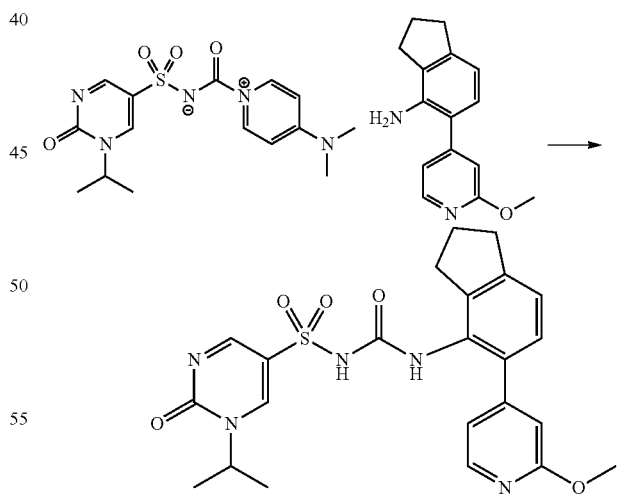

A suspension of 5-(2-methoxypyridin-4-yl)-2,3-dihydro-1H-inden-4-amine (0.033 g, 0.137 mmol) (Intermediate A4) and (4-(dimethylamino)pyridin-1-ium-1-carbonyl)((1-isopropyl-2-oxo-1,2-dihydropyrimidin-5-yl)sulfonyl)amide (Intermediate P139) (0.069 g, 0.123 mmol) in dry MeCN (2 mL) was stirred at 50° C. for 2 hours. Then the reaction mixture was concentrated in vacuo and the crude product was purified by prep-HPLC (column: Waters Xbridge C18, 19 mm*15 mm*5 µm; mobile phase: [A: water (0.1% NH₄HCO₃); B: MeCN]; B %: 10%-40%) to afford 1-isopropyl-N-((5-(2-methoxypyridin-4-yl)-2,3-dihydro-1H-inden-4-yl)carbamoyl)-2-oxo-1,2-dihydropyrimidine-5-sulfonamide (0.031 g, 52%) as a flocculent white solid.

The free acid (0.024 g, 0.050 mmol) was treated with 0.1 M NaOH (aq) (0.500 ml, 0.05 mmol) and the resultant solution was freeze-dried to afford the title compound (0.025 g, 99%) as a white solid.

$^1$H NMR (DMSO-d6) δ 8.65 (d, J=3.0 Hz, 1H), 8.35 (d, J=3.1 Hz, 1H), 7.98 (d, J=5.2 Hz, 1H), 7.24 (br s, 1H), 7.08 (d, J=7.7 Hz, 1H), 7.03 (d, J=7.6 Hz, 1H), 6.88 (dd, J=5.3, 1.4 Hz, 1H), 6.70 (t, J=1.0 Hz, 1H), 4.76 (sept, J=6.7 Hz, 1H), 3.82 (s, 3H), 2.88 (t, J=7.4 Hz, 2H), 2.70 (t, J=7.4 Hz, 2H), 1.94 (P, J=7.5 Hz, 2H), 1.30 (d, J=6.8 Hz, 6H).

LCMS: m/z 484.1 (M+H)⁺ (ES⁺); 482.1 (M−H)⁻ (ES⁻).

Example 179: 1-Isopropyl-N-((5-(2-methoxypyridin-4-yl)-2,3-dihydro-1H-inden-4-yl)carbamoyl)-2-oxo-1,2-dihydropyridine-4-sulfonamide, Sodium Salt

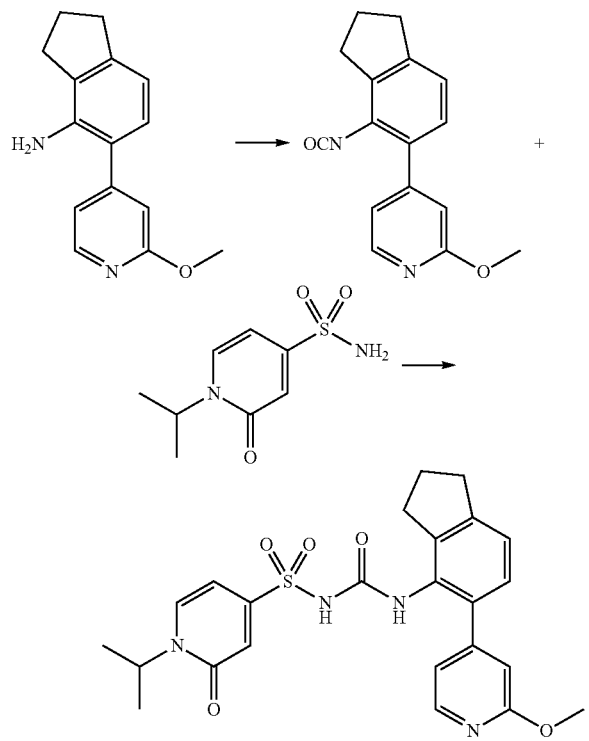

To a solution of 5-(2-methoxypyridin-4-yl)-2,3-dihydro-1H-inden-4-amine (Intermediate A4) (0.156 g, 0.65 mmol) in DCM (5 mL) and saturated aqueous NaHCO₃ (5 mL) was added a solution of bis(trichloromethyl) carbonate (0.079 g, 0.264 mmol) in toluene (1 mL) to the DCM layer without stirring. The reaction mixture was stirred for 1 hour, passed through a phase separator, dried (MgSO₄), filtered and concentrated in vacuo to afford crude isocyanate intermediate as an orange oil which was used without further purification. The crude isocyanate intermediate was dissolved in dry THF (11 mL).

A solution of 1-isopropyl-2-oxo-1,2-dihydropyridine-4-sulfonamide (Intermediate P140) (0.050 g, 0.224 mmol) in dry THF (3 mL) was treated with sodium tert-butoxide (2 M in THF) (0.120 ml, 0.24 mmol). The reaction mixture was stirred at room temperature for 1 hour, treated with a solution of the crude isocyanate intermediate in dry THF (4 mL) and then stirred at room temperature for 22 hours. The reaction mixture was concentrated in vacuo and the residue purified by reversed phase flash C18 chromatography (liquid load) (12 g cartridge, 5-50% MeCN/10 mM ammonium bicarbonate) to afford 1-isopropyl-N-((5-(2-methoxypyridin-4-yl)-2,3-dihydro-1H-inden-4-yl)carbamoyl)-2-oxo-1,2-dihydropyridine-4-sulfonamide (0.079 g, 70%) as a flocculent white solid. The free acid (0.071 g, 0.141 mmol) was treated with 0.1 M NaOH (aq) (1.410 ml, 0.141 mmol) and the mixture was freeze-dried to afford the title compound (0.073 g, 102%) as a white solid.

$^1$H NMR (DMSO-d6) δ 8.06 (dd, J=5.3, 0.7 Hz, 1H), 7.87 (dd, J=6.9, 2.1 Hz, 1H), 7.76 (dd, J=7.0, 2.1 Hz, 1H), 7.30 (br s, 1H), 7.06 (d, J=7.7 Hz, 1H), 7.03 (d, J=7.7 Hz, 1H), 6.94 (dd, J=5.3, 1.5 Hz, 1H), 6.76 (t, J=1.00 Hz, 1H), 6.30 (t, J=6.9 Hz, 1H), 5.14 (sept, J=6.8 Hz, 1H), 3.85 (s, 3H), 2.85 (t, J=7.4 Hz, 2H), 2.67 (t, J=7.4 Hz, 2H), 1.90 (p, J=7.5 Hz, 2H), 1.30 (d, J=6.8 Hz, 6H).

LCMS: m/z 483.1 (M+H)⁺ (ES⁺); 481.0 (M−H)⁻ (ES⁻).

Example 180: N-((1,2,3,5,6,7-Hexahydro-s-indacen-4-yl)carbamoyl)-1-isopropyl-2-oxo-1,2-dihydropyridine-4-sulfonamide, Sodium Salt

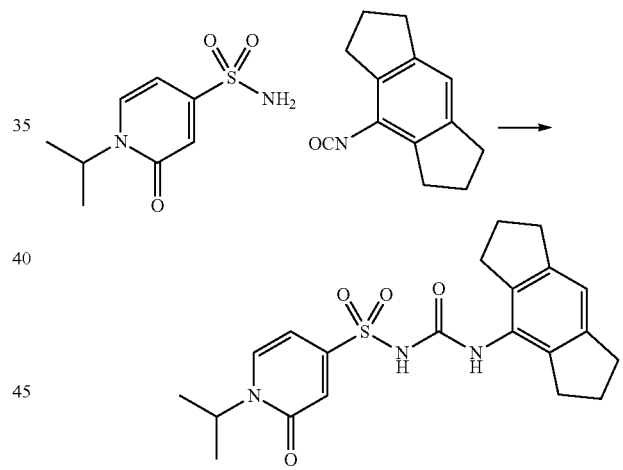

A solution of 1-isopropyl-2-oxo-1,2-dihydropyridine-4-sulfonamide (Intermediate P140) (0.05 g, 0.224 mmol) in dry THF (4 mL) was treated with 2 M sodium tert-butoxide in THF (0.12 ml, 0.240 mmol) under nitrogen. The resultant suspension was stirred at room temperature for 1 hour, then treated with a solution of 4-isocyanato-1,2,3,5,6,7-hexahydro-s-indacene (Intermediate A1) (0.049 g, 0.247 mmol) in dry THF (1 mL) and stirred for 18 hours. The reaction mixture was concentrated in vacuo and the residue was purified by reversed phase flash C18 chromatography (liquid load) (12 g cartridge, 0-75% MeCN/10 mM ammonium bicarbonate) to afford N-((1,2,3,5,6,7-hexahydro-s-indacen-4-yl)carbamoyl)-1-isopropyl-2-oxo-1,2-dihydropyridine-4-sulfonamide (0.059 g, 63%) as a flocculent white solid. The free acid (0.05 g, 0.119 mmol) was treated with 0.1 M NaOH (1.191 ml, 0.119 mmol) and the resultant solution was freeze-dried to afford the title compound (0.052 g, 99%) as a white solid.

¹H NMR (DMSO-d6) δ 7.88-7.84 (m, 2H), 7.47 (s, 1H), 6.75 (s, 1H), 6.33 (t, J=6.9 Hz, 1H), 5.11 (sept, J=6.8 Hz, 1H), 2.73 (t, J=7.4 Hz, 4H), 2.61 (t, J=7.4 Hz, 4H), 1.87 (p, J=7.4 Hz, 4H), 1.29 (d, J=6.9 Hz, 6H).

LCMS: m/z 438.3 (M+Na)⁺ (ES⁺); 414.2 (M−H)⁻ (ES⁻).

Example 181: N-((1,2,3,5,6,7-Hexahydro-s-indacen-4-yl)carbamoyl)-4-isopropyl-5-oxo-4,5-dihydropyrazine-2-sulfonamide, Sodium Salt

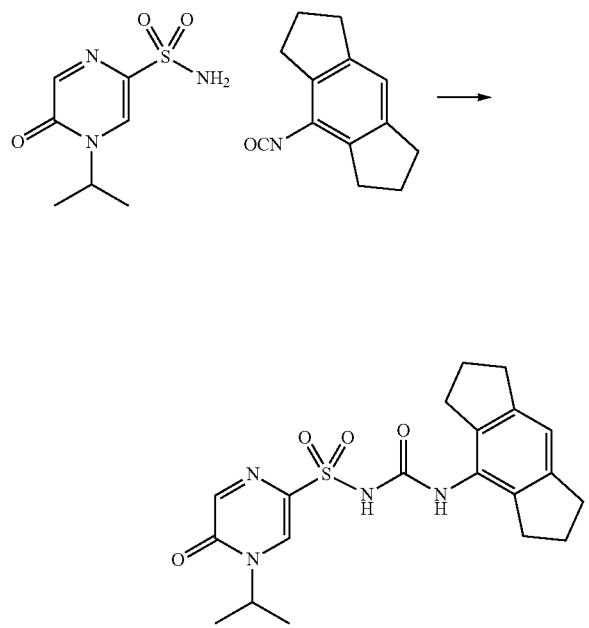

A solution of 4-isopropyl-5-oxo-4,5-dihydropyrazine-2-sulfonamide (Intermediate P133) (0.06 g, 0.273 mmol) in dry THF (4 mL) was treated with 2M sodium tert-butoxide in THF (0.15 ml, 0.300 mmol) under nitrogen. The resultant suspension was stirred at room temperature for 45 minutes, and then treated with a solution of 4-isocyanato-1,2,3,5,6,7-hexahydro-s-indacene (Intermediate A1) (0.061 g, 0.306 mmol) in dry THF (1 mL) and stirred for 21 hours. The reaction mixture was diluted with EtOAc (10 mL) and washed with water (2×2 mL). The aqueous layer was collected and retained. The organic layer was concentrated in vacuo and the residue was dissolved in MeCN (2 mL) and combined with the aqueous layer. The resultant suspension was filtered through cotton wool and then purified by reversed phase flash C18 chromatography (12 g cartridge, 5-75% MeCN/10 mM ammonium bicarbonate) to afford N-((1,2,3,5,6,7-hexahydro-s-indacen-4-yl)carbamoyl)-4-isopropyl-5-oxo-4,5-dihydropyrazine-2-sulfonamide (0.075 g, 66%) as a flocculent white solid. The free acid (0.05 g, 0.120 mmol) was treated with 0.1 M NaOH (1.200 ml, 0.120 mmol) and the resultant solution was freeze-dried to afford the title compound (00.0053 g, 101%) as a white solid.

¹H NMR (DMSO-d6) δ 7.96 (d, J=1.1 Hz, 1H), 7.90 (d, J=1.0 Hz, 1H), 7.46 (s, 1H), 6.76 (s, 1H), 4.88 (sept, J=6.8 Hz, 1H), 2.74 (t, J=7.4 Hz, 4H), 2.63 (t, J=7.3 Hz, 4H), 1.88 (p, J=7.4 Hz, 4H), 1.31 (d, J=6.8 Hz, 6H).

LCMS: m/z 417.3 (M+H)⁺ (ES⁺); 415.2 (M−H)⁻ (ES⁻).

Example 182: N-((1,2,3,5,6,7-Hexahydro-s-indacen-4-yl)carbamoyl)-1-isopropyl-2-oxo-1,2-dihydropyridine-3-sulfonamide

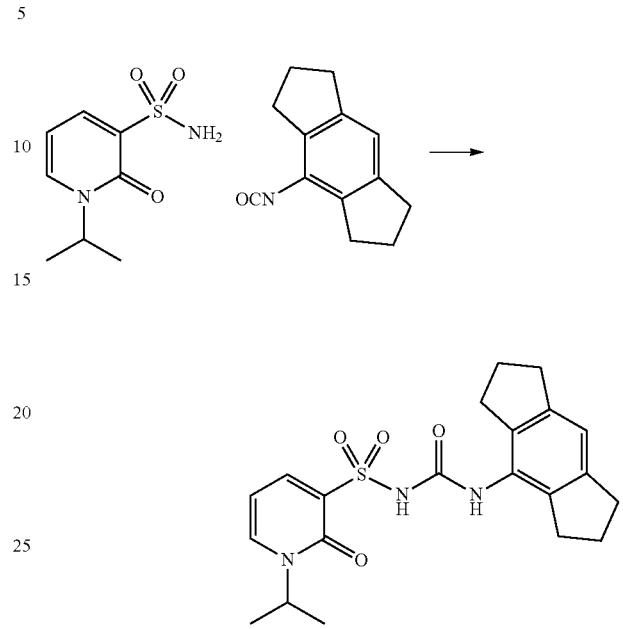

2 M Sodium tert-butoxide in THF (0.138 ml, 0.277 mmol) was added to a solution of 1-isopropyl-2-oxo-1,2-dihydropyridine-3-sulfonamide (Intermediate P141) (0.06 g, 0.264 mmol) in anhydrous THF (4 mL) at room temperature. The mixture was stirred for 1 hour before 4-isocyanato-1,2,3,5,6,7-hexahydro-s-indacene (Intermediate A1) (0.058 g, 0.290 mmol) was added in a single portion. The reaction mixture was stirred for 21 hours at room temperature, concentrated in vacuo, then redissolved in DMSO (1.5 mL) and purified by reversed phase flash C18 chromatography (12 g cartridge, 5-100% MeCN/10 mM ammonium bicarbonate) to afford the title compound (0.023 g, 21%) as a white solid.

¹H NMR (DMSO-d6) δ 8.19-8.00 (m, 3H), 6.89 (s, 1H), 6.46 (t, J=7.0 Hz, 1H), 5.11 (sept, J=6.8 Hz, 1H), 2.76 (t, J=7.4 Hz, 4H), 2.56 (t, J=7.2 Hz, 4H), 1.91 (p, J=7.4 Hz, 4H), 1.32 (d, J=6.8 Hz, 6H). One exchangeable proton not observed.

LCMS: m/z 416.2 (M+H)⁺ (ES⁺), 438.3 (M+Na)⁺ (ES⁺).

Example 183: (R)—N-((1,2,3,5,6,7-Hexahydro-s-indacen-4-yl)carbamoyl)-1-(2-hydroxypropyl)-6-oxo-1,6-dihydropyridine-3-sulfonamide

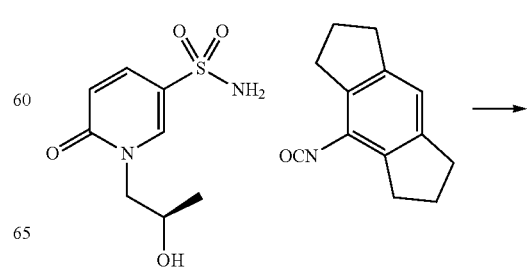

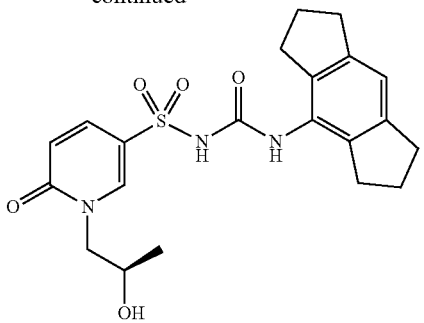

A solution of (R)-1-(2-hydroxypropyl)-6-oxo-1,6-dihydropyridine-3-sulfonamide (Intermediate P142) (0.047 g, 0.196 mmol) in dry THF (4 mL) was treated with 2M sodium tert-butoxide in THF (0.103 ml, 0.206 mmol) under nitrogen. The resultant suspension was stirred at room temperature for 1 hour, and then treated with a solution of 4-isocyanato-1,2,3,5,6,7-hexahydro-s-indacene (Intermediate A1) (0.043 g, 0.216 mmol) in dry THF (1 mL) and stirred for 20 hours. The reaction mixture was concentrated in vacuo to afford crude product as a green solid which was purified by prep-HPLC (column: Waters Xbridge C18, 19 mm*15 mm*5 μm; mobile phase: [A: water (0.1% NH$_4$HCO$_3$); B: MeCN]; B %: 10%-40%) to afford the title compound (0.016 g, 19%) as a flocculent white solid.

$^1$H NMR (DMSO-d6) δ 8.17 (d, J=2.6 Hz, 1H), 7.85 (br s, 1H), 7.75 (dd, J=9.6, 2.7 Hz, 1H), 6.88 (s, 1H), 6.44 (d, J=9.6 Hz, 1H), 4.92 (d, J=5.5 Hz, 1H), 4.04 (dd, J=12.9, 3.7 Hz, 1H), 3.85 (ddd, J=9.4, 7.0, 4.7 Hz, 1H), 3.64 (dd, J=12.9, 8.0 Hz, 1H), 2.77 (t, J=7.4 Hz, 4H), 2.60 (t, J=7.4 Hz, 4H), 1.92 (p, J=7.5 Hz, 4H), 1.06 (d, J=6.3 Hz, 3H). One exchangeable proton not observed.

LCMS: m/z 432.3 (M+H)$^+$ (ES$^+$); 430.1 (M−H)$^−$ (ES$^−$).

Example 184: 1-(2-(Dimethylamino)ethyl)-N-((1,2,3,5,6,7-hexahydro-s-indacen-4-yl)carbamoyl)-6-oxo-1,6-dihydropyridine-3-sulfonamide

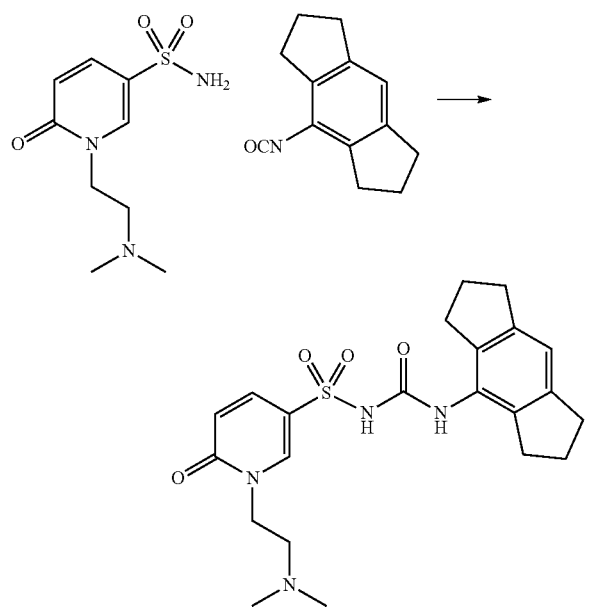

A solution of 1-(2-(dimethylamino)ethyl)-6-oxo-1,6-dihydropyridine-3-sulfonamide (Intermediate P143) (0.034 g, 0.100 mmol) in dry THF (3 mL) was treated with 2M sodium tert-butoxide in THF (0.07 ml, 0.140 mmol) under nitrogen. The resultant suspension was stirred at room temperature for 1 hour, and then treated with a solution of 4-isocyanato-1,2,3,5,6,7-hexahydro-s-indacene (Intermediate A1) (0.035 g, 0.176 mmol) in dry THF (1 mL) and stirred for 20 hours. The reaction mixture was concentrated in vacuo to afford crude product as an off white solid which was purified by reversed phase flash C18 chromatography (liquid load in water) (12 g cartridge, 5-75% MeCN/10 mM ammonium bicarbonate) to afford the title compound (0.017 g, 38%) as a flocculent white solid.

$^1$H NMR (DMSO-d6) δ 8.28 (d, J=2.6 Hz, 1H), 7.85 (s, 1H), 7.75 (dd, J=9.6, 2.7 Hz, 1H), 6.88 (s, 1H), 6.46 (d, J=9.6 Hz, 1H), 4.11 (t, J=6.3 Hz, 2H), 2.80-2.70 (m, 6H), 2.60 (t, J=7.4 Hz, 4H), 2.34 (s, 6H), 1.92 (p, J=7.4 Hz, 4H). One exchangeable proton not observed.

LCMS: m/z 445.3 (M+H)$^+$ (ES$^+$); 443.3 (M−H)$^−$ (ES$^−$).

Example 185: N-((1,2,3,5,6,7-Hexahydro-s-indacen-4-yl)carbamoyl)-1-isopropyl-6-oxo-1,6-dihydropyridine-3-sulfonamide, Sodium Salt

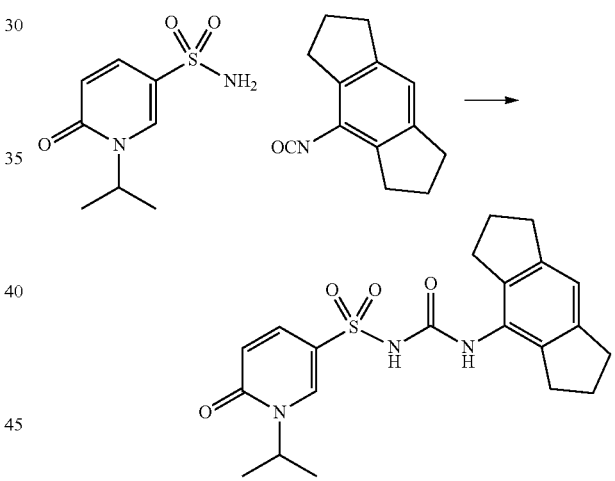

Sodium tert-butoxide (2 M in THF) (0.048 mL, 0.096 mmol) was added to a solution of 1-isopropyl-6-oxo-1,6-dihydropyridine-3-sulfonamide (Intermediate P132) (19.7 mg, 0.091 mmol) in THF (2 mL) and the reaction mixture was stirred at room temperature for 1 hour. Then 4-isocyanato-1,2,3,5,6,7-hexahydro-s-indacene (Intermediate A1) (20 mg, 0.100 mmol) was added and the reaction mixture was stirred at room temperature overnight. The resultant white precipitate was collected by filtration, washing with THF. The solid was dissolved in MeCN, filtered and dried in vacuo to afford the title compound (5 mg, 12%) as a white solid.

$^1$H NMR (DMSO-d6) δ 8.00 (d, J=2.5 Hz, 1H), 7.66 (dd, J=9.4, 2.5 Hz, 1H), 7.36 (s, 1H), 6.76 (s, 1H), 6.32 (d, J=9.3 Hz, 1H), 5.01 (sept, J=6.8 Hz, 1H), 2.75 (t, J=7.4 Hz, 4H), 2.63 (t, J=7.3 Hz, 4H), 1.88 (p, J=7.4 Hz, 4H), 1.28 (d, J=6.8 Hz, 6H).

LCMS: m/z 416.3 (M+H)$^+$ (ES$^+$).

Example 186: 1-Ethyl-N-((7-fluoro-5-(2-methoxy-pyridin-4-yl)-2,3-dihydro-1H-inden-4-yl)carbamoyl)piperidine-4-sulfonamide, Potassium Salt

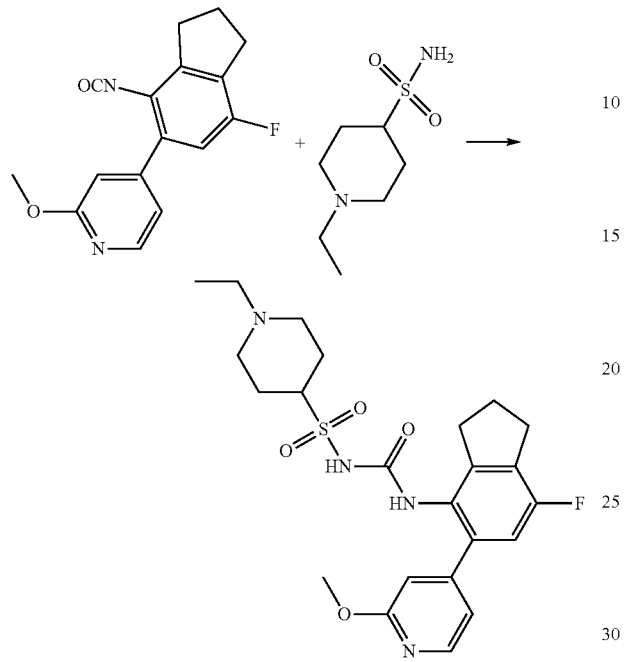

To a solution of 1-ethylpiperidine-4-sulfonamide (Intermediate P6; 90 mg, 0.37 mmol) in THF (5 mL) was added potassium tert-butoxide (49 mg, 0.44 mmol). The mixture was stirred at room temperature for 45 minutes. Then 4-(7-fluoro-4-isocyanato-2,3-dihydro-1H-inden-5-yl)-2-methoxypyridine (Intermediate A11; 90 mg, 0.32 mmol) was added and the mixture was stirred for 2 hours room temperature. The reaction mixture was concentrated in vacuo and DMSO (0.5-1 mL) was added. The mixture (filtered over cotton wool when solids were present) was submitted for purification by reversed phase column chromatography (see "Experimental Methods", "Purification Method 1") to afford the title compound (18 mg, to %) as a white solid.

$^1$H NMR (methanol-d$_4$) δ 8.10 (d, 1H), 7.03 (d, 1H), 6.87 (s, 1H), 6.84 (s, 1H), 3.92 (s, 3H), 3.23 (m, 2H), 3.07 (m, 1H), 3.00 (m, 4H), 2.68 (m, 2H), 2.32-2.08 (m, 4H), 2.03 (m, 2H), 1.86 (m, 2H), 1.18 (t, 3H).

LCMS: m/z 477 (M+H)$^+$ (ES$^+$); 475 (M−H)$^−$ (ES$^−$).

Example 187: 1-(sec-Butyl)-N-((4-chloro-2,6-diisopropylphenyl)carbamoyl) azetidine-3-sulfonamide, Potassium Salt

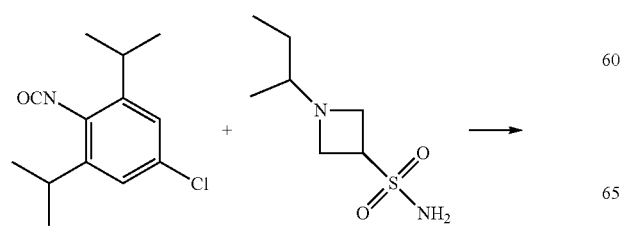

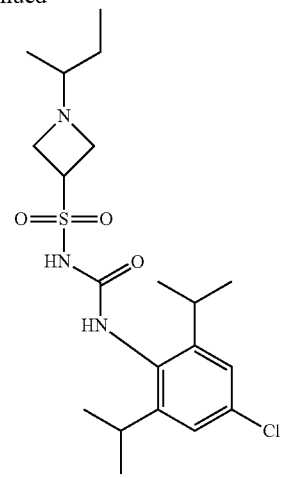

Prepared as described for 1-ethyl-N-((7-fluoro-5-(2-methoxypyridin-4-yl)-2,3-dihydro-1H-inden-4-yl)carbamoyl)piperidine-4-sulfonamide, potassium salt (Example 186) using 5-chloro-2-isocyanato-1,3-diisopropylbenzene (Intermediate A15) and 1-(sec-butyl)azetidine-3-sulfonamide (Intermediate P107) to afford the title compound (25%) as a white solid.

$^1$H NMR (CD$_3$OD) δ 7.08 (m, 2H), 4.28 (t, 1H), 3.70 (t, 2H), 3.58 (t, 2H), 3.24 (m, 2H), 2.42 (d, 1H), 1.55 (s, 1H), 1.18 (d, 13H), 0.95 (d, 3H), 0.89 (t, 3H).

LCMS: m/z 431 (M+H)$^+$ (ES$^+$); 429 (M−H)$^−$ (ES$^−$).

Example 188: 1-Ethyl-N-((5-(2-methoxypyridin-4-yl)-2,3-dihydro-1H-inden-4-yl)carbamoyl)piperidine-4-sulfonamide, Potassium Salt

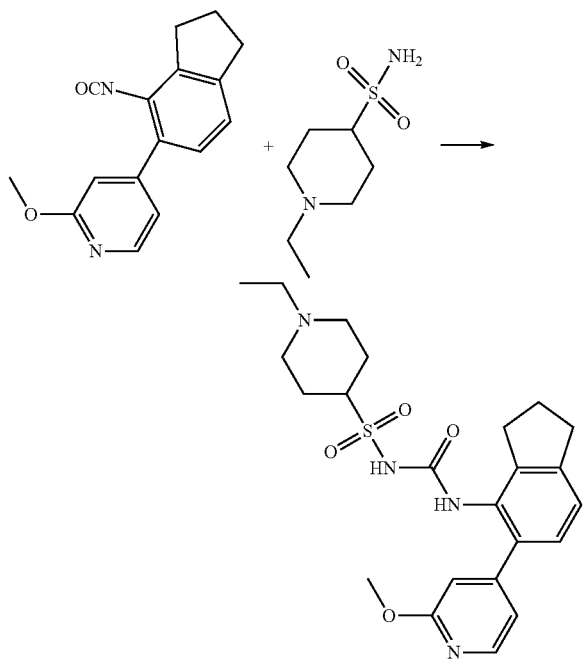

Prepared as described for 1-ethyl-N-((7-fluoro-5-(2-methoxypyridin-4-yl)-2,3-dihydro-1H-inden-4-yl)carbamoyl)piperidine-4-sulfonamide, potassium salt (Example 186) using 4-(4-isocyanato-2,3-dihydro-1H-inden-5-yl)-2-methoxypyridine (Intermediate A8) and 1-ethylpiperidine-4-sulfonamide (Intermediate P6) to afford the title compound (54 mg, 30%) as a white solid.

$^1$H NMR (methanol-d$_4$) δ 8.08 (d, 1H), 7.25-7.08 (m, 2H), 7.03 (dd, 1H), 6.86 (s, 1H), 3.92 (s, 3H), 3.39-3.17 (m, 3H), 2.95 (m, 4H), 2.71 (q, 2H), 2.33 (t, 2H), 2.22-1.97 (m, 4H), 1.97-1.72 (m, 2H), 1.18 (t, 3H).

LCMS: m/z 459 (M+H)$^+$ (ES$^+$); 457 (M-H)$^-$ (ES$^-$).

Example 189: 1-Ethyl-N-((1,2,3,7-tetrahydro-s-indacen-4-yl)carbamoyl) piperidine-4-sulfonamide, Potassium Salt

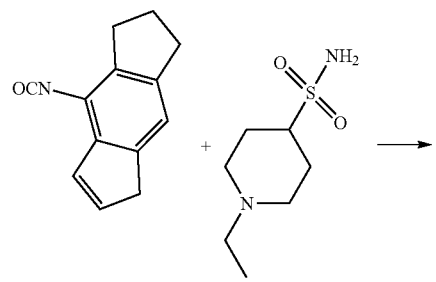

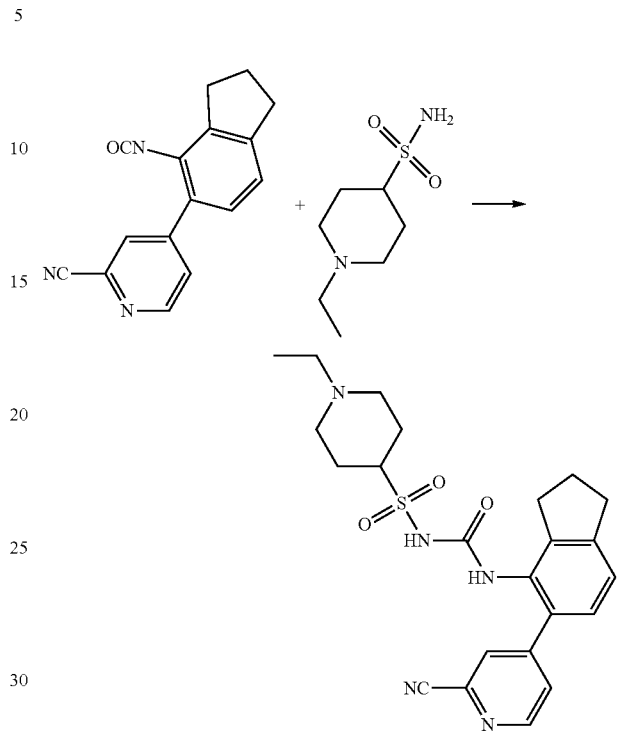

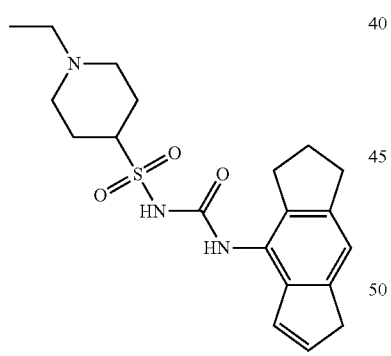

Prepared as described for 1-ethyl-N-((7-fluoro-5-(2-methoxypyridin-4-yl)-2,3-dihydro-1H-inden-4-yl)carbamoyl)piperidine-4-sulfonamide, potassium salt (Example 186) using 8-isocyanato-1,2,3,5-tetrahydro-s-indacene (Intermediate A14) and 1-ethylpiperidine-4-sulfonamide (Intermediate P6) to afford the title compound (77 mg, 34%) as a white solid.

$^1$H NMR (methanol-d$_4$) (mixture of isomers) δ 7.14, 7.06 (s, 1H), 6.91, 6.77 (m, 1H), 6.46, 6.41 (m, 1H), 3.64-3.44 (m, 2H), 3.31 (m, 2H), 3.23 (m, 1H), 2.89 (m, 4H), 2.74-2.54 (m, 2H), 2.31 (d, 2H), 2.25-1.85 (m, 6H), 1.16 (t, 3H).

LCMS: m/z 390 (M+H)$^+$ (ES$^+$); 388 (M-H)$^-$ (ES$^-$).

Example 190: N-((5-(2-Cyanopyridin-4-yl)-2,3-dihydro-1H-inden-4-yl) carbamoyl)-1-ethylpiperidine-4-sulfonamide, Potassium Salt Prepared as described for 1-ethyl-N-((7-fluoro-5-(2-methoxypyridin-4-yl)-2,3-dihydro-1H-inden-4-yl)carbamoyl)piperidine-4-sulfonamide, potassium salt (Example 186) using 4-(4-isocyanato-2,3-dihydro-H-inden-5-yl)picolinonithoxypyridine (Intermediate A12) and 1-ethylpiperidine-4-sulfonamide (Intermediate P6) to afford the title compound (18 mg, 18%) as a white solid.

$^1$H NMR (methanol-d$_4$) δ 8.66 (dd, 1H), 7.95 (d, 1H), 76.8873 (dd, 1H), 7.20 (q, 2H), 3.55 (m, 1H), 3.09 (q, 2H), 2.98 (m, 4H), 2.85 (m, 4H), 2.13 (m, 2H), 2.1-1.97 (d, 6H)), 1.31 (t, 3H).

LCMS: m/z 454 (M+H)$^+$ (ES$^+$); 452 (M-H)$^-$ (ES$^-$).

Example 191: 1-Ethyl-N-((4-fluoro-2-isopropyl-6-(2-methoxypyridin-4-yl) phenyl)carbamoyl)piperidine-4-sulfonamide, Potassium Salt

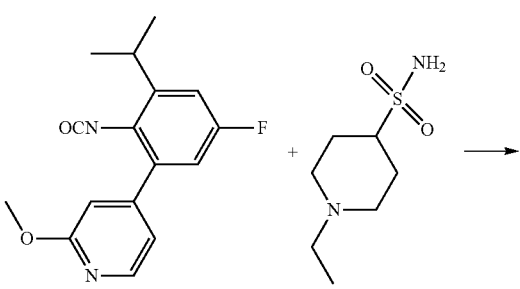

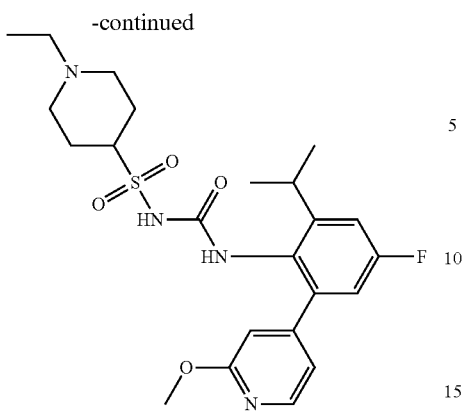

Prepared as described for 1-ethyl-N-((7-fluoro-5-(2-methoxypyridin-4-yl)-2,3-dihydro-1H-inden-4-yl)carbamoyl)piperidine-4-sulfonamide, potassium salt (Example 186) using 4-(5-fluoro-2-isocyanato-3-isopropylphenyl)-2-methoxypyridine (Intermediate A7) and 1-ethylpiperidine-4-sulfonamide (Intermediate P6) to afford the title compound (23 mg, 14%) as a white solid.

$^1$H NMR (methanol-$d_4$) δ 8.09 (d, 1H), 7.06 (dd, 2H), 6.88 (m, 2H), 3.92 (s, 3H), 3.72 (m, 1H), 3.19 (m, 1H), 3.08 (m, 2H), 2.49 (d, 2H), 1.87 (m, 6H), 1.23 (d, 6H), 1.12 (t, 3H).

LCMS: m/z 479 (M+H)$^+$ (ES$^+$); 477 (M-H)$^-$ (ES$^-$).

Example 192: 1-Ethyl-N-((5-(pyridin-4-yl)-2,3-dihydro-1H-inden-4-yl) carbamoyl)piperidine-4-sulfonamide, Potassium Salt

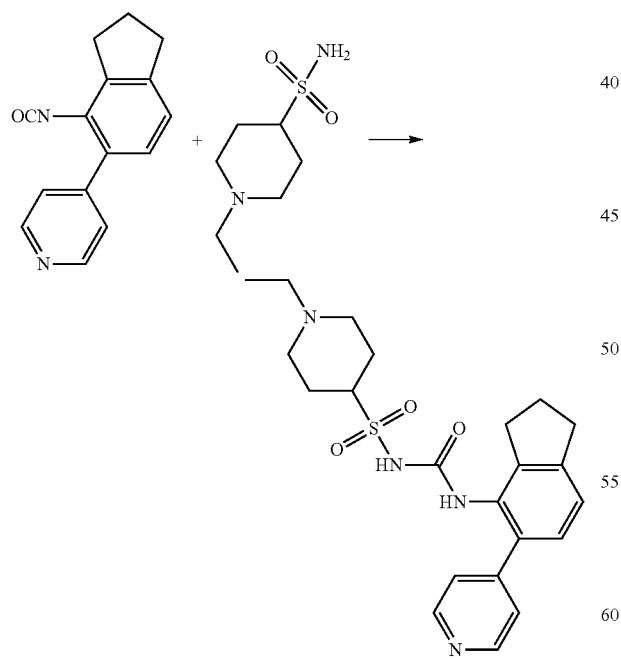

Prepared as described for 1-ethyl-N-((7-fluoro-5-(2-methoxypyridin-4-yl)-2,3-dihydro-1H-inden-4-yl)carbamoyl)piperidine-4-sulfonamide, potassium salt (Example 186) using 4-(4-isocyanato-2,3-dihydro-1H-inden-5-yl)pyridine (Intermediate A13) and 1-ethylpiperidine-4-sulfonamide (Intermediate P6) to afford the title compound (11 mg, 13%) as a white solid.

$^1$H NMR (methanol-$d_4$) δ 8.55-8.42 (m, 2H), 7.58-7.44 (m, 2H), 7.24-7.05 (m, 2H), 3.22 (d, 2H), 3.07 (m, 1H), 2.97 (m, 4H), 2.65 (t, 2H), 2.23 (t, 2H), 2.10 (m, 2H), 2.04-1.67 (m, 4H), 1.18 (t, 3H).

LCMS: m/z 429 (M+H)$^+$ (ES$^+$); 427 (M-H)$^-$ (ES$^-$).

Example 193: 1-(Ethyl-d5)-N-((1,2,3,5,6,7-hexahydro-s-indacen-4-yl) carbamoyl)piperidine-4-sulfonamide, Potassium Salt

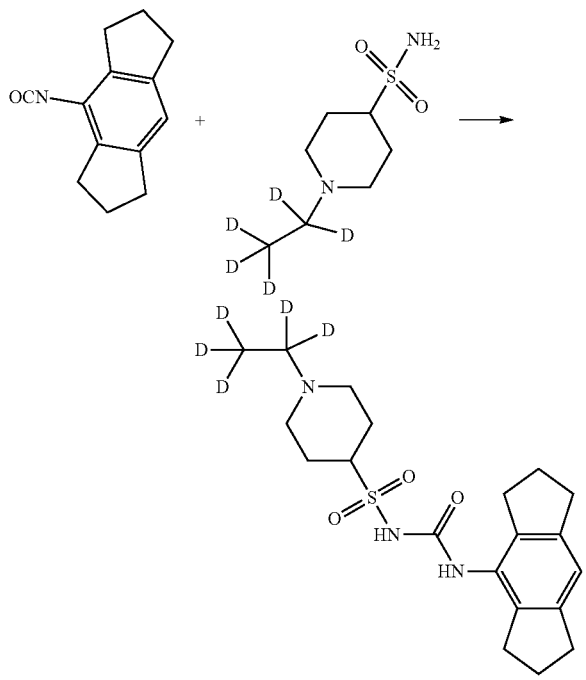

Prepared as described for 1-ethyl-N-((7-fluoro-5-(2-methoxypyridin-4-yl)-2,3-dihydro-1H-inden-4-yl)carbamoyl)piperidine-4-sulfonamide, potassium salt (Example 186) using 4-isocyanato-1,2,3,5,6,7-hexahydro-s-indacene (Intermediate A1) and 1-(ethyl-d5)piperidine-4-sulfonamide (Intermediate P145) to afford the title compound (75 mg, 38%) as a white solid.

$^1$H NMR (methanol-$d_4$) δ 6.87 (s, 1H), 3.44 (m, 1H), 3.16 (d, 2H), 2.82 (m, 8H), 2.15 (m, 4H), 2.10-1.84 (m, 6H).

LCMS: m/z 397 (M+H)$^+$ (ES$^+$); 395 (M-H)$^-$ (ES$^-$).

Example 194: 1-Ethyl-N-((1,2,3,5,6,7-hexahydro-s-indacen-4-yl)carbamoyl) azepane-4-sulfonamide, Potassium Salt

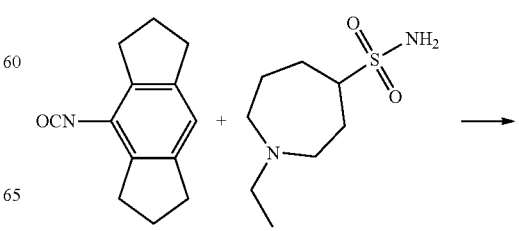

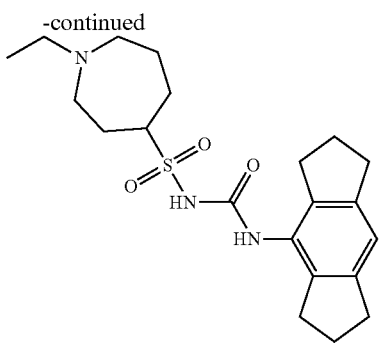

Prepared as described for 1-ethyl-N-((7-fluoro-5-(2-methoxypyridin-4-yl)-2,3-dihydro-1H-inden-4-yl)carbamoyl)piperidine-4-sulfonamide, potassium salt (Example 186) using 4-isocyanato-1,2,3,5,6,7-hexahydro-s-indacene (Intermediate A1) and 1-ethylazepane-4-sulfonamide (Intermediate P144) to afford the title compound (17 mg, 27%) as a white solid.

$^1$H NMR (methanol-$d_4$) δ 6.89 (s, 1H), 3.72 (dp, 1H), 3.37-3.18 (m, 2H), 3.13-2.91 (m, 3H), 2.85 (dq, 8H), 2.41 (ddt, 1H), 2.24 (ddd, 2H), 2.03 (m, 6H), 1.92-1.70 (m, 2H), 1.21 (t, 3H).

LCMS: m/z 406 (M+H)$^+$ (ES$^+$); 404 (M−H)$^−$ (ES$^−$).

Example 195: N-((1,2,3,5,6,7-hexahydro-s-indacen-4-yl)carbamoyl)-1-methylazepane-4-sulfonamide, Potassium Salt

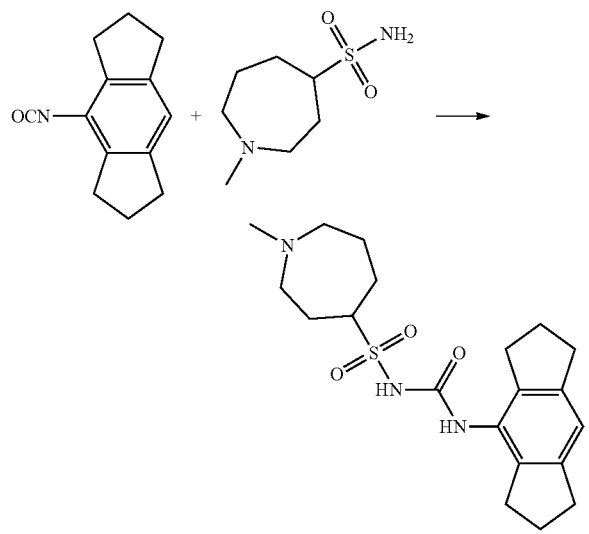

Prepared as described for 1-ethyl-N-((7-fluoro-5-(2-methoxypyridin-4-yl)-2,3-dihydro-1H-inden-4-yl)carbamoyl)piperidine-4-sulfonamide, potassium salt (Example 186) using 4-isocyanato-1,2,3,5,6,7-hexahydro-s-indacene (Intermediate A1) and 1-methylazepane-4-sulfonamide (prepared like Intermediate P144) to afford the title compound (11 mg, 9%) as a white solid.

$^1$H NMR (methanol-$d_4$) δ 6.89 (s, 1H), 3.83-3.66 (m, 1H), 3.14-2.95 (m, 4H), 2.83 (m, 8H), 2.66 (s, 3H), 2.47-2.19 (m, 2H), 2.18-1.93 (m, 6H), 1.83 (dd, 2H).

LCMS: m/z 392 (M+H)$^+$ (ES$^+$).

Examples—Biological Studies

NLRP3 and Pyroptosis

It is well established that the activation of NLRP3 leads to cell pyroptosis and this feature plays an important part in the manifestation of clinical disease (Yan-gang Liu et al., Cell Death & Disease, 2017, 8(2), e2579; Alexander Wree et al., Hepatology, 2014, 59(3), 898-910; Alex Baldwin et al., Journal of Medicinal Chemistry, 2016, 59(5), 1691-1710; Ema Ozaki et al., Journal of Inflammation Research, 2015, 8, 15-27; Zhen Xie & Gang Zhao, Neuroimmunology Neuroinflammation, 2014, 1(2), 60-65; Mattia Cocco et al., Journal of Medicinal Chemistry, 2014, 57(24), 10366-10382; T. Satoh et al., Cell Death & Disease, 2013, 4, e644). Therefore, it is anticipated that inhibitors of NLRP3 will block pyroptosis, as well as the release of pro-inflammatory cytokines (e.g. IL-1β) from the cell.

THP-1 Cells: Culture and Preparation

THP-1 cells (ATCC #TIB-202) were grown in RPMI containing L-glutamine (Gibco #11835) supplemented with 1 mM sodium pyruvate (Sigma #S8636) and penicillin (100 units/ml)/streptomycin (0.1 mg/ml) (Sigma #P4333) in 10% Fetal Bovine Serum (FBS) (Sigma #F0804). The cells were routinely passaged and grown to confluency (~$10^6$ cells/ml). On the day of the experiment, THP-1 cells were harvested and resuspended into RPMI medium (without FBS). The cells were then counted and viability (>90%) checked by Trypan blue (Sigma #T8154). Appropriate dilutions were made to give a concentration of 625,000 cells/ml. To this diluted cell solution was added LPS (Sigma #L4524) to give a 1 g/ml Final Assay Concentration (FAC). 40 μl of the final preparation was aliquoted into each well of a 96-well plate. The plate thus prepared was used for compound screening.

THP-1 Cells Pyroptosis Assay

The following method step-by-step assay was followed for compound screening.

1. Seed THP-1 cells (25,000 cells/well) containing 1.0 μg/ml LPS in 40 μl of RPMI medium (without FBS) in 96-well, black walled, clear bottom cell culture plates coated with poly-D-lysine (VWR #734-0317)
2. Add 51 compound (8 points half-log dilution, with 10 μM top dose) or vehicle (DMSO 0.1% FAC) to the appropriate wells
3. Incubate for 3 hrs at 37° C. and 5% $CO_2$
4. Add 5 μl nigericin (Sigma #N7143) (FAC 5 μM) to all wells
5. Incubate for 1 hr at 37° C. and 5% $CO_2$
6. At the end of the incubation period, spin plates at 300×g for 3 mins and remove supernatant
7. Then add 50 μl of resazurin (Sigma #R7017) (FAC 100 μM resazurin in RPMI medium without FBS) and incubate plates for a further 1-2 hrs at 37° C. and 5% $CO_2$
8. Plates were read in an Envision reader at Ex 560 nm and Em 590 nm
9. $IC_{50}$ data is fitted to a non-linear regression equation (log inhibitor vs response-variable slope 4-parameters)

96-Well Plate Map

| | 1 | 2 | 3 | 4 | 5 | 6 | 7 | 8 | 9 | 10 | 11 | 12 |
|---|---|---|---|---|---|---|---|---|---|---|---|---|
| A | High | Comp 1 | Comp 2 | Comp 3 | Comp 4 | Comp 5 | Comp 6 | Comp 7 | Comp 8 | Comp 9 | Comp 10 | Low |
| B | High | Comp 1 | Comp 2 | Comp 3 | Comp 4 | Comp 5 | Comp 6 | Comp 7 | Comp 8 | Comp 9 | Comp 10 | Low |
| C | High | Comp 1 | Comp 2 | Comp 3 | Comp 4 | Comp 5 | Comp 6 | Comp 7 | Comp 8 | Comp 9 | Comp 10 | Low |
| D | High | Comp 1 | Comp 2 | Comp 3 | Comp 4 | Comp 5 | Comp 6 | Comp 7 | Comp 8 | Comp 9 | Comp 10 | Low |
| E | High | Comp 1 | Comp 2 | Comp 3 | Comp 4 | Comp 5 | Comp 6 | Comp 7 | Comp 8 | Comp 9 | Comp 10 | Low |
| F | High | Comp 1 | Comp 2 | Comp 3 | Comp 4 | Comp 5 | Comp 6 | Comp 7 | Comp 8 | Comp 9 | Comp 10 | Low |
| G | High | Comp 1 | Comp 2 | Comp 3 | Comp 4 | Comp 5 | Comp 6 | Comp 7 | Comp 8 | Comp 9 | Comp 10 | Low |
| H | High | Comp 1 | Comp 2 | Comp 3 | Comp 4 | Comp 5 | Comp 6 | Comp 7 | Comp 8 | Comp 9 | Comp 10 | Low |

High  MCC950 (10 uM)  
Low  Drug free control  
Compound 8-point half-log dilution The results of the pyroptosis assay performed are summarised in Table 1 below as THP $IC_{50}$.

Human Whole Blood IL1β Release Assay

For systemic delivery, the ability to inhibit NLRP3 when the compounds are present within the bloodstream is of great importance. For this reason, the NLRP3 inhibitory activity of a number of compounds in human whole blood was investigated in accordance with the following protocol.

Human whole blood in Li-heparin tubes was obtained from healthy donors from a volunteer donor panel.

1. Plate out 80 μl of whole blood containing 1 μg/ml of LPS in 96-well, clear bottom cell culture plate (Corning #3585)
2. Add 10 μl compound (8 points half-log dilution with 10 μM top dose) or vehicle (DMSO 0.1% FAC) to the appropriate wells
3. Incubate for 3 hrs at 37° C., 5% $CO_2$
4. Add lop nigericin (Sigma #N7143) (10 μM FAC) to all wells
5. Incubate for 1 hr at 37° C., 5% $CO_2$
6. At the end of the incubation period, spin plates at 300×g for 5 mins to pellet cells and remove 20 μl of supernatant and add to 96-well v-bottom plates for IL-1β analysis (note: these plates containing the supernatants can be stored at −80° C. to be analysed at a later date)
7. IL-1β was measured according to the manufacturer protocol (Perkin Elmer-AlphaLisa IL-1 Kit AL220F-5000)
8. $IC_{50}$ data is fitted to a non-linear regression equation (log inhibitor vs response-variable slope 4-parameters)

The results of the human whole blood assay are summarised in Table 1 below as HWB $IC_{50}$.

TABLE 1

NLRP3 inhibitory activity (≤1 μM = '+++', ≤10 μM = '++', >10 μM = '+', not determined = 'ND').

| Example No | THP $IC_{50}$ | HWB $IC_{50}$ |
|---|---|---|
| 1 | ++ | ++ |
| 2 | ++ | ++ |
| 3 | ++ | ++ |
| 4 | ++ | ++ |
| 5 | +++ | ++ |
| 6 | +++ | +++ |
| 7 | +++ | ++ |
| 8 | ++ | +++ |
| 9 | +++ | +++ |
| 10 | ++ | ND |
| 11 | ++ | ND |
| 12 | ++ | ND |
| 13 | +++ | + |
| 14 | ++ | ND |
| 15 | ++ | ND |
| 16 | ++ | ++ |
| 17 | ++ | ND |
| 18 | +++ | +++ |
| 19 | ++ | ND |
| 20 | ++ | ND |
| 21 | ++ | ND |
| 22 | ++ | ND |
| 23 | ++ | ND |
| 24 | +++ | +++ |
| 25 | ++ | ND |
| 26 | ++ | ND |
| 27 | ++ | ND |
| 28 | ++ | ND |
| 29 | ++ | ND |
| 30 | ++ | ND |
| 31 | +++ | +++ |
| 32 | ++ | ++ |
| 33 | ++ | ND |
| 34 | +++ | ++ |
| 35 | +++ | + |
| 36 | ++ | ND |
| 37 | +++ | +++ |
| 38 | ++ | ND |
| 39 | +++ | ++ |
| 40 | ++ | ND |
| 41 | +++ | +++ |
| 42 | ++ | ND |
| 43 | ++ | ND |
| 44 | ++ | ND |
| 45 | +++ | +++ |
| 46 | +++ | +++ |
| 47 | ++ | ND |
| 48 | ++ | ND |
| 49 | +++ | +++ |
| 50 | ++ | ND |
| 51 | ++ | ND |
| 52 | ++ | ND |
| 53 | +++ | +++ |
| 54 | ++ | ND |
| 55 | ++ | ND |
| 56 | ++ | ND |
| 57 | ++ | ND |
| 58 | ++ | ND |
| 59 | ++ | ND |
| 60 | ++ | ND |
| 61 | ++ | ND |
| 62 | ++ | ND |
| 63 | ++ | ND |
| 64 | ++ | ND |
| 65 | +++ | +++ |
| 66 | +++ | ND |
| 67 | ++ | ND |
| 68 | +++ | ND |
| 69 | +++ | ND |
| 70 | +++ | +++ |
| 71 | +++ | + |
| 72 | +++ | ++ |
| 73 | ++ | ND |
| 74 | ++ | ND |
| 75 | +++ | +++ |
| 76 | +++ | +++ |
| 77 | ++ | ND |

TABLE 1-continued

NLRP3 inhibitory activity (≤1 μM = '+++', ≤10 μM = '++', >10 μM = '+', not determined = 'ND').

| Example No | THP $IC_{50}$ | HWB $IC_{50}$ |
|---|---|---|
| 78 | ++ | ND |
| 79 | ++ | ND |
| 80 | ++ | ND |
| 81 | ++ | ND |
| 82 | ++ | ND |
| 83 | ++ | ND |
| 84 | +++ | ND |
| 85 | +++ | ND |
| 86 | ++ | ND |
| 87 | ++ | ND |
| 88 | +++ | ND |
| 89 | ++ | ND |
| 90 | +++ | +++ |
| 91 | ++ | ND |
| 92 | +++ | ++ |
| 93 | +++ | +++ |
| 94 | +++ | +++ |
| 95 | +++ | ++ |
| 96 | +++ | ++ |
| 97 | +++ | +++ |
| 98 | +++ | +++ |
| 99 | +++ | +++ |
| 100 | ++ | ND |
| 101 | +++ | +++ |
| 102 | ++ | ND |
| 103 | +++ | ++ |
| 104 | +++ | ND |
| 105 | +++ | + |
| 106 | ++ | ND |
| 107 | +++ | ND |
| 108 | +++ | +++ |
| 109 | +++ | +++ |
| 110 | ++ | ND |
| 111 | ++ | ND |
| 112 | ++ | ND |
| 113 | +++ | +++ |
| 114 | ++ | ND |
| 115 | ++ | ND |
| 116 | ++ | ND |
| 117 | +++ | ND |
| 118 | +++ | ND |
| 119 | ++ | ND |
| 120 | ++ | ND |
| 121 | +++ | +++ |
| 122 | +++ | +++ |
| 123 | ++ | ND |
| 124 | +++ | ++ |
| 125 | +++ | ++ |
| 126 | ++ | ++ |
| 127 | ++ | ND |
| 128 | ++ | ND |
| 129 | ++ | ND |
| 130 | +++ | +++ |
| 131 | +++ | ++ |
| 132 | +++ | +++ |
| 133 | +++ | +++ |
| 134 | +++ | ++ |
| 135 | +++ | ++ |
| 136 | ++ | ND |
| 137 | +++ | ++ |
| 138 | +++ | +++ |
| 139 | ++ | ND |
| 140 | +++ | ND |
| 141 | +++ | ++ |
| 142 | +++ | ND |
| 143 | ++ | ND |
| 144 | +++ | ++ |
| 145 | +++ | ++ |
| 146 | ++ | ND |
| 147 | ++ | ND |
| 148 | ++ | ND |
| 149 | ++ | ND |
| 150 | +++ | ND |
| 151 | +++ | ND |
| 152 | +++ | +++ |
| 153 | +++ | +++ |
| 154 | +++ | +++ |
| 155 | +++ | +++ |
| 156 | +++ | +++ |
| 157 | ++ | ND |
| 158 | +++ | +++ |
| 159 | +++ | +++ |
| 160 | +++ | +++ |
| 161 | ++ | ND |
| 162 | +++ | +++ |
| 163 | +++ | +++ |
| 164 | +++ | +++ |
| 165 | ++ | ND |
| 166 | ++ | ND |
| 167 | +++ | +++ |
| 168 | +++ | ND |
| 169 | ++ | ND |
| 170 | ++ | ++ |
| 171 | +++ | ND |
| 172 | +++ | +++ |
| 173 | +++ | +++ |
| 174 | +++ | +++ |
| 175 | +++ | ND |
| 176 | ++ | ND |
| 177 | ++ | ND |
| 178 | +++ | +++ |
| 179 | +++ | ND |
| 180 | ++ | ND |
| 181 | +++ | +++ |
| 182 | ++ | ND |
| 183 | +++ | ND |
| 184 | ++ | ND |
| 185 | +++ | ++ |
| 186 | ++ | ND |
| 187 | ++ | ND |
| 188 | ++ | ND |
| 189 | +++ | ++ |
| 190 | ++ | ND |
| 191 | ++ | ++ |
| 192 | ++ | ++ |
| 193 | +++ | +++ |
| 194 | +++ | +++ |
| 195 | +++ | ND |

PK Protocol

Pharmacokinetic parameters were determined in male Sprague Dawley rats (Charles River, UK, 250-300 g; or Vital River Laboratory Animal Technology Co Ltd, Beijing, China, 7-9 weeks old). Animals were individually housed during the study and maintained under a 12 h light/dark cycle. Animals had free access to food and water except that orally dosed animals were food deprived overnight prior to the study.

For intravenous administration, compounds were formulated as a solution in water or DMSO:PBS [10:90] in 2 mL/kg dosing volume and administered via tail vein. For oral administration, compounds were formulated as a solution in water or DMSO:water [10:90] in 5 mL/kg dosing volume and administered orally.

Serial blood samples (about 120-300 μL) were taken from each animal at each of 8 time-points post dose (0.083, 0.25, 0.5, 1, 2, 4, 8 and 24 h). Samples were held on ice for no longer than 30 minutes before centrifugation (10,000 rpm (8,385 g) for 3 minutes; or 5,696 rpm (3,000 g) for 15 minutes) for plasma generation. Plasma was frozen on dry ice prior to bioanalysis. PK parameters were generated from LC-MS/MS data using Dotmatics or Phoenix WinNonlin 6.3 software.

TABLE 2

| | | PK data (intravenous administration) | | | |
|---|---|---|---|---|---|
| Example No | Dose (mg/kg) | AUC (ng·hr/mL) | $T_{1/2}$ (hr) | $V_{dss}$ (L/kg) | Cl (mL/min·kg) |
| 1 | 1 | 1949.4 | 1.2 | 0.58 | 8.5 |
| 6 | 1 | 2344.0 | 2.7 | 0.61 | 7.2 |
| 9 | 1 | 2669.0 | 3.9 | 0.63 | 6.5 |
| 18 | 1 | 1531.6 | 0.9 | 0.42 | 10.9 |
| 31 | 1 | 2753.6 | 4.5 | 0.47 | 6.1 |
| 37 | 1.46 | 2247.9 | 2.1 | 0.59 | 10.8 |
| 41 | 1 | 1853.9 | 2.9 | 0.78 | 9.1 |
| 45 | 0.66 | 703.1 | 3.3 | 2.06 | 15.6 |
| 46 | 1 | 2077.2 | 1.2 | 0.45 | 8.2 |
| 70 | 1.86 | 2552.9 | 1.7 | 0.53 | 12.1 |
| 76 | 1 | 2647.5 | 1.0 | 0.25 | 6.3 |
| 94 | 2.09 | 1407.8 | 1.1 | 1.62 | 25.2 |
| 99 | 1 | 1670.9 | 0.6 | 0.42 | 10.0 |
| 109 | 1 | 1732.0 | 1.3 | 0.64 | 9.6 |
| 153 | 1 | 510.7 | 1.1 | 1.21 | 32.6 |
| 156 | 1 | 1518.0 | 1.0 | 0.31 | 11.0 |

TABLE 3

| | | | PK data (oral administration) | | | | |
|---|---|---|---|---|---|---|---|
| Example No | Dose (mg/kg) | $C_{max}$ (ng/mL) | AUC (ng·hr/mL) | $T_{max}$ (hr) | $T_{1/2}$ (hr) | Cl (mL/min·kg) | Bioavailability |
| 6 | 3 | 1768.6 | 5395.0 | 0.5 | 2.7 | 9.3 | 76.7 |
| 46 | 3 | 1330.0 | 3513.7 | 0.67 | 1.4 | 14.6 | 56.4 |

As is evident from the results presented in Table 1, surprisingly in spite of the structural differences versus the prior art compounds, the compounds of the invention show high levels of NLRP3 inhibitory activity in the pyroptosis assay and in particular in the human whole blood assay.

As is evident from the results presented in Tables 2 and 3, the compounds of the invention show advantageous pharmacokinetic properties, for example half-life $T_{1/2}$, area under the curve AUC, clearance Cl and/or bioavailability, compared to the prior art compounds.

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. A compound of formula (I):

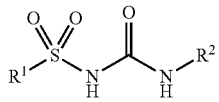

Formula (I)

or a pharmaceutically acceptable salt, solvate or prodrug thereof, wherein:

Q is selected from O or S;

$R^1$ is a non-aromatic heterocyclic group comprising at least one ring nitrogen atom, wherein $R^1$ is attached to the sulfur atom of the sulfonylurea group by a ring carbon atom, and wherein $R^1$ may optionally be substituted; and $R^2$ is a cyclic group substituted at the α-position, wherein $R^2$ may optionally be further substituted.

2. The compound or pharmaceutically acceptable salt, solvate or prodrug as claimed in claim 1, wherein $R^1$ is a monocyclic or bicyclic non-aromatic heterocyclic group, wherein $R^1$ may optionally be substituted.

3. The compound or pharmaceutically acceptable salt, solvate or prodrug as claimed in claim 2, wherein $R^1$ is a 4-, 5-, 6- or 7-membered monocyclic non-aromatic heterocyclic group or a 7-, 8-, 9- or 10-membered bicyclic non-aromatic heterocyclic group, wherein $R^1$ may optionally be substituted.

4. The compound or pharmaceutically acceptable salt, solvate or prodrug as claimed in claim 1, wherein the non-aromatic heterocyclic group of $R^1$ is fully saturated.

5. The compound or pharmaceutically acceptable salt, solvate or prodrug as claimed in claim 1, wherein $R^1$ comprises one, two or three ring nitrogen, oxygen or sulfur atoms.

6. The compound or pharmaceutically acceptable salt, solvate or prodrug as claimed in claim 5, wherein $R^1$ comprises one or two ring nitrogen or oxygen atoms.

7. The compound or pharmaceutically acceptable salt, solvate or prodrug as claimed in claim 6, wherein $R^1$ comprises one or two ring nitrogen atoms.

8. The compound or pharmaceutically acceptable salt, solvate or prodrug as claimed in claim 1, wherein $R^1$ is selected from:

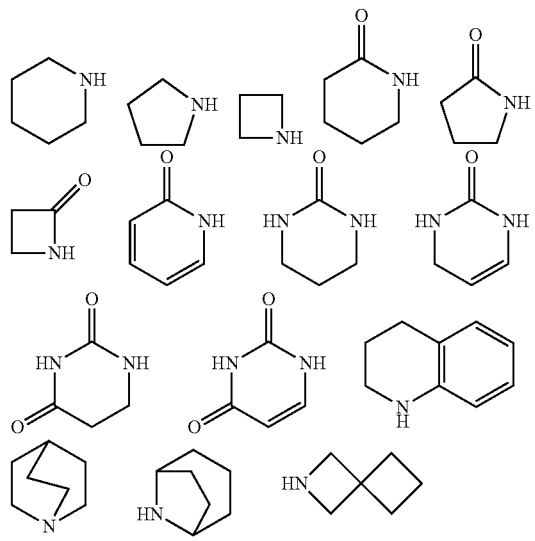

wherein $R^1$ is attached to the sulfur atom of the sulfonylurea group by a non-aromatic ring carbon atom, and wherein $R^1$ may optionally be substituted or further substituted.

9. The compound or pharmaceutically acceptable salt, solvate or prodrug as claimed in claim 1, wherein $R^1$ is substituted with one or more substituents independently selected from halo; —CN; —NO$_2$; —N$_3$; —R$^\beta$; —OH;

—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; —NR$^\beta$—R$^\alpha$—N(R$^\beta$)$_2$; a C$_3$-C$_7$ cycloalkyl group optionally substituted with one or more C$_1$-C$_3$ alkyl or C$_1$-C$_3$ haloalkyl groups; a C$_3$-C$_7$ cycloalkenyl group optionally substituted with one or more C$_1$-C$_3$ alkyl or C$_1$-C$_3$ haloalkyl groups; or a 3- to 7-membered non-aromatic heterocyclic group optionally substituted with one or more C$_1$-C$_6$ alkyl or C$_1$-C$_3$ haloalkyl groups; oxo (=O); or a C$_1$-C$_4$ alkylene bridge;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, and wherein any —R$^\beta$ may optionally be substituted with one or more C$_1$-C$_3$ alkyl, C$_1$-C$_3$ haloalkyl, C$_3$-C$_7$ cycloalkyl, —O(C$_1$-C$_3$ alkyl), halo, —CN, —C≡CH or oxo (=O) groups.

10. The compound or pharmaceutically acceptable salt, solvate or prodrug as claimed in claim 9, wherein R$^1$ is substituted on one or more ring nitrogen atoms with a substituent independently selected from halo; —CN; —NO$_2$; —N$_3$; —R$^\beta$; —OH; —OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; a C$_3$-C$_7$ cycloalkyl group optionally substituted with one or more C$_1$-C$_3$ alkyl or C$_1$-C$_3$ haloalkyl groups; a C$_3$-C$_7$ cycloalkenyl group optionally substituted with one or more C$_1$-C$_3$ alkyl or C$_1$-C$_3$ haloalkyl groups;

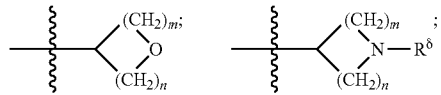

oxo (=O); or a C$_1$-C$_4$ alkylene bridge;

wherein each —R$^\alpha$— is independently selected from an alkylene, alkenylene or alkynylene group, wherein the alkylene, alkenylene or alkynylene group contains from 1 to 6 carbon atoms in its backbone, and wherein the alkylene, alkenylene or alkynylene group may optionally be substituted with one or more halo and/or —R$^\beta$ groups;

wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, and wherein any —R$^\beta$ may optionally be substituted with one or more C$_1$-C$_3$ alkyl, C$_1$-C$_3$ haloalkyl, C$_3$-C$_7$ cycloalkyl, —O(C$_1$-C$_3$ alkyl), halo, —CN, —C≡CH or oxo (=O) groups;

wherein each —R$^\delta$ is independently selected from a C$_1$-C$_6$ alkyl or C$_1$-C$_3$ haloalkyl group;

wherein each m is independently selected from 1, 2 or 3; and wherein each n is independently selected from 1, 2 or 3.

11. The compound or pharmaceutically acceptable salt, solvate or prodrug as claimed in claim 1, wherein R$^2$ is an aryl or a heteroaryl group, wherein the aryl or the heteroaryl group is substituted at the α-position, and wherein R$^2$ may optionally be further substituted.

12. The compound or pharmaceutically acceptable salt, solvate or prodrug as claimed in claim 11, wherein R$^2$ is an aryl or a heteroaryl group, wherein the aryl or the heteroaryl group is substituted at the α and α' positions, and wherein R$^2$ may optionally be further substituted.

13. The compound or pharmaceutically acceptable salt, solvate or prodrug as claimed in claim 12, wherein R$^2$ is a fused aryl or a fused heteroaryl group, wherein a first cycloalkyl, cycloalkenyl, non-aromatic heterocyclic, aryl or heteroaryl ring is fused to the aryl or heteroaryl group across the α,β positions and a second cycloalkyl, cycloalkenyl, non-aromatic heterocyclic, aryl or heteroaryl ring is fused to the aryl or heteroaryl group across the α',β' positions, and wherein R$^2$ may optionally be further substituted.

14. The compound or pharmaceutically acceptable salt, solvate or prodrug as claimed in claim 1, wherein R$^2$ is a cyclic group substituted at the α and α' positions, wherein R$^2$ may optionally be further substituted.

15. The compound or pharmaceutically acceptable salt, solvate or prodrug as claimed in claim 1, wherein Q is O.

16. The compound or pharmaceutically acceptable salt, solvate or prodrug as claimed in claim 1, which is (a) a compound selected from the group consisting of:

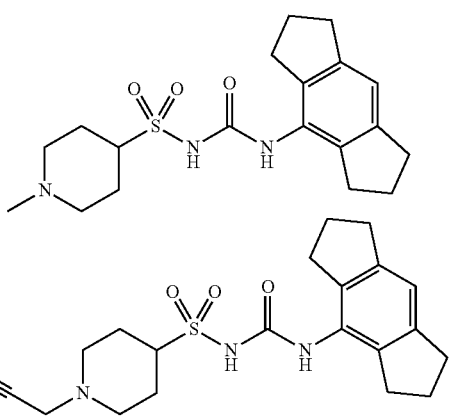

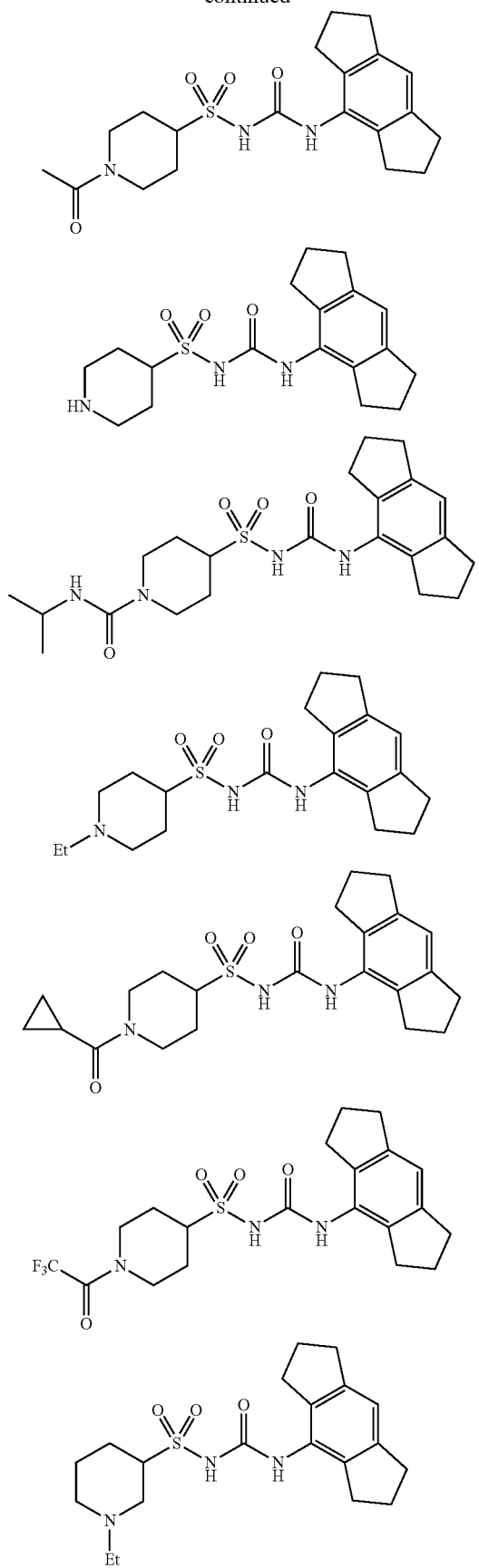
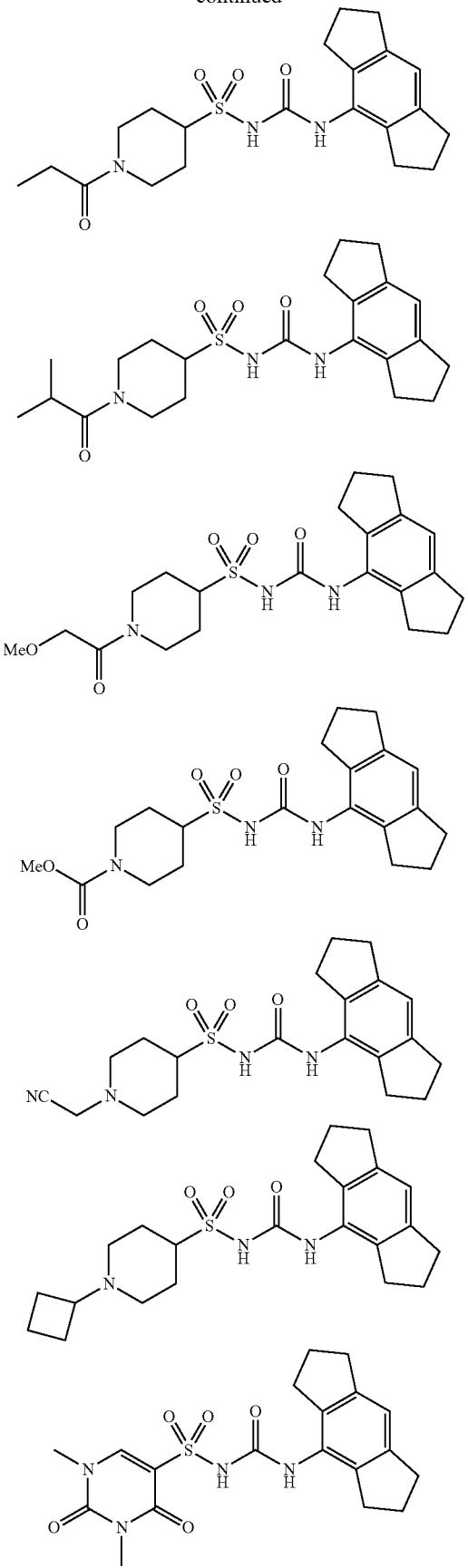

409
-continued
410
-continued
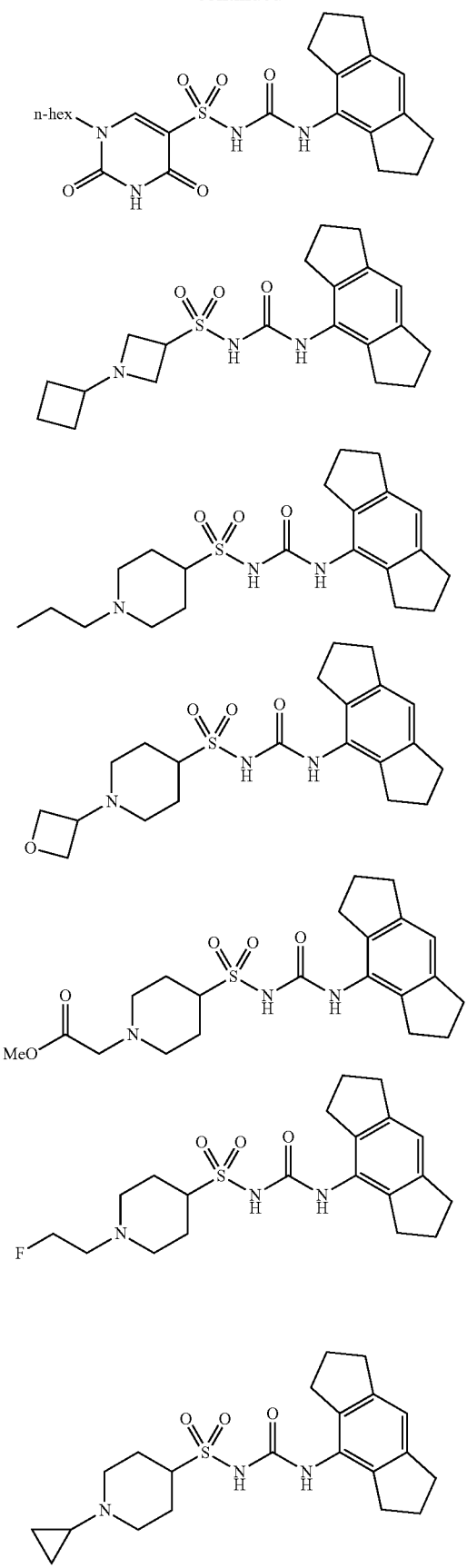
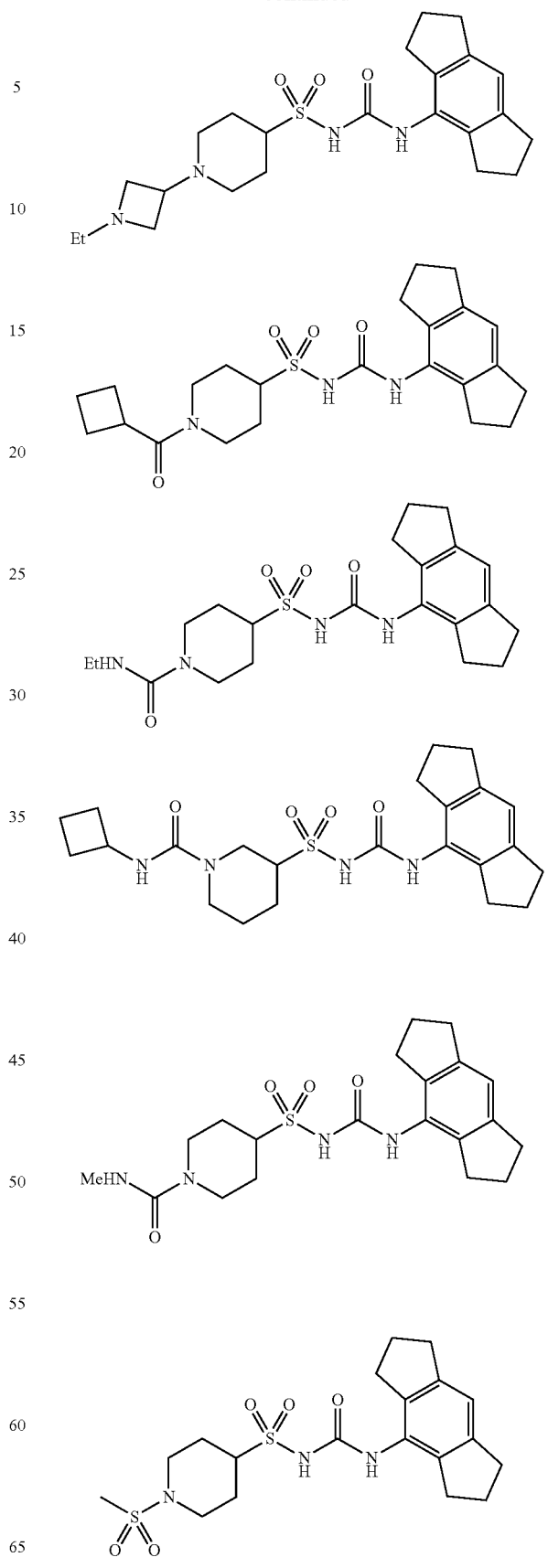

411
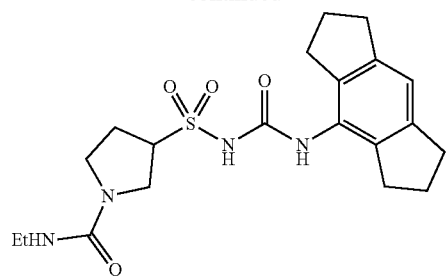
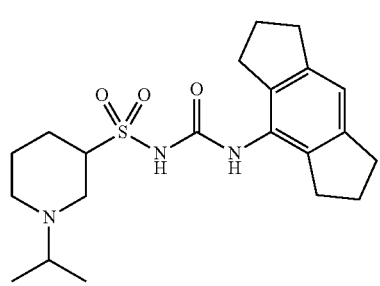
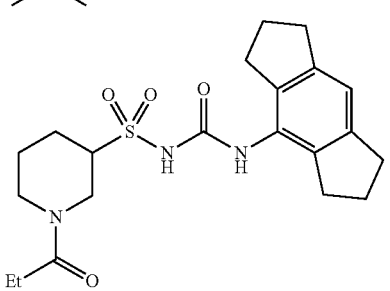
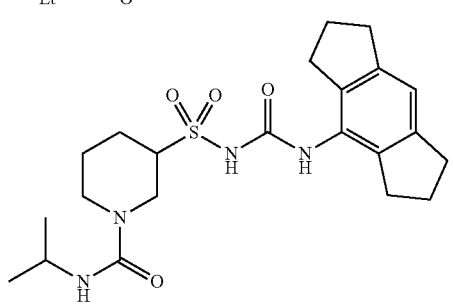
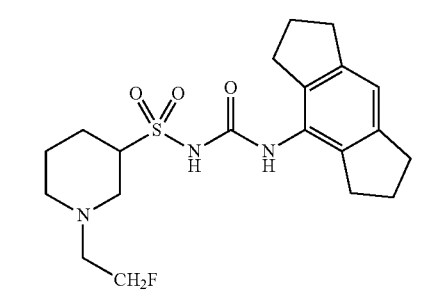
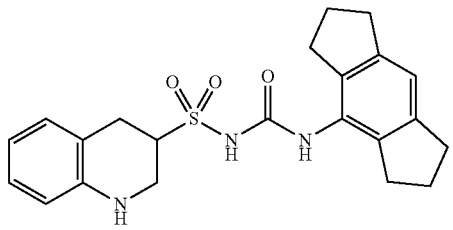
412
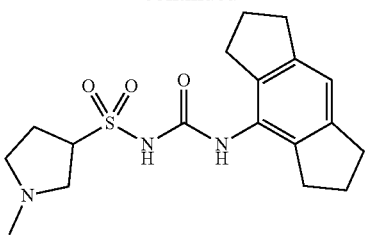
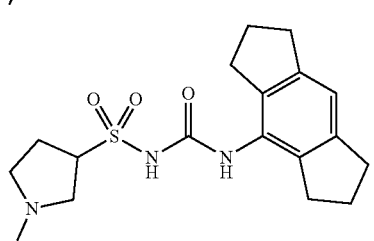
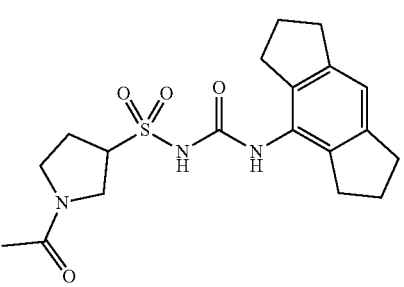
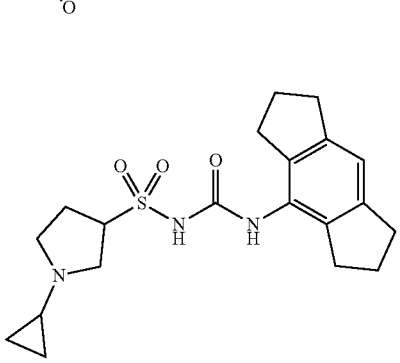
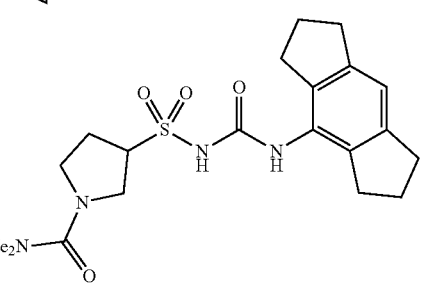
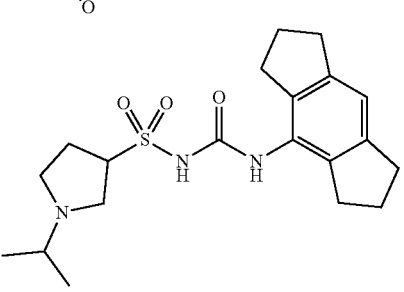

413
-continued
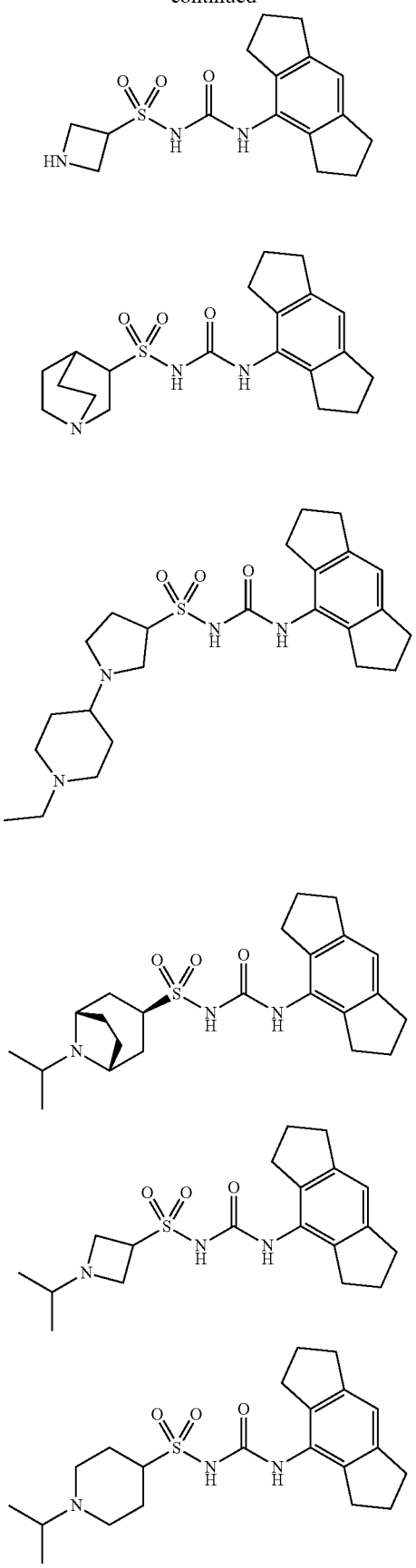
414
-continued
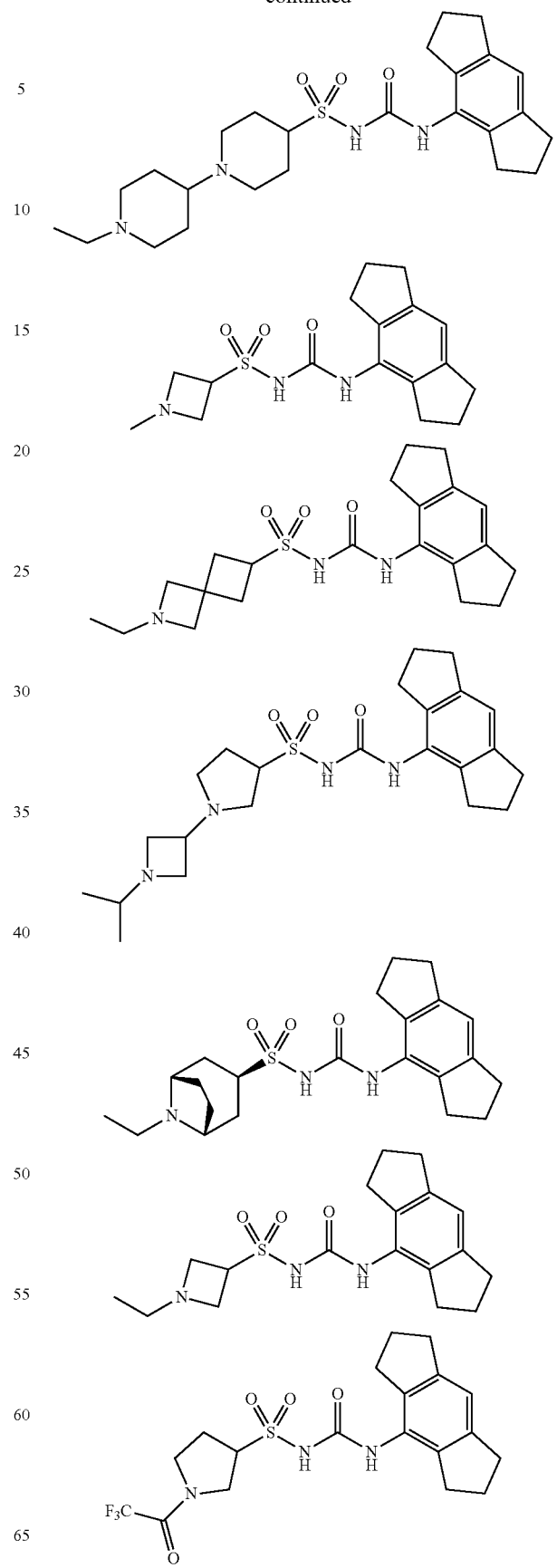

415
-continued
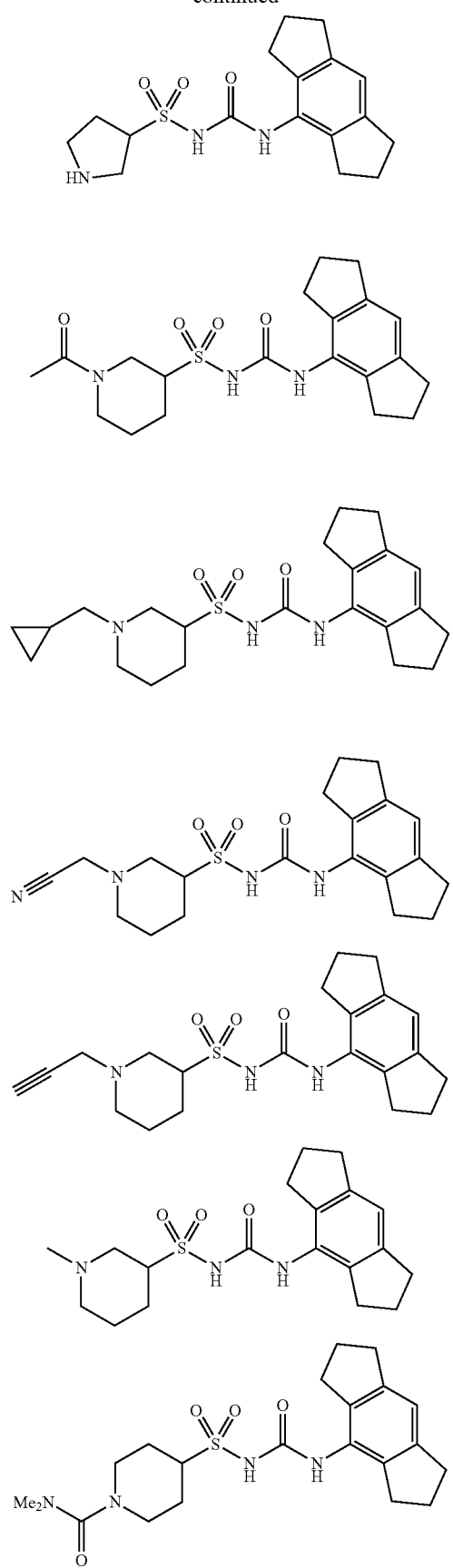
416
-continued
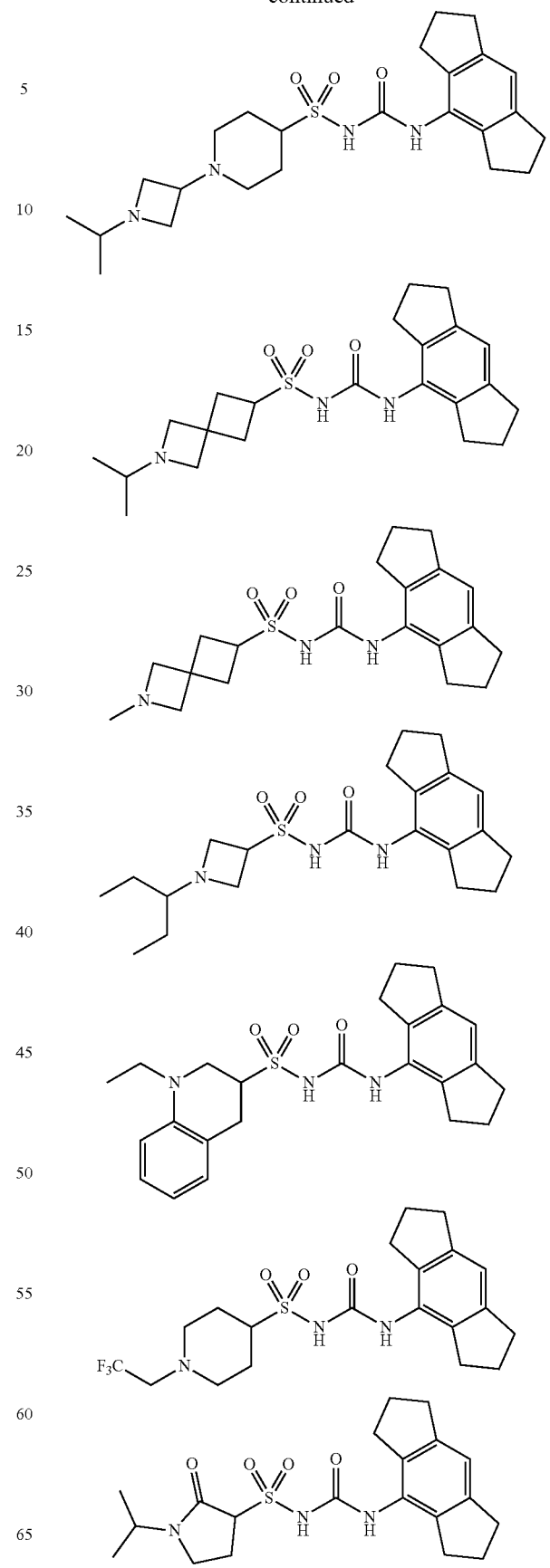

417
-continued
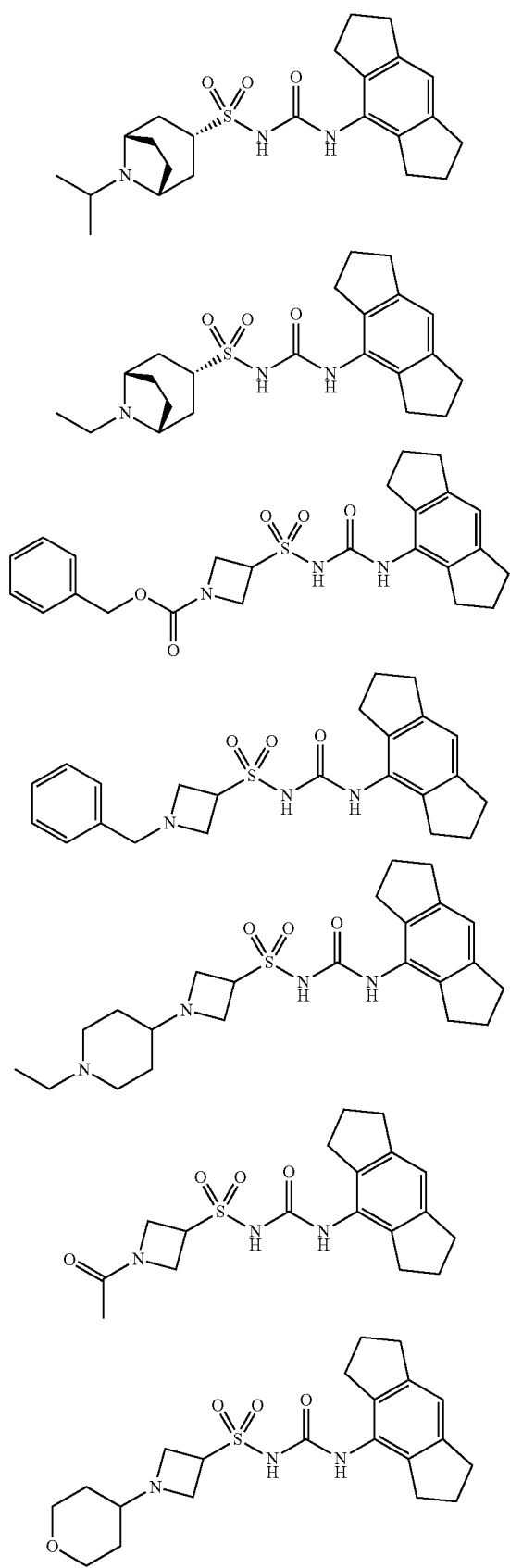
418
-continued
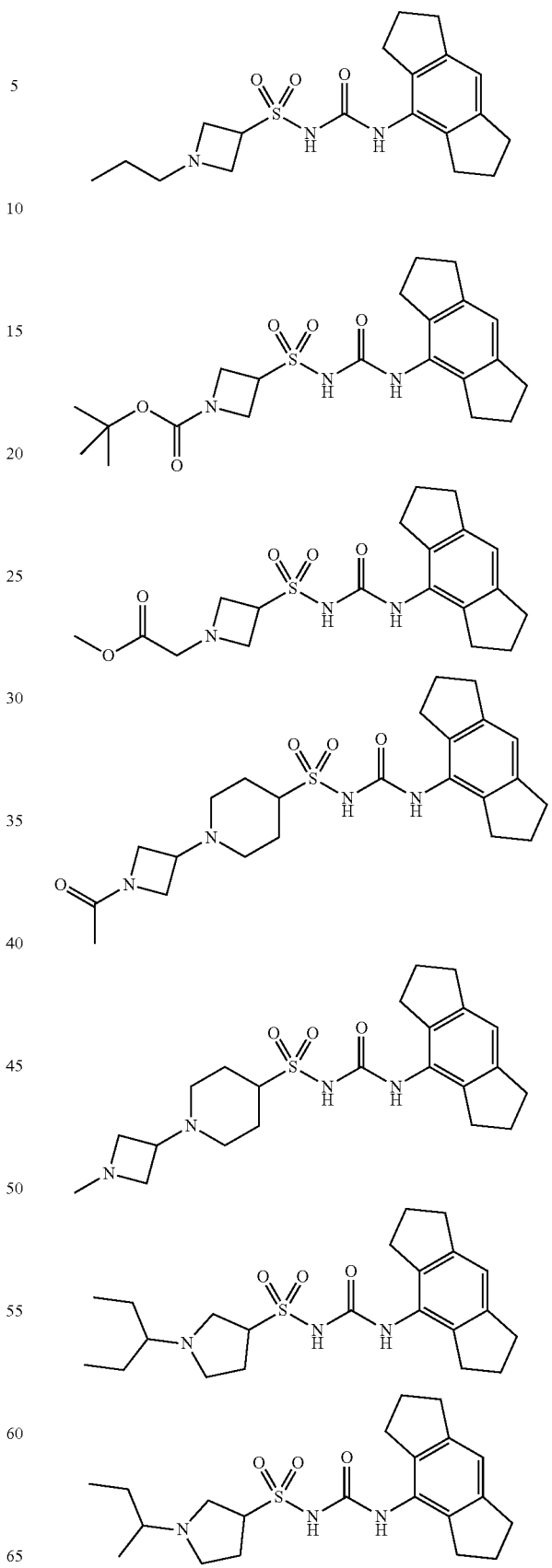

419
-continued
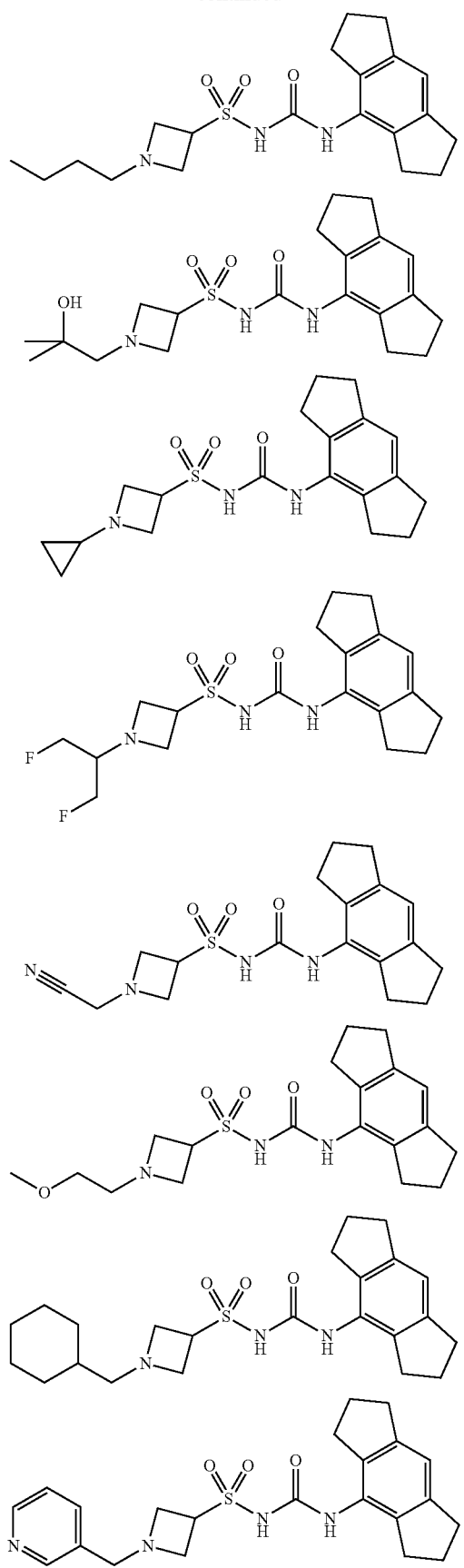
420
-continued
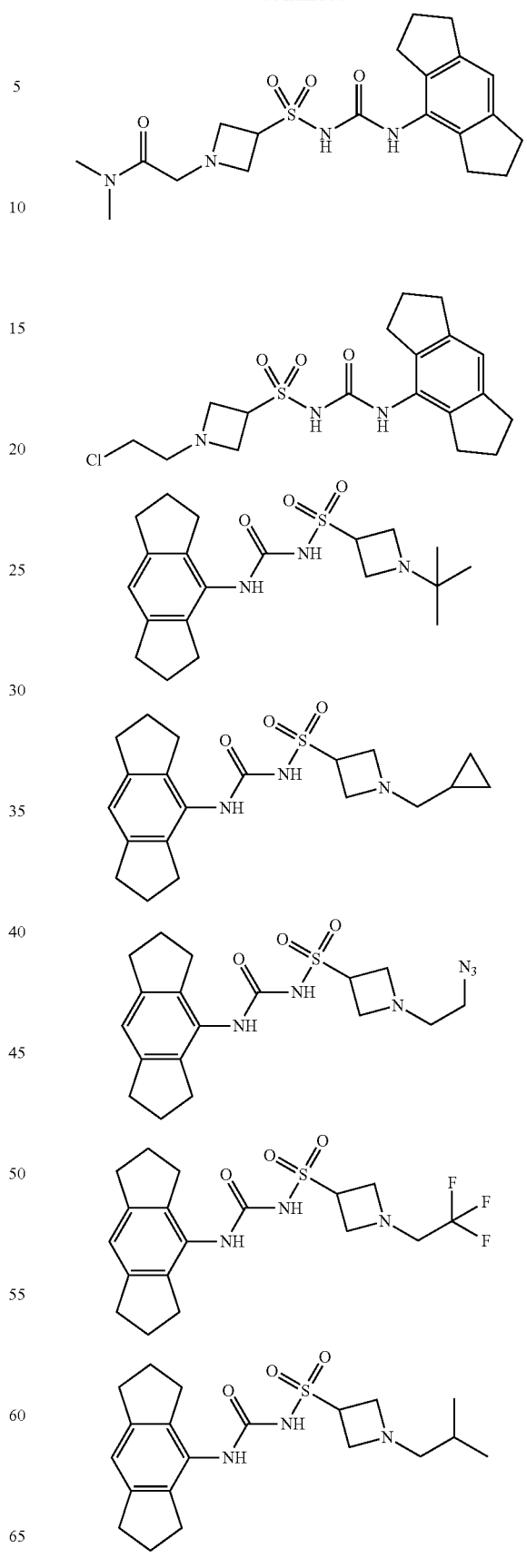

421
-continued
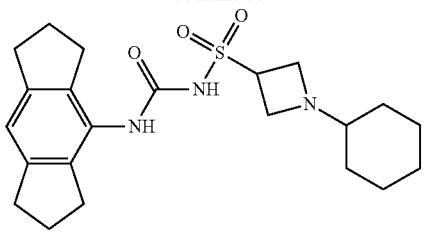
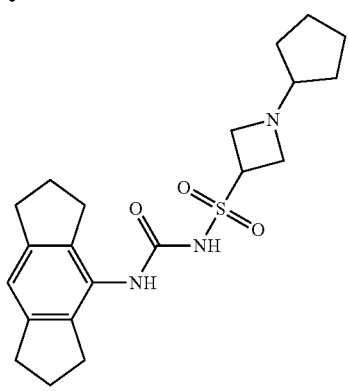
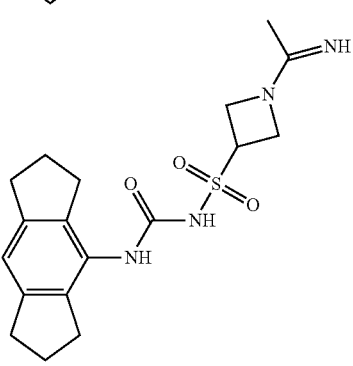
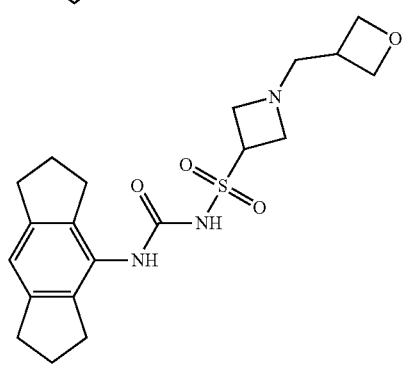
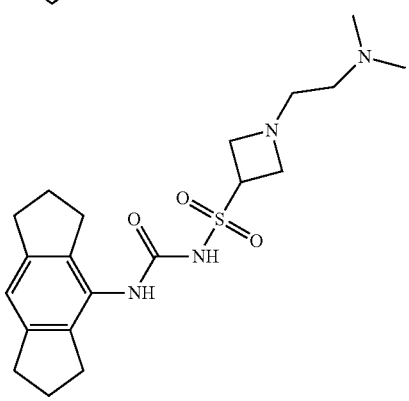
422
-continued
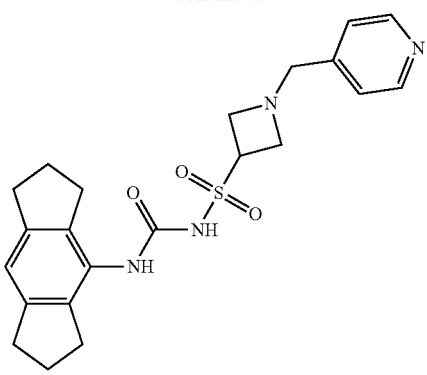
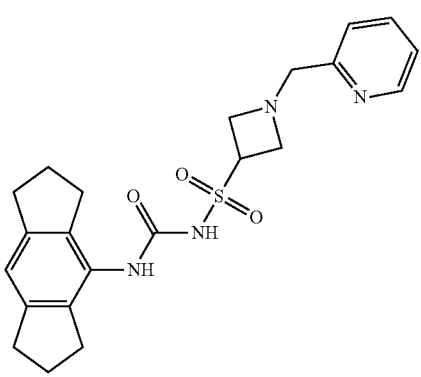
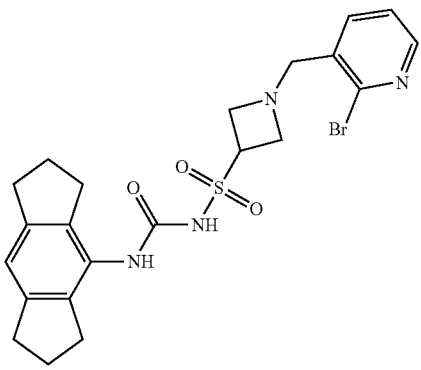
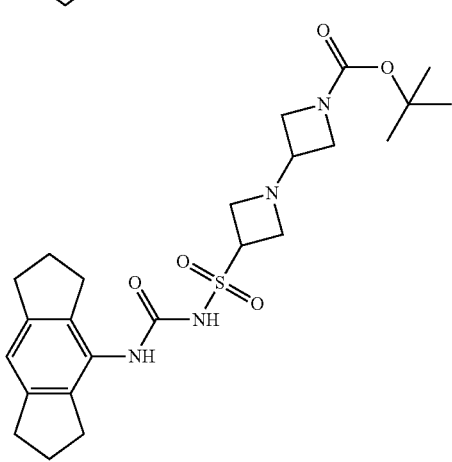

423
-continued
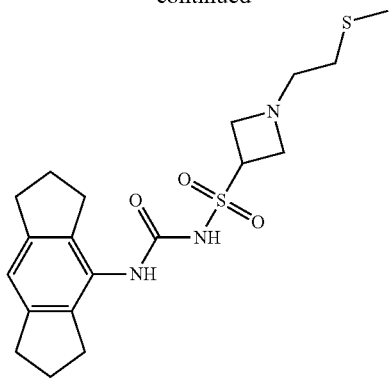
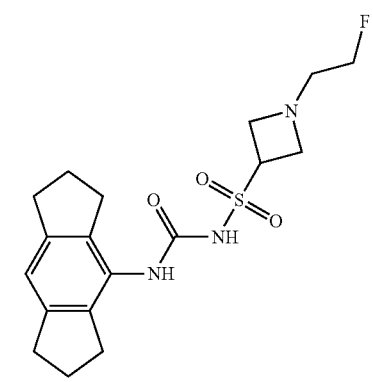
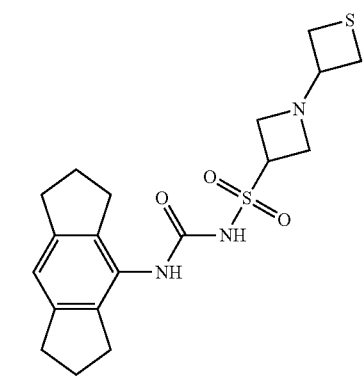
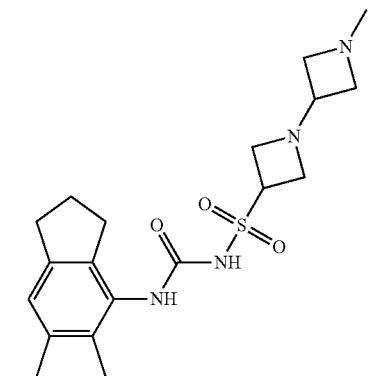
424
-continued
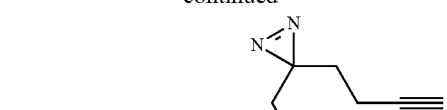
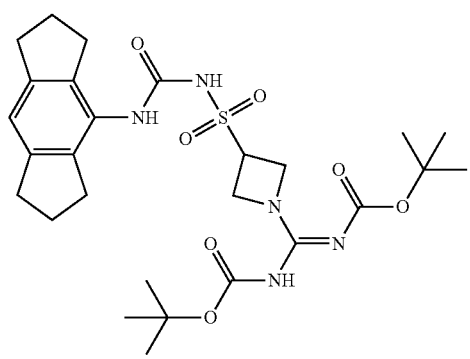
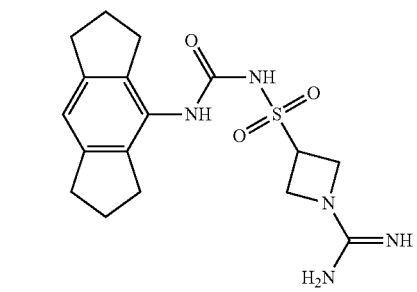
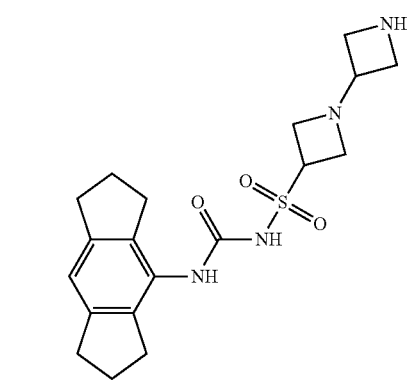

425
-continued
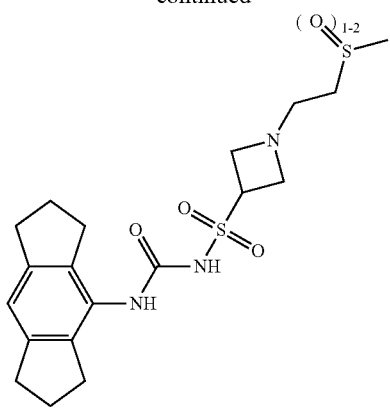
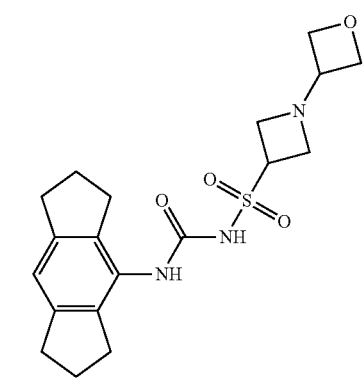
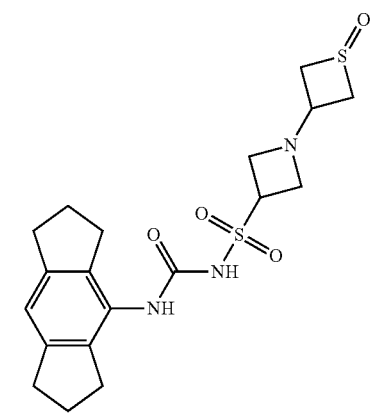
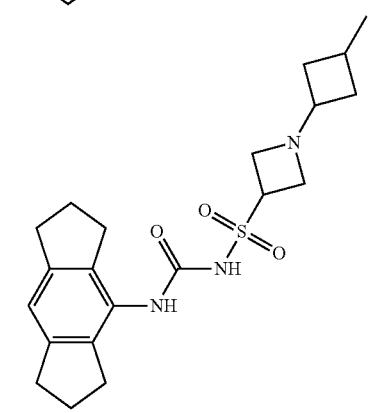
426
-continued
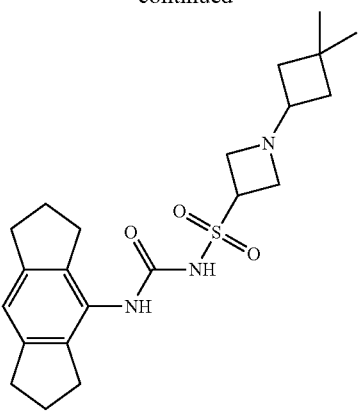
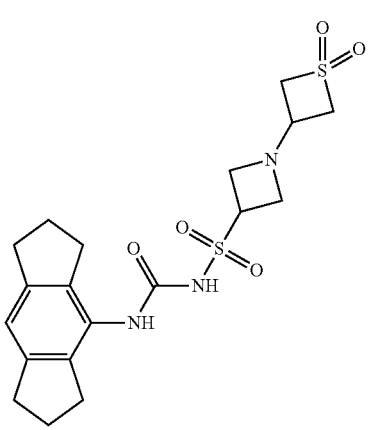
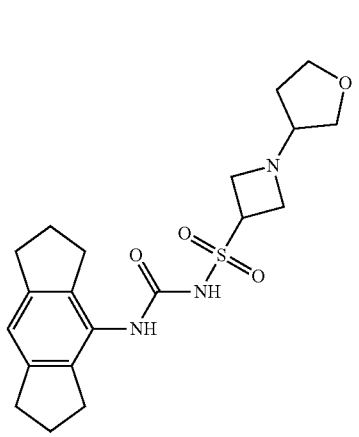
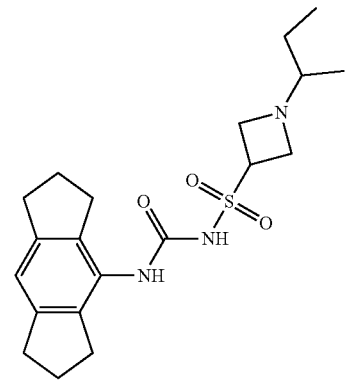

427
-continued
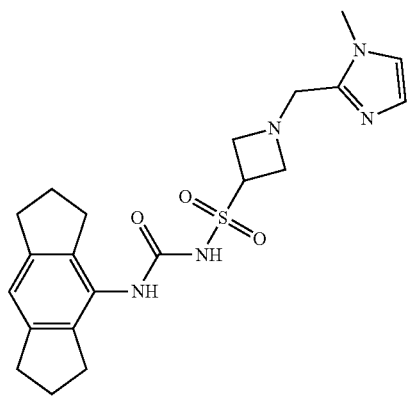
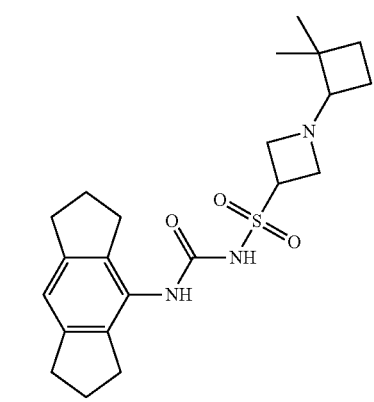
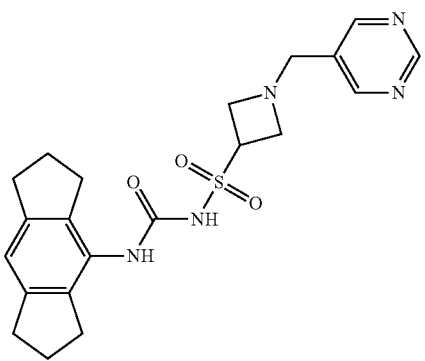
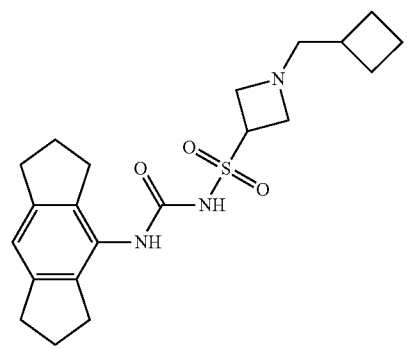
428
-continued
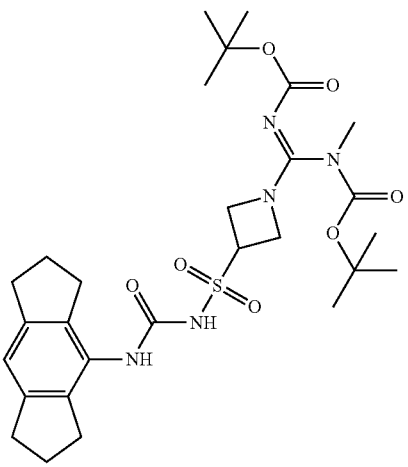
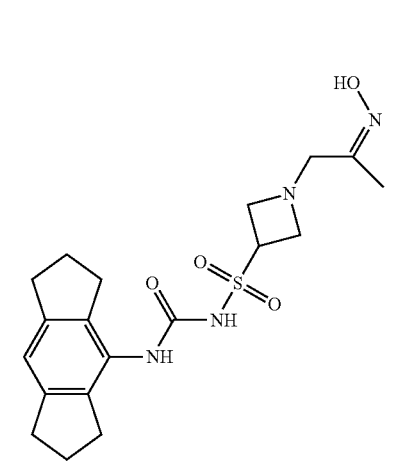
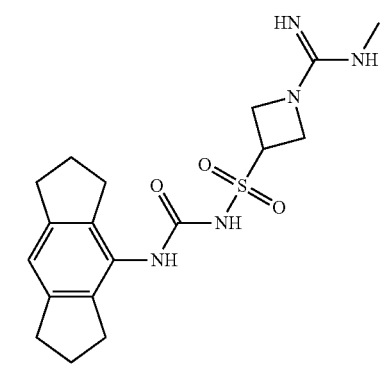
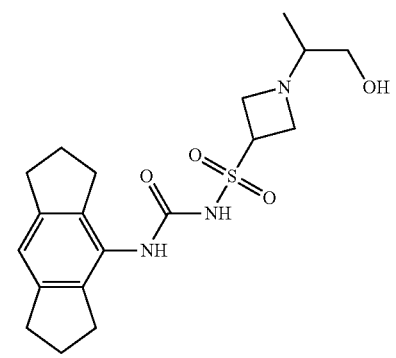

429
-continued
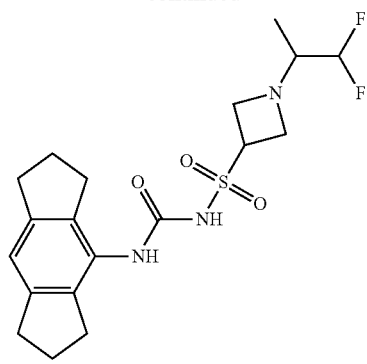
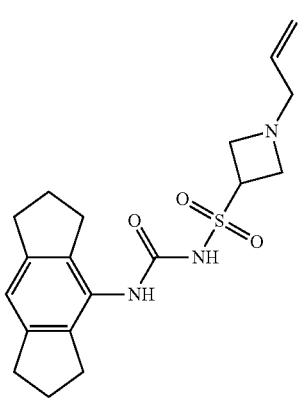
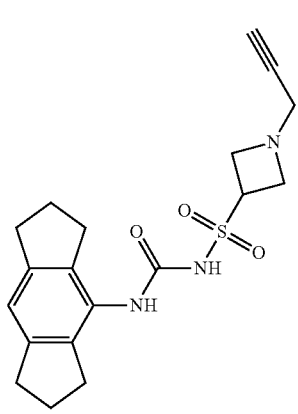
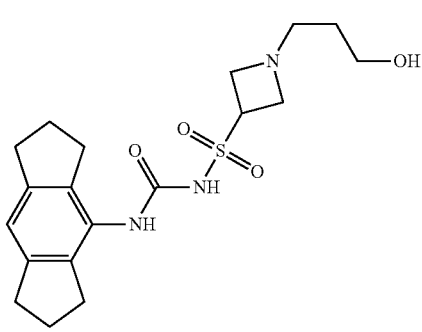
430
-continued
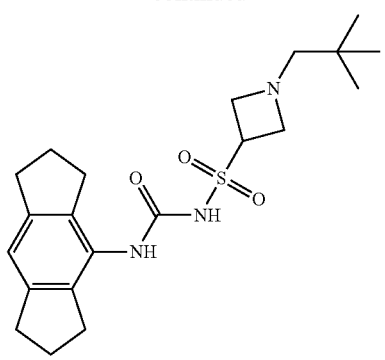
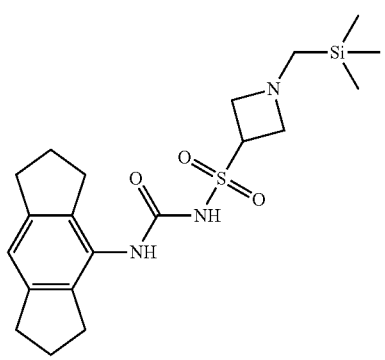
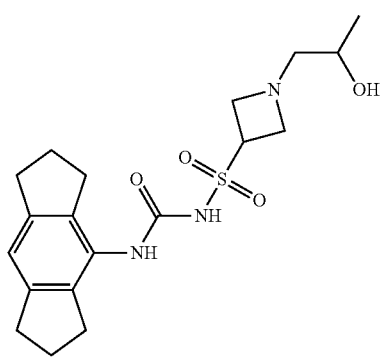
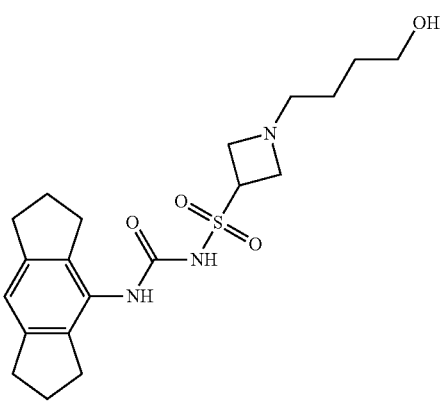

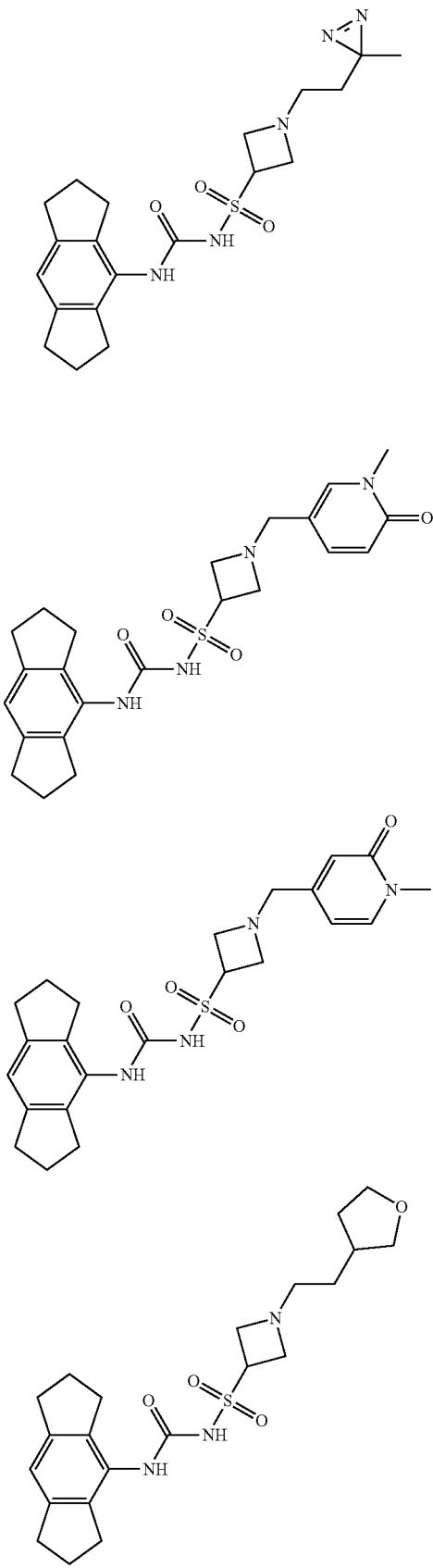
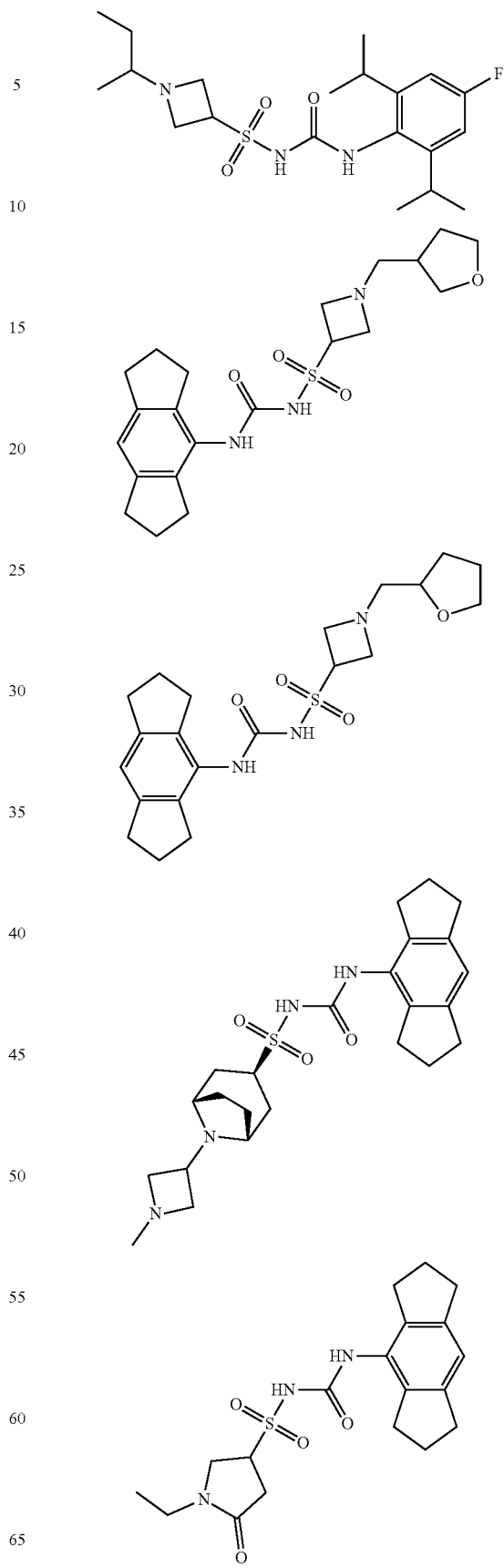

433 -continued 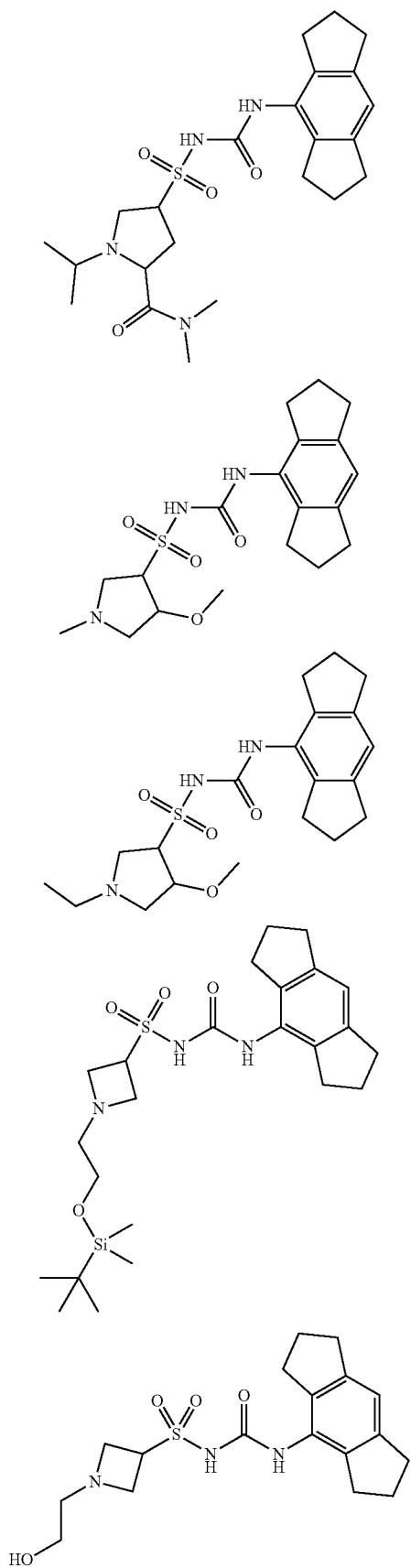
434 -continued 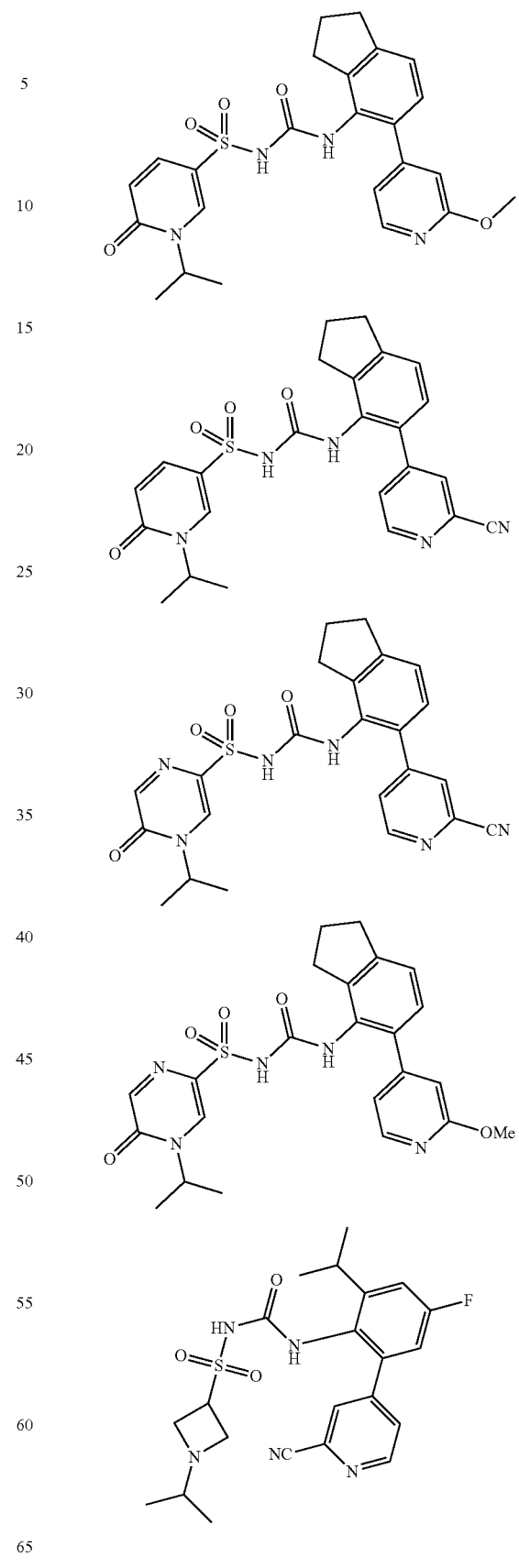

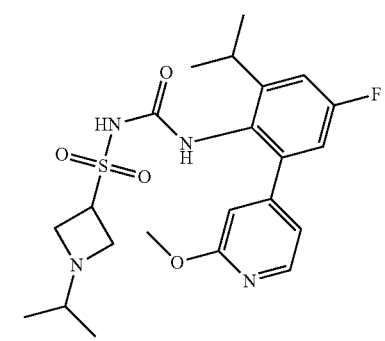
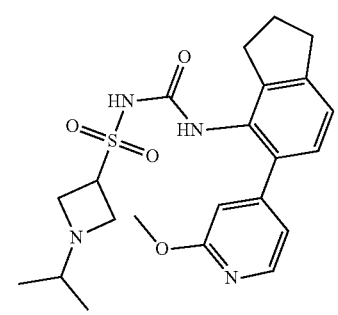
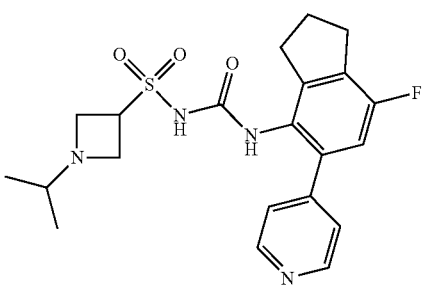
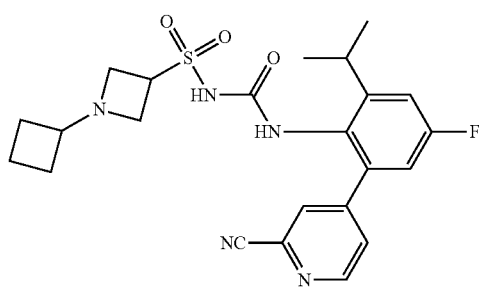
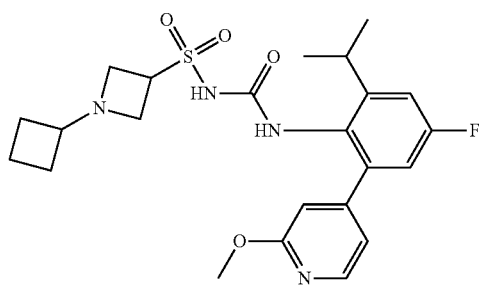
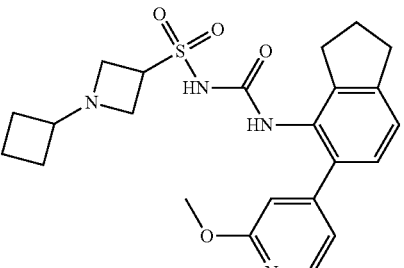
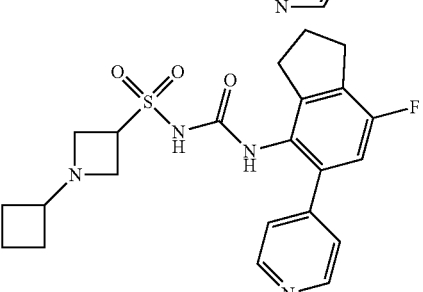
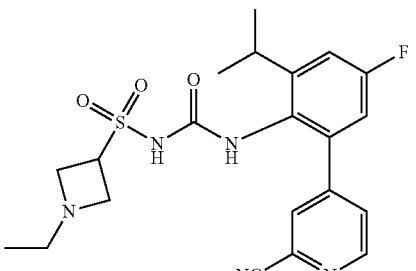
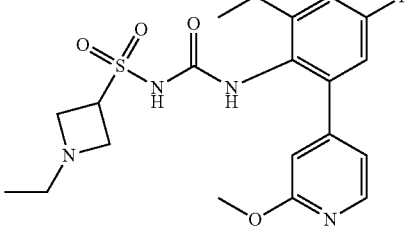
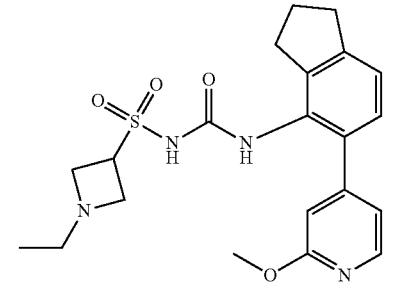
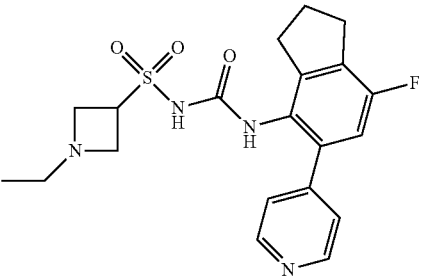

437
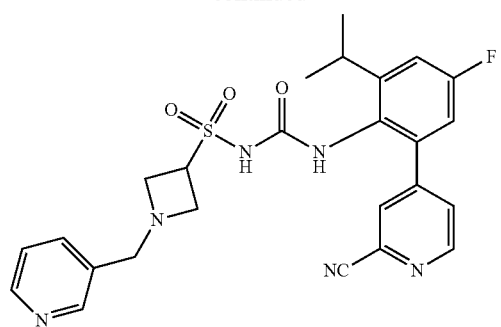
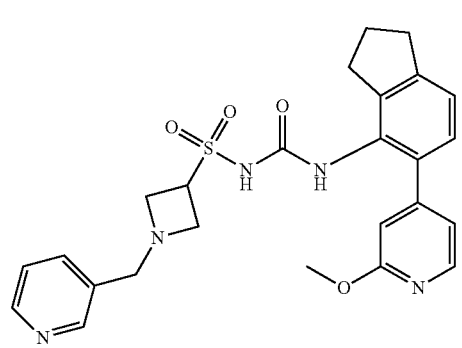
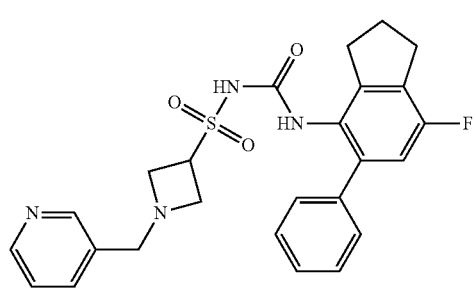
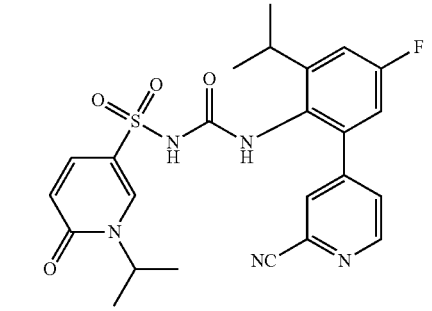
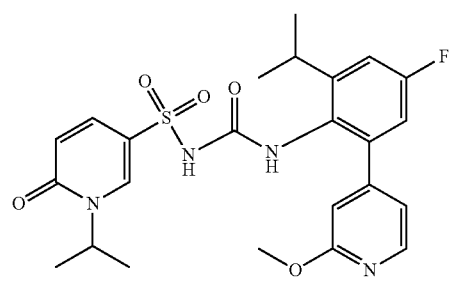
438
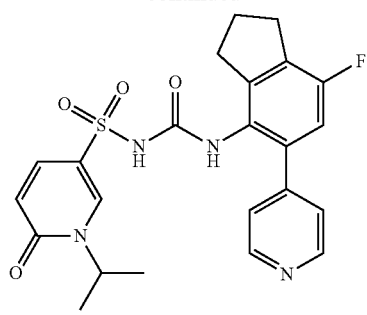
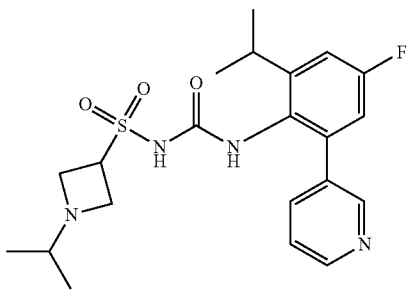
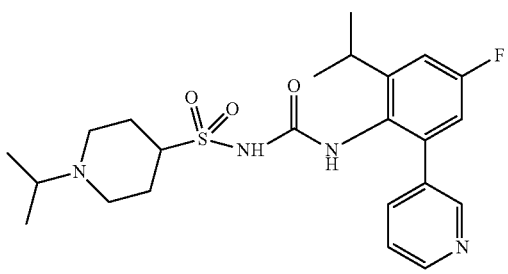
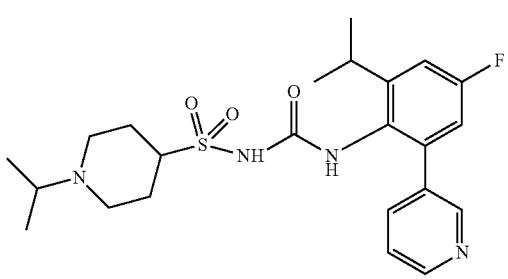
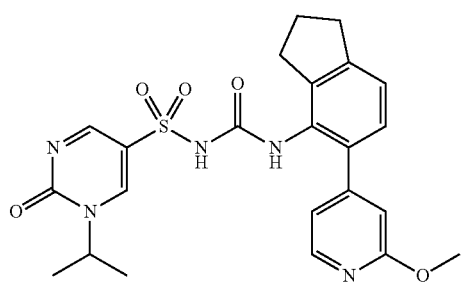
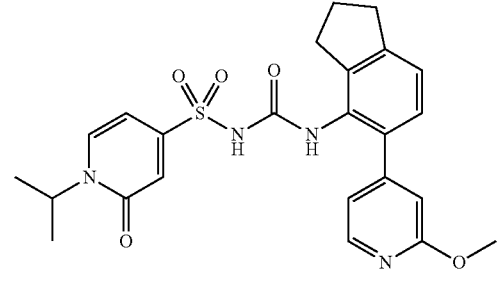

439
-continued
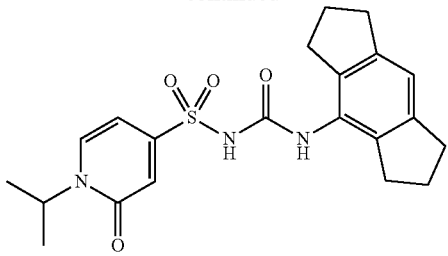
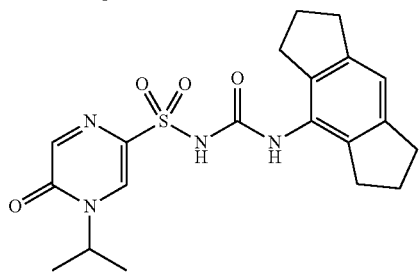
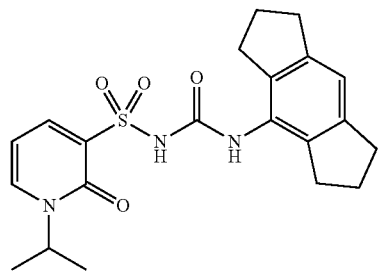
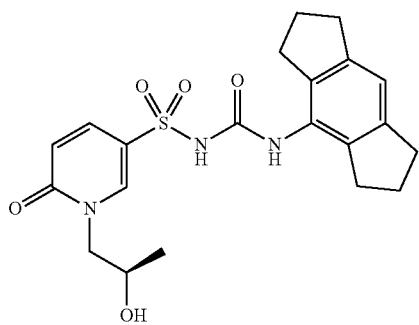
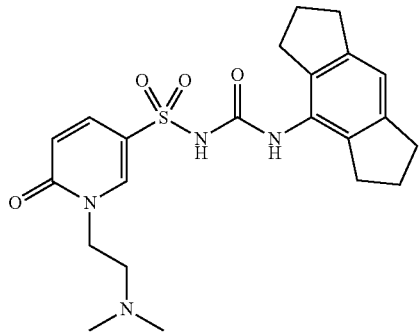
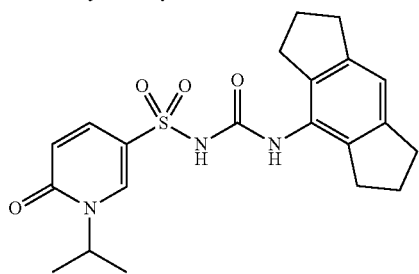
440
-continued
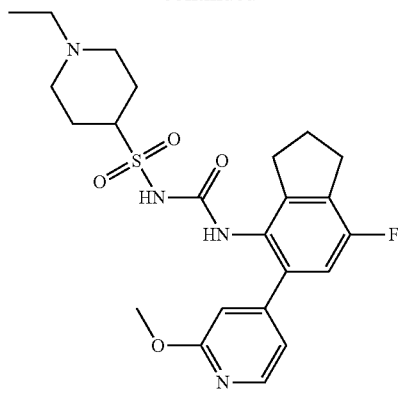
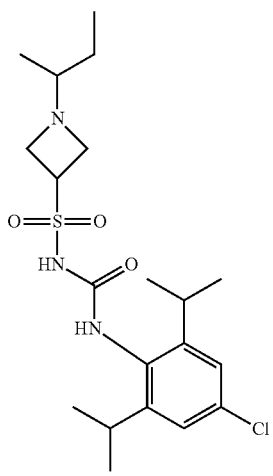
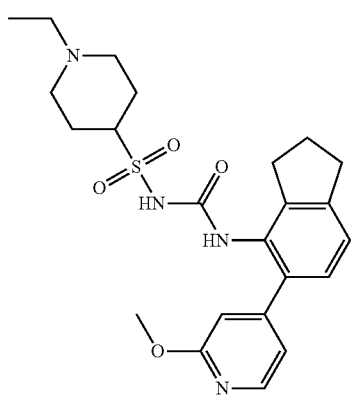
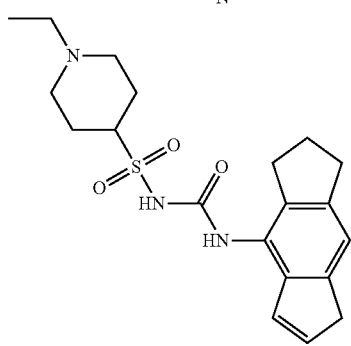

441
-continued

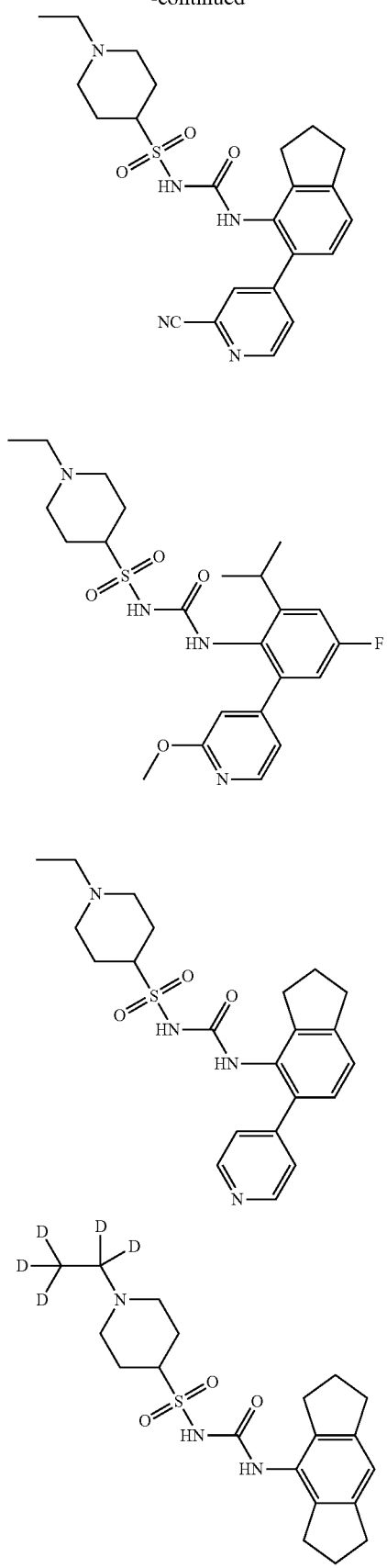

442
-continued

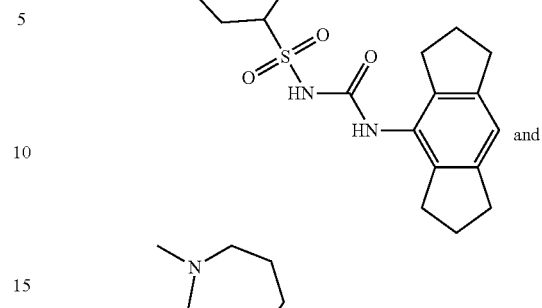

or (b) a pharmaceutically acceptable salt, solvate or prodrug of the selected compound.

17. The compound or pharmaceutically acceptable salt, solvate or prodrug as claimed in claim 1, which is the compound:

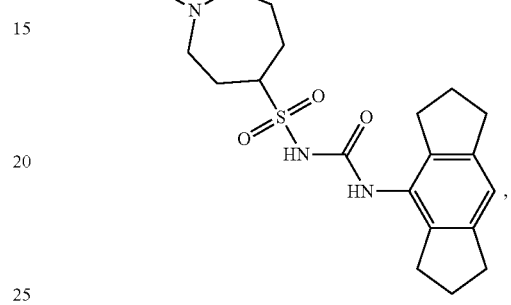

or a pharmaceutically acceptable salt, solvate or prodrug thereof.

18. The compound or pharmaceutically acceptable salt, solvate or prodrug as claimed in claim 1, which is the compound:

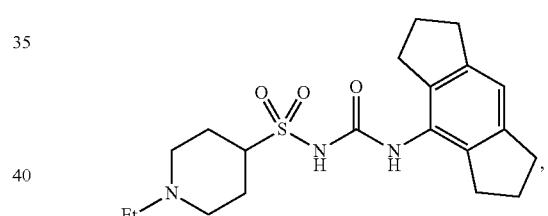

or a pharmaceutically acceptable salt, solvate or prodrug thereof.

19. The compound or pharmaceutically acceptable salt, solvate or prodrug as claimed in claim 1, which is the compound:

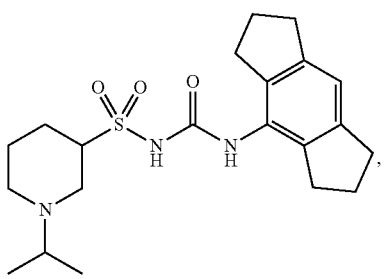 [SMILES: CC(C)N1CCCC(S(=O)(=O)NC(=O)Nc2c3c(cc4c2CCC4)CCC3)C1]

or a pharmaceutically acceptable salt, solvate or prodrug thereof.

20. The compound or pharmaceutically acceptable salt, solvate or prodrug as claimed in claim 1, which is the compound:

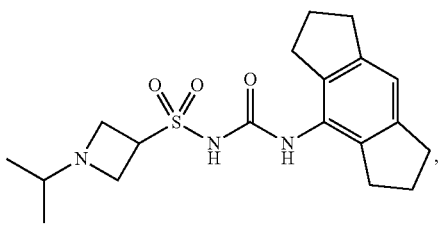 [SMILES: CC(C)N1CC(S(=O)(=O)NC(=O)Nc2c3c(cc4c2CCC4)CCC3)C1]

or a pharmaceutically acceptable salt, solvate or prodrug thereof.

21. The compound or pharmaceutically acceptable salt, solvate or prodrug as claimed in claim 1, which is the compound, pharmaceutically acceptable salt or solvate.

22. The compound or pharmaceutically acceptable salt, solvate or prodrug as claimed in claim 16, which is the compound, pharmaceutically acceptable salt or solvate.

23. The compound or pharmaceutically acceptable salt or solvate as claimed in claim 21, which is the compound:

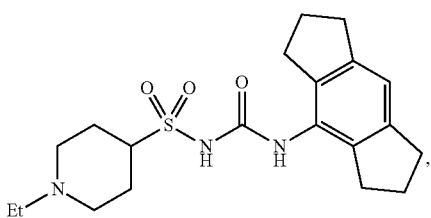 [SMILES: CCN1CCC(S(=O)(=O)NC(=O)Nc2c3c(cc4c2CCC4)CCC3)CC1]

or a pharmaceutically acceptable salt or solvate thereof.

24. The compound or pharmaceutically acceptable salt or solvate as claimed in claim 21, which is the compound:

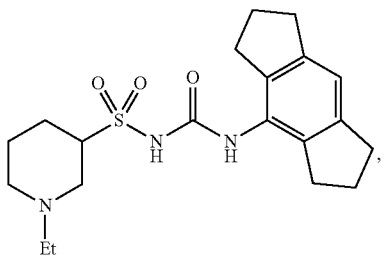 [SMILES: CCN1CCCC(S(=O)(=O)NC(=O)Nc2c3c(cc4c2CCC4)CCC3)C1]

or a pharmaceutically acceptable salt or solvate thereof.

25. The compound or pharmaceutically acceptable salt or solvate as claimed in claim 21, which is the compound:

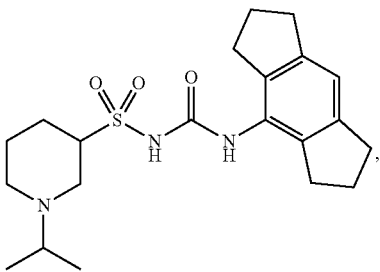

or a pharmaceutically acceptable salt or solvate thereof.

26. The compound or pharmaceutically acceptable salt or solvate as claimed in claim 21, which is the compound:

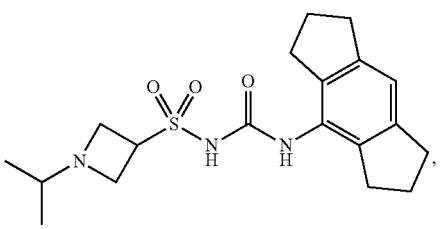 [SMILES: CC(C)N1CC(S(=O)(=O)NC(=O)Nc2c3c(cc4c2CCC4)CCC3)C1]

or a pharmaceutically acceptable salt or solvate thereof.

27. A pharmaceutical composition comprising the compound or the pharmaceutically acceptable salt, solvate or prodrug as claimed in claim 1, and a pharmaceutically acceptable excipient.

28. A pharmaceutical composition comprising the compound or the pharmaceutically acceptable salt or solvate as claimed in claim 21, and a pharmaceutically acceptable excipient.

29. A method of treating, delaying onset of, or reducing risk of a disease, disorder or condition in a subject, the method comprising the step of administering an effective amount of the compound or the pharmaceutically acceptable salt, solvate or prodrug as claimed in claim 1 to the subject, thereby treating, delaying onset of, or reducing risk of the disease, disorder or condition, wherein the disease, disorder or condition is responsive to NLRP3 inhibition.

30. The method of claim 29, wherein the disease, disorder or condition is selected from:
  (i) inflammation;
  (ii) an auto-immune disease;
  (iii) cancer;
  (iv) an infection;
  (v) a central nervous system disease;
  (vi) a metabolic disease;
  (vii) a cardiovascular disease;
  (viii) a respiratory disease;
  (ix) a liver disease;
  (x) a renal disease;
  (xi) an ocular disease;
  (xii) a skin disease;
  (xiii) a lymphatic condition;
  (xiv) a psychological disorder;
  (xv) graft versus host disease;
  (xvi) allodynia; and (xvii) any disease where an individual has been determined to carry a germline or somatic non-silent mutation in NLRP3.

31. The method of claim 29, wherein the disease, disorder or condition is selected from:
(i) cryopyrin-associated periodic syndromes (CAPS);
(ii) Muckle-Wells syndrome (MWS);
(iii) familial cold autoinflammatory syndrome (FCAS);
(iv) neonatal onset multisystem inflammatory disease (NOMID);
(v) familial Mediterranean fever (FMF);
(vi) pyogenic arthritis, pyoderma gangrenosum and acne syndrome (PAPA);
(vii) hyperimmunoglobulinemia D and periodic fever syndrome (HIDS);
(viii) Tumour Necrosis Factor (TNF) Receptor-Associated Periodic Syndrome (TRAPS);
(ix) systemic juvenile idiopathic arthritis;
(x) adult-onset Still's disease (AOSD);
(xi) relapsing polychondritis;
(xii) Schnitzler's syndrome;
(xiii) Sweet's syndrome;
(xiv) Behcet's disease;
(xv) anti-synthetase syndrome;
(xvi) deficiency of interleukin 1 receptor antagonist (DIRA); and
(xvii) haploinsufficiency of A20 (HA20).

32. The method as claimed in claim 29, wherein the compound is administered as a pharmaceutical composition further comprising a pharmaceutically acceptable excipient.

33. A method of inhibiting NLRP3 in a subject, comprising administering the compound or a pharmaceutically acceptable salt, solvate or prodrug thereof as claimed in claim 1 to the subject thereby inhibiting NLRP3.

34. A method of analysing inhibition of NLRP3 or an effect of inhibition of NLRP3 by a compound, comprising contacting a cell or non-human animal with the compound or a pharmaceutically acceptable salt, solvate or prodrug thereof as claimed in claim 1, and analysing inhibition of NLRP3 or an effect of inhibition of NLRP3 in the cell or non-human animal by the compound.

35. A method of treating, delaying onset of, or reducing risk of a disease, disorder or condition in a subject, the method comprising the step of administering an effective amount of the compound or the pharmaceutically acceptable salt or solvate as claimed in claim 21 to the subject, thereby treating, delaying onset of, or reducing risk of the disease, disorder or condition, wherein the disease, disorder or condition is responsive to NLRP3 inhibition.

36. A method of inhibiting $NLRP_3$ in a subject, comprising administering the compound or a pharmaceutically acceptable salt or solvate thereof as claimed in claim 21 to the subject thereby inhibiting $NLRP_3$.

37. A method of analysing inhibition of $NLRP_3$ or an effect of inhibition of $NLRP_3$ by a compound, comprising contacting a cell or non-human animal with the compound or a pharmaceutically acceptable salt or solvate thereof as claimed in claim 21 and analysing inhibition of $NLRP_3$ or an effect of inhibition of $NLRP_3$ in the cell or non-human animal by the compound.

* * * * *

UNITED STATES PATENT AND TRADEMARK OFFICE
CERTIFICATE OF CORRECTION

PATENT NO. : 11,465,992 B2
APPLICATION NO. : 16/629006
DATED : October 11, 2022
INVENTOR(S) : Matthew Cooper et al.

Page 1 of 1

It is certified that error appears in the above-identified patent and that said Letters Patent is hereby corrected as shown below:

On the Title Page

In Column 1, item (72), under Inventors, Line 3, delete "MacLeod," and insert -- Macleod --, therefor.

In the Claims

In Column 403, Lines 52-57, Claim 1, delete " 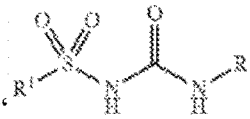 " and insert -- 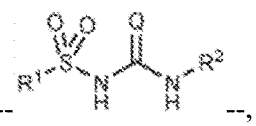 --, therefor.

In Column 405, Line 20, Claim 9, delete "groups; or" and insert -- groups; --, therefor.

In Column 446, Line 20, Claim 36, delete "NLRP$_3$" and insert -- NLRP3 --, therefor.

In Column 446, Line 23, Claim 36, delete "NLRP$_3$." and insert -- NLRP3. --, therefor.

In Column 446, Line 24, Claim 37, delete "NLRP$_3$" and insert -- NLRP3 --, therefor.

In Column 446, Line 25, Claim 37, delete "NLRP$_3$" and insert -- NLRP3 --, therefor.

In Column 446, Line 28, Claim 37, delete "NLRP$_3$" and insert -- NLRP3 --, therefor.

In Column 446, Line 28, Claim 37, delete "claim 21" and insert -- claim 21, --, therefor.

In Column 446, Line 29, Claim 37, delete "NLRP$_3$" and insert -- NLRP3 --, therefor.

Signed and Sealed this
Thirteenth Day of August, 2024

Katherine Kelly Vidal
*Director of the United States Patent and Trademark Office*